(12) United States Patent
Gong et al.

(10) Patent No.: US 9,073,922 B2
(45) Date of Patent: Jul. 7, 2015

(54) PYRROLO[2,3-B]PYRIDINE CDK9 KINASE INHIBITORS

(71) Applicant: AbbVie Inc., North Chicago, IL (US)

(72) Inventors: Jianchun Gong, Deerfield, IL (US); Zhi-Fu Tao, Vernon Hills, IL (US); Thomas D. Penning, Elmhurst, IL (US); Andrew J. Souers, Libertyville, IL (US); Yunsong Tong, Libertyville, IL (US); Guidong Zhu, Gurnee, IL (US)

(73) Assignee: AbbVie, Inc., North Chicago, IL (US)

( * ) Notice: Subject to any disclaimer, the term of this patent is extended or adjusted under 35 U.S.C. 154(b) by 0 days.

(21) Appl. No.: 14/207,886

(22) Filed: Mar. 13, 2014

(65) Prior Publication Data

US 2014/0275027 A1 Sep. 18, 2014

Related U.S. Application Data

(60) Provisional application No. 61/904,842, filed on Nov. 15, 2013.

(51) Int. Cl.

| | |
|---|---|
| *C07D 401/10* | (2006.01) |
| *A61K 31/437* | (2006.01) |
| *A61K 31/4353* | (2006.01) |
| *C07D 471/04* | (2006.01) |
| *A61K 31/497* | (2006.01) |
| *A61K 31/5377* | (2006.01) |

(52) U.S. Cl.
CPC ............ *C07D 471/04* (2013.01); *A61K 31/437* (2013.01); *A61K 31/497* (2013.01); *A61K 31/5377* (2013.01)

(58) Field of Classification Search
CPC . C07D 401/10; A61K 31/437; A61K 31/4353
USPC .......................................... 546/113; 514/300
See application file for complete search history.

(56) References Cited

U.S. PATENT DOCUMENTS

| | | | |
|---|---|---|---|
| 7,282,588 B2 * | 10/2007 | Dhanak et al. ............... | 546/133 |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |

FOREIGN PATENT DOCUMENTS

| | | |
|---|---|---|
| WO | 9507271 A1 | 3/1995 |
| WO | 9710223 A1 | 3/1997 |
| WO | 03000695 | 1/2003 |
| WO | 2005099353 A2 | 10/2005 |
| WO | 2006008754 A1 | 1/2006 |
| WO | 2006017443 | 2/2006 |
| WO | 2008049856 A2 | 5/2008 |
| WO | 2008079918 | 7/2008 |
| WO | 2008128072 | 10/2008 |
| WO | 2008145688 | 12/2008 |
| WO | 2009047359 A1 | 4/2009 |
| WO | 2010003133 | 1/2010 |
| WO | 2010020675 | 2/2010 |
| WO | 2013/157021 | 10/2013 |

OTHER PUBLICATIONS

Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes Metabolism, 1997, vol. 23 (3), pp. 251-257.
Blagojevic N., et al., In "Dosimetry & Treatment Planning for Neutron Capture Therapy", Zamenhof R, et al., Edition, 1994, Advanced Medical Publishing, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Coley W., et al., "Novel HIV-1 Therapeutics Through Targeting Altered Host Cell Pathways.," Expert Opinion on Biological Therapy, 2009, vol. 9 (11), pp. 1369-1382.
Czajka, D. M. et al., "Effect of Deuterium Oxide on the Reproductive Potential of Mice," Annals of the New York Academy of Sciences, 1960, vol. 84, pp. 770-779.

(Continued)

*Primary Examiner* — Niloofar Rahmani
(74) *Attorney, Agent, or Firm* — Chanqxia Sun

(57) ABSTRACT

Disclosed are compounds of Formula (IIIa),

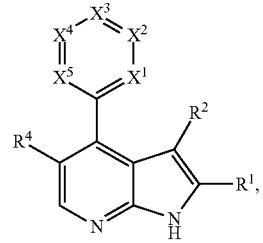

(IIIa)

wherein $R^1, R^2, R^3, X^1, X^2, X^3, X^4, X^5$, have any of the values defined therefore in the specification, and pharmaceutically acceptable salts thereof. The compounds may be used as agents in the treatment of diseases, including cancer. Also provided are pharmaceutical compositions comprising one or more compounds of Formula (IIIa).

8 Claims, No Drawings

(56) References Cited

OTHER PUBLICATIONS

Czajka, D. M. et al., "Physiological Effects of Deuterium on Dogs," American Journal of Physiology, 1961, vol. 201 (2), pp. 357-362.
Foster, A. B. et al., "Deuterium Isotope Effects in the Metabolism of Drugs and Xenobiotics: Implications for Drug Design," Advances in Drug Research, 1985, vol. 14, pp. 2-36.
"IUPAC 1974 Recommendations for Section E, Fundamental Stereochemistry," Pure and Applied Chemistry, 1976, vol. 45, pp. 10-13.
Kato, S. et al., "Synthesis of Deuterated Mosapride Citrate," Journal of Labelled Compounds and Radiopharmaceuticals, 1995, vol. 36 (10), pp. 927-932.
Krystof V., et al., "Pharmacological Targeting of CDK9 in Cardiac Hypertrophy.," Medicinal Research Reviews, 2010, vol. 30 (4), pp. 646-666.
Kushner D.J., et al., "Pharmacological Uses and Perspectives of Heavy Water and Deuterated Compounds.," Canadian Journal of Physiology and Pharmacology, 1999, vol. 77 (2), pp. 79-88.
Lizondo, J. et al., "Linezolid: Oxazolidinone antibacterial," Drugs of the Future, 1996, vol. 21 (11), pp. 1116-1123.
Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Malumbres M., et al., "Cell Cycle, CDKs and Cancer: a Changing Paradigm.," Nature Reviews Cancer, 2009, vol. 9 (3), pp. 153-166.
Miyaura N., et al., "Palladium-Catalyzed Cross-Coupling Reactions of Organoboron Compounds," Chemical Reviews, 1995, vol. 95 (7), pp. 2457-2483.
Prescott, Ed., Methods in Cell Biology, vol. XIV, Academic Press, New York, 1976, pp. 33.
Sutton, V.R. et al., "Bcl-2 Prevents Apoptosis Induced by Perforin and Granzyme B, but not That Mediated by Whole Cytotoxic Lymphocytes," Journal of Immunology, 1997, vol. 158 (12), pp. 5783-5790.
Suzuki A, "Recent Advances in the Cross-Coupling Reactions of Organoboron Derivatives with Organic Electrophiles," Journal of Organometallic Chemistry, 1999, vol. 576, pp. 147-168.
Thomson, J.F., "Physiological Effects of D20 in Mammals," Annals of the New York Academy of Sciences, 1960, vol. 84, pp. 736-744.
Wang S., et al., "Cyclin-dependent kinase 9: a key Transcriptional Regulator and Potential Drug Target in Oncology, Virology and Cardiology.," Trends in Pharmacological Sciences, 2009, vol. 29 (6), pp. 302-312.
The International Search Report and Written Opinion for PCT/US2014/025740 mailed May 27, 2014.
The International Search Report and Written Opinion for PCT/US2014/025670 mailed May 22, 2014.

\* cited by examiner

PYRROLO[2,3-B]PYRIDINE CDK9 KINASE INHIBITORS

BACKGROUND OF THE INVENTION

Cyclin-dependent kinases (CDKs) are serine/threonine protein kinases whose activity depends on binding and activation by cyclin partners. These heterodimeric complexes can phosphorylate various substrates involved in the control of transcription and cell-cycle progression in response to different stimuli. CDK8 and CDK9 have key roles in the control of transcription by RNA polymerase II. CDK9 responds specifically to several cytokines, including tumor necrosis factor and interleukin-6, indicating that it might have special roles in the regulation of a variety of physiological processes, especially immune responses, inflammation, cell activation, and differentiation.

Deregulated CDK activity is a hallmark of human cancer, and a variety of genetic and epigenetic events, such as over expression of cyclins, diminished levels of CDK inhibiting proteins or gain-of function mutations in CDK, have been described to cause increased activity of these enzymes and provide a selective growth advantage in tumor cells. CDK9 inhibition causes rapid depletion of short-lived mRNA transcripts and their associated protein products. Many genes encoding proteins involved in cell growth, proliferation, and tumor development (Myc, Cyclin D1, and Mcl-1) are characterized by short-lived mRNAs and proteins and hence the consequences of CDK9 inhibition include anti-proliferative and pro-apoptotic effects through loss of function at many cellular pathways. Tumor types that are dependent on labile pro-survival proteins (e.g., Mcl-1), which includes multiple myeloma, CLL, breast, melanoma and pancreatic cancers as well as the MYC-driven tumors (multiple cancer types) would be susceptible to CDK9 inhibition. CDK9 inhibitors might also be effective in combination with standard of care in tumors in which NF-κB is constitutively active and contributing to chemo resistance. This includes hematologic malignancies as well as solid tumors (breast, colorectal, prostate, melanoma and pancreatic). Thus, CDK9 inhibition targets multiple cancer-relevant pathways by inhibition of a single protein and thereby renders CDK9 as an attractive target for anti-cancer therapy. (Nature Reviews Cancer: 2009, 9, 153-166).

CDK9 inhibitors can also find therapeutic application in cardiology and virology as many viruses depend on the infected host for transcription of their genome. (Cyclin-dependent kinase 9: a key transcriptional regulator and potential drug target in oncology, virology and cardiology. Trends in Pharmacol. Sci. 2009, 29. 302-312; Pharmacological targeting of CDK9 in cardiac hypertrophy. Med Res. Rev. 2010 30:646-66; Novel HIV-1 therapeutics through targeting altered host cell pathways. Expert Opin Biol Ther. 2009 9:1369-82).

CDK9 inhibitors have also been reported as potential therapeutics for the treatment of chronic, inflammatory and neuropathic pain (WO2008/049856; WO2009/047359).

In view of the above, there is a need in the art for small molecule therapeutics that can inhibit the activity of CDK9. The present invention fulfills at least this need.

SUMMARY OF THE INVENTION

In one aspect, the present invention relates to compounds of Formula (IIIa) or a pharmaceutically acceptable salt thereof,

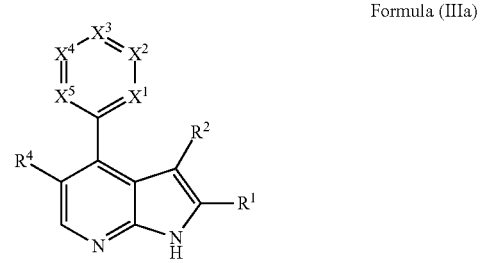

Formula (IIIa)

wherein
one of $X^1$, $X^2$, $X^3$, $X^4$, and $X^5$ is N; and the remaining are $CR^{3A}$; or
two of $X^1$, $X^2$, $X^3$, $X^4$, and $X^5$ are N; and the remaining are $CR^{3A}$;

$R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $S(O)(N)R^5SO_2R^5$, $C(O)H$, $C(O)OH$, $(O)$, $OH$, $CN$, $NO_2$, F, Cl, Br and I;

$R^2$ is selected from the group consisting of hydrogen, $C_1$-$C_4$ alkyl, $NO_2$, $CN$, $C(O)NH_2$, $C(O)OR^{2A}$, F, Cl, Br, and I;

$R^{2A}$ is selected from the group consisting of $C_1$-$C_6$ alkyl, $C_2$-$C_6$ alkenyl, and $C_2$-$C_6$ alkynyl;

$R^{3A}$, at each occurrence, is each independently selected from the group consisting of H, $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, $(O)$, $OH$, $CN$, $NO_2$, F, Cl, Br and I;

$R^4$ is selected from the group consisting of $R^{4A}$, $OR^{4A}$, $C(O)NH_2$, $CN$, F, Cl, Br, and I;

$R^{4A}$ is selected from the group consisting of hydrogen, $C_1$-$C_6$ alkyl, $C_2$-$C_6$ alkenyl, and $C_2$-$C_6$ alkynyl;

$R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $B(OH)_2$, $C(O)H$, $C(O)OH$, OH, CN, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, (O), OH, CN, $NO_2$, F, Cl, Br and I;

$R^6$, at each occurrence, is independently selected from the group consisting of $C_1$-$C_6$ alkyl, $C_2$-$C_6$ alkenyl, $C_2$-$C_6$ alkynyl, phenyl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, CN, $NO_2$, F, Cl, Br and I; wherein each $R^6$ phenyl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, (O), OH, CN, $NO_2$, F, Cl, Br and I;

$R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $NH_2$, $NHR^{13}$, $N(R^{13})_2$, $C(O)H$, $C(O)OH$, OH, CN, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, (O), OH, CN, $NO_2$, F, Cl, Br and I;

$R^8$, at each occurrence, is independently selected from the group consisting of $C_1$-$C_6$ alkyl, $C_2$-$C_6$ alkenyl, $C_2$-$C_6$ alkynyl, and heterocycloalkyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)NR^{8A}SO_2R^{8A}$, $NH_2$, $C(O)H$, $C(O)OH$, OH, CN, $NO_2$, F, Cl, Br and I; wherein each $R^8$ heterocycloalkyl is optionally substituted with one or more substituents independently selected from the group consisting of $NH_2$, $C(O)H$, $C(O)OH$, OH, CN, $NO_2$, F, Cl, Br and I;

$R^{8A}$, at each occurrence, is independently selected from the group consisting of $C_1$-$C_6$ alkyl, $C_2$-$C_6$ alkenyl, and $C_2$-$C_6$ alkynyl;

$R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, (O), OH, CN, $NO_2$, F, Cl, Br and I;

$R^{10}$, at each occurrence, is independently selected from the group consisting of $C_1$-$C_6$ alkyl, $C_2$-$C_6$ alkenyl, and $C_2$-$C_6$ alkynyl; wherein each $R^{10}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, OH, CN, $NO_2$, F, Cl, Br and I;

$R^{11}$, at each occurrence, is independently selected from the group consisting of $C_1$-$C_6$ alkyl, $C_2$-$C_6$ alkenyl, $C_2$-$C_6$ alkynyl, aryl, and heteroaryl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $OR^{11A}$, $NH_2$, $NHR^{11A}$, $N(R^{11A})_2$, $C(O)H$, $C(O)OH$, OH, CN, $NO_2$, F, Cl, Br and I; wherein each $R^{11}$ aryl and heteroaryl is optionally substituted with one or more substituents independently selected from the group consisting of $C_1$-$C_6$ alkyl, $C_1$-$C_6$ haloalkyl, $NH_2$, $C(O)H$, $C(O)OH$, OH, CN, $NO_2$, F, Cl, Br and I;

$R^{11A}$, at each occurrence, is independently selected from the group consisting of $C_1$-$C_6$ alkyl, $C_2$-$C_6$ alkenyl, and $C_2$-$C_6$ alkynyl;

$R^{12}$, at each occurrence, is independently selected from the group consisting of $C_1$-$C_6$ alkyl, $C_2$-$C_6$ alkenyl, and $C_2$-$C_6$ alkynyl; wherein each $R^{12}$ $C_1$-$C_6$ alkyl, $C_2$-$C_6$ alkenyl, and $C_2$-$C_6$ alkynyl is optionally substituted with one or more substituents independently selected from the group consisting of $NH_2$, $NHR^{14}$, $N(R^{14})_2$, $C(O)H$, $C(O)OH$, OH, CN, $NO_2$, F, Cl, Br and I;

$R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, cycloalkyl, cycloalkenyl, and heterocycloalkyl, heterocycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of $R^{15}$, $OR^{15}$, $C(O)H$, $C(O)OH$, OH, CN, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $R^{16}$, $OR^{16}$, $C(O)H$, $C(O)OH$, (O), OH, CN, $NO_2$, F, Cl, Br and I;

$R^{14}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl;

$R^{15}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl; wherein each $R^{15}$ $C_1$-$C_6$ alkyl, $C_2$-$C_6$ alkenyl, and $C_2$-$C_6$ alkynyl is optionally substituted with one or more $OCH_3$; and $R^{16}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl.

In one embodiment of Formula (IIIa), $R^2$ is hydrogen, $R^4$ is $R^{4A}$, and $R^{4A}$ is hydrogen. In another embodiment of Formula (IIIa), $R^2$ is hydrogen, $R^4$ is $R^{4A}$, $R^{4A}$ is hydrogen; and $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, tetrahydropyridinyl, cyclohexyl, and cyclohexenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NHC(O)OR^5$, $NR^5SO_2NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $S(O)(N)R^5SO_2R^5$, $C(O)H$, $C(O)OH$, (O), OH, CN, $NO_2$, F, Cl, Br and I. In another embodiment of Formula (IIIa), $R^2$ is hydrogen, $R^4$ is $R^{4A}$, $R^{4A}$ is hydrogen; and $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$. In another embodiment of Formula (IIIa), $R^2$ is hydrogen, $R^4$ is $R^{4A}$, $R^{4A}$ is hydrogen; and $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are unsubstituted. In another embodiment of Formula (IIIa), $R^2$ is hydrogen, $R^4$ is $R^{4A}$, $R^{4A}$ is hydrogen; $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $S(O)(N)R^5SO_2R^5$, $C(O)H$, $C(O)OH$, (O), OH, CN, $NO_2$, F, Cl, Br and I; and $X^1$ is N; and $X^2$, $X^3$, $X^4$, and $X^5$ are $C$—$R^{3A}$. In another embodiment of Formula (IIIa), $R^2$ is hydrogen, $R^4$ is $R^{4A}$, $R^{4A}$ is hydrogen; $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $S(O)(N)R^5SO_2R^5$, $C(O)H$, $C(O)OH$, (O), OH, CN, $NO_2$, F, Cl, Br and I; $X^2$ is N; $X^4$ is N; and $X^2$, $X^3$, and $X^5$ are $C$—$R^{3A}$. In another embodiment of Formula (IIIa), $R^2$ is hydrogen, $R^4$ is $R^{4A}$, $R^{4A}$ is hydrogen; $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $S(O)(N)R^5SO_2R^5$, $C(O)H$, $C(O)OH$, (O), OH, CN, $NO_2$, F, Cl, Br and I; $X^1$ is N; and $X^2$, $X^3$, $X^4$, and $X^5$ are $C$—$R^{3A}$; and $R^{3A}$, at each occurrence, is independently selected from the group consisting of H, $R^6$, $OR^6$, $NH_2$, NHR⁶, N(R⁶)₂, NHC(O)R⁶, C(O)NHR⁶, F, and Cl. In another embodiment of Formula (IIIa), R² is hydrogen, R⁴ is R⁴ᴬ, R⁴ᴬ is hydrogen; R¹ is selected from the group consisting of pyrrolidinyl, morpholinyl, piperidinyl, 1,2,3,6-tetrahydropyridinyl, cyclohexyl, and cyclohexenyl; wherein the R¹ pyrrolidinyl, morpholinyl, piperidinyl, 1,2,3,6-tetrahydropyridinyl, cyclohexyl, and cyclohexenyl are optionally substituted with one or more substituents independently selected from the group consisting of R⁵, OR⁵, SR⁵, S(O)R⁵, SO₂R⁵, C(O)R⁵, CO(O)R⁵, OC(O)R⁵, OC(O)OR⁵, NH₂, NHR⁵, N(R⁵)₂, NHC(O)R⁵, NR⁵C(O)R⁵, SO₂NHC(O)R⁵, SO₂NR⁵C(O)R⁵, NHS(O)₂R⁵, NR⁵S(O)₂R⁵, NHC(O)OR⁵, NR⁵C(O)OR⁵, SO₂NHC(O)OR⁵, SO₂NR⁵C(O)OR⁵, NHSO₂NHC(O)OR⁵, NHSO₂NR⁵C(O)OR⁵, NR⁵SO₂NR⁵C(O)OR⁵, NR⁵SO₂NHC(O)OR⁵, NHC(O)NH₂, NHC(O)NHR⁵, NHC(O)N(R⁵)₂, NR⁵C(O)NHR⁵, NR⁵C(O)N(R⁵)₂, OC(O)NH₂, OC(O)NHR⁵, OC(O)N(R⁵)₂, OC(O)NHSO₂R⁵, OC(O)NR⁵SO₂R⁵, C(O)NH₂, C(O)NHR⁵, C(O)N(R⁵)₂, C(O)NHOH, C(O)NHOR⁵, C(O)NHSO₂R⁵, C(O)NR⁵SO₂R⁵, SO₂NH₂, SO₂NHR⁵, SO₂N(R⁵)₂, OSO₂NH₂, OSO₂NHR⁵, OSO₂N(R⁵)₂, C(O)NHCN, C(O)NR⁵CN, S(O)(N)R⁵, S(O)(N)R⁵SO₂R⁵, C(O)H, C(O)OH, (O), OH, CN, NO₂, F, Cl, Br and I; X² is N; X⁴ is N; and X², X³, and X⁵ are C—R³ᴬ; and R³ᴬ, at each occurrence, is independently selected from the group consisting of H, R⁶, OR⁶, NH₂, NHR⁶, N(R⁶)₂, NHC(O)R⁶, C(O)NHR⁶, F, and Cl. In another embodiment of Formula (IIIa), R² is hydrogen, R⁴ is R⁴ᴬ, R⁴ᴬ is hydrogen; R¹ is selected from the group consisting of pyrrolidinyl, morpholinyl, piperidinyl, 1,2,3,6-tetrahydropyridinyl, cyclohexyl, and cyclohexenyl; wherein the R¹ pyrrolidinyl, morpholinyl, piperidinyl, 1,2,3,6-tetrahydropyridinyl, cyclohexyl, and cyclohexenyl are optionally substituted with one or more substituents independently selected from the group consisting of R⁵, OR⁵, SR⁵, S(O)R⁵, SO₂R⁵, C(O)R⁵, CO(O)R⁵, OC(O)R⁵, OC(O)OR⁵, NH₂, NHR⁵, N(R⁵)₂, NHC(O)R⁵, NR⁵C(O)R⁵, SO₂NHC(O)R⁵, SO₂NR⁵C(O)R⁵, NHS(O)₂R⁵, NR⁵S(O)₂R⁵, NHC(O)OR⁵, NR⁵C(O)OR⁵, SO₂NHC(O)OR⁵, SO₂NR⁵C(O)OR⁵, NHSO₂NHC(O)OR⁵, NHSO₂NR⁵C(O)OR⁵, NR⁵SO₂NR⁵C(O)OR⁵, NR⁵SO₂NHC(O)OR⁵, NHC(O)NH₂, NHC(O)NHR⁵, NHC(O)N(R⁵)₂, NR⁵C(O)NHR⁵, NR⁵C(O)N(R⁵)₂, OC(O)NH₂, OC(O)NHR⁵, OC(O)N(R⁵)₂, OC(O)NHSO₂R⁵, OC(O)NR⁵SO₂R⁵, C(O)NH₂, C(O)NHR⁵, C(O)N(R⁵)₂, C(O)NHOH, C(O)NHOR⁵, C(O)NHSO₂R⁵, C(O)NR⁵SO₂R⁵, SO₂NH₂, SO₂NHR⁵, SO₂N(R⁵)₂, OSO₂NH₂, OSO₂NHR⁵, OSO₂N(R⁵)₂, C(O)NHCN, C(O)NR⁵CN, S(O)(N)R⁵, S(O)(N)R⁵SO₂R⁵, C(O)H, C(O)OH, (O), OH, CN, NO₂, F, Cl, Br and I; X² is N; X⁴ is N; and X², X³, and X⁵ are C—R³ᴬ; R³ᴬ, at each occurrence, is independently selected from the group consisting of H, R⁶, OR⁶, NH₂, NHR⁶, N(R⁶)₂, NHC(O)R⁶, C(O)NHR⁶, F, and Cl; and R⁶, at each occurrence, is independently selected from the group consisting of C₁-C₆ alkyl, phenyl, and heteroaryl; wherein each R⁶ C₁-C₆ alkyl, C₂-C₆ alkenyl, and C₂-C₆ alkynyl is optionally substituted with one or more substituents independently selected from the group consisting of R⁹, SR⁹, and OH; wherein each R⁶ phenyl and heteroaryl is optionally substituted with one or more substituents independently selected from the group consisting of NH₂, and Cl.

Still another embodiment pertains to compounds of Formula (IIIa), selected from the group consisting of:
5-methoxy-6-[2-(piperidin-3-yl)-1H-pyrrolo[2,3-b]pyridin-4-yl]pyridin-2-amine;
N-benzyl-5-chloro-6-[2-(piperidin-3-yl)-1H-pyrrolo[2,3-b]pyridin-4-yl]pyridin-2-amine;
N-benzyl-5-chloro-6-[2-(1-methylpiperidin-3-yl)-1H-pyrrolo[2,3-b]pyridin-4-yl]pyridin-2-amine;
N-benzyl-6-[2-(1-methylpiperidin-3-yl)-1H-pyrrolo[2,3-b]pyridin-4-yl]pyridin-2-amine;
N-benzyl-5-methoxy-6-[2-(piperidin-3-yl)-1H-pyrrolo[2,3-b]pyridin-4-yl]pyridin-2-amine;
N-benzyl-5-chloro-6-{2-[1-(propan-2-ylsulfonyl)piperidin-3-yl]-1H-pyrrolo[2,3-b]pyridin-4-yl}pyridin-2-amine;
methyl 3-{4-[6-(benzylamino)-3-chloropyridin-2-yl]-1H-pyrrolo[2,3-b]pyridin-2-yl}piperidine-1-carboxylate;
4-(3-methoxypyridin-2-yl)-2-(piperidin-4-yl)-1H-pyrrolo[2,3-b]pyridine;
5-methoxy-6-[2-(piperidin-4-yl)-1H-pyrrolo[2,3-b]pyridin-4-yl]pyridin-2-amine;
4-(6-fluoro-3-methoxypyridin-2-yl)-2-(piperidin-4-yl)-1H-pyrrolo[2,3-b]pyridine;
4-(4-methoxypyridin-3-yl)-2-(1-methylpiperidin-4-yl)-1H-pyrrolo[2,3-b]pyridine;
N-benzyl-5-chloro-6-[2-(piperidin-4-yl)-1H-pyrrolo[2,3-b]pyridin-4-yl]pyridin-2-amine;
5-chloro-N-(3-fluorobenzyl)-6-[2-(piperidin-4-yl)-1H-pyrrolo[2,3-b]pyridin-4-yl]pyridin-2-amine;
5-chloro-6-[2-(piperidin-4-yl)-1H-pyrrolo[2,3-b]pyridin-4-yl]-N-(pyridin-3-ylmethyl)pyridin-2-amine;
5-chloro-N-(4-chlorobenzyl)-6-[2-(piperidin-4-yl)-1H-pyrrolo[2,3-b]pyridin-4-yl]pyridin-2-amine;
5-chloro-N-(2,5-difluorobenzyl)-6-[2-(piperidin-4-yl)-1H-pyrrolo[2,3-b]pyridin-4-yl]pyridin-2-amine;
5-chloro-N-[(5-fluoropyridin-3-yl)methyl]-6-[2-(piperidin-4-yl)-1H-pyrrolo[2,3-b]pyridin-4-yl]pyridin-2-amine;
5-chloro-N-(2-fluorobenzyl)-6-[2-(piperidin-4-yl)-1H-pyrrolo[2,3-b]pyridin-4-yl]pyridin-2-amine;
5-chloro-N-(3,4-difluorobenzyl)-6-[2-(piperidin-4-yl)-1H-pyrrolo[2,3-b]pyridin-4-yl]pyridin-2-amine;
5-chloro-6-[2-(piperidin-4-yl)-1H-pyrrolo[2,3-b]pyridin-4-yl]-N-(pyridin-4-ylmethyl)pyridin-2-amine;
5-chloro-N-[(1-oxidopyridin-3-yl)methyl]-6-[2-(piperidin-4-yl)-1H-pyrrolo[2,3-b]pyridin-4-yl]pyridin-2-amine;
5-chloro-N-(piperidin-4-ylmethyl)-6-[2-(piperidin-4-yl)-1H-pyrrolo[2,3-b]pyridin-4-yl]pyridin-2-amine;
5-chloro-N-(piperidin-3-ylmethyl)-6-[2-(piperidin-4-yl)-1H-pyrrolo[2,3-b]pyridin-4-yl]pyridin-2-amine;
4-(3-chloro-6-phenylpyridin-2-yl)-2-(piperidin-4-yl)-1H-pyrrolo[2,3-b]pyridine;
N-{5-chloro-6-[2-(piperidin-4-yl)-1H-pyrrolo[2,3-b]pyridin-4-yl]pyridin-2-yl}benzamide;
N-benzyl-5-chloro-N-methyl-6-[2-(piperidin-4-yl)-1H-pyrrolo[2,3-b]pyridin-4-yl]pyridin-2-amine;
N-benzyl-5-chloro-N-ethyl-6-[2-(piperidin-4-yl)-1H-pyrrolo[2,3-b]pyridin-4-yl]pyridin-2-amine;
5-chloro-6-[2-(piperidin-4-yl)-1H-pyrrolo[2,3-b]pyridin-4-yl]-N-(tetrahydro-2H-pyran-4-ylmethyl)pyridin-2-amine;
5-chloro-6-[2-(piperidin-4-yl)-1H-pyrrolo[2,3-b]pyridin-4-yl]-N-(tetrahydro-2H-pyran-3-ylmethyl)pyridin-2-amine;
N-benzyl-5-chloro-4-[2-(piperidin-4-yl)-1H-pyrrolo[2,3-b]pyridin-4-yl]pyridin-2-amine;
N-benzyl-5-chloro-6-[2-(1-methylpiperidin-4-yl)-1H-pyrrolo[2,3-b]pyridin-4-yl]pyridin-2-amine;
5-chloro-N-[(1S)-1-phenylethyl]-6-[2-(piperidin-4-yl)-1H-pyrrolo[2,3-b]pyridin-4-yl]pyridin-2-amine;
N-benzyl-6-[2-(1-methylpiperidin-4-yl)-1H-pyrrolo[2,3-b]pyridin-4-yl]pyridin-2-amine;
5-chloro-N-(3-fluorobenzyl)-6-[2-(1-methylpiperidin-4-yl)-1H-pyrrolo[2,3-b]pyridin-4-yl]pyridin-2-amine;
4-[6-(benzyloxy)-3-chloropyridin-2-yl]-2-(piperidin-4-yl)-1H-pyrrolo[2,3-b]pyridine;
N-benzyl-5-chloro-6-[2-(pyrrolidin-3-yl)-1H-pyrrolo[2,3-b]pyridin-4-yl]pyridin-2-amine;

5-chloro-6-[2-(pyrrolidin-3-yl)-1H-pyrrolo[2,3-b]pyridin-4-yl]-N-(tetrahydro-2H-pyran-4-ylmethyl)pyridin-2-amine;
N-benzyl-5-chloro-6-[2-(morpholin-2-yl)-1H-pyrrolo[2,3-b]pyridin-4-yl]pyridin-2-amine;
N-benzyl-6-[5-chloro-2-(piperidin-3-yl)-1H-pyrrolo[2,3-b]pyridin-4-yl]pyridin-2-amine;
5-chloro-4-(6-fluoropyridin-2-yl)-2-(piperidin-3-yl)-1H-pyrrolo[2,3-b]pyridine;
N-benzyl-6-[5-chloro-2-(piperidin-3-yl)-1H-pyrrolo[2,3-b]pyridin-4-yl]pyridin-2-amine;
6-[5-chloro-2-(piperidin-3-yl)-1H-pyrrolo[2,3-b]pyridin-4-yl]-N-(tetrahydro-2H-pyran-4-ylmethyl)pyridin-2-amine;
N-benzyl-6-[5-chloro-2-(1-methylpiperidin-3-yl)-1H-pyrrolo[2,3-b]pyridin-4-yl]pyridin-2-amine;
methyl 3-{4-[6-(b enzylamino)pyridin-2-yl]-5-chloro-1H-pyrrolo[2,3-b]pyridin-2-yl}piperidine-1-carboxylate;
N-benzyl-6-{5-chloro-2-[1-(propan-2-ylsulfonyl)piperidin-3-yl]-1H-pyrrolo[2,3-b]pyridin-4-yl}pyridin-2-amine;
6-[2-(3-aminocyclohexyl)-5-chloro-1H-pyrrolo[2,3-b]pyridin-4-yl]-N-benzylpyridin-2-amine;
6-[2-(piperidin-4-yl)-1H-pyrrolo[2,3-b]pyridin-4-yl]-N-(tetrahydro-2H-pyran-4-ylmethyl)pyridin-2-amine;
6-[2-(1-methylpiperidin-4-yl)-1H-pyrrolo[2,3-b]pyridin-4-yl]-N-(tetrahydro-2H-pyran-4-ylmethyl)pyridin-2-amine;
6-[2-(1-methylpiperidin-4-yl)-1H-pyrrolo[2,3-b]pyridin-4-yl]-N-(3-phenylpropyl)pyridin-2-amine;
6-[2-(1-methylpiperidin-4-yl)-1H-pyrrolo[2,3-b]pyridin-4-yl]-N-(pyridin-3-ylmethyl)pyridin-2-amine;
6-[2-(1-methylpiperidin-4-yl)-1H-pyrrolo[2,3-b]pyridin-4-yl]-N-[2-(phenylsulfanyl)ethyl]pyridin-2-amine;
N-(cyclopropylmethyl)-6-[2-(1-methylpiperidin-4-yl)-1H-pyrrolo[2,3-b]pyridin-4-yl]pyridin-2-amine;
N-[(2,2-dimethyltetrahydro-2H-pyran-4-yl)methyl]-6-[2-(1-methylpiperidin-4-yl)-1H-pyrrolo[2,3-b]pyridin-4-yl]pyridin-2-amine;
N-benzyl-N-methyl-6-[2-(1-methylpiperidin-4-yl)-1H-pyrrolo[2,3-b]pyridin-4-yl]pyridin-2-amine;
N-(3-chlorobenzyl)-6-[2-(1-methylpiperidin-4-yl)-1H-pyrrolo[2,3-b]pyridin-4-yl]pyridin-2-amine;
N-(2,6-difluorobenzyl)-6-[2-(1-methylpiperidin-4-yl)-1H-pyrrolo[2,3-b]pyridin-4-yl]pyridin-2-amine;
6-[2-(1-methylpiperidin-4-yl)-1H-pyrrolo[2,3-b]pyridin-4-yl]-N-[(1S)-1-phenylethyl]pyridin-2-amine;
N-(1,3-benzodioxol-5-ylmethyl)-6-[2-(1-methylpiperidin-4-yl)-1H-pyrrolo[2,3-b]pyridin-4-yl]pyridin-2-amine;
5-chloro-6-[2-(piperidin-4-yl)-1H-pyrrolo[2,3-b]pyridin-4-yl]pyridin-2-amine;
N-[2-(phenylsulfanyl)ethyl]-6-[2-(piperidin-4-yl)-1H-pyrrolo[2,3-b]pyridin-4-yl]pyridin-2-amine;
5-chloro-6-[2-(1-methylpiperidin-4-yl)-1H-pyrrolo[2,3-b]pyridin-4-yl]pyridin-2-amine;
3-chloro-$N^2$-{5-chloro-6-[2-(1-methylpiperidin-4-yl)-1H-pyrrolo[2,3-b]pyridin-4-yl]pyridin-2-yl}pyridine-2,6-diamine;
5-chloro-6-[2-(1-methylpiperidin-4-yl)-1H-pyrrolo[2,3-b]pyridin-4-yl]-N-(tetrahydro-2H-pyran-4-ylmethyl)pyridin-2-amine;
N-(2-phenylethyl)-6-[2-(piperidin-4-yl)-1H-pyrrolo[2,3-b]pyridin-4-yl]pyridin-2-amine;
N-methyl-6-[2-(1-methylpiperidin-4-yl)-1H-pyrrolo[2,3-b]pyridin-4-yl]-N-(2-phenylethyl)pyridin-2-amine;
N-(2-chlorobenzyl)-6-[2-(piperidin-4-yl)-1H-pyrrolo[2,3-b]pyridin-4-yl]pyridin-2-amine;
N-(2-chlorobenzyl)-6-[2-(1-methylpiperidin-4-yl)-1H-pyrrolo[2,3-b]pyridin-4-yl]pyridin-2-amine;
N-(2-chlorobenzyl)-N-methyl-6-[2-(1-methylpiperidin-4-yl)-1H-pyrrolo[2,3-b]pyridin-4-yl]pyridin-2-amine;
1-[2-({6-[2-(piperidin-4-yl)-1H-pyrrolo[2,3-b]pyridin-4-yl]pyridin-2-yl}amino)ethyl]pyrrolidin-2-one;
1-[2-(methyl{6-[2-(1-methylpiperidin-4-yl)-1H-pyrrolo[2,3-b]pyridin-4-yl]pyridin-2-yl}amino)ethyl]pyrrolidin-2-one;
6-[2-(1-methylpiperidin-4-yl)-1H-pyrrolo[2,3-b]pyridin-4-yl]-N-(2-phenylethyl)pyridin-2-amine;
1-[2-({6-[2-(1-methylpiperidin-4-yl)-1H-pyrrolo[2,3-b]pyridin-4-yl]pyridin-2-yl}amino)ethyl]pyrrolidin-2-one;
5-chloro-N-(cyclopropylmethyl)-6-[2-(1-methylpiperidin-4-yl)-1H-pyrrolo[2,3-b]pyridin-4-yl]pyridin-2-amine;
N-{4-[2-(dimethylamino)ethoxy]benzyl}-6-[2-(1-methylpiperidin-4-yl)-1H-pyrrolo[2,3-b]pyridin-4-yl]pyridin-2-amine;
5-chloro-N-[(2,2-dimethyltetrahydro-2H-pyran-4-yl)methyl]-6-[2-(1-methylpiperidin-4-yl)-1H-pyrrolo[2,3-b]pyridin-4-yl]pyridin-2-amine;
5-chloro-6-[2-(1-methylpiperidin-4-yl)-1H-pyrrolo[2,3-b]pyridin-4-yl]-N-(pyridin-4-ylmethyl)pyridin-2-amine;
6-[2-(1-methylpiperidin-4-yl)-1H-pyrrolo[2,3-b]pyridin-4-yl]-N-(1H-pyrazol-3-ylmethyl)pyridin-2-amine;
N-(2,3-dihydro-1H-isoindol-5-ylmethyl)-6-[2-(1-methylpiperidin-4-yl)-1H-pyrrolo[2,3-b]pyridin-4-yl]pyridin-2-amine;
6-[2-(1-methylpiperidin-4-yl)-1H-pyrrolo[2,3-b]pyridin-4-yl]-N-[(1-methylpyrrolidin-3-yl)methyl]pyridin-2-amine;
N-(1H-indol-6-ylmethyl)-6-[2-(1-methylpiperidin-4-yl)-1H-pyrrolo[2,3-b]pyridin-4-yl]pyridin-2-amine;
5-chloro-6-[2-(1-methylpiperidin-4-yl)-1H-pyrrolo[2,3-b]pyridin-4-yl]-N-[4-(methylsulfonyl)benzyl]pyridin-2-amine;
4-[({5-chloro-6-[2-(1-methylpiperidin-4-yl)-1H-pyrrolo[2,3-b]pyridin-4-yl]pyridin-2-yl}amino)methyl]benzenesulfonamide;
4-[({5-chloro-6-[2-(1-methylpiperidin-4-yl)-1H-pyrrolo[2,3-b]pyridin-4-yl]pyridin-2-yl}amino)methyl]benzamide;
6-[2-(1-methylpiperidin-4-yl)-1H-pyrrolo[2,3-b]pyridin-4-yl]-N-[2-(morpholin-4-yl)ethyl]pyridin-2-amine;
2-({6-[2-(1-methylpiperidin-4-yl)-1H-pyrrolo[2,3-b]pyridin-4-yl]pyridin-2-yl}amino)ethanol;
5-chloro-6-[2-(1-methylpiperidin-4-yl)-1H-pyrrolo[2,3-b]pyridin-4-yl]-N-(piperidin-4-ylmethyl)pyridin-2-amine;
tert-butyl 3-[({5-chloro-6-[2-(1-methylpiperidin-4-yl)-1H-pyrrolo[2,3-b]pyridin-4-yl]pyridin-2-yl}amino)methyl]pyrrolidine-1-carboxylate;
5-chloro-N-[(1,1-dioxidotetrahydro-2H-thiopyran-4-yl)methyl]-6-[2-(1-methylpiperidin-4-yl)-1H-pyrrolo[2,3-b]pyridin-4-yl]pyridin-2-amine;
{3-[({5-chloro-6-[2-(1-methylpiperidin-4-yl)-1H-pyrrolo[2,3-b]pyridin-4-yl]pyridin-2-yl}amino)methyl]phenoxy}acetic acid;
{4-[({5-chloro-6-[2-(1-methylpiperidin-4-yl)-1H-pyrrolo[2,3-b]pyridin-4-yl]pyridin-2-yl}amino)methyl]phenoxy}acetic acid;
1-{4-[({5-chloro-6-[2-(1-methylpiperidin-4-yl)-1H-pyrrolo[2,3-b]pyridin-4-yl]pyridin-2-yl}amino)methyl]piperidin-1-yl}ethanone;
5-chloro-6-[2-(1-methylpiperidin-4-yl)-1H-pyrrolo[2,3-b]pyridin-4-yl]-N-(4H-1,2,4-triazol-3-ylmethyl)pyridin-2-amine;
5-chloro-6-[2-(1-methylpiperidin-4-yl)-1H-pyrrolo[2,3-b]pyridin-4-yl]-N-[3-(methylsulfonyl)benzyl]pyridin-2-amine;
(3S,5R)-5-[({5-chloro-6-[2-(piperidin-4-yl)-1H-pyrrolo[2,3-b]pyridin-4-yl]pyridin-2-yl}amino)methyl]pyrrolidin-3-ol;

N-benzyl-5-chloro-6-(2-cyclohexyl-1H-pyrrolo[2,3-b]pyridin-4-yl)pyridin-2-amine;

5-chloro-N-{[(2S,4S)-4-fluoropyrrolidin-2-yl]methyl}-6-[2-(piperidin-4-yl)-1H-pyrrolo[2,3-b]pyridin-4-yl]pyridin-2-amine;

4-[({5-chloro-4-[2-(piperidin-4-yl)-1H-pyrrolo[2,3-b]pyridin-4-yl]pyridin-2-yl}amino)methyl]tetrahydro-2H-pyran-4-carbonitrile;

5-chloro-N-{[(2S)-4,4-difluoropyrrolidin-2-yl]methyl}-6-[2-(piperidin-4-yl)-1H-pyrrolo[2,3-b]pyridin-4-yl]pyridin-2-amine;

N-benzyl-5-chloro-N-methyl-6-[2-(piperidin-3-yl)-1H-pyrrolo[2,3-b]pyridin-4-yl]pyridin-2-amine;

5-chloro-N-(3,4-difluorobenzyl)-6-[2-(piperidin-3-yl)-1H-pyrrolo[2,3-b]pyridin-4-yl]pyridin-2-amine;

5-chloro-N-(3-fluorobenzyl)-6-[2-(piperidin-3-yl)-1H-pyrrolo[2,3-b]pyridin-4-yl]pyridin-2-amine;

5-chloro-N-(4-fluorobenzyl)-6-[2-(piperidin-3-yl)-1H-pyrrolo[2,3-b]pyridin-4-yl]pyridin-2-amine;

N-benzyl-5-chloro-4-[2-(piperidin-3-yl)-1H-pyrrolo[2,3-b]pyridin-4-yl]pyridin-2-amine;

5-chloro-N-(2-fluorobenzyl)-6-[2-(piperidin-3-yl)-1H-pyrrolo[2,3-b]pyridin-4-yl]pyridin-2-amine;

5-chloro-6-[2-(piperidin-3-yl)-1H-pyrrolo[2,3-b]pyridin-4-yl]-N-(pyridin-3-ylmethyl)pyridin-2-amine;

4-[3-chloro-6-(pyridin-3-ylmethoxy)pyridin-2-yl]-2-(piperidin-3-yl)-1H-pyrrolo[2,3-b]pyridine;

5-chloro-N-[(5-fluoropyridin-3-yl)methyl]-6-[2-(piperidin-3-yl)-1H-pyrrolo[2,3-b]pyridin-4-yl]pyridin-2-amine;

N-benzyl-5-fluoro-4-[2-(piperidin-3-yl)-1H-pyrrolo[2,3-b]pyridin-4-yl]pyridin-2-amine;

N-benzyl-4-fluoro-6-[2-(piperidin-3-yl)-1H-pyrrolo[2,3-b]pyridin-4-yl]pyridin-2-amine;

N-benzyl-4-[5-chloro-2-(piperidin-3-yl)-1H-pyrrolo[2,3-b]pyridin-4-yl]pyridin-2-amine;

5-chloro-N-(3-fluorobenzyl)-4-[2-(piperidin-4-yl)-1H-pyrrolo[2,3-b]pyridin-4-yl]pyridin-2-amine;

6-[2-(3-aminocyclohexyl)-1H-pyrrolo[2,3-b]pyridin-4-yl]-N-(3-fluorobenzyl)pyridin-2-amine;

4-(6-fluoropyridin-2-yl)-2-(1,2,3,6-tetrahydropyridin-4-yl)-1H-pyrrolo[2,3-b]pyridine;

4-(6-fluoropyridin-2-yl)-2-[1-(methylsulfonyl)-1,2,3,6-tetrahydropyridin-4-yl]-1H-pyrrolo[2,3-b]pyridine;

N-(2,6-difluorobenzyl)-6-{2-[1-(methylsulfonyl)-1,2,3,6-tetrahydropyridin-4-yl]-1H-pyrrolo[2,3-b]pyridin-4-yl}pyridin-2-amine;

N-(2-chlorobenzyl)-6-{2-[1-(methylsulfonyl)-1,2,3,6-tetrahydropyridin-4-yl]-1H-pyrrolo[2,3-b]pyridin-4-yl}pyridin-2-amine;

N-(cyclopropylmethyl)-6-{2-[1-(methylsulfonyl)-1,2,3,6-tetrahydropyridin-4-yl]-1H-pyrrolo[2,3-b]pyridin-4-yl}pyridin-2-amine;

N-benzyl-6-{2-[1-(methylsulfonyl)piperidin-4-yl]-1H-pyrrolo[2,3-b]pyridin-4-yl}pyrazin-2-amine;

N-benzyl-6-[2-(piperidin-4-yl)-1H-pyrrolo[2,3-b]pyridin-4-yl]pyrazin-2-amine;

6-[2-(piperidin-4-yl)-1H-pyrrolo[2,3-b]pyridin-4-yl]-N-(tetrahydro-2H-pyran-4-ylmethyl)pyrazin-2-amine;

N-(3,5-difluorobenzyl)-6-[2-(piperidin-4-yl)-1H-pyrrolo[2,3-b]pyridin-4-yl]pyrazin-2-amine;

N-(3-fluorobenzyl)-6-[2-(piperidin-4-yl)-1H-pyrrolo[2,3-b]pyridin-4-yl]pyrazin-2-amine;

6-[2-(piperidin-4-yl)-1H-pyrrolo[2,3-b]pyridin-4-yl]-N-(pyridin-3-ylmethyl)pyrazin-2-amine;

6-[2-(piperidin-4-yl)-1H-pyrrolo[2,3-b]pyridin-4-yl]-N-(pyridin-4-ylmethyl)pyrazin-2-amine;

N-(3,4-difluorobenzyl)-6-[2-(piperidin-4-yl)-1H-pyrrolo[2,3-b]pyridin-4-yl]pyrazin-2-amine;

1-[4-(4-{6-[(3,5-difluorobenzyl)amino]pyrazin-2-yl}-1H-pyrrolo[2,3-b]pyridin-2-yl)piperidin-1-yl]-2-hydroxyethanone;

1-[4-(4-{6-[(3-fluorobenzyl)amino]pyrazin-2-yl}-1H-pyrrolo[2,3-b]pyridin-2-yl)piperidin-1-yl]-2-hydroxyethanone;

1-(4-{4-[6-(benzylamino)pyrazin-2-yl]-1H-pyrrolo[2,3-b]pyridin-2-yl}piperidin-1-yl)-2-hydroxyethanone;

N-benzyl-N-methyl-6-[2-(1-methylpiperidin-4-yl)-1H-pyrrolo[2,3-b]pyridin-4-yl]pyrazin-2-amine;

N-benzyl-6-[2-(1-methylpiperidin-4-yl)-1H-pyrrolo[2,3-b]pyridin-4-yl]pyrazin-2-amine;

1-(4-{4-[6-(benzylamino)pyrazin-2-yl]-1H-pyrrolo[2,3-b]pyridin-2-yl}piperidin-1-yl)ethanone;

3-(4-{4-[6-(benzylamino)pyrazin-2-yl]-1H-pyrrolo[2,3-b]pyridin-2-yl}piperidin-1-yl)propane-1,2-diol;

ethyl[(4-{4-[6-(benzylamino)pyrazin-2-yl]-1H-pyrrolo[2,3-b]pyridin-2-yl}piperidin-1-yl)sulfonyl]carbamate;

4-(6-chloro-3-fluoropyridin-2-yl)-2-(piperidin-4-yl)-1H-pyrrolo[2,3-b]pyridine;

4-{6-[(3-fluorobenzyl)oxy]pyrazin-2-yl}-2-(piperidin-4-yl)-1H-pyrrolo[2,3-b]pyridine;

N-(3-fluorobenzyl)-6-[2-(1-methylpiperidin-4-yl)-1H-pyrrolo[2,3-b]pyridin-4-yl]pyrazin-2-amine;

1-[4-(4-{6-[(3-fluorobenzyl)amino]pyrazin-2-yl}-1H-pyrrolo[2,3-b]pyridin-2-yl)piperidin-1-yl]ethanone;

4-{6-[(3-fluorobenzyl)oxy]pyrazin-2-yl}-2-(1-methylpiperidin-4-yl)-1H-pyrrolo[2,3-b]pyridine;

N-benzyl-6-[2-(1,2,3,6-tetrahydropyridin-4-yl)-1H-pyrrolo[2,3-b]pyridin-4-yl]pyrazin-2-amine;

1-[4-(4-{6-[(3-fluorobenzyl)oxy]pyrazin-2-yl}-1H-pyrrolo[2,3-b]pyridin-2-yl)piperidin-1-yl]-2-hydroxyethanone;

3-[4-(4-{6-[(3-fluorobenzyl)oxy]pyrazin-2-yl}-1H-pyrrolo[2,3-b]pyridin-2-yl)piperidin-1-yl]propane-1,2-diol;

ethyl {[4-(4-{6-[(3-fluorobenzyl)amino]pyrazin-2-yl}-1H-pyrrolo[2,3-b]pyridin-2-yl)piperidin-1-yl]sulfonyl}carbamate;

4-{4-[6-(benzylamino)pyrazin-2-yl]-1H-pyrrolo[2,3-b]pyridin-2-yl}-N-methylpiperidine-1-carboxamide;

4-(4-{6-[(3-fluorobenzyl)amino]pyrazin-2-yl}-1H-pyrrolo[2,3-b]pyridin-2-yl)-N-methylpiperidine-1-carboxamide;

4-{6-[(3-fluorobenzyl)oxy]pyrazin-2-yl}-2-[1-(methylsulfonyl)piperidin-4-yl]-1H-pyrrolo[2,3-b]pyridine;

1-[4-(4-{6-[(3-fluorobenzyl)oxy]pyrazin-2-yl}-1H-pyrrolo[2,3-b]pyridin-2-yl)piperidin-1-yl]ethanone;

4-(4-{6-[(3-fluorobenzyl)oxy]pyrazin-2-yl}-1H-pyrrolo[2,3-b]pyridin-2-yl)-N-methylpiperidine-1-carboxamide;

1-[4-{4-[6-(benzylamino)pyrazin-2-yl]-1H-pyrrolo[2,3-b]pyridin-2-yl}-3,6-dihydropyridin-1(2H)-yl]-2-hydroxyethanone;

N-(3-fluorobenzyl)-6-[2-(1,2,3,6-tetrahydropyridin-4-yl)-1H-pyrrolo[2,3-b]pyridin-4-yl]pyrazin-2-amine;

3-[4-(4-{6-[(3-fluorobenzyl)amino]pyrazin-2-yl}-1H-pyrrolo[2,3-b]pyridin-2-yl)-3,6-dihydropyridin-1(2H)-yl]propane-1,2-diol;

4-{6-[(3-fluorobenzyl)oxy]pyrazin-2-yl}-2-(1,2,3,6-tetrahydropyridin-4-yl)-1H-pyrrolo[2,3-b]pyridine;

4-(4-{6-[(3-fluorobenzyl)amino]pyrazin-2-yl}-1H-pyrrolo[2,3-b]pyridin-2-yl)-N-methyl-3,6-dihydropyridine-1(2H)-carboxamide;

6-[2-(1-methylpiperidin-4-yl)-1H-pyrrolo[2,3-b]pyridin-4-yl]-N-(pyridin-3-ylmethyl)pyrazin-2-amine;

3-[4-(4-{6-[(pyridin-3-ylmethyl)amino]pyrazin-2-yl}-1H-pyrrolo[2,3-b]pyridin-2-yl)piperidin-1-yl]propane-1,2-diol;

2-hydroxy-1-[4-(4-{6-[(pyridin-3-ylmethyl)amino]pyrazin-2-yl}-1H-pyrrolo[2,3-b]pyridin-2-yl)piperidin-1-yl]ethanone;

N-methyl-4-(4-{6-[(pyridin-3-ylmethyl)amino]pyrazin-2-yl}-1H-pyrrolo[2,3-b]pyridin-2-yl)piperidine-1-carboxamide;

1-[4-(4-{6-[(3-fluorobenzyl)amino]pyrazin-2-yl}-1H-pyrrolo[2,3-b]pyridin-2-yl)-3,6-dihydropyridin-1(2H)-yl]-2-hydroxyethanone;

4-{6-[(3-fluorobenzyl)oxy]pyrazin-2-yl}-2-[1-(methylsulfonyl)-1,2,3,6-tetrahydropyridin-4-yl]-1H-pyrrolo[2,3-b]pyridine;

3,5-difluoro-N-(3-fluorobenzyl)-6-[2-(piperidin-4-yl)-1H-pyrrolo[2,3-b]pyridin-4-yl]pyridin-2-amine;

4-(4-{6-[(3-fluorobenzyl)oxy]pyrazin-2-yl}-1H-pyrrolo[2,3-b]pyridin-2-yl)-N-methyl-3,6-dihydropyridine-1(2H)-carboxamide;

1-[4-(4-{6-[(3-fluorobenzyl)oxy]pyrazin-2-yl}-1H-pyrrolo[2,3-b]pyridin-2-yl)-3,6-dihydropyridin-1(2H)-yl]-2-hydroxyethanone;

3,5-difluoro-N-(3-fluorobenzyl)-6-{2-[1-(methylsulfonyl)-1,2,3,6-tetrahydropyridin-4-yl]-1H-pyrrolo[2,3-b]pyridin-4-yl}pyridin-2-amine;

4-(4-{3,5-difluoro-6-[(3-fluorobenzyl)amino]pyridin-2-yl}-1H-pyrrolo[2,3-b]pyridin-2-yl)-N-methylpiperidine-1-carboxamide;

1-[4-(4-{3,5-difluoro-6-[(3-fluorobenzyl)amino]pyridin-2-yl}-1H-pyrrolo[2,3-b]pyridin-2-yl)piperidin-1-yl]-2-hydroxyethanone;

4-{4-[6-(benzylamino)pyrazin-2-yl]-1H-pyrrolo[2,3-b]pyridin-2-yl}cyclohex-3-ene-1-carboxylic acid;

4-{4-[6-(benzylamino)pyrazin-2-yl]-1H-pyrrolo[2,3-b]pyridin-2-yl}-N-methylcyclohex-3-ene-1-carboxamide;

4-(4-{6-[(3-fluorobenzyl)amino]pyrazin-2-yl}-1H-pyrrolo[2,3-b]pyridin-2-yl)cyclohex-3-ene-1-carboxylic acid;

4-(4-{6-[(3-fluorobenzyl)oxy]pyrazin-2-yl}-1H-pyrrolo[2,3-b]pyridin-2-yl)cyclohex-3-ene-1-carboxylic acid;

4-(4-{6-[(3-fluorobenzyl)oxy]pyrazin-2-yl}-1H-pyrrolo[2,3-b]pyridin-2-yl)-N-methylcyclohex-3-ene-1-carboxamide;

4-(4-{6-[(3-fluorobenzyl)oxy]pyrazin-2-yl}-1H-pyrrolo[2,3-b]pyridin-2-yl)cyclohex-3-ene-1-carboxamide;

4-(4-{6-[(3-fluorobenzyl)amino]pyrazin-2-yl}-1H-pyrrolo[2,3-b]pyridin-2-yl)cyclohex-3-ene-1-carboxamide;

4-{4-[6-(benzylamino)pyrazin-2-yl]-1H-pyrrolo[2,3-b]pyridin-2-yl}cyclohex-3-ene-1-carboxamide;

N-methyl-5-[2-(1,2,3,6-tetrahydropyridin-4-yl)-1H-pyrrolo[2,3-b]pyridin-4-yl]pyridine-2-carboxamide; or a pharmaceutically acceptable salt thereof.

In another aspect, the present invention relates to pharmaceutical compositions comprising a pharmaceutically acceptable excipient and a therapeutically effective amount of a compound of Formula (IIIa) or a pharmaceutically acceptable salt thereof.

In another aspect, the present invention relates to methods of treating cancer in a patient, comprising administering to a patient suffering from a cancer a therapeutically effective amount of a compound of Formula (IIIa), or a pharmaceutically acceptable salt thereof. In certain embodiments, the cancer is selected from the group consisting of acoustic neuroma, acute leukemia, acute lymphoblastic leukemia, acute myelogenous leukemia, acute t-cell leukemia, basal cell carcinoma, bile duct carcinoma, bladder cancer, brain cancer, breast cancer, bronchogenic carcinoma, Burkitt's lymphoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, dysplasias, metaplasias, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophoblastic disease, glioblastoma, head and neck cancer, heavy chain disease, hemangioblastoma, hepatoma, hepatocellular cancer, hormone insensitive prostate cancer, leiomyosarcoma, liposarcoma, lung cancer, lymphangioendothelio-sarcoma, lymphangiosarcoma, lymphoblastic leukemia, lymphoma, malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors, stomach cancer, squamous cell carcinoma, synovioma, sweat gland carcinoma, testicular cancer, thyroid cancer, Waldenström's macroglobulinemia, testicular tumors, uterine cancer, and Wilms' tumor. In certain embodiments, the methods further comprise administering a therapeutically effective amount of at least one additional therapeutic agent.

DETAILED DESCRIPTION OF THE INVENTION

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated radical of an alkane typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of alkyls include methyl, ethyl, n-propyl, isopropyl, n-butyl, isobutyl, sec-butyl, tert-butyl, pentyl, isoamyl, hexyl, pentan-3-yl), 2,2-dimethylpropan-2-yl), heptan-4-yl, and 2,6-dimethylheptan-4-yl, and the like. The term "$C_1$-$C_6$ alkyl" refers to an alkyl substituent containing from 1 to 6 carbon atoms and "$C_1$-$C_3$ alkyl" refers to an alkyl substituent containing from 1 to 3 carbon atoms.

The term "alkenyl" (alone or in combination with another term(s)) means a straight- or branched-chain radical of an alkene containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl(vinyl), 2-propenyl, 3-propenyl, 1,4-pentadienyl, 1,4-butadienyl, 1-butenyl, 2-butenyl, and 3-butenyl and the like. The term "$C_2$-$C_6$ alkenyl" means an alkenyl group containing 2-6 carbon atoms.

The term "alkynyl" (alone or in combination with another term(s)) means a straight- or branched-chain radical of an an alkyne containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like. The term "$C_2$-$C_6$ alkynyl" means an alkynyl group of 2 to 6 carbon atoms.

The term "cycloalkyl" (alone or in combination with another term(s)) means a saturated cyclic hydrocarbyl substituent containing from 3 or more carbon ring atoms ("ring atoms" are the atoms bound together to form the ring or rings of a cyclic substituent). A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic (contain more than one ring). Examples of polycyclic cycloalkyls include bridged, fused, and spirocyclic cycloalkyls.

The term "$C_3$-$C_7$ cycloalkyl" (alone or in combination with another term(s)) means a saturated cyclic radical of a monocyclic cycloalkane containing from 3 to 7 carbon ring atoms. Examples of monocyclic cycloalkyl groups include, but are not limited to, cyclopropyl (cyclopropanyl), cyclobutyl (cyclobutanyl), cyclopentyl (cyclopentanyl), cyclopentenyl, cyclohexyl (cyclohexanyl), and cycloheptyl.

The term "cycloalkenyl" (alone or in combination with another term(s)) means a partially unsaturated cyclic hydrocarbyl substituent containing from 4 or more carbon ring atoms ("ring atoms" are the atoms bound together to form the ring or rings of a cyclic substituent). A cycloalkenyl may be a single carbon ring, which typically contains from 4 to 8 carbon ring atoms and more typically from 4 to 6 ring atoms. Examples of single-ring cycloalkenyls include cyclobutenyl, cyclopentenyl, and cyclohexenyl. A cycloalkenyl may alternatively be polycyclic (contain more than one ring). Examples of polycyclic cycloalkenyls include bridged, fused, and spirocyclic cycloalkenyls.

The term "$C_5$-$C_7$ cycloalkenyl" (alone or in combination with another term(s)) means a partially unsaturated monocylic cycloalkane radical containing from 5 to 7 carbon ring atoms. Examples of single-ring cycloalkenyls include cyclopentenyl, cyclohexenyl, and cycloheptenyl.

The term "heterocycloalkyl" (alone or in combination with another term(s)) means a non-aromatic saturated monocyclic or polycyclic heterocycloalkane radical having carbon atoms and 1 or more heteroatoms independently selected from S, N or O, wherein when two O atoms or one O atom and one S atom are present, the two O atoms or one O atom and one S atom are not bonded to each other, respectively. A heterocycloalkyl may be a single carbon ring, which typically contains from 3 to 8 ring atoms and more typically from 3 to 6 ring atoms. Examples of single-ring heterocycloalkyls include oxetanyl, azetidinyl, thietanyl, tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, 3-pyrrolinyl, tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, trithianyl, azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl, azocanyl, thiocanyl, oxocanyl, tetrahydro-2H-thiopyranyl 1,1-dioxide and 3,4,5,6-tetrahydro-2H-oxocinyl. A heterocycloalkyl may alternatively be polycyclic (contain more than one ring). Examples of polycyclic heterocycloalkyls include bridged, fused, and spirocyclic heterocycloalkyls in which at least one ring is a heterocycloalkyl and the others are heterocycloalkyl, or cycloalkyl rings.

The term "heterocycloalkenyl" (alone or in combination with another term(s)) means a non-aromatic partially unsaturated monocyclic or polycyclic heterocycloalkene radical having carbon atoms and 1 or more heteroatoms independently selected from S, N or O, wherein when two O atoms or one O atom and one S atom are present, the two O atoms or one O atom and one S atom are not bonded to each other, respectively. A heterocycloalkenyl may be a single carbon ring, which typically contains from 3 to 8 ring atoms and more typically from 3 to 6 ring atoms. Examples of single-ring heterocycloalkenyls include 1,2,3,6-tetrahydropyridinyl, and 4,5-dihydro-1H-imidazolyl. A heterocycloalkenyl may alternatively be polycyclic (contain more than one ring). Examples of polycyclic heterocycloalkenyls include bridged, fused, and spirocyclic heterocycloalkenyls in which at least one ring is a heterocycloalkenyl and the others are heterocycloalkenyl, heterocycloalkyl, cycloalkenyl or cycloalkyl rings. Alternatively, a polycyclic heterocycloalkenyl may consist of one or more heterocycloalkyl rings and one or more cycloalkenyl rings. Examples of polycyclic heterocycloalkenyls include 8-azabicyclo[3.2.1]oct-2-enyl, and 1,2,3,3a,4,6a-hexahydrocyclopenta[c]pyrrolyl.

The term "5 to 7-membered heterocycloalkyl" (alone or in combination with another term(s)) means a non-aromatic monocyclic radical having carbon atoms and 1 to 3 heteroatoms independently selected from S, N or O, wherein when two O atoms or one O atom and one S atom are present, the two O atoms or one O atom and one S atom are not bonded to each other, respectively.

The term "4-membered monocyclic heterocycloalkyl" (alone or in combination with another term(s)) means a 4-membered, monocyclic radical having 3 carbon atoms and 1 heteroatom selected from the group consisting of: 1 O; 1 S; and 1 N. Illustrative examples of 4-membered monocyclic heterocycloalkyls include oxetanyl, azetidinyl, and thietanyl.

The term "5-membered monocyclic heterocycloalkyl" (alone or in combination with another term(s)) means a 5-membered, monocyclic radical having from 1 to 4 carbon atoms and from 1 to 3 heteroatoms selected from the group consisting of: 1 O; 1 S; 1 N; 2 N; 3 N; 1 S and 1 N; 1 S, and 2 N; 1 O and 1 N; and 1 O and 2 N. Illustrative examples of 5-membered monocyclic heterocycloalkyls include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl.

The term "6-membered monocyclic heterocycloalkyl" (alone or in combination with another term(s)) means a 6-membered, monocyclic radical having from 3 to 5 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 6-membered monocyclic heterocycloalkyls include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, and trithianyl.

The term "7-membered monocyclic heterocycloalkyl" (alone or in combination with another term(s)) means a 7-membered, monocyclic radical having from 5 or 6 carbon atoms and from 1 to 3 heteroatoms selected from the group consisting of: 1 O; 2 O; 1 S; 2 S; 1 N; 2 N; 1 S, 1 O, and 1 N; 1 S and 1 N; 1 S and 2 N; 1 S and 1O; 1 S and 2 O; 1 O and 1 N; and 1 O and 2 N. Illustrative examples of 7-membered monocyclic heterocycloalkyls include azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl.

The term "8-membered monocyclic heterocycloalkyl" (alone or in combination with another term(s)) means a 8-membered, monocyclic radical having from 5 to 7 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1O; 1 S and 2 O; 1 O and 1 N; and 1 O and 2 N. Illustrative examples of 8-membered monocyclic heterocycloalkyls include azocanyl, thiocanyl, oxocanyl, 3,4,5,6-tetrahydro-2H-oxocinyl, etc.

The nitrogen and sulfur heteroatoms in the heterocycloalkyl rings may optionally be oxidized (e.g. 1,1-dioxidotetrahydrothienyl, 1,2-dioxido-1,2-thiazolidinyl, 1,1-dioxidothiomorpholinyl)) and the nitrogen atoms may optionally be quarternized. Unless otherwise indicated, the foregoing heterocycloalkyls can be C-attached or N-attached where such is possible and which results in the creation of a stable structure. For example, piperidinyl can be piperidin-1-yl (N-attached) or piperidin-4-yl (C-attached).

The term "aryl" (alone or in combination with another term(s)) means an aromatic hydrocarbon radical. Furthermore, the term "aryl" includes polycyclic aryl groups, such as bicyclic, e.g., naphthyl. Typical aryl groups include phenyl, and naphthyl. The term aryl also includes a "9- to 12-membered bicyclic aryl," which is a ring structure formed by the fusion of a benzene ring to: (1) a cycloalkyl or cycloalkenyl (e.g., indanyl; 1,2,3,4-tetrahydro-naphthalenyl; 6,7,8,9-tetrahydro-5H-benzocycloheptenyl, etc.); (2) another benzene ring (e.g., naphthalenyl); wherein the fusion junctions are at adjacent carbons on the benzene ring; or (3) a heterocycloalkyl or heterocycloalkenyl (e.g., benzo[d][1,3]dioxolyl, isoindolinyl).

The term "heteroaryl" (alone or in combination with another term(s)) means a monocyclic 5 or 6 membered heteroaryl or a bicyclic heteroaryl.

The term "5-membered heteroaryl" (alone or in combination with another term(s)) means a 5-membered, monocyclic, aromatic ring radical having from 1 to 4 carbon atoms and from 1 to 4 heteroatoms selected from the group consisting of: 1 O; 1 S; 1 N; 2 N; 3 N; 4 N; 1 S and 1 N; 1 S and 2 N; 1 O and 1 N; and 1 O and 2 N. Illustrative examples of 5-membered heteroaryls include, but are not limited to, furanyl, 2-furanyl, 3-furanyl, imidazolyl, isoxazolyl, isothiazolyl, oxadiazolyl, oxazolyl, pyrazolyl, pyrrolyl, 2- or 3-pyrrolyl, thienyl, 2-thienyl, 3-thienyl, tetrazolyl, thiazolyl, thiadiazolyl, and triazolyl.

The term "6-membered heteroaryl" (alone or in combination with another term(s)) means a 6-membered, monocyclic, aromatic ring radical having from 3 to 5 carbon atoms and from 1 to 3 heteroatoms selected from the group consisting of: 1 N; 2 N; and 3 N. Illustrative examples of 6-membered heteroaryls include, but are not limited to, pyridinyl, 2-, 3-, or 4-pyridinyl, pyrimidinyl, 2-, 4-, or 5-pyrimidinyl, pyrazinyl, pyridazinyl, 3- or 4-pyridazinyl, 2-pyrazinyl, and triazinyl.

The term "bicyclic heteroaryl" (alone or in combination with another term(s)) means a ring structure formed by the fusion of 5- or 6-membered heteroaryl to: (1) an independently selected 5-membered heteroaryl; (2) an independently selected 6-membered heteroaryl (e.g., naphthyridinyl, pteridinyl, phthalazinyl, purinyl, etc.); (3) a cycloalkyl or cycloalkenyl; (4) a heterocycloalkyl or heterocycloalkenyl; or (5) a benzene ring (e.g., benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, and isoquinolinyl), wherein the fusion junctions are at adjacent ring atoms. The fusion junctions may be at nitrogen (e.g., indolizine) or carbon atoms in the 5- or 6-membered heteroaryl.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical. If a substituent is described as being optionally substituted with one or more non-hydrogen radicals, that substituent may be either (1) not substituted; or (2) substituted by up to the maximum number of substitutable positions on the substituent. Thus, for example, if a substituent is described as a heteroaryl optionally substituted with one or more non-hydrogen radicals, then any heteroaryl with 3 substitutable positions would be optionally substituted by one, two or three non-hydrogen radicals. To illustrate, tetrazolyl (which has only one substitutable position) would be optionally substituted with up to one non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat," "treating," and "treatment" refer to a method of alleviating or abrogating a disease and/or its attendant symptoms.

The terms "prevent," "preventing," and "prevention" refer to a method of preventing the onset of a disease and/or its attendant symptoms or barring a subject from acquiring a disease. As used herein, "prevent," "preventing," and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl may also be designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of CDK9 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.,* 36(10):927-932 (1995); Kushner et al., *Can. J. Physiol. Pharmacol.,* 77, 79-88 (1999)).

In addition, non-radio active isotope containing drugs, such as deuterated drugs called "heavy drugs," can be used for the treatment of diseases and conditions related to CDK9 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Compounds

Suitable groups for $R^1$, $R^2$, $R^3$, and $R^4$, in compounds of Formula (I); $R^1$, $R^2$, $R^4$, $X^1$, $X^2$, $X^3$, $X^4$, and $X^5$ in compounds of Formula (III) and Formula (IIIa); $R^1$, $R^2$, $R^{3A}$, $R^{3B}$, and $R^4$ in compounds of Formula (IVa); and $R^1$, $R^2$, $R^{3A}$, and $R^4$ in compounds of Formula (Va); are independently selected. The described embodiments of the present invention may be combined. Such combination is contemplated and within the scope of the present invention. For example, it is contemplated that embodiments for any of $R^1$, $R^2$, $R^3$, and $R^4$, in compounds of Formula (I) can be combined with embodiments defined for any other of $R^1$, $R^2$, $R^3$, and $R^4$ in compounds of Formula (I).

In one aspect, the present invention relates to compounds of Formula (I) or a pharmaceutically acceptable salt thereof,

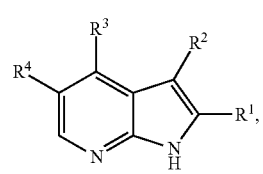

Formula (I)

wherein
$R^1$ is selected from the group consisting of $C_4$-$C_7$ cycloalkyl, $C_5$-$C_7$cycloalkenyl, a 5-7 membered heterocycloalkyl, and a 5-7 membered heterocycloalkenyl; each of which may be substituted with one, two, or three substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $OH$, $CN$, $NO_2$, F, Cl, Br and I;
$R^2$ is hydrogen or $C_1$-$C_4$ alkyl;
$R^3$ is selected from the group consisting of phenyl, pyridinyl, pyrazinyl, pyrimidinyl, and pyridazinyl; wherein the $R^3$ phenyl, pyridinyl, pyrazinyl, pyrimidinyl, and pyridazinyl are substituted with one, two, or three substituents independently selected from the group consisting of $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, $OH$, $CN$, $NO_2$, F, Cl, Br and I;
$R^4$ is selected from the group consisting of hydrogen, CN, F, Cl, Br, and I;
$R^5$, at each occurrence, is independently selected from the group consisting of $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_7$ cycloalkyl, and $C_5$-$C_7$ cycloalkenyl; wherein each $R^5$ $C_1$-$C_8$ alkyl, $C_2$-$C_6$ alkenyl, and $C_2$-$C_6$ alkynyl is optionally substituted with one, two, or three substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $OH$, $CN$, $NO_2$, F, Cl, Br and I; wherein each $R^5$ aryl, $C_3$-$C_7$ cycloalkyl, $C_5$-$C_7$ cycloalkenyl, heteroaryl, 5 to 7 membered heterocycloalkyl, and 5 to 7 membered heterocycloalkenyl is optionally substituted with one, two, or three substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $OH$, $CN$, $NO_2$, F, Cl, Br and I;

$R^6$, at each occurrence, is independently selected from the group consisting of $C_1$-$C_6$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_7$ cycloalkyl, and $C_5$-$C_7$ cycloalkenyl; wherein each $R^6$ $C_1$-$C_6$ alkyl, $C_2$-$C_6$ alkenyl, and $C_2$-$C_6$ alkynyl is optionally substituted with one, two, or three substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $OH$, $CN$, $NO_2$, F, Cl, Br and I; wherein each $R^6$ aryl, $C_4$-$C_7$ cycloalkyl, $C_5$-$C_7$ cycloalkenyl, heteroaryl, heterocycloalkyl, and heterocycloalkenyl is optionally substituted with one, two, three, or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $OH$, $CN$, $NO_2$, F, Cl, Br and I;

$R^7$, at each occurrence, is independently selected from the group consisting of $C_1$-$C_6$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_7$ cycloalkyl, and $C_5$-$C_7$ cycloalkenyl; wherein each $R^7$ $C_1$-$C_6$ alkyl, $C_2$-$C_6$ alkenyl, and $C_2$-$C_6$ alkynyl is optionally substituted with one, two, or three substituents independently selected from the group consisting of aryl, heteroaryl, $C_3$-$C_7$ cycloalkyl, $C_5$-$C_7$ cycloalkenyl, 5 to 7 membered heterocycloalkyl, 5 to 7 membered heterocycloalkenyl, $NH_2$, $NHR^{13}$, $N(R^{13})_2$, $C(O)H$, $C(O)OH$, $OH$, $CN$, $NO_2$, F, Cl, Br and I; wherein each $R^7$ aryl, $C_3$-$C_7$ cycloalkyl, $C_5$-$C_7$ cycloalkenyl, heteroaryl, 5 to 7 membered heterocycloalkyl, and 5 to 7 membered heterocycloalkenyl is optionally substituted with one, two, or three substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $OH$, $CN$, $NO_2$, F, Cl, Br and I;

$R^8$, at each occurrence, is independently selected from the group consisting of $C_1$-$C_6$ alkyl, $C_2$-$C_6$ alkenyl, and $C_2$-$C_6$ alkynyl;

$R^9$, at each occurrence, is independently selected from the group consisting of $C_1$-$C_6$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_7$ cycloalkyl, and $C_5$-$C_7$ cycloalkenyl; wherein each $R^9$ aryl, $C_3$-$C_7$ cycloalkyl, $C_5$-$C_7$ cycloalkenyl, heteroaryl, 5 to 7 membered heterocycloalkyl, and heterocycloalkenyl is optionally substituted with one, two, or three substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $OH$, $CN$, $NO_2$, F, Cl, Br and I;

$R^{10}$, at each occurrence, is independently selected from the group consisting of $C_1$-$C_6$ alkyl, $C_2$-$C_6$ alkenyl, and $C_2$-$C_6$ alkynyl;

$R^{11}$, at each occurrence, is independently selected from the group consisting of $C_1$-$C_6$ alkyl, $C_2$-$C_6$ alkenyl, and $C_2$-$C_6$ alkynyl;

$R^{12}$, at each occurrence, is independently selected from the group consisting of $C_1$-$C_6$ alkyl, $C_2$-$C_6$ alkenyl, and $C_2$-$C_6$ alkynyl; wherein each $R^{12}$ $C_1$-$C_6$ alkyl, $C_2$-$C_6$ alkenyl, and $C_2$-$C_6$ alkynyl is optionally substituted with one, two, or three substituents independently selected from the group consisting of $NH_2$, $NHR^{13}$, $N(R^{13})_2$, $C(O)H$, $C(O)OH$, $OH$, $CN$, $NO_2$, F, Cl, Br and I; and $R^{13}$, at each occurrence, is independently selected from the group consisting of $C_1$-$C_6$ alkyl, $C_2$-$C_6$ alkenyl, and $C_2$-$C_6$ alkynyl.

In certain embodiments, $R^2$ is hydrogen, and $R^4$ is hydrogen. In certain embodiments, $R^1$ is selected from the group consisting of azetidinyl, pyrrolidinyl, morpholinyl, tetrahydropyranyl, tetrahydropyridinyl, piperidinyl, cyclohexanyl, or azepanyl; wherein the $R^1$ azetidinyl, pyrrolidinyl, morpholinyl, tetrahydropyranyl, tetrahydropyridinyl, piperidinyl, cyclohexanyl, and azepanyl are optionally substituted with one, two, three, or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $OH$, $CN$, $NO_2$, F, Cl, Br and I. In certain embodiments, $R^1$ is selected from the group consisting of azetidinyl, pyrrolidinyl, morpholinyl, tetrahydropyranyl, tetrahydropyridinyl, piperidinyl, cyclohexanyl, or azepanyl; wherein the $R^1$ azetidinyl, pyrrolidinyl, morpholinyl, tetrahydropyranyl, tetrahydropyridinyl, piperidinyl, cyclohexanyl, and azepanyl are optionally substituted with one or two substituents independently selected from the group consisting of $R^5$, $SO_2R^5$, $C(O)R^5$, $CO(O)R^5$, $NH_2$, $NHR^5$, $C(O)NHR^5$, $SO_2NH_2$, and OH. In certain embodiments, $R^1$ is selected from the group consisting of: azetidinyl, pyrrolidinyl, morpholinyl, tetrahydropyranyl, tetrahydropyridinyl, piperidinyl, cyclohexanyl, or azepanyl; wherein the $R^1$ azetidinyl, pyrrolidinyl, morpholinyl, tetrahydropyranyl, tetrahydropyridinyl, piperidinyl, cyclohexanyl, and azepanyl are unsubstituted. In certain embodiments, $R^3$ is selected from the group consisting of phenyl and pyridinyl; wherein the $R^3$ phenyl, and pyridinyl are substituted with one, two, or three substituents independently selected from the group consisting of: $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, OH, CN, $NO_2$, F, Cl, Br and I. In certain embodiments, $R^3$ is selected from the group consisting of phenyl and pyridinyl; wherein the $R^3$ phenyl, and pyridinyl are substituted with one, two, or three substituents independently selected from the group consisting of $R^6$, $OR^6$, $NH_2$, $NHR^6$, $N(R^6)_2$, $NHC(O)R^6$, $NHS(O)_2R^6$, CN, F, Cl, Br and I. In certain embodiments, $R^3$ is selected from the group consisting of phenyl and pyridinyl; wherein the $R^3$ phenyl, and pyridinyl are substituted with one, or two substituents independently selected from the group consisting of $OR^6$, $NHR^6$, F, and Cl. In certain embodiments, $R^3$ is selected from the group consisting of:

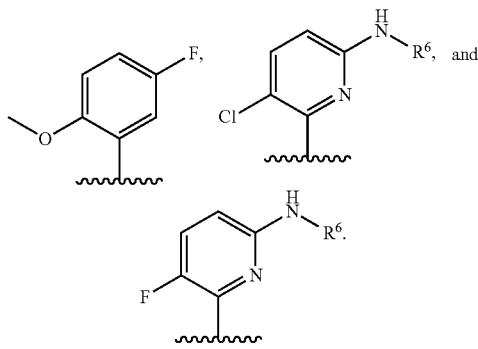

In certain embodiments, $R^6$, at each occurrence, is independently selected from the group consisting of $C_1$-$C_6$ alkyl, aryl, heteroaryl, 5 to 7 membered heterocycloalkenyl, and $C_3$-$C_7$ cycloalkyl; wherein each $R^6$ $C_1$-$C_6$ alkyl is optionally substituted with one substituent independently selected from the group consisting of $R^9$, $SR^9$, and OH; wherein each $R^6$ aryl, $C_3$-$C_7$ cycloalkyl, and heteroaryl is optionally substituted with one or two substituents independently selected from the group consisting of $NH_2$, F, Cl, Br and I.

In certain embodiments, a compound of formula I is selected from the group consisting of:
4-(5-fluoro-2-methoxyphenyl)-2-(piperidin-3-yl)-1H-pyrrolo[2,3-b]pyridine;
4-(4-fluoro-2-methoxyphenyl)-2-(piperidin-3-yl)-1H-pyrrolo[2,3-b]pyridine;
4-(5-fluoro-2-methoxyphenyl)-2-[(3S)-piperidin-3-yl]-1H-pyrrolo[2,3-b]pyridine;
4-(5-fluoro-2-methoxyphenyl)-2-[(3R)-piperidin-3-yl]-1H-pyrrolo[2,3-b]pyridine;
4-[5-(4,5-dihydro-1H-imidazol-2-yl)-2-methoxyphenyl]-2-(piperidin-3-yl)-1H-pyrrolo[2,3-b]pyridine;
4-(5-cyclopropyl-2-methoxyphenyl)-2-(piperidin-3-yl)-1H-pyrrolo[2,3-b]pyridine;
4-(4-fluoro-2-methoxyphenyl)-2-(1-methylpiperidin-3-yl)-1H-pyrrolo[2,3-b]pyridine;
4-(5-fluoro-2-methoxyphenyl)-2-(1-methylpiperidin-3-yl)-1H-pyrrolo[2,3-b]pyridine;
1-{3-[4-(5-fluoro-2-methoxyphenyl)-1H-pyrrolo[2,3-b]pyridin-2-yl]piperidin-1-yl}ethanone;
4-(5-fluoro-2-methoxyphenyl)-2-(piperidin-4-yl)-1H-pyrrolo[2,3-b]pyridine;
4-(4-fluoro-2-methoxyphenyl)-2-(piperidin-4-yl)-1H-pyrrolo[2,3-b]pyridine;
4-(4-chloro-2-methoxyphenyl)-2-(piperidin-4-yl)-1H-pyrrolo[2,3-b]pyridine;
4-(4,5-difluoro-2-methoxyphenyl)-2-(piperidin-4-yl)-1H-pyrrolo[2,3-b]pyridine;
4-(5-chloro-2-methoxyphenyl)-2-(piperidin-4-yl)-1H-pyrrolo[2,3-b]pyridine;
4-(2-methoxy-5-methylphenyl)-2-(piperidin-4-yl)-1H-pyrrolo[2,3-b]pyridine;
4-(3-chloro-2-methoxyphenyl)-2-(piperidin-4-yl)-1H-pyrrolo[2,3-b]pyridine;
4-(2-methoxyphenyl)-2-(piperidin-4-yl)-1H-pyrrolo[2,3-b]pyridine;
4-(5-fluoro-2-methoxyphenyl)-2-(1-methylpiperidin-4-yl)-1H-pyrrolo[2,3-b]pyridine;
4-(4-fluoro-2-methoxyphenyl)-2-(1-methylpiperidin-4-yl)-1H-pyrrolo[2,3-b]pyridine;
4-(2-methoxy-5-methylphenyl)-2-(1-methylpiperidin-4-yl)-1H-pyrrolo[2,3-b]pyridine;
N-{4-chloro-3-[2-(piperidin-4-yl)-1H-pyrrolo[2,3-b]pyridin-4-yl]phenyl}benzenesulfonamide;
N-benzyl-4-fluoro-3-[2-(piperidin-4-yl)-1H-pyrrolo[2,3-b]pyridin-4-yl]aniline;
N-benzyl-4-chloro-3-[2-(piperidin-4-yl)-1H-pyrrolo[2,3-b]pyridin-4-yl]aniline;
4-(5-fluoro-2-methoxyphenyl)-2-(pyrrolidin-3-yl)-1H-pyrrolo[2,3-b]pyridine;
4-(4-fluoro-2-methoxyphenyl)-2-(pyrrolidin-3-yl)-1H-pyrrolo[2,3-b]pyridine;
4-(5-fluoro-2-methoxyphenyl)-2-[(3S)-pyrrolidin-3-yl]-1H-pyrrolo[2,3-b]pyridine;
4-(5-fluoro-2-methoxyphenyl)-2-[(3R)-pyrrolidin-3-yl]-1H-pyrrolo[2,3-b]pyridine;
4-(5-fluoro-2-methoxyphenyl)-2-(1-methylpyrrolidin-3-yl)-1H-pyrrolo[2,3-b]pyridine;
4-(4-fluoro-2-methoxyphenyl)-2-(morpholin-2-yl)-1H-pyrrolo[2,3-b]pyridine;
4-(5-fluoro-2-methoxyphenyl)-2-(morpholin-2-yl)-1H-pyrrolo[2,3-b]pyridine;
4-(4-fluoro-2-methoxyphenyl)-2-(4-methylmorpholin-2-yl)-1H-pyrrolo[2,3-b]pyridine;
4-(5-fluoro-2-methoxyphenyl)-2-(4-methylmorpholin-2-yl)-1H-pyrrolo[2,3-b]pyridine;
2-(5,5-dimethylmorpholin-2-yl)-4-(5-fluoro-2-methoxyphenyl)-1H-pyrrolo[2,3-b]pyridine;
2-(5,5-dimethylmorpholin-2-yl)-4-(4-fluoro-2-methoxyphenyl)-1H-pyrrolo[2,3-b]pyridine;
4-(4-chloro-2-methoxyphenyl)-2-(5,5-dimethylmorpholin-2-yl)-1H-pyrrolo[2,3-b]pyridine;

trans-4-[4-(5-fluoro-2-methoxyphenyl)-1H-pyrrolo[2,3-b]pyridin-2-yl]cyclohexanamine;
3-[4-(5-fluoro-2-methoxyphenyl)-1H-pyrrolo[2,3-b]pyridin-2-yl]cyclohexanamine;
4-(5-fluoro-2-methoxyphenyl)-3-methyl-2-(piperidin-4-yl)-1H-pyrrolo[2,3-b]pyridine;
5-chloro-4-(3-fluorophenyl)-2-(piperidin-3-yl)-1H-pyrrolo[2,3-b]pyridine;
3-[5-chloro-4-(3-fluorophenyl)-1H-pyrrolo[2,3-b]pyridin-2-yl]cyclohexanamine;
4-(5-fluoro-2-methoxyphenyl)-2-(1,2,3,6-tetrahydropyridin-4-yl)-1H-pyrrolo[2,3-b]pyridine;
4-(5-fluoro-2-methoxyphenyl)-2-(pyrrolidin-2-yl)-1H-pyrrolo[2,3-b]pyridine;
2-cyclohexyl-4-(5-fluoro-2-methoxyphenyl)-1H-pyrrolo[2,3-b]pyridine;
1-{2-[4-(5-fluoro-2-methoxyphenyl)-1H-pyrrolo[2,3-b]pyridin-2-yl]pyrrolidin-1-yl}ethanone;
1-{4-[4-(5-fluoro-2-methoxyphenyl)-1H-pyrrolo[2,3-b]pyridin-2-yl]-3,6-dihydropyridin-1(2H)-yl}ethanone;
1-{4-[4-(5-fluoro-2-methoxyphenyl)-1H-pyrrolo[2,3-b]pyridin-2-yl]-3,6-dihydropyridin-1(2H)-yl}-2-hydroxyethanone;
4-(5-fluoro-2-methoxyphenyl)-2-(1-methylpyrrolidin-2-yl)-1H-pyrrolo[2,3-b]pyridine;
1-{3-[4-(5-fluoro-2-methoxyphenyl)-1H-pyrrolo[2,3-b]pyridin-2-yl]pyrrolidin-1-yl}ethanone;
2-{3-[4-(5-fluoro-2-methoxyphenyl)-1H-pyrrolo[2,3-b]pyridin-2-yl]pyrrolidin-1-yl}ethanol;
4-(5-fluoro-2-methoxyphenyl)-2-[1-(tetrahydro-2H-pyran-4-yl)pyrrolidin-3-yl]-1H-pyrrolo[2,3-b]pyridine;
4-(5-fluoro-2-methoxyphenyl)-2-[1-(pyridin-2-ylmethyl)pyrrolidin-3-yl]-1H-pyrrolo[2,3-b]pyridine;
4-(5-fluoro-2-methoxyphenyl)-2-[1-(pyridin-3-ylmethyl)pyrrolidin-3-yl]-1H-pyrrolo[2,3-b]pyridine;
4-(5-fluoro-2-methoxyphenyl)-2-[1-(pyridin-4-ylmethyl)pyrrolidin-3-yl]-1H-pyrrolo[2,3-b]pyridine;
4-(5-fluoro-2-methoxyphenyl)-2-[1-(tetrahydro-2H-pyran-3-ylmethyl)pyrrolidin-3-yl]-1H-pyrrolo[2,3-b]pyridine;
tert-butyl (2-{3-[4-(5-fluoro-2-methoxyphenyl)-1H-pyrrolo[2,3-b]pyridin-2-yl]pyrrolidin-1-yl}ethyl)carbamate;
tert-butyl 3-[4-(5-fluoro-2-methoxyphenyl)-1H-pyrrolo[2,3-b]pyridin-2-yl]-1,3'-bipyrrolidine-1'-carboxylate;
4-(5-fluoro-2-methoxyphenyl)-2-[1-(tetrahydro-2H-pyran-4-ylmethyl)pyrrolidin-3-yl]-1H-pyrrolo[2,3-b]pyridine;
4-(5-fluoro-2-methoxyphenyl)-2-{1-[2-(morpholin-4-yl)ethyl]pyrrolidin-3-yl}-1H-pyrrolo[2,3-b]pyridine;
4-(5-fluoro-2-methoxyphenyl)-2-[1-(methylsulfonyl)-1,2,3,6-tetrahydropyridin-4-yl]-1H-pyrrolo[2,3-b]pyridine;
methyl 4-({trans-4-[4-(5-fluoro-2-methoxyphenyl)-1H-pyrrolo[2,3-b]pyridin-2-yl]cyclohexyl}amino)butanoate;
ethyl 2-[({trans-4-[4-(5-fluoro-2-methoxyphenyl)-1H-pyrrolo[2,3-b]pyridin-2-yl]cyclohexyl}amino)methyl]cyclopropanecarboxylate;
trans-4-[4-(5-fluoro-2-methoxyphenyl)-1H-pyrrolo[2,3-b]pyridin-2-yl]-N-[2-(morpholin-4-yl)ethyl]cyclohexanamine;
3-({trans-4-[4-(5-fluoro-2-methoxyphenyl)-1H-pyrrolo[2,3-b]pyridin-2-yl]cyclohexyl}amino)propane-1,2-diol;
2-{3-[4-(5-fluoro-2-methoxyphenyl)-1H-pyrrolo[2,3-b]pyridin-2-yl]pyrrolidin-1-yl}ethanamine;
3-[4-(5-fluoro-2-methoxyphenyl)-1H-pyrrolo[2,3-b]pyridin-2-yl]-1,3'-bipyrrolidine;
4-[4-(5-fluoro-2-methoxyphenyl)-1H-pyrrolo[2,3-b]pyridin-2-yl]piperidin-4-ol;
benzyl(3-{3-[4-(5-fluoro-2-methoxyphenyl)-1H-pyrrolo[2,3-b]pyridin-2-yl]piperidin-1-yl}propyl)carbamate;
2-{3-[4-(5-fluoro-2-methoxyphenyl)-1H-pyrrolo[2,3-b]pyridin-2-yl]piperidin-1-yl}ethanol;
3-{3-[4-(5-fluoro-2-methoxyphenyl)-1H-pyrrolo[2,3-b]pyridin-2-yl]piperidin-1-yl}propan-1-amine;
4-(5-fluoro-2-methoxyphenyl)-2-[1-(2-methoxy ethyl)piperidin-3-yl]-1H-pyrrolo[2,3-b]pyridine;
4-({trans-4-[4-(5-fluoro-2-methoxyphenyl)-1H-pyrrolo[2,3-b]pyridin-2-yl]cyclohexyl}amino)butanoic acid;
1-{4-[4-(5-fluoro-2-methoxyphenyl)-1H-pyrrolo[2,3-b]pyridin-2-yl]piperidin-1-yl}ethanone;
1-{4-[4-(5-fluoro-2-methoxyphenyl)-1H-pyrrolo[2,3-b]pyridin-2-yl]piperidin-1-yl}-2-hydroxyethanone;
3-methoxy-4-[2-(piperidin-3-yl)-1H-pyrrolo[2,3-b]pyridin-4-yl]benzonitrile;
2-[({trans-4-[4-(5-fluoro-2-methoxyphenyl)-1H-pyrrolo[2,3-b]pyridin-2-yl]cyclohexyl}amino)methyl]cyclopropanecarboxylic acid;
2-(azetidin-3-yl)-4-(5-fluoro-2-methoxyphenyl)-1H-pyrrolo[2,3-b]pyridine;
1-{4-[4-(5-fluoro-2-methoxyphenyl)-1H-pyrrolo[2,3-b]pyridin-2-yl]piperidin-1-yl}-2-(4-hydroxypiperidin-1-yl)ethanone;
4-(5-fluoro-2-methoxyphenyl)-2-[1-(methylsulfonyl)piperidin-4-yl]-1H-pyrrolo[2,3-b]pyridine;
3-{4-[4-(5-fluoro-2-methoxyphenyl)-1H-pyrrolo[2,3-b]pyridin-2-yl]piperidin-1-yl}propane-1,2-diol;
5-chloro-6-[2-(1-methylpiperidin-4-yl)-1H-pyrrolo[2,3-b]pyridin-4-yl]-N-(piperidin-4-ylmethyl)pyridin-2-amine;
4-[4-(5-fluoro-2-methoxyphenyl)-1H-pyrrolo[2,3-b]pyridin-2-yl]tetrahydro-2H-pyran-4-ol;
4-(5-fluoro-2-methoxyphenyl)-2-[1-(pyridin-4-ylmethyl)azetidin-3-yl]-1H-pyrrolo[2,3-b]pyridine;
1-{3-[4-(5-fluoro-2-methoxyphenyl)-1H-pyrrolo[2,3-b]pyridin-2-yl]azetidin-1-yl}ethanone;
2-{3-[4-(5-fluoro-2-methoxyphenyl)-1H-pyrrolo[2,3-b]pyridin-2-yl]azetidin-1-yl}ethanamine;
4-(5-fluoro-2-methoxyphenyl)-2-[1-(tetrahydro-2H-pyran-4-ylmethyl)azetidin-3-yl]-1H-pyrrolo[2,3-b]pyridine;
4-(5-fluoro-2-methoxyphenyl)-2-{1-[2-(morpholin-4-yl)ethyl]azetidin-3-yl}-1H-pyrrolo[2,3-b]pyridine;
2-{3-[4-(5-fluoro-2-methoxyphenyl)-1H-pyrrolo[2,3-b]pyridin-2-yl]azetidin-1-yl}ethanol;
4-fluoro-3-[2-(1-methylpiperidin-4-yl)-1H-pyrrolo[2,3-b]pyridin-4-yl]-N-(tetrahydro-2H-pyran-4-ylmethyl)aniline;
1-{4-[4-(5-fluoro-2-methoxyphenyl)-1H-pyrrolo[2,3-b]pyridin-2-yl]piperidin-1-yl}-2-(piperidin-1-yl)ethanone;
1-{4-[4-(5-fluoro-2-methoxyphenyl)-1H-pyrrolo[2,3-b]pyridin-2-yl]piperidin-1-yl}-2-(morpholin-4-yl)ethanone;
1-{4-[4-(5-fluoro-2-methoxyphenyl)-1H-pyrrolo[2,3-b]pyridin-2-yl]piperidin-1-yl}-2-[(4-hydroxycyclohexyl)amino]ethanone;
1-{4-[4-(5-fluoro-2-methoxyphenyl)-1H-pyrrolo[2,3-b]pyridin-2-yl]piperidin-1-yl}-2-[(2-hydroxyethyl)amino]ethanone;
4-(5-fluoro-2-methoxyphenyl)-2-(1-methylazetidin-3-yl)-1H-pyrrolo[2,3-b]pyridine;
4-(5-fluoro-2-methoxyphenyl)-2-[1-(methylsulfonyl)azetidin-3-yl]-1H-pyrrolo[2,3-b]pyridine;
3-{4-[4-(5-fluoro-2-methoxyphenyl)-1H-pyrrolo[2,3-b]pyridin-2-yl]-3,6-dihydropyridin-1(2H)-yl}propane-1,2-diol;
4-fluoro-3-[2-(piperidin-4-yl)-1H-pyrrolo[2,3-b]pyridin-4-yl]aniline;
4-fluoro-3-[2-(1-methylpiperidin-4-yl)-1H-pyrrolo[2,3-b]pyridin-4-yl]-N-(pyridin-4-ylmethyl)aniline;

4-fluoro-3-[2-(1-methylpiperidin-4-yl)-1H-pyrrolo[2,3-b]pyridin-4-yl]-N-[4-(methylsulfonyl)benzyl]aniline;
4-[({4-fluoro-3-[2-(1-methylpiperidin-4-yl)-1H-pyrrolo[2,3-b]pyridin-4-yl]phenyl}amino)methyl]benzamide;
2-(azepan-3-yl)-4-(5-fluoro-2-methoxyphenyl)-1H-pyrrolo[2,3-b]pyridine;
N-benzyl-3-[5-chloro-2-(piperidin-4-yl)-1H-pyrrolo[2,3-b]pyridin-4-yl]-4-fluoroaniline;
N-benzyl-4-chloro-3-[2-(piperidin-3-yl)-1H-pyrrolo[2,3-b]pyridin-4-yl]aniline;
4-(4,5-difluoro-2-methoxyphenyl)-2-(piperidin-3-yl)-1H-pyrrolo[2,3-b]pyridine;
N-benzyl-4-fluoro-3-[2-(piperidin-3-yl)-1H-pyrrolo[2,3-b]pyridin-4-yl]aniline; and
4-fluoro-N-(3-fluorobenzyl)-3-[2-(piperidin-3-yl)-1H-pyrrolo[2,3-b]pyridin-4-yl]aniline; or a pharmaceutically acceptable salt thereof.

In certain embodiments, a compound of formula I is selected from the group consisting of:
5-methoxy-6-[2-(piperidin-3-yl)-1H-pyrrolo[2,3-b]pyridin-4-yl]pyridin-2-amine;
N-benzyl-5-chloro-6-[2-(piperidin-3-yl)-1H-pyrrolo[2,3-b]pyridin-4-yl]pyridin-2-amine;
N-benzyl-5-chloro-6-[2-(1-methylpiperidin-3-yl)-1H-pyrrolo[2,3-b]pyridin-4-yl]pyridin-2-amine;
N-benzyl-6-[2-(1-methylpiperidin-3-yl)-1H-pyrrolo[2,3-b]pyridin-4-yl]pyridin-2-amine;
N-benzyl-5-methoxy-6-[2-(piperidin-3-yl)-1H-pyrrolo[2,3-b]pyridin-4-yl]pyridin-2-amine;
N-benzyl-5-chloro-6-{2-[1-(propan-2-ylsulfonyl)piperidin-3-yl]-1H-pyrrolo[2,3-b]pyridin-4-yl}pyridin-2-amine;
methyl 3-{4-[6-(benzylamino)-3-chloropyridin-2-yl]-1H-pyrrolo[2,3-b]pyridin-2-yl}piperidine-1-carboxylate;
4-(3-methoxypyridin-2-yl)-2-(piperidin-4-yl)-1H-pyrrolo[2,3-b]pyridine;
5-methoxy-6-[2-(piperidin-4-yl)-1H-pyrrolo[2,3-b]pyridin-4-yl]pyridin-2-amine;
4-(6-fluoro-3-methoxypyridin-2-yl)-2-(piperidin-4-yl)-1H-pyrrolo[2,3-b]pyridine;
4-(4-methoxypyridin-3-yl)-2-(1-methylpiperidin-4-yl)-1H-pyrrolo[2,3-b]pyridine;
N-benzyl-5-chloro-6-[2-(piperidin-4-yl)-1H-pyrrolo[2,3-b]pyridin-4-yl]pyridin-2-amine;
5-chloro-N-(3-fluorobenzyl)-6-[2-(piperidin-4-yl)-1H-pyrrolo[2,3-b]pyridin-4-yl]pyridin-2-amine;
5-chloro-6-[2-(piperidin-4-yl)-1H-pyrrolo[2,3-b]pyridin-4-yl]-N-(pyridin-3-ylmethyl)pyridin-2-amine;
5-chloro-N-(4-chlorobenzyl)-6-[2-(piperidin-4-yl)-1H-pyrrolo[2,3-b]pyridin-4-yl]pyridin-2-amine;
5-chloro-N-(2,5-difluorobenzyl)-6-[2-(piperidin-4-yl)-1H-pyrrolo[2,3-b]pyridin-4-yl]pyridin-2-amine;
5-chloro-N-[(5-fluoropyridin-3-yl)methyl]-6-[2-(piperidin-4-yl)-1H-pyrrolo[2,3-b]pyridin-4-yl]pyridin-2-amine;
5-chloro-N-(2-fluorobenzyl)-6-[2-(piperidin-4-yl)-1H-pyrrolo[2,3-b]pyridin-4-yl]pyridin-2-amine;
5-chloro-N-(3,4-difluorobenzyl)-6-[2-(piperidin-4-yl)-1H-pyrrolo[2,3-b]pyridin-4-yl]pyridin-2-amine;
5-chloro-6-[2-(piperidin-4-yl)-1H-pyrrolo[2,3-b]pyridin-4-yl]-N-(pyridin-4-ylmethyl)pyridin-2-amine;
5-chloro-N-[(1-oxidopyridin-3-yl)methyl]-6-[2-(piperidin-4-yl)-1H-pyrrolo[2,3-b]pyridin-4-yl]pyridin-2-amine;
5-chloro-N-(piperidin-4-ylmethyl)-6-[2-(piperidin-4-yl)-1H-pyrrolo[2,3-b]pyridin-4-yl]pyridin-2-amine;
5-chloro-N-(piperidin-3-ylmethyl)-6-[2-(piperidin-4-yl)-1H-pyrrolo[2,3-b]pyridin-4-yl]pyridin-2-amine;
4-(3-chloro-6-phenylpyridin-2-yl)-2-(piperidin-4-yl)-1H-pyrrolo[2,3-b]pyridine;
N-{5-chloro-6-[2-(piperidin-4-yl)-1H-pyrrolo[2,3-b]pyridin-4-yl]pyridin-2-yl}benzamide;
N-benzyl-5-chloro-N-methyl-6-[2-(piperidin-4-yl)-1H-pyrrolo[2,3-b]pyridin-4-yl]pyridin-2-amine;
N-benzyl-5-chloro-N-ethyl-6-[2-(piperidin-4-yl)-1H-pyrrolo[2,3-b]pyridin-4-yl]pyridin-2-amine;
5-chloro-6-[2-(piperidin-4-yl)-1H-pyrrolo[2,3-b]pyridin-4-yl]-N-(tetrahydro-2H-pyran-4-ylmethyl)pyridin-2-amine;
5-chloro-6-[2-(piperidin-4-yl)-1H-pyrrolo[2,3-b]pyridin-4-yl]-N-(tetrahydro-2H-pyran-3-ylmethyl)pyridin-2-amine;
N-benzyl-5-chloro-4-[2-(piperidin-4-yl)-1H-pyrrolo[2,3-b]pyridin-4-yl]pyridin-2-amine;
N-benzyl-5-chloro-6-[2-(1-methylpiperidin-4-yl)-1H-pyrrolo[2,3-b]pyridin-4-yl]pyridin-2-amine;
5-chloro-N-[(1S)-1-phenylethyl]-6-[2-(piperidin-4-yl)-1H-pyrrolo[2,3-b]pyridin-4-yl]pyridin-2-amine;
N-benzyl-6-[2-(1-methylpiperidin-4-yl)-1H-pyrrolo[2,3-b]pyridin-4-yl]pyridin-2-amine;
5-chloro-N-(3-fluorobenzyl)-6-[2-(1-methylpiperidin-4-yl)-1H-pyrrolo[2,3-b]pyridin-4-yl]pyridin-2-amine;
4-[6-(benzyloxy)-3-chloropyridin-2-yl]-2-(piperidin-4-yl)-1H-pyrrolo[2,3-b]pyridine;
N-benzyl-5-chloro-6-[2-(pyrrolidin-3-yl)-1H-pyrrolo[2,3-b]pyridin-4-yl]pyridin-2-amine;
5-chloro-6-[2-(pyrrolidin-3-yl)-1H-pyrrolo[2,3-b]pyridin-4-yl]-N-(tetrahydro-2H-pyran-4-ylmethyl)pyridin-2-amine;
N-benzyl-5-chloro-6-[2-(morpholin-2-yl)-1H-pyrrolo[2,3-b]pyridin-4-yl]pyridin-2-amine;
N-benzyl-6-[5-chloro-2-(piperidin-4-yl)-1H-pyrrolo[2,3-b]pyridin-4-yl]pyridin-2-amine;
5-chloro-4-(6-fluoropyridin-2-yl)-2-(piperidin-3-yl)-1H-pyrrolo[2,3-b]pyridine;
N-benzyl-6-[5-chloro-2-(piperidin-3-yl)-1H-pyrrolo[2,3-b]pyridin-4-yl]pyridin-2-amine;
6-[5-chloro-2-(piperidin-3-yl)-1H-pyrrolo[2,3-b]pyridin-4-yl]-N-(tetrahydro-2H-pyran-4-ylmethyl)pyridin-2-amine;
N-benzyl-6-[5-chloro-2-(1-methylpiperidin-3-yl)-1H-pyrrolo[2,3-b]pyridin-4-yl]pyridin-2-amine;
methyl 3-{4-[6-(b enzylamino)pyridin-2-yl]-5-chloro-1H-pyrrolo[2,3-b]pyridin-2-yl}piperidine-1-carboxylate;
N-benzyl-6-{5-chloro-2-[1-(propan-2-ylsulfonyl)piperidin-3-yl]-1H-pyrrolo[2,3-b]pyridin-4-yl}pyridin-2-amine;
6-[2-(3-aminocyclohexyl)-5-chloro-1H-pyrrolo[2,3-b]pyridin-4-yl]-N-benzylpyridin-2-amine;
6-[2-(piperidin-4-yl)-1H-pyrrolo[2,3-b]pyridin-4-yl]-N-(tetrahydro-2H-pyran-4-ylmethyl)pyridin-2-amine;
6-[2-(1-methylpiperidin-4-yl)-1H-pyrrolo[2,3-b]pyridin-4-yl]-N-(tetrahydro-2H-pyran-4-ylmethyl)pyridin-2-amine;
6-[2-(1-methylpiperidin-4-yl)-1H-pyrrolo[2,3-b]pyridin-4-yl]-N-(3-phenylpropyl)pyridin-2-amine;
6-[2-(1-methylpiperidin-4-yl)-1H-pyrrolo[2,3-b]pyridin-4-yl]-N-(pyridin-3-ylmethyl)pyridin-2-amine;
6-[2-(1-methylpiperidin-4-yl)-1H-pyrrolo[2,3-b]pyridin-4-yl]-N-[2-(phenylsulfanyl)ethyl]pyridin-2-amine;
N-(cyclopropylmethyl)-6-[2-(1-methylpiperidin-4-yl)-1H-pyrrolo[2,3-b]pyridin-4-yl]pyridin-2-amine;
N-[(2,2-dimethyltetrahydro-2H-pyran-4-yl)methyl]-6-[2-(1-methylpiperidin-4-yl)-1H-pyrrolo[2,3-b]pyridin-4-yl]pyridin-2-amine;
N-benzyl-N-methyl-6-[2-(1-methylpiperidin-4-yl)-1H-pyrrolo[2,3-b]pyridin-4-yl]pyridin-2-amine;
N-(3-chlorobenzyl)-6-[2-(1-methylpiperidin-4-yl)-1H-pyrrolo[2,3-b]pyridin-4-yl]pyridin-2-amine;
N-(2,6-difluorobenzyl)-6-[2-(1-methylpiperidin-4-yl)-1H-pyrrolo[2,3-b]pyridin-4-yl]pyridin-2-amine;
6-[2-(1-methylpiperidin-4-yl)-1H-pyrrolo[2,3-b]pyridin-4-yl]-N-[(1S)-1-phenylethyl]pyridin-2-amine;

N-(1,3-benzodioxol-5-ylmethyl)-6-[2-(1-methylpiperidin-4-yl)-1H-pyrrolo[2,3-b]pyridin-4-yl]pyridin-2-amine;
5-chloro-6-[2-(piperidin-4-yl)-1H-pyrrolo[2,3-b]pyridin-4-yl]pyridin-2-amine;
N-[2-(phenylsulfanyl)ethyl]-6-[2-(piperidin-4-yl)-1H-pyrrolo[2,3-b]pyridin-4-yl]pyridin-2-amine;
5-chloro-6-[2-(1-methylpiperidin-4-yl)-1H-pyrrolo[2,3-b]pyridin-4-yl]pyridin-2-amine;
3-chloro-N²-{5-chloro-6-[2-(1-methylpiperidin-4-yl)-1H-pyrrolo[2,3-b]pyridin-4-yl]pyridin-2-yl}pyridine-2,6-diamine;
5-chloro-6-[2-(1-methylpiperidin-4-yl)-1H-pyrrolo[2,3-b]pyridin-4-yl]-N-(tetrahydro-2H-pyran-4-ylmethyl)pyridin-2-amine;
N-(2-phenylethyl)-6-[2-(piperidin-4-yl)-1H-pyrrolo[2,3-b]pyridin-4-yl]pyridin-2-amine;
N-methyl-6-[2-(1-methylpiperidin-4-yl)-1H-pyrrolo[2,3-b]pyridin-4-yl]-N-(2-phenylethyl)pyridin-2-amine;
N-(2-chlorobenzyl)-6-[2-(piperidin-4-yl)-1H-pyrrolo[2,3-b]pyridin-4-yl]pyridin-2-amine;
N-(2-chlorobenzyl)-6-[2-(1-methylpiperidin-4-yl)-1H-pyrrolo[2,3-b]pyridin-4-yl]pyridin-2-amine;
N-(2-chlorobenzyl)-N-methyl-6-[2-(1-methylpiperidin-4-yl)-1H-pyrrolo[2,3-b]pyridin-4-yl]pyridin-2-amine;
1-[2-({6-[2-(piperidin-4-yl)-1H-pyrrolo[2,3-b]pyridin-4-yl]pyridin-2-yl}amino)ethyl]pyrrolidin-2-one;
1-[2-(methyl {6-[2-(1-methylpiperidin-4-yl)-1H-pyrrolo[2,3-b]pyridin-4-yl]pyridin-2-yl}amino)ethyl]pyrrolidin-2-one;
6-[2-(1-methylpiperidin-4-yl)-1H-pyrrolo[2,3-b]pyridin-4-yl]-N-(2-phenylethyl)pyridin-2-amine;
1-[2-({6-[2-(1-methylpiperidin-4-yl)-1H-pyrrolo[2,3-b]pyridin-4-yl]pyridin-2-yl}amino)ethyl]pyrrolidin-2-one;
5-chloro-N-(cyclopropylmethyl)-6-[2-(1-methylpiperidin-4-yl)-1H-pyrrolo[2,3-b]pyridin-4-yl]pyridin-2-amine;
N-{4-[2-(dimethylamino)ethoxy]benzyl}-6-[2-(1-methylpiperidin-4-yl)-1H-pyrrolo[2,3-b]pyridin-4-yl]pyridin-2-amine;
5-chloro-N-[(2,2-dimethyltetrahydro-2H-pyran-4-yl)methyl]-6-[2-(1-methylpiperidin-4-yl)-1H-pyrrolo[2,3-b]pyridin-4-yl]pyridin-2-amine;
5-chloro-6-[2-(1-methylpiperidin-4-yl)-1H-pyrrolo[2,3-b]pyridin-4-yl]-N-(pyridin-4-ylmethyl)pyridin-2-amine;
6-[2-(1-methylpiperidin-4-yl)-1H-pyrrolo[2,3-b]pyridin-4-yl]-N-(1H-pyrazol-3-ylmethyl)pyridin-2-amine;
N-(2,3-dihydro-1H-isoindol-5-ylmethyl)-6-[2-(1-methylpiperidin-4-yl)-1H-pyrrolo[2,3-b]pyridin-4-yl]pyridin-2-amine;
6-[2-(1-methylpiperidin-4-yl)-1H-pyrrolo[2,3-b]pyridin-4-yl]-N-[(1-methylpyrrolidin-3-yl)methyl]pyridin-2-amine;
N-(1H-indol-6-ylmethyl)-6-[2-(1-methylpiperidin-4-yl)-1H-pyrrolo[2,3-b]pyridin-4-yl]pyridin-2-amine;
5-chloro-6-[2-(1-methylpiperidin-4-yl)-1H-pyrrolo[2,3-b]pyridin-4-yl]-N-[4-(methylsulfonyl)benzyl]pyridin-2-amine;
4-[({5-chloro-6-[2-(1-methylpiperidin-4-yl)-1H-pyrrolo[2,3-b]pyridin-4-yl]pyridin-2-yl}amino)methyl]benzenesulfonamide;
4-[({5-chloro-6-[2-(1-methylpiperidin-4-yl)-1H-pyrrolo[2,3-b]pyridin-4-yl]pyridin-2-yl}amino)methyl]benzamide;
6-[2-(1-methylpiperidin-4-yl)-1H-pyrrolo[2,3-b]pyridin-4-yl]-N-[2-(morpholin-4-yl)ethyl]pyridin-2-amine;
2-({6-[2-(1-methylpiperidin-4-yl)-1H-pyrrolo[2,3-b]pyridin-4-yl]pyridin-2-yl}amino)ethanol;
tert-butyl 3-[({5-chloro-6-[2-(1-methylpiperidin-4-yl)-1H-pyrrolo[2,3-b]pyridin-4-yl]pyridin-2-yl}amino)methyl]pyrrolidine-1-carboxylate;
5-chloro-N-[(1,1-dioxidotetrahydro-2H-thiopyran-4-yl)methyl]-6-[2-(1-methylpiperidin-4-yl)-1H-pyrrolo[2,3-b]pyridin-4-yl]pyridin-2-amine;
{3-[({5-chloro-6-[2-(1-methylpiperidin-4-yl)-1H-pyrrolo[2,3-b]pyridin-4-yl]pyridin-2-yl}amino)methyl]phenoxy}acetic acid;
{4-[({5-chloro-6-[2-(1-methylpiperidin-4-yl)-1H-pyrrolo[2,3-b]pyridin-4-yl]pyridin-2-yl}amino)methyl]phenoxy}acetic acid;
1-{4-[({5-chloro-6-[2-(1-methylpiperidin-4-yl)-1H-pyrrolo[2,3-b]pyridin-4-yl]pyridin-2-yl}amino)methyl]piperidin-1-yl}ethanone;
5-chloro-6-[2-(1-methylpiperidin-4-yl)-1H-pyrrolo[2,3-b]pyridin-4-yl]-N-(4H-1,2,4-triazol-3-ylmethyl)pyridin-2-amine;
5-chloro-6-[2-(1-methylpiperidin-4-yl)-1H-pyrrolo[2,3-b]pyridin-4-yl]-N-[3-(methylsulfonyl)benzyl]pyridin-2-amine;
(3S,5R)-5-[({5-chloro-6-[2-(piperidin-4-yl)-1H-pyrrolo[2,3-b]pyridin-4-yl]pyridin-2-yl}amino)methyl]pyrrolidin-3-ol;
N-benzyl-5-chloro-6-(2-cyclohexyl-1H-pyrrolo[2,3-b]pyridin-4-yl)pyridin-2-amine;
5-chloro-N-{[(2S,4S)-4-fluoropyrrolidin-2-yl]methyl}-6-[2-(piperidin-4-yl)-1H-pyrrolo[2,3-b]pyridin-4-yl]pyridin-2-amine;
4-[({5-chloro-4-[2-(piperidin-4-yl)-1H-pyrrolo[2,3-b]pyridin-4-yl]pyridin-2-yl}amino)methyl]tetrahydro-2H-pyran-4-carbonitrile;
5-chloro-N-{[(2S)-4,4-difluoropyrrolidin-2-yl]methyl}-6-[2-(piperidin-4-yl)-1H-pyrrolo[2,3-b]pyridin-4-yl]pyridin-2-amine;
N-benzyl-5-chloro-N-methyl-6-[2-(piperidin-3-yl)-1H-pyrrolo[2,3-b]pyridin-4-yl]pyridin-2-amine;
5-chloro-N-(3,4-difluorobenzyl)-6-[2-(piperidin-3-yl)-1H-pyrrolo[2,3-b]pyridin-4-yl]pyridin-2-amine;
5-chloro-N-(3-fluorobenzyl)-6-[2-(piperidin-3-yl)-1H-pyrrolo[2,3-b]pyridin-4-yl]pyridin-2-amine;
5-chloro-N-(4-fluorobenzyl)-6-[2-(piperidin-3-yl)-1H-pyrrolo[2,3-b]pyridin-4-yl]pyridin-2-amine;
N-benzyl-5-chloro-4-[2-(piperidin-3-yl)-1H-pyrrolo[2,3-b]pyridin-4-yl]pyridin-2-amine;
5-chloro-N-(2-fluorobenzyl)-6-[2-(piperidin-3-yl)-1H-pyrrolo[2,3-b]pyridin-4-yl]pyridin-2-amine;
5-chloro-6-[2-(piperidin-3-yl)-1H-pyrrolo[2,3-b]pyridin-4-yl]-N-(pyridin-3-ylmethyl)pyridin-2-amine;
4-[3-chloro-6-(pyridin-3-ylmethoxy)pyridin-2-yl]-2-(piperidin-3-yl)-1H-pyrrolo[2,3-b]pyridine;
5-chloro-N-[(5-fluoropyridin-3-yl)methyl]-6-[2-(piperidin-3-yl)-1H-pyrrolo[2,3-b]pyridin-4-yl]pyridin-2-amine;
N-benzyl-5-fluoro-4-[2-(piperidin-3-yl)-1H-pyrrolo[2,3-b]pyridin-4-yl]pyridin-2-amine;
N-benzyl-4-fluoro-6-[2-(piperidin-3-yl)-1H-pyrrolo[2,3-b]pyridin-4-yl]pyridin-2-amine; and
N-benzyl-4-[5-chloro-2-(piperidin-3-yl)-1H-pyrrolo[2,3-b]pyridin-4-yl]pyridin-2-amine; or a pharmaceutically acceptable salt thereof.

Embodiments of Formula (I)

In one aspect, the present invention relates to compounds of Formula (I) or a pharmaceutically acceptable salt thereof,

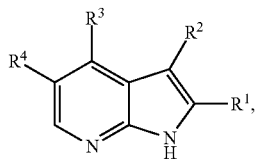

Formula (I)

wherein
- R¹ is selected from the group consisting of cycloalkyl, cycloalkenyl, heterocycloalkyl, and heterocycloalkenyl; wherein the R¹ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $C(O)H$, $C(O)OH$, $(O)$, $OH$, $CN$, $NO_2$, $F$, $Cl$, $Br$ and $I$;
- R² is selected from the group consisting of hydrogen, $C_1$-$C_4$ alkyl, $NO_2$, $CN$, $C(O)NH_2$, and $C(O)OR^{2A}$;
- $R^{2A}$ is selected from the group consisting of alkyl, alkenyl, and alkynyl;
- R³ is selected from the group consisting of phenyl, pyridinyl, pyrazinyl, pyrimidinyl, and pyridazinyl; wherein the R³ phenyl, pyridinyl, pyrazinyl, pyrimidinyl, and pyridazinyl are optionally substituted with one or more substituents independently selected from the group consisting of $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, $(O)$, $OH$, $CN$, $NO_2$, $F$, $Cl$, $Br$ and $I$;
- R⁴ is selected from the group consisting of hydrogen, $R^{4A}$, $OR^{4A}$, $C(O)NH_2$, $CN$, $F$, $Cl$, $Br$, and $I$;
- $R^{4A}$ is selected from the group consisting of haloalkyl, alkyl, alkenyl, and alkynyl;
- R⁵, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each R⁵ $C_1$-$C_8$ alkyl, $C_2$-$C_6$ alkenyl, and $C_2$-$C_6$ alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $OH$, $CN$, $NO_2$, $F$, $Cl$, $Br$ and $I$; wherein each R⁵ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $(O)$, $OH$, $CN$, $NO_2$, $F$, $Cl$, $Br$ and $I$;
- R⁶, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each R⁶ $C_1$-$C_6$ alkyl, $C_2$-$C_6$ alkenyl, and $C_2$-$C_6$ alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $OH$, $CN$, $NO_2$, $F$, $Cl$, $Br$ and $I$; wherein each R⁶ aryl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $(O)$, $OH$, $CN$, $NO_2$, $F$, $Cl$, $Br$ and $I$;
- R⁷, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each R⁷ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, cycloalkyl, cycloalkenyl, heterocycloalkyl, heterocycloalkenyl, $NH_2$, $NHR^{13}$, $N(R^{13})_2$, $C(O)H$, $C(O)OH$, $OH$, $CN$, $NO_2$, $F$, $Cl$, $Br$ and $I$; wherein each R⁷ aryl, cycloalkyl, cycloalkenyl, heteroaryl, heterocycloalkyl, and heterocycloalkenyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $(O)$, $OH$, $CN$, $NO_2$, $F$, $Cl$, $Br$ and $I$;
- R⁸, at each occurrence, is independently selected from the group consisting of $C_1$-$C_6$ alkyl, $C_2$-$C_6$ alkenyl, and $C_2$-$C_6$ alkynyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NH_2$, C(O)H, C(O)OH, OH, CN, $NO_2$, F, Cl, Br and I;

$R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, NHC(O)$OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, C(O)NHOH, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, C(O)H, C(O)OH, (O), OH, CN, $NO_2$, F, Cl, Br and I;

$R^{10}$, at each occurrence, is independently selected from the group consisting of $C_1$-$C_6$ alkyl, $C_2$-$C_6$ alkenyl, and $C_2$-$C_6$ alkynyl; wherein each $R^{10}$ $C_1$-$C_6$ alkyl, $C_2$-$C_6$ alkenyl, and $C_2$-$C_6$ alkynyl is optionally substituted with one or more substituents independently selected from the group consisting of $NH_2$, C(O)H, C(O)OH, OH, CN, $NO_2$, F, Cl, Br and I;

$R^{11}$, at each occurrence, is independently selected from the group consisting of $C_1$-$C_6$ alkyl, $C_2$-$C_6$ alkenyl, and $C_2$-$C_6$ alkynyl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $NH_2$, C(O)H, C(O)OH, OH, CN, $NO_2$, F, Cl, Br and I;

$R^{12}$, at each occurrence, is independently selected from the group consisting of $C_1$-$C_6$ alkyl, $C_2$-$C_6$ alkenyl, and $C_2$-$C_6$ alkynyl; wherein each $R^{12}$ $C_1$-$C_6$ alkyl, $C_2$-$C_6$ alkenyl, and $C_2$-$C_6$ alkynyl is optionally substituted with one or more substituents independently selected from the group consisting of $NH_2$, $NHR^{13}$, $N(R^{13})_2$, C(O)H, C(O)OH, OH, CN, $NO_2$, F, Cl, Br and I; and $R^{13}$, at each occurrence, is independently selected from the group consisting of $C_1$-$C_6$ alkyl, $C_2$-$C_6$ alkenyl, and $C_2$-$C_6$ alkynyl.

In one embodiment of Formula (I), $R^2$ is selected from the group consisting of hydrogen, $C_1$-$C_4$ alkyl, $NO_2$, CN, C(O)$NH_2$, and C(O)$OR^{2A}$; and $R^{2A}$ is selected from the group consisting of alkyl, alkenyl, and alkynyl. In another embodiment of Formula (I), $R^2$ is selected from the group consisting of hydrogen, $C_1$-$C_4$ alkyl, $NO_2$, CN, C(O)$NH_2$, and C(O)$OR^{2A}$; and $R^{2A}$ is alkyl. In another embodiment of Formula (I), $R^2$ is selected from the group consisting of hydrogen, $C_1$-$C_4$ alkyl, and CN. In another embodiment of Formula (I), $R^2$ is selected from the group consisting of hydrogen, $CH_3$, and CN. In another embodiment of Formula (I), $R^2$ is hydrogen. In another embodiment of Formula (I), $R^2$ is $CH_3$. In another embodiment of Formula (I), $R^2$ is CN.

In one embodiment of Formula (I), $R^4$ is selected from the group consisting of hydrogen, $R^{4A}$, $OR^{4A}$, C(O)$NH_2$, CN, F, Cl, Br, and I; and $R^{4A}$ is selected from the group consisting of haloalkyl, alkyl, alkenyl, and alkynyl. In another embodiment of Formula (I), $R^4$ is selected from the group consisting of hydrogen, $R^{4A}$, $OR^{4A}$, C(O)$NH_2$, CN, F, and Cl; and $R^{4A}$ is selected from the group consisting of haloalkyl and alkyl. In another embodiment of Formula (I), $R^4$ is selected from the group consisting of hydrogen, CN, F, and Cl. In another embodiment of Formula (I), $R^4$ is hydrogen. In another embodiment of Formula (I), $R^4$ is CN. In another embodiment of Formula (I), $R^4$ is F. In another embodiment of Formula (I), $R^4$ is Cl.

In one embodiment of Formula (I), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, C(O)NHOH, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, C(O)NHCN, $C(O)NR^5CN$, $S(O)(N)R^5$, C(O)H, C(O)OH, (O), OH, CN, $NO_2$, F, Cl, Br and I. In another embodiment of Formula (I), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, C(O)NHCN, $S(O)(N)R^5$, C(O)OH, and OH. In another embodiment of Formula (I), $R^1$ is cycloalkyl; wherein the $R^1$ cycloalkyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, C(O)NHCN, $S(O)(N)R^5$, C(O)OH, and OH. In another embodiment of Formula (I), $R^1$ is cycloalkenyl; wherein the $R^1$ cycloalkenyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, C(O)NHCN, $S(O)(N)R^5$, C(O)OH, and OH. In another embodiment of Formula (I), $R^1$ is heterocycloalkyl; wherein the $R^1$ heterocycloalkyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, C(O)NHCN, $S(O)(N)R^5$, C(O)OH, and OH. In another embodiment of Formula (I), $R^1$ is heterocycloalkenyl; wherein the $R^1$ heterocycloalkenyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, C(O)NHCN, $S(O)(N)R^5$, C(O)OH, and OH. In another embodiment of Formula (I), $R^1$ is selected from the group consisting of azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl wherein the $R^1$ azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $C(O)H$, $C(O)OH$, $(O)$, $OH$, $CN$, $NO_2$, F, Cl, Br and I. In another embodiment of Formula (I), $R^1$ is selected from the group consisting of azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl wherein the $R^1$ azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH. In another embodiment of Formula (I), $R^1$ is selected from the group consisting of azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl wherein the $R^1$ azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are unsubstituted.

In one embodiment of Formula (I), $R^3$ is selected from the group consisting of phenyl, pyridinyl, pyrazinyl, pyrimidinyl, and pyridazinyl; wherein the $R^3$ phenyl, pyridinyl, pyrazinyl, pyrimidinyl, and pyridazinyl are optionally substituted with one or more substituents independently selected from the group consisting of $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, $(O)$, $OH$, $CN$, $NO_2$, F, Cl, Br and I. In another embodiment of Formula (I), $R^3$ is selected from the group consisting of phenyl and pyridinyl; wherein the $R^3$ phenyl and pyridinyl are optionally substituted with one or more substituents independently selected from the group consisting of $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, $(O)$, $OH$, $CN$, $NO_2$, F, Cl, Br and I. In another embodiment of Formula (I), $R^3$ is selected from the group consisting of phenyl and pyridinyl; wherein the $R^3$ phenyl and pyridinyl are optionally substituted with one or more substituents independently selected from the group consisting of $R^6$, $OR^6$, $NH_2$, $NHR^6$, $N(R^6)_2$, $NHC(O)R^6$, $NHS(O)_2R^6$, CN, F, and Cl. In another embodiment of Formula (I), $R^3$ is selected from the group consisting of phenyl and pyridinyl; wherein the $R^3$ phenyl, and pyridinyl are substituted with one, or two substituents independently selected from the group consisting of $OR^6$, $NHR^6$, F, and Cl. In another embodiment of Formula (I), $R^3$ is selected from the group consisting of:

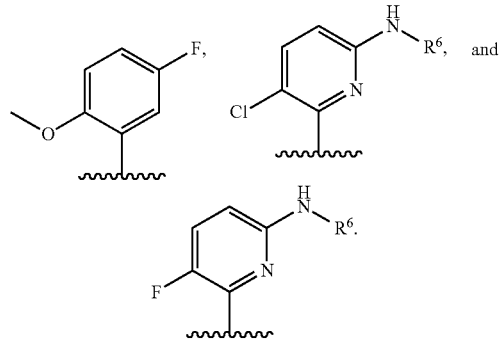

In one embodiment of Formula (I), $R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $OH$, $CN$, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $(O)$, $OH$, $CN$, $NO_2$, F, Cl, Br and I. In another embodiment of Formula (I), $R^5$, at each occurrence, is independently selected from the group consisting of $C_1$-$C_8$ alkyl, heteroaryl, heterocycloalkyl, and cycloalkyl; wherein each $R^5$ $C_1$-$C_8$ alkyl is optionally substituted with one or more substituents independently selected from the group consisting of $R^7$, $OR^7$, $C(O)R^7$, $CO(O)R^7$, $NH_2$, $NHR^7$, $NHC(O)OR^7$, $C(O)NH_2$, $C(O)NHR^7$, $C(O)N(R^7)_2$, $SO_2NHR^7$, $C(O)OH$, OH, and CN; wherein each $R^5$ cycloalkyl, heteroaryl, and heterocycloalkyl is optionally substituted with one or more substituents independently selected from the group consisting of $R^8$, $CO(O)R^8$, $C(O)OH$, and OH.

In one embodiment of Formula (I), $R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $OH$, $CN$, $NO_2$, $F$, $Cl$, $Br$ and $I$; wherein each $R^6$ aryl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $(O)$, $OH$, $CN$, $NO_2$, $F$, $Cl$, $Br$ and $I$. In another embodiment of Formula (I), $R^6$, at each occurrence, is independently selected from the group consisting of $C_1$-$C_6$ alkyl, aryl, heteroaryl, heterocycloalkenyl, and cycloalkyl; wherein each $R^6$ $C_1$-$C_6$ alkyl is optionally substituted with one or more substituents independently selected from the group consisting of $R^9$, $SR^9$, and $OH$; wherein each $R^6$ heteroaryl is optionally substituted with one or more substituents independently selected from the group consisting of $NH_2$, $F$, $Cl$, $Br$ and $I$. In another embodiment of Formula (I), $R^6$, at each occurrence, is independently selected from the group consisting of $C_1$-$C_6$ alkyl, aryl, heteroaryl, heterocycloalkenyl, and cycloalkyl; wherein each $R^6$ $C_1$-$C_6$ alkyl is optionally substituted with one or more substituents independently selected from the group consisting of $R^9$, $SR^9$, and $OH$; wherein each $R^6$ heteroaryl is optionally substituted with one or more substituents independently selected from the group consisting of $NH_2$, and $Cl$.

In one embodiment of Formula (I), $R^8$, at each occurrence, is independently selected from the group consisting of $C_1$-$C_6$ alkyl, $C_2$-$C_6$ alkenyl, and $C_2$-$C_6$ alkynyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, $OH$, $CN$, $NO_2$, $F$, $Cl$, $Br$ and $I$. In another embodiment of Formula (I), $R^8$, at each occurrence, is independently $C_1$-$C_6$ alkyl; wherein each $R^8$ $C_1$-$C_6$ alkyl is optionally substituted with one or more $C(O)OH$.

In one embodiment of Formula (I), $R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2$ $R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $(O)$, $OH$, $CN$, $NO_2$, $F$, $Cl$, $Br$ and $I$. In another embodiment of Formula (I), $R^9$, at each occurrence, is independently selected from the group consisting of aryl, heteroaryl, heterocycloalkyl, and cycloalkyl; wherein each $R^9$ aryl, heteroaryl, and heterocycloalkyl is optionally substituted with one or more substituents independently selected from the group consisting of $R^{12}$, $OR^{12}$, $SO_2R^{12}$, $C(O)R^{12}$, $CO(O)R^{12}$, $C(O)NH_2$, $SO_2NH_2$, $OH$, $CN$, $F$, and $Cl$.

In one embodiment of Formula (I), $R^{11}$, at each occurrence, is independently selected from the group consisting of $C_1$-$C_6$ alkyl, $C_2$-$C_6$ alkenyl, and $C_2$-$C_6$ alkynyl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, $OH$, $CN$, $NO_2$, $F$, $Cl$, $Br$ and $I$. In another embodiment of Formula (I), $R^{11}$, at each occurrence, is $C_1$-$C_6$ alkyl; wherein each $R^{11}$ $C_1$-$C_6$ alkyl is optionally substituted with one or more $OH$.

In one embodiment of Formula (I), $R^{12}$, at each occurrence, is independently selected from the group consisting of $C_1$-$C_6$ alkyl, $C_2$-$C_6$ alkenyl, and $C_2$-$C_6$ alkynyl; wherein each $R^{12}$ $C_1$-$C_6$ alkyl, $C_2$-$C_6$ alkenyl, and $C_2$-$C_6$ alkynyl is optionally substituted with one or more substituents independently selected from the group consisting of $NH_2$, $NHR^{13}$, $N(R^{13})_2$, $C(O)H$, $C(O)OH$, $OH$, $CN$, $NO_2$, $F$, $Cl$, $Br$ and $I$. In another embodiment of Formula (I), $R^{12}$, at each occurrence, is $C_1$-$C_6$ alkyl; wherein each $R^{12}$ $C_1$-$C_6$ alkyl is optionally substituted with one or more substituents independently selected from the group consisting of $N(R^{13})_2$, and $C(O)OH$.

In one embodiment of Formula (I), $R^{13}$, at each occurrence, is independently selected from the group consisting of $C_1$-$C_6$ alkyl, $C_2$-$C_6$ alkenyl, and $C_2$-$C_6$ alkynyl. In another embodiment of Formula (I), $R^{13}$, at each occurrence, is $C_1$-$C_6$ alkyl.

In one embodiment of Formula (I), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and $OH$; $R^2$ is selected from the group consisting of hydrogen, $C_1$-$C_4$ alkyl, and $CN$; $R^3$ is selected from the group consisting of phenyl, and pyridinyl; wherein the $R^3$ phenyl, and pyridinyl are optionally substituted with one or more substituents independently selected from the group consisting of $R^6$, $OR^6$, $NH_2$, $NHR^6$, $N(R^6)_2$, $NHC(O)R^6$, $NHS(O)_2$ $R^6$, $CN$, $F$, and $Cl$; $R^4$ is selected from the group consisting of hydrogen, $CN$, $F$, and $Cl$; $R^5$, at each occurrence, is independently selected from the group consisting of $C_1$-$C_8$ alkyl, heteroaryl, heterocycloalkyl, and cycloalkyl; wherein each $R^5$ $C_1$-$C_8$ alkyl, is optionally substituted with one or more substituents independently selected from the group consisting of $R^7$, $OR^7$, $C(O)R^7$, $CO(O)R^7$, $NH_2$, $NHR^7$, $NHC(O)OR^7$, $C(O)NH_2$, $C(O)NHR^7$, $C(O)N(R^7)_2$, $SO_2NHR^7$, $C(O)OH$, $OH$, and $CN$; wherein each $R^5$ cycloalkyl, heteroaryl, and heterocycloalkyl is optionally substituted with one or more substituents independently selected from the group consisting of $R^8$, $CO(O)R^8$, $C(O)OH$, and $OH$; $R^6$, at each occurrence, is independently selected from the group consisting of $C_1$-$C_6$ alkyl, aryl, heteroaryl, heterocycloalkyl, and cycloalkyl; wherein each $R^6$ $C_1$-$C_6$ alkyl is optionally substituted with one or more substituents independently selected from the group consisting of $R^9$, $SR^9$, and $OH$; wherein each $R^6$ heteroaryl is optionally substituted with one or more substituents independently selected from the group consisting of $NH_2$, and $Cl$; $R^7$, at each occurrence, is independently selected from the group consisting of $C_1$-$C_6$ alkyl, aryl, heteroaryl, heterocycloalkyl, and cycloalkyl; wherein each $R^7$ $C_1$-$C_6$ alkyl is optionally substituted with one or more substituents independently selected from the group consisting of aryl and OH; wherein each $R^7$ aryl, cycloalkyl, and heterocycloalkyl is optionally substituted with one or more substituents independently selected from the group consisting of $R^{11}$, $CO(O)R^{11}$, $NHC(O)R^{11}$, $C(O)NH_2$, $C(O)OH$, and OH; $R^8$, at each occurrence, is independently $C_1$-$C_6$ alkyl; wherein each $R^8$ $C_1$-$C_6$ alkyl is optionally substituted with one or more $C(O)OH$; $R^9$, at each occurrence, is independently selected from the group consisting of aryl, heteroaryl, heterocycloalkyl, and cycloalkyl; wherein each $R^9$ aryl, cycloalkyl, heteroaryl, and heterocycloalkyl is optionally substituted with one or more substituents independently selected from the group consisting of $R^{12}$, $OR^{12}$, $SO_2R^{12}$, $C(O)R^{12}$, $CO(O)R^{12}$, $C(O)NH_2$, $SO_2NH_2$, OH, CN, F, and Cl; $R^{11}$, at each occurrence, is independently selected from the group consisting of $C_1$-$C_6$ alkyl; wherein each $R^{11}$ $C_1$-$C_6$ alkyl is optionally substituted with one or more OH; $R^{12}$, at each occurrence, is independently $C_1$-$C_6$ alkyl; wherein each $R^{12}$ $C_1$-$C_6$ alkyl is optionally substituted with one or more substituents independently selected from the group consisting of $N(R^{13})_2$, and $C(O)OH$; and $R^{13}$, at each occurrence, is $C_1$-$C_6$ alkyl.

Still another embodiment pertains to compounds of Formula (I), selected from the group consisting of: Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, and pharmaceutically acceptable salts thereof.

Embodiments of Formula (III)

In another aspect, the present invention relates to compounds of Formula (III) or a pharmaceutically acceptable salt thereof,

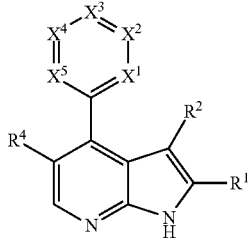

Formula (III)

wherein
one of $X^1$, $X^2$, $X^3$, $X^4$, and $X^5$ is N; and the remaining are C—$R^{3A}$; or
two of $X^1$, $X^2$, $X^3$, $X^4$, and $X^5$ are N; and the remaining are C—$R^{3A}$;
$R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $C(O)H$, $C(O)OH$, (O), OH, CN, $NO_2$, F, Cl, Br and I;
$R^2$ is selected from the group consisting of hydrogen, $C_1$-$C_4$ alkyl, $NO_2$, CN, $C(O)NH_2$, and $C(O)OR^{2A}$;
$R^{2A}$ is selected from the group consisting of alkyl, alkenyl, and alkynyl;
$R^{3A}$, at each occurrence, is each independently selected from the group consisting of H, $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, (O), OH, CN, $NO_2$, F, Cl, Br and I;
$R^4$ is selected from the group consisting of hydrogen, $R^{4A}$, $OR^{4A}$, $C(O)NH_2$, CN, F, Cl, Br, and I;
$R^{4A}$ is selected from the group consisting of haloalkyl, alkyl, alkenyl, and alkynyl;
$R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, OH, CN, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)$ $N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, (O), OH, CN, $NO_2$, F, Cl, Br and I;

$R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, CN, $NO_2$, F, Cl, Br and I; wherein each $R^6$ aryl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, (O), OH, CN, $NO_2$, F, Cl, Br and I;

$R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, cycloalkyl, cycloalkenyl, heterocycyloalkyl, heterocycloalkenyl, $NH_2$, $NHR^{13}$, $N(R^{13})_2$, $C(O)H$, $C(O)OH$, OH, CN, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, (O), OH, CN, $NO_2$, F, Cl, Br and I;

$R^8$, at each occurrence, is independently selected from the group consisting of $C_1$-$C_6$ alkyl, $C_2$-$C_6$ alkenyl, and $C_2$-$C_6$ alkynyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, OH, CN, $NO_2$, F, Cl, Br and I;

$R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, (O), OH, CN, $NO_2$, F, Cl, Br and I;

$R^{10}$, at each occurrence, is independently selected from the group consisting of $C_1$-$C_6$ alkyl, $C_2$-$C_6$ alkenyl, and $C_2$-$C_6$ alkynyl; wherein each $R^{10}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, OH, CN, $NO_2$, F, Cl, Br and I;

$R^{11}$, at each occurrence, is independently selected from the group consisting of $C_1$-$C_6$ alkyl, $C_2$-$C_6$ alkenyl, and $C_2$-$C_6$ alkynyl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, OH, CN, $NO_2$, F, Cl, Br and I;

$R^{12}$, at each occurrence, is independently selected from the group consisting of $C_1$-$C_6$ alkyl, $C_2$-$C_6$ alkenyl, and $C_2$-$C_6$ alkynyl; wherein each $R^{12}$ $C_1$-$C_6$ alkyl, $C_2$-$C_6$ alkenyl, and $C_2$-$C_6$ alkynyl is optionally substituted with one or more substituents independently selected from the group consisting of $NH_2$, $NHR^{13}$, $N(R^{13})_2$, $C(O)H$, $C(O)OH$, OH, CN, $NO_2$, F, Cl, Br and I; and $R^{13}$, at each occurrence, is independently selected from the group consisting of $C_1$-$C_6$ alkyl, $C_2$-$C_6$ alkenyl, and $C_2$-$C_6$ alkynyl.

In one embodiment of Formula (III), $R^2$ is selected from the group consisting of hydrogen, $C_1$-$C_4$ alkyl, $NO_2$, CN, $C(O)NH_2$, and $C(O)OR^{2A}$; and $R^{2A}$ is selected from the group consisting of alkyl, alkenyl, and alkynyl. In another embodiment of Formula (III), $R^2$ is selected from the group consisting of hydrogen, $C_1$-$C_4$ alkyl, $NO_2$, CN, $C(O)NH_2$, and $C(O)OR^{2A}$; and $R^{2A}$ is alkyl. In another embodiment of Formula (III), $R^2$ is selected from the group consisting of hydrogen, $C_1$-$C_4$ alkyl, and CN. In another embodiment of Formula (III), $R^2$ is selected from the group consisting of hydrogen, $CH_3$, and CN. In another embodiment of Formula (III), $R^2$ is hydrogen. In another embodiment of Formula (III), $R^2$ is $CH_3$. In another embodiment of Formula (III), $R^2$ is CN.

In one embodiment of Formula (III), $R^4$ is selected from the group consisting of hydrogen, $R^{4A}$, $OR^{4A}$, $C(O)NH_2$, CN, F, Cl, Br, and I; and $R^{4A}$ is selected from the group consisting of haloalkyl, alkyl, alkenyl, and alkynyl. In another embodiment of Formula (III), $R^4$ is selected from the group consisting of hydrogen, $R^{4A}$, $OR^{4A}$, $C(O)NH_2$, CN, F, and Cl; and $R^{4A}$ is selected from the group consisting of haloalkyl and alkyl. In another embodiment of Formula (III), $R^4$ is selected from the group consisting of hydrogen, CN, F, and Cl. In another embodiment of Formula (III), $R^4$ is hydrogen. In another embodiment of Formula (III), $R^4$ is CN. In another embodiment of Formula (III), $R^4$ is F. In another embodiment of Formula (III), $R^4$ is Cl.

In one embodiment of Formula (III), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)$ $R^5$, $SO_2NR^5C(O)R^5$, $NHS(O)_2R^5$, $NR^5S(O)_2R^5$, $NHC(O)$ $OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $C(O)H$, $C(O)OH$, (O), OH, CN, $NO_2$, F, Cl, Br and I. In another embodiment of Formula (III), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH. In another embodiment of Formula (III), $R^1$ is cycloalkyl; wherein the $R^1$ cycloalkyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH. In another embodiment of Formula (III), $R^1$ is cycloalkenyl; wherein the $R^1$ cycloalkenyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH. In another embodiment of Formula (III), $R^1$ is heterocycloalkyl; wherein the $R^1$ heterocycloalkyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH. In another embodiment of Formula (III), $R^1$ is heterocycloalkenyl; wherein the $R^1$ heterocycloalkenyl is optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH. In another embodiment of Formula (III), $R^1$ is selected from the group consisting of azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl wherein the $R^1$ azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)$ $NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $C(O)H$, $C(O)OH$, (O), OH, CN, $NO_2$, F, Cl, Br and I. In another embodiment of Formula (III), $R^1$ is selected from the group consisting of azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl wherein the $R^1$ azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH. In another embodiment of Formula (III), $R^1$ is selected from the group consisting of azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl wherein the $R^1$ azetidinyl, pyrrolidinyl, morpholinyl, tetrahydro-2H-pyranyl, piperidinyl, 1,2,3,6-tetrahydropyridinyl, cyclohexyl, cyclohexenyl, azepanyl, 8-azabicyclo[3.2.1]oct-2-enyl, and 1,2,3,3a,4,6a-hexahydrocyclopenta[c]pyrrolyl are unsubstituted.

In one embodiment of Formula (III), $X^1$ is N; and $X^2$, $X^3$, $X^4$, and $X^5$ are C—$R^{3A}$. In another embodiment of Formula (III), $X^2$ is N; and $X^1$, $X^3$, $X^4$, and $X^5$ are C—$R^{3A}$. In another embodiment of Formula (III), $X^3$ is N; and $X^1$, $X^2$, $X^4$, and $X^5$ are C—$R^{3A}$. In another embodiment of Formula (III), $X^1$ is N; $X^2$ is C—$NHR^6$, $X^3$ and $X^4$ are C—H, and $X^5$ is C—Cl. In another embodiment of Formula (III), $X^1$ is N; $X^2$ is C—$NHR^6$, $X^3$ and $X^4$ are C—H, and $X^5$ is C—F.

In one embodiment of Formula (III), $R^{3A}$, at each occurrence, is independently selected from the group consisting of H, $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, (O), OH, CN, $NO_2$, F, Cl, Br and I. In another embodiment of Formula (III), $R^{3A}$, at each occurrence, is independently selected from the group consisting of H, $R^6$, $OR^6$, $NH_2$, $NHR^6$, $N(R^6)_2$, $NHC(O)R^6$, $NHS(O)_2R^6$, CN, F, Cl, Br and I. In another embodiment of Formula (III), $R^{3A}$, at each occurrence, is independently selected from the group consisting of H, $R^6$, $OR^6$, $NH_2$, $NHR^6$, $N(R^6)_2$, $NHC(O)R^6$, $NHS(O)_2R^6$, CN, F, and Cl. In another embodiment of Formula (III), $R^{3A}$, at each occurrence, is independently selected from the group consisting of H, $R^6$, $OR^6$, $NH_2$, $NHR^6$, $N(R^6)_2$, $NHC(O)R^6$, F, and Cl.

In one embodiment of Formula (III), $R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N$ ($R^7$)$_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, OH, CN, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, (O), OH, CN, $NO_2$, F, Cl, Br and I. In another embodiment of Formula (III), $R^5$, at each occurrence, is independently selected from the group consisting of $C_1$-$C_8$ alkyl, heteroaryl, heterocycloalkyl, and cycloalkyl; wherein each $R^5$ $C_1$-$C_8$ alkyl is optionally substituted with one or more substituents independently selected from the group consisting of $R^7$, $OR^7$, $C(O)R^7$, $CO(O)R^7$, $NH_2$, $NHR^7$, $NHC(O)OR^7$, $C(O)NH_2$, $C(O)NHR^7$, $C(O)N(R^7)_2$, $SO_2NHR^7$, $C(O)OH$, OH, and CN; wherein each $R^5$ cycloalkyl, heteroaryl, and heterocycloalkyl is optionally substituted with one or more substituents independently selected from the group consisting of $R^8$, $CO(O)R^8$, $C(O)OH$, and OH.

In one embodiment of Formula (III), $R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, CN, $NO_2$, F, Cl, Br and I; wherein each $R^6$ aryl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2 R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, (O), OH, CN, $NO_2$, F, Cl, Br and I. In another embodiment of Formula (III), $R^6$, at each occurrence, is independently selected from the group consisting of $C_1$-$C_6$ alkyl, aryl, heteroaryl, heterocycloalkenyl, and cycloalkyl; wherein each $R^6$ $C_1$-$C_6$ alkyl is optionally substituted with one or more substituents independently selected from the group consisting of $R^9$, $SR^9$, and OH; wherein each $R^6$ heteroaryl is optionally substituted with one or more substituents independently selected from the group consisting of $NH_2$, F, Cl, Br and I. In another embodiment of Formula (III), $R^6$, at each occurrence, is independently selected from the group consisting of $C_1$-$C_6$ alkyl, aryl, heteroaryl, heterocycloalkenyl, and cycloalkyl; wherein each $R^6$ $C_1$-$C_6$ alkyl is optionally substituted with one or more substituents independently selected from the group consisting of $R^9$, $SR^9$, and OH; wherein each $R^6$ heteroaryl is optionally substituted with one or more substituents independently selected from the group consisting of $NH_2$ and Cl.

In one embodiment of Formula (III), $R^8$, at each occurrence, is independently selected from the group consisting of $C_1$-$C_6$ alkyl, $C_2$-$C_6$ alkenyl, and $C_2$-$C_6$ alkynyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, OH, CN, $NO_2$, F, Cl, Br and I. In another embodiment of Formula (III), $R^8$, at each occurrence, is independently $C_1$-$C_6$ alkyl; wherein each $R^8$ $C_1$-$C_6$ alkyl is optionally substituted with one or more $C(O)OH$.

In one embodiment of Formula (III), $R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, (O), OH, CN, $NO_2$, F, Cl, Br and I. In another embodiment of Formula (III), $R^9$, at each occurrence, is independently selected from the group consisting of aryl, heteroaryl, heterocycloalkyl, and cycloalkyl; wherein each $R^9$ aryl, heteroaryl, and heterocycloalkyl is optionally substituted with one or more substituents independently selected from the group consisting of $R^{12}$, $OR^{12}$, $SO_2R^{12}$, $C(O)R^{12}$, $CO(O)R^{12}$, $C(O)NH_2$, $SO_2NH_2$, OH, CN, F, and Cl.

In one embodiment of Formula (III), $R^{11}$, at each occurrence, is independently selected from the group consisting of $C_1$-$C_6$ alkyl, $C_2$-$C_6$ alkenyl, and $C_2$-$C_6$ alkynyl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, OH, CN, $NO_2$, F, Cl, Br and I. In another embodiment of Formula (III), $R^{11}$, at each occurrence, is $C_1$-$C_6$ alkyl; wherein each $R^{11}$ $C_1$-$C_6$ alkyl is optionally substituted with one or more OH.

In one embodiment of Formula (III), $R^{12}$, at each occurrence, is independently selected from the group consisting of $C_1$-$C_6$ alkyl, $C_2$-$C_6$ alkenyl, and $C_2$-$C_6$ alkynyl; wherein each $R^{12}$ $C_1$-$C_6$ alkyl, $C_2$-$C_6$ alkenyl, and $C_2$-$C_6$ alkynyl is optionally substituted with one or more substituents independently selected from the group consisting of $NH_2$, $NHR^{13}$, $N(R^{13})_2$, $C(O)H$, $C(O)OH$, OH, CN, $NO_2$, F, Cl, Br and I. In another embodiment of Formula (III), $R^{12}$, at each occurrence, is $C_1$-$C_6$ alkyl; wherein each $R^{12}$ $C_1$-$C_6$ alkyl is optionally substituted with one or more substituents independently selected from the group consisting of $N(R^{13})_2$, and $C(O)OH$.

In one embodiment of Formula (III), $R^{13}$, at each occurrence, is independently selected from the group consisting of $C_1$-$C_6$ alkyl, $C_2$-$C_6$ alkenyl, and $C_2$-$C_6$ alkynyl. In another embodiment of Formula (III), $R^{13}$, at each occurrence, is $C_1$-$C_6$ alkyl.

In one embodiment of Formula (III), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $SO_2R^5$, $C(O)R^5$, $CO(O)R^5$, $NH_2$, $NHR^5$, $SO_2NHC(O)OR^5$, $NHSO_2NHC(O)OR^5$, $C(O)NHR^5$, $SO_2NH_2$, $C(O)NHCN$, $S(O)(N)R^5$, $C(O)OH$, and OH; $R^2$ is selected from the group consisting of hydrogen, $C_1$-$C_4$ alkyl, and CN; one of $X^1$, $X^2$, $X^3$, $X^4$, and $X^5$ is N; and the remaining are C—$R^{3A}$; $R^{3A}$, at each occurrence, is independently selected from the group consisting of H, $R^6$, $OR^6$, $NH_2$, $NHR^6$, $N(R^6)_2$, $NHC(O)R^6$, $NHS(O)_2R^6$, F, and Cl; $R^4$ is selected from the group consisting of hydrogen, CN, F, and Cl; $R^5$, at each occurrence, is independently selected from the group consisting of $C_1$-$C_8$ alkyl, heteroaryl, heterocycloalkyl, and cycloalkyl; wherein each $R^5$ $C_1$-$C_8$ alkyl, is optionally substituted with one or more substituents independently selected from the group consisting of $R^7$, $OR^7$, $C(O)R^7$, $CO(O)R^7$, $NH_2$, $NHR^7$, $NHC(O)R^7$, $C(O)NH_2$, $C(O)NHR^7$, $C(O)N(R^7)_2$, $SO_2NHR^7$, $C(O)OH$, OH, and CN; wherein each $R^5$ cycloalkyl, heteroaryl, and heterocycloalkyl is optionally substituted with one or more substituents independently selected from the group consisting of $R^8$, $CO(O)R^8$, $C(O)OH$, and OH; $R^6$, at each occurrence, is independently selected from the group consisting of $C_1$-$C_6$ alkyl, aryl, heteroaryl, heterocycloalkenyl, and cycloalkyl; wherein each $R^6$ $C_1$-$C_6$ alkyl is optionally substituted with one or more substituents independently selected from the group consisting of $R^9$, $SR^9$, and OH; wherein each $R^6$ heteroaryl is optionally substituted with one or more substituents independently selected from the group consisting of $NH_2$, and Cl; $R^7$, at each occurrence, is independently selected from the group consisting of $C_1$-$C_6$ alkyl, aryl, heteroaryl, heterocycloalkyl, and cycloalkyl; wherein each $R^7$ $C_1$-$C_6$ alkyl is optionally substituted with one or more substituents independently selected from the group consisting of aryl and OH; wherein each $R^7$ aryl, cycloalkyl, and heterocycloalkyl is optionally substituted with one or more substituents independently selected from the group consisting of $R^{11}$, $CO(O)R^{11}$, $NHC(O)R^{11}$, $C(O)NH_2$, $C(O)OH$, and OH; $R^8$, at each occurrence, is independently $C_1$-$C_6$ alkyl; wherein each $R^8$ $C_1$-$C_6$ alkyl is optionally substituted with one or more $C(O)OH$; $R^9$, at each occurrence, is independently selected from the group consisting of aryl, heteroaryl, heterocycloalkyl, and cycloalkyl; wherein each $R^9$ aryl, cycloalkyl, heteroaryl, and heterocycloalkyl is optionally substituted with one or more substituents independently selected from the group consisting of $R^{12}$, $OR^{12}$, $SO_2R^{12}$, $C(O)R^{12}$, $CO(O)R^{12}$, $C(O)NH_2$, $SO_2NH_2$, OH, CN, F, and Cl; $R^{11}$, at each occurrence, is independently selected from the group consisting of $C_1$-$C_6$ alkyl; wherein each $R^{11}$ $C_1$-$C_6$ alkyl is optionally substituted with one or more OH; $R^{12}$, at each occurrence, is independently $C_1$-$C_6$ alkyl; wherein each $R^{12}$ $C_1$-$C_6$ alkyl is optionally substituted with one or more substituents independently selected from the group consisting of $N(R^{13})_2$, and $C(O)OH$; and $R^{13}$, at each occurrence, is $C_1$-$C_6$ alkyl.

Still another embodiment pertains to compounds of Formula (III), selected from the group consisting of: Examples 5, 11, 12, 13, 14, 15, 16, 20, 21, 26, 31, 32, 33, 34, 35, 36, 37, 38, 39, 40, 41, 42, 43, 44, 45, 46, 47, 48, 49, 52, 54, 55, 56, 57, 58, 64, 65, 70, 77, 79, 80, 81, 82, 83, 84, 86, 88, 89, 90, 91, 92, 93, 95, 96, 97, 102, 104, 105, 106, 107, 132, 133, 134, 138, 139, 140, 141, 142, 143, 144, 150, 151, 152, 153, 154, 155, 156, 157, 158, 159, 160, 161, 162, 163, 164, 165, 173, 174, 175, 176, 177, 178, 188, 192, 194, 196, 197, 198, 200, 202, 203, 204, 205, 207, 208, 209, 210, 211, 212, 213, or a pharmaceutically acceptable salt thereof.

In another aspect, the present invention relates to compounds of Formula (IIIa) or a pharmaceutically acceptable salt thereof,

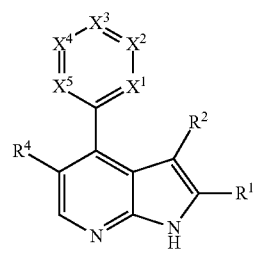

Formula (IIIa)

wherein
one of $X^1$, $X^2$, $X^3$, $X^4$, and $X^5$ is N; and the remaining are $CR^{3A}$; or
two of $X^1$, $X^2$, $X^3$, $X^4$, and $X^5$ are N; and the remaining are $CR^{3A}$;
$R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $S(O)(N)R^5SO_2R^5$, $C(O)H$, $C(O)OH$, (O), OH, CN, $NO_2$, F, Cl, Br and I;
$R^2$ is selected from the group consisting of hydrogen, $C_1$-$C_4$ alkyl, $NO_2$, CN, $C(O)NH_2$, $C(O)OR^{2A}$, F, Cl, Br, and I;
$R^{2A}$ is selected from the group consisting of $C_1$-$C_6$ alkyl, $C_2$-$C_6$ alkenyl, and $C_2$-$C_6$ alkynyl;
$R^{3A}$, at each occurrence, is each independently selected from the group consisting of H, $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, (O), OH, CN, $NO_2$, F, Cl, Br and I;
$R^4$ is selected from the group consisting of $R^{4A}$, $OR^{4A}$, $C(O)NH_2$, CN, F, Cl, Br, and I;
$R^{4A}$ is selected from the group consisting of hydrogen, $C_1$-$C_6$ alkyl, $C_2$-$C_6$ alkenyl, and $C_2$-$C_6$ alkynyl;
$R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each R⁵ C₁-C₈ alkyl, C₂-C₆ alkenyl, and C₂-C₆ alkynyl is optionally substituted with one or more substituents independently selected from the group consisting of R⁷, OR⁷, SR⁷, S(O)R⁷, SO₂R⁷, C(O)R⁷, CO(O)R⁷, OC(O)R⁷, OC(O)OR⁷, NH₂, NHR⁷, N(R⁷)₂, NHC(O)R⁷, NR⁷C(O)R⁷, NHS(O)₂R⁷, NR⁷S(O)₂R⁷, NHC(O)OR⁷, NR⁷C(O)OR⁷, NHC(O)NH₂, NHC(O)NHR⁷, NHC(O)N(R⁷)₂, NR⁷C(O)NHR⁷, NR⁷C(O)N(R⁷)₂, C(O)NH₂, C(O)NHR⁷, C(O)N(R⁷)₂, C(O)NHOH, C(O)NHOR⁷, C(O)NHSO₂R⁷, C(O)NR⁷SO₂R⁷, SO₂NH₂, SO₂NHR⁷, SO₂N(R⁷)₂, B(OH)₂, C(O)H, C(O)OH, OH, CN, NO₂, F, Cl, Br and I; wherein each R⁵ aryl, cycloalkyl, cycloalkenyl, heteroaryl, heterocycloalkyl, and heterocycloalkenyl is optionally substituted with one or more substituents independently selected from the group consisting of R⁸, OR⁸, SR⁸, S(O)R⁸, SO₂R⁸, C(O)R⁸, CO(O)R⁸, OC(O)R⁸, OC(O)OR⁸, NH₂, NHR⁸, N(R⁸)₂, NHC(O)R⁸, NR⁸C(O)R⁸, NHS(O)₂R⁸, NR⁸S(O)₂R⁸, NHC(O)OR⁸, NR⁸C(O)OR⁸, NHC(O)NH₂, NHC(O)NHR⁸, NHC(O)N(R⁸)₂, NR⁸C(O)NHR⁸, NR⁸C(O)N(R⁸)₂, C(O)NH₂, C(O)NHR⁸, C(O)N(R⁸)₂, C(O)NHOH, C(O)NHOR⁸, C(O)NHSO₂R⁸, C(O)NR⁸SO₂R⁸, SO₂NH₂, SO₂NHR⁸, SO₂N(R⁸)₂, C(O)H, C(O)OH, (O), OH, CN, NO₂, F, Cl, Br and I;

R⁶, at each occurrence, is independently selected from the group consisting of C₁-C₆ alkyl, C₂-C₆ alkenyl, C₂-C₆ alkynyl, phenyl, heteroaryl, heterocycloalkyl, heterocycloalkenyl, cycloalkyl, and cycloalkenyl; wherein each R⁶ C₁-C₆ alkyl, C₂-C₆ alkenyl, and C₂-C₆ alkynyl is optionally substituted with one or more substituents independently selected from the group consisting of R⁹, OR⁹, SR⁹, S(O)R⁹, SO₂R⁹, C(O)R⁹, CO(O)R⁹, OC(O)R⁹, OC(O)OR⁹, NH₂, NHR⁹, N(R⁹)₂, NHC(O)R⁹, NR⁹C(O)R⁹, NHS(O)₂R⁹, NR⁹S(O)₂R⁹, NHC(O)OR⁹, NR⁹C(O)OR⁹, NHC(O)NH₂, NHC(O)NHR⁹, NHC(O)N(R⁹)₂, NR⁹C(O)NHR⁹, NR⁹C(O)N(R⁹)₂, C(O)NH₂, C(O)NHR⁹, C(O)N(R⁹)₂, C(O)NHOH, C(O)NHOR⁹, C(O)NHSO₂R⁹, C(O)NR⁹SO₂R⁹, SO₂NH₂, SO₂NHR⁹, SO₂N(R⁹)₂, C(O)H, C(O)OH, OH, CN, NO₂, F, Cl, Br and I; wherein each R⁶ phenyl, cycloalkyl, cycloalkenyl, heteroaryl, heterocycloalkyl, and heterocycloalkenyl is optionally substituted with one or more substituents independently selected from the group consisting of R¹⁰, OR¹⁰, SR¹⁰, S(O)R¹⁰, SO₂R¹⁰, C(O)R¹⁰, CO(O)R¹⁰, OC(O)R¹⁰, OC(O)OR¹⁰, NH₂, NHR¹⁰, N(R¹⁰)₂, NHC(O)R¹⁰, NR¹⁰C(O)R¹⁰, NHS(O)₂R¹⁰, NR¹⁰S(O)₂R¹⁰, NHC(O)OR¹⁰, NR¹⁰C(O)OR¹⁰, NHC(O)NH₂, NHC(O)NHR¹⁰, NHC(O)N(R¹⁰)₂, NR¹⁰C(O)NHR¹⁰, NR¹⁰C(O)N(R¹⁰)₂, C(O)NH₂, C(O)NHR¹⁰, C(O)N(R¹⁰)₂, C(O)NHOH, C(O)NHOR¹⁰, C(O)NHSO₂R¹⁰, C(O)NR¹⁰SO₂R¹⁰, SO₂NH₂, SO₂NHR¹⁰, SO₂N(R¹⁰)₂, C(O)H, C(O)OH, (O), OH, CN, NO₂, F, Cl, Br and I;

R⁷, at each occurrence, is independently selected from the group consisting of C₁-C₆ alkyl, C₂-C₆ alkenyl, C₂-C₆ alkynyl, aryl, heteroaryl, heterocycloalkyl, heterocycloalkenyl, cycloalkyl, and cycloalkenyl; wherein each R⁷ C₁-C₆ alkyl, C₂-C₆ alkenyl, and C₂-C₆ alkynyl is optionally substituted with one or more substituents independently selected from the group consisting of R¹³, OR¹³, NH₂, NHR¹³, N(R¹³)₂, C(O)H, C(O)OH, OH, CN, NO₂, F, Cl, Br and I; wherein each R⁷ aryl, cycloalkyl, cycloalkenyl, heteroaryl, heterocycloalkyl, and heterocycloalkenyl is optionally substituted with one or more substituents independently selected from the group consisting of R¹¹, OR¹¹, SR¹¹, S(O)R¹¹, SO₂R¹¹, C(O)R¹¹, CO(O)R¹¹, OC(O)R¹¹, OC(O)OR¹¹, NH₂, NHR¹¹, N(R¹¹)₂, NHC(O)R¹¹, NR¹¹C(O)R¹¹, NHS(O)₂R¹¹, NR¹¹S(O)₂R¹¹, NHC(O)OR¹¹, NR¹¹C(O)OR¹¹, NHC(O)NH₂, NHC(O)NHR¹¹, NHC(O)N(R¹¹)₂, NR¹¹C(O)NHR¹¹, NR¹¹C(O)N(R¹¹)₂, C(O)NH₂, C(O)NHR¹¹, C(O)N(R¹¹)₂, C(O)NHOH, C(O)NHOR¹¹, C(O)NHSO₂R¹¹, C(O)NR¹¹SO₂R¹¹, SO₂NH₂, SO₂NHR¹¹, SO₂N(R¹¹)₂, C(O)H, C(O)OH, (O), OH, CN, NO₂, F, Cl, Br and I;

R⁸, at each occurrence, is independently selected from the group consisting of C₁-C₆ alkyl, C₂-C₆ alkenyl, C₂-C₆ alkynyl, and heterocycloalkyl; wherein each R⁸ C₁-C₆ alkyl, C₂-C₆ alkenyl, and C₂-C₆ alkynyl is optionally substituted with one or more substituents independently selected from the group consisting of aryl, heteroaryl, SO₂R⁸ᴬ, C(O)OR⁸ᴬ, C(O)NH₂, C(O)NHR⁸ᴬ, C(O)N(R⁸ᴬ)₂, C(O)NHSO₂R⁸ᴬ, C(O)NR⁸ᴬSO₂R⁸ᴬ, NH₂, C(O)H, C(O)OH, OH, CN, NO₂, F, Cl, Br and I; wherein each R⁸ heterocycloalkyl is optionally substituted with one or more substituents independently selected from the group consisting of NH₂, C(O)H, C(O)OH, OH, CN, NO₂, F, Cl, Br and I;

R⁸ᴬ, at each occurrence, is independently selected from the group consisting of C₁-C₆ alkyl, C₂-C₆ alkenyl, and C₂-C₆ alkynyl;

R⁹, at each occurrence, is independently selected from the group consisting of C₁-C₆ alkyl, C₂-C₆ alkenyl, C₂-C₆ alkynyl, aryl, heteroaryl, heterocycloalkyl, heterocycloalkenyl, cycloalkyl, and cycloalkenyl; wherein each R⁹ aryl, cycloalkyl, cycloalkenyl, heteroaryl, heterocycloalkyl, and heterocycloalkenyl is optionally substituted with one or more substituents independently selected from the group consisting of R¹², OR¹², SR¹², S(O)R¹², SO₂R¹², C(O)R¹², CO(O)R¹², OC(O)R¹², OC(O)OR¹², NH₂, NHR¹², N(R¹²)₂, NHC(O)R¹², NR¹²C(O)R¹², NHS(O)₂R¹², NR¹²S(O)₂R¹², NHC(O)OR¹², NR¹²C(O)OR¹², NHC(O)NH₂, NHC(O)NHR¹², NHC(O)N(R¹²)₂, NR¹²C(O)NHR¹², NR¹²C(O)N(R¹²)₂, C(O)NH₂, C(O)NHR¹², C(O)N(R¹²)₂, C(O)NHOH, C(O)NHOR¹², C(O)NHSO₂R¹², C(O)NR¹²SO₂R¹², SO₂NH₂, SO₂NHR¹², SO₂N(R¹²)₂, C(O)H, C(O)OH, (O), OH, CN, NO₂, F, Cl, Br and I;

R¹⁰, at each occurrence, is independently selected from the group consisting of C₁-C₆ alkyl, C₂-C₆ alkenyl, and C₂-C₆ alkynyl; wherein each R¹⁰ C₁-C₆ alkyl, C₂-C₆ alkenyl, and C₂-C₆ alkynyl is optionally substituted with one or more substituents independently selected from the group consisting of NH₂, C(O)H, C(O)OH, OH, CN, NO₂, F, Cl, Br and I;

R¹¹, at each occurrence, is independently selected from the group consisting of C₁-C₆ alkyl, C₂-C₆ alkenyl, C₂-C₆ alkynyl, aryl, and heteroaryl; wherein each R¹¹ C₁-C₆ alkyl, C₂-C₆ alkenyl, and C₂-C₆ alkynyl is optionally substituted with one or more substituents independently selected from the group consisting of OR¹¹ᴬ, NH₂, NHR¹¹ᴬ, N(R¹¹ᴬ)₂, C(O)H, C(O)OH, OH, CN, NO₂, F, Cl, Br and I; wherein each R¹¹ aryl and heteroaryl is optionally substituted with one or more substituents independently selected from the group consisting of C₁-C₆ alkyl, C₁-C₆ haloalkyl, NH₂, C(O)H, C(O)OH, OH, CN, NO₂, F, Cl, Br and I;

R¹¹ᴬ, at each occurrence, is independently selected from the group consisting of C₁-C₆ alkyl, C₂-C₆ alkenyl, and C₂-C₆ alkynyl;

R¹², at each occurrence, is independently selected from the group consisting of C₁-C₆ alkyl, C₂-C₆ alkenyl, and C₂-C₆ alkynyl; wherein each R¹² C₁-C₆ alkyl, C₂-C₆ alkenyl, and C₂-C₆ alkynyl is optionally substituted with one or more substituents independently selected from the group consisting of $NH_2$, $NHR^{14}$, $N(R^{14})_2$, C(O)H, C(O)OH, OH, CN, $NO_2$, F, Cl, Br and I;

$R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, cycloalkyl, cycloalkenyl, and heterocycloalkyl, heterocycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of $R^{15}$, $OR^{15}$, C(O)H, C(O)OH, OH, CN, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $R^{16}$, $OR^{16}$, C(O)H, C(O)OH, (O), OH, CN, $NO_2$, F, Cl, Br and I;

$R^{14}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl;

$R^{15}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl; wherein each $R^{15}$ $C_1$-$C_6$ alkyl, $C_2$-$C_6$ alkenyl, and $C_2$-$C_6$ alkynyl is optionally substituted with one or more $OCH_3$; and $R^{16}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl.

In one embodiment of Formula (IIIa), $R^2$ is selected from the group consisting of hydrogen, $C_1$-$C_4$ alkyl, $NO_2$, CN, $C(O)NH_2$, $C(O)OR^{2A}$, F, Cl, Br, and I; and $R^{2A}$ is selected from the group consisting of $C_1$-$C_6$ alkyl, $C_2$-$C_6$ alkenyl, and $C_2$-$C_6$ alkynyl. In another embodiment of Formula (IIIa), $R^2$ is selected from the group consisting of hydrogen, F, Cl, Br, and I. In another embodiment of Formula (IIIa), $R^2$ is hydrogen.

In one embodiment of Formula (IIIa), $R^4$ is selected from the group consisting of $R^{4A}$, $OR^{4A}$, $C(O)NH_2$, CN, F, Cl, Br, and I; and $R^{4A}$ is selected from the group consisting of hydrogen, $C_1$-$C_6$ alkyl, $C_2$-$C_6$ alkenyl, and $C_2$-$C_6$ alkynyl. In another embodiment of Formula (IIIa), $R^4$ is selected from the group consisting of $R^{4A}$, F, Cl, Br, and I; and $R^{4A}$ is hydrogen. In another embodiment of Formula (IIIa), $R^4$ is $R^{4A}$; and $R^{4A}$ is hydrogen. In another embodiment of Formula (IIIa), $R^4$ is selected from the group consisting of F, Cl, Br, and I. In another embodiment of Formula (IIIa), $R^4$ is Cl.

In one embodiment of Formula (IIIa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, C(O)NHOH, $C(O)NHOR^5$, $C(O)NHSO_2R^5$, C(O) $NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, C(O)NHCN, $C(O)NR^5CN$, $S(O)(N)R^5$, $S(O)(N)R^5SO_2R^5$, C(O)H, C(O)OH, (O), OH, CN, $NO_2$, F, Cl, Br and I. In another embodiment of Formula (IIIa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $SO_2R^5$, $C(O)R^5$, $CO(O)R^5$, $NH_2$, $SO_2NHC(O)$ $OR^5$, $C(O)NH_2$, $C(O)NHR^5$, and C(O)OH. In another embodiment of Formula (IIIa), $R^1$ is cycloalkyl; wherein the $R^1$ cycloalkyl is optionally substituted with one or more substituents independently selected from the group consisting of $R^5$, $SO_2R^5$, $C(O)R^5$, $CO(O)R^5$, $NH_2$, $SO_2NHC(O)OR^5$, C(O) $NH_2$, $C(O)NHR^5$, and C(O)OH. In another embodiment of Formula (IIIa), $R^1$ is cycloalkenyl; wherein the $R^1$ cycloalkenyl is optionally substituted with one or more substituents independently selected from the group consisting of $R^5$, $SO_2R^5$, $C(O)R^5$, $CO(O)R^5$, $NH_2$, $SO_2NHC(O)OR^5$, C(O) $NH_2$, $C(O)NHR^5$, and C(O)OH. In another embodiment of Formula (IIIa), $R^1$ is heterocycloalkyl; wherein the $R^1$ heterocycloalkyl is optionally substituted with one or more substituents independently selected from the group consisting of $R^5$, $SO_2R^5$, $C(O)R^5$, $CO(O)R^5$, $NH_2$, $SO_2NHC(O)OR^5$, C(O) $NH_2$, $C(O)NHR^5$, and C(O)OH. In another embodiment of Formula (IIIa), $R^1$ heterocycloalkenyl; wherein the $R^1$ heterocycloalkenyl is optionally substituted with one or more substituents independently selected from the group consisting of $R^5$, $SO_2R^5$, $C(O)R^5$, $CO(O)R^5$, $NH_2$, $SO_2NHC(O)OR^5$, C(O) $NH_2$, $C(O)NHR^5$, and C(O)OH. In another embodiment of Formula (IIIa), $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, NHC $(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, OC(O) $NR^5SO_2R^5$, $C(O)NH_2$, $C(O)NHR^5$, $C(O)N(R^5)_2$, C(O) NHOH, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, C(O)NHCN, $C(O)NR^5CN$, $S(O)(N)R^5$, $S(O)(N)R^5SO_2R^5$, C(O)H, C(O)OH, (O), OH, CN, $NO_2$, F, Cl, Br and I. In another embodiment of Formula (IIIa), $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are optionally substituted with one or more substituents independently selected from the group consisting of $R^5$, $SO_2R^5$, $C(O)R^5$, $CO(O)R^5$, $NH_2$, $SO_2NHC(O)$ $OR^5$, $C(O)NH_2$, $C(O)NHR^5$, and C(O)OH. In another embodiment of Formula (IIIa), $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are unsubstituted.

In one embodiment of Formula (IIIa), $X^1$ is N; and $X^2$, $X^3$, $X^4$, and $X^5$ are C—$R^{3A}$. In another embodiment of Formula (IIIa), $X^2$ is N; $X^4$ is N; and $X^2$, $X^3$, and $X^5$ are C—$R^{3A}$. In another embodiment of Formula (IIIa), $X^2$ is N; and $X^1$, $X^3$, $X^4$, and $X^5$ are C—$R^{3A}$. In another embodiment of Formula (IIIa), $X^3$ is N; and $X^1$, $X^3$, $X^4$, and $X^5$ are C—$R^{3A}$.

In one embodiment of Formula (IIIa), $R^{3A}$, at each occurrence, is independently selected from the group consisting of H, $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, $(O)$, $OH$, $CN$, $NO_2$, F, Cl, Br and I. In another embodiment of Formula (IIIa), $R^{3.4}$, at each occurrence, is independently selected from the group consisting of H, $R^6$, $OR^6$, $NH_2$, $NHR^6$, $N(R^6)_2$, $NHC(O)R^6$, $C(O)NHR^6$, F, and Cl.

In one embodiment of Formula (IIIa), $X^1$ is N; $X^2$ is $C$—$R^{3.4}$; and $R^{3.4}$ is independently selected from the group consisting of H, $R^6$, $OR^6$, $NH_2$, $NHR^6$, $N(R^6)_2$, $NHC(O)R^6$, $C(O)NHR^6$, F, and Cl; $X^3$ is $C$—$R^{3.4}$; and $R^{3.4}$ is independently H or F; $X^4$ is $C$—$R^{3.4}$; and $R^{3.4}$ is independently H or F; and $X^5$ is $C$—$R^{3.4}$; and $R^{3.4}$ is independently $OR^6$, H, F, or Cl.

In one embodiment of Formula (IIIa), $R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $B(OH)_2$, $C(O)H$, $C(O)OH$, OH, CN, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $(O)$, OH, CN, $NO_2$, F, Cl, Br and I. In another embodiment of Formula (IIIa), $R^5$, at each occurrence, is independently $C_1$-$C_8$ alkyl; wherein each $R^5$ $C_1$-$C_8$ alkyl is optionally substituted with one or more OH.

In one embodiment of Formula (IIIa), $R^6$, at each occurrence, is independently selected from the group consisting of $C_1$-$C_6$ alkyl, $C_2$-$C_6$ alkenyl, $C_2$-$C_6$ alkynyl, phenyl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, CN, $NO_2$, F, Cl, Br and I; wherein each $R^6$ phenyl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $(O)$, OH, CN, $NO_2$, F, Cl, Br and I. In another embodiment of Formula (IIIa), $R^6$, at each occurrence, is independently selected from the group consisting of $C_1$-$C_6$ alkyl, phenyl, and heteroaryl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of $R^9$, $SR^9$, and OH; wherein each $R^6$ phenyl and heteroaryl is optionally substituted with one or more substituents independently selected from the group consisting of $NH_2$, and Cl.

In one embodiment of Formula (IIIa), $R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $NH_2$, $NHR^{13}$, $N(R^{13})_2$, $C(O)H$, $C(O)OH$, OH, CN, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $(O)$, OH, CN, $NO_2$, F, Cl, Br and I.

In one embodiment of Formula (IIIa), $R^8$, at each occurrence, is independently selected from the group consisting of $C_1$-$C_6$ alkyl, $C_2$-$C_6$ alkenyl, $C_2$-$C_6$ alkynyl, and heterocycloalkyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, $SO_2R^{8.4}$, $C(O)OR^{8.4}$, $C(O)NH_2$, $C(O)NHR^{8.4}$, $C(O)N(R^{8.4})_2$, $C(O)NHSO_2R^{8.4}$, $C(O)NR^{8.4}SO_2R^{8.4}$, $NH_2$, $C(O)H$, $C(O)OH$, OH, CN, $NO_2$, F, Cl, Br and I; wherein each $R^8$ heterocycloalkyl is optionally substituted with one or more substituents independently selected from the group consisting of $NH_2$, $C(O)H$, $C(O)OH$, OH, CN, $NO_2$, F, Cl, Br and I.

In one embodiment of Formula (IIIa), $R^{8.4}$, at each occurrence, is independently selected from the group consisting of $C_1$-$C_6$ alkyl, $C_2$-$C_6$ alkenyl, and $C_2$-$C_6$ alkynyl.

In one embodiment of Formula (IIIa), $R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)$ NHSO$_2$R$^{12}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, (O), OH, CN, NO$_2$, F, Cl, Br and I. In another embodiment of Formula (IIIa), R$^9$, at each occurrence, is independently selected from the group consisting of aryl, heteroaryl, heterocycloalkyl, and cycloalkyl; wherein each R$^9$ aryl, cycloalkyl, heteroaryl, and heterocycloalkyl is optionally substituted with one or more substituents independently selected from the group consisting of R$^{12}$, OR$^{12}$, SO$_2$R$^{12}$, C(O)R$^{12}$, CO(O)R$^{12}$, C(O)NH$_2$, SO$_2$NH$_2$, (O), OH, CN, F, and Cl.

In one embodiment of Formula (IIIa), R$^{10}$, at each occurrence, is independently selected from the group consisting of C$_1$-C$_6$ alkyl, C$_2$-C$_6$ alkenyl, and C$_2$-C$_6$ alkynyl; wherein each R$^{10}$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)H, C(O)OH, OH, CN, NO$_2$, F, Cl, Br and I.

In one embodiment of Formula (IIIa), R$^{11}$, at each occurrence, is independently selected from the group consisting of C$_1$-C$_6$ alkyl, C$_2$-C$_6$ alkenyl, C$_2$-C$_6$ alkynyl, aryl, and heteroaryl; wherein each R$^{11}$ C$_1$-C$_6$ alkyl, C$_2$-C$_6$ alkenyl, and C$_2$-C$_6$ alkynyl is optionally substituted with one or more substituents independently selected from the group consisting of OR$^{11A}$, NH$_2$, NHR$^{11A}$, N(R$^{11A}$)$_2$, C(O)H, C(O)OH, OH, CN, NO$_2$, F, Cl, Br and I; wherein each R$^{11}$ aryl and heteroaryl is optionally substituted with one or more substituents independently selected from the group consisting of C$_1$-C$_6$ alkyl, C$_1$-C$_6$ haloalkyl, NH$_2$, C(O)H, C(O)OH, OH, CN, NO$_2$, F, Cl, Br and I.

In one embodiment of Formula (IIIa), R$^{11A}$, at each occurrence, is independently selected from the group consisting of C$_1$-C$_6$ alkyl, C$_2$-C$_6$ alkenyl, and C$_2$-C$_6$ alkynyl.

In one embodiment of Formula (IIIa), R$^{12}$, at each occurrence, is independently selected from the group consisting of C$_1$-C$_6$ alkyl, C$_2$-C$_6$ alkenyl, and C$_2$-C$_6$ alkynyl; wherein each R$^{12}$ C$_1$-C$_6$ alkyl, C$_2$-C$_6$ alkenyl, and C$_2$-C$_6$ alkynyl is optionally substituted with one or more substituents independently selected from the group consisting of NH$_2$, NHR$^{14}$, N(R$^{14}$)$_2$, C(O)H, C(O)OH, OH, CN, NO$_2$, F, Cl, Br and I. In another embodiment of Formula (IIIa), R$^{12}$, at each occurrence, is independently C$_1$-C$_6$ alkyl; wherein each R$^{12}$ C$_1$-C$_6$ alkyl is optionally substituted with one or more substituents independently selected from the group consisting of N(R$^{14}$)$_2$, and C(O)OH.

In one embodiment of Formula (IIIa), R$^{13}$, at each occurrence, is independently selected from the group consisting of C$_1$-C$_6$ alkyl, C$_2$-C$_6$ alkenyl, C$_2$-C$_6$ alkynyl, aryl, heteroaryl, cycloalkyl, cycloalkenyl, and heterocycloalkyl, heterocycloalkenyl; wherein each R$^{13}$ C$_1$-C$_6$ alkyl, C$_2$-C$_6$ alkenyl, and C$_2$-C$_6$ alkynyl is optionally substituted with one or more substituents independently selected from the group consisting of R$^{15}$, OR$^{15}$, C(O)H, C(O)OH, OH, CN, NO$_2$, F, Cl, Br and I; wherein each R$^{13}$ aryl, cycloalkyl, cycloalkenyl, heteroaryl, heterocycloalkyl, and heterocycloalkenyl is optionally substituted with one or more substituents independently selected from the group consisting of R$^{16}$, OR$^{16}$, C(O)H, C(O)OH, (O), OH, CN, NO$_2$, F, Cl, Br and I.

In one embodiment of Formula (IIIa), R$^{14}$, at each occurrence, is independently selected from the group consisting of C$_1$-C$_6$ haloalkyl, C$_1$-C$_6$ alkyl, C$_2$-C$_6$ alkenyl, and C$_2$-C$_6$ alkynyl. In another embodiment of Formula (IIIa), R$^{14}$, at each occurrence, is independently C$_1$-C$_6$ alkyl.

In one embodiment of Formula (IIIa), R$^{15}$, at each occurrence, is independently selected from the group consisting of C$_1$-C$_6$ haloalkyl, C$_1$-C$_6$ alkyl, C$_2$-C$_6$ alkenyl, and C$_2$-C$_6$ alkynyl; wherein each R$^{15}$ C$_1$-C$_6$ alkyl, C$_2$-C$_6$ alkenyl, and C$_2$-C$_6$ alkynyl is optionally substituted with one or more OCH$_3$.

In one embodiment of Formula (IIIa), R$^{16}$, at each occurrence, is independently selected from the group consisting of C$_1$-C$_6$ haloalkyl, C$_1$-C$_6$ alkyl, C$_2$-C$_6$ alkenyl, and C$_2$-C$_6$ alkynyl.

In one embodiment of Formula (IIIa), one of X$^1$, X$^2$, X$^3$, X$^4$, and X$^5$ is N; and the remaining are CR$^{3A}$; or X$^1$ and X$^4$ are N; and X$^2$, X$^3$, and X$^5$ are CR$^{3A}$;

R$^1$ is selected from the group consisting of cycloalkyl, cycloalkenyl, heterocycloalkyl, and heterocycloalkenyl; wherein the R$^1$ cycloalkyl, cycloalkenyl, heterocycloalkyl and heterocycloalkenyl are optionally substituted with one or more substituents independently selected from the group consisting of R$^5$, SO$_2$R$^5$, C(O)R$^5$, CO(O)R$^5$, NH$_2$, SO$_2$NHC(O)OR$^5$, C(O)NH$_2$, C(O)NHR$^5$, and C(O)OH;

R$^2$ is hydrogen;

R$^{3A}$, at each occurrence, is each independently selected from the group consisting of H, R$^6$, OR$^6$, NH$_2$, NHR$^6$, N(R$^6$)$_2$, NHC(O)R$^6$, C(O)NHR$^6$, F, and Cl;

R$^4$ is selected from the group consisting of R$^{4A}$ and Cl;

R$^{4A}$ is hydrogen;

R$^5$, at each occurrence, is independently C$_1$-C$_8$ alkyl; wherein each R$^5$ C$_1$-C$_8$ alkyl, is optionally substituted with one or more OH;

R$^6$, at each occurrence, is independently selected from the group consisting of C$_1$-C$_6$ alkyl, phenyl, and heteroaryl; wherein each R$^6$ C$_1$-C$_6$ alkyl is optionally substituted with one or more substituents independently selected from the group consisting of R$^9$, SR$^9$, and OH; wherein each R$^6$ phenyl and heteroaryl is optionally substituted with one or more substituents independently selected from the group consisting of NH$_2$ and Cl;

R$^9$, at each occurrence, is independently selected from the group consisting of aryl, heteroaryl, heterocycloalkyl and cycloalkyl; wherein each R$^9$ aryl, cycloalkyl, heteroaryl, and heterocycloalkyl is optionally substituted with one or more substituents independently selected from the group consisting of R$^{12}$, OR$^{12}$, SO$_2$R$^{12}$, C(O)R$^{12}$, CO(O)R$^{12}$, C(O)NH$_2$, SO$_2$NH$_2$, (O), OH, CN, F, and Cl;

R$^{12}$, at each occurrence, is independently C$_1$-C$_6$ alkyl; wherein each R$^{12}$ C$_1$-C$_6$ alkyl is optionally substituted with one or more substituents independently selected from the group consisting of N(R$^{14}$)$_2$ and C(O)OH; and R$^{14}$, at each occurrence, is independently C$_1$-C$_6$ alkyl.

Still another embodiment pertains to compounds of Formula (IIIa), selected from the group consisting of:

5-methoxy-6-[2-(piperidin-3-yl)-1H-pyrrolo[2,3-b]pyridin-4-yl]pyridin-2-amine;

N-benzyl-5-chloro-6-[2-(piperidin-3-yl)-1H-pyrrolo[2,3-b]pyridin-4-yl]pyridin-2-amine;

N-benzyl-5-chloro-6-[2-(1-methylpiperidin-3-yl)-1H-pyrrolo[2,3-b]pyridin-4-yl]pyridin-2-amine;

N-benzyl-6-[2-(1-methylpiperidin-3-yl)-1H-pyrrolo[2,3-b]pyridin-4-yl]pyridin-2-amine;

N-benzyl-5-methoxy-6-[2-(piperidin-3-yl)-1H-pyrrolo[2,3-b]pyridin-4-yl]pyridin-2-amine;

N-benzyl-5-chloro-6-{2-[1-(propan-2-ylsulfonyl)piperidin-3-yl]-1H-pyrrolo[2,3-b]pyridin-4-yl}pyridin-2-amine;

methyl 3-{4-[6-(benzylamino)-3-chloropyridin-2-yl]-1H-pyrrolo[2,3-b]pyridin-2-yl}piperidine-1-carboxylate;

4-(3-methoxypyridin-2-yl)-2-(piperidin-4-yl)-1H-pyrrolo[2,3-b]pyridine;

5-methoxy-6-[2-(piperidin-4-yl)-1H-pyrrolo[2,3-b]pyridin-4-yl]pyridin-2-amine;

4-(6-fluoro-3-methoxypyridin-2-yl)-2-(piperidin-4-yl)-1H-pyrrolo[2,3-b]pyridine;

4-(4-methoxypyridin-3-yl)-2-(1-methylpiperidin-4-yl)-1H-pyrrolo[2,3-b]pyridine;

N-benzyl-5-chloro-6-[2-(piperidin-4-yl)-1H-pyrrolo[2,3-b]pyridin-4-yl]pyridin-2-amine;

5-chloro-N-(3-fluorobenzyl)-6-[2-(piperidin-4-yl)-1H-pyrrolo[2,3-b]pyridin-4-yl]pyridin-2-amine;

5-chloro-6-[2-(piperidin-4-yl)-1H-pyrrolo[2,3-b]pyridin-4-yl]-N-(pyridin-3-ylmethyl)pyridin-2-amine;

5-chloro-N-(4-chlorobenzyl)-6-[2-(piperidin-4-yl)-1H-pyrrolo[2,3-b]pyridin-4-yl]pyridin-2-amine;

5-chloro-N-(2,5-difluorobenzyl)-6-[2-(piperidin-4-yl)-1H-pyrrolo[2,3-b]pyridin-4-yl]pyridin-2-amine;

5-chloro-N-[(5-fluoropyridin-3-yl)methyl]-6-[2-(piperidin-4-yl)-1H-pyrrolo[2,3-b]pyridin-4-yl]pyridin-2-amine;

5-chloro-N-(2-fluorobenzyl)-6-[2-(piperidin-4-yl)-1H-pyrrolo[2,3-b]pyridin-4-yl]pyridin-2-amine;

5-chloro-N-(3,4-difluorobenzyl)-6-[2-(piperidin-4-yl)-1H-pyrrolo[2,3-b]pyridin-4-yl]pyridin-2-amine;

5-chloro-6-[2-(piperidin-4-yl)-1H-pyrrolo[2,3-b]pyridin-4-yl]-N-(pyridin-4-ylmethyl)pyridin-2-amine;

5-chloro-N-[(1-oxidopyridin-3-yl)methyl]-6-[2-(piperidin-4-yl)-1H-pyrrolo[2,3-b]pyridin-4-yl]pyridin-2-amine;

5-chloro-N-(piperidin-4-ylmethyl)-6-[2-(piperidin-4-yl)-1H-pyrrolo[2,3-b]pyridin-4-yl]pyridin-2-amine;

5-chloro-N-(piperidin-3-ylmethyl)-6-[2-(piperidin-4-yl)-1H-pyrrolo[2,3-b]pyridin-4-yl]pyridin-2-amine;

4-(3-chloro-6-phenylpyridin-2-yl)-2-(piperidin-4-yl)-1H-pyrrolo[2,3-b]pyridine;

N-{5-chloro-6-[2-(piperidin-4-yl)-1H-pyrrolo[2,3-b]pyridin-4-yl]pyridin-2-yl}benzamide;

N-benzyl-5-chloro-N-methyl-6-[2-(piperidin-4-yl)-1H-pyrrolo[2,3-b]pyridin-4-yl]pyridin-2-amine;

N-benzyl-5-chloro-N-ethyl-6-[2-(piperidin-4-yl)-1H-pyrrolo[2,3-b]pyridin-4-yl]pyridin-2-amine;

5-chloro-6-[2-(piperidin-4-yl)-1H-pyrrolo[2,3-b]pyridin-4-yl]-N-(tetrahydro-2H-pyran-4-ylmethyl)pyridin-2-amine;

5-chloro-6-[2-(piperidin-4-yl)-1H-pyrrolo[2,3-b]pyridin-4-yl]-N-(tetrahydro-2H-pyran-3-ylmethyl)pyridin-2-amine;

N-benzyl-5-chloro-4-[2-(piperidin-4-yl)-1H-pyrrolo[2,3-b]pyridin-4-yl]pyridin-2-amine;

N-benzyl-5-chloro-6-[2-(1-methylpiperidin-4-yl)-1H-pyrrolo[2,3-b]pyridin-4-yl]pyridin-2-amine;

5-chloro-N-[(1S)-1-phenylethyl]-6-[2-(piperidin-4-yl)-1H-pyrrolo[2,3-b]pyridin-4-yl]pyridin-2-amine;

N-benzyl-6-[2-(1-methylpiperidin-4-yl)-1H-pyrrolo[2,3-b]pyridin-4-yl]pyridin-2-amine;

5-chloro-N-(3-fluorobenzyl)-6-[2-(1-methylpiperidin-4-yl)-1H-pyrrolo[2,3-b]pyridin-4-yl]pyridin-2-amine;

4-[6-(benzyloxy)-3-chloropyridin-2-yl]-2-(piperidin-4-yl)-1H-pyrrolo[2,3-b]pyridine;

N-benzyl-5-chloro-6-[2-(pyrrolidin-3-yl)-1H-pyrrolo[2,3-b]pyridin-4-yl]pyridin-2-amine;

5-chloro-6-[2-(pyrrolidin-3-yl)-1H-pyrrolo[2,3-b]pyridin-4-yl]-N-(tetrahydro-2H-pyran-4-ylmethyl)pyridin-2-amine;

N-benzyl-5-chloro-6-[2-(morpholin-2-yl)-1H-pyrrolo[2,3-b]pyridin-4-yl]pyridin-2-amine;

N-benzyl-6-[5-chloro-2-(piperidin-4-yl)-1H-pyrrolo[2,3-b]pyridin-4-yl]pyridin-2-amine;

5-chloro-4-(6-fluoropyridin-2-yl)-2-(piperidin-3-yl)-1H-pyrrolo[2,3-b]pyridine;

N-benzyl-6-[5-chloro-2-(piperidin-3-yl)-1H-pyrrolo[2,3-b]pyridin-4-yl]pyridin-2-amine;

6-[5-chloro-2-(piperidin-3-yl)-1H-pyrrolo[2,3-b]pyridin-4-yl]-N-(tetrahydro-2H-pyran-4-ylmethyl)pyridin-2-amine;

N-benzyl-6-[5-chloro-2-(1-methylpiperidin-3-yl)-1H-pyrrolo[2,3-b]pyridin-4-yl]pyridin-2-amine;

methyl 3-{4-[6-(benzylamino)pyridin-2-yl]-5-chloro-1H-pyrrolo[2,3-b]pyridin-2-yl}piperidine-1-carboxylate;

N-benzyl-6-{5-chloro-2-[1-(propan-2-ylsulfonyl)piperidin-3-yl]-1H-pyrrolo[2,3-b]pyridin-4-yl}pyridin-2-amine;

6-[2-(3-aminocyclohexyl)-5-chloro-1H-pyrrolo[2,3-b]pyridin-4-yl]-N-benzylpyridin-2-amine;

6-[2-(piperidin-4-yl)-1H-pyrrolo[2,3-b]pyridin-4-yl]-N-(tetrahydro-2H-pyran-4-ylmethyl)pyridin-2-amine;

6-[2-(1-methylpiperidin-4-yl)-1H-pyrrolo[2,3-b]pyridin-4-yl]-N-(tetrahydro-2H-pyran-4-ylmethyl)pyridin-2-amine;

6-[2-(1-methylpiperidin-4-yl)-1H-pyrrolo[2,3-b]pyridin-4-yl]-N-(3-phenylpropyl)pyridin-2-amine;

6-[2-(1-methylpiperidin-4-yl)-1H-pyrrolo[2,3-b]pyridin-4-yl]-N-(pyridin-3-ylmethyl)pyridin-2-amine;

6-[2-(1-methylpiperidin-4-yl)-1H-pyrrolo[2,3-b]pyridin-4-yl]-N-[2-(phenylsulfanyl)ethyl]pyridin-2-amine;

N-(cyclopropylmethyl)-6-[2-(1-methylpiperidin-4-yl)-1H-pyrrolo[2,3-b]pyridin-4-yl]pyridin-2-amine;

N-[(2,2-dimethyltetrahydro-2H-pyran-4-yl)methyl]-6-[2-(1-methylpiperidin-4-yl)-1H-pyrrolo[2,3-b]pyridin-4-yl]pyridin-2-amine;

N-benzyl-N-methyl-6-[2-(1-methylpiperidin-4-yl)-1H-pyrrolo[2,3-b]pyridin-4-yl]pyridin-2-amine;

N-(3-chlorobenzyl)-6-[2-(1-methylpiperidin-4-yl)-1H-pyrrolo[2,3-b]pyridin-4-yl]pyridin-2-amine;

N-(2,6-difluorobenzyl)-6-[2-(1-methylpiperidin-4-yl)-1H-pyrrolo[2,3-b]pyridin-4-yl]pyridin-2-amine;

6-[2-(1-methylpiperidin-4-yl)-1H-pyrrolo[2,3-b]pyridin-4-yl]-N-[(1S)-1-phenylethyl]pyridin-2-amine;

N-(1,3-benzodioxol-5-ylmethyl)-6-[2-(1-methylpiperidin-4-yl)-1H-pyrrolo[2,3-b]pyridin-4-yl]pyridin-2-amine;

5-chloro-6-[2-(piperidin-4-yl)-1H-pyrrolo[2,3-b]pyridin-4-yl]pyridin-2-amine;

N-[2-(phenylsulfanyl)ethyl]-6-[2-(piperidin-4-yl)-1H-pyrrolo[2,3-b]pyridin-4-yl]pyridin-2-amine;

5-chloro-6-[2-(1-methylpiperidin-4-yl)-1H-pyrrolo[2,3-b]pyridin-4-yl]pyridin-2-amine;

3-chloro-N$^2$-{5-chloro-6-[2-(1-methylpiperidin-4-yl)-1H-pyrrolo[2,3-b]pyridin-4-yl]pyridin-2-yl}pyridine-2,6-diamine;

5-chloro-6-[2-(1-methylpiperidin-4-yl)-1H-pyrrolo[2,3-b]pyridin-4-yl]-N-(tetrahydro-2H-pyran-4-ylmethyl)pyridin-2-amine;

N-(2-phenylethyl)-6-[2-(piperidin-4-yl)-1H-pyrrolo[2,3-b]pyridin-4-yl]pyridin-2-amine;

N-methyl-6-[2-(1-methylpiperidin-4-yl)-1H-pyrrolo[2,3-b]pyridin-4-yl]-N-(2-phenylethyl)pyridin-2-amine;

N-(2-chlorobenzyl)-6-[2-(piperidin-4-yl)-1H-pyrrolo[2,3-b]pyridin-4-yl]pyridin-2-amine;

N-(2-chlorobenzyl)-6-[2-(1-methylpiperidin-4-yl)-1H-pyrrolo[2,3-b]pyridin-4-yl]pyridin-2-amine;

N-(2-chlorobenzyl)-N-methyl-6-[2-(1-methylpiperidin-4-yl)-1H-pyrrolo[2,3-b]pyridin-4-yl]pyridin-2-amine;

1-[2-({6-[2-(piperidin-4-yl)-1H-pyrrolo[2,3-b]pyridin-4-yl]pyridin-2-yl}amino)ethyl]pyrrolidin-2-one;

1-[2-(methyl {6-[2-(1-methylpiperidin-4-yl)-1H-pyrrolo[2,3-b]pyridin-4-yl]pyridin-2-yl}amino)ethyl]pyrrolidin-2-one;

6-[2-(1-methylpiperidin-4-yl)-1H-pyrrolo[2,3-b]pyridin-4-yl]-N-(2-phenylethyl)pyridin-2-amine;

1-[2-({6-[2-(1-methylpiperidin-4-yl)-1H-pyrrolo[2,3-b]pyridin-4-yl]pyridin-2-yl}amino)ethyl]pyrrolidin-2-one;

5-chloro-N-(cyclopropylmethyl)-6-[2-(1-methylpiperidin-4-yl)-1H-pyrrolo[2,3-b]pyridin-4-yl]pyridin-2-amine;

N-{4-[2-(dimethylamino)ethoxy]benzyl}-6-[2-(1-methylpiperidin-4-yl)-1H-pyrrolo[2,3-b]pyridin-4-yl]pyridin-2-amine;

5-chloro-N-[(2,2-dimethyltetrahydro-2H-pyran-4-yl)methyl]-6-[2-(1-methylpiperidin-4-yl)-1H-pyrrolo[2,3-b]pyridin-4-yl]pyridin-2-amine;
5-chloro-6-[2-(1-methylpiperidin-4-yl)-1H-pyrrolo[2,3-b]pyridin-4-yl]-N-(pyridin-4-ylmethyl)pyridin-2-amine;
6-[2-(1-methylpiperidin-4-yl)-1H-pyrrolo[2,3-b]pyridin-4-yl]-N-(1H-pyrazol-3-ylmethyl)pyridin-2-amine;
N-(2,3-dihydro-1H-isoindol-5-ylmethyl)-6-[2-(1-methylpiperidin-4-yl)-1H-pyrrolo[2,3-b]pyridin-4-yl]pyridin-2-amine;
6-[2-(1-methylpiperidin-4-yl)-1H-pyrrolo[2,3-b]pyridin-4-yl]-N-[(1-methylpyrrolidin-3-yl)methyl]pyridin-2-amine;
N-(1H-indol-6-ylmethyl)-6-[2-(1-methylpiperidin-4-yl)-1H-pyrrolo[2,3-b]pyridin-4-yl]pyridin-2-amine;
5-chloro-6-[2-(1-methylpiperidin-4-yl)-1H-pyrrolo[2,3-b]pyridin-4-yl]-N-[4-(methylsulfonyl)benzyl]pyridin-2-amine;
4-[({5-chloro-6-[2-(1-methylpiperidin-4-yl)-1H-pyrrolo[2,3-b]pyridin-4-yl]pyridin-2-yl}amino)methyl]benzenesulfonamide;
4-[({5-chloro-6-[2-(1-methylpiperidin-4-yl)-1H-pyrrolo[2,3-b]pyridin-4-yl]pyridin-2-yl}amino)methyl]benzamide;
6-[2-(1-methylpiperidin-4-yl)-1H-pyrrolo[2,3-b]pyridin-4-yl]-N-[2-(morpholin-4-yl)ethyl]pyridin-2-amine;
2-({6-[2-(1-methylpiperidin-4-yl)-1H-pyrrolo[2,3-b]pyridin-4-yl]pyridin-2-yl}amino)ethanol;
5-chloro-6-[2-(1-methylpiperidin-4-yl)-1H-pyrrolo[2,3-b]pyridin-4-yl]-N-(piperidin-4-ylmethyl)pyridin-2-amine;
tert-butyl 3-[({5-chloro-6-[2-(1-methylpiperidin-4-yl)-1H-pyrrolo[2,3-b]pyridin-4-yl]pyridin-2-yl}amino)methyl]pyrrolidine-1-carboxylate;
5-chloro-N-[(1,1-dioxidotetrahydro-2H-thiopyran-4-yl)methyl]-6-[2-(1-methylpiperidin-4-yl)-1H-pyrrolo[2,3-b]pyridin-4-yl]pyridin-2-amine;
{3-[({5-chloro-6-[2-(1-methylpiperidin-4-yl)-1H-pyrrolo[2,3-b]pyridin-4-yl]pyridin-2-yl}amino)methyl]phenoxy}acetic acid;
{4-[({5-chloro-6-[2-(1-methylpiperidin-4-yl)-1H-pyrrolo[2,3-b]pyridin-4-yl]pyridin-2-yl}amino)methyl]phenoxy}acetic acid;
1-{4-[({5-chloro-6-[2-(1-methylpiperidin-4-yl)-1H-pyrrolo[2,3-b]pyridin-4-yl]pyridin-2-yl}amino)methyl]piperidin-1-yl}ethanone;
5-chloro-6-[2-(1-methylpiperidin-4-yl)-1H-pyrrolo[2,3-b]pyridin-4-yl]-N-(4H-1,2,4-triazol-3-ylmethyl)pyridin-2-amine;
5-chloro-6-[2-(1-methylpiperidin-4-yl)-1H-pyrrolo[2,3-b]pyridin-4-yl]-N-[3-(methylsulfonyl)benzyl]pyridin-2-amine;
(3S,5R)-5-[({5-chloro-6-[2-(piperidin-4-yl)-1H-pyrrolo[2,3-b]pyridin-4-yl]pyridin-2-yl}amino)methyl]pyrrolidin-3-ol;
N-benzyl-5-chloro-6-(2-cyclohexyl-1H-pyrrolo[2,3-b]pyridin-4-yl)pyridin-2-amine;
5-chloro-N-{[(2S,4S)-4-fluoropyrrolidin-2-yl]methyl}-6-[2-(piperidin-4-yl)-1H-pyrrolo[2,3-b]pyridin-4-yl]pyridin-2-amine;
4-[({5-chloro-4-[2-(piperidin-4-yl)-1H-pyrrolo[2,3-b]pyridin-4-yl]pyridin-2-yl}amino)methyl]tetrahydro-2H-pyran-4-carbonitrile;
5-chloro-N-{[(2S)-4,4-difluoropyrrolidin-2-yl]methyl}-6-[2-(piperidin-4-yl)-1H-pyrrolo[2,3-b]pyridin-4-yl]pyridin-2-amine;
N-benzyl-5-chloro-N-methyl-6-[2-(piperidin-3-yl)-1H-pyrrolo[2,3-b]pyridin-4-yl]pyridin-2-amine;
5-chloro-N-(3,4-difluorobenzyl)-6-[2-(piperidin-3-yl)-1H-pyrrolo[2,3-b]pyridin-4-yl]pyridin-2-amine;
5-chloro-N-(3-fluorobenzyl)-6-[2-(piperidin-3-yl)-1H-pyrrolo[2,3-b]pyridin-4-yl]pyridin-2-amine;
5-chloro-N-(4-fluorobenzyl)-6-[2-(piperidin-3-yl)-1H-pyrrolo[2,3-b]pyridin-4-yl]pyridin-2-amine;
N-benzyl-5-chloro-4-[2-(piperidin-3-yl)-1H-pyrrolo[2,3-b]pyridin-4-yl]pyridin-2-amine;
5-chloro-N-(2-fluorobenzyl)-6-[2-(piperidin-3-yl)-1H-pyrrolo[2,3-b]pyridin-4-yl]pyridin-2-amine;
5-chloro-6-[2-(piperidin-3-yl)-1H-pyrrolo[2,3-b]pyridin-4-yl]-N-(pyridin-3-ylmethyl)pyridin-2-amine;
4-[3-chloro-6-(pyridin-3-ylmethoxy)pyridin-2-yl]-2-(piperidin-3-yl)-1H-pyrrolo[2,3-b]pyridine;
5-chloro-N-[(5-fluoropyridin-3-yl)methyl]-6-[2-(piperidin-3-yl)-1H-pyrrolo[2,3-b]pyridin-4-yl]pyridin-2-amine;
N-benzyl-5-fluoro-4-[2-(piperidin-3-yl)-1H-pyrrolo[2,3-b]pyridin-4-yl]pyridin-2-amine;
N-benzyl-4-fluoro-6-[2-(piperidin-3-yl)-1H-pyrrolo[2,3-b]pyridin-4-yl]pyridin-2-amine;
N-benzyl-4-[5-chloro-2-(piperidin-3-yl)-1H-pyrrolo[2,3-b]pyridin-4-yl]pyridin-2-amine;
5-chloro-N-(3-fluorobenzyl)-4-[2-(piperidin-4-yl)-1H-pyrrolo[2,3-b]pyridin-4-yl]pyridin-2-amine;
6-[2-(3-aminocyclohexyl)-1H-pyrrolo[2,3-b]pyridin-4-yl]-N-(3-fluorobenzyl)pyridin-2-amine;
4-(6-fluoropyridin-2-yl)-2-(1,2,3,6-tetrahydropyridin-4-yl)-1H-pyrrolo[2,3-b]pyridine;
4-(6-fluoropyridin-2-yl)-2-[1-(methylsulfonyl)-1,2,3,6-tetrahydropyridin-4-yl]-1H-pyrrolo[2,3-b]pyridine;
N-(2,6-difluorobenzyl)-6-{2-[1-(methylsulfonyl)-1,2,3,6-tetrahydropyridin-4-yl]-1H-pyrrolo[2,3-b]pyridin-4-yl}pyridin-2-amine;
N-(2-chlorobenzyl)-6-{2-[1-(methylsulfonyl)-1,2,3,6-tetrahydropyridin-4-yl]-1H-pyrrolo[2,3-b]pyridin-4-yl}pyridin-2-amine;
N-(cyclopropylmethyl)-6-{2-[1-(methylsulfonyl)-1,2,3,6-tetrahydropyridin-4-yl]-1H-pyrrolo[2,3-b]pyridin-4-yl}pyridin-2-amine;
N-benzyl-6-{2-[1-(methylsulfonyl)piperidin-4-yl]-1H-pyrrolo[2,3-b]pyridin-4-yl}pyrazin-2-amine;
N-benzyl-6-[2-(piperidin-4-yl)-1H-pyrrolo[2,3-b]pyridin-4-yl]pyrazin-2-amine;
6-[2-(piperidin-4-yl)-1H-pyrrolo[2,3-b]pyridin-4-yl]-N-(tetrahydro-2H-pyran-4-ylmethyl)pyrazin-2-amine;
N-(3,5-difluorobenzyl)-6-[2-(piperidin-4-yl)-1H-pyrrolo[2,3-b]pyridin-4-yl]pyrazin-2-amine;
N-(3-fluorobenzyl)-6-[2-(piperidin-4-yl)-1H-pyrrolo[2,3-b]pyridin-4-yl]pyrazin-2-amine;
6-[2-(piperidin-4-yl)-1H-pyrrolo[2,3-b]pyridin-4-yl]-N-(pyridin-3-ylmethyl)pyrazin-2-amine;
6-[2-(piperidin-4-yl)-1H-pyrrolo[2,3-b]pyridin-4-yl]-N-(pyridin-4-ylmethyl)pyrazin-2-amine;
N-(3,4-difluorobenzyl)-6-[2-(piperidin-4-yl)-1H-pyrrolo[2,3-b]pyridin-4-yl]pyrazin-2-amine;
1-[4-(4-{6-[(3,5-difluorobenzyl)amino]pyrazin-2-yl}-1H-pyrrolo[2,3-b]pyridin-2-yl)piperidin-1-yl]-2-hydroxyethanone;
1-[4-(4-{6-[(3-fluorobenzyl)amino]pyrazin-2-yl}-1H-pyrrolo[2,3-b]pyridin-2-yl)piperidin-1-yl]-2-hydroxyethanone;
1-(4-{4-[6-(benzylamino)pyrazin-2-yl]-1H-pyrrolo[2,3-b]pyridin-2-yl}piperidin-1-yl)-2-hydroxyethanone;
N-benzyl-N-methyl-6-[2-(1-methylpiperidin-4-yl)-1H-pyrrolo[2,3-b]pyridin-4-yl]pyrazin-2-amine;
N-benzyl-6-[2-(1-methylpiperidin-4-yl)-1H-pyrrolo[2,3-b]pyridin-4-yl]pyrazin-2-amine;
1-(4-{4-[6-(benzylamino)pyrazin-2-yl]-1H-pyrrolo[2,3-b]pyridin-2-yl}piperidin-1-yl)ethanone;

3-(4-{4-[6-(benzylamino)pyrazin-2-yl]-1H-pyrrolo[2,3-b]pyridin-2-yl}piperidin-1-yl)propane-1,2-diol;

ethyl[(4-{4-[6-(benzylamino)pyrazin-2-yl]-1H-pyrrolo[2,3-b]pyridin-2-yl}piperidin-1-yl)sulfonyl]carbamate;

4-(6-chloro-3-fluoropyridin-2-yl)-2-(piperidin-4-yl)-1H-pyrrolo[2,3-b]pyridine;

4-{6-[(3-fluorobenzyl)oxy]pyrazin-2-yl}-2-(piperidin-4-yl)-1H-pyrrolo[2,3-b]pyridine;

N-(3-fluorobenzyl)-6-[2-(1-methylpiperidin-4-yl)-1H-pyrrolo[2,3-b]pyridin-4-yl]pyrazin-2-amine;

1-[4-(4-{6-[(3-fluorobenzyl)amino]pyrazin-2-yl}-1H-pyrrolo[2,3-b]pyridin-2-yl)piperidin-1-yl]ethanone;

4-{6-[(3-fluorobenzyl)oxy]pyrazin-2-yl}-2-(1-methylpiperidin-4-yl)-1H-pyrrolo[2,3-b]pyridine;

N-benzyl-6-[2-(1,2,3,6-tetrahydropyridin-4-yl)-1H-pyrrolo[2,3-b]pyridin-4-yl]pyrazin-2-amine;

1-[4-(4-{6-[(3-fluorobenzyl)oxy]pyrazin-2-yl}-1H-pyrrolo[2,3-b]pyridin-2-yl)piperidin-1-yl]-2-hydroxyethanone;

3-[4-(4-{6-[(3-fluorobenzyl)oxy]pyrazin-2-yl}-1H-pyrrolo[2,3-b]pyridin-2-yl)piperidin-1-yl]propane-1,2-diol;

ethyl {[4-(4-{6-[(3-fluorobenzyl)amino]pyrazin-2-yl}-1H-pyrrolo[2,3-b]pyridin-2-yl)piperidin-1-yl]sulfonyl}carbamate;

4-{4-[6-(benzylamino)pyrazin-2-yl]-1H-pyrrolo[2,3-b]pyridin-2-yl}-N-methylpiperidine-1-carboxamide;

4-(4-{6-[(3-fluorobenzyl)amino]pyrazin-2-yl}-1H-pyrrolo[2,3-b]pyridin-2-yl)-N-methylpiperidine-1-carboxamide;

4-{6-[(3-fluorobenzyl)oxy]pyrazin-2-yl}-2-[1-(methylsulfonyl)piperidin-4-yl]-1H-pyrrolo[2,3-b]pyridine;

1-[4-(4-{6-[(3-fluorobenzyl)oxy]pyrazin-2-yl}-1H-pyrrolo[2,3-b]pyridin-2-yl)piperidin-1-yl]ethanone;

4-(4-{6-[(3-fluorobenzyl)oxy]pyrazin-2-yl}-1H-pyrrolo[2,3-b]pyridin-2-yl)-N-methylpiperidine-1-carboxamide;

1-[4-{4-[6-(b enzylamino)pyrazin-2-yl]-1H-pyrrolo[2,3-b]pyridin-2-yl}-3,6-dihydropyridin-1(2H)-yl]-2-hydroxyethanone;

N-(3-fluorobenzyl)-6-[2-(1,2,3,6-tetrahydropyridin-4-yl)-1H-pyrrolo[2,3-b]pyridin-4-yl]pyrazin-2-amine;

3-[4-(4-{6-[(3-fluorobenzyl)amino]pyrazin-2-yl}-1H-pyrrolo[2,3-b]pyridin-2-yl)-3,6-dihydropyridin-1(2H)-yl]propane-1,2-diol;

4-{6-[(3-fluorobenzyl)oxy]pyrazin-2-yl}-2-(1,2,3,6-tetrahydropyridin-4-yl)-1H-pyrrolo[2,3-b]pyridine;

4-(4-{6-[(3-fluorobenzyl)amino]pyrazin-2-yl}-1H-pyrrolo[2,3-b]pyridin-2-yl)-N-methyl-3,6-dihydropyridine-1(2H)-carboxamide;

6-[2-(1-methylpiperidin-4-yl)-1H-pyrrolo[2,3-b]pyridin-4-yl]-N-(pyridin-3-ylmethyl)pyrazin-2-amine;

3-[4-(4-{6-[(pyridin-3-ylmethyl)amino]pyrazin-2-yl}-1H-pyrrolo[2,3-b]pyridin-2-yl)piperidin-1-yl]propane-1,2-diol;

2-hydroxy-1-[4-(4-{6-[(pyridin-3-ylmethyl)amino]pyrazin-2-yl}-1H-pyrrolo[2,3-b]pyridin-2-yl)piperidin-1-yl]ethanone;

N-methyl-4-(4-{6-[(pyridin-3-ylmethyl)amino]pyrazin-2-yl}-1H-pyrrolo[2,3-b]pyridin-2-yl)piperidine-1-carboxamide;

1-[4-(4-{6-[(3-fluorobenzyl)amino]pyrazin-2-yl}-1H-pyrrolo[2,3-b]pyridin-2-yl)-3,6-dihydropyridin-1(2H)-yl]-2-hydroxyethanone;

4-{6-[(3-fluorobenzyl)oxy]pyrazin-2-yl}-2-[1-(methylsulfonyl)-1,2,3,6-tetrahydropyridin-4-yl]-1H-pyrrolo[2,3-b]pyridine;

3,5-difluoro-N-(3-fluorobenzyl)-6-[2-(piperidin-4-yl)-1H-pyrrolo[2,3-b]pyridin-4-yl]pyridin-2-amine;

4-(4-{6-[(3-fluorobenzyl)oxy]pyrazin-2-yl}-1H-pyrrolo[2,3-b]pyridin-2-yl)-N-methyl-3,6-dihydropyridine-1(2H)-carboxamide;

1-[4-(4-{6-[(3-fluorobenzyl)oxy]pyrazin-2-yl}-1H-pyrrolo[2,3-b]pyridin-2-yl)-3,6-dihydropyridin-1(2H)-yl]-2-hydroxyethanone;

3,5-difluoro-N-(3-fluorobenzyl)-6-{2-[1-(methylsulfonyl)-1,2,3,6-tetrahydropyridin-4-yl]-1H-pyrrolo[2,3-b]pyridin-4-yl}pyridin-2-amine;

4-(4-{3,5-difluoro-6-[(3-fluorobenzyl)amino]pyridin-2-yl}-1H-pyrrolo[2,3-b]pyridin-2-yl)-N-methylpiperidine-1-carboxamide;

1-[4-(4-{3,5-difluoro-6-[(3-fluorobenzyl)amino]pyridin-2-yl}-1H-pyrrolo[2,3-b]pyridin-2-yl)piperidin-1-yl]-2-hydroxyethanone;

4-{4-[6-(benzylamino)pyrazin-2-yl]-1H-pyrrolo[2,3-b]pyridin-2-yl}cyclohex-3-ene-1-carboxylic acid;

4-{4-[6-(benzylamino)pyrazin-2-yl]-1H-pyrrolo[2,3-b]pyridin-2-yl}-N-methylcyclohex-3-ene-1-carboxamide;

4-(4-{6-[(3-fluorobenzyl)amino]pyrazin-2-yl}-1H-pyrrolo[2,3-b]pyridin-2-yl)cyclohex-3-ene-1-carboxylic acid;

4-(4-{6-[(3-fluorobenzyl)oxy]pyrazin-2-yl}-1H-pyrrolo[2,3-b]pyridin-2-yl)cyclohex-3-ene-1-carboxylic acid;

4-(4-{6-[(3-fluorobenzyl)oxy]pyrazin-2-yl}-1H-pyrrolo[2,3-b]pyridin-2-yl)-N-methylcyclohex-3-ene-1-carboxamide;

4-(4-{6-[(3-fluorobenzyl)oxy]pyrazin-2-yl}-1H-pyrrolo[2,3-b]pyridin-2-yl)cyclohex-3-ene-1-carboxamide;

4-(4-{6-[(3-fluorobenzyl)amino]pyrazin-2-yl}-1H-pyrrolo[2,3-b]pyridin-2-yl)cyclohex-3-ene-1-carboxamide;

4-{4-[6-(benzylamino)pyrazin-2-yl]-1H-pyrrolo[2,3-b]pyridin-2-yl}cyclohex-3-ene-1-carboxamide;

N-methyl-5-[2-(1,2,3,6-tetrahydropyridin-4-yl)-1H-pyrrolo[2,3-b]pyridin-4-yl]pyridine-2-carboxamide; or a pharmaceutically acceptable salt thereof.

In another aspect, the present invention relates to compounds of Formula (IVa) or a pharmaceutically acceptable salt thereof,

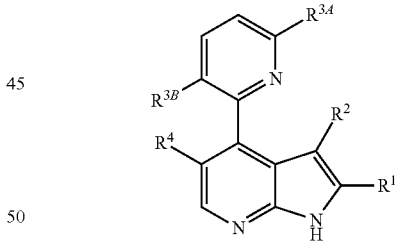

Formula (IVa)

wherein $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, OC(O)NH₂, OC(O)NHR⁵, OC(O)N(R⁵)₂, OC(O) NHSO₂R⁵, OC(O)NR⁵SO₂R⁵, C(O)NH₂, C(O)NHR⁵, C(O)N(R⁵)₂, C(O)NHOH, C(O)NHOR⁵, C(O) NHSO₂R⁵, C(O)NR⁵SO₂R⁵, SO₂NH₂, SO₂NHR⁵, SO₂N(R⁵)₂, OSO₂NH₂, OSO₂NHR⁵, OSO₂N(R⁵)₂, C(O)NHCN, C(O)NR⁵CN, S(O)(N)R⁵, S(O)(N) R⁵SO₂R⁵, C(O)H, C(O)OH, (O), OH, CN, NO₂, F, Cl, Br and I;

R² is selected from the group consisting of hydrogen, C₁-C₄ alkyl, NO₂, CN, C(O)NH₂, C(O)OR²·⁴, F, Cl, Br, and I;

R²·⁴ is selected from the group consisting of C₁-C₆ alkyl, C₂-C₆ alkenyl, and C₂-C₆ alkynyl;

R³·⁴ and R³·ᴮ, at each occurrence, are each independently selected from the group consisting of H, R⁶, OR⁶, SR⁶, S(O)R⁶, C(O)R⁶, CO(O)R⁶, OC(O)R⁶, OC(O)OR⁶, NH₂, NHR⁶, N(R⁶)₂, NHC(O)R⁶, NR⁶C(O)R⁶, NHS (O)₂ R⁶, NR⁶S(O)₂R⁶, NHC(O)OR⁶, NR⁶C(O)OR⁶, NHC(O)NH₂, NHC(O)NHR⁶, NHC(O)N(R⁶)₂, NR⁶C (O)NHR⁶, NR⁶C(O)N(R⁶)₂, C(O)NH₂, C(O)NHR⁶, C(O)N(R⁶)₂, C(O)NHOH, C(O)NHOR⁶, C(O) NHSO₂R⁶, C(O)NR⁶SO₂R⁶, C(O)H, C(O)OH, (O), OH, CN, NO₂, F, Cl, Br and I;

R⁴ is selected from the group consisting of R⁴·⁴, OR⁴·⁴, C(O)NH₂, CN, F, Cl, Br, and I;

R⁴·⁴ is selected from the group consisting of hydrogen, C₁-C₆ alkyl, C₂-C₆ alkenyl, and C₂-C₆ alkynyl;

R⁵, at each occurrence, is independently selected from the group consisting of C₁-C₈ alkyl, C₂-C₆ alkenyl, C₂-C₆ alkynyl, aryl, heteroaryl, heterocycloalkyl, heterocycloalkenyl, cycloalkyl, and cycloalkenyl; wherein each R⁵ C₁-C₈ alkyl, C₂-C₆ alkenyl, and C₂-C₆ alkynyl is optionally substituted with one or more substituents independently selected from the group consisting of R⁷, OR⁷, SR⁷, S(O)R⁷, SO₂R⁷, C(O)R⁷, CO(O)R⁷, OC(O) R⁷, OC(O)OR⁷, NH₂, NHR⁷, N(R⁷)₂, NHC(O)R⁷, NR⁷C(O)R⁷, NHS(O)₂R⁷, NR⁷S(O)₂R⁷, NHC(O)OR⁷, NR⁷C(O)OR⁷, NHC(O)NH₂, NHC(O)NHR⁷, NHC(O) N(R⁷)₂, NR⁷C(O)NHR⁷, NR⁷C(O)N(R⁷)₂, C(O)NH₂, C(O)NHR⁷, C(O)N(R⁷)₂, C(O)NHOH, C(O)NHOR⁷, C(O)NHSO₂R⁷, C(O)NR⁷SO₂R⁷, SO₂NH₂, SO₂NHR⁷, SO₂N(R⁷)₂, B(OH)₂, C(O)H, C(O)OH, OH, CN, NO₂, F, Cl, Br and I; wherein each R⁵ aryl, cycloalkyl, cycloalkenyl, heteroaryl, heterocycloalkyl, and heterocycloalkenyl is optionally substituted with one or more substituents independently selected from the group consisting of R⁸, OR⁸, SR⁸, S(O)R⁸, SO₂R⁸, C(O)R⁸, CO(O)R⁸, OC(O)R⁸, OC(O)OR⁸, NH₂, NHR⁸, N(R⁸)₂, NHC(O)R⁸, NR⁸C(O)R⁸, NHS(O)₂R⁸, NR⁸S(O)₂R⁸, NHC(O)OR⁸, NR⁸C(O)OR⁸, NHC(O)NH₂, NHC(O) NHR⁸, NHC(O)N(R⁸)₂, NR⁸C(O)NHR⁸, NR⁸C(O)N (R⁸)₂, C(O)NH₂, C(O)NHR⁸, C(O)N(R⁸)₂, C(O) NHOH, C(O)NHOR⁸, C(O)NHSO₂R⁸, C(O) NR⁸SO₂R⁸, SO₂NH₂, SO₂NHR⁸, SO₂N(R⁸)₂, C(O)H, C(O)OH, (O), OH, CN, NO₂, F, Cl, Br and I;

R⁶, at each occurrence, is independently selected from the group consisting of C₁-C₆ alkyl, C₂-C₆ alkenyl, C₂-C₆ alkynyl, phenyl, heteroaryl, heterocycloalkyl, heterocycloalkenyl, cycloalkyl, and cycloalkenyl; wherein each R⁶ C₁-C₆ alkyl, C₂-C₆ alkenyl, and C₂-C₆ alkynyl is optionally substituted with one or more substituents independently selected from the group consisting of R⁹, OR⁹, SR⁹, S(O)R⁹, SO₂R⁹, C(O)R⁹, CO(O)R⁹, OC(O) R⁹, OC(O)OR⁹, NH₂, NHR⁹, N(R⁹)₂, NHC(O)R⁹, NR⁹C(O)R⁹, NHS(O)₂R⁹, NR⁹S(O)₂R⁹, NHC(O)OR⁹, NR⁹C(O)OR⁹, NHC(O)NH₂, NHC(O)NHR⁹, NHC(O) N(R⁹)₂, NR⁹C(O)NHR⁹, NR⁹C(O)N(R⁹)₂, C(O)NH₂, C(O)NHR⁹, C(O)N(R⁹)₂, C(O)NHOH, C(O)NHOR⁹, C(O)NHSO₂R⁹, C(O)NR⁹SO₂R⁹, SO₂NH₂, SO₂NHR⁹, SO₂N(R⁹)₂, C(O)H, C(O)OH, OH, CN, NO₂, F, Cl, Br and I; wherein each R⁶ phenyl, cycloalkyl, cycloalkenyl, heteroaryl, heterocycloalkyl, and heterocycloalkenyl is optionally substituted with one or more substituents independently selected from the group consisting of R¹⁰, OR¹⁰, SR¹⁰, S(O)R¹⁰, SO₂R¹⁰, C(O)R¹⁰, CO(O) R¹⁰, OC(O)R¹⁰, OC(O)OR¹⁰, NH₂, NHR¹⁰, N(R¹⁰)₂, NHC(O)R¹⁰, NR¹⁰C(O)R¹⁰, NHS(O)₂R¹⁰, NR¹⁰S(O)₂ R¹⁰, NHC(O)OR¹⁰, NR¹⁰C(O)OR¹⁰, NHC(O)NH₂, NHC(O)NHR¹⁰, NHC(O)N(R¹⁰)₂, NR¹⁰C(O)NHR¹⁰, NR¹⁰C(O)N(R¹⁰)₂, C(O)NH₂, C(O)NHR¹⁰, C(O)N (R¹⁰)₂, C(O)NHOH, C(O)NHOR¹⁰, C(O)NHSO₂R¹⁰, C(O)NR¹⁰SO₂R¹⁰, SO₂NH₂, SO₂NHR¹⁰, SO₂N(R¹⁰)₂, C(O)H, C(O)OH, (O), OH, CN, NO₂, F, Cl, Br and I;

R⁷, at each occurrence, is independently selected from the group consisting of C₁-C₆ alkyl, C₂-C₆ alkenyl, C₂-C₆ alkynyl, aryl, heteroaryl, heterocycloalkyl, heterocycloalkenyl, cycloalkyl, and cycloalkenyl; wherein each R⁷ C₁-C₆ alkyl, C₂-C₆ alkenyl, and C₂-C₆ alkynyl is optionally substituted with one or more substituents independently selected from the group consisting of R¹³, OR¹³, NH₂, NHR¹³, N(R¹³)₂, C(O)H, C(O)OH, OH, CN, NO₂, F, Cl, Br and I; wherein each R⁷ aryl, cycloalkyl, cycloalkenyl, heteroaryl, heterocycloalkyl, and heterocycloalkenyl is optionally substituted with one or more substituents independently selected from the group consisting of R¹¹, OR¹¹, SR¹¹, S(O)R¹¹, SO₂R¹¹, C(O)R¹¹, CO(O)R¹¹, OC(O)R¹¹, OC(O)OR¹¹, NH₂, NHR¹¹, N(R¹¹)₂, NHC(O)R¹¹, NR¹¹C(O)R¹¹, NHS(O)₂R¹¹, NR¹¹S(O)₂R¹¹, NHC(O)OR¹¹, NR¹¹C (O)OR¹¹, NHC(O)NH₂, NHC(O)NHR¹¹, NHC(O)N (R¹¹)₂, NR¹¹C(O)NHR¹¹, NR¹¹C(O)N(R¹¹)₂, C(O) NH₂, C(O)NHR¹¹, C(O)N(R¹¹)₂, C(O)NHOH, C(O) NHOR¹¹, C(O)NHSO₂R¹¹, C(O)NR¹¹SO₂R¹¹, SO₂NH₂, SO₂NHR¹¹, SO₂N(R¹¹)₂, C(O)H, C(O)OH, (O), OH, CN, NO₂, F, Cl, Br and I;

R⁸, at each occurrence, is independently selected from the group consisting of C₁-C₆ alkyl, C₂-C₆ alkenyl, C₂-C₆ alkynyl, and heterocycloalkyl; wherein each R⁸ C₁-C₆ alkyl, C₂-C₆ alkenyl, and C₂-C₆ alkynyl is optionally substituted with one or more substituents independently selected from the group consisting of aryl, heteroaryl, SO₂R⁸·⁴, C(O)OR⁸·⁴, C(O)NH₂, C(O)NHR⁸·⁴, C(O)N (R⁸·⁴)₂, C(O)NHSO₂R⁸·⁴, C(O)NR⁸·⁴SO₂R⁸·⁴, NH₂, C(O)H, C(O)OH, OH, CN, NO₂, F, Cl, Br and I; wherein each R⁸ heterocycloalkyl is optionally substituted with one or more substituents independently selected from the group consisting of NH₂, C(O)H, C(O)OH, OH, CN, NO₂, F, Cl, Br and I;

R⁸·⁴, at each occurrence, is independently selected from the group consisting of C₁-C₆ alkyl, C₂-C₆ alkenyl, and C₂-C₆ alkynyl;

R⁹, at each occurrence, is independently selected from the group consisting of C₁-C₆ alkyl, C₂-C₆ alkenyl, C₂-C₆ alkynyl, aryl, heteroaryl, heterocycloalkyl, heterocycloalkenyl, cycloalkyl, and cycloalkenyl; wherein each R⁹ aryl, cycloalkyl, cycloalkenyl, heteroaryl, heterocycloalkyl, and heterocycloalkenyl is optionally substituted with one or more substituents independently selected from the group consisting of R¹², OR¹², SR¹², S(O)R¹², SO₂R¹², C(O)R¹², CO(O)R¹², OC(O)R¹², OC(O)OR¹², NH₂, NHR¹², N(R¹²)₂, NHC(O)R¹², NR¹²C(O)R¹², NHS(O)₂R¹², NR¹²S(O)₂R¹², NHC(O) OR¹², NR¹²C(O)OR¹², NHC(O)NH₂, NHC(O)NHR¹², NHC(O)N(R¹²)₂, NR¹²C(O)NHR¹², NR¹²C(O)

$N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $(O)$, $OH$, $CN$, $NO_2$, $F$, $Cl$, $Br$ and $I$;

$R^{10}$, at each occurrence, is independently selected from the group consisting of $C_1$-$C_6$ alkyl, $C_2$-$C_6$ alkenyl, and $C_2$-$C_6$ alkynyl; wherein each $R^{10}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, $OH$, $CN$, $NO_2$, $F$, $Cl$, $Br$ and $I$;

$R^{11}$, at each occurrence, is independently selected from the group consisting of $C_1$-$C_6$ alkyl, $C_2$-$C_6$ alkenyl, $C_2$-$C_6$ alkynyl, aryl, and heteroaryl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $OR^{11A}$, $NH_2$, $NHR^{11A}$, $N(R^{11A})_2$, $C(O)H$, $C(O)OH$, $OH$, $CN$, $NO_2$, $F$, $Cl$, $Br$ and $I$; wherein each $R^{11}$ aryl and heteroaryl is optionally substituted with one or more substituents independently selected from the group consisting of $C_1$-$C_6$ alkyl, $C_1$-$C_6$ haloalkyl, $NH_2$, $C(O)H$, $C(O)OH$, $OH$, $CN$, $NO_2$, $F$, $Cl$, $Br$ and $I$;

$R^{11A}$, at each occurrence, is independently selected from the group consisting of $C_1$-$C_6$ alkyl, $C_2$-$C_6$ alkenyl, and $C_2$-$C_6$ alkynyl;

$R^{12}$, at each occurrence, is independently selected from the group consisting of $C_1$-$C_6$ alkyl, $C_2$-$C_6$ alkenyl, and $C_2$-$C_6$ alkynyl; wherein each $R^{12}$ $C_1$-$C_6$ alkyl, $C_2$-$C_6$ alkenyl, and $C_2$-$C_6$ alkynyl is optionally substituted with one or more substituents independently selected from the group consisting of $NH_2$, $NHR^{14}$, $N(R^{14})_2$, $C(O)H$, $C(O)OH$, $OH$, $CN$, $NO_2$, $F$, $Cl$, $Br$ and $I$;

$R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, cycloalkyl, cycloalkenyl, and heterocycloalkyl, heterocycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of $R^{15}$, $OR^{15}$, $C(O)H$, $C(O)OH$, $OH$, $CN$, $NO_2$, $F$, $Cl$, $Br$ and $I$; wherein each $R^{13}$ aryl, cycloalkyl, cycloalkenyl, heteroaryl, heterocycloalkyl, and heterocycloalkenyl is optionally substituted with one or more substituents independently selected from the group consisting of $R^{16}$, $OR^{16}$, $C(O)H$, $C(O)OH$, $(O)$, $OH$, $CN$, $NO_2$, $F$, $Cl$, $Br$ and $I$;

$R^{14}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl;

$R^{15}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl; wherein each $R^{15}$ $C_1$-$C_6$ alkyl, $C_2$-$C_6$ alkenyl, and $C_2$-$C_6$ alkynyl is optionally substituted with one or more $OCH_3$; and $R^{16}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl.

In one embodiment of Formula (IVa), $R^2$ is selected from the group consisting of hydrogen, $C_1$-$C_4$ alkyl, $NO_2$, $CN$, $C(O)NH_2$, $C(O)OR^{2A}$, $F$, $Cl$, $Br$, and $I$; and $R^{2A}$ is selected from the group consisting of $C_1$-$C_6$ alkyl, $C_2$-$C_6$ alkenyl, and $C_2$-$C_6$ alkynyl. In another embodiment of Formula (IVa), $R^2$ is selected from the group consisting of hydrogen, $F$, $Cl$, $Br$, and $I$. In another embodiment of Formula (IVa), $R^2$ is hydrogen.

In one embodiment of Formula (IVa), $R^4$ is selected from the group consisting of $R^{4A}$, $OR^{4A}$, $C(O)NH_2$, $CN$, $F$, $Cl$, $Br$, and $I$; and $R^{4A}$ is selected from the group consisting of hydrogen, $C_1$-$C_6$ alkyl, $C_2$-$C_6$ alkenyl, and $C_2$-$C_6$ alkynyl. In another embodiment of Formula (IVa), $R^4$ is selected from the group consisting of $R^{4A}$, $F$, $Cl$, $Br$, and $I$; and $R^{4A}$ is hydrogen. In another embodiment of Formula (IVa), $R^4$ is $R^{4A}$; and $R^{4A}$ is hydrogen. In another embodiment of Formula (IVa), $R^4$ is selected from the group consisting of $F$, $Cl$, $Br$, and $I$. In another embodiment of Formula (IVa), $R^4$ is $Cl$.

In one embodiment of Formula (IVa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $S(O)(N)R^5SO_2R^5$, $C(O)H$, $C(O)OH$, $(O)$, $OH$, $CN$, $NO_2$, $F$, $Cl$, $Br$ and $I$. In another embodiment of Formula (IVa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$. In another embodiment of Formula (IVa), $R^1$ is cycloalkyl; wherein the $R^1$ cycloalkyl is optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$. In another embodiment of Formula (IVa), $R^1$ is cycloalkenyl; wherein the $R^1$ cycloalkenyl is optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$. In another embodiment of Formula (IVa), $R^1$ is heterocycloalkyl; wherein the $R^1$ heterocycloalkyl is optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$. In another embodiment of Formula (IVa), $R^1$ heterocycloalkenyl; wherein the $R^1$ heterocycloalkenyl is optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$. In another embodiment of Formula (IVa), $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $S(O)(N)R^5SO_2R^5$, $C(O)H$, $C(O)OH$, $(O)$, $OH$, $CN$, $NO_2$, F, Cl, Br and I. In another embodiment of Formula (IVa), $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$. In another embodiment of Formula (IVa), $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are unsubstituted.

In one embodiment of Formula (IVa), $R^{3A}$ and $R^{3B}$, at each occurrence, are independently selected from the group consisting of H, $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, $(O)$, $OH$, $CN$, $NO_2$, F, Cl, Br and I. In another embodiment of Formula (IVa), $R^{3A}$ and $R^{3B}$, at each occurrence, are independently selected from the group consisting of H, $R^6$, $OR^6$, $NH_2$, $NHR^6$, $N(R^6)_2$, $NHC(O)R^6$, $C(O)NHR^6$, F, and Cl.

In one embodiment of Formula (IVa), $R^{3A}$ is independently selected from the group consisting of $R^6$, $OR^6$, $NH_2$, $NHR^6$, $N(R^6)_2$, $NHC(O)R^6$, $C(O)NHR^6$, F, and Cl; and $R^{3B}$ is independently H, $OR^6$, F, or Cl. In another embodiment of Formula (IVa), $R^{3A}$ is independently selected from the group consisting of $NH_2$, $NHR^6$, $N(R^6)_2$, $NHC(O)R^6$, and $C(O)NHR^6$; and $R^{3B}$ is independently H, $OR^6$, F, or Cl. In another embodiment of Formula (IVa), $R^{3A}$ is $NHR^6$; and $R^{3B}$ is independently H, $OR^6$, F, or Cl.

In one embodiment of Formula (IVa), $R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $B(OH)_2$, $C(O)H$, $C(O)OH$, $OH$, $CN$, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $(O)$, $OH$, $CN$, $NO_2$, F, Cl, Br and I. In another embodiment of Formula (IVa), $R^5$, at each occurrence, is independently $C_1$-$C_8$ alkyl; wherein each $R^5$ $C_1$-$C_8$ alkyl is optionally substituted with one or more OH.

In one embodiment of Formula (IVa), $R^6$, at each occurrence, is independently selected from the group consisting of $C_1$-$C_6$ alkyl, $C_2$-$C_6$ alkenyl, $C_2$-$C_6$ alkynyl, phenyl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $OH$, $CN$, $NO_2$, F, Cl, Br and I; wherein each $R^6$ phenyl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $(O)$, $OH$, $CN$, $NO_2$, F, Cl, Br and I. In another embodiment of Formula (IVa), $R^6$, at each occurrence, is independently selected from the group consisting of $C_1$-$C_6$ alkyl, phenyl, and heteroaryl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of $R^9$, $SR^9$, and $OH$; wherein each $R^6$ phenyl and heteroaryl is optionally substituted with one or more substituents independently selected from the group consisting of $NH_2$, and Cl.

In one embodiment of Formula (IVa), $R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $NH_2$, $NHR^{13}$, $N(R^{13})_2$, $C(O)H$, $C(O)OH$, $OH$, $CN$, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $(O)$, $OH$, $CN$, $NO_2$, F, Cl, Br and I.

In one embodiment of Formula (IVa), $R^8$, at each occurrence, is independently selected from the group consisting of $C_1$-$C_6$ alkyl, $C_2$-$C_6$ alkenyl, $C_2$-$C_6$ alkynyl, and heterocycloalkyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)NR^{8A}SO_2R^{8A}$, $NH_2$, $C(O)H$, $C(O)OH$, OH, CN, $NO_2$, F, Cl, Br and I; wherein each $R^8$ heterocycloalkyl is optionally substituted with one or more substituents independently selected from the group consisting of $NH_2$, $C(O)H$, $C(O)OH$, OH, CN, $NO_2$, F, Cl, Br and I.

In one embodiment of Formula (IVa), $R^{8A}$, at each occurrence, is independently selected from the group consisting of $C_1$-$C_6$ alkyl, $C_2$-$C_6$ alkenyl, and $C_2$-$C_6$ alkynyl.

In one embodiment of Formula (IVa), $R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, (O), OH, CN, $NO_2$, F, Cl, Br and I. In another embodiment of Formula (IVa), $R^9$, at each occurrence, is independently selected from the group consisting of aryl, heteroaryl, heterocycloalkyl, and cycloalkyl; wherein each $R^9$ aryl, cycloalkyl, heteroaryl, and heterocycloalkyl is optionally substituted with one or more substituents independently selected from the group consisting of $R^{12}$, $OR^{12}$, $SO_2R^{12}$, $C(O)R^{12}$, $CO(O)R^{12}$, $CO(O)NH_2$, $SO_2NH_2$, (O), OH, CN, F, and Cl.

In one embodiment of Formula (IVa), $R^{10}$, at each occurrence, is independently selected from the group consisting of $C_1$-$C_6$ alkyl, $C_2$-$C_6$ alkenyl, and $C_2$-$C_6$ alkynyl; wherein each $R^{10}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, OH, CN, $NO_2$, F, Cl, Br and I.

In one embodiment of Formula (IVa), $R^{11}$, at each occurrence, is independently selected from the group consisting of $C_1$-$C_6$ alkyl, $C_2$-$C_6$ alkenyl, $C_2$-$C_6$ alkynyl, aryl, and heteroaryl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $OR^{11A}$, $NH_2$, $NHR^{11A}$, $N(R^{11A})_2$, $C(O)H$, $C(O)OH$, OH, CN, $NO_2$, F, Cl, Br and I; wherein each $R^{11}$ aryl and heteroaryl is optionally substituted with one or more substituents independently selected from the group consisting of $C_1$-$C_6$ alkyl, $C_1$-$C_6$ haloalkyl, $NH_2$, $C(O)H$, $C(O)OH$, OH, CN, $NO_2$, F, Cl, Br and I.

In one embodiment of Formula (IVa), $R^{11A}$, at each occurrence, is independently selected from the group consisting of $C_1$-$C_6$ alkyl, $C_2$-$C_6$ alkenyl, and $C_2$-$C_6$ alkynyl.

In one embodiment of Formula (IVa), $R^{12}$, at each occurrence, is independently selected from the group consisting of $C_1$-$C_6$ alkyl, $C_2$-$C_6$ alkenyl, and $C_2$-$C_6$ alkynyl; wherein each $R^{12}$ $C_1$-$C_6$ alkyl, $C_2$-$C_6$ alkenyl, and $C_2$-$C_6$ alkynyl is optionally substituted with one or more substituents independently selected from the group consisting of $NH_2$, $NHR^{14}$, $N(R^{14})_2$, $C(O)H$, $C(O)OH$, OH, CN, $NO_2$, F, Cl, Br and I. In another embodiment of Formula (IVa), $R^{12}$, at each occurrence, is independently $C_1$-$C_6$ alkyl; wherein each $R^{12}$ $C_1$-$C_6$ alkyl is optionally substituted with one or more substituents independently selected from the group consisting of $N(R^{14})_2$, and $C(O)OH$.

In one embodiment of Formula (IVa), $R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, cycloalkyl, cycloalkenyl, and heterocycloalkyl, heterocycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of $R^{15}$, $OR^{15}$, $C(O)H$, $C(O)OH$, OH, CN, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $R^{16}$, $OR^{16}$, $C(O)H$, $C(O)OH$, (O), OH, CN, $NO_2$, F, Cl, Br and I.

In one embodiment of Formula (IVa), $R^{14}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl. In another embodiment of Formula (IVa), $R^{14}$, at each occurrence, is independently $C_1$-$C_6$ alkyl.

In one embodiment of Formula (IVa), $R^{15}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl; wherein each $R^{15}$ $C_1$-$C_6$ alkyl, $C_2$-$C_6$ alkenyl, and $C_2$-$C_6$ alkynyl is optionally substituted with one or more $OCH_3$.

In one embodiment of Formula (IVa), $R^{16}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl.

In one embodiment of Formula (IVa), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$;

$R^2$ is hydrogen;

$R^{3A}$ and $R^{3B}$, at each occurrence, are each independently selected from the group consisting of H, $R^6$, $OR^6$, $NH_2$, $NHR^6$, $N(R^6)_2$, $NHC(O)R^6$, $C(O)NHR^6$, F, and Cl;

$R^4$ is selected from the group consisting of $R^{4A}$ and Cl;

$R^{4A}$ is hydrogen;

$R^5$, at each occurrence, is independently $C_1$-$C_8$ alkyl; wherein each $R^5$ $C_1$-$C_8$ alkyl, is optionally substituted with one or more OH;

$R^6$, at each occurrence, is independently selected from the group consisting of $C_1$-$C_6$ alkyl, phenyl, and heteroaryl; wherein each $R^6$ $C_1$-$C_6$ alkyl is optionally substituted with one or more substituents independently selected from the group consisting of $R^9$, $SR^9$, and OH; wherein each $R^6$ phenyl and heteroaryl is optionally substituted with one or more substituents independently selected from the group consisting of $NH_2$ and Cl;

$R^9$, at each occurrence, is independently selected from the group consisting of aryl, heteroaryl, heterocycloalkyl and cycloalkyl; wherein each $R^9$ aryl, cycloalkyl, heteroaryl, and heterocycloalkyl is optionally substituted with one or more substituents independently selected from the group consisting of $R^{12}$, $OR^{12}$, $SO_2R^{12}$, $C(O)R^{12}$, $CO(O)R^{12}$, $C(O)NH_2$, $SO_2NH_2$, (O), OH, CN, F, and Cl;

$R^{12}$, at each occurrence, is independently $C_1$-$C_6$ alkyl; wherein each $R^{12}$ $C_1$-$C_6$ alkyl is optionally substituted with one or more substituents independently selected from the group consisting of $N(R^{14})_2$ and C(O)OH; and $R^{14}$, at each occurrence, is independently $C_1$-$C_6$ alkyl.

Still another embodiment pertains to compounds of Formula (IVa), selected from the group consisting of:

5-methoxy-6-[2-(piperidin-3-yl)-1H-pyrrolo[2,3-b]pyridin-4-yl]pyridin-2-amine;
N-benzyl-5-chloro-6-[2-(piperidin-3-yl)-1H-pyrrolo[2,3-b]pyridin-4-yl]pyridin-2-amine;
N-benzyl-5-chloro-6-[2-(1-methylpiperidin-3-yl)-1H-pyrrolo[2,3-b]pyridin-4-yl]pyridin-2-amine;
N-benzyl-6-[2-(1-methylpiperidin-3-yl)-1H-pyrrolo[2,3-b]pyridin-4-yl]pyridin-2-amine;
N-benzyl-5-methoxy-6-[2-(piperidin-3-yl)-1H-pyrrolo[2,3-b]pyridin-4-yl]pyridin-2-amine;
N-benzyl-5-chloro-6-{2-[1-(propan-2-ylsulfonyl)piperidin-3-yl]-1H-pyrrolo[2,3-b]pyridin-4-yl}pyridin-2-amine;
methyl 3-{4-[6-(benzylamino)-3-chloropyridin-2-yl]-1H-pyrrolo[2,3-b]pyridin-2-yl}piperidine-1-carboxylate;
4-(3-methoxypyridin-2-yl)-2-(piperidin-4-yl)-1H-pyrrolo[2,3-b]pyridine;
5-methoxy-6-[2-(piperidin-4-yl)-1H-pyrrolo[2,3-b]pyridin-4-yl]pyridin-2-amine;
4-(6-fluoro-3-methoxypyridin-2-yl)-2-(piperidin-4-yl)-1H-pyrrolo[2,3-b]pyridine;
N-benzyl-5-chloro-6-[2-(piperidin-4-yl)-1H-pyrrolo[2,3-b]pyridin-4-yl]pyridin-2-amine;
5-chloro-N-(3-fluorobenzyl)-6-[2-(piperidin-4-yl)-1H-pyrrolo[2,3-b]pyridin-4-yl]pyridin-2-amine;
5-chloro-6-[2-(piperidin-4-yl)-1H-pyrrolo[2,3-b]pyridin-4-yl]-N-(pyridin-3-ylmethyl)pyridin-2-amine;
5-chloro-N-(4-chlorobenzyl)-6-[2-(piperidin-4-yl)-1H-pyrrolo[2,3-b]pyridin-4-yl]pyridin-2-amine;
5-chloro-N-(2,5-difluorobenzyl)-6-[2-(piperidin-4-yl)-1H-pyrrolo[2,3-b]pyridin-4-yl]pyridin-2-amine;
5-chloro-N-[(5-fluoropyridin-3-yl)methyl]-6-[2-(piperidin-4-yl)-1H-pyrrolo[2,3-b]pyridin-4-yl]pyridin-2-amine;
5-chloro-N-(2-fluorobenzyl)-6-[2-(piperidin-4-yl)-1H-pyrrolo[2,3-b]pyridin-4-yl]pyridin-2-amine;
5-chloro-N-(3,4-difluorobenzyl)-6-[2-(piperidin-4-yl)-1H-pyrrolo[2,3-b]pyridin-4-yl]pyridin-2-amine;
5-chloro-6-[2-(piperidin-4-yl)-1H-pyrrolo[2,3-b]pyridin-4-yl]-N-(pyridin-4-ylmethyl)pyridin-2-amine;
5-chloro-N-[(1-oxidopyridin-3-yl)methyl]-6-[2-(piperidin-4-yl)-1H-pyrrolo[2,3-b]pyridin-4-yl]pyridin-2-amine;
5-chloro-N-(piperidin-4-ylmethyl)-6-[2-(piperidin-4-yl)-1H-pyrrolo[2,3-b]pyridin-4-yl]pyridin-2-amine;
5-chloro-N-(piperidin-3-ylmethyl)-6-[2-(piperidin-4-yl)-1H-pyrrolo[2,3-b]pyridin-4-yl]pyridin-2-amine;
4-(3-chloro-6-phenylpyridin-2-yl)-2-(piperidin-4-yl)-1H-pyrrolo[2,3-b]pyridine;
N-{5-chloro-6-[2-(piperidin-4-yl)-1H-pyrrolo[2,3-b]pyridin-4-yl]pyridin-2-yl}benzamide;
N-benzyl-5-chloro-N-methyl-6-[2-(piperidin-4-yl)-1H-pyrrolo[2,3-b]pyridin-4-yl]pyridin-2-amine;
N-benzyl-5-chloro-N-ethyl-6-[2-(piperidin-4-yl)-1H-pyrrolo[2,3-b]pyridin-4-yl]pyridin-2-amine;
5-chloro-6-[2-(piperidin-4-yl)-1H-pyrrolo[2,3-b]pyridin-4-yl]-N-(tetrahydro-2H-pyran-4-ylmethyl)pyridin-2-amine;
5-chloro-6-[2-(piperidin-4-yl)-1H-pyrrolo[2,3-b]pyridin-4-yl]-N-(tetrahydro-2H-pyran-3-ylmethyl)pyridin-2-amine;
N-benzyl-5-chloro-6-[2-(1-methylpiperidin-4-yl)-1H-pyrrolo[2,3-b]pyridin-4-yl]pyridin-2-amine;
5-chloro-N-[(1S)-1-phenylethyl]-6-[2-(piperidin-4-yl)-1H-pyrrolo[2,3-b]pyridin-4-yl]pyridin-2-amine;
N-benzyl-6-[2-(1-methylpiperidin-4-yl)-1H-pyrrolo[2,3-b]pyridin-4-yl]pyridin-2-amine;
5-chloro-N-(3-fluorobenzyl)-6-[2-(1-methylpiperidin-4-yl)-1H-pyrrolo[2,3-b]pyridin-4-yl]pyridin-2-amine;
4-[6-(benzyloxy)-3-chloropyridin-2-yl]-2-(piperidin-4-yl)-1H-pyrrolo[2,3-b]pyridine;
N-benzyl-5-chloro-6-[2-(pyrrolidin-3-yl)-1H-pyrrolo[2,3-b]pyridin-4-yl]pyridin-2-amine;
5-chloro-6-[2-(pyrrolidin-3-yl)-1H-pyrrolo[2,3-b]pyridin-4-yl]-N-(tetrahydro-2H-pyran-4-ylmethyl)pyridin-2-amine;
N-benzyl-5-chloro-6-[2-(morpholin-2-yl)-1H-pyrrolo[2,3-b]pyridin-4-yl]pyridin-2-amine;
N-benzyl-6-[5-chloro-2-(piperidin-4-yl)-1H-pyrrolo[2,3-b]pyridin-4-yl]pyridin-2-amine;
5-chloro-4-(6-fluoropyridin-2-yl)-2-(piperidin-3-yl)-1H-pyrrolo[2,3-b]pyridine;
N-benzyl-6-[5-chloro-2-(piperidin-3-yl)-1H-pyrrolo[2,3-b]pyridin-4-yl]pyridin-2-amine;
6-[5-chloro-2-(piperidin-3-yl)-1H-pyrrolo[2,3-b]pyridin-4-yl]-N-(tetrahydro-2H-pyran-4-ylmethyl)pyridin-2-amine;
N-benzyl-6-[5-chloro-2-(1-methylpiperidin-3-yl)-1H-pyrrolo[2,3-b]pyridin-4-yl]pyridin-2-amine;
methyl 3-{4-[6-(benzylamino)pyridin-2-yl]-5-chloro-1H-pyrrolo[2,3-b]pyridin-2-yl}piperidine-1-carboxylate;
N-benzyl-6-{5-chloro-2-[1-(propan-2-ylsulfonyl)piperidin-3-yl]-1H-pyrrolo[2,3-b]pyridin-4-yl}pyridin-2-amine;
6-[2-(3-aminocyclohexyl)-5-chloro-1H-pyrrolo[2,3-b]pyridin-4-yl]-N-benzylpyridin-2-amine;
6-[2-(piperidin-4-yl)-1H-pyrrolo[2,3-b]pyridin-4-yl]-N-(tetrahydro-2H-pyran-4-ylmethyl)pyridin-2-amine;
6-[2-(1-methylpiperidin-4-yl)-1H-pyrrolo[2,3-b]pyridin-4-yl]-N-(tetrahydro-2H-pyran-4-ylmethyl)pyridin-2-amine;
6-[2-(1-methylpiperidin-4-yl)-1H-pyrrolo[2,3-b]pyridin-4-yl]-N-(3-phenylpropyl)pyridin-2-amine;
6-[2-(1-methylpiperidin-4-yl)-1H-pyrrolo[2,3-b]pyridin-4-yl]-N-(pyridin-3-ylmethyl)pyridin-2-amine;
6-[2-(1-methylpiperidin-4-yl)-1H-pyrrolo[2,3-b]pyridin-4-yl]-N-[2-(phenylsulfanyl)ethyl]pyridin-2-amine;
N-(cyclopropylmethyl)-6-[2-(1-methylpiperidin-4-yl)-1H-pyrrolo[2,3-b]pyridin-4-yl]pyridin-2-amine;
N-[(2,2-dimethyltetrahydro-2H-pyran-4-yl)methyl]-6-[2-(1-methylpiperidin-4-yl)-1H-pyrrolo[2,3-b]pyridin-4-yl]pyridin-2-amine;
N-benzyl-N-methyl-6-[2-(1-methylpiperidin-4-yl)-1H-pyrrolo[2,3-b]pyridin-4-yl]pyridin-2-amine;
N-(3-chlorobenzyl)-6-[2-(1-methylpiperidin-4-yl)-1H-pyrrolo[2,3-b]pyridin-4-yl]pyridin-2-amine;
N-(2,6-difluorobenzyl)-6-[2-(1-methylpiperidin-4-yl)-1H-pyrrolo[2,3-b]pyridin-4-yl]pyridin-2-amine;
6-[2-(1-methylpiperidin-4-yl)-1H-pyrrolo[2,3-b]pyridin-4-yl]-N-[(1S)-1-phenylethyl]pyridin-2-amine;
N-(1,3-benzodioxol-5-ylmethyl)-6-[2-(1-methylpiperidin-4-yl)-1H-pyrrolo[2,3-b]pyridin-4-yl]pyridin-2-amine;
5-chloro-6-[2-(piperidin-4-yl)-1H-pyrrolo[2,3-b]pyridin-4-yl]pyridin-2-amine;
N-[2-(phenylsulfanyl)ethyl]-6-[2-(piperidin-4-yl)-1H-pyrrolo[2,3-b]pyridin-4-yl]pyridin-2-amine;
5-chloro-6-[2-(1-methylpiperidin-4-yl)-1H-pyrrolo[2,3-b]pyridin-4-yl]pyridin-2-amine;
3-chloro-$N^2$-{5-chloro-6-[2-(1-methylpiperidin-4-yl)-1H-pyrrolo[2,3-b]pyridin-4-yl]pyridin-2-yl}pyridine-2,6-diamine;
5-chloro-6-[2-(1-methylpiperidin-4-yl)-1H-pyrrolo[2,3-b]pyridin-4-yl]-N-(tetrahydro-2H-pyran-4-ylmethyl)pyridin-2-amine;
N-(2-phenylethyl)-6-[2-(piperidin-4-yl)-1H-pyrrolo[2,3-b]pyridin-4-yl]pyridin-2-amine;

N-methyl-6-[2-(1-methylpiperidin-4-yl)-1H-pyrrolo[2,3-b]
   pyridin-4-yl]-N-(2-phenylethyl)pyridin-2-amine;
N-(2-chlorobenzyl)-6-[2-(piperidin-4-yl)-1H-pyrrolo[2,3-b]
   pyridin-4-yl]pyridin-2-amine;
N-(2-chlorobenzyl)-6-[2-(1-methylpiperidin-4-yl)-1H-pyrrolo[2,3-b]pyridin-4-yl]pyridin-2-amine;
N-(2-chlorobenzyl)-N-methyl-6-[2-(1-methylpiperidin-4-yl)-1H-pyrrolo[2,3-b]pyridin-4-yl]pyridin-2-amine;
1-[2-({6-[2-(piperidin-4-yl)-1H-pyrrolo[2,3-b]pyridin-4-yl]pyridin-2-yl}amino)ethyl]pyrrolidin-2-one;
1-[2-(methyl {6-[2-(1-methylpiperidin-4-yl)-1H-pyrrolo[2,3-b]pyridin-4-yl]pyridin-2-yl}amino)ethyl]pyrrolidin-2-one;
6-[2-(1-methylpiperidin-4-yl)-1H-pyrrolo[2,3-b]pyridin-4-yl]-N-(2-phenylethyl)pyridin-2-amine;
1-[2-({6-[2-(1-methylpiperidin-4-yl)-1H-pyrrolo[2,3-b]pyridin-4-yl]pyridin-2-yl}amino)ethyl]pyrrolidin-2-one;
5-chloro-N-(cyclopropylmethyl)-6-[2-(1-methylpiperidin-4-yl)-1H-pyrrolo[2,3-b]pyridin-4-yl]pyridin-2-amine;
N-{4-[2-(dimethylamino)ethoxy]benzyl}-6-[2-(1-methylpiperidin-4-yl)-1H-pyrrolo[2,3-b]pyridin-4-yl]pyridin-2-amine;
5-chloro-N-[(2,2-dimethyltetrahydro-2H-pyran-4-yl)methyl]-6-[2-(1-methylpiperidin-4-yl)-1H-pyrrolo[2,3-b]pyridin-4-yl]pyridin-2-amine;
5-chloro-6-[2-(1-methylpiperidin-4-yl)-1H-pyrrolo[2,3-b]pyridin-4-yl]-N-(pyridin-4-ylmethyl)pyridin-2-amine;
6-[2-(1-methylpiperidin-4-yl)-1H-pyrrolo[2,3-b]pyridin-4-yl]-N-(1H-pyrazol-3-ylmethyl)pyridin-2-amine;
N-(2,3-dihydro-1H-isoindol-5-ylmethyl)-6-[2-(1-methylpiperidin-4-yl)-1H-pyrrolo[2,3-b]pyridin-4-yl]pyridin-2-amine;
6-[2-(1-methylpiperidin-4-yl)-1H-pyrrolo[2,3-b]pyridin-4-yl]-N-[(1-methylpyrrolidin-3-yl)methyl]pyridin-2-amine;
N-(1H-indol-6-ylmethyl)-6-[2-(1-methylpiperidin-4-yl)-1H-pyrrolo[2,3-b]pyridin-4-yl]pyridin-2-amine;
5-chloro-6-[2-(1-methylpiperidin-4-yl)-1H-pyrrolo[2,3-b]pyridin-4-yl]-N-[4-(methylsulfonyl)benzyl]pyridin-2-amine;
4-[({5-chloro-6-[2-(1-methylpiperidin-4-yl)-1H-pyrrolo[2,3-b]pyridin-4-yl]pyridin-2-yl}amino)methyl]benzenesulfonamide;
4-[({5-chloro-6-[2-(1-methylpiperidin-4-yl)-1H-pyrrolo[2,3-b]pyridin-4-yl]pyridin-2-yl}amino)methyl]benzamide;
6-[2-(1-methylpiperidin-4-yl)-1H-pyrrolo[2,3-b]pyridin-4-yl]-N-[2-(morpholin-4-yl)ethyl]pyridin-2-amine;
2-({6-[2-(1-methylpiperidin-4-yl)-1H-pyrrolo[2,3-b]pyridin-4-yl]pyridin-2-yl}amino)ethanol;
5-chloro-6-[2-(1-methylpiperidin-4-yl)-1H-pyrrolo[2,3-b]pyridin-4-yl]-N-(piperidin-4-ylmethyl)pyridin-2-amine;
tert-butyl 3-[({5-chloro-6-[2-(1-methylpiperidin-4-yl)-1H-pyrrolo[2,3-b]pyridin-4-yl]pyridin-2-yl}amino)methyl]pyrrolidine-1-carboxylate;
5-chloro-N-[(1,1-dioxidotetrahydro-2H-thiopyran-4-yl)methyl]-6-[2-(1-methylpiperidin-4-yl)-1H-pyrrolo[2,3-b]pyridin-4-yl]pyridin-2-amine;
{3-[({5-chloro-6-[2-(1-methylpiperidin-4-yl)-1H-pyrrolo[2,3-b]pyridin-4-yl]pyridin-2-yl}amino)methyl]phenoxy}acetic acid;
{4-[({5-chloro-6-[2-(1-methylpiperidin-4-yl)-1H-pyrrolo[2,3-b]pyridin-4-yl]pyridin-2-yl}amino)methyl]phenoxy}acetic acid;
1-{4-[({5-chloro-6-[2-(1-methylpiperidin-4-yl)-1H-pyrrolo[2,3-b]pyridin-4-yl]pyridin-2-yl}amino)methyl]piperidin-1-yl}ethanone;
5-chloro-6-[2-(1-methylpiperidin-4-yl)-1H-pyrrolo[2,3-b]pyridin-4-yl]-N-(4H-1,2,4-triazol-3-ylmethyl)pyridin-2-amine;
5-chloro-6-[2-(1-methylpiperidin-4-yl)-1H-pyrrolo[2,3-b]pyridin-4-yl]-N-[3-(methylsulfonyl)benzyl]pyridin-2-amine;
(3S,5R)-5-[({5-chloro-6-[2-(piperidin-4-yl)-1H-pyrrolo[2,3-b]pyridin-4-yl]pyridin-2-yl}amino)methyl]pyrrolidin-3-ol;
N-benzyl-5-chloro-6-(2-cyclohexyl-1H-pyrrolo[2,3-b]pyridin-4-yl)pyridin-2-amine;
5-chloro-N-{[(2S,4S)-4-fluoropyrrolidin-2-yl]methyl}-6-[2-(piperidin-4-yl)-1H-pyrrolo[2,3-b]pyridin-4-yl]pyridin-2-amine;
5-chloro-N-{[(2S)-4,4-difluoropyrrolidin-2-yl]methyl}-6-[2-(piperidin-4-yl)-1H-pyrrolo[2,3-b]pyridin-4-yl]pyridin-2-amine;
N-benzyl-5-chloro-N-methyl-6-[2-(piperidin-3-yl)-1H-pyrrolo[2,3-b]pyridin-4-yl]pyridin-2-amine;
5-chloro-N-(3,4-difluorobenzyl)-6-[2-(piperidin-3-yl)-1H-pyrrolo[2,3-b]pyridin-4-yl]pyridin-2-amine;
5-chloro-N-(3-fluorobenzyl)-6-[2-(piperidin-3-yl)-1H-pyrrolo[2,3-b]pyridin-4-yl]pyridin-2-amine;
5-chloro-N-(4-fluorobenzyl)-6-[2-(piperidin-3-yl)-1H-pyrrolo[2,3-b]pyridin-4-yl]pyridin-2-amine;
5-chloro-N-(2-fluorobenzyl)-6-[2-(piperidin-3-yl)-1H-pyrrolo[2,3-b]pyridin-4-yl]pyridin-2-amine;
5-chloro-6-[2-(piperidin-3-yl)-1H-pyrrolo[2,3-b]pyridin-4-yl]-N-(pyridin-3-ylmethyl)pyridin-2-amine;
4-[3-chloro-6-(pyridin-3-ylmethoxy)pyridin-2-yl]-2-(piperidin-3-yl)-1H-pyrrolo[2,3-b]pyridine;
5-chloro-N-[(5-fluoropyridin-3-yl)methyl]-6-[2-(piperidin-3-yl)-1H-pyrrolo[2,3-b]pyridin-4-yl]pyridin-2-amine;
N-benzyl-4-fluoro-6-[2-(piperidin-3-yl)-1H-pyrrolo[2,3-b]pyridin-4-yl]pyridin-2-amine;
6-[2-(3-aminocyclohexyl)-1H-pyrrolo[2,3-b]pyridin-4-yl]-N-(3-fluorobenzyl)pyridin-2-amine;
4-(6-fluoropyridin-2-yl)-2-(1,2,3,6-tetrahydropyridin-4-yl)-1H-pyrrolo[2,3-b]pyridine;
4-(6-fluoropyridin-2-yl)-2-[1-(methylsulfonyl)-1,2,3,6-tetrahydropyridin-4-yl]-1H-pyrrolo[2,3-b]pyridine;
N-(2,6-difluorobenzyl)-6-{2-[1-(methylsulfonyl)-1,2,3,6-tetrahydropyridin-4-yl]-1H-pyrrolo[2,3-b]pyridin-4-yl}pyridin-2-amine;
N-(2-chlorobenzyl)-6-{2-[1-(methylsulfonyl)-1,2,3,6-tetrahydropyridin-4-yl]-1H-pyrrolo[2,3-b]pyridin-4-yl}pyridin-2-amine;
N-(cyclopropylmethyl)-6-{2-[1-(methylsulfonyl)-1,2,3,6-tetrahydropyridin-4-yl]-1H-pyrrolo[2,3-b]pyridin-4-yl}pyridin-2-amine;
4-(6-chloro-3-fluoropyridin-2-yl)-2-(piperidin-4-yl)-1H-pyrrolo[2,3-b]pyridine;
3,5-difluoro-N-(3-fluorobenzyl)-6-[2-(piperidin-4-yl)-1H-pyrrolo[2,3-b]pyridin-4-yl]pyridin-2-amine;
3,5-difluoro-N-(3-fluorobenzyl)-6-{2-[1-(methylsulfonyl)-1,2,3,6-tetrahydropyridin-4-yl]-1H-pyrrolo[2,3-b]pyridin-4-yl}pyridin-2-amine;
4-(4-{3,5-difluoro-6-[(3-fluorobenzyl)amino]pyridin-2-yl}-1H-pyrrolo[2,3-b]pyridin-2-yl)-N-methylpiperidine-1-carboxamide;
1-[4-(4-{3,5-difluoro-6[(3-fluorobenzyl)amino]pyridin-2-yl}-1H-pyrrolo[2,3-b]pyridin-2-yl)piperidin-1-yl]-2-hydroxyethanone; or a pharmaceutically acceptable salt thereof.

In another aspect, the present invention relates to compounds of Formula (Va) or a pharmaceutically acceptable salt thereof,

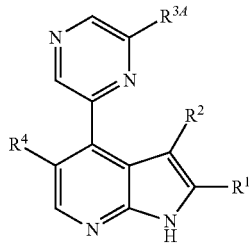

Formula (Va)

wherein

R¹ is selected from the group consisting of cycloalkyl, cycloalkenyl, heterocycloalkyl, and heterocycloalkenyl; wherein the R¹ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $S(O)(N)R^5SO_2R^5$, $C(O)H$, $C(O)OH$, (O), OH, CN, $NO_2$, F, Cl, Br and I;

R² is selected from the group consisting of hydrogen, $C_1$-$C_4$ alkyl, $NO_2$, CN, $C(O)NH_2$, $C(O)OR^{2A}$, F, Cl, Br, and I;

$R^{2A}$ is selected from the group consisting of $C_1$-$C_6$ alkyl, $C_2$-$C_6$ alkenyl, and $C_2$-$C_6$ alkynyl;

$R^{3A}$ is independently selected from the group consisting of H, $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, (O), OH, CN, $NO_2$, F, Cl, Br and I;

R⁴ is selected from the group consisting of $R^{4A}$, $OR^{4A}$, $C(O)NH_2$, CN, F, Cl, Br, and I;

$R^{4A}$ is selected from the group consisting of hydrogen, $C_1$-$C_6$ alkyl, $C_2$-$C_6$ alkenyl, and $C_2$-$C_6$ alkynyl;

R⁵, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)$ $N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $B(OH)_2$, $C(O)H$, $C(O)OH$, OH, CN, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, (O), OH, CN, $NO_2$, F, Cl, Br and I;

R⁶, at each occurrence, is independently selected from the group consisting of $C_1$-$C_6$ alkyl, $C_2$-$C_6$ alkenyl, $C_2$-$C_6$ alkynyl, phenyl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, CN, $NO_2$, F, Cl, Br and I; wherein each $R^6$ phenyl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{16}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, (O), OH, CN, $NO_2$, F, Cl, Br and I;

R⁷, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $NH_2$, $NHR^{13}$, $N(R^{13})_2$, $C(O)H$, $C(O)OH$, OH, CN, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, (O), OH, CN, $NO_2$, F, Cl, Br and I;

R⁸, at each occurrence, is independently selected from the group consisting of $C_1$-$C_6$ alkyl, $C_2$-$C_6$ alkenyl, $C_2$-$C_6$ alkynyl, and heterocycloalkyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)NR^{8A}SO_2R^{8A}$, $NH_2$, $C(O)H$, $C(O)OH$, $OH$, $CN$, $NO_2$, $F$, $Cl$, $Br$ and $I$; wherein each $R^8$ heterocycloalkyl is optionally substituted with one or more substituents independently selected from the group consisting of $NH_2$, $C(O)H$, $C(O)OH$, $OH$, $CN$, $NO_2$, $F$, $Cl$, $Br$ and $I$;

$R^{8A}$, at each occurrence, is independently selected from the group consisting of $C_1$-$C_6$ alkyl, $C_2$-$C_6$ alkenyl, and $C_2$-$C_6$ alkynyl;

$R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $(O)$, $OH$, $CN$, $NO_2$, $F$, $Cl$, $Br$ and $I$;

$R^{10}$, at each occurrence, is independently selected from the group consisting of $C_1$-$C_6$ alkyl, $C_2$-$C_6$ alkenyl, and $C_2$-$C_6$ alkynyl; wherein each $R^{10}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, $OH$, $CN$, $NO_2$, $F$, $Cl$, $Br$ and $I$;

$R^{11}$, at each occurrence, is independently selected from the group consisting of $C_1$-$C_6$ alkyl, $C_2$-$C_6$ alkenyl, $C_2$-$C_6$ alkynyl, aryl, and heteroaryl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $OR^{11A}$, $NH_2$, $NHR^{11A}$, $N(R^{11A})_2$, $C(O)H$, $C(O)OH$, $OH$, $CN$, $NO_2$, $F$, $Cl$, $Br$ and $I$; wherein each $R^{11}$ aryl and heteroaryl is optionally substituted with one or more substituents independently selected from the group consisting of $C_1$-$C_6$ alkyl, $C_1$-$C_6$ haloalkyl, $NH_2$, $C(O)H$, $C(O)OH$, $OH$, $CN$, $NO_2$, $F$, $Cl$, $Br$ and $I$;

$R^{11A}$, at each occurrence, is independently selected from the group consisting of $C_1$-$C_6$ alkyl, $C_2$-$C_6$ alkenyl, and $C_2$-$C_6$ alkynyl;

$R^{12}$, at each occurrence, is independently selected from the group consisting of $C_1$-$C_6$ alkyl, $C_2$-$C_6$ alkenyl, and $C_2$-$C_6$ alkynyl; wherein each $R^{12}$ $C_1$-$C_6$ alkyl, $C_2$-$C_6$ alkenyl, and $C_2$-$C_6$ alkynyl is optionally substituted with one or more substituents independently selected from the group consisting of $NH_2$, $NHR^{14}$, $N(R^{14})_2$, $C(O)H$, $C(O)OH$, $OH$, $CN$, $NO_2$, $F$, $Cl$, $Br$ and $I$;

$R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, cycloalkyl, cycloalkenyl, and heterocycloalkyl, heterocycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of $R^{15}$, $OR^{15}$, $C(O)H$, $C(O)OH$, $OH$, $CN$, $NO_2$, $F$, $Cl$, $Br$ and $I$; wherein each $R^{13}$ aryl, cycloalkyl, cycloalkenyl, heteroaryl, heterocycloalkyl, and heterocycloalkenyl is optionally substituted with one or more substituents independently selected from the group consisting of $R^{16}$, $OR^{16}$, $C(O)H$, $C(O)OH$, $(O)$, $OH$, $CN$, $NO_2$, $F$, $Cl$, $Br$ and $I$;

$R^{14}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl;

$R^{15}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl; wherein each $R^{15}$ $C_1$-$C_6$ alkyl, $C_2$-$C_6$ alkenyl, and $C_2$-$C_6$ alkynyl is optionally substituted with one or more $OCH_3$; and $R^{16}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl.

In one embodiment of Formula (Va), $R^2$ is selected from the group consisting of hydrogen, $C_1$-$C_4$ alkyl, $NO_2$, $CN$, $C(O)NH_2$, $C(O)OR^{2A}$, $F$, $Cl$, $Br$, and $I$; and $R^{2A}$ is selected from the group consisting of $C_1$-$C_6$ alkyl, $C_2$-$C_6$ alkenyl, and $C_2$-$C_6$ alkynyl. In another embodiment of Formula (Va), $R^2$ is selected from the group consisting of hydrogen, $F$, $Cl$, $Br$, and $I$. In another embodiment of Formula (Va), $R^2$ is hydrogen.

In one embodiment of Formula (Va), $R^4$ is selected from the group consisting of $R^{4A}$, $OR^{4A}$, $C(O)NH_2$, $CN$, $F$, $Cl$, $Br$, and $I$; and $R^{4A}$ is selected from the group consisting of hydrogen, $C_1$-$C_6$ alkyl, $C_2$-$C_6$ alkenyl, and $C_2$-$C_6$ alkynyl. In another embodiment of Formula (Va), $R^4$ is selected from the group consisting of $R^{4A}$, $F$, $Cl$, $Br$, and $I$; and $R^{4A}$ is hydrogen. In another embodiment of Formula (Va), $R^4$ is $R^{4A}$; and $R^{4A}$ is hydrogen. In another embodiment of Formula (Va), $R^4$ is selected from the group consisting of $F$, $Cl$, $Br$, and $I$. In another embodiment of Formula (Va), $R^4$ is $Cl$.

In one embodiment of Formula (Va), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $S(O)(N)R^5SO_2R^5$, $C(O)H$, $C(O)OH$, $(O)$, $OH$, $CN$, $NO_2$, $F$, $Cl$, $Br$ and $I$. In another embodiment of Formula (Va), $R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$. In another embodiment of Formula (Va), $R^1$ is cycloalkyl; wherein the $R^1$ cycloalkyl is optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$. In another embodiment of Formula (Va), $R^1$ is cycloalkenyl; wherein the $R^1$ cycloalkenyl is optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$. In another embodiment of Formula (Va), $R^1$ is heterocycloalkyl; wherein the $R^1$ heterocycloalkyl is optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$. In another embodiment of Formula (Va), $R^1$ heterocycloalkenyl; wherein the $R^1$ heterocycloalkenyl is optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$. In another embodiment of Formula (Va), $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $S(O)(N)R^5SO_2R^5$, $C(O)H$, $C(O)OH$, (O), OH, CN, $NO_2$, F, Cl, Br and I. In another embodiment of Formula (Va), $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$. In another embodiment of Formula (Va), $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are unsubstituted.

In one embodiment of Formula (Va), $R^{3,4}$ is independently selected from the group consisting of H, $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, (O), OH, CN, $NO_2$, F, Cl, Br and I. In another embodiment of Formula (Va), $R^{3,4}$ is independently selected from the group consisting of H, $R^6$, $OR^6$, $NH_2$, $NHR^6$, $N(R^6)_2$, $NHC(O)R^6$, $C(O)NHR^6$, F, and Cl.

In one embodiment of Formula (Va), $R^{3,4}$ is independently selected from the group consisting of $R^6$, $OR^6$, $NH_2$, $NHR^6$, $N(R^6)_2$, $NHC(O)R^6$, $C(O)NHR^6$, F, and Cl. In another embodiment of Formula (Va), $R^{3,4}$ is independently selected from the group consisting of $NH_2$, $NHR^6$, $N(R^6)_2$, $NHC(O)R^6$, and $C(O)NHR^6$. In another embodiment of Formula (Va), $R^{3,4}$ is $NHR^6$.

In one embodiment of Formula (Va), $R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $B(OH)_2$, $C(O)H$, $C(O)OH$, OH, CN, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, (O), OH, CN, $NO_2$, F, Cl, Br and I. In another embodiment of Formula (Va), $R^5$, at each occurrence, is independently $C_1$-$C_8$ alkyl; wherein each $R^5$ $C_1$-$C_8$ alkyl is optionally substituted with one or more OH.

In one embodiment of Formula (Va), $R^6$, at each occurrence, is independently selected from the group consisting of $C_1$-$C_6$ alkyl, $C_2$-$C_6$ alkenyl, $C_2$-$C_6$ alkynyl, phenyl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, CN, $NO_2$, F, Cl, Br and I; wherein each $R^6$ phenyl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, (O), OH, CN, $NO_2$, F, Cl, Br and I. In another embodiment of Formula (Va), $R^6$, at each occurrence, is independently selected from the group consisting of $C_1$-$C_6$ alkyl, phenyl, and heteroaryl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of $R^9$, $SR^9$, and OH; wherein each $R^6$ phenyl and heteroaryl is optionally substituted with one or more substituents independently selected from the group consisting of $NH_2$, and Cl.

In one embodiment of Formula (Va), $R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $NH_2$, $NHR^{13}$, $N(R^{13})_2$, C(O)H, C(O)OH, OH, CN, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^{11}$, $OR^{11}$, $SR^{11}$, $S(O)R^{11}$, $SO_2R^{11}$, $C(O)R^{11}$, CO(O)$R^{11}$, $OC(O)R^{11}$, $OC(O)OR^{11}$, $NH_2$, $NHR^{11}$, $N(R^{11})_2$, NHC(O)$R^{11}$, $NR^{11}C(O)R^{11}$, $NHS(O)_2R^{11}$, $NR^{11}S(O)_2R^{11}$, NHC(O)$OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, C(O)NHOH, C(O)N-$HOR^{11}$, $C(O)NHSO_2R^{11}$, $C(O)NR^{11}SO_2R^{11}$, $SO_2NH_2$, $SO_2NHR^{11}$, $SO_2N(R^{11})_2$, C(O)H, C(O)OH, (O), OH, CN, $NO_2$, F, Cl, Br and I.

In one embodiment of Formula (Va), $R^8$, at each occurrence, is independently selected from the group consisting of $C_1$-$C_6$ alkyl, $C_2$-$C_6$ alkenyl, $C_2$-$C_6$ alkynyl, and heterocycloalkyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)NR^{8A}SO_2R^{8A}$, $NH_2$, C(O)H, C(O)OH, OH, CN, $NO_2$, F, Cl, Br and I; wherein each $R^8$ heterocycloalkyl is optionally substituted with one or more substituents independently selected from the group consisting of $NH_2$, C(O)H, C(O)OH, OH, CN, $NO_2$, F, Cl, Br and I.

In one embodiment of Formula (Va), $R^{8A}$, at each occurrence, is independently selected from the group consisting of $C_1$-$C_6$ alkyl, $C_2$-$C_6$ alkenyl, and $C_2$-$C_6$ alkynyl.

In one embodiment of Formula (Va), $R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, C(O)NHOH, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, C(O)H, C(O)OH, (O), OH, CN, $NO_2$, F, Cl, Br and I. In another embodiment of Formula (Va), $R^9$, at each occurrence, is independently selected from the group consisting of aryl, heteroaryl, heterocycloalkyl, and cycloalkyl; wherein each $R^9$ aryl, cycloalkyl, heteroaryl, and heterocycloalkyl is optionally substituted with one or more substituents independently selected from the group consisting of $R^{12}$, $OR^{12}$, $SO_2R^{12}$, $C(O)R^{12}$, $CO(O)R^{12}$, $C(O)NH_2$, $SO_2NH_2$, (O), OH, CN, F, and Cl.

In one embodiment of Formula (Va), $R^{10}$, at each occurrence, is independently selected from the group consisting of $C_1$-$C_6$ alkyl, $C_2$-$C_6$ alkenyl, and $C_2$-$C_6$ alkynyl; wherein each $R^{10}$ $C_1$-$C_6$ alkyl, $C_2$-$C_6$ alkenyl, and $C_2$-$C_6$ alkynyl is optionally substituted with one or more substituents independently selected from the group consisting of $NH_2$, C(O)H, C(O)OH, OH, CN, $NO_2$, F, Cl, Br and I.

In one embodiment of Formula (Va), $R^{11}$, at each occurrence, is independently selected from the group consisting of $C_1$-$C_6$ alkyl, $C_2$-$C_6$ alkenyl, $C_2$-$C_6$ alkynyl, aryl, and heteroaryl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $OR^{11A}$, $NH_2$, $NHR^{11A}$, $N(R^{11A})_2$, C(O)H, C(O)OH, OH, CN, $NO_2$, F, Cl, Br and I; wherein each $R^{11}$ aryl and heteroaryl is optionally substituted with one or more substituents independently selected from the group consisting of $C_1$-$C_6$ alkyl, $C_1$-$C_6$ haloalkyl, $NH_2$, C(O)H, C(O)OH, OH, CN, $NO_2$, F, Cl, Br and I.

In one embodiment of Formula (Va), $R^{11A}$, at each occurrence, is independently selected from the group consisting of $C_1$-$C_6$ alkyl, $C_2$-$C_6$ alkenyl, and $C_2$-$C_6$ alkynyl.

In one embodiment of Formula (Va), $R^{12}$, at each occurrence, is independently selected from the group consisting of $C_1$-$C_6$ alkyl, $C_2$-$C_6$ alkenyl, and $C_2$-$C_6$ alkynyl; wherein each $R^{12}$ $C_1$-$C_6$ alkyl, $C_2$-$C_6$ alkenyl, and $C_2$-$C_6$ alkynyl is optionally substituted with one or more substituents independently selected from the group consisting of $NH_2$, $NHR^{14}$, $N(R^{14})_2$, C(O)H, C(O)OH, OH, CN, $NO_2$, F, Cl, Br and I. In another embodiment of Formula (Va), $R^{12}$, at each occurrence, is independently $C_1$-$C_6$ alkyl; wherein each $R^{12}$ $C_1$-$C_6$ alkyl is optionally substituted with one or more substituents independently selected from the group consisting of $N(R^{14})_2$, and C(O)OH.

In one embodiment of Formula (Va), $R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, cycloalkyl, cycloalkenyl, and heterocycloalkyl, heterocycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of $R^{15}$, $OR^{15}$, C(O)H, C(O)OH, OH, CN, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $R^{16}$, $OR^{16}$, C(O)H, C(O)OH, (O), OH, CN, $NO_2$, F, Cl, Br and I.

In one embodiment of Formula (Va), $R^{14}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl. In another embodiment of Formula (Va), $R^{14}$, at each occurrence, is independently $C_1$-$C_6$ alkyl.

In one embodiment of Formula (Va), $R^{15}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl; wherein each $R^{15}$ $C_1$-$C_6$ alkyl, $C_2$-$C_6$ alkenyl, and $C_2$-$C_6$ alkynyl is optionally substituted with one or more $OCH_3$.

In one embodiment of Formula (Va), $R^{16}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl.

In one embodiment of Formula (Va),
$R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and C(O)OH;

R² is hydrogen;

R³·⁴ is independently selected from the group consisting of H, R⁶, OR⁶, NH₂, NHR⁶, N(R⁶)₂, NHC(O)R⁶, C(O)NHR⁶, F, and Cl;

R⁴ is selected from the group consisting of R⁴·⁴ and Cl;

R⁴·⁴ is hydrogen;

R⁵, at each occurrence, is independently C₁-C₈ alkyl; wherein each R⁵ C₁-C₈ alkyl, is optionally substituted with one or more OH;

R⁶, at each occurrence, is independently selected from the group consisting of C₁-C₆ alkyl, phenyl, and heteroaryl; wherein each R⁶ C₁-C₆ alkyl is optionally substituted with one or more substituents independently selected from the group consisting of R⁹, SR⁹, and OH; wherein each R⁶ phenyl and heteroaryl is optionally substituted with one or more substituents independently selected from the group consisting of NH₂ and Cl;

R⁹, at each occurrence, is independently selected from the group consisting of aryl, heteroaryl, heterocycloalkyl and cycloalkyl; wherein each R⁹ aryl, cycloalkyl, heteroaryl, and heterocycloalkyl is optionally substituted with one or more substituents independently selected from the group consisting of R¹², OR¹², SO₂R¹², C(O)R¹², CO(O)R¹², C(O)NH₂, SO₂NH₂, (O), OH, CN, F, and Cl;

R¹², at each occurrence, is independently C₁-C₆ alkyl; wherein each R¹² C₁-C₆ alkyl is optionally substituted with one or more substituents independently selected from the group consisting of N(R¹⁴)₂ and C(O)OH; and R¹⁴, at each occurrence, is independently C₁-C₆ alkyl.

Still another embodiment pertains to compounds of Formula (Va), selected from the group consisting of:

N-benzyl-6-{2-[1-(methylsulfonyl)piperidin-4-yl]-1H-pyrrolo[2,3-b]pyridin-4-yl}pyrazin-2-amine;
N-benzyl-6-[2-(piperidin-4-yl)-1H-pyrrolo[2,3-b]pyridin-4-yl]pyrazin-2-amine;
6-[2-(piperidin-4-yl)-1H-pyrrolo[2,3-b]pyridin-4-yl]-N-(tetrahydro-2H-pyran-4-ylmethyl)pyrazin-2-amine;
N-(3,5-difluorobenzyl)-6-[2-(piperidin-4-yl)-1H-pyrrolo[2,3-b]pyridin-4-yl]pyrazin-2-amine;
N-(3-fluorobenzyl)-6-[2-(piperidin-4-yl)-1H-pyrrolo[2,3-b]pyridin-4-yl]pyrazin-2-amine;
6-[2-(piperidin-4-yl)-1H-pyrrolo[2,3-b]pyridin-4-yl]-N-(pyridin-3-ylmethyl)pyrazin-2-amine;
6-[2-(piperidin-4-yl)-1H-pyrrolo[2,3-b]pyridin-4-yl]-N-(pyridin-4-ylmethyl)pyrazin-2-amine;
N-(3,4-difluorobenzyl)-6-[2-(piperidin-4-yl)-1H-pyrrolo[2,3-b]pyridin-4-yl]pyrazin-2-amine;
1-[4-(4-{6-[(3,5-difluorobenzyl)amino]pyrazin-2-yl}-1H-pyrrolo[2,3-b]pyridin-2-yl)piperidin-1-yl]-2-hydroxyethanone;
1-[4-(4-{6-[(3-fluorobenzyl)amino]pyrazin-2-yl}-1H-pyrrolo[2,3-b]pyridin-2-yl)piperidin-1-yl]-2-hydroxyethanone;
1-(4-{4-[6-(benzylamino)pyrazin-2-yl]-1H-pyrrolo[2,3-b]pyridin-2-yl}piperidin-1-yl)-2-hydroxyethanone;
N-benzyl-N-methyl-6-[2-(1-methylpiperidin-4-yl)-1H-pyrrolo[2,3-b]pyridin-4-yl]pyrazin-2-amine;
N-benzyl-6-[2-(1-methylpiperidin-4-yl)-1H-pyrrolo[2,3-b]pyridin-4-yl]pyrazin-2-amine;
1-(4-{4-[6-(benzylamino)pyrazin-2-yl]-1H-pyrrolo[2,3-b]pyridin-2-yl}piperidin-1-yl)ethanone;
3-(4-{4-[6-(benzylamino)pyrazin-2-yl]-1H-pyrrolo[2,3-b]pyridin-2-yl}piperidin-1-yl)propane-1,2-diol;
ethyl[(4-{4-[6-(benzylamino)pyrazin-2-yl]-1H-pyrrolo[2,3-b]pyridin-2-yl}piperidin-1-yl)sulfonyl]carbamate;
4-{6-[(3-fluorobenzyl)oxy]pyrazin-2-yl}-2-(piperidin-4-yl)-1H-pyrrolo[2,3-b]pyridine;
N-(3-fluorobenzyl)-6-[2-(1-methylpiperidin-4-yl)-1H-pyrrolo[2,3-b]pyridin-4-yl]pyrazin-2-amine;
1-[4-(4-{6-[(3-fluorobenzyl)amino]pyrazin-2-yl}-1H-pyrrolo[2,3-b]pyridin-2-yl)piperidin-1-yl]ethanone;
4-{6-[(3-fluorobenzyl)oxy]pyrazin-2-yl}-2-(1-methylpiperidin-4-yl)-1H-pyrrolo[2,3-b]pyridine;
N-benzyl-6-[2-(1,2,3,6-tetrahydropyridin-4-yl)-1H-pyrrolo[2,3-b]pyridin-4-yl]pyrazin-2-amine;
1-[4-(4-{6-[(3-fluorobenzyl)oxy]pyrazin-2-yl}-1H-pyrrolo[2,3-b]pyridin-2-yl)piperidin-1-yl]-2-hydroxyethanone;
3-[4-(4-{6-[(3-fluorobenzyl)oxy]pyrazin-2-yl}-1H-pyrrolo[2,3-b]pyridin-2-yl)piperidin-1-yl]propane-1,2-diol;
ethyl {[4-(4-{6-[(3-fluorobenzyl)amino]pyrazin-2-yl}-1H-pyrrolo[2,3-b]pyridin-2-yl)piperidin-1-yl]sulfonyl}carbamate;
4-{4-[6-(benzylamino)pyrazin-2-yl]-1H-pyrrolo[2,3-b]pyridin-2-yl}-N-methylpiperidine-1-carboxamide;
4-(4-{6-[(3-fluorobenzyl)amino]pyrazin-2-yl}-1H-pyrrolo[2,3-b]pyridin-2-yl)-N-methylpiperidine-1-carboxamide;
4-{6-[(3-fluorobenzyl)oxy]pyrazin-2-yl}-2-[1-(methylsulfonyl)piperidin-4-yl]-1H-pyrrolo[2,3-b]pyridine;
1-[4-(4-{6-[(3-fluorobenzyl)oxy]pyrazin-2-yl}-1H-pyrrolo[2,3-b]pyridin-2-yl)piperidin-1-yl]ethanone;
4-(4-{6-[(3-fluorobenzyl)oxy]pyrazin-2-yl}-1H-pyrrolo[2,3-b]pyridin-2-yl)-N-methylpiperidine-1-carboxamide;
1-[4-{4-[6-(benzylamino)pyrazin-2-yl]-1H-pyrrolo[2,3-b]pyridin-2-yl}-3,6-dihydropyridin-1(2H)-yl]-2-hydroxyethanone;
N-(3-fluorobenzyl)-6-[2-(1,2,3,6-tetrahydropyridin-4-yl)-1H-pyrrolo[2,3-b]pyridin-4-yl]pyrazin-2-amine;
3-[4-(4-{6-[(3-fluorobenzyl)amino]pyrazin-2-yl}-1H-pyrrolo[2,3-b]pyridin-2-yl)-3,6-dihydropyridin-1(2H)-yl]propane-1,2-diol;
4-{6-[(3-fluorobenzyl)oxy]pyrazin-2-yl}-2-(1,2,3,6-tetrahydropyridin-4-yl)-1H-pyrrolo[2,3-b]pyridine;
4-(4-{6-[(3-fluorobenzyl)amino]pyrazin-2-yl}-1H-pyrrolo[2,3-b]pyridin-2-yl)-N-methyl-3,6-dihydropyridine-1(2H)-carboxamide;
6-[2-(1-methylpiperidin-4-yl)-1H-pyrrolo[2,3-b]pyridin-4-yl]-N-(pyridin-3-ylmethyl)pyrazin-2-amine;
3-[4-(4-{6-[(pyridin-3-ylmethyl)amino]pyrazin-2-yl}-1H-pyrrolo[2,3-b]pyridin-2-yl)piperidin-1-yl]propane-1,2-diol;
2-hydroxy-1-[4-(4-{6-[(pyridin-3-ylmethyl)amino]pyrazin-2-yl}-1H-pyrrolo[2,3-b]pyridin-2-yl)piperidin-1-yl]ethanone;
N-methyl-4-(4-{6-[(pyridin-3-ylmethyl)amino]pyrazin-2-yl}-1H-pyrrolo[2,3-b]pyridin-2-yl)piperidine-1-carboxamide;
1-[4-(4-{6-[(3-fluorobenzyl)amino]pyrazin-2-yl}-1H-pyrrolo[2,3-b]pyridin-2-yl)-3,6-dihydropyridin-1(2H)-yl]-2-hydroxyethanone;
4-{6-[(3-fluorobenzyl)oxy]pyrazin-2-yl}-2-[1-(methylsulfonyl)-1,2,3,6-tetrahydropyridin-4-yl]-1H-pyrrolo[2,3-b]pyridine;
4-(4-{6-[(3-fluorobenzyl)oxy]pyrazin-2-yl}-1H-pyrrolo[2,3-b]pyridin-2-yl)-N-methyl-3,6-dihydropyridine-1(2H)-carboxamide;
1-[4-(4-{6-[(3-fluorobenzyl)oxy]pyrazin-2-yl}-1H-pyrrolo[2,3-b]pyridin-2-yl)-3,6-dihydropyridin-1(2H)-yl]-2-hydroxyethanone;
4-{4-[6-(benzylamino)pyrazin-2-yl]-1H-pyrrolo[2,3-b]pyridin-2-yl}cyclohex-3-ene-1-carboxylic acid;
4-{4-[6-(benzylamino)pyrazin-2-yl]-1H-pyrrolo[2,3-b]pyridin-2-yl}-N-methylcyclohex-3-ene-1-carboxamide;

4-(4-{6-[(3-fluorobenzyl)amino]pyrazin-2-yl}-1H-pyrrolo[2,3-b]pyridin-2-yl)cyclohex-3-ene-1-carboxylic acid;

4-(4-{6-[(3-fluorobenzyl)oxy]pyrazin-2-yl}-1H-pyrrolo[2,3-b]pyridin-2-yl)cyclohex-3-ene-1-carboxylic acid;

4-(4-{6-[(3-fluorobenzyl)oxy]pyrazin-2-yl}-1H-pyrrolo[2,3-b]pyridin-2-yl)-N-methylcyclohex-3-ene-1-carboxamide;

4-(4-{6-[(3-fluorobenzyl)oxy]pyrazin-2-yl}-1H-pyrrolo[2,3-b]pyridin-2-yl)cyclohex-3-ene-1-carboxamide;

4-(4-{6-[(3-fluorobenzyl)amino]pyrazin-2-yl}-1H-pyrrolo[2,3-b]pyridin-2-yl)cyclohex-3-ene-1-carboxamide;

4-{4-[6-(benzylamino)pyrazin-2-yl]-1H-pyrrolo[2,3-b]pyridin-2-yl}cyclohex-3-ene-1-carboxamide; or a pharmaceutically acceptable salt thereof.

In another aspect, the present invention relates to pharmaceutical compositions comprising a pharmaceutically acceptable excipient and a therapeutically effective amount of a compound of Formula (IIIa) or a pharmaceutically acceptable salt thereof.

In another aspect, the present invention relates to methods of treating cancer in a patient, comprising administering to a patient suffering from a cancer a therapeutically effective amount of a compound of Formula (IIIa), or a pharmaceutically acceptable salt thereof. In certain embodiments, the cancer is selected from the group consisting of acoustic neuroma, acute leukemia, acute lymphoblastic leukemia, acute myelogenous leukemia, acute t-cell leukemia, basal cell carcinoma, bile duct carcinoma, bladder cancer, brain cancer, breast cancer, bronchogenic carcinoma, Burkitt's lymphoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, dysplasias, metaplasias, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer, lymphangioendothelio-sarcoma, lymphangiosarcoma, lymphoblastic leukemia, lymphoma, malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung cancer, solid tumors, stomach cancer, squamous cell carcinoma, synovioma, sweat gland carcinoma, testicular cancer, thyroid cancer, Waldenström's macroglobulinemia, testicular tumors, uterine cancer, and Wilms' tumor. In certain embodiments, the methods further comprise administering a therapeutically effective amount of at least one additional therapeutic agent.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula I. In certain embodiments, the compound of formula I may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula I can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula I may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds of formula I, or pharmaceutically acceptable salts thereof, and pharmaceutical compositions comprising a compound of formula I, or a pharmaceutically acceptable salt thereof, can be administered to a subject suffering from a CDK9-mediated disorder or condition. A "CDK9-mediated disorder or condition" is characterized by the participation of one or more CDK9 kinases in the inception, manifestation of one or more symptoms or disease markers, severity, or progression of a disorder or condition. An example of a CDK9-mediated disorder or condition is cancer, including cancers such as, not limited to, acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

The term "administering" or "administered" refers to the method of contacting a compound with a subject. Thus, the compounds of formula I can be administered by injection, that is, intravenously, intramuscularly, intracutaneously, subcutaneously, intraduodenally, parentally, or intraperitoneally. In certain embodiments, a compound of formula I may be administered orally. Also, the compounds described herein can be administered by inhalation, for example, intranasally. Additionally, the compounds of formula I can be administered transdermally, topically, via implantation, transdermally, topically, and via implantation. In certain embodiments, the compounds of the formula I may be delivered orally. The compounds can also be delivered rectally, bucally, intravaginally, ocularly, andially, or by insufflation. CDK9-mediated disorders and conditions can be treated prophylactically, acutely, and chronically using compounds of formula I, depending on the nature of the disorder or condition. Typically, the host or subject in each of these methods is human, although other mammals can also benefit from the administration of a compound of formula I.

The compounds of formula I can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 bifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Schemes and Experimentals

The following abbreviations have the meanings indicated. ADDP means 1,1'-(azodicarbonyl)dipiperidine; AD-mix-β means a mixture of (DHQD)$_2$PHAL, K$_3$Fe(CN)$_6$, K$_2$CO$_3$, and K$_2$SO$_4$; 9-BBN means 9-borabicyclo(3.3.1)nonane; Boc means tert-butoxycarbonyl; (DHQD)$_2$PHAL means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-BH$_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; and PPh$_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

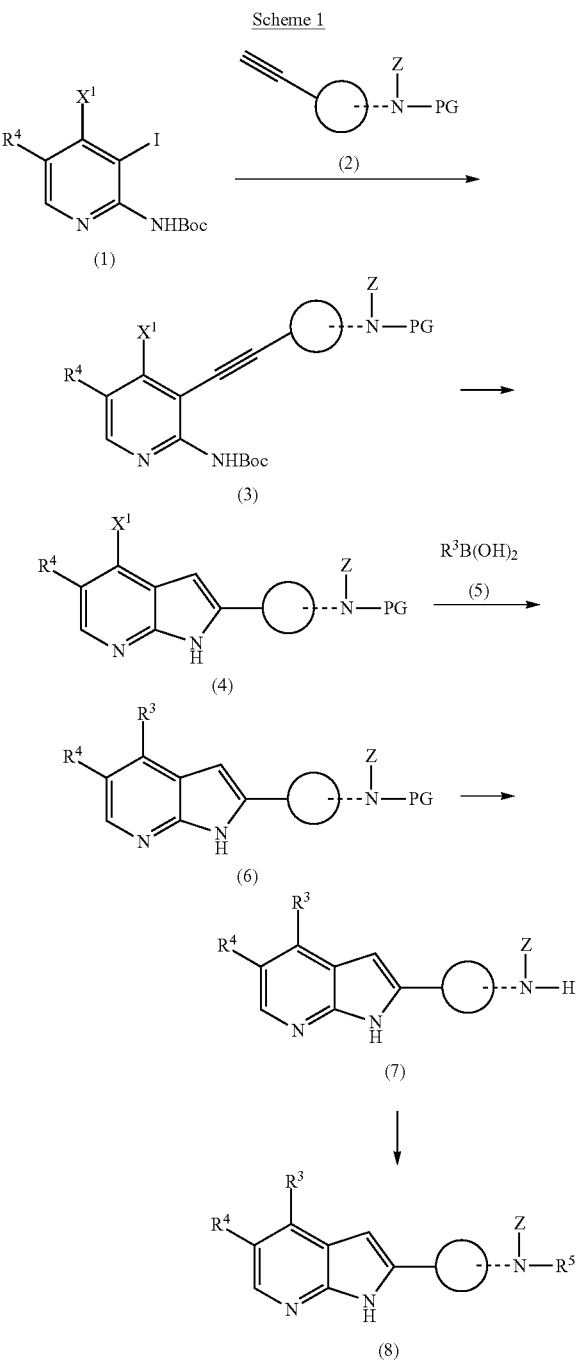

Scheme 1

As shown in Scheme 1, compounds of formula (3) can be prepared by reacting compounds of formula (1), wherein $X^1$ is Br or Cl, $R^4$ is as described for Formula (I) herein and BOC is tert-butoxycarbonyl, with compounds of formula (2), wherein ◯ is a carbocycle or heterocycle with --- indicating the N can be within the ring (Z is absent) or outside of the ring (Z is H) and PG is a suitable protecting group, in the presence of copper (I) iodide, a catalyst such as, but not limited to, bis(triphenylphosphine)palladium(II) chloride, and a base such as, but not limited to, triethylamine. The reaction is typically performed at room temperature in a solvent such as, but not limited to, tetrahydrofuran. Compounds of formula (3) can be reacted with potassium tert-butoxide in the presence of 18-crown-6 to provide compounds of formula (4).

The reaction is typically performed at an elevated temperature (e.g., 60-110° C.) in a solvent such as, but not limited to, toluene. Compounds of formula (4) can be reacted with a boronic acid of formula (5), wherein $R^3$ is

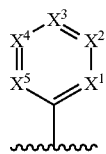

as described herein for Formula (IIIa), under Suzuki coupling reaction conditions (N. Miyama and A. Suzuki, Chem. Rev. 1995, 95:2457-2483, J. Organomet. Chem. 1999, 576:147-148) to provide compounds of formula (6). For example, the coupling reaction may be conducted in the presence of a palladium catalyst and a base, and optionally in the presence of a ligand, and in a suitable solvent at elevated temperature (about 80° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), bis(triphenylphosphine)palladium(II) dichloride, and palladium(II)acetate. Examples of suitable bases that may be employed include, but not limited to, carbonates or phosphates of sodium, potassium, and cesium, acetates of sodium or potassium, and cesium fluoride. Examples of suitable ligands include, but are not limited to, 1,3,5,7-tetramethyl-6-phenyl-2,4,8-trioxa-6-phosphaadamante, 2-dicyclohexylphosphino-2',4',6'-triisopropylbiphenyl (X-phos), and 1,1'-bis(diphenylphosphanyl) ferrocene. Non-limiting examples of suitable solvent include methanol, ethanol, dimethoxyethane, N,N-dimethylformamide, dimethylsulfoxide, dioxane, tetrahydropyran, and water, or a mixture thereof.

Compounds of formula (7), which are representative of compounds of Formula (IIIa), can be prepared by deprotecting compounds of formula (6) under conditions described herein (e.g. with an acid such as hydrochloric acid in a solvent such as ethanol or ethyl acetate or trifluoroacetic acid in a solvent such as dichloromethane). Compounds of formula (8), which are representative of compounds of Formula (IIIa) and wherein $R^5$ is as described herein in Formula (IIIa), can be prepared from compounds of formula (7) by various processes such as alkylation under reductive amination conditions using an appropriate ketone or aldehyde; acylation using an appropriate acid chloride or other activated carboxylic acid; sulfonation using an appropriate sulfonyl chloride; carboxamidation using an appropriate activated carbamate; and sulfonamidation using an appropriate sulfonylamide.

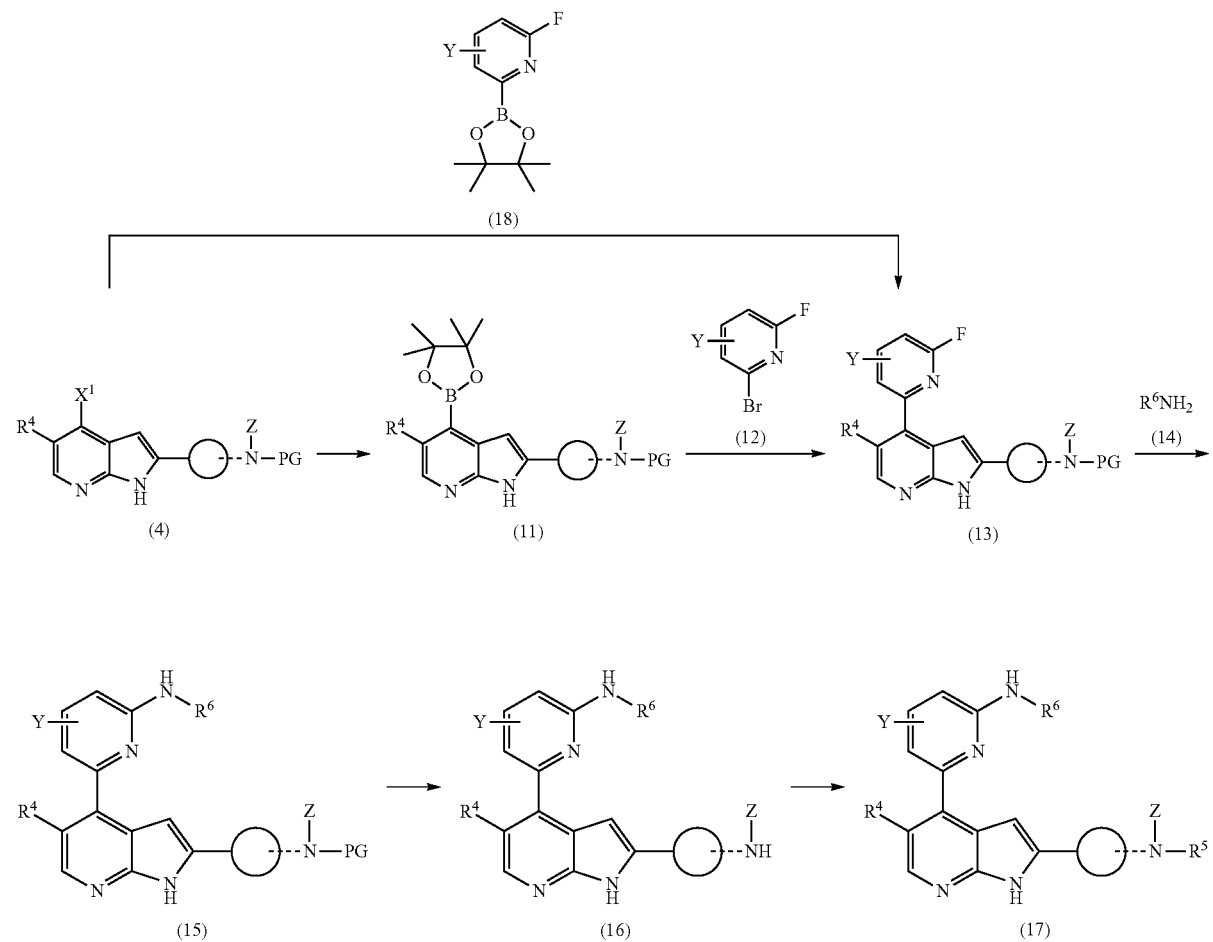

Scheme 2

Compounds of formula (4) can be reacted with potassium acetate and 4,4,4',4',5,5,5',5'-octamethyl-2,2'-bi(1,3,2-dioxaborolane) in the presence of a catalyst such as, but not limited to, palladium acetate, and a ligand such as, but not limited to, 2-dicyclohexylphosphino)biphenyl to provide compounds of formula (11). The reaction is typically performed at an elevated temperature (e.g., 100-110° C.) in a solvent such as, but not limited to, 1,4-dioxane. Compounds of formula (13) can be prepared by reacting compounds of formula (11) with compounds of formula (12), wherein Y is $R^{3A}$ as described in Formula (IIIa) herein, under Suzuki Coupling reaction conditions described above in Scheme 1. Alternatively, compounds of formula (4) can be reacted with compounds of formula (18), wherein Y is $R^{3A}$ as described in Formula (IIIa) herein under Suzuki Coupling reaction conditions to provide compounds of formula (13). Compounds of formula (15) can be prepared by reacting compounds of formula (13) with compounds of formula (14) wherein $R^6$ is as described herein for Formula (IIIa). The reaction is typically performed at an elevated temperature (e.g., 100-110° C.). Compounds of formula (16), which are representative of compounds of Formula (IIIa), can be prepared by deprotecting compounds of formula (15) under conditions described herein and known to those skilled in the art and readily available in the literature as described above in Scheme 1. Compounds of formula (17), which are representative of compounds of Formula (IIIa) and wherein $R^5$ is as described herein in Formula (IIIa), can be prepared from compounds of formula (16) as described above in Scheme 1.

Compounds of formula (11) can be reacted with compounds of formula (19), wherein $R^3$ is as described in Scheme 1 and $X^n$ is an appropriate halide or triflate, under Suzuki Coupling reaction conditions described above in Scheme 1 to provide compounds of formula (20). Compounds of formula (21), which are representative of compounds of Formula (IIIa), can be prepared by deprotecting compounds of formula (20) under conditions described herein and as described above in Scheme 1. Compounds of formula (23), which are representative of compounds of Formula (IIIa) and wherein $R^5$ is as described herein in Formula (IIIa), can be prepared from compounds of formula (21) by various processes known to those skilled in the art and described herein.

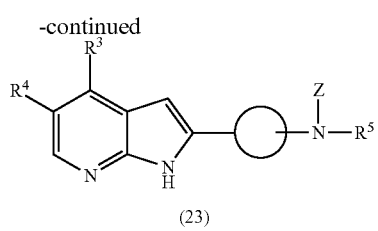

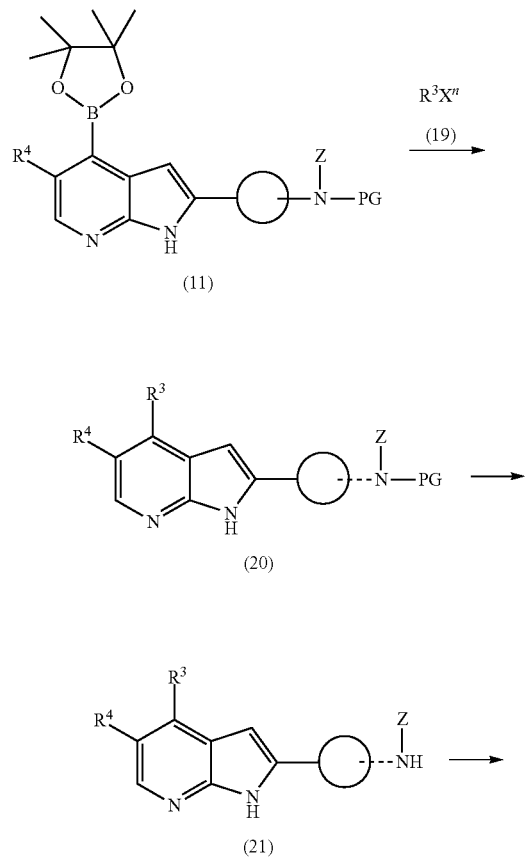

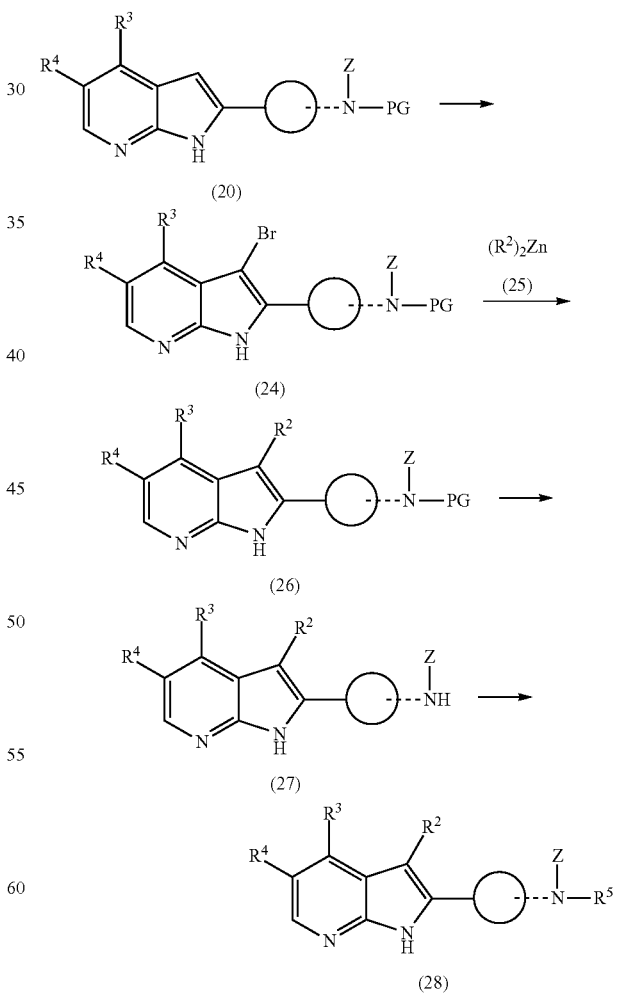

As shown in Scheme 4, compounds of formula (20), wherein $R^3$ is as described in Scheme 1, can be reacted with N-bromosuccinimide to provide compounds of formula (24).

The addition is typically performed at low temperature before warming up to ambient temperature in a solvent such as, but not limited to, N,N-dimethylformamide. Compounds of formula (26) can be prepared reacting compounds of formula (24) with compounds of formula (25) wherein $R^2$ is as described herein, in the presence of a catalyst such as, but not limited to, [1,1'-bis(diphenylphosphino)ferrocene]dichloropalladium(II), dichloromethane adduct. The reaction is typically performed at an elevated temperature (e.g., 100° C.) in a solvent such as, but not limited to, 1,4-dioxane. Compounds of formula (27), which are representative of compounds of Formula (IIIa), can be prepared can be prepared by deprotecting compounds of formula (26) as described above in Scheme 1. Compounds of formula (28), which are representative of compounds of Formula (IIIa) and wherein $R^5$ is as described herein in Formula (IIIa), can be prepared from compounds of formula (27) as described above in Scheme 1

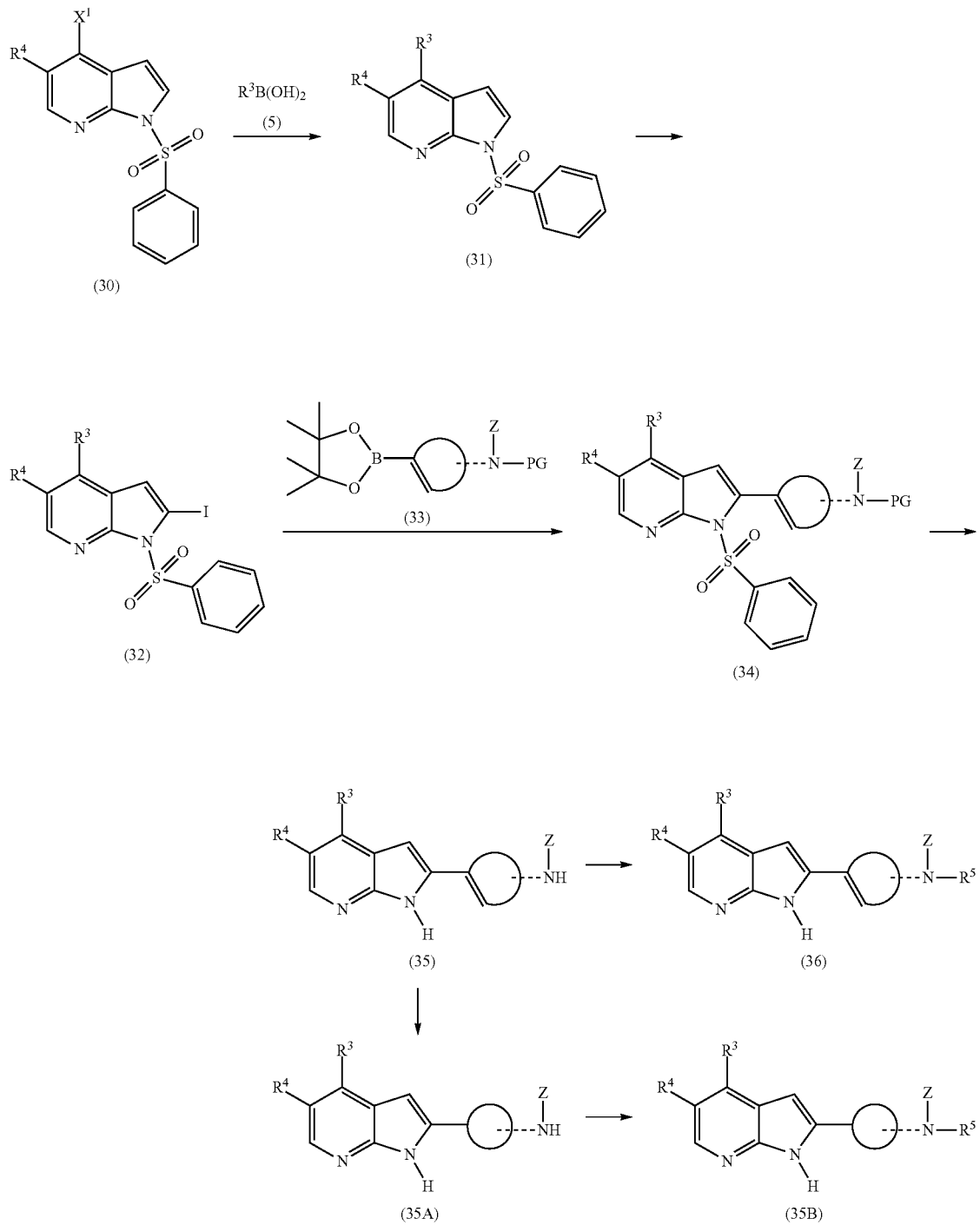

Scheme 5

Compounds of formula (30), wherein $X^1$ is Cl or Br, $R^4$ is as described for Formula (I) herein, can be reacted with compounds of formula (5) under Suzuki Coupling reaction conditions described above in Scheme 1 to provide compounds of formula (31). Compounds of formula (31) can be treated with lithium diisopropylamide at low temperature followed by iodine to provide compounds of formula (32). The reaction is typically performed in a solvent such as, but not limited to, tetrahydrofuran, heptane, ethylbenzene, or mixtures thereof. Compounds of formula (32) can be reacted with compounds of formula (33) wherein ◯ is a cycloalkenyl or heterocycloakenyl ring with ------ indicating the N can be within the ring (Z is absent) or outside of the ring (Z is H) and PG is a suitable protecting group, under Suzuki Coupling reaction conditions described above in Scheme 1 to provide compounds of formula (34). Compounds of formula (34) can be reacted with sodium hydroxide in dioxane at an elevated temperature (e.g., 80-90° C.) followed by deprotection as described above in Scheme 1 to provide compounds of formula (35) which are representative of compounds of Formula (IIIa). Compounds of formula (36), which are representative of compounds of Formula (IIIa) and wherein $R^5$ is as described herein in Formula (IIIa), can be prepared from compounds of formula (35) by various processes known to those skilled in the art and described herein.

Alternatively, as shown in Scheme 5, compounds of formula (35) can be treated with palladium hydroxide on carbon in the presence of hydrogen gas to provide compounds of formula (35A) which are representative of compounds of Formula (IIIa). The reaction is typically performed at an elevated temperature (e.g., 50° C.) in a solvent such as but not limited to ethanol. Compounds of formula (35B), which are representative of compounds of Formula (IIIa) and wherein $R^5$ is as described herein in Formula (IIIa), can be prepared from compounds of formula (35A) by various processes known to those skilled in the art and described herein.

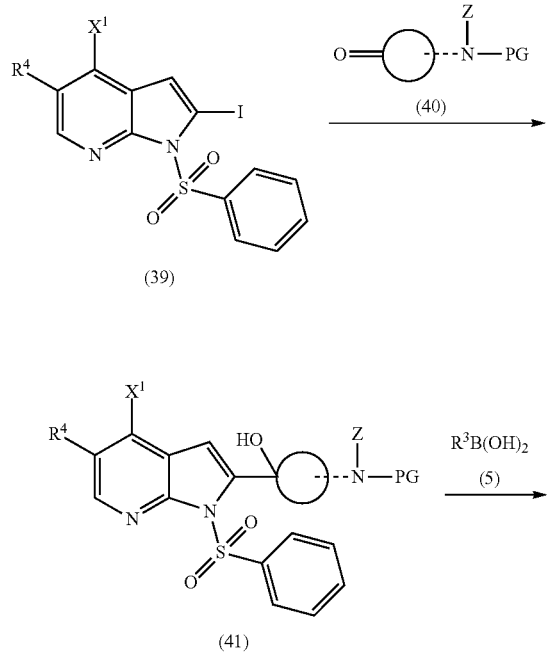

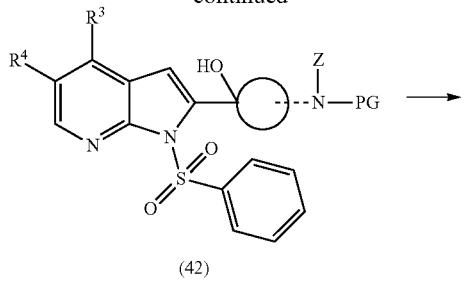

As shown in Scheme 6, compounds of formula (39) can be treated with n-butyllithium followed by compounds of formula (40), wherein ◯ is a carbocycle or heterocycle with ------ indicating the N can be within the ring (X is absent) or outside of the ring (X is H) and PG is a suitable protecting group, to provide compounds of formula (41). The reaction is typically performed at low temperature in a solvent such as, but not limited to, tetrahydrofuran, hexanes, or mixtures thereof. Compounds of formula (42) can be prepared by reacting compounds of formula (41) with compounds of formula (5) under Suzuki Coupling reaction conditions described above in Scheme 1. Compounds of formula (42) can be treated with aqueous sodium hydroxide in a solvent such as dioxane to provide compounds of formula (43). Compounds of formula (44), which are representative of compounds of Formula (IIIa), can be prepared can be prepared by deprotecting compounds of formula (43) as described above in Scheme 1. Compounds of formula (45), which are representative of compounds of Formula (IIIa) and wherein $R^5$ is as described herein in Formula (IIIa), can be prepared from compounds of formula (44) by various processes as described above in Scheme 1.

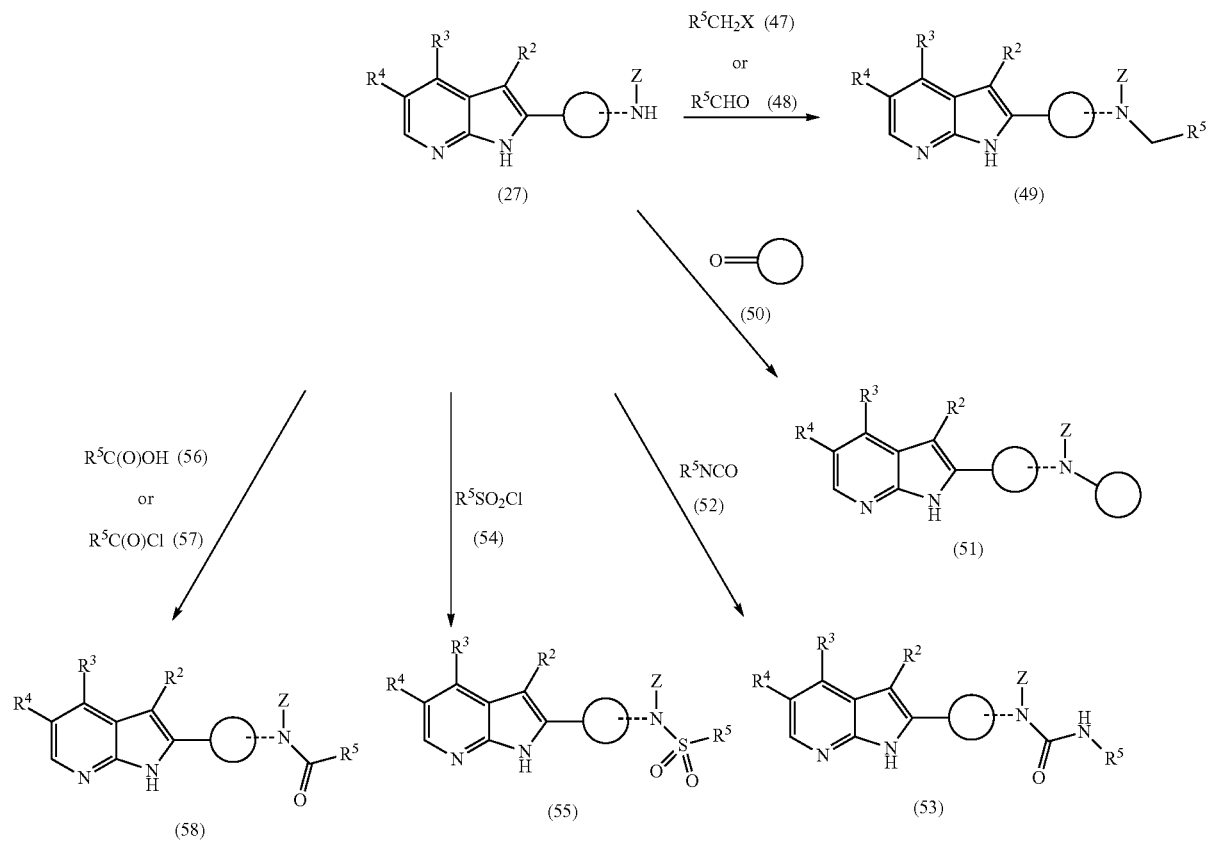

Scheme 7

Compounds of formula (49), which are representative of compounds of Formula (IIIa), can be prepared by reacting compounds of formula (27), wherein $R^3$ is as described in Scheme 1, with compounds of formula (47) or (48) under appropriate alkylation or reductive amination conditions. Compounds of formula (51), which are representative of compounds of Formula (IIIa), can be prepared by reacting compounds of formula (27) with compounds of the formula (50) under appropriate reductive amination conditions. Compounds of formula (53), which are representative of compounds of Formula (IIIa), can be prepared by reacting compounds of formula (27) with compounds of formula (52) under appropriate urea formation conditions. Compounds of formula (55), which are representative of compounds of Formula (IIIa), can be prepared by reacting compounds of formula (27) with compounds of formula (54) under appropriate sulfonamidation conditions. Compounds of formula (58), which are representative of compounds of Formula (IIIa), can be prepared by reacting compounds of formula (27) with compounds of formula (56) or formula (57) under appropriate acylation conditions.

EXPERIMENTALS

The following examples are presented to provide what is believed to be the most useful and readily understood description of procedures and conceptual aspects of this invention. Each exemplified compound and intermediate was named using ACD/ChemSketch 2012 Release ((Build 59026, 3 Sep. 2012), Advanced Chemistry Development Inc., Toronto, Ontario), or ChemDraw® Ver. 9.0.7 (CambridgeSoft, Cambridge, Mass.).

Example 1

4-(5-fluoro-2-methoxyphenyl)-2-(piperidin-3-yl)-1H-pyrrolo[2,3-b]pyridine

Example 1A tert-butyl (4-chloro-3-iodopyridin-2-yl)carbamate tert-Butyl (4-chloropyridin-2-yl)carbamate (10 g, 43.7 mmol) and tetramethylethylenediamine (12 mL) in anhydrous tetrahydrofuran (200 mL) was cooled to −70° C. and treated dropwise with a solution of 2.5M n-butyllithium (52 mL, 131 mmol) in hexane over a period of 30 minutes. The mixture was stirred at −70° C. for 1 hour and treated dropwise with a solution of iodine (27 g, 109 mmol) in anhydrous tetrahydrofuran at −70° C. After the addition, the mixture was stirred at the −70° C. for 30 minutes and was allowed to warm to room temperature. The mixture was treated with saturated sodium hydrogensulfite solution (200 mL) and stirred for 30 minutes. The mixture was extracted with ethyl acetate (100×3 mL) and the organic layer was washed with water and brine solution (200 mL each) and dried over anhydrous sodium sulfate. Filtration and concentration under vacuum and recrystallization with ethyl acetate-hexane afforded the title compound. LCMS: 298.9 (M+H—NCOOH)$^+$.

Example 1B tert-butyl 3-(hydroxymethyl)piperidine-1-carboxylate

To a solution of piperidin-3-ylmethanol (5 g, 43.4 mmol) in dichloromethane (100 mL) was added di-tert-butyldicarbonate (11.09 mL, 47.8 mmol) at 0° C. and the mixture was stirred at room temperature for 12 hours. The mixture was concentrated under vacuum to afford the crude product which was purified by column chromatography (silica gel, 40% ethyl acetate in hexane) to afford the title compound.

Example 1C tert-Butyl 3-formylpiperidine-1-carboxylate

To a solution of Example 1B (5 g, 23.22 mmol) in dichloromethane (50 mL) was added pyridinium chlorochromate (10.01 g, 46.4 mmol) and the mixture was stirred for 12 hours. The mixture was filtered and concentrated to afford crude product which was purified by column chromatography (silica gel, 40% ethyl acetate in hexane) to afford the title compound. $^1$H NMR (300 MHz, CDCl$_3$): δ 1.44 (s, 9H), 1.5-1.54 (m, 1H), 1.66-1.69 (m, 2H), 1.9-2.0 (m, 1H), 2.38-2.46 (m, 1H), 3.04-3.12 (m, 1H), 2.38-3.36 (m, 1H), 3.6-3.68 (m, 1H), 3.88-4.0 (m, 1H), 9.7 (s, 1H).

Example 1D tert-Butyl 3-ethynylpiperidine-1-carboxylate

To solution of Example 1C (2 g, 9.38 mmol) in methanol (20 mL) was added potassium carbonate (3.89 g, 28.1 mmol) and the mixture was stirred for 30 minutes. Dimethyl 1-diazo-2-oxopropylphosphonate (3.60 g, 18.76 mmol) was added and the mixture was stirred for 12 hours. The mixture was filtered through diatomaceous earth and concentrated to afford crude material which was purified by column chromatography (silica gel, 15% ethyl acetate in hexane) to afford the title compound. $^1$H NMR (300 MHz, CDCl$_3$): δ 1.41 (s, 9H), 1.55-1.59 (m, 1H), 1.67-1.69 (m, 2H), 1.96-1.99 (m, 1H), 2.06-2.07 (m, 1H), 2.43-2.44 (m, 1H), 2.93-3.02 (m, 2H), 3.69-3.75 (m, 1H), 3.9-4.0 (m, 1H).

Example 1E tert-Butyl 3-((2-(((tert-butoxycarbonyl)amino)-4-chloropyridin-3-yl)ethynyl)piperidine-1-carboxylate To a degassed solution of product of Example 1A (2.033 g, 5.73 mmol) in tetrahydrofuran (15 mL) was added copper (I) iodide (46 mg, 0.239 mmol) and bis(triphenylphosphine)palladium(II) chloride (168 mg, 0.239 mmol) followed by triethylamine (1.998 mL, 14.33 mmol) and Example 1D (1 g, 4.78 mmol). The mixture was stirred for 12 hours at room temperature, filtered through diatomaceous earth, and washed with ethyl acetate. The combined organic layers were washed with water and brine (50 mL each) and were dried over sodium sulfate. Concentration afforded crude product which was purified by column chromatography (silica gel, 15% ethyl acetate in hexane) to afford the title compound. LCMS: 436.2 (M+H)

Example 1F tert-butyl 3-(4-chloro-1H-pyrrolo[2,3-b]pyridin-2-yl)piperidine-1-carboxylate To a solution of product of Example 1E (250 mg, 0.573 mmol) in toluene (5 mL) was added potassium tert-butoxide (161 mg, 1.434 mmol) followed by 18-crown-6 (15 mg, 0.057 mmol) and the mixture was heated at 65° C. for 12 hours. The mixture was dissolved in ethyl acetate (25 mL), washed with water and brine, and dried over anhydrous sodium sulfate. Filtration followed by concentration of the filtrate afforded crude product which was purified by column chromatography (silica gel, 40% ethyl acetate in hexane) to afford the title compound. LCMS: 336.0 (M+H-Boc)$^+$.

Example 1G tert-Butyl 3-(4-(5-fluoro-2-methoxyphenyl)-1H-pyrrolo[2,3-b]pyridin-2-yl)piperidine-1-carboxylate To Example 1F (150 mg, 0.447 mmol) in 1,4-dioxane (6 mL) was added cesium carbonate (437 mg, 1.340 mmol) followed by 5-fluoro-2-methoxyphenylboronic acid (114 mg, 0.670 mmol). The mixture was degassed with nitrogen and tricyclohexylphosphine (6.26 mg, 0.022 mmol) and bis(triphenylphosphine)palladium(II) chloride (16 mg, 0.022 mmol) were added. The mixture was heated at 100° C. for 2 hours, diluted with ethyl acetate, and filtered through diatomaceous earth. The organic layer was washed with water and brine (50 mL each) and dried over sodium sulfate. Filtration and concentration afforded crude product which was purified by column chromatography (silica gel, 40% ethyl acetate in hexane) to afford the title compound. LCMS: 514.2 (M+H)$^+$.

Example 1H

4-(5-fluoro-2-methoxyphenyl)-2-(piperidin-3-yl)-1H-pyrrolo[2,3-b]pyridine

To Example 1G (100 mg, 0.235 mmol) in dichloromethane (2 mL) was added hydrogen chloride in ethyl acetate (2 mL, 0.235 mmol) and the mixture was stirred for 2 hours. Concentration afforded crude product which was purified by preparative HPLC (Zorbax XDB C-18 (32) column with gradient elution from 0.1% trifluoroacetic acid in water to 1:1 methanol/acetonitrile) to afford the title compound as the trifluoroacetate salt. LCMS: 326.1 (M+H)$^+$. $^1$H NMR (400 MHz, DMSO-d$_6$): δ 1.74-1.76 (m, 2H), 1.92 (s, 1H), 2.12-2.16 (m, 1H), 3.13-3.20 (m, 2H), 3.55-3.57 (m, 3H), 3.76 (s, 1H), 6.13 (d, 1.6 Hz, 1H), 7.10 (d, J=4.8 Hz, 1H), 7.22-7.25 (m, 2H), 7.29-7.32 (m, 1H), 8.23 (d, J=5.2 Hz, 1H), 8.6-8.7 (m, 1H), 11.9 (s, 1H).

Example 2

4-(4-fluoro-2-methoxyphenyl)-2-(piperidin-3-yl)-1H-pyrrolo[2,3-b]pyridine

Example 2A tert-Butyl 3-(4-(4-fluoro-2-methoxyphenyl)-1H-pyrrolo[2,3-b]pyridin-2-yl)piperidine-1-carboxylate The title compound was prepared using the procedure described in Example 1G, using 4-fluoro-2-methoxyphenylboronic acid (114 mg, 0.670 mmol) in place of 5-fluoro-2-methoxyphenylboronic acid. LCMS: 426.0 (M+H)$^+$.

Example 2B 4-(4-fluoro-2-methoxyphenyl)-2-(piperidin-3-yl)-1H-pyrrolo[2,3-b]pyridine The title compound was prepared using the procedure described in Example 1H, using Example 2A (100 mg, 0.235 mmol) in place of Example 1G. LCMS: 325.9 (M+H)$^+$. $^1$H NMR (400 MHz, DMSO-d$_6$): δ 1.73-1.77 (m, 1H), 2.17-2.20 (m, 1H), 2.86-2.89 (m, 1H), 3.18-3.21 (m, 1H), 3.31-3.41 (m, 2H), 3.47-3.58 (m, 2H), 3.84 (s, 3H), 6.32 (s, 1H), 7.01 (t, J=8.4 Hz, 1H), 7.22 (d, J=11.6 Hz, 1H), 7.34 (d, J=5.2 Hz, 1H), 7.52 (t, J=7.6 Hz, 1H), 8.35 (d, J=5.6 Hz, 1H), 9.31-9.35 (m, 1H), 12.7 (s, 1H).

Example 3

4-(5-fluoro-2-methoxyphenyl)-2-[(3S)-piperidin-3-yl]-1H-pyrrolo[2,3-b]pyridine

The racemic product of Example 1H (100 mg, 0.307 mmol) was resolved using a Chiralpak AD-H HPLC column to afford the title compound. (Absolute stereochemistry was arbitrarily assigned.) LCMS: 325.9 (M+H)$^+$. $^1$H NMR (400 MHz, CD$_3$OD): δ 1.62-1.82 (m, 3H), 2.16-2.18 (m, 1H), 2.59-2.79 (m, 2H), 2.91-2.96 (m, 3H), 3.03-3.06 (m, 2H), 3.75 (s, 3H), 6.04 (s, 1H), 7.07 (dd, J=1.2, 5.2 Hz, 1H), 7.11-7.16 (m, 3H), 8.09 (d, J=5.2 Hz, 1H).

Example 4

4-(5-fluoro-2-methoxyphenyl)-2-[(3R)-piperidin-3-yl]-1H-pyrrolo[2,3-b]pyridine

The racemic product of Example 1H (100 mg, 0.307 mmol) was resolved using a Chiralpak AD-H HPLC column to afford the title compound. (Absolute stereochemistry was arbitrarily assigned.) LCMS: 325.9 (M+H)$^+$. $^1$H NMR (400 MHz, CD$_3$OD): δ 1.63-1.71 (m, 2H), 1.78-1.81 (m, 1H), 2.15-2.18 (m, 1H), 2.60-2.79 (m, 2H), 2.93-3.06 (m, 2H), 3.33-3.61 (m, 1H), 3.75 (s, 3H), 6.03 (d, J=0.8 Hz, 1H), 7.06 (d, J=5.2 Hz, 1H), 7.12-7.15 (m, 3H), 8.09 (d, J=5.2 Hz, 1H).

Example 5

5-methoxy-6-[2-(piperidin-3-yl)-1H-pyrrolo[2,3-b]pyridin-4-yl]pyridin-2-amine

Example 5A tert-butyl 3-(4-(4,4,5,5-tetramethyl-1,3,2-dioxaborolan-2-yl)-1H-pyrrolo[2,3-b]pyridin-2-yl)piperidine-1-carboxylate To a solution of product of Example 1F (200 mg, 0.596 mmol) in 1,4-dioxane (10 mL) was added 4,4,4',4',5,5,5',5'-octamethyl-2,2'-bi(1,3,2-dioxaborolane) (227 mg, 0.893 mmol) and potassium acetate (175 mg, 1.787 mmol) and the mixture was degassed with nitrogen for 5 minutes. 2-Dicyclohexylphosphino)biphenyl (10.44 mg, 0.030 mmol) and palladium acetate (6.69 mg, 0.030 mmol) were added and the mixture was heated at 100° C. for 12 hours. The mixture was filtered through diatomaceous earth and concentrated. The crude product was dissolved in ethyl acetate, washed with water and brine, dried over anhydrous sodium sulfate, filtered, and concentrated to afford crude title compound. Purification by column chromatography (silica gel, 60% ethyl acetate in hexane) afforded the title compound. LCMS: 346.3 (M+H-Boc acid)$^+$.

Example 5B tert-butyl 3-(4-(6-amino-3-methoxypyridin-2-yl)-1H-pyrrolo[2,3-b]pyridin-2-yl)piperidine-1-carboxylate The product of Example 5A (200 mg, 0.468 mmol) in N,N-dimethylformamide (8 mL) was treated with sodium bicarbonate (0.118 g, 1.404 mmol) in 0.5 mL water followed by the addition of 6-bromo-5-methoxypyridin-2-amine (170 mg, 0.86 mmol). The mixture was degassed with nitrogen and [1,1'-bis(di tert butyl phosphino)ferrocene]palladium(II) dichloride (21 mg, 0.033 mmol) was added. The mixture was heated at 100° C. for 12 hours, diluted with ethyl acetate and filtered through diatomaceous earth. The combined organic layers were washed with water and brine (25 mL each), dried over sodium sulfate, filtered, and concentrated to afford the crude product. Purification by column chromatography (silica gel, 60% ethyl acetate-hexane) afforded the title compound. LCMS: 424.0 (M+H)$^+$.

Example 5C 5-methoxy-6-(2-(piperidin-3-yl)-1H-pyrrolo[2,3-b]pyridin-4-yl)pyridin-2-amine Example 5B (0.1 g, 0.236 mmol) was treated with hydrogen chloride in ethyl acetate (2 mL) as described in Example 1H to afford the title compound as the trifluoroacetate salt. LCMS: 324.1 (M+H)$^+$. $^1$H NMR (400 MHz, DMSO-d$_6$): δ 1.69-1.77 (m, 2H), 1.90-1.93 (m, 1H), 2.12-2.15 (m, 1H), 2.84-2.87 (m, 1H), 3.04-3.23 (m, 2H), 3.32-3.38 (m, 2H), 3.53-3.56 (m, 2H), 3.74 (s, 3H), 6.29 (s, 1H), 6.98 (d, J=7.2 Hz, 1H), 7.26 (d, J=4.8 Hz, 1H), 7.95 (brs, 1H), 8.29 (d, J=4.8 Hz, 1H), 8.72 (m, 1H), 12.0 (s, 1H).

Example 6

4-[5-(4,5-dihydro-1H-imidazol-2-yl)-2-methoxyphenyl]-2-(piperidin-3-yl)-1H-pyrrolo[2,3-b]pyridine

Example 6A 2-(3-bromo-4-methoxyphenyl)-4,5-dihydro-1H-imidazole

To a solution of 3-bromo-4-methoxybenzonitrile (1 g, 4.72 mmol) in 10 mL of ethane-1,2-diamine was added sulfur (0.121 g, 3.77 mmol) and the mixture was heated at 110° C. overnight. The mixture was cooled, quenched with water and extracted with ethyl acetate. The organic layer was washed with water and brine (25 mL each), dried over sodium sulfate, filtered, and concentrated to afford the title compound. LCMS: 257 (M+2)$^+$.

Example 6B tert-butyl 2-(3-bromo-4-methoxyphenyl)-4,5-dihydro-1H-imidazole-1-carboxylate A solution of Example 6A (700 mg, 2.74 mmol) in dichloromethane (10 mL) was cooled to 0° C. and triethylamine (833 mg, 8.23 mmol) and di-tert-butyl dicarbonate (898 mg, 4.12 mmol) were added. The mixture was stirred at room temperature for 2 hours and diluted with dichloromethane. The organic layer was washed with water and brine, dried over sodium sulfate, filtered, and concentrated to afford the crude product. Purification by column chromatography (silica gel, 15% ethyl acetate in hexane) afforded the title compound. LCMS: 357 (M+2)$^+$.

Example 6C tert-butyl 2-(4-methoxy-3-(4,4,5,5-tetramethyl-1,3,2-dioxaborolan-2-yl)phenyl)-4,5-dihydro-1H-imidazole-1-carboxylate A mixture of Example 6B (500 mg, 1.408 mmol), potassium acetate (414 mg, 4.22 mmol) and 4,4,4',4',5,5,5',5'-octamethyl-2,2'-bi(1,3,2-dioxaborolane) (429 mg, 1.689 mmol) in 1,4-dioxane (5 mL) was degassed with nitrogen for 5 minutes and [1,1'-bis(diphenylphosphino)ferrocene]dichloropalladium(II) dichloromethane adduct (57.5 mg, 0.070 mmol) was added. The mixture was heated at 100° C. for 12 hours, cooled, and concentrated and the residue purified by column chromatography (silica gel, 30% ethyl acetate in hexane) to afford the title compound. LCMS: 403 (M+H)$^+$.

Example 6D tert-butyl 3-(4-(5-(1-(tert-butoxycarbonyl)-4,5-dihydro-1H-imidazol-2-yl)-2-methoxyphenyl)-1H-pyrrolo[2,3-b]pyridin-2-yl)piperidine-1-carboxylate The title compound was prepared using the procedure described in Example 1G, using Example 6C (270 mg, 0.670 mmol) in place of 5-fluoro-2-methoxyphenylboronic acid. LCMS: 476.3 (M+H–Boc)$^+$.

Example 6E 4-(5-(4,5-dihydro-1H-imidazol-2-yl)-2-methoxyphenyl)-2-(piperidin-3-yl)-1H-pyrrolo[2,3-b]pyridine To Example 6D (150 mg, 0.261 mmol) in ethanol (2 mL) was added hydrogen chloride in ethanol (2 mL) and the mixture was stirred for 2 hours. Concentration and purification by preparative HPLC (Agilent AD/PP/C18-15/033 reversed phase column and gradient elution from water to 1:1 methanol/acetonitrile over 30 minutes) afforded the title compound as the hydrochloride salt. LCMS: 376.1 (M+H)$^+$. $^1$H NMR (400 MHz, DMSO-d$_6$): δ 1.69-1.87 (m, 4H), 2.12-2.15 (m, 1H), 2.82-2.83 (m, 1H), 3.10-3.13 (m, 2H), 3.27-3.29 (m, 2H), 3.41-3.52 (m, 3H), 3.98 (s, 3H), 6.16 (s, 1H), 7.16 (d, J=4.8 Hz, 1H), 7.50 (d, J=8.8 Hz, 1H), 8.08 (d, J=2.4 Hz, 1H), 8.99 (dd, J=2.4, 8.8 Hz, 1H), 8.28 (d, J=5.2 Hz, 1H), 9.28 (brs, 1H), 10.63 (s, 1H), 12.2 (s, 1H).

Example 7

4-(5-cyclopropyl-2-methoxyphenyl)-2-(piperidin-3-yl)-1H-pyrrolo[2,3-b]pyridine

Example 7A tert-butyl 3-(4-(5-cyclopropyl-2-methoxyphenyl)-1H-pyrrolo[2,3-b]pyridin-2-yl)piperidine-1-carboxylate Example 5A (200 mg, 0.468 mmol) in N,N-dimethylformamide (8 mL) was treated with sodium bicarbonate (0.118 g, 1.404 mmol) in 0.5 mL water followed by the addition of 2-bromo-4-cyclopropyl-1-methoxybenzene (158 mg, 0.702 mmol). The mixture was degassed with nitrogen and [1,1'-bis(di tert butyl phosphino)ferrocene]palladium(II) dichloride (21 mg, 0.033 mmol) was added. The mixture was subjected to microwave irradiation using a Biotage Initiator at 100° C. for 1 hour, diluted with ethyl acetate, and filtered through diatomaceous earth. The organic layer was washed with water and brine (25 mL each), dried over sodium sulfate, filtered, and concentrated to afford the crude product. Purification by column chromatography (silica gel, 40% ethyl acetate-hexane) afforded the title compound. LCMS: 448.0 (M+H)$^+$.

Example 7B 4-(5-cyclopropyl-2-methoxyphenyl)-2-(piperidin-3-yl)-1H-pyrrolo[2,3-b]pyridine The title compound was prepared as the trifluoroacetate salt using the procedure described in Example 1H, using Example 7A (120 mg, 0.219 mmol) in place of Example 1G. LCMS: 348.6 (M+H)$^+$. $^1$H NMR (400 MHz, DMSO-d$_6$): δ 0.61-0.65 (m, 2H), 0.8-0.94 (m, 2H), 1.21-1.72 (m, 1H), 1.67-1.75 (m, 2H), 1.89-1.95 (m, 2H), 2.84-2.86 (m, 2H), 3.08-3.16 (m, 3H), 3.7 (s, 3H), 6.03 (s, 1H), 7.02-7.08 (m, 3H), 7.14 (dd, J=2, 8.8 Hz, 1H), 8.17 (d, J=5.2 Hz, 1H), 8.71 (brs, 1H), 11.8 (s, 1H).

Example 8

4-(4-fluoro-2-methoxyphenyl)-2-(1-methylpiperidin-3-yl)-1H-pyrrolo[2,3-b]pyridine Example 2A (220 mg, 0.517 mmol) in 5 mL anhydrous tetrahydrofuran was cooled to 0° C. and 1M lithium aluminium hydride in tetrahydrofuran (2.068 mL, 2.068 mmol) was added under inert atmosphere. The mixture was warmed to room temperature and heated to 60° C. for 2 hours. The mixture was cooled to 0° C. and ethyl acetate and saturated ammonium chloride solution was added. After stirring for 30 minutes, the mixture was extracted with ethyl acetate and the organic layer was washed with water and brine (25 mL each). The organic layer was dried over sodium sulfate, filtered, and concentrated to afford the title compound. LCMS: 340.3 (M+H)$^+$. $^1$H NMR (400 MHz, DMSO-d$_6$): δ 1.58-1.72 (m, 2H), 1.88-2.0 (m, 2H), 2.2 (s, 3H), 2.73-2.76 (m, 2H), 2.92-3.02 (m, 3H), 3.78 (s, 3H), 5.95 (s, 1H), 6.89-6.99 (m, 2H), 7.08 (dd, J=2.4, 11.6 Hz, 1H), 7.38-7.42 (m, 1H), 8.12 (d, J=4.8 Hz, 1H), 11.6 (s, 1H).

Example 9

4-(5-fluoro-2-methoxyphenyl)-2-(1-methylpiperidin-3-yl)-1H-pyrrolo[2,3-b]pyridine The title compound was prepared using the procedure described in Example 8, using Example 1G (150 mg, 0.353 mmol) in place of Example 2A. LCMS: 340.0 (M+H)$^+$. $^1$H NMR (400 MHz, DMSO-d$_6$): δ 1.55-1.58 (m, 2H), 1.88 (s, 1H), 1.96-2.01 (m, 2H), 2.17 (s, 3H), 2.66-2.73 (m, 2H), 2.9-3.0 (m. 2H), 3.72 (s, 3H), 5.95 (d, J=1.2 Hz, 1H), 6.9 (d, J=4.8 Hz, 1H), 7.15-7.28 (m, 3H), 8.12 (d, J=5.2 Hz, 1H), 11.6 (s, 1H).

Example 10

1-{3-[4-(5-fluoro-2-methoxyphenyl)-1H-pyrrolo[2,3-b]pyridin-2-yl]piperidin-1-yl}ethanone

Example 10A

3-ethynylpiperidine

To Example 1D (1 g, 4.78 mmol) in dichloromethane (20 mL) was added trifluoroacetic acid (1.841 mL, 23.89 mmol) and the mixture was stirred at room temperature for 12 hours. Concentration afforded the title compound.

Example 10B

1-(3-ethynylpiperidin-1-yl)ethanone

To Example 10A (0.5 g, 4.58 mmol) in dichloromethane (10 mL) was added triethylamine (1.915 mL, 13.74 mmol) followed by acetic anhydride (0.519 mL, 5.50 mmol) and the mixture was stirred at room temperature for 4 hours. After concentration, the residue was dissolved in ethyl acetate, washed with water and brine, dried over anhydrous sodium sulfate, filtered, and concentrated to afford crude product. Purification by column chromatography (silica gel, 60% ethyl acetate in hexane) afforded the title compound. LCMS: 152.1 (M+H)$^+$.

Example 10C tert-butyl (3-((1-acetylpiperidin-3-yl)ethynyl)-4-chloropyridin-2-yl)carbamate The title compound was prepared using the procedure described in Example 1E, using Example 10B (277 mg, 1.83 mmol) in place of Example 1D. LCMS: 378 (M+H)$^+$.

Example 10D

1-(3-(4-chloro-1H-pyrrolo[2,3-b]pyridin-2-yl)piperidin-1-yl)ethanone

The title compound was prepared using the procedure described in Example 1F, using Example 10C (300 mg, 0.794 mmol) in place of Example 1E. LCMS: 278.4 (M+H)$^+$.

Example 10E

1-(3-(4-(5-fluoro-2-methoxyphenyl)-1H-pyrrolo[2,3-b]pyridin-2-yl)piperidin-1-yl)ethanone The title compound was prepared as the trifluoroacetate salt using the procedure described in Example 1G, using Example 10D (150 mg, 0.54 mmol) in place of Example 1F. LCMS: 368 (M+H)$^+$. $^1$H NMR (400 MHz, DMSO-d$_6$): δ 1.2-1.5 (m, 2H), 1.71-1.77 (m, 2H), 2.05 (s, 3H), 2.8-2.9 (m, 2H), 3.08-3.17 (m, 1H), 3.73 (s, 3H), 4.02-4.05 (m, 1H), 4.32-4.35 (m. 1H), 6.09 (s, 1H), 7.09 (t, J=6 Hz, 1H), 7.18-7.30 (m, 3H), 8.19 (d, J=5.2 Hz, 1H), 11.8 (s, 1H).

Example 11

N-benzyl-5-chloro-6-[2-(piperidin-3-yl)-1H-pyrrolo[2,3-b]pyridin-4-yl]pyridin-2-amine

Example 11A

6-bromo-5-chloropyridin-2-amine

To a solution of 6-bromopyridin-2-amine (1 g, 5.78 mmol) in acetonitrile (10 mL) was added N-chlorosuccinimide (0.849 g, 6.36 mmol) and the mixture was heated at 80° C. for 12 hours. The mixture was filtered through diatomaceous earth and concentrated and the residue was dissolved in ethyl acetate and washed with water and brine. Drying over anhydrous sodium sulfate, filtration, concentration and purification by column chromatography (silica gel, 30% ethyl acetate in hexane) afforded the title compound. LCMS: 209.1 (M+2)$^+$.

Example 11B

N-benzyl-6-bromo-5-chloropyridin-2-amine

A solution of Example 11A (500 mg, 2.410 mmol) in 1,2-dichloroethane (10 mL) and acetic acid (5 mL) was treated with benzaldehyde (281 mg, 2.65 mmol) and the mixture was stirred at room temperature for 2 hours. Sodium triacetoxyborohydride (2.043 g, 9.64 mmol) was added and the mixture was stirred at room temperature for 12 hours. The mixture was diluted with water (25 mL), treated with saturated sodium bicarbonate solution, extracted with ethyl acetate, and washed with water and brine. The organic layer was dried over anhydrous sodium sulfate, filtered, and concentrated to afford the crude title compound. Purification by column chromatography (silica gel, 15% ethyl acetate in hexane) afforded the title compound.

Example 11C tert-butyl 3-(4-(6-(benzylamino)-3-chloropyridin-2-yl)-1H-pyrrolo[2,3-b]pyridin-2-yl)piperidine-1-carboxylate Example 5A (200 mg, 0.468 mmol) in dioxane (8 mL) was treated with sodium bicarbonate (0.118 g, 1.404 mmol) in 0.5 mL water followed by the addition of Example 11B (0.167 g, 0.562 mmol). The mixture was degassed with nitrogen and [1,1'-bis(di tert butyl phosphino)ferrocene]palladium(II) dichloride (21 mg, 0.033 mmol) was added. The mixture was heated at 100° C. for 2 hours, diluted with ethyl acetate, and filtered through diatomaceous earth. The organic layer was washed with water and brine (25 mL each), dried over anhydrous sodium sulfate, filtered, and concentrated to afford the crude product. Purification by column chromatography (silica gel, 4% methanol in dichloromethane) afforded the title compound. LCMS: 418 (M+H)$^+$.

Example 11D

N-benzyl-5-chloro-6-(2-(piperidin-3-yl)-1H-pyrrolo[2,3-b]pyridin-4-yl)pyridin-2-amine The title compound was prepared using the procedure described in Example 1H, using Example 11C (150 mg, 0.290 mmol) in place of Example 1G. LCMS: 417.9 (M+H)$^+$. $^1$H NMR (400 MHz, DMSO-d$_6$): δ 1.56-1.59 (m, 2H), 1.86-1.90

(m, 1H), 2.0-2.03 (m, 1H), 2.8-2.83 (m, 1H), 2.97-3.12 (m, 2H), 3.29-3.38 (m, 2H), 4.46 (s, 2H), 5.9 (s, 1H), 6.63 (d, J=9.2 Hz, 1H), 7.1 (d, J=4.8 Hz, 1H), 7.23-7.34 (m, 5H), 7.46 (brs, 1H), 7.60 (d, J=8.8 Hz, 1H), 8.21 (d, J=5.2 Hz, 1H), 8.55 (brs, 1H), 11.8 (s, 1H).

Example 12

N-benzyl-5-chloro-6-[2-(1-methylpiperidin-3-yl)-1H-pyrrolo[2,3-b]pyridin-4-yl]pyridin-2-amine A solution of Example 11C (200 mg, 0.386 mmol) in tetrahydrofuran (5 mL) was cooled to −10° C. and 1M lithium aluminum hydride in tetrahydrofuran (2 mL) was added. The mixture was stirred at room temperature for 12 hours, cooled to 0° C. and quenched with aqueous ammonium chloride. The mixture was extracted with ethyl acetate and the organic layer was washed with water and brine (25 mL each). Drying over anhydrous sodium sulfate, filtration, concentration, and purification by preparative HPLC (Agilent AD/PP/C18-15/033 reversed phase column and gradient elution from 0.01% trifluoroacetic acid in water to 1:1 methanol/acetonitrile over 60 minutes) afforded the title compound as the trifluoroacetate salt. LCMS: 431.9 (M+H)$^+$. $^1$H NMR (400 MHz, CD$_3$OD): δ 1.31-1.35 (m, 2H), 1.63-1.67 (m, 1H), 1.91-2.22 (m, 3H), 2.93 (s, 3H), 3.06-3.15 (m, 1H), 3.58-3.61 (m, 1H), 3.73-3.76 (m, 1H), 4.57 (s, 2H), 6.27 (s, 1H), 6.66 (dd, J=3.6, 9.2 Hz, 1H), 7.33-7.37 (m, 5H), 7.60 (d, J=8.8 Hz, 1H), 8.28 (s, 2H).

Example 13

N-benzyl-6-[2-(1-methylpiperidin-3-yl)-1H-pyrrolo[2,3-b]pyridin-4-yl]pyridin-2-amine The title compound was isolated as a trifluoroacetate salt as a byproduct from Example 12. LCMS: 398.3 (M+H)$^+$. $^1$H NMR (400 MHz, CD$_3$OD): δ 1.70-1.73 (m, 1H), 1.96-1.99 (m, 2H), 2.14-2.27 (m, 2H), 2.96 (s, 3H), 3.01-3.02 (m, 1H), 3.12-3.18 (m, 1H), 3.62-3.65 (m, 1H), 3.79-3.82 (m, 1H), 4.76 (s, 2H), 6.78 (s, 1H), 7.01 (d, J=8.8 Hz, 1H), 7.35 (d, J=7.2 Hz, 2H), 7.40-7.48 (m, 4H), 7.56 (d, J=5.6 Hz, 1H), 7.92 (d, J=7.6 Hz, 1H), 8.37 (d, J=5.6 Hz, 1H).

Example 14

N-benzyl-5-methoxy-6-[2-(piperidin-3-yl)-1H-pyrrolo[2,3-b]pyridin-4-yl]pyridin-2-amine

Example 14A

N-benzyl-6-bromo-5-methoxypyridin-2-amine

The title compound was prepared using the procedure described in Example 11B, using 6-bromo-5-methoxypyridin-2-amine (800 mg, 3.94 mmol) in place of Example 11A. LCMS: 292.9 (M+H)$^+$.

Example 14B tert-butyl 3-(4-(6-(benzylamino)-3-methoxypyridin-2-yl)-1H-pyrrolo[2,3-b]pyridin-2-yl)piperidine-1-carboxylate The title compound was prepared using the procedure described in Example 5B, using Example 14A (123 mg, 0.421 mmol) in place of 6-bromo-5-methoxypyridin-2-amine. LCMS: 514.2 (M+H)$^+$.

Example 14C

N-benzyl-5-methoxy-6-(2-(piperidin-3-yl)-1H-pyrrolo[2,3-b]pyridin-4-yl)pyridin-2-amine The title compound was prepared as the trifluoroacetate salt using the procedure described in Example 1H, using Example 14B (80 mg, 0.156 mmol) in place of Example 1G. LCMS: 414.1 (M+H)$^+$. $^1$H NMR (400 MHz, DMSO-d$_6$): δ 1.57-1.59 (m, 1H), 1.7-1.78 (m, 1H), 1.89-2.04 (m, 2H), 2.82-2.99 (m, 2H), 3.10-3.13 (m, 1H), 3.33-3.42 (m, 1H), 3.49-3.52 (m, 1H), 3.71 (s, 3H), 4.54 (s, 2H), 6.27 (s, 1H), 6.71 (d, J=8.8 Hz, 1H), 7.28-7.37 (m, 6H), 7.54 (d, J=9.2 Hz, 1H), 8.21 (d, J=5.6 Hz, 1H), 8.73-8.88 (m, 2H), 11.8 (s, 1H).

Example 15

N-benzyl-5-chloro-6-{2-[1-(propan-2-ylsulfonyl)piperidin-3-yl]-1H-pyrrolo[2,3-b]pyridin-4-yl}pyridin-2-amine

Example 15A 3-ethynyl-1-(isopropylsulfonyl)piperidine

To a solution of Example 10A (500 mg, 4.58 mmol) in dichloromethane (10 mL) was added triethylamine (2.55 mL, 18.32 mmol) followed by propane-2-sulfonyl chloride (1.306 g, 9.16 mmol) and the mixture was stirred for 3 hours. The mixture was concentrated and the residue was dissolved in ethyl acetate, washed with water and brine, dried over anhydrous sodium sulfate, filtered, and concentrated. Purification by column chromatography (silica gel, 30% ethyl acetate in hexane) afforded the title compound. LCMS: 216.2 (M+H-Boc)$^+$.

Example 15B tert-butyl (4-chloro-3-((1-(isopropylsulfonyl)piperidin-3-yl)ethynyl)pyridin-2-yl)carbamate The title compound was prepared using the procedure described in Example 1E, using Example 15A (395 mg, 1.833 mmol) in place of Example 1D. LCMS: 342.4 (M+H-Boc)$^+$.

Example 15C 4-chloro-2-(1-(isopropylsulfonyl)piperidin-3-yl)-1H-pyrrolo[2,3-b]pyridine The title compound was prepared using the procedure described in Example 1F, using Example 15B (550 mg, 1.24 mmol) in place of Example 1E. LCMS: 341.8 (M+H)$^+$.

Example 15D 2-(1-(isopropylsulfonyl)piperidin-3-yl)-4-(4,4,5,5-tetramethyl-1,3,2-dioxaborolan-2-yl)-1H-pyrrolo[2,3-b]pyridine The title compound was prepared using the procedure described in Example 5A, using Example 15C (200 mg, 0.585 mmol) in place of Example 1F. LCMS: 352.0 (M+H)$^+$.

Example 15E

N-benzyl-5-chloro-6-(2-(1-(isopropylsulfonyl)piperidin-3-yl)-1H-pyrrolo[2,3-b]pyridin-4-yl)pyridin-2-amine The title compound was prepared using the procedure described in Example 5B, using Example 15D (200 mg, 0.461 mmol) in place of Example 5A and Example 11B (165 mg, 0.554 mmol) in place of the 6-bromo-5-methoxypyridin-2-amine. LCMS: 524.1 (M+H)+. $^1$H NMR (400 MHz, DMSO-$d_6$): δ 1.20 (dd, J=2.4, 6.8 Hz, 7H), 1.50-1.55 (m, 2H), 1.76-1.96 (m, 2H), 2.85-2.95 (m, 3H), 3.64-3.82 (m, 2H), 4.47 (d, J=5.2 Hz, 2H), 5.98 (s, 1H), 6.63 (d, J=8.8 Hz, 1H), 6.97 (s, 1H), 7.11 (d, J=4.8 Hz, 1H), 7.22-7.34 (m, 5H), 7.44-7.47 (m, 1H), 7.60 (d, J=8.8 Hz, 1H), 8.17 (d, J=4.8 Hz, 1H), 11.7 (s, 1H).

Example 16 methyl 3-{4-[6-(benzylamino)-3-chloropyridin-2-yl]-1H-pyrrolo[2,3-b]pyridin-2-yl}piperidine-1-carboxylate

Example 16A methyl 3-ethynylpiperidine-1-carboxylate

To a solution of Example 10A (500 mg, 4.58 mmol) in dichloromethane (10 mL) was added triethylamine (2.55 mL, 18.32 mmol) followed by methyl chloroformate (0.532 mL, 6.87 mmol) and the mixture was stirred at room temperature for 3 hours. The mixture was diluted with water and dichloromethane and the organic layer was separated and washed with water and brine. After drying over sodium sulfate, filtration, and concentration, the residue was purified by column chromatography (silica gel, 20% ethyl acetate in hexane) to afford the title compound. LCMS: 168.3 (M+H)+.

Example 16B methyl 3-((2-((tert-butoxycarbonyl)amino)-4-chloropyridin-3-yl)ethynyl)piperidine-1-carboxylate The title compound was prepared using the procedure described in Example 1E, using Example 16A (424 mg, 2.54 mmol) in place of Example 1D. LCMS: 294 (M+H-Boc)+.

Example 16C methyl 3-(4-chloro-1H-pyrrolo[2,3-b]pyridin-2-yl)piperidine-1-carboxylate The title compound was prepared using the procedure described in Example 1F, using Example 16B (800 mg, 2.031 mmol) in place of Example 1E. LCMS: 294 (M+H)+.

Example 16D methyl 3-(4-(4,4,5,5-tetramethyl-1,3,2-dioxaborolan-2-yl)-1H-pyrrolo[2,3-b]pyridin-2-yl)piperidine-1-carboxylate The title compound was prepared using the procedure described in Example 5A, using Example 16C (200 mg, 0.681 mmol) in place of Example 1F. LCMS: 304 (M+H-boronic acid)+.

Example 16E methyl 3-(4-(6-(benzylamino)-3-chloropyridin-2-yl)-1H-pyrrolo[2,3-b]pyridin-2-yl)piperidine-1-carboxylate The title compound was prepared using the procedure described in Example 5B, using Example 16D (150 mg, 0.389 mmol)) in place of Example 5A and Example 11B (139 mg, 0.467 mmol)) in place of the product of 6-bromo-5-methoxy-pyridin-2-amine. LCMS: 476.1 (M+H)+. $^1$H NMR (400 MHz, DMSO-$d_6$): δ 1.44-1.69 (m, 3H), 1.94-1.97 (m, 1H), 2.77-2.80 (m, 3H), 3.59 (s, 3H), 3.91-3.94 (m, 2H), 4.48 (s, 2H), 6.0 (s, 1H), 6.66 (d, J=9.2 Hz, 1H), 7.18-7.31 (m, 6H), 7.62 (d, J=8.8 Hz, 2H), 8.22 (d, J=5.2 Hz, 1H), 11.8 (s, 1H).

Example 17

4-(5-fluoro-2-methoxyphenyl)-2-(piperidin-4-yl)-1H-pyrrolo[2,3-b]pyridine

Example 17A tert-butyl 4-(hydroxymethyl)piperidine-1-carboxylate

The title compound was prepared using the procedure described in Example 1B, using piperidin-4-ylmethanol (5 g, 43.4 mmol) in place of piperidin-3-ylmethanol.

Example 17B tert-butyl 4-formylpiperidine-1-carboxylate

The title compound was prepared using the procedure described in Example 1C, using Example 17A (5 g, 23.22 mmol) in place of Example 1B. LCMS: 213.9 (M+H)+.

Example 17C tert-butyl 4-ethynylpiperidine-1-carboxylate

The title compound was prepared using the procedure described in Example 1D, using Example 17B (1 g, 4.69 mmol) in place of Example 1C. LCMS: 110 (M+H-Boc)+.

Example 17D tert-butyl 4-((2-((tert-butoxycarbonyl)amino)-4-chloropyridin-3-yl)ethynyl)piperidine-1-carboxylate The title compound was prepared using the procedure described in Example 1E, using Example 17C in place of Example 1D. LCMS: 335.9 (M+H-Boc)+.

Example 17E tert-butyl 4-(4-chloro-1H-pyrrolo[2,3-b]pyridin-2-yl)piperidine-1-carboxylate The title compound was prepared using the procedure described in Example 1F, using Example 17D (800 mg, 1.835 mmol) in place of Example 1E. LCMS: 335.8 (M+H)+.

Example 17F tert-butyl 4-(4-(5-fluoro-2-methoxyphenyl)-1H-pyrrolo[2,3-b]pyridin-2-yl)piperidine-1-carboxylate The title compound was prepared using the procedure described in Example 1G, using Example 17E (300 mg, 0.893 mmol) in place of Example 1F. LCMS: 425.9 (M+H)$^+$.

Example 17G 4-(5-fluoro-2-methoxyphenyl)-2-(piperidin-4-yl)-1H-pyrrolo[2,3-b]pyridine The title compound was prepared using the procedure described in Example 1H, using Example 17F (100 mg, 0.235 mmol) in place of Example 1G. LCMS: 326 (M+H)$^+$. $^1$H NMR (400 MHz, DMSO-d$_6$/D$_2$O): δ 1.77-1.80 (m, 2H), 2.20-2.23 (m, 2H), 3.0-3.06 (m, 3H), 3.33-3.36 (m, 2H), 3.73 (s, 3H), 6.02 (s, 1H), 7.07 (d, J=5.2 Hz, 1H), 7.18-7.22 (m, 2H), 7.25-7.28 (m, 1H), 8.19 (d, J=4.8 Hz, 1H).

Example 18

4-(4-fluoro-2-methoxyphenyl)-2-(piperidin-4-yl)-1H-pyrrolo[2,3-b]pyridine

Example 18A tert-Butyl 4-(4-(4-fluoro-2-methoxyphenyl)-1H-pyrrolo[2,3-b]pyridin-2-yl)piperidine-1-carboxylate The title compound was prepared using the procedure described in Example 1G, using Example 17E (300 mg, 0.893 mmol) in place of Example 1F and 4-fluoro-2-methoxyphenylboronic acid (228 mg, 1.340 mmol) in place of 5-fluoro-2-methoxyphenylboronic acid. LCMS: 425.9 (M+H)$^+$.

Example 18B 4-(4-fluoro-2-methoxyphenyl)-2-(piperidin-4-yl)-1H-pyrrolo[2,3-b]pyridine The title compound was prepared as the trifluoroacetate salt using the procedure described in Example 1H, using Example 18A (100 mg, 0.235 mmol) in place of Example 1G. LCMS: 341.9 (M+H)$^+$. $^1$H NMR (400 MHz, DMSO-d$_6$): δ 1.7-1.83 (m, 2H), 2.20-2.23 (m, 2H), 3.0-3.09 (m, 3H), 3.34-3.37 (m, 2H), 3.78 (s, 3H), 5.99 (d, J=1.6 Hz, 1H), 7.04 (d, J=4.8 Hz, 1H), 7.16 (dd, J=2, 8 Hz, 1H), 7.28 (d, J=2 Hz, 1H), 7.39 (d, J=8.4 Hz, 1H), 8.18 (d, J=4.8 Hz, 1H), 8.32 (brs, 1H), 11.80 (s, 1H).

Example 19

4-(4-chloro-2-methoxyphenyl)-2-(piperidin-4-yl)-1H-pyrrolo[2,3-b]pyridine

Example 19A tert-butyl 4-(4-(4-chloro-2-methoxyphenyl)-1H-pyrrolo[2,3-b]pyridin-2-yl)piperidine-1-carboxylate The title compound was prepared using the procedure described in Example 1G, using Example 17E (200 mg, 0.596 mmol) in place of Example 1F and 4-chloro-2-methoxyphenylboronic acid (167 mg, 0.893 mmol) in place of 5-fluoro-2-methoxyphenylboronic acid. LCMS: 441.8 (M+H)$^+$.

Example 19B 4-(4-chloro-2-methoxyphenyl)-2-(piperidin-4-yl)-1H-pyrrolo[2,3-b]pyridine To a solution of Example 19A (100 mg, 0.235 mmol) in 2 mL ethanol was added 2 mL ethanolic HCl at 0° C. and the mixture was stirred at ambient temperature for 2 hours. The mixture was concentrated and the crude material was purified by preparative HPLC (Zorbax XDB C-18 (32) analytical reversed phase column and gradient elution from 0.1% trifluoroacetic acid in water to 1:1 of methanol/acetonitrile over 20 minutes) to afford the title compound as the trifluoroacetate salt. LCMS: 341.9 (M+H)$^+$. $^1$H NMR (400 MHz, DMSO-d$_6$): δ 1.7-1.83 (m, 2H), 2.20-2.23 (m, 2H), 3.0-3.09 (m, 3H), 3.34-3.37 (m, 2H), 3.78 (s, 3H), 5.99 (d, J=1.6 Hz, 1H), 7.04 (d, J=4.8 Hz, 1H), 7.16 (dd, J=2, 8 Hz, 1H), 7.28 (d, J=2 Hz, 1H), 7.39 (d, J=8.4 Hz, 1H), 8.18 (d, J=4.8 Hz, 1H), 8.32 (brs, 1H), 11.80 (s, 1H).

Example 20

4-(3-methoxypyridin-2-yl)-2-(piperidin-4-yl)-1H-pyrrolo[2,3-b]pyridine

Example 20A tert-butyl 4-(4-(3-methoxypyridin-2-yl)-1H-pyrrolo[2,3-b]pyridin-2-yl)piperidine-1-carboxylate The title compound was prepared using the procedure described in Example 1G, using Example 17E (200 mg, 0.596 mmol) in place of Example 1F and 4-methoxypyridin-3-ylboronic acid (137 mg, 0.893 mmol) in place of 5-fluoro-2-methoxyphenylboronic acid. LCMS: 308.9 (M+H)$^+$.

Example 20B 4-(3-methoxypyridin-2-yl)-2-(piperidin-4-yl)-1H-pyrrolo[2,3-b]pyridine The title compound was prepared as the acetate salt using the procedure described in Example 6E, using Example 20A (120 mg, 0.294 mmol) in place of Example 6D. LCMS: 308.9 (M+H)$^+$. $^1$H NMR (400 MHz, DMSO-d$_6$): δ 1.62-1.72 (m, 2H), 2.04-2.08 (m, 2H), 2.72-2.8 (m, 2H), 2.9-2.94 (m, 1H), 3.14-3.17 (m, 2H), 3.83 (s, 3H), 5.95 (s, 1H), 7.04 (d, J=5.2 Hz, 1H), 7.24 (d, J=6 Hz, 1H), 8.16 (d, J=4.8 Hz, 1H), 8.42 (s, 1H), 8.52 (d, J=5.6 Hz, 1H), 11.62 (s, 1H).

Example 21

5-methoxy-6-[2-(piperidin-4-yl)-1H-pyrrolo[2,3-b]pyridin-4-yl]pyridin-2-amine

Example 21A tert-butyl 4-(4-(4,4,5,5-tetramethyl-1,3,2-dioxaborolan-2-yl)-1H-pyrrolo[2,3-b]pyridin-2-yl)piperidine-1-carboxylate The title compound was prepared using the procedure described in Example 5A, using Example 17E (100 mg, 0.298 mmol) in place of Example 1F. LCMS: 428.4 (M+H)$^+$.

Example 21B tert-butyl 4-(4-(6-amino-3-methoxypyridin-2-yl)-1H-pyrrolo[2,3-b]pyridin-2-yl)piperidine-1-carboxylate The title compound was prepared using the procedure described in Example 5B, using Example 21A (200 mg, 468 mmol) in place of Example 5A. LCMS: 424.3 (M+H)$^+$.

Example 21C 5-methoxy-6-(2-(piperidin-4-yl)-1H-pyrrolo[2,3-b]pyridin-4-yl)pyridin-2-amine The title compound was prepared as the trifluoroacetate salt using the procedure described in Example 1H, using Example 21B (80 mg, 0.189 mmol) in place of Example 1G. LCMS: 324.2 (M+H)$^+$. $^1$H NMR (400 MHz, DMSO-d$_6$): δ 1.76-1.86 (m, 2H), 2.22-2.25 (m, 2H), 2.97-3.20 (m, 3H), 3.36-3.39 (m, 2H), 3.75 (s, 3H), 6.19 (s, 1H), 7.02-7.02 (m, 1H), 7.24 (d, J=5.2 Hz, 1H), 8.01 (brs, 1H), 8.29 (d, J=5.2 Hz, 1H), 8.43 (brs, 1H), 12.0 (s, 1H).

Example 22

4-(4,5-difluoro-2-methoxyphenyl)-2-(piperidin-4-yl)-1H-pyrrolo[2,3-b]pyridine

Example 22A tert-butyl 4-(4-(4,5-difluoro-2-methoxyphenyl)-1H-pyrrolo[2,3-b]pyridin-2-yl)piperidine-1-carboxylate The title compound was prepared using the procedure described in Example 1G, using Example 17E (250 mg, 0.744 mmol) in place of Example 1F and 4,5-difluoro-2-methoxyphenylboronic acid (210 mg, 1.117 mmol) in place of 5-fluoro-2-methoxyphenylboronic acid. LCMS: 444.2 (M+H)$^+$.

Example 22B 4-(4,5-difluoro-2-methoxyphenyl)-2-(piperidin-4-yl)-1H-pyrrolo[2,3-b]pyridine The title compound was prepared as the acetate salt using the procedure described in Example 6E, using Example 22A (150 mg, 0.338 mmol) in place of Example 6D. LCMS: 344.2 (M+H)$^+$. $^1$H NMR (400 MHz, DMSO-d$_6$): δ 1.52-1.61 (m, 2H), 1.93-1.99 (m, 2H), 2.66-2.67 (m, 3H), 3.03-3.06 (m, 2H), 3.75 (s, 3H), 5.94 (s, 1H), 6.99 (dd, J=0.8, 4.8 Hz, 1H), 7.32-7.37 (m, 1H), 7.42-7.47 (m, 1H), 8.12 (d, J=4.8 Hz, 1H), 11.60 (s, 1H).

Example 23

4-(5-chloro-2-methoxyphenyl)-2-(piperidin-4-yl)-1H-pyrrolo[2,3-b]pyridine

Example 23A tert-butyl 4-(4-(5-chloro-2-methoxyphenyl)-1H-pyrrolo[2,3-b]pyridin-2-yl)piperidine-1-carboxylate The title compound was prepared using the procedure described in Example 1G, using Example 17E (250 mg, 0.744 mmol) in place of Example 1F and 5-chloro-2-methoxyphenylboronic acid (167 mg, 0.893 mmol) in place of 5-fluoro-2-methoxyphenylboronic acid. LCMS: 442.2 (M+H)$^+$.

Example 23B 4-(5-chloro-2-methoxyphenyl)-2-(piperidin-4-yl)-1H-pyrrolo[2,3-b]pyridine The title compound was prepared as the trifluoroacetate salt using the procedure described in Example 6E, using Example 23A (160 mg, 0.362 mmol) in place of Example 6D. LCMS: 342.2 (M+H)$^+$. $^1$H NMR (400 MHz, DMSO-d$_6$): δ 1.76-1.82 (m, 2H), 2.19-2.22 (m, 2H), 2.98-3.08 (m, 3H), 3.33-3.36 (m, 2H), 3.74 (s, 3H), 5.98 (d, J=1.2 Hz, 1H), 7.06 (d, J=4.8 Hz, 1H), 7.21 (d, J=8.8 Hz, 1H), 7.36 (d, J=2.8 Hz, 1H), 7.48 (dd, J=2.8, 8.8 Hz, 1H), 8.19 (d, J=5.2 Hz, 1H), 8.66 (brs, 1H), 11.8 (s, 1H).

Example 24

4-(2-methoxy-5-methylphenyl)-2-(piperidin-4-yl)-1H-pyrrolo[2,3-b]pyridine

Example 24A tert-butyl 4-(4-(2-methoxy-5-methylphenyl)-1H-pyrrolo[2,3-b]pyridin-2-yl)piperidine-1-carboxylate The title compound was prepared using the procedure described in Example 1G, using Example 17E (200 mg, 0.596 mmol) in place of Example 1F and 2-methoxy-5-methylphenylboronic acid (148 mg, 0.893 mmol) in place of 5-fluoro-2-methoxyphenylboronic acid. LCMS: 422.6 (M+H)$^+$.

Example 24B 4-(2-methoxy-5-methylphenyl)-2-(piperidin-4-yl)-1H-pyrrolo[2,3-b]pyridine The title compound was prepared as the hydrochloride salt using the procedure described in Example 1H, using Example 24A (100 mg, 0.237 mmol) in place of Example 1G. LCMS: 322.3 (M+H)$^+$. $^1$H NMR (400 MHz, DMSO-d$_6$): δ 1.80-1.88 (m, 2H), 2.21-2.25 (m, 2H), 2.32 (s, 3H), 2.98-3.16 (m, H), 3.32-3.36 (m, H), 3.73 (s, 3H), 6.13 (s, 1H), 7.12 (d, J=8.4 Hz, 1H), 7.22-7.31 (m, 3H), 8.27 (d, J=5.6 Hz, 1H), 8.72 (m, 1H), 12.4 (s, 1H).

Example 25

4-(3-chloro-2-methoxyphenyl)-2-(piperidin-4-yl)-1H-pyrrolo[2,3-b]pyridine

Example 25A tert-butyl 4-(4-(3-chloro-2-methoxyphenyl)-1H-pyrrolo[2,3-b]pyridin-2-yl)piperidine-1-carboxylate The title compound was prepared using the procedure described in Example 1G, using Example 17E (300 mg, 0.893 mmol) in place of Example 1F and 2-(3-chloro-2-methoxyphenyl)-4,4,5,5-tetramethyl-1,3,2-dioxaborolane (240 mg, 0.893 mmol) in place of 5-fluoro-2-methoxyphenylboronic acid. LCMS: 442.1 (M+H)$^+$.

Example 25B 4-(3-chloro-2-methoxyphenyl)-2-(piperidin-4-yl)-1H-pyrrolo[2,3-b]pyridine The title compound was prepared as the trifluoroacetate salt using the procedure described in Example 6E, using Example 25A (300 mg, 0.679 mmol) in place of Example 6D. LCMS: 342.1 (M+H)$^+$. $^1$H NMR (400 MHz, DMSO-d$_6$): δ 1.77-1.80 (m, 2H), 2.21-2.24 (m, 2H), 3.03-3.08 (m, 3H), 3.35-3.39 (m, 5H), 6.03 (d, J=1.6 Hz, 1H), 7.12 (d, J=5.2 Hz, 1H), 7.29 (t, J=8.0 Hz, 1H), 7.43 (dd, J=1.6, 7.6 Hz, 1H), 7.60 (dd, J=1.6, 8.0 Hz, 1H), 8.24 (d, J=5.2 Hz, 1H), 8.66 (brs, 1H), 11.8 (s, 1H).

Example 26

4-(6-fluoro-3-methoxypyridin-2-yl)-2-(piperidin-4-yl)-1H-pyrrolo[2,3-b]pyridine

Example 26A tert-butyl 4-(4-(6-fluoro-3-methoxypyridin-2-yl)-1H-pyrrolo[2,3-b]pyridin-2-yl)piperidine-1-carboxylate The title compound was prepared using the procedure described in Example 7A, using Example 21A (933 mg, 2.18 mmol) in place of Example 5A and 2-bromo-6-fluoro-3-methoxypyridine (300 mg, 1.456 mmol) in place of 2-bromo-4-cyclopropyl-1-methoxybenzene. LCMS: 427.3 (M+H)$^+$.

Example 26B 4-(6-fluoro-3-methoxypyridin-2-yl)-2-(piperidin-4-yl)-1H-pyrrolo[2,3-b]pyridine The title compound was prepared as the acetate salt using the procedure described in Example 6E, using Example 26A (200 mg, 0.469 mmol) in place of Example 6D, and purified using preparative HPLC (Zorbax XDB C-18 column with elution with 77/23 10M ammonium acetate in water/acetonitrile). LCMS: 327.1 (M+H)$^+$. $^1$H NMR (400 MHz, CD$_3$OD): δ 1.97-1.98 (m, 2H), 2.32-2.35 (m, 2H), 3.10-3.18 (m, 3H), 3.46-3.49 (m, 2H), 3.90 (s, 3H), 6.45 (s, 1H), 7.13 (dd, J=3.6, 8.8 Hz, 1H), 7.45 (d, J=4.8 Hz, 1H), 7.81 (d, J=6.4 Hz, 1H), 8.20 (d, J=5.2 Hz, 1H).

Example 27

4-(2-methoxyphenyl)-2-(piperidin-4-yl)-1H-pyrrolo[2,3-b]pyridine

Example 27A tert-butyl 4-(4-(2-methoxyphenyl)-1H-pyrrolo[2,3-b]pyridin-2-yl)piperidine-1-carboxylate The title compound was prepared using the procedure described in Example 1G, using Example 17E (100 mg, 0.298 mmol) in place of Example 1F and 2-methoxyphenylboronic acid (54.3 mg, 0.357 mmol) in place of the product of 5-fluoro-2-methoxyphenylboronic acid.

Example 27B 4-(2-methoxyphenyl)-2-(piperidin-4-yl)-1H-pyrrolo[2,3-b]pyridine

The title compound was prepared as the trifluoroacetate salt using the procedure described in Example 6E, using Example 27A (120 mg, 0.294 mmol) in place of Example 6D, and purified using preparative HPLC (Zorbax XDB C-18 column with gradient elution from 0.1% trifluoroacetic acid in water to 1:1 methanol/acetonitrile) LCMS: 308.3 (M+H)$^+$. $^1$H NMR (400 MHz, DMSO-d$_6$): δ 1.74-1.79 (m, 2H), 2.18-2.22 (m, 2H), 3.01-3.06 (m, 3H), 3.32-3.35 (m, 2H), 3.73 (s, 3H), 5.95 (s, 1H), 7.02-7.09 (m, 2H), 7.18 (d, J=8 Hz, 1H), 7.35-7.44 (m, 2H), 8.15 (d, J=4.8 Hz, 1H), 8.23 (brs, 1H), 11.80 (s, 1H).

Example 28

4-(5-fluoro-2-methoxyphenyl)-2-(1-methylpiperidin-4-yl)-1H-pyrrolo[2,3-b]pyridine The title compound was prepared using the procedure described in Example 8, using Example 17F (150 mg, 0.353 mmol) in place of Example 2A. LCMS: 340.0 (M+H)$^+$. $^1$H NMR (400 MHz, DMSO-d$_6$): δ 1.66-1.70 (m, 2H), 1.95-2.17 (m, 2H), 2.17 (s, 3H), 2.64-2.67 (m, 3H), 2.82-2.84 (m, 2H), 3.73 (s, 3H), 5.9 (d, J=1.2 Hz, 1H), 7.01 (d, J=4.8 Hz, 1H), 7.16-7.20 (m, 2H), 7.20-7.26 (m, 1H), 8.13 (d, J=4.8 Hz, 1H), 11.60 (s, 1H).

Example 29

4-(4-fluoro-2-methoxyphenyl)-2-(1-methylpiperidin-4-yl)-1H-pyrrolo[2,3-b]pyridine The title compound was prepared as the trifluoroacetate salt using the procedure described in Example 8, using Example 18A (150 mg, 0.353 mmol) in place of Example 2A. LCMS: 340.2 (M+H)$^+$. $^1$H NMR (400 MHz, DMSO-d$_6$): δ 1.77-1.80 (m, 2H), 2.26-2.30 (m, 2H), 2.8 (d, J=4 Hz, 3H), 2.99-3.16 (m, 3H), 3.51-3.54 (m, 2H), 3.77 (s, 3H), 6.0 (s, 1H), 6.92 (t, J=7.2 Hz, 1H), 7.05-7.13 (m, 2H), 7.40 (d, J=7.2 Hz, 1H), 8.19 (d, J=4.4 Hz, 1H), 11.80 (s, 1H).

Example 30

4-(2-methoxy-5-methylphenyl)-2-(1-methylpiperidin-4-yl)-1H-pyrrolo[2,3-b]pyridine The title compound was prepared using the procedure described in Example 8, using Example 24A (80 mg, 0.19 mmol) in place of Example 2A. LCMS: 336.2 (M+H)$^+$. $^1$H NMR (400 MHz, DMSO-d$_6$): δ 1.66-1.70 (m, 2H), 1.93-1.99 (m, 3H), 2.18 (s, 3H), 2.30 (s, 3H), 2.63-2.67 (m, 2H), 2.82-2.85 (m, 2H), 3.70 (s, 3H), 5.9 (s, 1H), 6.95 (d, J=4.8 Hz, 1H), 7.06 (d, J=8.4 Hz, 1H), 7.16 (d, J=1.6 Hz, 1H), 7.21 (dd, J=2, 8.4 Hz, 2H), 8.1 (d, J=5.2 Hz, 1H), 11.60 (s, 1H).

Example 31

4-(4-methoxypyridin-3-yl)-2-(1-methylpiperidin-4-yl)-1H-pyrrolo[2,3-b]pyridine

Example 31A tert-butyl 4-(4-(4-methoxypyridin-3-yl)-1H-pyrrolo[2,3-b]pyridin-2-yl)piperidine-1-carboxylate The title compound was prepared using the procedure described in Example 7A, using Example 17E (93 mg, 0.276 mmol) in place of 2-bromo-4-cyclopropyl-1-methoxybenzene and (4-methoxypyridin-3-yl)boronic acid (78 mg, 0.332 mmol) in place of Example 5A. LCMS: 409.2 (M+H)$^+$.

Example 31B 4-(4-methoxypyridin-3-yl)-2-(1-methylpiperidin-4-yl)-1H-pyrrolo[2,3-b]pyridine The title compound was prepared as the acetate salt using the procedure described in Example 8, using Example 31A (100 mg, 0.24 mmol) in place of Example 2A. LCMS: 323.1 (M+H)$^+$. $^1$H NMR (400 MHz, CD$_3$OD): δ 1.87-1.90 (m, 2H), 2.17-2.19 (m, 2H), 2.47-2.51 (m, 5H), 2.99-3.16 (m, 1H), 3.14-3.19 (m, 2H), 3.93 (s, 3H), 6.09 (s, 1H), 7.13 (d, J=5.2 Hz, 1H), 7.28 (d, J=6 Hz, 1H), 8.17 (d, J=5.2 Hz, 1H), 8.45 (s, 1H), 8.51 (d, J=5.6 Hz, 1H).

Example 32

N-benzyl-5-chloro-6-[2-(piperidin-4-yl)-1H-pyrrolo[2,3-b]pyridin-4-yl]pyridin-2-amine Example 32A tert-butyl 4-(4-(6-(benzylamino)-3-chloropyridin-2-yl)-1H-pyrrolo[2,3-b]pyridin-2-yl)piperidine-1-carboxylate The title compound was prepared using the procedure described in Example 5B, using Example 21A (200 mg, 0.468 mmol) in place of Example 5A and Example 11B (167 mg, 0.562 mmol) in place of 6-bromo-5-methoxypyridin-2-amine. LCMS: 418.1 (M+H)$^+$.

Example 32B

N-benzyl-5-chloro-6-(2-(piperidin-4-yl)-1H-pyrrolo[2,3-b]pyridin-4-yl)pyridin-2-amine The title compound was prepared as the trifluoroacetate salt using the procedure described in Example 1H, using Example 32A (100 mg, 0.193 mmol) in place of Example 1G. LCMS: 417.8 (M+H)$^+$. $^1$H NMR (400 MHz, DMSO-d$_6$): δ 1.65-1.75 (m, 2H), 2.11-2.14 (m, 2H), 2.97-3.06 (m, 3H), 3.32-3.38 (m, 2H), 4.47 (s, 2H), 5.99 (s, 1H), 6.64 (d, J=8.8 Hz, 1H), 7.12 (d, J=4.8 Hz, 1H), 7.24-7.34 (m, 5H), 7.46-7.61 (m, 2H), 8.19-8.31 (m, 2H), 11.70 (s, 1H).

Example 33

5-chloro-N-(3-fluorobenzyl)-6-[2-(piperidin-4-yl)-1H-pyrrolo[2,3-b]pyridin-4-yl]pyridin-2-amine Example 33A 6-bromo-5-chloro-N-(3-fluorobenzyl)pyridin-2-amine The title compound was prepared using the procedure described in Example 11B, using 3-fluorobenzaldehyde (329 mg, 2.65 mmol) in place of benzaldehyde. LCMS: 316.9 (M+H)$^+$.

Example 33B tert-butyl 4-(4-(3-chloro-6-((3-fluorobenzyl)amino)pyridin-2-yl)-1H-pyrrolo[2,3-b]pyridin-2-yl)piperidine-1-carboxylate The title compound was prepared using the procedure described in Example 5B, using Example 33A (288 mg, 0.913 mmol) in place of 6-bromo-5-methoxypyridin-2-amine and Example 21A (300 mg, 0.702 mmol) in place of Example 5A. LCMS: 536.3 (M+H)$^+$.

Example 33C 5-chloro-N-(3-fluorobenzyl)-6-(2-(piperidin-4-yl)-1H-pyrrolo[2,3-b]pyridin-4-yl)pyridin-2-amine The title compound was prepared as the trifluoroacetate salt using the procedure described in Example 1H, using Example 33B (100 mg, 0.187 mmol) in place of Example 1G. LCMS: 436.2 (M+H)$^+$. $^1$H NMR (400 MHz, DMSO-d$_6$): δ 1.67-1.70 (m, 2H), 2.06-2.12 (m, 2H), 2.98-3.01 (m, 3H), 3.30-3.33 (m, 2H), 4.46 (s, 2H), 5.93 (s, 1H), 6.64 (d, J=8.8 Hz, 1H), 7.05-7.12 (m, 4H), 7.33-7.34 (m, 1H), 7.46-7.52 (m, 1H), 7.60 (d, J=8.8 Hz, 1H), 8.17 (d, J=5.2 Hz, 1H), 8.22-8.28 (m, 1H), 11.70 (s, 1H).

Example 34

5-chloro-6-[2-(piperidin-4-yl)-1H-pyrrolo[2,3-b]pyridin-4-yl]-N-(pyridin-3-ylmethyl)pyridin-2-amine Example 34A 6-bromo-5-chloro-N-(pyridin-3-ylmethyl)pyridin-2-amine The title compound was prepared using the procedure described in Example 11B, using nicotinaldehyde (568 mg, 5.30 mmol) in place of benzaldehyde. LCMS: 298 (M+2)$^+$.

Example 34B tert-butyl 4-(4-(3-chloro-6-((pyridin-3-ylmethyl)amino)pyridin-2-yl)-1H-pyrrolo[2,3-b]pyridin-2-yl)piperidine-1-carboxylate The title compound was prepared using the procedure described in Example 7A, using Example 21A (644 mg, 1.507 mmol) in place of Example 5A and Example 34A (300 mg, 1.005 mmol) in place of 2-bromo-4-cyclopropyl-1-methoxybenzene. LCMS: 519.3 (M+H)$^+$.

Example 34C 5-chloro-6-(2-(piperidin-4-yl)-1H-pyrrolo[2,3-b]pyridin-4-yl)-N-(pyridin-3-ylmethyl)pyridin-2-amine The title compound was prepared as the trifluoroacetate salt using the procedure described in Example 6E, using Example 34B (200 mg, 0.385 mmol) in place of Example 6D, and purified using preparative HPLC (Zorbax XDB C-18 column with gradient elution from 0.1% trifluoroacetic acid in water to acetonitrile). LCMS: 418.8 (M+H)$^+$. $^1$H NMR (400 MHz, DMSO-d$_6$): δ 1.72-1.78 (m, 2H), 2.14-2.17 (m, 2H), 2.99-3.09 (m, 3H), 3.35-3.38 (m, 2H), 4.59 (s, 2H), 5.93 (s, 1H), 6.72 (d, J=8.8 Hz, 1H), 7.03 (d, J=5.2 Hz, 1H), 7.66

(d, J=8.8 Hz, 1H), 7.77-7.81 (m, 1H), 8.20-8.22 (m, 2H), 8.38-8.42 (m, 1H), 8.70-8.71 (m, 3H), 11.80 (s, 1H).

Example 35

5-chloro-N-(4-chlorobenzyl)-6-[2-(piperidin-4-yl)-1H-pyrrolo[2,3-b]pyridin-4-yl]pyridin-2-amine Example 35A 6-bromo-5-chloro-N-(4-chlorobenzyl)pyridin-2-amine The title compound was prepared using the procedure described in Example 11B, using 4-chlorobenzaldehyde (237 mg, 1.687 mmol) in place of benzaldehyde. LCMS: 332 (M+3)$^+$.

Example 35B tert-butyl 4-(4-(3-chloro-6-((4-chlorobenzyl)amino)pyridin-2-yl)-1H-pyrrolo[2,3-b]pyridin-2-yl)piperidine-1-carboxylate The title compound was prepared using the procedure described in Example 5B, using Example 35A (200 mg, 0.602 mmol) in place of 6-bromo-5-methoxypyridin-2-amine and Example 21A (386 mg, 0.904 mmol) in place of Example 5A. LCMS: 554.2 (M+3)$^+$.

Example 35C 5-chloro-N-(4-chlorobenzyl)-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 35B (145 mg, 0.262 mmol) in place of Example 6D, and purified using preparative HPLC (Zorbax XDB C-18 column with gradient elution from 0.1% trifluoroacetic acid in water to acetonitrile) LCMS: 452.1 (M+H)$^+$. $^1$H NMR (400 MHz, DMSO-d$_6$): δ 1.69-1.72 (m, 2H), 2.09-2.14 (m, 2H), 2.67 (s, 1H), 4.46 (d, J=5.6 Hz, 2H), 5.93 (s, 1H), 6.65 (d, J=8.8 Hz, 1H), 7.11 (d, J=5.2 Hz, 1H), 7.32 (d, J=8.4 Hz, 2H), 7.39 (d, J=8.8 Hz, 2H), 7.51-7.52 (m, 1H), 7.62 (d, J=8.8 Hz, 1H), 8.2 (d, J=4.8 Hz, 1H), 8.3-8.34 (m, 1H), 11.80 (s, 1H).

Example 36

5-chloro-N-(2,5-difluorobenzyl)-6-[2-(piperidin-4-yl)-1H-pyrrolo[2,3-b]pyridin-4-yl]pyridin-2-amine Example 36A 6-bromo-5-chloro-N-(2,5-difluorobenzyl)pyridin-2-amine To Example 11A (350 mg, 1.687 mmol) and 2,5-difluorobenzaldehyde (288 mg, 2.028 mmol) was added titanium isopropoxide (1579 mg, 5.56 mmol) and the mixture was stirred at room temperature for 16 hours. Methanol was added, the mixture was cooled to 0° C. and sodium borohydride (354 mg, 8.45 mmol) was added in portions maintaining the 0° C. temperature. After stirring at room temperature for 3 hours, the mixture was cooled to 10° C. and quenched with saturated ammonium chloride solution. The solution was extracted with ethyl acetate (20 mL×2) and the combined organic layers washed with water and brine (25 mL each), dried over sodium sulfate, filtered, and concentrated to afford the crude title compound.

Example 36B tert-butyl 4-(4-(3-chloro-6-((2,5-difluorobenzyl)amino)pyridin-2-yl)-1H-pyrrolo[2,3-b]pyridin-2-yl)piperidine-1-carboxylate The title compound was prepared using the procedure described in Example 5B, using Example 36A (100 mg, 0.299 mmol) in place of 6-bromo-5-methoxypyridin-2-amine and Example 21A (147 mg, 0.598 mmol) in place of Example 5A. LCMS: 454.2 (M+H)$^+$.

Example 36C 5-chloro-N-(2,5-difluorobenzyl)-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 36B (120 mg, 0.216 mmol) in place of Example 6D, and purified using preparative HPLC (Zorbax XDB C-18 column with gradient elution from 0.1% trifluoroacetic acid in water to 1:1 methanol/acetonitrile). LCMS: 454.2 (M+H)$^+$. $^1$H NMR (400 MHz, DMSO-d$_6$): δ 1.66-1.74 (m, 2H), 2.11-2.14 (m, 2H), 2.97-3.06 (m, 3H), 3.31-3.34 (m, 2H), 4.47 (d, J=5.2 Hz, 2H), 5.92 (s, 1H), 6.69 (d, J=8.8 Hz, 1H), 7.06 (d, J=4.8 Hz, 1H), 7.11-7.24 (m, 3H), 7.48 (d, J=5.6 Hz, 1H), 7.63 (d, J=8.8 Hz, 1H), 8.18 (d, J=4.8 Hz, 1H), 8.69 (brs, 1H), 11.8 (s, 1H).

Example 37

5-chloro-N-[(5-fluoropyridin-3-yl)methyl]-6-[2-(piperidin-4-yl)-1H-pyrrolo[2,3-b]pyridin-4-yl]pyridin-2-amine Example 37A 6-bromo-5-chloro-N-((5-fluoropyridin-3-yl)methyl)pyridin-2-amine The title compound was prepared using the procedure described in Example 36A, using 5-fluoro nicotinaldehyde (212 mg, 1.70 mmol) in place of 2,5-difluorobenzaldehyde.

Example 37B tert-butyl 4-(4-(3-chloro-6-(((5-fluoropyridin-3-yl)methyl)amino)pyridin-2-yl)-1H-pyrrolo[2,3-b]pyridin-2-yl)piperidine-1-carboxylate The title compound was prepared using the procedure described in Example 5B, using Example 37A (192 mg, 0.556 mmol) in place of 6-bromo-5-methoxypyridin-2-amine and Example 21A (110 mg, 0.348 mmol) in place of Example 5A. LCMS: 437 (M+H-Boc)$^+$.

Example 37C 5-chloro-N-((5-fluoropyridin-3-yl)methyl)-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 37B (130 mg, 0.242 mmol) in place of Example 6D, and purified using preparative HPLC (Zorbax XDB C-18 column with gradient elution from 0.1% trifluoroacetic acid in water to 1:1 methanol/acetonitrile). LCMS: 437.15 (M+H)$^+$. $^1$H NMR (400 MHz, CD$_3$OD): δ 1.91-1.97 (m, 2H), 2.30-2.33 (m, 2H), 3.17-3.23 (m, 3H), 3.51-3.54 (m, 2H), 4.62 (s, 2H), 6.23 (s, 1H), 6.71 (d, J=8.8 Hz, 1H), 7.34 (s, 1H), 7.63 (d, J=8.4 Hz, 2H), 8.29-8.38 (m, 3H).

Example 38

5-chloro-N-(2-fluorobenzyl)-6-[2-(piperidin-4-yl)-1H-pyrrolo[2,3-b]pyridin-4-yl]pyridin-2-amine Example 38A 6-bromo-5-chloro-N-(2-fluorobenzyl)pyridin-2-amine The title compound was prepared using the procedure described in Example 11B, using 2-fluorobenzaldehyde (197 mg, 1.591 mmol) in place of benzaldehyde. LCMS: 316.9 (M+H)$^+$.

Example 38B tert-butyl 4-(4-(3-chloro-6-((2-fluorobenzyl)amino)pyridin-2-yl)-1H-pyrrolo[2,3-b]pyridin-2-yl)piperidine-1-carboxylate The title compound was prepared using the procedure described in Example 7A, using Example 38A (200 mg, 0.634 mmol) in place of 2-bromo-4-cyclopropyl-1-methoxybenzene and Example 21A (406 mg, 0.951 mmol) in place of Example 5A. LCMS: 536.2 (M+H)$^+$.

Example 38C 5-chloro-N-(2-fluorobenzyl)-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 38B (125 mg, 0.233 mmol) in place of Example 6D, and purified using preparative HPLC (Zorbax XDB C-18 column with gradient elution from 0.1% trifluoroacetic acid in water to 1:1 methanol/acetonitrile). LCMS: 436.2 (M+H)$^+$. $^1$H NMR (400 MHz, DMSO-d$_6$): δ 1.65-1.76 (m, 2H), 2.12-2.15 (m, 2H), 2.99-3.08 (s, 3H), 3.34-3.37 (m, 2H), 4.52 (s, 2H), 5.97 (s, 1H), 6.68 (d, J=8.8 Hz, 1H), 7.12 (d, J=4.8 Hz, 1H), 7.15-7.20 (m, 2H), 7.29-7.39 (m, 2H), 7.46 (brs, 1H), 7.63 (d, J=8.8 Hz, 1H), 8.20 (d, J=5.2 Hz, 1H), 8.60-8.62 (m, 1H) 11.77 (s, 1H).

Example 39

5-chloro-N-(3,4-difluorobenzyl)-6-[2-(piperidin-4-yl)-1H-pyrrolo[2,3-b]pyridin-4-yl]pyridin-2-amine Example 39A 6-bromo-5-chloro-N-(3,4-difluorobenzyl)pyridin-2-amine The title compound was prepared using the procedure described in Example 11B, using 3,4-difluorobenzaldehyde (468 mg, 3.29 mmol) in place of benzaldehyde.

Example 39B tert-butyl 4-(4-(3-chloro-6-((3,4-difluorobenzyl)amino)pyridin-2-yl)-1H-pyrrolo[2,3-b]pyridin-2-yl)piperidine-1-carboxylate The title compound was prepared using the procedure described in Example 7A, using Example 39A (150 mg, 0.45 mmol) in place of 2-bromo-4-cyclopropyl-1-methoxybenzene and Example 21A (380 mg, 0.89 mmol) in place of Example 5A.

Example 39C 5-chloro-N-(3,4-difluorobenzyl)-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 39B (80 mg, 0.14 mmol) in place of Example 6D, and purified using preparative HPLC (Zorbax XDB C-18 column with gradient elution from 0.1% trifluoroacetic acid in water to 1:1 methanol/acetonitrile). LCMS: 454.1 (M+H)$^+$. $^1$H NMR (400 MHz, CD$_3$OD): δ 1.88-1.96 (m, 2H), 2.25-2.34 (m, 2H), 3.14-3.19 (m, 3H), 3.49-3.50 (m, 2H), 4.53 (s, 2H), 6.21 (s, 1H), 6.68 (d, J=8.8 Hz, 1H), 7.10-7.18 (m, 1H), 7.20-7.26 (m, 2H), 7.35 (d, J=5.2 Hz, 1H), 7.62 (d, J=8.8 Hz, 1H), 8.28 (d, J=5.6 Hz, 1H).

Example 40

5-chloro-6-[2-(piperidin-4-yl)-1H-pyrrolo[2,3-b]pyridin-4-yl]-N-(pyridin-4-ylmethyl)pyridin-2-amine Example 40A 6-bromo-5-chloro-N-(pyridin-4-ylmethyl)pyridin-2-amine The title compound was prepared using the procedure described in Example 11B, using isonicotinaldehyde (620 mg, 5.78 mmol) in place of benzaldehyde. LCMS: 299.9 (M+3)$^+$.

Example 40B tert-butyl 4-(4-(3-chloro-6-((pyridin-4-ylmethyl)amino)pyridin-2-yl)-1H-pyrrolo[2,3-b]pyridin-2-yl)piperidine-1-carboxylate The title compound was prepared using the procedure described in Example 7A, using Example 40A (200 mg, 0.67 mmol) in place of 2-bromo-4-cyclopropyl-1-methoxybenzene and Example 21A (380 mg, 0.89 mmol) in place of Example 5A. LCMS: 519.3 (M+H)$^+$.

Example 40C 5-chloro-6-(2-(piperidin-4-yl)-1H-pyrrolo[2,3-b]pyridin-4-yl)-N-(pyridin-4-ylmethyl)pyridin-2-amine The title compound was prepared as the trifluoroacetate salt using the procedure described in Example 1H, using Example 40B (70 mg, 0.113 mmol) in place of Example 1G. LCMS: 419.1 (M+H)$^+$. $^1$H NMR (400 MHz, DMSO-d$_6$/D$_2$O): δ 1.66-1.69 (m, 2H), 2.08-2.11 (m, 2H), 2.97-3.04 (m, 3H), 3.33-3.38 (m, 2H), 4.69 (s, 2H), 5.82 (s, 1H), 6.77 (d, J=8.8 Hz, 1H), 6.92 (d, J=5.2 Hz, 1H), 7.69 (d, J=9.2 Hz, 1H), 7.82 (d, J=6.8 Hz, 2H), 8.14 (d, J=4.8 Hz, 1H), 8.73 (d, J=6.4 Hz, 2H).

Example 41

5-chloro-N-[(1-oxidopyridin-3-yl)methyl]-6-[2-(piperidin-4-yl)-1H-pyrrolo[2,3-b]pyridin-4-yl]pyridin-2-amine

Example 41A 3-(((6-bromo-5-chloropyridin-2-yl)amino)methyl) pyridine 1-oxide The title compound was prepared using the procedure described in Example 11B, using 3-formylpyridine 1-oxide (653 mg, 5.30 mmol) in place of benzaldehyde. LCMS: 315.7 $(M+H)^+$.

Example 41B 3-(((6-(2-(1-(tert-butoxycarbonyl)piperidin-4-yl)-1H-pyrrolo[2,3-b]pyridin-4-yl)-5-chloropyridin-2-yl) amino)methyl)pyridine 1-oxide The title compound was prepared using the procedure described in Example 7A, using Example 41A (300 mg, 0.954 mmol) in place of 2-bromo-4-cyclopropyl-1-methoxybenzene and Example 21A (380 mg, 0.89 mmol) in place of Example 5A. LCMS: 535.1 $(M+H)^+$.

Example 41C 5-chloro-N-[(1-oxidopyridin-3-yl)methyl]-6-[2-(piperidin-4-yl)-1H-pyrrolo[2,3-b]pyridin-4-yl]pyridin-2-amine The title compound was prepared as the trifluoroacetate salt using the procedure described in Example 6E, using Example 41B (150 mg, 0.280 mmol) in place of Example 6D, and purified using preparative HPLC (Zorbax XDB C-18 column with gradient elution from 0.1% trifluoroacetic acid in water to 1:1 methanol/acetonitrile). LCMS: 435.1 $(M+H)^+$. $^1$H NMR (400 MHz, DMSO-$d_6$/$D_2O$): δ 1.62-1.65 (m, 2H), 2.09-2.12 (m, 2H), 2.99-3.05 (m, 3H), 3.35-3.38 (m, 2H), 4.47 (s, 2H), 5.82 (s, 1H), 6.72 (d, J=8.8 Hz, 1H), 7.14 (d, J=5.2 Hz, 1H), 7.36-7.47 (m, 2H), 7.66 (d, J=8.8 Hz, 1H), 8.18-8.22 (m, 3H).

Example 42

5-chloro-N-(piperidin-4-ylmethyl)-6-[2-(piperidin-4-yl)-1H-pyrrolo[2,3-b]pyridin-4-yl]pyridin-2-amine

Example 42A tert-butyl 4-(((6-bromo-5-chloropyridin-2-yl)amino) methyl)piperidine-1-carboxylate The title compound was prepared using the procedure described in Example 11B, using tert-butyl 4-formylpiperidine-1-carboxylate (514 mg, 2.410 mmol) in place of benzaldehyde. LCMS: 304.9 $(M+H-Boc)^+$.

Example 42B tert-butyl 4-((((6-(2-(1-(tert-butoxycarbonyl)piperidin-4-yl)-1H-pyrrolo[2,3-b]pyridin-4-yl)-5-chloropyridin-2-yl)amino)methyl)piperidine-1-carboxylate The title compound was prepared using the procedure described in Example 5B, using Example 21A (200 mg, 0.468 mmol) in place of Example 5A and Example 42A (246 mg, 0.608 mmol) in place of 6-bromo-5-methoxypyridin-2-amine. LCMS: 625.4 $(M+H)^+$.

Example 42C 5-chloro-N-(piperidin-4-ylmethyl)-6-[2-(piperidin-4-yl)-1H-pyrrolo[2,3-b]pyridin-4-yl]pyridin-2-amine The title compound was prepared as the trifluoroacetate salt using the procedure described in Example 1H, using Example 42B (120 mg, 0.192 mmol) in place of Example 1G. LCMS: 425.5 $(M+H)^+$. $^1$H NMR (400 MHz, DMSO-$d_6$): δ 1.24-1.32 (m, 2H), 1.74-1.82 (m, 2H), 2.21-2.24 (m, 2H), 2.78-2.89 (m, 2H), 3.01-3.10 (m, 4H), 3.16-3.17 (m, 2H), 3.24-3.27 (m, 2H), 3.35-3.38 (m, 2H), 3.96 (s, 2H), 6.06 (s, 1H), 6.60 (d, J=8.8 Hz, 1H), 7.07 (brs, 1H), 7.12 (d, J=4.8 Hz, 1H), 7.59 (d, J=8.8 Hz, 1H), 8.17 (brs, 1H), 8.22 (d, J=5.2 Hz, 1H), 8.52 (brs, 1H), 11.8 (s, 1H).

Example 43

5-chloro-N-(piperidin-3-ylmethyl)-6-[2-(piperidin-4-yl)-1H-pyrrolo[2,3-b]pyridin-4-yl]pyridin-2-amine

Example 43A tert-butyl 3-(((6-bromo-5-chloropyridin-2-yl)amino) methyl)piperidine-1-carboxylate The title compound was prepared using the procedure described in Example 11B, using tert-butyl 3-formylpiperidine-1-carboxylate (514 mg, 2.410 mmol) in place of benzaldehyde. LCMS: 306 $(M+2-Boc)^+$.

Example 43B tert-butyl 3-((((6-(2-(1-(tert-butoxycarbonyl)piperidin-4-yl)-1H-pyrrolo[2,3-b]pyridin-4-yl)-5-chloropyridin-2-yl)amino)methyl)piperidine-1-carboxylate The title compound was prepared using the procedure described in Example 5B, using Example 21A (200 mg, 0.468 mmol) in place of Example 5A and Example Example 43A (246 mg, 0.608 mmol) in place of 6-bromo-5-methoxypyridin-2-amine. LCMS: 625.3 $(M+H)^+$.

Example 43C 5-chloro-N-(piperidin-3-ylmethyl)-6-(2-(piperidin-4-yl)-1H-pyrrolo[2,3-b]pyridin-4-yl)pyridin-2-amine The title compound was prepared as the trifluoroacetate salt using the procedure described in Example 1H, using Example 43B (120 mg, 0.192 mmol) in place of Example 1G. LCMS: 425.2 $(M+H)^+$. $^1$H NMR (400 MHz, DMSO-$d_6$/

D$_2$O): δ 1.5-1.6 (m, 1H), 1.76-1.80 (m, 4H), 1.9-1.97 (m, 1H), 2.21-2.24 (m, 2H), 2.67-2.77 (m, 2H), 3.01-3.23 (m, 10H), 6.06 (s, 1H), 6.61 (d, J=8.8 Hz, 1H), 7.13 (d, J=4.8 Hz, 1H), 7.60 (d, J=8.8 Hz, 1H), 8.22 (d, J=4.8 Hz, 1H).

Example 44

4-(3-chloro-6-phenylpyridin-2-yl)-2-(piperidin-4-yl)-1H-pyrrolo[2,3-b]pyridine

Example 44A 2-bromo-3-chloro-6-phenylpyridine

To a degassed solution of 2-bromo-3-chloro-6-iodopyridine (350 mg, 1.099 mmol) and phenylboronic acid (134 mg, 1.099 mmol), saturated potassium carbonate solution (5.50 mL, 5.50 mmol) in acetonitrile (5 mL) was added tetrakistriphenylphosphine palladium (63.5 mg, 0.055 mmol) and the mixture heated at 70° C. for 2 hours. The mixture was cooled and filtered through diatomaceous earth. The filtrate was concentrated and the residue washed with diethyl ether to afford the crude title compound. LCMS: 267 (M+H)$^+$.

Example 44B tert-butyl 4-(4-(3-chloro-6-phenylpyridin-2-yl)-1H-pyrrolo[2,3-b]pyridin-2-yl)piperidine-1-carboxylate The title compound was prepared using the procedure described in Example 5B, using Example 21A (300 mg, 0.468 mmol) in place of Example 5A and Example 44A (300 mg, 1.117 mmol) in place of 6-bromo-5-methoxypyridin-2-amine. LCMS: 489 (M+H)$^+$.

Example 44C 4-(3-chloro-6-phenylpyridin-2-yl)-2-(piperidin-4-yl)-1H-pyrrolo[2,3-b]pyridine The title compound was prepared as the trifluoroacetate salt using the procedure described in Example 6E, using Example 44B (150 mg, 0.306 mmol) in place of Example 6D, and purified using preparative HPLC (Zorbax XDB C-18 column with gradient elution from 0.1% trifluoroacetic acid in water to 1:1 methanol/acetonitrile). LCMS: 389.2 (M+H)$^+$. $^1$H NMR (400 MHz, DMSO-d$_6$): δ 1.77-1.80 (m, 2H), 2.22-2.26 (m, 2H), 3.03-3.1 (m, 3H) 3.35-3.36 (m, 2H), 6.12 (s, 1H), 7.28 (d, J=4.8 Hz, 1H), 7.48-7.53 (m, 3H), 8.11-8.13 (m, 3H), 8.20 (d, J=8.4 Hz, 1H), 8.30 (d, J=5.2 Hz, 1H), 8.6 (brs, 1H), 11.9 (s, 1H).

Example 45

N-{5-chloro-6-[2-(piperidin-4-yl)-1H-pyrrolo[2,3-b]pyridin-4-yl]pyridin-2-yl}benzamide Example 45A N-(6-bromo-5-chloropyridin-2-yl)benzamide To a solution of Example 11A (400 mg, 1.928 mmol) in dichloromethane (20 mL) was added pyridine (0.468 mL, 5.78 mmol) followed by benzoyl chloride (0.325 g, 2.314 mmol) and the mixture was stirred for 2 hours. The mixture was concentrated and the residue was dissolved in ethyl acetate, washed with sodium bicarbonate solution, water and brine, and dried over anhydrous sodium sulfate. Filtration, concentration and purification by column chromatography (silica gel, 10% ethyl acetate in hexane) afforded the title compound. LCMS: 311 (M+H)$^+$.

Example 45B tert-butyl 4-(4-(6-benzamido-3-chloropyridin-2-yl)-1H-pyrrolo[2,3-b]pyridin-2-yl)piperidine-1-carboxylate The title compound was prepared using the procedure described in Example 5B, using Example 21A (200 mg, 0.468 mmol) in place of Example 5A and Example 45A (190 mg, 0.608 mmol) in place of 6-bromo-5-methoxypyridin-2-amine. LCMS: 532.8 (M+H)$^+$.

Example 45C

N-(5-chloro-6-(2-(piperidin-4-yl)-1H-pyrrolo[2,3-b]pyridin-4-yl)pyridin-2-yl)benzamide The title compound was prepared as the trifluoroacetate salt using the procedure described in Example 1H, using Example 45B (100 mg, 0.188 mmol) in place of Example 1G. LCMS: 432.4 (M+H)$^+$. $^1$H NMR (400 MHz, DMSO-d$_6$): δ 1.74-1.83 (m, 2H), 2.21-2.24 (m, 2H), 2.99-3.07 (m, 3H), 3.33-3.36 (m, 2H), 6.08 (s, 1H), 7.18 (d, J=4.4 Hz, 1H), 7.48-7.62 (m, 3H), 8.03 (d, J=7.6 Hz, 2H), 8.14 (d, J=8.8 Hz, 1H), 8.27-8.30 (m, 2H), 8.62 (brs, 1H), 11.0 (s, 1H), 11.8 (s, 1H).

Example 46

N-benzyl-5-chloro-N-methyl-6-[2-(piperidin-4-yl)-1H-pyrrolo[2,3-b]pyridin-4-yl]pyridin-2-amine Example 46A N-benzyl-6-bromo-5-chloro-N-methylpyridin-2-amine To a solution of trifluoroacetic acid (1 mL) in dichloromethane (5 mL) was added sodium borohydride (185 mg, 4.40 mmol) at 0° C. and the mixture was stirred at 0° C. for 15 minutes. Example 11B (100 mg, 0.33 mmol) and paraformaldehyde (100 mg, 3.35 mmol) in dichloromethane were added and the mixture was stirred at room temperature for 1 hour. The mixture was quenched with sodium bicarbonate solution and the aqueous layer was extracted with dichloromethane, separated and concentrated. Purification by column chromatography (silica gel, 30% ethyl acetate in hexane) afforded the title compound. LCMS: 313 (M+3)$^+$.

Example 46B tert-butyl 4-(4-(6-(benzyl(methyl)amino)-3-chloropyridin-2-yl)-1H-pyrrolo[2,3-b]pyridin-2-yl)piperidine-1-carboxylate In 20 mL microwave vial Example 46A (50 mg, 0.16 mmol) was dissolved in 0.5 mL water and 2 mL dioxane. Sodium carbonate (51 mg, 0.48 mmol) in 1 mL of water was added followed by the addition of Example 21A (83 mg, 0.241). The mixture was degassed with nitrogen for 10 minutes and tetrakistriphenylphosphine (6.1 mg, 0.005 mmol) was added. After heating at 100° C. overnight, the mixture was diluted with ethyl acetate (50 mL) and washed with water (50×3 mL) followed by brine solution (25 mL). The organic layer was dried over anhydrous sodium sulfate, filtered, and concentrated to afford the title compound. LCMS: 533 (M+2)$^+$.

Example 46C

N-benzyl-5-chloro-N-methyl-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 46B (120 mg, 0.225 mmol) in place of Example 6D, and purified using preparative HPLC (AG/AD/PP/C-18 column with gradient elution from 0.1% trifluoroacetic acid in water to 1:1 methanol/acetonitrile). LCMS: 432.2 (M+H)$^+$. $^1$H NMR (400 MHz, DMSO-d$_6$): δ 1.62-1.68 (m, 2H), 2.06-2.12 (m, 2H), 2.99-3.05 (m, 8H), 3.8 (s, 2H), 6.03 (s, 1H), 6.78 (d, J=8.8 Hz, 1H), 7.17-7.21 (m, 3H), 7.22-7.25 (m, 1H), 7.31-7.33 (m, 2H), 7.73 (d, J=8.8 Hz, 1H), 8.2 (d, J=4.8 Hz, 2H), 8.5 (brs, 1H), 11.7 (s, 1H).

Example 47

N-benzyl-5-chloro-N-ethyl-6-[2-(piperidin-4-yl)-1H-pyrrolo[2,3-b]pyridin-4-yl]pyridin-2-amine Example 47A N-benzyl-6-bromo-5-chloro-N-ethylpyridin-2-amine To a stirred solution of trifluoroacetic acid (1 mL) in dichloromethane (10 mL) was added sodium borohydride (185 mg, 4.40 mmol) at 0° C. and the mixture stirred at 0° C. for 15 minutes. Example 11B (100 mg, 0.33 mmol) and acetaldehyde (149 mg, 3.35 mmol) in dichloromethane were added and the mixture was stirred at room temperature for 1 hour. The mixture was quenched with sodium bicarbonate solution and the aqueous layer was extracted with dichloromethane. The organic layer was separated and concentrated and the residue was purified by column chromatography (silica gel, 30% ethyl acetate in hexane) to afford the title compound. LCMS: 327 (M+3)$^+$.

Example 47B tert-butyl 4-(4-(6-(benzyl(ethyl)amino)-3-chloropyridin-2-yl)-1H-pyrrolo[2,3-b]pyridin-2-yl)piperidine-1-carboxylate The title compound was prepared using the procedure described in Example 46B using Example 47A (200 mg, 0.615 mmol) in place of Example 46A. LCMS: 546.3 (M+H)$^+$.

Example 47C

N-benzyl-5-chloro-N-ethyl-6-(2-(piperidin-4-yl)-1H-pyrrolo[2,3-b]pyridin-4-yl)pyridin-2-amine The title compound was prepared as the trifluoroacetate salt using the procedure described in Example 6E, using Example 47B (300 mg, 0.549 mmol) in place of Example 6D, and purified using preparative HPLC (Zorbax XDB C-18 column with gradient elution from 0.1% trifluoroacetic acid in water to acetonitrile). LCMS: 446.2 (M+H)$^+$. $^1$H NMR (400 MHz, CD$_3$OD): δ 1.20 (t, J=7.2 Hz, 3H), 1.81-1.84 (m, 2H), 2.22-2.25 (m, 2H), 3.11-3.18 (m, 3H), 3.45-3.49 (m, 2H), 3.58-3.63 (m, 2H), 4.91 (s, 2H), 6.28 (s, 1H), 6.72 (d, J=9.2 Hz, 1H), 7.26-7.28 (m, 3H), 7.32-7.36 (m, 3H), 7.64 (d, J=9.2 Hz, 1H), 8.23 (d, J=4 Hz, 1H).

Example 48

5-chloro-6-[2-(piperidin-4-yl)-1H-pyrrolo[2,3-b]pyridin-4-yl]-N-(tetrahydro-2H-pyran-4-ylmethyl)pyridin-2-amine Example 48A 6-bromo-5-chloro-N-((tetrahydro-2H-pyran-4-yl)methyl)pyridin-2-amine The title compound was prepared using the procedure described in Example 11B, using tetrahydro-2H-pyran-4-carbaldehyde (132 mg, 1.157 mmol) in place of benzaldehyde. LCMS: 306.9 (M+H)$^+$.

Example 48B tert-butyl 4-(4-(3-chloro-6-(((tetrahydro-2H-pyran-4-yl)methyl)amino)pyridin-2-yl)-1H-pyrrolo[2,3-b]pyridin-2-yl)piperidine-1-carboxylate The title compound was prepared using the procedure described in Example 5B, using Example 21A (100 mg, 0.234 mmol) in place of Example 5A and Example 48A (107 mg, 0.351 mmol) in place of 6-bromo-5-methoxypyridin-2-amine. LCMS: 526.4 (M+H)$^+$.

Example 48C 5-chloro-6-(2-(piperidin-4-yl)-1H-pyrrolo[2,3-b]pyridin-4-yl)-N-((tetrahydro-2H-pyran-4-yl)methyl)pyridin-2-amine The title compound as prepared as the trifluoroacetate salt using the procedure described in Example 1H, using Example 48B (80 mg, 0.152 mmol) in place of Example 1G. LCMS: 427.15 (M+H)$^+$. $^1$H NMR (400 MHz, DMSO-d$_6$/D$_2$O): δ 1.16-1.23 (m, 2H), 1.59-1.62 (m, 2H), 1.76-1.80 (m, 2H), 2.21-2.25 (m, 2H), 3.02-3.13 (m, 4H), 3.23-3.28 (m, 2H), 3.35-3.38 (m 2H), 3.57-3.59 (m, 2H), 3.83 (d, J=10 Hz, 2H), 6.11 (s, 1H), 6.61 (d, J=8.8 Hz, 1H), 7.16 (d, J=5.2 Hz, 1H), 7.57 (d, J=9.2 Hz, 1H), 8.23 (d, J=5.2 Hz, 1H).

Example 49

5-chloro-6-[2-(piperidin-4-yl)-1H-pyrrolo[2,3-b]pyridin-4-yl]-N-(tetrahydro-2H-pyran-3-ylmethyl)pyridin-2-amine Example 49A 6-bromo-5-chloro-N-((tetrahydro-2H-pyran-3-yl)methyl)pyridin-2-amine The title compound was prepared using the procedure described in Example 11B, using tetrahydro-2H-pyran-3-carbaldehyde (303 mg, 2.65 mmol) in place of benzaldehyde. LCMS: 308 (M+3)$^+$.

Example 49B tert-butyl 4-(4-(3-chloro-6-(((tetrahydro-2H-pyran-3-yl)methyl)amino)pyridin-2-yl)-1H-pyrrolo[2,3-b]pyridin-2-yl)piperidine-1-carboxylate The title compound was prepared using the procedure described in Example 5B, using Example 21A (200 mg, 0.468 mmol) in place of Example 5A and Example 49A (215 mg, 0.702 mmol) in place of 6-bromo-5-methoxypyridin-2-amine. LCMS: 527.1 (M+H)$^+$.

Example 49C 5-chloro-6-[2-(piperidin-4-yl)-1H-pyrrolo[2,3-b]pyridin-4-yl]-N-(tetrahydro-2H-pyran-3-ylmethyl)pyridin-2-amine The title compound was prepared as the trifluoroacetate salt using the procedure described in Example 1H, using Example 49B (130 mg, 0.247 mmol) in place of Example 1G. LCMS: 426.3 (M+H)$^+$. $^1$H NMR (400 MHz, DMSO-d$_6$/D$_2$O): δ 1.16-1.33 (m, 2H), 1.39-1.57 (m, 2H), 1.75-1.82 (m, 4H), 2.22-2.25 (m, 2H), 3.02-3.11 (m, 5H), 3.26-3.37 (m, 3H), 3.69-3.79 (m, 2H), 6.10 (s, 1H), 6.59 (d, J=8.8 Hz, 1H), 7.15 (d, J=5.2 Hz, 1H), 7.57 (d, J=8.8 Hz, 1H), 8.23 (d, J=4.8 Hz, 1H).

Example 50

N-{4-chloro-3-[2-(piperidin-4-yl)-1H-pyrrolo[2,3-b]pyridin-4-yl]phenyl}benzenesulfonamide

Example 50A

N-(3-bromo-4-chlorophenyl)benzenesulfonamide

To a solution of 3-bromo-4-chloroaniline (200 mg, 0.969 mmol) in dichloromethane (5 mL) was added triethylamine (0.374 mL, 2.91 mmol). The solution was cooled to 0° C. and benzenesulfonyl chloride (188 mg, 1.066 mmol) was added dropwise. After stirring at room temperature for 12 hours, the mixture was extracted with dichloromethane and the organic layer washed with water and brine (25 mL each). Drying over sodium sulfate, filtration and concentration afforded the title compound. LCMS: 346.1 (M+H)$^+$.

Example 50B tert-butyl 4-(4-(2-chloro-5-(phenylsulfonamido)phenyl)-1H-pyrrolo[2,3-b]pyridin-2-yl)piperidine-1-carboxylate The title compound was prepared using the procedure described in Example 7A, using Example 50A (200 mg, 0.577 mmol) in place of 2-bromo-4-cyclopropyl-1-methoxybenzene and Example 21A (370 mg, 0.865 mmol) in place of Example 5A. LCMS: 567.2 (M+H)$^+$.

Example 50C

N-(4-chloro-3-(2-(piperidin-4-yl)-1H-pyrrolo[2,3-b]pyridin-4-yl)phenyl)benzenesulfonamide The title compound was prepared as the trifluoroacetate salt using the procedure described in Example 6E, using Example 50B (150 mg, 0.265 mmol) in place of Example 6D, and purified using preparative HPLC (Zorbax XDB C-18 column with gradient elution from 0.1% trifluoroacetic acid in water to 1:1 methanol/acetonitrile). LCMS: 467.2 (M+H)$^+$. $^1$H NMR (400 MHz, DMSO-d$_6$): δ 1.71-1.80 (m, 2H), 2.19-2.23 (m, 2H), 3.05-3.07 (m, 5H), 5.75 (s, 1H), 6.93 (d, J=4.8 Hz, 1H), 7.18-7.20 (m, 2H), 7.52 (d, J=9.2 Hz, 1H), 7.58-7.70 (m, 3H), 7.78 (d, J=8 Hz, 2H), 8.20 (d, J=5.2 Hz, 1H), 8.60 (brs, 1H), 10.6 (s, 1H), 11.8 (s, 1H).

Example 51

N-benzyl-4-fluoro-3-[2-(piperidin-4-yl)-1H-pyrrolo[2,3-b]pyridin-4-yl]aniline

Example 51A

N-benzyl-3-bromo-4-fluoroaniline

The title compound was prepared using the procedure described in Example 11B, using 2-bromo-4-fluoroaniline (2 g, 10.4 mmol) in place of the Example 11A. LCMS: 281.9 (M+3)$^+$.

Example 51B

N-benzyl-4-fluoro-3-(4,4,5,5-tetramethyl-1,3,2-dioxaborolan-2-yl)aniline

The title compound was prepared using the procedure described in Example 6C, using Example 51A (500 mg, 1.77 mmol) in place of the Example 6B. LCMS: 328.1 (M+H)$^+$.

Example 51C tert-butyl 4-(4-(5-(benzylamino)-2-fluorophenyl)-1H-pyrrolo[2,3-b]pyridin-2-yl)piperidine-1-carboxylate The title compound was prepared using the procedure described in Example 1G, using Example 17E (250 mg, 0.71 mmol) in place of the Example 1F and Example 51B (351 mg, 1.06 mmol) in place of 5-fluoro-2-methoxyphenylboronic acid. LCMS: 501.4 (M+H)$^+$.

Example 51D

N-benzyl-4-fluoro-3-(2-(piperidin-4-yl)-1H-pyrrolo[2,3-b]pyridin-4-yl)aniline

The title compound was prepared as the trifluoroacetate salt using the procedure described in Example 6E, using Example 51C (200 mg, 0.399 mmol) in place of Example 6D, and purified using preparative HPLC (SEMI C-18 column with gradient elution from 0.1% trifluoroacetic acid in water to acetonitrile). LCMS: 401 (M+H)$^+$. $^1$H NMR (400 MHz, CD$_3$OD): δ 1.92-1.96 (m, 2H), 2.31-2.34 (m, 1H), 3.17-3.23 (m, 3H), 3.52-3.55 (m, 2H), 4.39 (s, 2H), 6.27 (s, 1H), 6.82-6.89 (m, 2H), 7.09-7.14 (m, 1H), 7.28-7.42 (m, 6H), 8.27 (wd, J=5.2 Hz, 1H).

Example 52

N-benzyl-5-chloro-4-[2-(piperidin-4-yl)-1H-pyrrolo[2,3-b]pyridin-4-yl]pyridin-2-amine

Example 52A 4-bromo-5-chloropyridin-2-amine

To a solution of 4-bromopyridin-2-amine (500 mg, 2.89 mmol) in N,N-dimethylformamide (5 mL) was added N-chlorosuccinimide (463 mg, 3.47 mmol) and the mixture was stirred at room temperature for 12 hours. The mixture was filtered through diatomaceous earth and concentrated and the residue was dissolved in ethyl acetate. The solution was washed with water and brine, dried over anhydrous sodium sulfate, filtered, and concentrated to afford the crude title compound. Purification by column chromatography (silica gel, 30% ethyl acetate in hexane) afforded the title compound.

Example 52B

N-benzyl-4-bromo-5-chloropyridin-2-amine

The title compound was prepared using the procedure described in Example 11B, using Example 52A (600 mg, 2.89 mmol) in place of Example 11A. LCMS: 298.9 (M+3)$^+$.

Example 52C tert-butyl 4-(4-(2-(benzylamino)-5-chloropyridin-4-yl)-1H-pyrrolo[2,3-b]pyridin-2-yl)piperidine-1-carboxylate The title compound was prepared using the procedure described in Example 5B, using Example 52B (300 mg, 1.008 mmol) in place of 6-bromo-5-methoxypyridin-2-amine and Example 21A (200 mg, 0.468 mmol) in place of Example 5A. LCMS: 518.3 (M+H)$^+$.

Example 52D

N-benzyl-5-chloro-4-(2-(piperidin-4-yl)-1H-pyrrolo[2,3-b]pyridin-4-yl)pyridin-2-amine The title compound was prepared as the trifluoroacetate salt using the procedure described in Example 6E, using Example 52C (160 mg, 0.309 mmol) in place of Example 6D, and purified using preparative HPLC (X-bridge C-18 column with gradient elution from 0.1% trifluoroacetic acid in water to 1:1 methanol/acetonitrile). LCMS: 417.9 (M+H)$^+$. $^1$H NMR (400 MHz, DMSO-d$_6$): δ 1.76-1.78 (m, 2H), 2.19-2.22 (m, 2H), 3.0-3.09 (m, 5H), 4.50 (d, J=5.6 Hz, 2H), 5.94 (s, 1H), 6.60 (s, 1H), 7.01 (d, J=4.8 Hz, 1H), 7.25-7.27 (m, 1H), 7.31-7.35 (m, 3H), 7.43-7.46 (m, 1H), 8.14 (s, 1H), 8.23 (d, J=4.8 Hz, 1H), 8.26-8.3 (m, 1H), 8.56-8.6 (m, 1H), 11.90 (s, 1H).

Example 53

N-benzyl-4-chloro-3-[2-(piperidin-4-yl)-1H-pyrrolo[2,3-b]pyridin-4-yl]aniline

Example 53A

N-benzyl-3-bromo-4-chloroaniline

The title compound was prepared using the procedure described in Example 11B, using 3-bromo-4-chloroaniline (600 mg, 2.91 mmol) in place of Example 11A. LCMS: 297 (M+3)$^+$.

Example 53B tert-butyl 4-(4-(5-(benzylamino)-2-chlorophenyl)-1H-pyrrolo[2,3-b]pyridin-2-yl)piperidine-1-carboxylate The title compound was prepared using the procedure described in Example 5B, using Example 53A (300 mg, 1.01 mmol) in place of 6-bromo-5-methoxypyridin-2-amine and Example 21A (200 mg, 0.468 mmol) in place of Example 5A. LCMS: 517.3 (M+H)$^+$.

Example 53C

N-benzyl-4-chloro-3-(2-(piperidin-4-yl)-1H-pyrrolo[2,3-b]pyridin-4-yl)aniline

The title compound was prepared as the trifluoroacetate salt using the procedure described in Example 6E, using Example 53B (110 mg, 0.213 mmol) in place of Example 6D, and purified using preparative HPLC (AG/AD/PP/C-18 column with gradient elution from 0.1% trifluoroacetic acid in water to 1:1 methanol/acetonitrile). LCMS: 417.1 (M+H)$^+$. $^1$H NMR (400 MHz, DMSO-d$_6$): δ 1.7-1.76 (m, 2H), 2.14-2.17 (m, 2H), 3.01-3.04 (m, 5H), 4.26 (s, 2H), 5.77 (s, 1H), 6.59-6.68 (m, 3H), 6.91 (d, J=4.8 Hz, 1H), 7.22-7.24 (m, 2H), 7.29-7.33 (m, 4H), 8.15-8.24 (m, 2H), 11.80 (s, 1H).

Example 54

N-benzyl-5-chloro-6-[2-(1-methylpiperidin-4-yl)-1H-pyrrolo[2,3-b]pyridin-4-yl]pyridin-2-amine The title compound was prepared as the trifluoroacetate salt using the procedure described in Example 8, substituting Example 32A (100 mg, 0.193 mmol) in place of Example 2A, and purified using preparative HPLC (Zorbax XDB C-18 column with gradient elution from 0.1% trifluoroacetic acid in water to 1:1 methanol/acetonitrile). LCMS: 432.3 (M+H)$^+$. $^1$H NMR (400 MHz, DMSO-d$_6$): δ 1.7-1.73 (m, 2H), 2.16-2.19 (m, 2H), 2.8 (s, 3H), 2.9-3.0 (m, 2H), 3.06-3.09 (m, 2H), 3.49-3.52 (m, 1H), 4.47 (s, 2H), 5.97 (s, 1H), 6.64 (d, J=8.8 Hz, 1H), 7.12 (d, J=5.2 Hz, 1H), 7.25-7.26 (m, 1H), 7.31-7.32 (m, 4H), 7.5 (brs, 1H), 7.61 (d, J=8.8 Hz, 1H), 8.20 (d, J=5.2 Hz, 1H), 11.80 (s, 1H).

Example 55

5-chloro-N-[(1S)-1-phenylethyl]-6-[2-(piperidin-4-yl)-1H-pyrrolo[2,3-b]pyridin-4-yl]pyridin-2-amine Example 55A (S)-6-bromo-N-(1-phenylethyl)pyridin-2-amine A mixture of 2-bromo-6-fluoropyridine (500 mg, 2.84 mmol) and (S)-(−)-1-phenylethylamine (0.435 mL, 3.41 mmol) were heated at 100° C. for 12 hours. The mixture was cooled to room temperature, dissolved in ethyl acetate, washed with water and brine, dried over anhydrous sodium sulfate, filtered, and concentrated. Purification by column chromatography (silica gel, 6% ethyl acetate-hexane) afforded the title compound.

Example 55B (S)-6-bromo-5-chloro-N-(1-phenylethyl)pyridin-2-amine

The title compound was prepared using the procedure described in Example 52A, using Example 55A (500 mg, 1.804 mmol) in place of 4-bromopyridin-2-amine

Example 55C (S)-tert-butyl 4-(4-(3-chloro-6-((1-phenylethyl)amino)pyridin-2-yl)-1H-pyrrolo[2,3-b]pyridin-2-yl)piperidine-1-carboxylate The title compound was prepared using the procedure described in Example 5B, using Example 21A (200 mg, 0.468 mmol) in place of Example 5A and Example 55B (190 mg, 0.608 mmol) in place of 6-bromo-5-methoxypyridin-2-amine.

Example 55D 5-chloro-N-[(1S)-1-phenylethyl]-6-[2-(piperidin-4-yl)-1H-pyrrolo[2,3-b]pyridin-4-yl]pyridin-2-amine The title compound was prepared as the trifluoroacetate salt using the procedure described in Example 6E, using Example 55C (150 mg, 0.282 mmol) in place of Example 6D, and purified using preparative HPLC (Zorbax XDB C-18 column with gradient elution from 0.1% trifluoroacetic acid in water to 1:1 methanol/acetonitrile). LCMS: 432.2 (M+H)$^+$. $^1$H NMR (400 MHz, DMSO-d$_6$): δ 1.61 (d, J=6.8 Hz, 3H), 1.76-1.87 (m, 2H), 2.18-2.19 (m, 2H), 3.09-3.10 (m, 2H), 3.37-3.39 (m, 3H), 5.49 (t, J=7.6 Hz, 1H), 6.58 (s, 1H), 6.77 (d, J=8 Hz, 1H), 7.18-7.24 (m, 2H), 7.32 (t, J=7.2 Hz, 2H), 7.40 (d (J=5.2 Hz), 1H), 7.46 (d, J=7.6 Hz, 2H), 7.76 (d, J=8 Hz, 1H), 8.19 (d, J=5.2 Hz, 1H), 8.57 (brs, 1H), 11.80 (s, 1H).

Example 56

N-benzyl-6-[2-(1-methylpiperidin-4-yl)-1H-pyrrolo[2,3-b]pyridin-4-yl]pyridin-2-amine The title compound was prepared as the trifluoroacetate salt using the procedure described in Example 8, using Example 32A (100 mg, 0.193 mmol) in place of Example 2A, and purified using preparative HPLC (Zorbax XDB C-18 column with gradient elution from 0.1% trifluoroacetic acid in water to 1:1 methanol/acetonitrile). Dechlorination occurred under the reaction conditions. LCMS: 398.2 (M+H)$^+$. $^1$H NMR (400 MHz, DMSO-d$_6$): δ 1.70-1.73 (m, 2H), 2.16-2.19 (m, 2H), 2.77-2.81 (m, 3H), 3.06-3.09 (m, 3H), 3.49-3.52 (m, 2H), 4.64 (s, 2H), 6.65-6.66 (m, 2H), 7.19-7.25 (m, 2H), 7.31-7.38 (m, 4H), 7.47 (d, J=5.2 Hz, 1H), 7.52-7.58 (m, 1H), 8.20 (d, J=5.2 Hz, 1H), 11.80 (s, 1H).

Example 57

5-chloro-N-(3-fluorobenzyl)-6-[2-(1-methylpiperidin-4-yl)-1H-pyrrolo[2,3-b]pyridin-4-yl]pyridin-2-amine The title compound was prepared as the trifluoroacetate salt using the procedure described in Example 8, using Example 33B (100 mg, 0.187 mmol) in place of Example 2A, and purified using preparative HPLC (Zorbax XDB C-18 column with gradient elution from 0.1% trifluoroacetic acid in water to 1:1 methanol/acetonitrile). LCMS: 449.8 (M+H)$^+$. $^1$H NMR (400 MHz, DMSO-d$_6$): δ 1.68-1.71 (m, 2H), 2.06 (s, 3H), 2.14-2.18 (m, 2H), 2.76-2.79 (m, 2H), 3.04-3.08 (m, 2H), 3.47-3.50 (m, 1H), 4.46 (s, 2H), 5.91 (s, 1H), 6.64 (d, J=8.8 Hz, 1H), 7.05-7.13 (m, 3H), 7.33-7.34 (m, 1H), 7.5 (brs, 1H), 7.60 (d, J=8.8 Hz, 1H), 8.18 (d, J=5.2 Hz, 1H), 9.3 (brs, 1H), 11.70 (s, 1H).

Example 58

4-[6-(benzyloxy)-3-chloropyridin-2-yl]-2-(piperidin-4-yl)-1H-pyrrolo[2,3-b]pyridine

Example 58A 2-bromo-3-chloro-6-fluoropyridine

To a solution of 6-bromo-5-chloropyridin-2-amine (1 g, 4.82 mmol) in dichloromethane (10 mL) at 0° C. added tert-butylnitrite (1.145 mL, 9.64 mmol) followed by pyridine hydrofluoride (3 mL, 9.64 mmol) and the mixture was stirred at 0° C. for 30 minutes. The mixture was quenched with water and extracted with dichloromethane. The organic layer was washed with water and brine (25 mL each), dried over sodium sulfate, filtered, and concentrated to afford of the title compound. $^1$H NMR (400 MHz, CDCl$_3$): δ 6.90-6.93 (m, 1H), 7.80-7.84 (m, 1H).

Example 58B 6-(benzyloxy)-2-bromo-3-chloropyridine

To a solution of benzyl alcohol (55.5 mg, 0.513 mmol) in tetrahydrofuran (5 mL) at 0° C. was added potassium tert-butoxide (57.6 mg, 0.513 mmol) and the mixture was stirred at 0° C. for 2 hours. The mixture was cooled to −78° C. and a solution of 2-bromo-3-chloro-6-fluoropyridine (120 mg, 0.570 mmol) in 2 mL tetrahydrofuran was added. After stirring at −78° C. for 1 hour the mixture was diluted with ethyl acetate and water. The organic layer was separated, washed with water and brine, dried over sodium sulfate and concentrated. Purification by column chromatography (silica gel, 20% ethyl acetate in hexane) afforded the title compound. LCMS: 299.9 (M+3)$^+$.

Example 58C tert-butyl 4-(4-(6-(benzyloxy)-3-chloropyridin-2-yl)-1H-pyrrolo[2,3-b]pyridin-2-yl)piperidine-1-carboxylate The title compound was prepared using the procedure described in Example 7A, using Example 58B (100 mg, 0.335 mmol) in place of 2-bromo-4-cyclopropyl-1-methoxybenzene and Example 21A (215 mg, 0.502 mmol) in place of Example 5A. LCMS: 520.1 (M+H)$^+$.

Example 58D 4-(6-(benzyloxy)-3-chloropyridin-2-yl)-2-(piperidin-4-yl)-1H-pyrrolo[2,3-b]pyridine The title compound was prepared as the trifluoroacetate salt using the procedure described in Example 6E, using Example 58C (100 mg, 0.193 mmol) in place of Example 6D, and purified using preparative HPLC (Zorbax XDB C-18 column with gradient elution from 0.1% trifluoroacetic acid in water to 1:1 methanol/acetonitrile). LCMS: 419.2 (M+H)$^+$. $^1$H NMR (400 MHz, DMSO-d$_6$): δ 1.76-1.81 (m, 2H), 2.19-2.22 (m, 2H), 3.0-3.09 (m, 4H), 3.35-3.37 (m, 1H), 5.35 (s, 2H), 6.09 (s, 1H), 7.05 (d, J=8.8 Hz, 1H), 7.22 (d, J=4.8 Hz, 1H), 7.32-7.45 (m, 5H), 8.02 (d, J=8.8 Hz, 1H), 8.60 (brs, 1H), 9.31-9.35 (m, 1H), 11.8 (s, 1H).

Example 59

4-(5-fluoro-2-methoxyphenyl)-2-(pyrrolidin-3-yl)-1H-pyrrolo[2,3-b]pyridine

Example 59A tert-butyl 3-ethynylpyrrolidine-1-carboxylate

The title compound was prepared using the procedure described in Example 1D, using tert-butyl 3-formylpyrrolidine-1-carboxylate (1.1 g, 5.52 mmol) in place of Example 1C.

Example 59B tert-butyl 3-((2-((tert-butoxycarbonyl)amino)-4-chloropyridin-3-yl)ethynyl)pyrrolidine-1-carboxylate The title compound was prepared using the procedure described in Example 1E, using Example 59A (413 mg, 2.115 mmol) in place of Example 1A. LCMS: 422.1 (M+H).

Example 59C tert-butyl 3-(4-chloro-1H-pyrrolo[2,3-b]pyridin-2-yl)pyrrolidine-1-carboxylate The title compound was prepared using the procedure described in Example 1F, using Example 59B (430 mg, 1.019 mmol) in place of Example 1E. LCMS: 322.1 (M+H).

Example 59D tert-butyl 2-(1-(tert-butoxycarbonyl)pyrrolidin-3-yl)-4-chloro-1H-pyrrolo[2,3-b]pyridine-1-carboxylate N,N-Dimethylpyridin-4-amine (0.087 g, 0.715 mmol) was added to a solution of Example 59C (230 mg, 0.715 mmol) in 5 mL tetrahydrofuran at room temperature followed by the drop wise addition of di-tert-butyl dicarbonate (0.156 g, 0.715 mmol). After stirring at room temperature for 3 hours, the mixture was partitioned between ethyl acetate and water (20 mL each). The organic layer was dried over anhydrous sodium sulfate, filtered, and concentrated to afford the title compound. LCMS: 322.1 (M+H-Boc).

Example 59E tert-butyl 2-(1-(tert-butoxycarbonyl)pyrrolidin-3-yl)-4-(5-fluoro-2-methoxyphenyl)-1H-pyrrolo[2,3-b]pyridine-1-carboxylate The title compound was prepared using the procedure described in Example 7A, using Example 59D (200 mg, 0.474 mmol) in place of Example 5A and 5-fluoro-2-methoxyphenylboronic acid (131 mg, 0.521 mmol) in place of 2-bromo-4-cyclopropyl-1-methoxybenzene. LCMS: 412.1 (M+H-Boc).

Example 59F

4-(5-fluoro-2-methoxyphenyl)-2-(pyrrolidin-3-yl)-1H-pyrrolo[2,3-b]pyridine

The title compound was prepared as the hydrochloride salt using the procedure described in Example 1H, using Example 59E (100 mg, 0.195 mmol) in place of Example 1G, and was purified by crystallization from acetonitrile/methanol. LCMS: 312.2 (M+H)$^+$. $^1$H NMR (400 MHz, DMSO-d$_6$/D$_2$O): δ 2.06-2.11 (m, 1H), 2.37-2.41 (m, 2H), 3.24-3.32 (m, 4H), 6.3 (s, 1H), 7.19-7.24 (m, 4H), 7.27-7.30 (m, 1H), 8.25 (d, J=5.2 Hz, 1H).

Example 60

4-(4-fluoro-2-methoxyphenyl)-2-(pyrrolidin-3-yl)-1H-pyrrolo[2,3-b]pyridine

Example 60A tert-butyl 2-(1-(tert-butoxycarbonyl)pyrrolidin-3-yl)-4-(4-fluoro-2-methoxyphenyl)-1H-pyrrolo[2,3-b]pyridine-1-carboxylate The title compound was prepared using the procedure described in Example 7A, using Example 59D (100 mg, 0.31 mmol) in place of Example 5A and 4-fluoro-2-methoxyphenylboronic acid (63 mg, 0.37 mmol) in place of 2-bromo-4-cyclopropyl-1-methoxybenzene. LCMS: 412.9 (M+H).

Example 60B

4-(4-fluoro-2-methoxyphenyl)-2-(pyrrolidin-3-yl)-1H-pyrrolo[2,3-b]pyridine

The title compound was prepared as the hydrochloride salt using the procedure described in Example 1H, using Example 60A (60 mg, 0.11 mmol) in place of Example 1G, and was purified by crystallization from acetonitrile/methanol. LCMS: 312.2 (M+H)$^+$. $^1$H NMR (400 MHz, DMSO-d$_6$/D$_2$O): δ 2.05-2.14 (m, 1H), 2.32-2.41 (m, 2H), 3.25-3.38 (m, 4H), 3.80 (s, 3H), 6.27 (s, 1H), 6.93 (t, J=8.4 Hz, 1H), 7.112-7.18 (m, 2H) 7.438 (t, J=7.6 Hz, 1H) 8.24 (d, J=5.2 Hz, 1H).

Example 61

4-(5-fluoro-2-methoxyphenyl)-2-[(3S)-pyrrolidin-3-yl]-1H-pyrrolo[2,3-b]pyridine The racemic product of Example 59F (100 mg, 0.321 mmol) was resolved using a Chiralpak AD-H HPLC column to afford the title compound. (absolute stereochemistry arbitrarily assigned). LCMS: 311.9 (M+H)$^+$. $^1$H NMR (400 MHz, CD$_3$OD): δ 2.01-2.06 (m, 1H), 2.32-2.36 (m, 1H), 3.0-3.19 (m, 3H), 3.39-3.42 (m, 1H), 3.50-3.56 (m, 1H), 3.78 (s, 3H), 6.15 (s, 1H), 7.09-7.19 (m, 4H), 8.13 (d, J=5.2 Hz, 1H).

Example 62

4-(5-fluoro-2-methoxyphenyl)-2-[(3R)-pyrrolidin-3-yl]-1H-pyrrolo[2,3-b]pyridine The racemic product of Example 59F (100 mg, 0.321 mmol) was resolved using Chiralpak AD-H HPLC column to afford the title compound. (Absolute stereochemistry was arbitrarily assigned.) LCMS: 311.9 (M+H)$^+$. $^1$H NMR (400 MHz, CD$_3$OD): δ 1.3-1.4 (m, 2H), 2.6-2.7 (m, 1H), 3.05 (brs, 1H), 3.5-3.6 (m, 2H), 3.89 (s, 3H), 3.92-3.98 (m, 1H), 6.66-6.7 (m, 1H), 7.24-7.38 (m, 3H), 7.62-7.68 (m, 1H), 8.38-8.42 (m, 1H).

Example 63

4-(5-fluoro-2-methoxyphenyl)-2-(1-methylpyrrolidin-3-yl)-1H-pyrrolo[2,3-b]pyridine

Example 63A tert-butyl 3-(4-(5-fluoro-2-methoxyphenyl)-1H-pyrrolo[2,3-b]pyridin-2-yl)pyrrolidine-1-carboxylate The title compound was prepared using the procedure described in Example 7A, using Example 59C (100 mg, 0.31 mmol) in place of Example 5A and 5-fluoro-2-methoxyphenylboronic acid (63 mg, 0.37 mmol) in place of 2-bromo-4-cyclopropyl-1-methoxybenzene. LCMS: 413.0 (M+H-Boc).

Example 63B 4-(5-fluoro-2-methoxyphenyl)-2-(1-methylpyrrolidin-3-yl)-1H-pyrrolo[2,3-b]pyridine The title compound was prepared using the procedure described in Example 8, using Example 63A (50 mg, 0.12 mmol) in place of Example 2A. LCMS: 326.2 (M+H)$^+$. $^1$H NMR (400 MHz, DMSO-$d_6$): δ 2.86 (d, J=4.8 Hz, 2H), 3.23-3.47 (m, 3H), 3.60-3.70 (m, 3H), 3.76-3.79 (m, 5H), 6.37 (brs, 1H), 7.23-7.29 (m, 3H), 7.31-7.36 (m, 1H), 8.29 (d, J=5.2 Hz, 1H), 12.4 (s, 1H).

Example 64

N-benzyl-5-chloro-6-[2-(pyrrolidin-3-yl)-1H-pyrrolo[2,3-b]pyridin-4-yl]pyridin-2-amine

Example 64A tert-butyl 2-(1-(tert-butoxycarbonyl)pyrrolidin-3-yl)-4-(4,4,5,5-tetramethyl-1,3,2-dioxaborolan-2-yl)-1H-pyrrolo[2,3-b]pyridine-1-carboxylate The title compound was prepared using the procedure described in Example 5A, using Example 59D (160 mg, 0.379 mmol) in place of Example 1F. LCMS: 431.9 (M+H (boronic acid)).

Example 64B tert-butyl 3-(4-(6-(benzylamino)-3-chloropyridin-2-yl)-1H-pyrrolo[2,3-b]pyridin-2-yl)pyrrolidine-1-carboxylate The title compound was prepared using the procedure described in Example 7A, using Example 64A (150 mg, 0.292 mmol) in place of Example 5A and Example 11B (96 mg, 0.321 mmol) in place of 2-bromo-4-cyclopropyl-1-methoxybenzene. LCMS: 505.2 (M+H).

Example 64C

N-benzyl-5-chloro-6-(2-(pyrrolidin-3-yl)-1H-pyrrolo[2,3-b]pyridin-4-yl)pyridin-2-amine The title compound was prepared as the hydrochloride salt using the procedure described in Example 1H, using Example 64B (100 mg, 0.166 mmol) in place of Example 1G. LCMS: 404.1 (M+H)$^+$. $^1$H NMR (400 MHz, DMSO-$d_6$): δ 1.03-1.10 (m, 1H), 1.99-2.03 (m, 1H), 3.2-3.3 (m, 1H), 2.9-3.0 (m, 2H), 3.06-3.09 (m, 2H), 3.36-3.45 (m, 3H), 4.46 (s, 2H), 6.13 (s, 1H), 6.67 (d, J=8.8 Hz, 1H), 7.18 (d, J=5.2 Hz, 1H), 7.18-7.25 (m, 2H), 7.29-7.33 (m, 4H), 7.62 (d, J=8.8 Hz, 1H), 8.26 (d, J=4.8 Hz, 1H), 9.12-9.2 (m, 2H), 12.0 (s, 1H).

Example 65

5-chloro-6-[2-(pyrrolidin-3-yl)-1H-pyrrolo[2,3-b]pyridin-4-yl]-N-(tetrahydro-2H-pyran-4-ylmethyl)pyridin-2-amine

Example 65A tert-butyl 3-(4-chloro-1-tosyl-1H-pyrrolo[2,3-b]pyridin-2-yl)pyrrolidine-1-carboxylate To a solution of Example 59C (0.5 g, 1.554 mmol) in 20 mL tetrahydrofuran, was added sodium hydroxide (0.249 g, 6.22 mmol) and the mixture was stirred at room temperature for 1 hour. p-Toluenesulfonyl chloride (0.355 g, 1.865 mmol) and benzyltriethylammonium chloride (0.018 g, 0.078 mmol) were added and the mixture was stirred for 12 hours. Water was added and the mixture was extracted with dichloromethane. The organic layer was washed with water and brine, dried over sodium sulfate, filtered, and concentrated to afford the crude product which was purified by column chromatography (100-200 silica-gel in hexane and eluted with 15% ethyl acetate-hexane) to afford the title compound. LCMS: 475.1 (M+H)+.

Example 65B tert-butyl 3-(1-tosyl-4-(4,4,5,5-tetramethyl-1,3,2-dioxaborolan-2-yl)-1H-pyrrolo[2,3-b]pyridin-2-yl)pyrrolidine-1-carboxylate To Example 65A (0.25 g, 0.525 mmol) in 40 mL of 1,4-dioxane, was added 4,4,4',4',5,5,5',5'-octamethyl-2,2'-bi(1,3,2-dioxaborolane) (0.200 g, 0.788 mmol) and potassium acetate (0.155 g, 1.576 mmol). The mixture was purged with nitrogen for 5 minutes and 2-(dicyclohexylphosphino)biphenyl (0.018 g, 0.053 mmol) and palladium(II) acetate (0.012 g, 0.053 mmol) were added. After heating at 100° C. for 12 hours, the mixture was filtered through diatomaceous earth and concentrated. The residue was dissolved in ethyl acetate, washed with water and brine, dried over anhydrous sodium sulfate, filtered, and concentrated to afford the title compound, which was used without further purification.

Example 65C tert-butyl 3-(4-(3-chloro-6-((((tetrahydro-2H-pyran-4-yl)methyl)amino)pyridin-2-yl)-1-tosyl-1H-pyrrolo[2,3-b]pyridin-2-yl)pyrrolidine-1-carboxylate The title compound was prepared using the procedure described in Example 7A, using Example 65B (297 mg, 0.524 mmol) in place of Example 5A and Example 48A (160 mg, 0.524 mmol) in place of 2-bromo-4-cyclopropyl-1-methoxybenzene. LCMS: 666.8 (M+H)$^+$.

Example 65D tert-butyl 3-(4-(3-chloro-6-(((tetrahydro-2H-pyran-4-yl)methyl)amino)pyridin-2-yl)-1H-pyrrolo[2,3-b]pyridin-2-yl)pyrrolidine-1-carboxylate A solution of Example 65C (150 mg, 0.225 mmol) in dioxane (3 mL) and 10N aqueous sodium hydroxide (0.225 mL) was heated in sealed tube at 100° C. for 3 hours. The mixture was diluted with water and ethyl acetate. The organic layer was washed with water and brine (25 mL each), dried over sodium sulfate, filtered and concentrated to afford the title compound. LCMS: 512.55 (M+H)$^+$.

Example 65E 5-chloro-6-(2-(pyrrolidin-3-yl)-1H-pyrrolo[2,3-b]pyridin-4-yl)-N-((tetrahydro-2H-pyran-4-yl)methyl)pyridin-2-amine The title compound was prepared as the trifluoroacetate salt using the procedure described in Example 1H, using Example 65D (110 mg, 0.215 mmol) in place of Example 1G, and purified using preparative HPLC (X-bridge C-18 column with gradient elution from 0.1% trifluoroacetic acid in water to 1:1 methanol/acetonitrile). LCMS: 412.2 (M+H)$^+$. $^1$H NMR (400 MHz, DMSO-d$_6$/D$_2$O): δ 1.15-1.23 (m, 2H), 1.58-1.61 (m, 2H), 2.07-2.12 (m, 1H), 2.33-2.40 (m, 2H), 3.10 (d, J=6.8 Hz, 2H), 3.22-3.43 (m, 4H), 3.60-3.67 (m, 2H), 3.81-3.84 (m, 2H), 6.25 (s, 1H), 6.60 (d, J=8.8 Hz, 1H), 7.14 (d, J=4.8 Hz, 1H), 7.56 (d, J=9.2 Hz, 1H), 8.24 (d, J=4.8 Hz, 1H).

Example 66

4-(4-fluoro-2-methoxyphenyl)-2-(morpholin-2-yl)-1H-pyrrolo[2,3-b]pyridine

Example 66A tert-butyl 2-ethynylmorpholine-4-carboxylate

The title compound was prepared using the procedure described in Example 1D, using tert-butyl 2-formylmorpholine-4-carboxylate (300 mg, 1.394 mmol) in place of Example 1C. LCMS: 212.4 (M+H)$^+$.

Example 66B tert-butyl 2-((2-((tert-butoxycarbonyl)amino)-4-chloropyridin-3-yl)ethynyl)morpholine-4-carboxylate The title compound was prepared using the procedure described in Example 1E, using Example 66A (1.192 g, 5.64 mmol) in place of Example 1A and N,N-dimethylformamide as the solvent instead of tetrahydrofuran. LCMS: 437.2 (M+H)$^+$.

Example 66C tert-butyl 2-(4-chloro-1H-pyrrolo[2,3-b]pyridin-2-yl)morpholine-4-carboxylate The title compound was prepared using the procedure described in Example 1F, using Example 66B (400 mg, 0.913 mmol) in place of Example 1E. LCMS: 338 (M+H-Boc)$^+$.

Example 66D tert-butyl 2-(4-(4-fluoro-2-methoxyphenyl)-1H-pyrrolo[2,3-b]pyridin-2-yl)morpholine-4-carboxylate The title compound was prepared using the procedure described in Example 7A, using 4-fluoro-2-methoxyphenylboronic acid (91 mg, 0.53 mmol) in place of Example 5A and Example 66C (180 mg, 0.53 mmol) in place of 2-bromo-4-cyclopropyl-1-methoxybenzene.

Example 66E 4-(4-fluoro-2-methoxyphenyl)-2-(morpholin-2-yl)-1H-pyrrolo[2,3-b]pyridine The title compound was prepared as the hydrochloride salt using the procedure described in Example 1H, using Example 66D (90 mg, 0.21 mmol) in place of Example 1G, and was purified by crystallization from acetonitrile/methanol. LCMS: 328.1 (M+H)$^+$. $^1$H NMR (400 MHz, DMSO-d$_6$/D$_2$O): δ 3.06-3.08 (m, 1H), 3.27-3.38 (m, 2H), 3.5-3.58 (m, 1H), 3.76 (s, 3H), 4.08-4.11 (m, 2H), 4.89-4.92 (m, 1H), 6.29 (d, J=1.6 Hz, 1H), 6.89-6.94 (m, 1H), 7.06-7.13 (m, 2H), 7.37-7.41 (m, 1H), 8.2 (d, J=4.8 Hz, 1H).

Example 67

4-(5-fluoro-2-methoxyphenyl)-2-(morpholin-2-yl)-1H-pyrrolo[2,3-b]pyridine

Example 67A tert-butyl 2-(4-(5-fluoro-2-methoxyphenyl)-1H-pyrrolo[2,3-b]pyridin-2-yl)morpholine-4-carboxylate The title compound was prepared using the procedure described in Example 1G using Example 66C (150 mg, 0.45 mmol) in place of Example 1F. LCMS: 428.1 (M+H)$^+$.

Example 67B 4-(5-fluoro-2-methoxyphenyl)-2-(morpholin-2-yl)-1H-pyrrolo[2,3-b]pyridine The title compound was prepared as the trifluoroacetate salt using the procedure described in Example 1H, using Example 67A (80 mg, 0.2 mmol) in place of Example 1G, and purified using preparative HPLC (Zorbax XDB C-18 column with gradient elution from 0.1% trifluoroacetic acid in water to 1:1 methanol/acetonitrile). LCMS: 328.1 (M+H)$^+$. $^1$H NMR (400 MHz, DMSO-d$_6$/D$_2$O): δ 3.05-3.15 (m, 2H), 3.25-3.36 (m, 2H), 3.72 (s, 3H), 3.9-3.95 (m, 1H), 4.06-4.12 (m, 1H), 4.97 (d, J=9.6 Hz, 1H), 6.37 (s, 1H), 7.17-7.30 (m, 4H), 8.29 (d, J=5.2 Hz, 1H).

Example 68

4-(4-fluoro-2-methoxyphenyl)-2-(4-methylmorpholin-2-yl)-1H-pyrrolo[2,3-b]pyridine The title compound was prepared using the procedure described in Example 8, using Example 66D (50 mg, 0.117 mmol) in place of Example 2A. LCMS: 341.9 (M+H)$^+$. $^1$H NMR (400 MHz, DMSO-d$_6$): δ 2.1-2.14 (m, 2H), 2.24 (s, 3H), 2.64-2.67 (m, 1H), 2.94-2.97 (m, 1H), 3.63-3.69 (m, 1H), 3.76 (s, 3H), 3.87-3.90 (m, 1H), 4.65 (d, J=8.4 Hz, 1H), 6.11 (s, 1H), 6.88-6.93 (m, 1H), 7.01 (d, J=4.8 Hz, 1H), 7.08 (dd, J=2.4, 11.6 Hz, 1H), 7.39 (t, J=7.2 Hz, 1H), 8.17 (d, J=5.2 Hz, 1H), 11.7 (s, 1H).

Example 69

4-(5-fluoro-2-methoxyphenyl)-2-(4-methylmorpholin-2-yl)-1H-pyrrolo[2,3-b]pyridine The title compound was prepared using the procedure described in Example 8, using Example 67B (80 mg, 0.187 mmol) in place of Example 2A. LCMS: 342.2 (M+H)$^+$. $^1$H NMR (400 MHz, DMSO-d$_6$): δ 2.02-2.15 (m, 2H), 2.2 (s, 3H), 2.6-2.68 (m, 2H), 2.9-2.97 (m, 1H), 3.72 (s, 3H), 3.82-3.90 (m, 1H), 4.6-4.66 (m, 1H), 6.13 (s, 1H), 7.0-7.2 (m, 1H), 7.15-7.3 (m, 3H), 8.19-8.2 (m, 1H), 11.8 (s, 1H).

Example 70

N-benzyl-5-chloro-6-[2-(morpholin-2-yl)-1H-pyrrolo[2,3-b]pyridin-4-yl]pyridin-2-amine

Example 70A tert-butyl 2-(4-(4,4,5,5-tetramethyl-1,3,2-dioxaborolan-2-yl)-1H-pyrrolo[2,3-b]pyridin-2-yl)morpholine-4-carboxylate The title compound was prepared using the procedure described in Example 5A, using Example 66C (100 mg, 0.296 mmol) in place of Example 1F.

Example 70B tert-butyl 2-(4-(6-(benzylamino)-3-chloropyridin-2-yl)-1H-pyrrolo[2,3-b]pyridin-2-yl)morpholine-4-carboxylate The title compound was prepared using the procedure described in Example 7A, using Example 70A (72 mg, 0.14 mmol) in place of Example 5A and Example 11B (50 mg, 0.094 mmol) in place of 2-bromo-4-cyclopropyl-1-methoxybenzene.

Example 70C

N-benzyl-5-chloro-6-(2-(morpholin-2-yl)-1H-pyrrolo[2,3-b]pyridin-4-yl)pyridin-2-amine The title compound was prepared using the procedure described in Example 1H, using Example 70B (90 mg, 0.17 mmol) in place of Example 1G. LCMS: 420.0 (M+H)$^+$. $^1$H NMR (400 MHz, CD$_3$OD): δ 3.36-3.41 (m, 2H), 3.58-3.62 (m, 2H), 4.08-4.1 (m, 1H), 4.25-4.32 (m, 1H), 4.58 (s, 2H), 5.06-5.1 (m, 1H), 6.57 (s, 1H), 6.85-6.88 (m, 1H), 7.3-7.34 (m, 1H), 7.35-7.37 (m, 4H), 7.63 (d, J=5.6 Hz, 1H), 7.75 (d, J=9.2 Hz, 1H), 8.47 (d, J=1.4 Hz, 1H)

Example 71

2-(5,5-dimethylmorpholin-2-yl)-4-(5-fluoro-2-methoxyphenyl)-1H-pyrrolo[2,3-b]pyridine

Example 71A tert-butyl 2-formyl-5,5-dimethylmorpholine-4-carboxylate

To as solution of tert-butyl 2-(hydroxymethyl)-5,5-dimethylmorpholine-4-carboxylate (2.0 g, 8.15 mmol) in dichloromethane (25 mL) was added Dess-Martin periodinane (4.15 g, 9.78 mmol) slowly over 10 minutes and the mixture was stirred at room temperature 3 hours. Saturated sodium bicarbonate solution was added and the mixture extracted with dichloromethane. The dichloromethane layer was washed with water and brine, dried over sodium sulfate, filtered, and concentrated to afford the title compound. LCMS: 144.0 (M+H-Boc).

Example 71B tert-butyl 2-ethynyl-5,5-dimethylmorpholine-4-carboxylate

The title compound was prepared using the procedure described in Example 1D, using Example 71A (1.3 g, 5.34 mmol) in place of Example 1C. LCMS: 140.1 (M+H-Boc)$^+$.

Example 71C tert-butyl 2-((2-((tert-butoxycarbonyl)amino)-4-chloropyridin-3-yl)ethynyl)-5,5-dimethylmorpholine-4-carboxylate The title compound was prepared using the procedure described in Example 1E, using Example 71B (506 mg, 2.115 mmol) in place of Example 1D. LCMS: 140.1 (M+H-Boc)$^+$.

Example 71D tert-butyl 2-(4-chloro-1H-pyrrolo[2,3-b]pyridin-2-yl)-5,5-dimethylmorpholine-4-carboxylate The title compound was prepared using the procedure described in Example 1F, using Example 71C (500 mg, 1.367 mmol) in place of Example 1E.

Example 71E tert-butyl 2-(4-(5-fluoro-2-methoxyphenyl)-1H-pyrrolo[2,3-b]pyridin-2-yl)-5,5-dimethylmorpholine-4-carboxylate The title compound was prepared using the procedure described in Example 1G, using Example 71D (150 mg, 0.41 mmol) in place of Example 1F.

Example 71F 2-(5,5-dimethylmorpholin-2-yl)-4-(5-fluoro-2-methoxyphenyl)-1H-pyrrolo[2,3-b]pyridine The title compound was prepared as the trifluoroacetate salt using the procedure described in Example 6E, using Example 71E (100 mg, 0.235 mmol) in place of Example 6D, and purified using preparative HPLC (Zorbax XDB C-18 column with gradient elution from 0.1% trifluoroacetic acid in water to acetonitrile). LCMS: 356.1 (M+H)$^+$. $^1$H NMR (400 MHz, DMSO-d$_6$): δ 1.23-1.27 (m, 5H), 1.47 (s, 3H), 3.74 (s, 3H), 3.79-3.82 (m, 2H), 4.83-4.86 (m, 1H), 6.42 (s, 1H), 7.1 (d, J=4.8 Hz, 1H), 7.20-7.23 (m, 2H), 7.28-7.31 (m, 1H), 8.28 (d, J=4.8 Hz, 1H), 9.04 (brs, 1H), 12.0 (brs, 1H).

Example 72

2-(5,5-dimethylmorpholin-2-yl)-4-(4-fluoro-2-methoxyphenyl)-1H-pyrrolo[2,3-b]pyridine Example 72A tert-butyl 2-(4-(4-fluoro-2-methoxyphenyl)-1H-pyrrolo[2,3-b]pyridin-2-yl)-5,5-dimethylmorpholine-4-carboxylate The title compound was prepared using the procedure described in Example 1G, using Example 71D (150 mg, 0.41 mmol) in place of Example 1F and 4-fluoro-2-methoxyphenylboronic acid (91 mg, 0.533 mmol) in place of 5-fluoro-2-methoxyphenylboronic acid. LCMS: 456.2 (M+H)$^+$.

Example 72B 2-(5,5-dimethylmorpholin-2-yl)-4-(4-fluoro-2-methoxyphenyl)-1H-pyrrolo[2,3-b]pyridine The title compound was prepared as the trifluoroacetate salt using the procedure described in Example 6E, using Example 72A (150 mg, 0.329 mmol) in place of Example 6D, and purified using preparative HPLC (Zorbax XDB C-18 column with gradient elution from 0.1% trifluoroacetic acid in water to 1:1 methanol/acetonitrile). LCMS: 356.15 (M+H)$^+$. $^1$H NMR (400 MHz, CD$_3$OD): δ 1.44 (s, 3H), 1.61 (s, 3H), 3.49-3.57 (m, 1H), 3.62-3.68 (m, 1H), 3.84 (s, 3H), 3.91-3.96 (m, 2H), 5.10 (dd, J=2.4, 10.8 Hz, 1H), 6.55 (s, 1H), 6.88 (t, J=8 Hz, 1H), 7.02 (dd, J=2.8, 11.2 Hz, 1H), 7.35-7.39 (m, 1H), 7.49-7.52 (m, 1H), 8.31 (d, J=5.6 Hz, 1H).

Example 73

4-(4-chloro-2-methoxyphenyl)-2-(5,5-dimethylmorpholin-2-yl)-1H-pyrrolo[2,3-b]pyridine Example 73A tert-butyl 2-(4-(4-chloro-2-methoxyphenyl)-1H-pyrrolo[2,3-b]pyridin-2-yl)-5,5-dimethylmorpholine-4-carboxylate The title compound was prepared using the procedure described in Example 1G, using Example 71D (200 mg, 0.547 mmol) in place of Example 1F and 4-chloro-2-methoxyphenylboronic acid (132 mg, 0.711 mmol) in place of 5-fluoro-2-methoxyphenylboronic acid. LCMS: 472.2 (M+H)$^+$.

Example 73B 4-(4-chloro-2-methoxyphenyl)-2-(5,5-dimethylmorpholin-2-yl)-1H-pyrrolo[2,3-b]pyridine The title compound was prepared as the acetate salt using the procedure described in Example 6E, using Example 73A (150 mg, 0.329 mmol) in place of Example 6D, and purified using preparative HPLC (Zorbax XDB C-18 column with gradient elution from 10M ammonium acetate in water to 1:1 methanol/acetonitrile). LCMS: 372.2 (M+H)$^+$. $^1$H NMR (400 MHz, CD$_3$OD): δ 1.21 (s, 3H), 1.44 (s, 3H), 3.1-3.2 (m, 2H), 3.62-3.63 (m, 1H), 3.79 (s, 1H), 3.82 (s, 3H), 4.72-4.76 (m, 1H), 6.31 (s, 1H), 7.10-7.14 (m, 2H), 7.21 (d, J=2 Hz, 1H), 7.41 (d, J=8 Hz, 1H), 8.21 (d, J=4.8 Hz, Example 74 trans-4-[4-(5-fluoro-2-methoxyphenyl)-1H-pyrrolo[2,3-b]pyridin-2-yl]cyclohexanamine Example 74A tert-butyl(trans-4-ethynylcyclohexyl)carbamate The title compound was prepared using the procedure described in Example 1D, using tert-butyl trans-4-formylcyclohexylcarbamate (600 mg, 2.64 mmol) in place of Example 1C.

Example 74B tert-butyl[trans-4-({2-[(tert-butoxycarbonyl)amino]-4-chloropyridin-3-yl}ethynyl)cyclohexyl]carbamate The title compound was prepared using the procedure described in Example 1E, using Example 74A (348 mg, 1.558 mmol) in place of Example 1D. LCMS: 349.9 (M+H)$^+$.

Example 74C tert-butyl(trans-4-(4-chloro-1H-pyrrolo[2,3-b]pyridin-2-yl)cyclohexyl)carbamate A solution of Example 74B (150 mg, 0.429 mmol) in N,N-dimethylformamide (5 mL) was treated with potassium tert-butoxide (122 mg, 1.085 mmol) and the mixture was stirred at room temperature for 12 hours. The mixture was quenched with ice water and extracted into ethyl acetate (30 mL×2). The organic layer was washed with water and brine solution (25 mL each) and the organic layer was separated, dried over sodium sulfate, filtered, and concentrated to afford the title compound. LCMS: 250.1 (M+H)$^+$.

Example 74D trans-4-[4-(5-fluoro-2-methoxyphenyl)-1H-pyrrolo[2,3-b]pyridin-2-yl]cyclohexanamine The title compound was prepared as the acetate salt using the procedure described in Example 7A, using Example 74C (100 mg, 0.286 mmol) in place of Example 5A and 5-fluoro-2-methoxyphenylboronic acid (73 mg, 0.429 mmol) in place of 2-bromo-4-cyclopropyl-1-methoxybenzene, and purified using preparative HPLC (Zorbax XDB C-18 column with gradient elution from 10M ammonium acetate in water to 1:1 methanol/acetonitrile). LCMS: 340.2 (M+H)$^+$. $^1$H NMR (400 MHz, DMSO-d$_6$): δ 1.14-1.23 (m, 2H), 1.46-1.55 (m, 2H), 1.84-1.89 (m, 2H), 1.99-2.02 (m, 2H), 3.17 (s, 2H), 3.73-3.74 (m, 5H), 5.93 (s, 1H), 6.99-7.01 (m, 1H), 7.16-7.21 (m, 2H), 7.24-7.29 (m, 1H), 8.12-8.14 (m, 1H), 11.5 (s, 1H).

Example 75

3-[4-(5-fluoro-2-methoxyphenyl)-1H-pyrrolo[2,3-b]pyridin-2-yl]cyclohexanamine

Example 75A tert-butyl (3-formylcyclohexyl)carbamate

To a solution of tert-butyl 3-(hydroxymethyl)cyclohexylcarbamate (1.4 g, 6.11 mmol) in dimethylsulfoxide (10 mL)

was added triethylamine (1.853 g, 18.32 mmol) followed by the pyridine-sulfur trioxide (2.92 g, 18.32 mmol) in 5 mL of dimethylsulfoxide, and the mixture was stirred at room temperature for 1 hour. The mixture was quenched with ice water and extracted into ethyl acetate (30 mL×2). The organic layer was washed with water and brine solution (25 mL each), dried over sodium sulfate, filtered, and concentrated under reduced pressure to afford the title compound.

Example 75B tert-butyl (3-ethynylcyclohexyl)carbamate

The title compound was prepared using the procedure described in Example 1D, using Example 75A (1.3 g, 5.72 mmol) in place of Example 1C. LCMS: 124 (M+H-Boc)$^+$.

Example 75C tert-butyl[3-({2-[(tert-butoxycarbonyl)amino]-4-chloropyridin-3-yl}ethynyl)cyclohexyl]carbamate The title compound was prepared using the procedure described in Example 1E, using Example 75B (409 mg, 1.833 mmol) in place of Example 1D. LCMS: 450.2 (M+H)$^+$.

Example 75D tert-butyl (3-(4-chloro-1H-pyrrolo[2,3-b]pyridin-2-yl)cyclohexyl)carbamate The title compound was prepared using the procedure described in Example 74C, using Example 75C (550 mg, 1.222 mmol) in place of Example 74B. LCMS: 350.1 (M+H)$^+$.

Example 75E tert-butyl (3-(4-(5-fluoro-2-methoxyphenyl)-1H-pyrrolo[2,3-b]pyridin-2-yl)cyclohexyl)carbamate The title compound was prepared using the procedure described in Example 1H, using Example 75D (400 mg, 1.143 mmol) in place of Example 1G. LCMS: 340.2 (M+H-Boc)$^+$.

Example 75F 3-(4-(5-fluoro-2-methoxyphenyl)-1H-pyrrolo[2,3-b]pyridin-2-yl)cyclohexanamine The title compound was prepared as the trifluoroacetate salt using the procedure described in Example 6E, using Example 75E (400 mg, 0.910 mmol) in place of Example 6D, and purified using preparative HPLC (Zorbax XDB C-18 column with gradient elution from 0.1% trifluoroacetic acid in water to 1:1 methanol/acetonitrile). LCMS: 340.2 (M+H)$^+$.
$^1$H NMR (400 MHz, DMSO-d$_6$/D$_2$O): δ 1.21-1.54 (m, 4H), 1.84-2.03 (m, 3H), 2.21-2.24 (m, 1H), 2.84-2.90 (m, 1H), 3.13-3.18 (m, 1H), 3.72 (s, 3H), 5.01 (m, 1H), 7.14 (d, J=5.2 Hz, 1H), 7.19-7.23 (m, 2H), 7.26-7.31 (m, 1H), 8.20 (d, J=5.2 Hz, 1H).

Example 76

4-(5-fluoro-2-methoxyphenyl)-3-methyl-2-(piperidin-4-yl)-1H-pyrrolo[2,3-b]pyridine Example 76A tert-butyl 4-(3-bromo-4-(5-fluoro-2-methoxyphenyl)-1H-pyrrolo[2,3-b]pyridin-2-yl)piperidine-1-carboxylate To a solution of Example 17F (300 mg, 0.705 mmol) in N,N-dimethylformamide (3 mL) at 0° C. was added N-bromosuccinimide (188 mg, 1.058 mmol) and the mixture was stirred at room temperature for 3 hours. The mixture was diluted with water and ethyl acetate and the ethyl acetate layer was washed with water and brine, dried over sodium sulfate, filtered, and concentrated. Purification by column chromatography (silica gel, 15% ethyl acetate in hexane) afforded the title compound. LCMS: 506 (M+3)$^+$.

Example 76B tert-butyl 4-(4-(5-fluoro-2-methoxyphenyl)-3-methyl-1H-pyrrolo[2,3-b]pyridin-2-yl)piperidine-1-carboxylate To Example 76A (200 mg, 0.397 mmol) in 1,4-dioxane (6 mL) was added 1.2M dimethylzinc solution in toluene (0.991 ml, 1.190 mmol) followed by [1,1'-bis(diphenylphosphino)ferrocene]dichloropalladium(II), dichloromethane adduct (16.19 mg, 0.020 mmol) and the mixture was heated at 100° C. for 30 minutes. The mixture was cooled, quenched with ammonium chloride solution and extracted ethyl acetate. The organic layer was washed with water and brine, dried over sodium sulfate, filtered, and concentrated to afford the title compound. LCMS: 440.2 (M+H)$^+$.

Example 76C 4-(5-fluoro-2-methoxyphenyl)-3-methyl-2-(piperidin-4-yl)-1H-pyrrolo[2,3-b]pyridine The title compound was prepared as the trifluoroacetate salt using the procedure described in Example 6E, using Example 76B (100 mg, 0.228 mmol) in place of Example 6D, and purified using preparative HPLC (Zorbax XDB C-18 column with gradient elution from 0.1% trifluoroacetic acid in water to 1:1 methanol/acetonitrile). LCMS: 340.2 (M+H)$^+$.
$^1$H NMR (400 MHz, DMSO-d$_6$): δ 1.72 (s, 3H), 1.83-1.89 (m, 2H), 1.98-2.09 (m, 2H), 3.0-3.09 (m, 2H), 3.36-3.40 (m, 2H), 3.65 (s, 3H), 6.8 (d, J=4.8 Hz, 1H), 7.06 (dd, J=3.2, 8.8 Hz, 1H), 7.11-7.14 (m, 1H), 7.24-7.29 (m, 1H), 8.14 (d, J=4.8 Hz, 1H), 8.78 (d, J=8.4 Hz, 1H), 11.54 (s, 1H).

Example 77

N-benzyl-6-[5-chloro-2-(piperidin-4-yl)-1H-pyrrolo[2,3-b]pyridin-4-yl]pyridin-2-amine Example 77A 4-bromo-5-chloro-3-iodopyridin-2-amine A solution of Example 52A (3 g, 14.46 mmol) in N,N-dimethylformamide (60 mL) was heated to 40° C. and iodine chloride (2.82 g, 17.35 mmol) was added. After stirring at 40°

C. for 3 hours, a second lot of iodine chloride (2.82 g, 17.35 mmol) was added and the mixture was stirred overnight at 40° C. The mixture was cooled to room temperature and quenched with ice cold water. The mixture was extracted with ethyl acetate (100 mL×2) and the organic layer was washed with water and brine, dried over sodium sulfate, filtered, and concentrated. Purification by column chromatography (silica gel, 20% ethyl acetate in hexane) afforded the title compound. LCMS: 334.6 (M+H)$^+$.

Example 77B tert-butyl 4-((2-amino-4-bromo-5-chloropyridin-3-yl)ethynyl)piperidine-1-carboxylate The title compound was prepared using the procedure described in Example 1E, using Example 77A (1 g, 3.00 mmol) in place of Example 1A and Example 17C (942 mg, 4.50 mmol) in place of Example 1D. LCMS: 415.8 (M+H)$^+$.

Example 77C tert-butyl 4-(4-bromo-5-chloro-1H-pyrrolo[2,3-b]pyridin-2-yl)piperidine-1-carboxylate The title compound was prepared using the procedure described in Example 1F, using Example 77B (800 mg, 1.929 mmol) in place of Example 1E. LCMS: 415.8 (M+H)$^+$.

Example 77D tert-butyl 4-(5-chloro-4-(6-fluoropyridin-2-yl)-1H-pyrrolo[2,3-b]pyridin-2-yl)piperidine-1-carboxylate The title compound was prepared using the procedure described in Example 7A, using Example 77C (500 mg, 1.206 mmol) in place of 2-bromo-4-cyclopropyl-1-methoxybenzene and 2-fluoro-6-(4,4,5,5-tetramethyl-1,3,2-dioxaborolan-2-yl)pyridine (403 mg, 1.808 mmol) in place of Example 5A. LCMS: 331.0 (M+H).

Example 77E tert-butyl 4-(4-(6-(benzylamino)pyridin-2-yl)-5-chloro-1H-pyrrolo[2,3-b]pyridin-2-yl)piperidine-1-carboxylate Example 77D (150 mg, 0.348 mmol) was heated at 100° C. for 12 hours in sealed tube with benzyl amine (1 mL). The mixture was diluted with water and ethyl acetate and the ethyl acetate layer was washed with water and brine, dried over sodium sulfate, filtered and concentrated to afford the title compound. LCMS: 519.7 (M+H)$^+$.

Example 77F

N-benzyl-6-(5-chloro-2-(piperidin-4-yl)-1H-pyrrolo[2,3-b]pyridin-4-yl)pyridin-2-amine The title compound was prepared as the acetate salt using the procedure described in Example 1H, using Example 77E (160 mg, 0.309 mmol) in place of Example 1G. LCMS: 418.2 (M+H)$^+$. $^1$H NMR (400 MHz, DMSO-d$_6$/D$_2$O): δ 1.50-1.54 (m, 2H), 1.8-1.88 (m, 2H), 2.64-2.69 (m, 3H), 3.05-3.08 (m, 2H), 4.50 (s, 2H), 5.9 (s, 1H), 6.60 (d, J=8.4 Hz, 1H), 6.76 (d, J=7.2 Hz, 1H), 7.21 (brs, 1H), 7.30-7.31 (m, 4H), 7.54 (t, J=8 Hz, 1H), 8.16 (s, 1H).

Example 78

5-chloro-4-(3-fluorophenyl)-2-(piperidin-3-yl)-1H-pyrrolo[2,3-b]pyridine

Example 78A tert-butyl 3-((2-amino-4-bromo-5-chloropyridin-3-yl)ethynyl)piperidine-1-carboxylate The title compound was prepared using the procedure described in Example 1E, using Example 77A (286 mg, 0.858 mmol) in place of Example 1A. LCMS: 416 (M+H)$^+$.

Example 78B tert-butyl 3-(4-bromo-5-chloro-1H-pyrrolo[2,3-b]pyridin-2-yl)piperidine-1-carboxylate The title compound was prepared using the procedure described in Example 1F, using Example 78A (400 mg, 0.98 mmol) in place of Example 1E. LCMS: 415.8 (M+H)$^+$.

Example 78C tert-butyl 3-(5-chloro-4-(3-fluorophenyl)-1H-pyrrolo[2,3-b]pyridin-2-yl)piperidine-1-carboxylate To Example 78B (150 mg, 0.362 mmol) in 1 mL water and 4 mL dioxane was added potassium carbonate (125 mg, 0.904 mmol) in 1 mL of water followed by the addition of 3-fluorophenylboronic acid (55.7 mg, 0.398 mmol). The mixture was degassed with nitrogen for 10 minutes and tetrakistriphenylphosphine (20.90 mg, 0.018 mmol) was added. The mixture was heated overnight in a Biotage Initiator microwave at 100° C. The mixture was diluted with ethyl acetate (50 mL) and washed with water (50×3 mL) followed by brine solution (25 mL). The organic layer was dried over anhydrous sodium sulfate, filtered, and concentrated to afford the title compound. LCMS: 330.0 (M+H-Boc)$^+$.

Example 78D 5-chloro-4-(3-fluorophenyl)-2-(piperidin-3-yl)-1H-pyrrolo[2,3-b]pyridine The title compound was prepared as the trifluoroacetate salt using the procedure described in Example 6E, using Example 78C (120 mg, 0.279 mmol) in place of Example 6D, and purified using preparative HPLC (Zorbax XDB C-18 column with gradient elution from 0.1% trifluoroacetic acid in water to 1:1 methanol/acetonitrile). LCMS: 330.0 (M+H)$^+$. $^1$H NMR (400 MHz, DMSO-d$_6$/D$_2$O): δ 1.67-1.70 (m, 2H), 1.86-1.9 (m, 1H), 2.05-2.1 (m, 1H), 2.8-2.84 (m, 1H), 3.07-3.10 (m, 2H), 3.27 (d, J=12 Hz, 1H), 3.47-3.50 (m, 1H), 6.05 (s, 1H), 7.32-7.36 (m, 3H), 7.59-7.61 (m, 1H), 8.29 (s, 1H).

Example 79

5-chloro-4-(6-fluoropyridin-2-yl)-2-(piperidin-3-yl)-1H-pyrrolo[2,3-b]pyridine

Example 79A tert-butyl 3-(5-chloro-4-(6-fluoropyridin-2-yl)-1H-pyrrolo[2,3-b]pyridin-2-yl)piperidine-1-carboxylate The title compound was prepared using the procedure described in Example 5B, using Example 78B (150 mg, 362 mmol) in place of 6-bromo-5-methoxypyridin-2-amine and 2-fluoro-6-(4,4,5,5-tetramethyl-1,3,2-dioxaborolan-2-yl)pyridine (121 mg, 0.543 mmol) in place of Example 5A. LCMS: 430.9 (M+H)$^+$.

Example 79B 5-chloro-4-(6-fluoropyridin-2-yl)-2-(piperidin-3-yl)-1H-pyrrolo[2,3-b]pyridine The title compound was prepared using the procedure described in Example 1H, using Example 79A (100 mg, 0.232 mmol) in place of Example 1G. LCMS: 331 (M+H)$^+$. $^1$H NMR (400 MHz, DMSO-d$_6$): δ 1.66-1.85 (m, 3H), 2.08-2.12 (m, 1H), 2.81-2.83 (m, 1H), 3.07-3.16 (m, 1H), 3.22-3.28 (m, 2H), 3.48-3.51 (m, 1H), 6.15 (d, J=1.6 Hz, 1H), 7.33 (dd, J=2, 8 Hz, 1H), 7.65 (d, J=2, 7.2 Hz, 1H), 8.17-8.23 (m, 1H), 9.11-9.18 (m, 1H), 12.2 (s, 1H).

Example 80

N-benzyl-6-[5-chloro-2-(piperidin-3-yl)-1H-pyrrolo[2,3-b]pyridin-4-yl]pyridin-2-amine

Example 80A tert-butyl 3-(4-(6-(benzylamino)pyridin-2-yl)-5-chloro-1H-pyrrolo[2,3-b]pyridin-2-yl)piperidine-1-carboxylate The title compound was prepared using the procedure described in Example 77E, using Example 79A (80 mg, 0.186 mmol) in place of Example 77D. LCMS: 519 (M+H)$^+$.

Example 80B

N-benzyl-6-(5-chloro-2-(piperidin-3-yl)-1H-pyrrolo[2,3-b]pyridin-4-yl)pyridin-2-amine The title compound was prepared using the procedure described in Example 1H, using Example 80A (80 mg, 0.154 mmol) in place of Example 1G. LCMS: 417.9 (M+H)$^+$. $^1$H NMR (400 MHz, DMSO-d$_6$): δ 1.61-1.85 (m, 2H), 2.04-2.08 (m, 1H), 2.78-2.80 (m, 1H), 3.22-3.30 (m, 2H), 3.36-3.47 (m, 2H), 4.61 (s, 2H), 6.10 (s, 1H), 6.93 (brs, 2H), 7.30-7.38 (m, 6H), 7.9 (brs, 1H), 8.31 (s, 1H), 9.24 (brs, 1H), 12.2 (s, 1H).

Example 81

6-[5-chloro-2-(piperidin-3-yl)-1H-pyrrolo[2,3-b]pyridin-4-yl]-N-(tetrahydro-2H-pyran-4-ylmethyl)pyridin-2-amine

Example 81A tert-butyl 3-(5-chloro-4-(6-(((tetrahydro-2H-pyran-4-yl)methyl)amino)pyridin-2-yl)-1H-pyrrolo[2,3-b]pyridin-2-yl)piperidine-1-carboxylate The title compound was prepared using the procedure described in Example 77E, using Example 79A (25 mg, 0.058 mmol) in place of Example 77D and (tetrahydro-2H-pyran-4-yl)methanamine (53 mg, 0.464 mmol) in place of benzyl amine. LCMS: 527 (M+H)$^+$.

Example 81B 6-(5-chloro-2-(piperidin-3-yl)-1H-pyrrolo[2,3-b]pyridin-4-yl)-N-((tetrahydro-2H-pyran-4-yl)methyl)pyridin-2-amine The title compound was prepared as the hydrochloride salt using the procedure described in Example 1H, using Example 81A (15 mg, 0.029 mmol) in place of Example 1G. LCMS: 425.9 (M+H)$^+$. $^1$H NMR (400 MHz, DMSO-d$_6$/D$_2$O): δ 1.58-1.92 (m, 3H), 2.81-2.86 (m, 1H), 2.98-3.10 (m, 1H), 3.15-3.18 (m, 8H), 3.18-3.32 (m, 5H), 3.68-3.86 (m, 2H), 6.22 (s, 1H), 6.86 (d, J=6.8 Hz, 1H), 6.90-6.95 (m, 1H), 7.25-7.35 (m, 1H), 8.32 (s, 1H).

Example 82

N-benzyl-6-[5-chloro-2-(1-methylpiperidin-3-yl)-1H-pyrrolo[2,3-b]pyridin-4-yl]pyridin-2-amine The title compound was prepared using the procedure described in Example 8, using Example 80A (100 mg, 0.193 mmol) in place of Example 2A. LCMS: 433.15 (M+H)$^+$. $^1$H NMR (400 MHz, DMSO-d$_6$): δ 1.44-1.47 (m, 1H), 1.72-1.75 (m, 1H), 1.92-2.07 (m, 2H), 2.78 (s, 3H), 3.03-3.15 (m, 3H), 3.45-3.62 (m. 2H), 4.50 (s, 2H), 6.02 (s, 1H), 6.65-6.76 (m, 2H), 7.22-7.32 (m, 5H), 7.57-7.60 (m, 1H), 8.23 (s, 1H), 9.65 (brs, 1H), 12.0 (s, 1H).

Example 83 methyl 3-{4-[6-(benzylamino)pyridin-2-yl]-5-chloro-1H-pyrrolo[2,3-b]pyridin-2-yl}piperidine-1-carboxylate

Example 83A methyl 3-((2-amino-4-bromo-5-chloropyridin-3-yl)ethynyl)piperidine-1-carboxylate The title compound was prepared using the procedure described in Example 1E, using Example 77A (200 mg, 0.600 mmol) in place Example 1A and Example 16A (130 mg, 0.780 mmol) in place of Example 1D. LCMS: 373.8 (M+2)$^+$.

Example 83B methyl 3-(4-bromo-5-chloro-1H-pyrrolo[2,3-b]pyridin-2-yl)piperidine-1-carboxylate The title compound was prepared using the procedure described in Example 1F, using Example 83A (200 mg, 0.537 mmol) in place of Example 1E. LCMS: 373.8 (M+2)$^+$.

Example 83C methyl 3-(5-chloro-4-(6-fluoropyridin-2-yl)-1H-pyrrolo[2,3-b]pyridin-2-yl)piperidine-1-carboxylate The title compound was prepared using the procedure described in Example 5B, using Example 83B (100 mg, 0.268 mmol) in place of 6-bromo-5-methoxypyridin-2-amine and 2-fluoro-6-(4,4,5,5-tetramethyl-1,3,2-dioxaborolan-2-yl)pyridine (90 mg, 0.403 mmol) in place of Example 5A. LCMS: 389.1 (M+H)$^+$.

Example 83D methyl 3-(4-(6-(benzylamino)pyridin-2-yl)-5-chloro-1H-pyrrolo[2,3-b]pyridin-2-yl)piperidine-1-carboxylate The title compound was prepared as the trifluoroacetate salt using the procedure described in Example 77E, using Example 83C (90 mg, 0.231 mmol) in place of Example 77D, and purified using preparative HPLC (Zorbax XDB C-18 column with gradient elution from 0.1% trifluoroacetic acid in water to 1:1 methanol/acetonitrile). LCMS: 475.8 (M+H)$^+$. $^1$H NMR (400 MHz, DMSO-d$_6$): δ 1.41-1.69 (m, 4H), 1.96-1.98 (m, 1H), 2.75-3.0 (m, 4H), 3.59 (s, 3H), 4.58 (s, 2H), 6.0 (s. 1H), 6.77-6.85 (m, 2H), 7.22-7.34 (m, 5H), 7.67 (brs, 1H), 8.22 (s, 1H), 12.0 (s, 1H).

Example 84

N-benzyl-6-{5-chloro-2-[1-(propan-2-ylsulfonyl)piperidin-3-yl]-1H-pyrrolo[2,3-b]pyridin-4-yl}pyridin-2-amine

Example 84A 4-bromo-5-chloro-3-((1-(isopropylsulfonyl)piperidin-3-yl)ethynyl)pyridin-2-amine The title compound was prepared using the procedure described in Example 1E, using Example 77A (200 mg, 0.600 mmol) in place Example 1A and Example 15A (581 mg, 2.70 mmol) in place of Example 1D. LCMS: 422 (M+H)$^+$.

Example 84B 4-bromo-5-chloro-2-(1-(isopropylsulfonyl)piperidin-3-yl)-1H-pyrrolo[2,3-b]pyridine The title compound was prepared using the procedure described in Example 1F, using Example 84A (500 mg, 1.188 mmol) in place of Example 1E. LCMS: 421.0 (M+H)$^+$.

Example 84C 5-chloro-4-(6-fluoropyridin-2-yl)-2-(1-(isopropylsulfonyl)piperidin-3-yl)-1H-pyrrolo[2,3-b]pyridine The title compound was prepared using the procedure described in Example 7A, using Example 84B (200 mg, 0.475 mmol) in place of 2-bromo-4-cyclopropyl-1-methoxybenzene and 2-fluoro-6-(4,4,5,5-tetramethyl-1,3,2-dioxaborolan-2-yl)pyridine (159 mg, 0.713 mmol) in place of Example 5A. LCMS: 437.1 (M+H)$^+$.

Example 84D

N-benzyl-6-(5-chloro-2-(1-(isopropylsulfonyl)piperidin-3-yl)-1H-pyrrolo[2,3-b]pyridin-4-yl)pyridin-2-amine The title compound was prepared as the trifluoroacetate salt using the procedure described in Example 77E, using Example 84C (200 mg, 0.458 mmol) in place of Example 77D, and purified using preparative HPLC (AG/AD/PP/C-18 column with gradient elution from 0.1% trifluoroacetic acid in water to 1:1 methanol/acetonitrile). LCMS: 524.2 (M+H)$^+$. $^1$H NMR (400 MHz, DMSO-d$_6$): δ 1.20-1.22 (m, 7H), 1.5-1.51 (m, 2H), 1.76-1.77 (m, 1H), 1.98-2.0 (m, 1H), 2.87-2.94 (m, 2H), 3.64-3.67 (m. 2H), 3.79-3.81 (m, 1H), 4.54 (s, 2H), 6.02 (s, 1H), 6.63-6.72 (m, 1H), 6.82-6.86 (m, 1H), 7.2-7.3 (m, 2H), 7.3-7.38 (m, 4H), 7.6-7.64 (m, 1H), 8.22 (s, 1H), 12.0 (s, 1H).

Example 85

3-[5-chloro-4-(3-fluorophenyl)-1H-pyrrolo[2,3-b]pyridin-2-yl]cyclohexanamine

Example 85A tert-butyl (3-((2-amino-4-bromo-5-chloropyridin-3-yl)ethynyl)cyclohexyl)carbamate The title compound was prepared using the procedure described in Example 1E, using Example 77A (600 mg, 1.800 mmol) in place Example 1A and Example 75B (603 mg, 2.70 mmol) in place of Example 1D. LCMS: 374 (M+3-NCOOH)$^+$.

Example 85B tert-butyl (3-(4-bromo-5-chloro-1H-pyrrolo[2,3-b]pyridin-2-yl)cyclohexyl)carbamate The title compound was prepared using the procedure described in Example 1F, using Example 85A (600 mg, 1.39 mmol) in place of Example 1E. LCMS: 329.7 (M+H-Boc)$^+$.

Example 85C tert-butyl (3-(5-chloro-4-(3-fluorophenyl)-1H-pyrrolo[2,3-b]pyridin-2-yl)cyclohexyl)carbamate The title compound was prepared using the procedure described in Example 7A, using Example 85B (200 mg, 0.466 mmol) in place of 2-bromo-4-cyclopropyl-1-methoxybenzene and 3-fluorophenylboronic acid (98 mg, 0.700 mmol) in place of Example 5A. LCMS: 344 (M+H-Boc)$^+$.

Example 85D 3-(5-chloro-4-(3-fluorophenyl)-1H-pyrrolo[2,3-b]pyridin-2-yl)cyclohexanamine The title compound was prepared as the trifluoroacetate salt using the procedure described in Example 6E, using Example 85C (200 mg, 0.451 mmol) in place of Example 6D, and purified using preparative HPLC (ECLIPSE XDB C-18 column with gradient elution from 0.1% trifluoroacetic acid in water to acetonitrile). LCMS: 343.9 (M+H)$^+$. $^1$H NMR (400 MHz, DMSO-d$_6$/D$_2$O): δ 1.24-1.31 (m, 1H), 1.43-1.55 (m, 1H), 1.84-1.88 (m, 2H), 1.96-2.02 (m, 2H), 2.16-2.24 (m, 2H), 2.84-2.90 (m, 1H), 3.12-3.19 (m, 1H), 7.29-7.34 (m, 4H), 7.57-7.60 (m, 1H), 8.24 (s, 1H).

Example 86

6-[2-(3-aminocyclohexyl)-5-chloro-1H-pyrrolo[2,3-b]pyridin-4-yl]-N-benzylpyridin-2-amine

Example 86A tert-butyl (3-(5-chloro-4-(6-fluoropyridin-2-yl)-1H-pyrrolo[2,3-b]pyridin-2-yl)cyclohexyl)carbamate The title compound was prepared using the procedure described in Example 7A, using Example 85B (200 mg, 0.466 mmol) in place of 2-bromo-4-cyclopropyl-1-methoxybenzene and 2-fluoro-6-(4,4,5,5-tetramethyl-1,3,2-dioxaborolan-2-yl)pyridine (156 mg, 0.700 mmol) in place of Example 5A. LCMS: 345 (M+H-Boc)$^+$.

Example 86B tert-butyl (3-(4-(6-(benzylamino)pyridin-2-yl)-5-chloro-1H-pyrrolo[2,3-b]pyridin-2-yl)cyclohexyl) carbamate The title compound was prepared using the procedure described in Example 77E, using Example 86A (200 mg, 0.58 mmol) in place of Example 77D. LCMS: 432 (M+H-Boc)$^+$.

Example 86C 6-(2-(3-aminocyclohexyl)-5-chloro-1H-pyrrolo[2,3-b]pyridin-4-yl)-N-benzylpyridin-2-amine The title compound was prepared as the trifluoroacetate salt using the procedure described in Example 6E, using Example 86B (250 mg, 0.470 mmol) in place of Example 6D. LCMS: 432.0 (M+H)$^+$. $^1$H NMR (400 MHz, DMSO-d$_6$/D$_2$O): δ 1.22-1.29 (m, 2H), 1.38-1.47 (m, 2H), 1.8-1.86 (m, 2H), 1.94-1.97 (m, 1H), 2.14-2.17 (m, 1H), 2.76-2.79 (m, 1H), 3.11-3.17 (m, 1H), 4.51 (s, 2H), 5.89 (s, 1H), 6.70 (d, J=7.6 Hz, 1H), 6.8 (d, J=6.8 Hz, 1H), 7.23-7.25 (m, 1H), 7.32 (d, J=4 Hz, 4H), 7.63 (t, J=8 Hz, 1H), 8.20 (s, 1H).

Example 87

4-(5-fluoro-2-methoxyphenyl)-2-(1,2,3,6-tetrahydropyridin-4-yl)-1H-pyrrolo[2,3-b]pyridine

Example 87A 4-(5-fluoro-2-methoxyphenyl)-1-(phenylsulfonyl)-1H-pyrrolo[2,3-b]pyridine A suspension of 4-bromo-1-(phenylsulfonyl)-1H-pyrrolo[2,3-b]pyridine (10.00 g, 29.7 mmol), 5-fluoro-2-methoxyphenylboronic acid (5.54 g, 32.6 mmol), 2M aqueous potassium carbonate (66.7 mL, 133 mmol), and [1,1'-bis(diphenylphosphino)ferrocene]dichloropalladium(II) dichloromethane adduct (1.453 g, 1.779 mmol) in 1,2-dimethoxyethane (250 mL) was degassed with nitrogen and heated at 100° C. for 1.5 hours. The mixture was diluted with ethyl acetate and washed with aqueous sodium bicarbonate (twice) and brine. The organic layer was dried over magnesium sulfate, filtered, concentrated, and purified on silica gel using an ISCO Companion flash system eluting with heptane/ethyl acetate (75:25 to 60:40) to afford the title compound. MS (ESI$^+$) m/z 383.1 (M+H)$^+$.

Example 87B 4-(5-fluoro-2-methoxyphenyl)-2-iodo-1-(phenylsulfonyl)-1H-pyrrolo[2,3-b]pyridine To a solution of Example 87A (4.24 g, 11.09 mmol) in tetrahydrofuran at −78° C. was added dropwise 2M lithium diisopropylamide (8.32 mL, 16.63 mmol) in tetrahydrofuran/heptane/ethylbenzene. After 30 minutes, iodine (5.63 g, 22.18 mmol) in tetrahydrofuran (50 mL) was cannulated into the mixture. The mixture was stirred at −78° C. for 3 hours, quenched with aqueous sodium thiosulfate and extracted with ethyl acetate (twice). The combined organic layers were dried over magnesium sulfate, filtered, and concentrated until a precipitate formed. The solids were filtered, washed with ethyl acetate and dried under vacuum to afford the title compound. MS (ESI$^+$) m/z 508.9 (M+H)$^+$.

Example 87C tert-butyl 4-(4-(5-fluoro-2-methoxyphenyl)-1-(phenylsulfonyl)-1H-pyrrolo[2,3-b]pyridin-2-yl)-5,6-dihydropyridine-1(2H)-carboxylate A mixture of Example 87B (1.600 g, 3.15 mmol), tert-butyl 4-(4,4,5,5-tetramethyl-1,3,2-dioxaborolan-2-yl)-5,6-dihydropyridine-1(2H)-carboxylate (1.071 g, 3.46 mmol), tetrakistriphenylphosphine palladium (0.182 g, 0.157 mmol), and aqueous sodium bicarbonate solution (15 mL) in N,N-dimethylformamide (60 mL) was degassed with nitrogen and heated at 80° C. for 3 hours. After cooling, the mixture was quenched with water and brine and extracted with ethyl acetate (twice). The combined organic layers were washed with brine, dried over magnesium sulfate, filtered, concentrated, and purified on silica gel using an ISCO Companion flash system eluting with heptane/ethyl acetate (65:35 to 5:5) to afford the title compound. MS (ESI$^+$) m/z 564.1 (M+H)$^+$.

Example 87D 4-(5-fluoro-2-methoxyphenyl)-2-(1,2,3,6-tetrahydropyridin-4-yl)-1H-pyrrolo[2,3-b]pyridine A mixture of Example 87C (400.0 mg, 0.710 mmol) and 20% sodium hydroxide (0.7 mL) solution in dioxane (6 mL) was heated at 90° C. for 6 hours. The mixture was concentrated and the residue was treated with ethyl acetate and washed with water. The organic layer was dried over magnesium sulfate, filtered and concentrated until most of solvent was evaporated. The solids were filtered, washed with ethyl acetate/heptane, and dried under vacuum to afford the protected intermediate. The intermediate was dissolved in dichloromethane (8 mL) and treated with trifluoroacetic acid (0.547 mL, 7.10 mmol) and the mixture was stirred for 3 hours and concentrated. The residue was dissolved in 2.5 mL methanol and treated with 4 mL 1M hydrogen chloride in ether. After stirring for 15 minutes, the mixture was treated with ether. The solids were filtered, washed with ether, and dried under vacuum to afford the title compound as a hydrochloride salt. $^1$H NMR (400 MHz, CD$_3$OD) δ 2.93-2.83 (m, 2H), 3.50 (t, J=6.1 Hz, 2H), 3.83 (s, 3H), 4.01-3.96 (m, 2H), 6.65-6.59 (m, 1H), 6.74 (s, 1H), 7.38-7.21 (m, 3H), 7.58 (d, J=6.1 Hz, 1H), 8.36 (d, J=6.1 Hz, 1H). MS (ESI$^+$) m/z 324.1 (M+H)$^+$.

Example 88

6-[2-(piperidin-4-yl)-1H-pyrrolo[2,3-b]pyridin-4-yl]-N-(tetrahydro-2H-pyran-4-ylmethyl)pyridin-2-amine

Example 88A 2-fluoro-6-(4,4,5,5-tetramethyl-1,3,2-dioxaborolan-2-yl)pyridine To a solution of 2-bromo-6-fluoropyridine (5.0 g, 28.4 mmol) in 1,4-dioxane (150 mL) was added 4,4,4',4',5,5,5',5'-octamethyl-2,2'-bi(1,3,2-dioxaborolane) (8.6 g, 34.1 mmol), and potassium acetate (5.6 g, 56.8 mmol) followed by [1,1'- bis(diphenylphosphino)ferrocene]dichloropalladium(II) (1.2 g, 1.4 mmol) and the mixture was degassed with nitrogen. The mixture was heated at 110° C. for 10 hours, diluted with ethyl acetate and filtered through diatomaceous earth. The filtrate was concentrated and purified by column chromatography (silica gel, 20% ethyl acetate in hexane) to afford the title compound. LCMS: 224 (M+H)$^+$.

Example 88B tert-butyl 4-(4-(6-fluoropyridin-2-yl)-1H-pyrrolo[2,3-b]pyridin-2-yl)piperidine-1-carboxylate To a mixture of Example 17E (500 mg, 1.5 mmol); Example 88A (400 mg, 1.8 mmol) and dichlorobis(triphenylphosphine)palladium (52 mg, 0.07 mmol) in 7/3/2 1,2-dimethoxyethane/water/ethanol (15 mL) was added 2M sodium carbonate solution (1.1 mL) and the mixture was heated in a microwave reactor (Biotage Initiator) at 150° C. for 30 minutes. After cooling, the mixture was diluted with dichloromethane (100 mL) and filtered through diatomaceous earth. The filtrate was concentrated and purified by column chromatography (silica gel, 100% ethyl acetate) to afford the title compound. LCMS: 397 (M+H)$^+$.

Example 88C 6-(2-(piperidin-4-yl)-1H-pyrrolo[2,3-b]pyridin-4-yl)-N-((tetrahydro-2H-pyran-4-yl)methyl)pyridin-2-amine A mixture of Example 88B (40 mg, 0.1 mmol) and (tetrahydro-2H-pyran-4-yl)methanamine (116 mg, 1.0 mmol) in dimethylsulfoxide (1 mL) was heated in a sealed tube at 110° C. for 30 minutes. The mixture was diluted with dichloromethane (20 mL) and washed with water. The organic phase was concentrated and purified by column chromatography (silica gel, 10% methanol in ethyl acetate) to afford the Boc-protected intermediate. To the intermediate in dichloromethane (5 mL) was added trifluoroacetic acid (0.5 mL) and the mixture was stirred at room temperature for 1 hour. Concentration and purification by HPLC (Zorbax C-18, using a 0-100% gradient of water/acetonitrile, containing 0.1% trifluoroacetic acid) afforded the title compound. $^1$H NMR (400 MHz, DMSO-d$_6$): δ 1.13-1.41 (m, 2H), 1.63-1.73 (m, 2H), 1.74-1.95 (m, 3H), 2.28 (d, J=11.19 Hz, 2H), 2.99-3.18 (m, 3H), 3.20-3.35 (m, 4H), 3.39 (d, J=12.55 Hz, 2H), 3.88 (dd, J=11.19, 2.71 Hz, 2H), 6.68 (d, J=8.48 Hz, 1H), 6.79 (s, 1H), 7.18 (d, J=7.12 Hz, 1H), 7.50 (d, J=5.09 Hz, 1H), 7.55-7.68 (m, 1H), 8.26 (d, J=5.09 Hz, 1H). LCMS: 392 (M+H)$^+$.

Example 89

6-[2-(1-methylpiperidin-4-yl)-1H-pyrrolo[2,3-b]pyridin-4-yl]-N-(tetrahydro-2H-pyran-4-ylmethyl)pyridin-2-amine A solution of Example 88C (15 mg, 0.04 mmol) in methanol (2 mL) was treated with 37% formaldehyde in water (12 mg, 0.4 mmol) and the mixture was stirred at room temperature for 1 hour. Sodium cyanoborohydride (5 mg, 0.08 mmol) was added and the mixture was stirred at room temperature for 12 hours. The mixture was diluted with dichloromethane and washed with water. The organic phase was concentrated and purified by HPLC (Zorbax C-18, using a 0-100% gradient of water/acetonitrile, containing 0.1% trifluoroacetic acid) to afford the title compound. $^1$H NMR (400 MHz, DMSO-d$_6$): δ 1.17-1.38 (m, 2H), 1.64-1.73 (m, 2H), 1.77-1.96 (m, 4H), 2.34 (d, J=13.56 Hz, 4H), 2.83 (d, J=4.75 Hz, 3H), 3.00-3.20 (m, 4H), 3.56 (d, J=11.53 Hz, 2H), 3.88 (dd, J=10.68, 3.22 Hz, 2H), 6.68 (d, J=8.48 Hz, 1H), 6.77-6.83 (m, 1H), 7.18 (d, J=7.80 Hz, 1H), 7.50 (d, J=5.09 Hz, 1H), 7.58-7.63 (m, 1H), 8.24-8.27 (m, 1H). LCMS: 406 (M+H)$^+$.

Example 90

6-[2-(1-methylpiperidin-4-yl)-1H-pyrrolo[2,3-b]pyridin-4-yl]-N-(3-phenylpropyl)pyridin-2-amine 4-(6-fluoropyridin-2-yl)-2-(piperidin-4-yl)-1H-pyrrolo[2,3-b]pyridine Example 90A To a solution of Example 88B (136 mg, 0.34 mmol) in dichloromethane (15 ml) was added trifluoroacetic acid (1 mL) and the mixture was stirred at room temperature for 1 hour. Concentration and purification by HPLC (Zorbax C-18, using a 0-100% gradient of water/acetonitrile, containing 0.1% trifluoroacetic acid) afforded the title compound. LCMS: 297 (M+H)$^+$ 4-(6-fluoropyridin-2-yl)-2-(1-methylpiperidin-4-yl)-1H-pyrrolo[2,3-b]pyridine Example 90B The title compound was prepared using the procedure described in Example 89, using Example 90A (89 mg, 0.3 mmol) in place of Example 88C. LCMS: 311 (M+H)$^+$ Example 90C 6-[2-(1-methylpiperidin-4-yl)-1H-pyrrolo[2,3-b]pyridin-4-yl]-N-(3-phenylpropyl)pyridin-2-amine The title compound was prepared using the procedure described in Example 88C, using Example 90B (40 mg, 0.13 mmol) in place of Example 88B and 3-phenylpropan-1-amine (122 mg, 0.9 mmol) in place of (tetrahydro-2H-pyran-4-yl)methanamine. $^1$H NMR (400 MHz, DMSO-d$_6$): δ 1.74-2.00 (m, 4H), 2.32 (d, J=13.56 Hz, 2H), 2.65-2.74 (m, 2H), 2.83 (d, J=4.75 Hz, 3H), 2.96-3.21 (m, 3H), 3.41 (t, J=6.95 Hz, 2H), 3.54 (d, J=12.21 Hz, 2H), 6.66 (d, J=8.48 Hz, 1H), 6.76 (s, 1H), 7.11-7.36 (m, 6H), 7.49 (d, J=5.09 Hz, 1H), 7.61 (t, J=7.80 Hz, 1H), 8.25 (d, J=5.09 Hz, 1H). LCMS: 426 (M+H)$^+$.

Example 91

6-[2-(1-methylpiperidin-4-yl)-1H-pyrrolo[2,3-b]pyridin-4-yl]-N-(pyridin-3-ylmethyl)pyridin-2-amine The title compound was prepared using the procedure described in Example 88C, using Example 90B (40 mg, 0.13 mmol) in place of Example 88B and pyridin-3-ylmethanamine (139 mg, 1.3 mmol) in place of (tetrahydro-2H-pyran-4-yl)methanamine. $^1$H NMR (400 MHz, DMSO-d$_6$): δ 1.63-1.91 (m, 2H), 2.16-2.29 (m, 2H), 2.83 (s, 3H), 2.96 (d, J=11.87 Hz, 1H), 3.04-3.16 (m, 2H), 3.53 (d, J=11.87 Hz, 2H), 4.73 (s, 2H), 6.59 (s, 1H), 6.68 (d, J=8.14 Hz, 1H), 7.24 (d, J=7.46 Hz, 1H), 7.41-7.44 (m, 1H), 7.57-7.64 (m, 1H), 7.69 (dd, J=7.80, 5.09 Hz, 1H), 8.16 (d, J=7.80 Hz, 1H), 8.20 (d, J=5.09 Hz, 1H), 8.62 (dd, J=5.43, 1.36 Hz, 1H), 8.75 (s, 1H). LCMS: 399 (M+H)$^+$.

Example 92

6-[2-(1-methylpiperidin-4-yl)-1H-pyrrolo[2,3-b] pyridin-4-yl]-N-[2-(phenylsulfanyl)ethyl]pyridin-2-amine The title compound was prepared using the procedure as described in Example 88C, using Example 90B (35 mg, 0.11 mmol) in place of Example 88B and 2-(phenylthio)ethanamine (173 mg, 1 mmol) in place of (tetrahydro-2H-pyran-4-yl)methanamine. $^1$H NMR (400 MHz, DMSO-d$_6$): 1.66-1.87 (m, 2H), 2.17-2.31 (m, 2H), 2.83 (s, 3H), 2.91-3.21 (m, 6H), 3.30-3.43 (m, 1H), 3.54 (d, J=11.87 Hz, 2H), 6.59 (s, 1H), 6.69 (d, J=8.14 Hz, 1H), 7.26 (d, J=7.12 Hz, 1H), 7.43 (d, J=5.09
Hz, 1H), 7.58-7.65 (m, 2H), 7.75 (dd, J=7.97, 5.26 Hz, 1H), 8.21 (d, J=5.09 Hz, 2H), 8.60-8.70 (m, 1H), 8.78 (d, J=1.36 Hz, 1H). LCMS: 444 (M+H)$^+$.

Example 93

N-(cyclopropylmethyl)-6-[2-(1-methylpiperidin-4-yl)-1H-pyrrolo[2,3-b]pyridin-4-yl]pyridin-2-amine The title compound was prepared using the procedure described in Example 88C, using Example 90B (30 mg, 0.1 mmol) in place of Example 88B and cyclopropylmethanamine (69 mg, 1.0 mmol) in place of (tetrahydro-2H-pyran-4-yl)methanamine. $^1$H NMR (400 MHz, DMSO-d$_6$): δ 0.20-0.33 (m, 2H), 0.43-0.57 (m, 2H), 1.08-1.26 (m, 1H), 1.74-1.95 (m, 2H), 2.26-2.41 (m, 2H), 2.83 (d, J=4.75 Hz, 3H), 2.97-3.21 (m, 4H), 3.30 (d, J=6.78 Hz, 2H), 3.56 (d, J=11.87 Hz, 2H), 6.68 (d, J=6.44 Hz, 1H), 6.82 (s, 1H), 7.19 (d, J=7.12 Hz, 1H), 7.51 (d, J=5.09 Hz, 1H), 7.57-7.66 (m, 1H), 8.25 (d, J=5.09 Hz, 1H). LCMS: 444 (M+H)$^+$ Example 94

4-(5-fluoro-2-methoxyphenyl)-2-(pyrrolidin-2-yl)-1H-pyrrolo[2,3-b]pyridine

Example 94A tert-butyl 2-((2-(tert-butoxycarbonylamino)-4-chloropyridin-3-yl)ethynyl)pyrrolidine-1-carboxylate The title compound was prepared using the procedure described in Example 1E, using tert-butyl 2-ethynylpyrrolidine-1-carboxylate (2.5 g, 12.80 mmol) in place of Example 1D. MS (ESI$^+$) m/z 421.9 (M+H)$^+$.

Example 94B tert-butyl 2-(4-chloro-1H-pyrrolo[2,3-b]pyridin-2-yl) pyrrolidine-1-carboxylate The title compound was prepared using the procedure described in Example 1F, using Example 94A (2.5 g, 5.93 mmol) in place of Example 1E. MS (ESI$^+$) m/z 321.9 (M+H)$^+$.

Example 94C tert-butyl 2-(4-(5-fluoro-2-methoxyphenyl)-1H-pyrrolo[2,3-b]pyridin-2-yl)pyrrolidine-1-carboxylate To Example 94B (200 mg, 0.0.622 mmol) in tetrahydrofuran (1.5 mL) and water (0.5 mL) was added potassium phosphate (400 mg, 1.884 mmol) followed by 5-fluoro-2-methoxyphenylboronic acid (140 mg, 0.824 mmol). The mixture was degassed with nitrogen and [1,3-bis(2,6-diisopropylphenyl)imidazol-2-ylidene]chloro[3-phenylallyl]palladium(II) (40 mg, 0.062 mmol) was added. The mixture was subjected to microwave irradiation (Biotage Initiator) at 60° C. for 90 minutes. After dilution with ethyl acetate and filtration through diatomaceous earth, the organic layer was washed with water and brine (50 mL each) and dried over sodium sulfate, filtered, and concentrated. The residue dissolved in dichloromethane and purified by flash chromatography using a Grace, SF25-40 g column, eluting with 0-100% ethyl acetate/hexane, to afford the title compound. LCMS: 412.2 (M+H)$^+$.

Example 94D 4-(5-fluoro-2-methoxyphenyl)-2-(pyrrolidin-2-yl)-1H-pyrrolo[2,3-b]pyridine To Example 94C (30 mg, 0.073 mmol) in dichloromethane (1 mL) was added trifluoroacetic acid (1 mL, 12.98 mmol) and the mixture was stirred for 15 hours. The mixture was concentrated and purified by reverse phase flash chromatography (SiO$_2$—C18, 0-100% acetonitrile/water/0.1% trifluoroacetic acid) to yield the title compound as the trifluoroacetate salt. $^1$H NMR (500 MHz, DMSO-d$_6$) δ 2.47-1.95 (m, 4H), 3.34-3.30 (m, 2H), 3.74 (s, 3H), 4.88-4.71 (m, 1H), 6.45 (d, J=1.7, 1H), 7.13 (d, J=4.9, 1H), 7.26-7.17 (m, 2H), 7.34-7.26 (m, 1H), 8.30 (d, J=4.9, 1H), 8.87 (br. s, 1H), 9.41 (br. s, 1H), 11.97 (br. s, 1H). MS (ESI$^+$) m/z 312.2 (M+H)$^+$.

Example 95

N-[(2,2-dimethyltetrahydro-2H-pyran-4-yl)methyl]-6-[2-(1-methylpiperidin-4-yl)-1H-pyrrolo[2,3-b] pyridin-4-yl]pyridin-2-amine The title compound was prepared using the procedure described in Example 88C, using Example 90B (35 mg, 0.13 mmol) in place of Example 88B and (2,2-dimethyltetrahydro-2H-pyran-4-yl)methanamine (162 mg, 1.3 mmol) in place of (tetrahydro-2H-pyran-4-yl)methanamine. $^1$H NMR (400 MHz, DMSO-d$_6$): δ 0.99-1.11 (m, 2H), 1.14 (s, 6H), 1.67 (dd, J=13.22, 2.71 Hz, 2H), 1.76-1.94 (m, 2H), 1.95-2.11 (m, 1H), 2.20-2.30 (m, 1H), 2.35 (d, J=11.87 Hz, 2H), 2.83 (d, J=4.75 Hz, 3H), 2.97-3.21 (m, 4H), 3.26 (t, J=6.95 Hz, 2H), 3.56 (d, J=12.21 Hz, 2H), 6.64 (d, J=7.80 Hz, 1H), 6.78 (s, 1H), 7.17 (d, J=7.12 Hz, 1H), 7.50 (d, J=5.09 Hz, 1H), 7.54-7.60 (m, 1H), 8.24 (d, J=5.09 Hz, 1H). LCMS: 434 (M+H)$^+$.

Example 96

N-benzyl-N-methyl-6-[2-(1-methylpiperidin-4-yl)-1H-pyrrolo[2,3-b]pyridin-4-yl]pyridin-2-amine The title compound was prepared using the procedure described in Example 88C, using Example 90B (30 mg, 0.10 mmol) in place of Example 88B and N-methyl-1-phenylmethanamine (112 mg, 1.0 mmol) in place of (tetrahydro-2H- pyran-4-yl)methanamine. $^1$H NMR (400 MHz, DMSO-d$_6$): δ 1.52-1.80 (m, 2H), 2.15 (d, J=13.90 Hz, 2H), 2.67-2.77 (m, 1H), 2.81 (d, J=4.75 Hz, 3H), 2.95-3.10 (m, 4H), 3.13 (s, 3H), 4.95 (s, 2H), 6.65 (s, 1H), 6.74 (d, J=8.48 Hz, 1H), 7.27 (dd, J=6.44, 3.05 Hz, 3H), 7.33 (d, J=5.76 Hz, 2H), 7.45 (s, 1H), 7.49 (d, J=5.43 Hz, 1H), 7.64-7.73 (m, 1H), 8.20 (d, J=5.09 Hz, 1H). LCMS: 412 (M+H)$^+$.

Example 97

N-(3-chlorobenzyl)-6-[2-(1-methylpiperidin-4-yl)-1H-pyrrolo[2,3-b]pyridin-4-yl]pyridin-2-amine The title compound was prepared using the procedure described in Example 88C, using Example 90B (30 mg, 0.10 mmol) in place of Example 88B and (3-chlorophenyl)methanamine (137 mg, 1.0 mmol) in place of (tetrahydro-2H-pyran-4-yl)methanamine. $^1$H NMR (400 MHz, DMSO-d$_6$): δ 1.64-1.85 (m, 2H), 2.22 (d, J=13.90 Hz, 2H), 2.83 (d, J=4.75 Hz, 3H), 2.91-3.02 (m, 1H), 3.05-3.19 (m, 2H), 3.53 (d, J=11.53 Hz, 2H), 4.65 (s, 2H), 6.64 (d, J=2.37 Hz, 1H), 6.67 (s, 1H), 7.22 (d, J=7.12 Hz, 1H), 7.27-7.33 (m, 2H), 7.33-7.39 (m, 3H), 7.43 (s, 1H), 7.47 (d, J=5.43 Hz, 1H), 8.19-8.22 (m, 1H). LCMS: 412 (M+H)$^+$.

Example 98

2-cyclohexyl-4-(5-fluoro-2-methoxyphenyl)-1H-pyrrolo[2,3-b]pyridine

Example 98A tert-butyl (4-chloro-3-(cyclohexylethynyl)pyridin-2-yl)carbamate tert-Butyl 4-chloro-3-iodopyridin-2-ylcarbamate (1.0 g, 2.82 mmol) in 10 mL tetrahydrofuran was treated with copper (I) iodide (0.027 g, 0.141 mmol) and bis(triphenylphosphine)palladium(II) chloride (0.099 g, 0.141 mmol) and the mixture was purged with nitrogen for 5 minutes. Ethynylcyclohexane (0.472 mL, 3.67 mmol) and triethylamine (1.179 mL, 8.46 mmol) were added and the mixture was stirred overnight under nitrogen. The mixture was filtered through diatomaceous earth and the filtrate washed with aqueous citric acid (once), water (twice), and brine (once), dried over magnesium sulfate, filtered, and concentrated. Purification by flash chromatography (20% ethyl acetate/hexane) provided the title compound. MS (DCI) m/e 335/337 (M+H)$^+$.

Example 98B 4-chloro-2-cyclohexyl-1H-pyrrolo[2,3-b]pyridine

A solution of Example 98A (870 mg, 2.60 mmol) in 20 mL toluene was treated with potassium tert-butoxide (729 mg, 6.50 mmol) and 18-crown-6 (68.7 mg, 0.260 mmol) and the mixture was heated at 65° C. for 6 hours and at 85° C. overnight. The cooled mixture was partitioned between ethyl acetate and water. The layers were separated and the aqueous layer was extracted with ethyl acetate (twice). The combined organic extracts were rinsed with water (once) and brine (twice), dried over magnesium sulfate, filtered, and concentrated. The residue was suspended in diethyl ether and the solids were collected and rinsed with diethyl ether to afford the title compound. MS (DCI) m/e 235/237 (M+H)$^+$.

Example 98C 2-cyclohexyl-4-(5-fluoro-2-methoxyphenyl)-1H-pyrrolo[2,3-b]pyridine

A solution of Example 98B (200 mg, 0.852 mmol), (5-fluoro-2-methoxyphenyl)boronic acid (188 mg, 1.108 mmol), phenylallylchloro[1,3-bis(diisopropylphenyl)-2-imidazol-2-ylidene]palladium(II) (50 mg, 0.077 mmol) and potassium phosphate (543 mg, 2.56 mmol) in 8 mL 3:1 tetrahydrofuran:water was purged with nitrogen and heated under nitrogen at 60° C. for 4 hours. The cooled mixture was diluted with water and ethyl acetate and filtered through diatomaceous earth. The mixture was extracted into ethyl acetate (twice) and the combined extracts were rinsed with brine, dried over magnesium sulfate, filtered and concentrated. Purification by flash chromatography (1:1 ethyl acetate:hexanes) provided only a small amount of material. The column was washed with 10% methanol/dichloromethane and the remainder of the material eluted. The combined residue was suspended in diethyl ether and the solids were collected and rinsed with diethyl ether to afford the title compound. $^1$H NMR (300 MHz, DMSO-d$_6$) δ 1.20-1.48 (m, 5H) 1.64-1.76 (m, 3H) 1.99-2.02 (m, 2H) 2.70-2.73 (m, 1H) 3.72 (s, 3H) 5.92 (s, 1H) 6.99 (d, J=5.08 Hz, 1H) 7.15-7.27 (m, 3H) 8.12 (d, J=4.75 Hz, 1H) 11.50 (s, 1H). MS (DCI) m/e 325 (M+H)$^+$.

Example 99

1-{2-[4-(5-fluoro-2-methoxyphenyl)-1H-pyrrolo[2,3-b]pyridin-2-yl]pyrrolidin-1-yl}ethanone To a solution of Example 94D (0.035 g, 0.112 mmol) and triethylamine (0.1 mL, 0.717 mmol) in dichloromethane (2 mL), was slowly added acetyl chloride (1M in dichloromethane, 0.11 mL, 0.11 mmol) and the mixture was stirred at room temperature for 5 minutes. The mixture was concentrated and purified by reverse phase flash chromatography (SiO$_2$—C18, 10-100% acetonitrile/water/0.1% trifluoroacetic acid) to afford the title compound as the trifluoroacetate salt. $^1$H NMR (400 MHz, DMSO-d$_6$) δ 2.36-1.73 (m, 7H), 3.81-3.31 (m, 6H), 5.18 (dd, J=8.1, 6.5, 1H), 6.00 (dd, J=21.8, 1.2, 1H), 7.12 (dd, J=10.1, 5.1, 1H), 7.35-7.16 (m, 3H), 8.23 (d, J=5.1, 1H), 11.85 (d, J=49.2, 1H). MS (ESI$^+$) m/z 354.1 (M+H)$^+$.

Example 100

1-{4-[4-(5-fluoro-2-methoxyphenyl)-1H-pyrrolo[2,3-b]pyridin-2-yl]-3,6-dihydropyridin-1(2H)-yl}ethanone A mixture of Example 87 (30.0 mg, 0.076 mmol), (benzotriazol-1-yloxy)tripyrrolidinophosphonium hexafluorophosphate (47.3 mg, 0.091 mmol), triethylamine (0.042 mL, 0.303 mmol), and acetic acid (5.20 µl, 0.091 mmol) in N,N-dimethylformamide (1.2 mL) was stirred for 5 hours. The mixture was quenched with water and brine and extracted with ethyl acetate (twice). The combined organic layers were diluted with ethyl acetate until clear, washed with brine, dried over magnesium sulfate, filtered, and concentrated. The residue was triturated with ethyl acetate to afford the title compound. $^1$H NMR (400 MHz, DMSO) δ 1.17 (t, J=7.2 Hz, 2H), 2.04 (s, 1.5H), 2.07 (s, 1.5H), 3.67-3.58 (m, 2H), 3.74 (s, 3H), 4.22-4.11 (m, 2H), 6.25 (dd, J=6.4, 2.0 Hz, 1H), 6.51 (bs, 1H), 7.04

(d, J=4.9 Hz, 1H), 7.32-7.16 (m, 3H), 8.21 (d, J=5.0 Hz, 1H), 11.89-11.81 (m, 1H). MS (ESI+) m/z 366.1 (M+H)+.

Example 101

1-{4-[4-(5-fluoro-2-methoxyphenyl)-1H-pyrrolo[2,3-b]pyridin-2-yl]-3,6-dihydropyridin-1(2H)-yl}-2-hydroxyethanone The title compound was prepared as described in Example 100, using 2-hydroxyacetic acid in place of acetic acid. Purification by reverse-phase HPLC performed on a Zorbax RX-C18 column (250×21.2 mm, 7 μm particle size) using a gradient of 15% to 100% methanol: 0.1% aqueous trifluoroacetic acid afforded the title compound as a trifluoroacetic acid salt. $^1$H NMR (400 MHz, CD$_3$OD) δ 2.69-2.58 (m, 2H), 3.79-3.62 (m, 1H), 3.86-3.82 (m, 4H), 4.37-4.16 (m, 4H), 6.64-6.50 (m, 2H), 7.34-7.19 (m, 3H), 7.52 (d, J=6.1 Hz, 1H), 8.29 (d, J=6.1 Hz, 1H). MS (ESI+) m/z 382.2 (M+H)+.

Example 102

N-(2,6-difluorobenzyl)-6-[2-(1-methylpiperidin-4-yl)-1H-pyrrolo[2,3-b]pyridin-4-yl]pyridin-2-amine The title compound was prepared using the procedure described in Example 88C, using Example 90B (30 mg, 0.10 mmol) in place of Example 88B and (2,6-difluorophenyl)methanamine (138 mg, 1.0 mmol) in place of (tetrahydro-2H-pyran-4-yl)methanamine. $^1$H NMR (400 MHz, DMSO-d$_6$): δ 1.65-1.85 (m, 2H), 2.22 (d, J=13.22 Hz, 2H), 2.83 (d, J=4.75 Hz, 3H), 2.90-3.02 (m, 1H), 3.04-3.18 (m, 2H), 3.54 (d, J=12.21 Hz, 2H), 4.67 (s, 2H), 6.60 (d, J=1.36 Hz, 1H), 6.68 (d, J=8.14 Hz, 1H), 7.07-7.37 (m, 3H), 7.45 (d, J=5.09 Hz, 1H), 7.55-7.64 (m, 1H), 8.20 (d, J=5.09 Hz, 1H), 8.19 (s, 1H). LCMS: 434 (M+H)+.

Example 103

4-(5-fluoro-2-methoxyphenyl)-2-(1-methylpyrrolidin-2-yl)-1H-pyrrolo[2,3-b]pyridine To a solution of Example 94D (0.07 g, 0.130 mmol) and triethylamine (0.1 mL, 0.717 mmol) in methanol (5 mL), was added formaldehyde (37% in water) (0.2 mL, 2.69 mmol) and the mixture was stirred at room temperature for 1 hour. Sodium cyanoborohydride (0.03 g, 0.477 mmol) was added and the mixture was stirred at room temperature for 15 hours. Trifluoroacetic acid (1 mL) was then added and the mixture was stirred for 1 hour. Concentration and purification by reverse phase flash chromatography (SiO$_2$—C18, 0-100% acetonitrile/water/0.1% trifluoroacetic acid) afforded the title compound as the trifluoroacetate salt. $^1$H NMR (400 MHz, DMSO-d$_6$) δ 2.46-1.99 (m, 4H).), 2.82 (d, J=4.8, 3H), 3.74 (s, 3H), 4.65-4.48 (m, 1H), 6.57 (d, J=2.0, 1H), 7.16 (d, J=5.0, 1H), 7.36-7.19 (m, 3H), 8.33 (d, J=4.9, 1H), 9.70 (br.s, 1H), δ 12.05 (br. s, 1H). MS (ESI+) m/z 326.0 (M+H)+.

Example 104

6-[2-(1-methylpiperidin-4-yl)-1H-pyrrolo[2,3-b]pyridin-4-yl]-N-[(1S)-1-phenylethyl]pyridin-2-amine The title compound was prepared using the procedure described in Example 88C, using Example 90B (30 mg, 0.10 mmol) in place of Example 88B and (S)-1-phenylethanamine (117 mg, 1.0 mmol) in place of (tetrahydro-2H-pyran-4-yl) methanamine. $^1$H NMR (400 MHz, DMSO-d$_6$): δ 1.52 (d, J=7.02 Hz, 3H), 1.77-1.93 (m, 2H), 2.27 (d, J=14.34 Hz, 2H), 2.84 (d, J=3.97 Hz, 3H), 2.97-3.08 (m, 1H), 3.13 (d, J=12.21 Hz, 2H), 3.57 (d, J=11.60 Hz, 2H), 5.22 (d, J=6.71 Hz, 1H), 6.63 (s, 1H), 6.71 (d, J=8.24 Hz, 1H), 7.18-7.25 (m, 2H), 7.34 (t, J=7.63 Hz, 2H), 7.41-7.50 (m, 3H), 7.63 (t, J=7.93 Hz, 1H), 8.27 (d, J=5.49 Hz, 1H). LCMS: 412 (M+H)+.

Example 105

N-(1,3-benzodioxol-5-ylmethyl)-6-[2-(1-methylpiperidin-4-yl)-1H-pyrrolo[2,3-b]pyridin-4-yl]pyridin-2-amine The title compound was prepared using the procedure described in Example 88C, using Example 90B (30 mg, 0.10 mmol) in place of Example 88B and benzo[d][1,3]dioxol-5-ylmethanamine (146 mg, 1.0 mmol) in place of (tetrahydro-2H-pyran-4-yl)methanamine. $^1$H NMR (400 MHz, DMSO-d$_6$): δ 1.69-1.90 (m, 2H), 2.25 (d, J=13.12 Hz, 2H), 2.81 (d, J=3.97 Hz, 3H), 3.00 (t, J=12.05 Hz, 1H), 3.06-3.15 (m, 2H), 3.52 (d, J=11.90 Hz, 2H), 4.53 (s, 2H), 5.95 (s, 2H), 6.65 (d, J=8.54 Hz, 1H), 6.71 (s, 1H), 6.86 (s, 1H), 6.93 (s, 1H), 7.16 (s, 1H), 7.22 (t, J=6.87 Hz, 1H), 7.50 (d, J=5.19 Hz, 1H), 7.59 (t, J=7.78 Hz, 1H), 8.23 (d, J=5.19 Hz, 1H). LCMS: 442 (M+H)+.

Example 106

5-chloro-6-[2-(piperidin-4-yl)-1H-pyrrolo[2,3-b]pyridin-4-yl]pyridin-2-amine

Example 106A 6-bromo-5-chloropyridin-2-amine

To a solution of 6-bromopyridin-2-amine (10 g, 58 mmol) in acetonitrile (150 mL) was added 1-chloropyrrolidine-2,5-dione (8.1 g, 60 mmol) and the mixture was heated at 80° C. for 10 hours. The mixture was diluted with ethyl acetate (200 mL) and washed with water. The organic phase was concentrated and purified by column chromatography (silica gel, 30% ethyl acetate in hexane) to afford the title compound. LCMS: 208 (M+H)+.

Example 106B tert-butyl 6-bromo-5-chloropyridin-2-ylcarbamate

To a solution of Example 106A (7.1 g, 34.2 mmol) in dichloromethane (200 mL) was added di-tert-butyl dicarbonate (9 g, 68 mmol), triethylamine (6.9 g, 68 mmol), and 4-dimethylaminopyridine (1.04 g, 8.6 mmol) and the mixture was stirred at room temperature overnight. The mixture was diluted with ethyl acetate (200 mL) and washed with water. The organic phase was concentrated and purified by column chromatography (silica gel, 10% ethyl acetate in hexane) to afford the title compound. LCMS: 308 (M+H)+.

Example 106C 5-chloro-6-(2-(piperidin-4-yl)-1H-pyrrolo[2,3-b]pyridin-4-yl)pyridin-2-amine To a mixture of Example 21A (100 mg, 0.23 mmol); Example 106B (108 mg, 0.35 mmol), bis(triphenylphosphine)palladium(II)chloride (16 mg, 0.02 mmol), tricyclohexylphosphine (7 mg, 0.02 mmol) and cesium carbonate (230 mg, 0.7 mmol) was added dioxane (10 mL) and the mixture was degassed with nitrogen and heated at 110° C. for 10 hours. After cooling, the mixture was diluted with ethyl acetate (50 mL) and filtered through diatomaceous earth. The filtrate was concentrated and the residue was dissolved in dichloromethane (5 mL) and trifluoroacetic acid (0.5 mL). The mixture was stirred at room temperature for 2 hours, concentrated, and purified by HPLC (Zorbax C-18, using a 0-100% gradient of water/acetonitrile, containing 0.1% trifluoroacetic acid) to afford the title compound. $^1$H NMR (400 MHz, DMSO-$d_6$): δ 1.71-1.87 (m, 2H) 2.22 (d, J=12.82 Hz, 2H), 2.94-3.12 (m, 3H), 3.36 (d, J=12.51 Hz, 2H), 6.11 (s, 1H), 6.73 (d, J=8.85 Hz, 1H), 7.17 (d, J=4.88 Hz, 1H), 7.75 (d, J=8.85 Hz, 1H), 8.27 (d, J=4.88 Hz, 1H). LCMS: 327 (M+H)$^+$.

Example 107

N-[2-(phenylsulfanyl)ethyl]-6-[2-(piperidin-4-yl)-1H-pyrrolo[2,3-b]pyridin-4-yl]pyridin-2-amine The title compound was prepared using the procedure described in Example 88C, using 2-(phenylthio)ethanamine (146 mg, 1.0 mmol) in place of (tetrahydro-2H-pyran-4-yl)methanamine. $^1$H NMR (400 MHz, DMSO-$d_6$): δ 1.75-1.92 (m, 2H), 2.26 (d, J=12.21 Hz, 2H), 2.98-3.15 (m, 3H), 3.20-3.27 (m, 2H), 3.38 (d, J=12.51 Hz, 2H), 3.60-3.69 (m, 2H), 6.64 (d, J=8.24 Hz, 1H), 6.75 (s, 1H), 7.16 (d, J=7.32 Hz, 1H), 7.19-7.25 (m, 3H), 7.37 (d, J=7.32 Hz, 2H), 7.52 (d, J=5.19 Hz, 1H), 7.62 (t, J=7.93 Hz, 1H), 8.28 (d, J=5.19 Hz, 1H). LCMS: 430 (M+H)$^+$.

Example 108

1-{3-[4-(5-fluoro-2-methoxyphenyl)-1H-pyrrolo[2,3-b]pyridin-2-yl]pyrrolidin-1-yl}ethanone To a suspension of Example 59F (50 mg, 0.130 mmol) and triethylamine (0.091 mL, 0.651 mmol) in dichloromethane (2 mL) was added acetyl chloride (0.195 mL, 0.195 mmol) at room temperature. The mixture was stirred for 16 hours, concentrated, and purified by reverse phase flash chromatography (silica gel-C18, 15-60% acetonitrile/water/0.1% trifluoroacetic acid) to provide the title compound. $^1$H NMR (300 MHz, DMSO-$d_6$) δ 1.95 (d, J=4.1 Hz, 3H), 1.98-2.40 (m, 3H), 3.23-3.42 (m, 2H), 3.45-3.60 (m, 2H), 3.73 (s, 3H), 3.77-3.96 (m, 2H), 6.11 (dd, J=10.4, 1.7 Hz, 1H), 7.08 (dd, J=5.1, 1.6 Hz, 1H), 7.15-7.34 (m, 3H), 8.20 (d, J=5.1 Hz, 1H), 11.81 (s, 1H). MS (ESI$^+$) m/z 354.1 (M+H)$^+$.

Example 109

2-{3-[4-(5-fluoro-2-methoxyphenyl)-1H-pyrrolo[2,3-b]pyridin-2-yl]pyrrolidin-1-yl}ethanol Example 109A 2-(1-(2-((tert-butyldimethylsilyl)oxy)ethyl)pyrrolidin-3-yl)-4-(5-fluoro-2-methoxyphenyl)-1H-pyrrolo[2,3-b]pyridine To a solution of Example 59F (50 mg, 0.130 mmol) in dichloromethane (1 mL)/methanol (1 mL) was added triethylamine (0.036 mL, 0.260 mmol) followed by acetic acid (0.037 mL, 0.651 mmol) and (t-butyldimethylsilyloxy)acetaldehyde (0.050 mL, 0.260 mmol). After stirring for 5 minutes, MP-cyanoborohydride (2.49 mmol/g, 209 mg, 0.52 mmol) was added and the mixture was shaken for 16 hours at room temperature. The resin was filtered off, and washed with methanol/dichloromethane (2×3 mL). The crude mixture was concentrated and used in the next step without further purification. LCMS: 470.3 (M+H)$^+$.

Example 109B

2-{3-[4-(5-fluoro-2-methoxyphenyl)-1H-pyrrolo[2,3-b]pyridin-2-yl]pyrrolidin-1-yl}ethanol A solution of Example 109A (61.1 mg, 0.13 mmol) and trifluoroacetic acid (0.6 mL, 7.79 mmol) in dichloromethane (2 mL) was stirred at room temperature for 16 hours. The mixture was concentrated and purified by reverse phase flash chromatography (silica gel-C18, 15-60% acetonitrile/water/0.1% trifluoroacetic acid) to afford the title compound as the trifluoroacetate salt. $^1$H NMR (300 MHz, DMSO-$d_6$) δ 2.07-2.25 (m, 1H), 2.42 (d, J=7.7 Hz, 1H), 3.23-3.37 (m, 3H), 3.70 (d, J=5.2 Hz, 4H), 3.73 (s, 3H), 3.90 (dd, J=18.6, 7.5 Hz, 2H), 5.39 (s, 1H), 6.16-6.25 (m, 1H), 7.06 (d, J=5.0 Hz, 1H), 7.16-7.23 (m, 2H), 7.24-7.33 (m, 1H), 8.20 (d, J=5.0 Hz, 1H), 9.78 (s, 1H), 11.73 (s, 1H), 11.80 (s, 1H). MS (ESI$^+$) m/z 356.1 (M+H)$^+$.

Example 110

4-(5-fluoro-2-methoxyphenyl)-2-[1-(tetrahydro-2H-pyran-4-yl)pyrrolidin-3-yl]-1H-pyrrolo[2,3-b]pyridine To a solution of Example 59F (50 mg, 0.130 mmol) in dichloromethane (1 mL)/methanol (1 mL) was added triethylamine (0.036 mL, 0.260 mmol) followed by acetic acid (0.037 mL, 0.651 mmol) and tetrahydro-4H-pyran-4-one (0.024 mL, 0.260 mmol). After stirring for 5 minute, MP-cyanoborohydride (2.49 mmol/g, 209 mg, 0.52 mmol) was added and the mixture was shaken for 16 hours at room temperature. The resin was filtered off and washed with methanol/dichloromethane (2×3 mL). The crude mixture was concentrated and purified by reverse phase flash chromatography (silica gel-C18, 15-60% acetonitrile/water/0.1% trifluoroacetic acid) to afford the title compound as the trifluoroacetate salt. $^1$H NMR (300 MHz, DMSO-$d_6$) δ 1.48-1.69 (m, 2H), 1.93-2.36 (m, 4H), 3.20-3.49 (m, 6H), 3.73 (s, 3H), 3.79-4.01 (m, 3H), 6.23 (dd, J=4.3, 1.9 Hz, 1H), 7.07 (d, J=4.9 Hz, 1H), 7.15-7.33 (m, 3H), 8.17-8.24 (m, 1H), 9.72-9.95 (m, 1H), 11.72-11.84 (m, 1H). MS (ESI$^+$) m/z 396.1 (M+H)$^+$.

Example 111

4-(5-fluoro-2-methoxyphenyl)-2-[1-(pyridin-2-ylmethyl)pyrrolidin-3-yl]-1H-pyrrolo[2,3-b]pyridine The title compound was prepared as the trifluoroacetate salt using the procedure described in Example 110, using 2-pyridinecarboxaldehyde (0.025 mL, 0.260 mmol) in place of tetrahydro-4H-pyran-4-one. $^1$H NMR (300 MHz, DMSO-$d_6$) δ 2.16-2.32 (m, 1H), 3.73 (s, 3H), 3.75-3.90 (m, 3H), 4.65 (s, 2H), 6.21 (d, J=1.8 Hz, 1H), 7.07 (d, J=4.9 Hz, 1H), 7.16-7.25 (m, 2H), 7.23-7.34 (m, 1H), 7.44-7.55 (m, 2H), 7.93 (td, J=7.7, 1.8 Hz, 1H), 8.20 (d, J=4.9 Hz, 1H), 8.64-8.71 (m, 1H), 10.37-10.57 (m, 1H), 11.77 (bs, 1H). MS (ESI$^+$) m/z 403.0 (M+H)$^+$.

Example 112

4-(5-fluoro-2-methoxyphenyl)-2-[1-(pyridin-3-ylmethyl)pyrrolidin-3-yl]-1H-pyrrolo[2,3-b]pyridine The title compound was prepared as the trifluoroacetate salt using the procedure described in Example 110, using 3-pyridinecarboxaldehyde (0.025 mL, 0.260 mmol) in place of tetrahydro-4H-pyran-4-one. $^1$H NMR (400 MHz, DMSO-$d_6$) δ 1.85-2.41 (m, 1H), 3.16-3.64 (m, 4H), 4.53 (m, 2H), 6.24 (bs, 1H), 7.11 (d, J=5.0 Hz, 1H), 7.16-7.26 (m, 2H), 7.29 (td, J=8.6, 3.1 Hz, 1H), 7.59 (dd, J=7.9, 4.9 Hz, 1H), 8.07 (dt, J=7.9, 1.9 Hz, 1H), 8.23 (d, J=5.0 Hz, 1H), 8.70 (dd, J=4.9, 1.6 Hz, 1H), 8.78 (d, J=2.1 Hz, 1H), 10.41 (bs, 1H), 11.87-11.92 (m, 1H). MS (ESI$^+$) m/z 403.0 (M+H)$^+$.

Example 113

4-(5-fluoro-2-methoxyphenyl)-2-[1-(pyridin-4-ylmethyl)pyrrolidin-3-yl]-1H-pyrrolo[2,3-b]pyridine The title compound was prepared as the trifluoroacetate salt using the procedure described in Example 110, using 4-pyridinecarboxaldehyde (0.025 mL, 0.260 mmol) in place of tetrahydro-4H-pyran-4-one. $^1$H NMR (400 MHz, DMSO-$d_6$) δ 2.05-2.32 (m, 1H), 3.73 (s, 3H), 3.85-3.93 (m, 1H), 4.54 (s, 2H), 6.23 (s, 1H), 7.10 (d, J=5.0 Hz, 1H), 7.16-7.33 (m, 3H), 7.61-7.67 (m, 2H), 8.22 (d, J=5.0 Hz, 1H), 8.72-8.77 (m, 2H), 11.75-11.94 (m, 1H). MS (ESI$^+$) m/z 403.0 (M+H)$^+$.

Example 114

4-(5-fluoro-2-methoxyphenyl)-2-[1-(tetrahydro-2H-pyran-3-ylmethyl)pyrrolidin-3-yl]-1H-pyrrolo[2,3-b]pyridine The title compound was prepared as the trifluoroacetate salt using the procedure described in Example 110, using tetrahydro-pyran-3-carbaldehyde (29.7 mg, 0.260 mmol) in place of tetrahydro-4H-pyran-4-one. $^1$H NMR (400 MHz, DMSO-$d_6$) δ 1.22-1.40 (m, 1H), 1.42-1.57 (m, 1H), 1.56-1.65 (m, 1H), 1.82-1.90 (m, 1H), 1.91-2.50 (m, 4H), 2.87-3.44 (m, 5H), 3.74 (m, 3H), 3.72-4.09 (m, 4H), 6.20-6.26 (m, 1H), 7.09 (d, J=5.0 Hz, 1H), 7.17-7.25 (m, 2H), 7.29 (td, J=8.6, 3.1 Hz, 1H), 8.18-8.25 (m, 1H), 9.65-9.83 (m, 1H), 11.78-11.88 (m, 1H). MS (ESI$^+$) m/z 410.1 (M+H)$^+$.

Example 115 tert-butyl (2-{3-[4-(5-fluoro-2-methoxyphenyl)-1H-pyrrolo[2,3-b]pyridin-2-yl]pyrrolidin-1-yl}ethyl)carbamate The title compound was prepared as the trifluoroacetate salt using the procedure described in Example 110, using tert-butyl (2-oxoethyl)carbamate (83 mg, 0.520 mmol) in place of tetrahydro-4H-pyran-4-one. $^1$H NMR (400 MHz, DMSO-$d_6$) δ 1.35-1.42 (m, 9H), 2.01-2.28 (m, 1H), 3.25-3.32 (m, 5H), 3.73 (s, 3H), 3.75-4.34 (m, 4H), 6.18-6.25 (m, 1H), 7.05-7.11 (m, 2H), 7.16-7.25 (m, 2H), 7.29 (td, J=8.6, 3.1 Hz, 1H), 8.21 (dd, J=5.0, 1.8 Hz, 1H), 9.72-9.94 (m, 1H), 11.76-11.88 (m, 1H). MS (ESI$^+$) m/z 455.0 (M+H)$^+$.

Example 116 tert-butyl 3-[4-(5-fluoro-2-methoxyphenyl)-1H-pyrrolo[2,3-b]pyridin-2-yl]-1,3'-bipyrrolidine-1'-carboxylate The title compound was prepared as the trifluoroacetate salt using the procedure described in Example 110, using tert-butyl 3-oxopyrrolidine-1-carboxylate (48.2 mg, 0.260 mmol) in place of tetrahydro-4H-pyran-4-one. $^1$H NMR (400 MHz, DMSO-$d_6$) δ 1.32-1.44 (m, 9H), 1.66-2.46 (m, 4H), 2.39-2.65 (m, 2H), 3.20-3.32 (m, 3H), 3.64-3.85 (m, 4H), 3.86-4.04 (m, 4H), 6.25 (s, 1H), 7.08 (d, J=4.9 Hz, 1H), 7.17-7.25 (m, 2H), 7.24-7.33 (m, 1H), 8.21 (d, J=4.9 Hz, 1H), 10.31 (d, J=48.4 Hz, 1H), 11.75-11.88 (m, 1H). MS (ESI$^+$) m/z 481.0 (M+H)$^+$.

Example 117

4-(5-fluoro-2-methoxyphenyl)-2-[1-(tetrahydro-2H-pyran-4-ylmethyl)pyrrolidin-3-yl]-1H-pyrrolo[2,3-b]pyridine The title compound was prepared as the trifluoroacetate salt using the procedure described in Example 110, using tetrahydro-2H-pyran-4-carbaldehyde (29.7 mg, 0.260 mmol) in place of tetrahydro-4H-pyran-4-one. $^1$H NMR (400 MHz, DMSO-$d_6$) δ 1.10-1.34 (m, 2H), 1.34-1.81 (m, 2H), 1.86-2.35 (m, 2H), 2.37-2.60 (m, 1H), 3.15 (t, J=6.1 Hz, 2H), 3.27 (t, J=11.1, 9.2 Hz, 4H), 3.74 (s, 3H), 3.83-3.93 (m, 2H), 3.96-4.08 (m, 1H), 6.20-6.27 (m, 1H), 7.09 (d, J=5.0 Hz, 1H), 7.17-7.26 (m, 2H), 7.25-7.33 (m, 1H), 8.22 (d, J=5.0 Hz, 1H), 9.63-9.84 (m, 1H), 11.81-11.92 (m, 1H). MS (ESI$^+$) m/z 410.1 (M+H)$^+$.

Example 118

4-(5-fluoro-2-methoxyphenyl)-2-{1-[2-(morpholin-4-yl)ethyl]pyrrolidin-3-yl}-1H-pyrrolo[2,3-b]pyridine The title compound was prepared as the trifluoroacetate salt using the procedure described in Example 110, using 2-morpholinoacetaldehyde hydrochloride hydrate (47.8 mg, 0.260 mmol) in place of tetrahydro-4H-pyran-4-one. $^1$H NMR (400 MHz, DMSO-$d_6$) δ 2.13-2.26 (m, 1H), 2.45-2.57 (m, 1H), 2.64-3.39 (m, 8H), 3.73 (s, 3H), 3.77-3.92 (m, 4H), 6.21 (s, 1H), 7.09 (d, J=4.9 Hz, 1H), 7.17-7.24 (m, 2H), 7.29 (td, J=8.6, 3.1 Hz, 1H), 8.22 (d, J=4.9 Hz, 1H), 11.77-11.93 (m, 1H). MS (ESI$^+$) m/z 425.0 (M+H)$^+$.

Example 119

4-(5-fluoro-2-methoxyphenyl)-2-[1-(methylsulfonyl)-1,2,3,6-tetrahydropyridin-4-yl]-1H-pyrrolo[2,3-b]pyridine To a solution of Example 87 (35.0 mg, 0.088 mmol) in N,N-dimethylformamide (0.8 mL) was added methanesulfonyl chloride (0.011 mL, 0.141 mmol) and triethylamine (0.074 mL, 0.530 mmol). The mixture was stirred for 3 hours and treated with water. The solids were filtered, washed with water, and oven-dried to afford the title compound. $^1$H NMR (400 MHz, DMSO-$d_6$) δ 2.65-2.58 (m, 2H), 2.94 (s, 3H), 3.37 (t, J=5.7 Hz, 2H), 3.74 (s, 3H), 3.94-3.88 (m, 2H), 6.28 (d, J=2.0 Hz, 1H), 6.56-6.51 (m, 1H), 7.04 (d, J=4.9 Hz, 1H), 7.32-7.16 (m, 3H), 8.21 (d, J=4.9 Hz, 1H), 11.89-11.84 (m, 1H). MS (ESI$^+$) m/z 402.1 (M+H)$^+$.

Example 120 methyl 4-({trans-4-[4-(5-fluoro-2-methoxyphenyl)-1H-pyrrolo[2,3-b]pyridin-2-yl]cyclohexyl}amino)butanoate Example 74 (50.5 mg, 0.15 mmol), 4-oxobutanoic acid methyl ester (17.6 mg, 0.15 mmol) and acetic acid (0.08 mL, 1.4 mmol) were stirred in 2 mL methanol for 1 hour and sodium cyanoborohydride was added (15.9 mg, 0.25 mmol). The mixture was stirred at room temperature for 24 hours and was concentrated. The residue was purified by RP-HPLC using a gradient of 10:90 to 50:50 acetonitrile/0.1% trifluoroacetic acid in water to afford the title compound. $^1$H NMR (400 MHz, DMSO-d$_6$) δ 1.51 (m, 4H), 1.85 (m, 2H), 2.14 (m, 4H), 2.47 (t, 2H), 2.73 (m, 1H), 3.02 (m, 3H), 3.62 (s, 3H), 3.73 (s, 3H), 6.01 (s, 1H), 7.08 (d, 1H), 7.22 (m, 3H), 8.18 (d, 1H), 11.75 (br s, 1H), (ESI) m/e 440.1 (M+H)$^+$.

Example 121 ethyl 2-[({trans-4-[4-(5-fluoro-2-methoxyphenyl)-1H-pyrrolo[2,3-b]pyridin-2-yl]cyclohexyl}amino)methyl]cyclopropanecarboxylate The title compound was prepared using the procedure described in Example 120 using ethyl 2-formyl-1-cyclopropanecarboxylate in place of 4-oxobutanoic acid methyl ester. $^1$H NMR (400 MHz, DMSO-d$_6$) δ 1.07 (m, 2H), 1.20 (t, 3H), 1.53 (m, 5H), 1.79 (m, 1H), 2.14 (m, 4H), 2.75 (m, 1H), 2.99 (m, 3H), 3.73 (s, 3H), 4.09 (m, 2H), 6.02 (s, 1H), 7.08 (d, 1H), 7.22 (m, 3H), 8.18 (br d, 1H), 11.70 (br s, 1H). (ESI) m/e 466.1 (M+H)$^+$.

Example 122 trans-4-[4-(5-fluoro-2-methoxyphenyl)-1H-pyrrolo[2,3-b]pyridin-2-yl]-N-[2-(morpholin-4-yl)ethyl]cyclohexanamine The title compound was prepared using the procedure described in Example 120 using morpholin-4-yl-acetaldehyde monohydrate hydrochloride in place of 4-oxobutanoic acid methyl ester. $^1$H NMR (400 MHz, DMSO-d$_6$) δ 1.54 (m, 4H), 2.16 (m, 4H), 2.75 (m, 1H), 3.22 (m, 12H), 3.73 (s, 3H), 3.80 (m, 1H), 6.00 (s, 1H), 7.05 (d, 1H), 7.25 (m, 3H), 8.16 (d, 1H), 11.69 (br s, 1H). (ESI) m/e 453.1 (M+H)$^+$.

Example 123

3-({trans-4-[4-(5-fluoro-2-methoxyphenyl)-1H-pyrrolo[2,3-b]pyridin-2-yl]cyclohexyl}amino)propane-1,2-diol The title compound was prepared using the procedure described in Example 120 using DL-glyceraldehyde in place of 4-oxobutanoic acid methyl ester. $^1$H NMR (400 MHz, DMSO-d$_6$) δ 1.53 (m, 4H), 2.15 (m, 4H), 2.71 (m, 1H), 2.87 (m, 1H), 3.11 (m, 2H), 3.36 (m, 1H), 3.47 (m, 2H), 3.73 (s, 3H), 6.00 (s, 1H), 7.06 (d, 1H), 7.22 (m, 3H), 8.17 (d, 1H), 11.72 (br s, 1H). (ESI) m/e 414.1 (M+H)$^+$.

Example 124

2-{3-[4-(5-fluoro-2-methoxyphenyl)-1H-pyrrolo[2,3-b]pyridin-2-yl]pyrrolidin-1-yl}ethanamine The title compound was prepared as the trifluoroacetate salt using the procedure described in Example 109B, using Example 115 (0.025 mL, 0.260 mmol) in place of Example 109A. $^1$H NMR (300 MHz, DMSO-d$_6$) δ 1.44-2.36 (m, 2H), 3.07-3.67 (m, 9H), 3.73 (s, 1H), 6.21 (s, 1H), 7.07 (d, J=5.0 Hz, 1H), 7.15-7.33 (m, 3H), 8.00 (bs, 3H), 8.21 (d, J=4.9 Hz, 1H), 10.19 (bs, 1H), 11.69-11.86 (m, 1H). MS (ESI$^+$) m/z 355.0 (M+H)$^+$.

Example 125

3-[4-(5-fluoro-2-methoxyphenyl)-1H-pyrrolo[2,3-b]pyridin-2-yl]-1,3'-bipyrrolidine The title compound was prepared as the trifluoroacetate salt using the procedure described in Example 109B, using Example 116 (0.025 mL, 0.260 mmol) in place of Example 109A. $^1$H NMR (300 MHz, DMSO-d$_6$) δ 2.03-2.41 (m, 2H), 3.17-3.43 (m, 8H), 3.73 (s, 3H), 6.21 (s, 1H), 7.07 (d, J=4.9 Hz, 1H), 7.16-7.34 (m, 3H), 8.21 (d, J=4.9 Hz, 1H), 8.93-9.19 (m, 2H), 11.76-11.82 (m, 1H). MS (ESI$^+$) m/z 381.1 (M+H)$^+$.

Example 126

4-[4-(5-fluoro-2-methoxyphenyl)-1H-pyrrolo[2,3-b]pyridin-2-yl]piperidin-4-ol

Example 126A tert-butyl 4-(4-chloro-1-tosyl-1H-pyrrolo[2,3-b]pyridin-2-yl)-4-hydroxypiperidine-1-carboxylate To a solution of 4-chloro-2-iodo-1-tosyl-1H-pyrrolo[2,3-b]pyridine (200 mg, 0.462 mmol) in tetrahydrofuran (1.5 mL) at −78° C. was added 1.6 M n-butyllithium in hexanes (0.347 mL, 0.555 mmol) under nitrogen. The mixture was stirred for 10 minutes and tert-butyl 4-oxopiperidine-1-carboxylate (111 mg, 0.555 mmol) was added. The mixture was stirred at −78° C. for 1 hour and was slowly warmed to room temperature overnight. The mixture was quenched with water, extracted with ethyl acetate (2×5 mL) and the organic layer was dried over magnesium sulfate, filtered, and concentrated. Purification by flash chromatography (silica gel, 20-100% ethyl acetate/heptanes) afforded the title compound. MS (ESI$^+$) m/z 506.0 (M+H)$^+$.

Example 126B tert-butyl 4-(4-(5-fluoro-2-methoxyphenyl)-1-tosyl-1H-pyrrolo[2,3-b]pyridin-2-yl)-4-hydroxypiperidine-1-carboxylate A suspension of potassium phosphate (154 mg, 0.723 mmol), phenylallylchloro[1,3-bis(diisopropylphenyl)-2-imidazol-2-ylidene]palladium(II) (15.61 mg, 0.024 mmol), Example 126A (122 mg, 0.241 mmol) and (5-fluoro-2-methoxyphenyl)boronic acid (53.3 mg, 0.313 mmol) in tetrahydrofuran (1.5 mL) was heated under nitrogen at 60° C. for 150 minutes. The mixture was diluted with ethyl acetate, the water layer was separated and the organic layer was dried over magnesium sulfate, filtered and concentrated. The crude product was used in the next step without further purification. LCMS: 596.2 (M+H)$^+$.

Example 126C tert-butyl 4-(4-(5-fluoro-2-methoxyphenyl)-1H-pyrrolo[2,3-b]pyridin-2-yl)-4-hydroxypiperidine-1-carboxylate A suspension of Example 126B (0.144 g, 0.241 mmol) and 50% sodium hydroxide (0.064 mL, 1.205 mmol)/water (0.064 mL) in dioxane (1 mL) was heated at 80° C. for 4 hours. The mixture was diluted with ethyl acetate and dried over magnesium sulfate, filtered and concentrated. The crude mixture was used in the next step without further purification. LCMS: 442.2 (M+H)$^+$.

Example 126D

4-[4-(5-fluoro-2-methoxyphenyl)-1H-pyrrolo[2,3-b]pyridin-2-yl]piperidin-4-ol

The title compound was prepared as the trifluoroacetate salt using the procedure described in Example 109B, using Example 126C (0.025 mL, 0.260 mmol) in place of Example 109A. $^1$H NMR (300 MHz, DMSO-d$_6$) δ 1.59-1.77 (m, 2H), 1.85-2.05 (m, 2H), 2.95-3.13 (m, 2H), 3.13-3.40 (m, 2H), 3.73 (s, 3H), 3.99-4.13 (m, 1H), 7.05 (d, J=2.1 Hz, 1H), 7.13 (d, J=4.8 Hz, 1H), 7.20-7.37 (m, 3H), 8.17-8.32 (m, 1H), 8.33-8.39 (m, 1H), 8.41-8.56 (m, 2H), 12.16-12.22 (m, 1H). MS (ESI$^+$) m/z 369.2 (M+H)$^+$.

Example 127 benzyl (3-{3-[4-(5-fluoro-2-methoxyphenyl)-1H-pyrrolo[2,3-b]pyridin-2-yl]piperidin-1-yl}propyl)carbamate A solution of benzyl (3-oxopropyl)carbamate (153 mg, 0.738 mmol), Example 1H (80 mg, 0.246 mmol) and sodium triacetoxyborohydride (78 mg, 0.369 mmol) in dichloromethane (3 mL) was stirred overnight and the mixture was quenched with 5% aqueous sodium hydroxide (15 mL). The mixture was extracted with dichloromethane and the organic layer was dried over sodium sulfate, filtered, and concentrated. The residue was dissolved in a mixture of dimethylsulfoxide and methanol and loaded onto a C18 column, eluting with 40-80% acetonitrile in 0.1% trifluoroacetic acid/water to afford the title compound. LCMS: 517.24 (M+H)$^+$. $^1$H NMR (400 MHz, DMSO-d$_6$) δ 1.61 (m, 1H) 1.75-1.92 (m, 3H) 1.98 (d, 1H) 2.16 (d, 1H) 2.80-2.95 (m, 1H) 3.01-3.17 (m, 5H) 3.18-3.29 (m, 2H) 3.41 (t, 2H) 3.73 (s, 3H) 5.02 (s, 2H) 6.11 (d, 1H) 7.09 (d, 1H) 7.17-7.24 (m, 2H) 7.25-7.43 (m, 7H) 8.22 (d, 1H) 9.51 (s, 1H) 11.84 (s, 1H).

Example 128

2-{3-[4-(5-fluoro-2-methoxyphenyl)-1H-pyrrolo[2,3-b]pyridin-2-yl]piperidin-1-yl}ethanol Example 128A 2-(1-(2-(tert-butyldimethylsilyloxy)ethyl)piperidin-3-yl)-4-(5-fluoro-2-methoxyphenyl)-1H-pyrrolo[2,3-b]pyridine The title compound was prepared by using the procedure described in Example 127, using 2-((tert-butyldimethylsilyBoxy)acetaldehyde (86 mg, 0.49 mmol) in place of benzyl (3-oxopropyl)carbamate.

Example 128B 2-(3-(4-(5-fluoro-2-methoxyphenyl)-1H-pyrrolo[2,3-b]pyridin-2-yl)piperidin-1-yl)ethanol A solution of Example 128A (80 mg, 0.16 mmol)) in dichloromethane (2 mL) and methanol (2 mL) was treated with 37% hydrochloric acid (0.1 mL) for 10 minutes and concentrated. The residue was purified by reverse phase HPLC, and was eluted with 10-70% acetonitrile in 0.1% trifluoroacetic acid/water to afford the title compound. LCMS: 370.20 (M+H)$^+$. $^1$H NMR (400 MHz, DMSO-d$_6$) δ 1.56-1.69 (m, 1H) 1.83-2.01 (m, 2H) 2.16 (d, 1H) 2.85-2.99 (m, 1H) 3.14-3.23 (m, 3H) 3.26-3.40 (m, 2H) 3.74 (s, 3H) 3.75-3.80 (m, 2H) 6.11 (d, 1H) 7.09 (d, 1H) 7.18-7.24 (m, 2H) 7.25-7.32 (m, 1H) 8.22 (d, 1H) 9.55 (s, 1H) 11.88 (s, 1H).

Example 129

3-{3-[4-(5-fluoro-2-methoxyphenyl)-1H-pyrrolo[2,3-b]pyridin-2-yl]piperidin-1-yl}propan-1-amine To a solution of Example 127 (100 mg, 0.194 mmol) in tetrahydrofuran (20 mL) and methanol (10 mL) was added 20% palladium hydroxide on carbon (wet, 20 mg, 0.015 mmol). The mixture was heated under 50 psi hydrogen at 45° C. for 3 hours and cooled. The insoluble material was filtered off and the filtrate was concentrated. The residue was purified by reverse phase HPLC, and was eluted with 10-70% acetonitrile in 0.1% trifluoroacetic acid/water to afford the title compound. LCMS: 383.23 (M+H)$^+$. $^1$H NMR (400 MHz, DMSO-d$_6$) δ 1.58-1.74 (m, 3H) 1.82-1.93 (m, 1H) 1.95-2.07 (m, 2H) 2.18 (d, 1H) 2.81-2.97 (m, 4H) 3.14-3.23 (m, 2H) 3.48 (t, 2H) 3.74 (s, 3H) 6.10 (s, 1H) 7.08 (d, 1H) 7.17-7.23 (m, 2H) 7.25-7.34 (m, 1H) 8.22 (d, 1H) 10.17 (s, 1H) 11.88 (s, 1H).

Example 130

4-(5-fluoro-2-methoxyphenyl)-2-[1-(2-methoxyethyl)piperidin-3-yl]-1H-pyrrolo[2,3-b]pyridine The title compound was prepared using the procedure described in Example 127, using 2-methoxyacetaldehyde (27.3 mg, 0.37 mmol) in place of benzyl (3-oxopropyl)carbamate. LCMS: 384.21 (M+H)$^+$. $^1$H NMR (400 MHz, DMSO-d$_6$) δ 1.55-1.68 (m, 1H) 1.80-1.99 (m, 2H) 2.15 (d, 1H) 2.84-3.00 (m, 1H) 3.10-3.22 (m, 2H) 3.25-3.31 (m, 2H) 3.32 (s, 3H) 3.41-3.60 (m, 2H) 3.66-3.73 (m, 2H) 3.74 (s, 3H)

6.11 (d, 1H) 7.10 (d, 1H) 7.18-7.23 (m, 2H) 7.26-7.32 (m, 1H) 8.23 (d, 1H) 9.67 (s, 1H) 11.91 (s, 1H).

Example 131

4-({trans-4-[4-(5-fluoro-2-methoxyphenyl)-1H-pyrrolo[2,3-b]pyridin-2-yl]cyclohexyl}amino)butanoic acid Example 120 (31.4 mg, 0.07 mmol) and 1 mL 0.8 M lithium hydroxide were stirred in 2 mL tetrahydrofuran for 24 hours. The mixture was acidified to pH 2 with 2M hydrochloric acid, concentrated and purified by reverse phase HPLC using a gradient of 10:90 to 40:60 acetonitrile/0.1% trifluoroacetic acid in water to afford the title compound. $^1$H NMR (400 MHz, DMSO-$d_6$) δ 11.78 (s, 1H), 8.18 (d, 1H), 7.26 (m, 3H), 7.08 (d, 1H), 6.02 (s, 1H), 3.74 (s, 3H), 3.02 (m, 3H), 2.73 (m, 1H), 2.37 (t, 2H), 2.15 (m, 4H), 1.82 (m, 2H), 1.51 (m, 4H). (ESI) m/e 426.1 (M+H)$^+$.

Example 132

5-chloro-6-[2-(1-methylpiperidin-4-yl)-1H-pyrrolo[2,3-b]pyridin-4-yl]pyridin-2-amine Example 132A 4-chloro-2-(1-methylpiperidin-4-yl)-1H-pyrrolo[2,3-b]pyridine To a solution of Example 17E (200 mg, 0.6 mmol) in dichloromethane (10 mL) was added 0.5 mL trifluoroacetic acid and the mixture was stirred at room temperature for 2 hours. The mixture was concentrated, dissolved in dichloromethane (20 mL), washed with sodium bicarbonate solution and concentrated. The residue was dissolved in methanol (2 mL) and treated with formaldehyde (120 mg, 37% in water) and sodium cyanoborohydride (57 mg, 0.9 mmol). The mixture was stirred at room temperature for 2 hours, diluted with dichloromethane and the organic phase was washed with water and concentrated to afford the title compound. LCMS: 250 (M+H)$^+$.

Example 132B 2-(1-methylpiperidin-4-yl)-4-(4,4,5,5-tetramethyl-1,3,2-dioxaborolan-2-yl)-1H-pyrrolo[2,3-b]pyridine The title compound was prepared using the procedure described in Example 5A, using Example 132A (1.0 g, 4.0 mmol) in place of Example 1F. LCMS: 342 (M+H)$^+$.

Example 132C 5-chloro-6-(2-(1-methylpiperidin-4-yl)-1H-pyrrolo[2,3-b]pyridin-4-yl)pyridin-2-amine The title compound was prepared using the procedure described in Example 5B, using Example 132B (100 mg, 0.3 mmol) in place of Example 5A and Example 106A (94 mg, 0.45 mmol) in place of 6-bromo-5-methoxypyridin-2-amine. $^1$H NMR (400 MHz, DMSO-$d_6$): δ 1.82 (t, J=13.05 Hz, 2H), 2.20-2.33 (m, 2H), 2.81 (d, J=4.75 Hz, 3H), 2.91-3.19 (m, 3H), 3.45-3.60 (m, 2H), 6.04 (d, J=1.36 Hz, 1H), 6.59 (d, J=8.82 Hz, 1H), 7.08 (d, J=5.09 Hz, 1H), 7.61 (d, J=8.82 Hz, 1H), 8.22 (d, J=4.75 Hz, 1H). LCMS: 342 (M+H)$^+$.

Example 133

3-chloro-$N^2$-{5-chloro-6-[2-(1-methylpiperidin-4-yl)-1H-pyrrolo[2,3-b]pyridin-4-yl]pyridin-2-yl}pyridine-2,6-diamine The title compound was obtained as a byproduct from the procedure described in Example 132C. $^1$H NMR (400 MHz, DMSO-$d_6$): δ 2.22-2.39 (m, 2H), 2.80 (d, J=4.41 Hz, 3H), 2.94-3.19 (m, 3H), 3.51 (d, J=5.76 Hz, 2H), 3.81-3.91 (m, 2H), 6.06 (d, J=1.36 Hz, 1H), 6.11 (d, J=8.48 Hz, 1H), 7.17 (d, J=5.09 Hz, 1H), 7.43 (d, J=8.82 Hz, 1H), 7.92 (d, J=8.82 Hz, 1H), 8.25 (d, J=4.75 Hz, 1H), 8.31 (d, J=8.82 Hz, 1H). LCMS: 469 (M+H)$^+$.

Example 134

5-chloro-6-[2-(1-methylpiperidin-4-yl)-1H-pyrrolo[2,3-b]pyridin-4-yl]-N-(tetrahydro-2H-pyran-4-ylmethyl)pyridin-2-amine The title compound was prepared using the procedure described in Example 11B, using Example 132 (20 mg, 0.06 mmol) in place of Example 11A and tetrahydro-2H-pyran-4-carbaldehyde (10 mg, 0.09 mmol) in place of benzaldehyde. $^1$H NMR (400 MHz, DMSO-$d_6$): δ 1.11-1.30 (m, 4H), 1.61 (d, J=12.82 Hz, 2H), 1.72-1.89 (m, 2H), 2.29 (d, J=13.43 Hz, 2H), 2.81 (d, J=3.36 Hz, 3H), 3.06-3.17 (m, 4H), 3.21-3.31 (m, 2H), 3.54 (d, J=11.90 Hz, 2H), 3.84 (dd, J=11.14, 2.90 Hz, 2H), 6.10 (d, J=1.22 Hz, 1H), 6.60 (d, J=8.85 Hz, 1H), 7.14 (d, J=4.88 Hz, 1H), 7.55 (d, J=8.85 Hz, 1H), 8.22 (d, J=5.19 Hz, 1H). LCMS: 440 (M+H)$^+$.

Example 135

1-{4-[4-(5-fluoro-2-methoxyphenyl)-1H-pyrrolo[2,3-b]pyridin-2-yl]piperidin-1-yl}ethanone Example 135A tert-butyl 4-(4-(5-fluoro-2-methoxyphenyl)-1H-pyrrolo[2,3-b]pyridin-2-yl)piperidine-1-carboxylate A solution of Example 87C (2.35 g, 4.17 mmol) in ethanol (40 mL) was added to 20% palladium hydroxide on carbon (wet, 2.35 g, 1.707 mmol) in a stainless steel pressure bottle and was stirred at 50° C. for several days at 50 psi hydrogen. The mixture was filtered through a nylon membrane and concentrated. The residue was dissolved in 30 mL 1,4-dioxane and treated with 2 mL 20% sodium hydroxide. The mixture was heated at 90° C. for 4 hours and was concentrated. The residue was treated with water and extracted with ethyl acetate (twice). The combined organic layers were dried over magnesium sulfate, filtered, concentrated, and purified using an ISCO Companion flash system on silica eluting with dichloromethane/ethyl acetate (5:5 to 4:6) to afford the title compound. MS (ESI$^+$) m/z 425.9 (M+H)$^+$.

Example 135B 4-(5-fluoro-2-methoxyphenyl)-2-(piperidin-4-yl)-1H-pyrrolo[2,3-b]pyridine A solution of Example 135A (0.955 g, 2.24 mmol) in dichloromethane (20 mL) was treated with trifluoroacetic acid (1.73 mL, 22.4 mmol) and the mixture was stirred for 3 hours. After concentration, the residue was dissolved in 10

Example 135C

1-{4-[4-(5-fluoro-2-methoxyphenyl)-1H-pyrrolo[2,3-b]pyridin-2-yl]piperidin-1-yl}ethanone A mixture of Example 135B (50 mg, 0.126 mmol), (benzotriazol-1-yl-oxytripyrrolidinophosphonium hexafluorophosphate) (78 mg, 0.151 mmol), triethylamine (0.07 mL, 0.502 mmol), and acetic acid (8.62 µL, 0.151 mmol) in tetrahydrofuran (2 mL) was stirred for 5 hours. The mixture was quenched with water and brine and extracted with ethyl acetate (twice). The combined organic layers were diluted with ethyl acetate, washed with brine, dried over magnesium sulfate, filtered, concentrated and purified using an ISCO Companion flash system on silica eluting with methanol/ethyl acetate (gradient of 5:95 to 10:90) to afford the title compound. $^1$H NMR (500 MHz, CD$_3$OD) δ 1.65 (qd, J=12.5, 4.3 Hz, 2H), 2.05-2.16 (m, 5H), 2.79 (td, J=12.9, 2.9 Hz, 1H), 3.02-3.18 (m, 1H), 3.23.3.27 (m, 1H), 3.75 (s, 3H), 3.99-4.06 (m, 1H), 4.52-4.66 (m, 1H), 6.07 (d, J=0.8 Hz, 1H), 7.08 (d, J=5.0 Hz, 1H), 7.09-7.18 (m, 3H), 8.11 (d, J=5.0 Hz, 1H). MS (ESI$^+$) m/z 368.1 (M+H)$^+$.

Example 136

1-{4-[4-(5-fluoro-2-methoxyphenyl)-1H-pyrrolo[2,3-b]pyridin-2-yl]piperidin-1-yl}-2-hydroxyethanone The title compound was prepared as described in Example 135C, using 2-hydroxyacetic acid (0.196 mmol, 70% in water, 14.89 mg) in place of acetic acid. Purification by reverse-phase HPLC on a Zorbax RX-C18 column using a gradient of 15% to 100% methanol/0.1% aqueous trifluoroacetic acid afforded the title compound as a trifluoroacetic acid salt. $^1$H NMR (400 MHz, CD$_3$OD) δ 1.61-1.84 (m, 2H), 2.09-2.18 (m, 2H), 2.82-2.93 (m, 1H), 3.11-3.25 (m, 2H), 3.80 (s, 3H), 3.83-3.92 (m, 1H), 4.26 (d, J=5.7 Hz, 2H), 4.57-4.66 (m, 1H), 6.37 (d, J=0.8 Hz, 1H), 7.18-7.31 (m, 3H), 7.47 (d, J=5.9 Hz, 1H), 8.26 (d, J=5.9 Hz, 1H). MS (ESI$^+$) m/z 384.1 (M+H)$^+$.

Example 137

3-methoxy-4-[2-(piperidin-3-yl)-1H-pyrrolo[2,3-b]pyridin-4-yl]benzonitrile

Example 137A tert-butyl 3-(4-(4-cyano-2-methoxyphenyl)-1H-pyrrolo[2,3-b]pyridin-2-yl)piperidine-1-carboxylate A mixture of Example 1F (100 mg, 0.298 mmol), 4-cyano-2-methoxyphenylboronic acid (86 mg, 0.447 mmol), bis(triphenylphosphine)palladium chloride (12.54 mg, 0.018 mmol), tricyclohexylphosphine (5.01 mg, 0.018 mmol) and cesium carbonate (291 mg, 0.893 mmol) in dioxane (3 mL) was heated at 110° C. for 24 hours. Additional tricyclohexylphosphine (5.01 mg, 0.018 mmol), bis(triphenylphosphine)palladium chloride (12.54 mg, 0.018 mmol) and 4-cyano-2-methoxyphenylboronic acid (60 mg) were added and the mixture was heated at 120° C. for 24 hours and cooled. Insoluble material was filtered off and the filtrate was concentrated. The residue was purified by flash chromatography, and was eluted with 0-100% ethyl acetate in heptanes to afford the title compound.

Example 137B 3-methoxy-4-(2-(piperidin-3-yl)-1H-pyrrolo[2,3-b]pyridin-4-yl)benzonitrile A solution of Example 137A (75 mg, 0.17 mmol) in dichloromethane (3 mL) was treated with trifluoroacetic acid (1 mL) for 10 minutes and was concentrated. The residue was purified by reverse phase HPLC, eluted with 10-70% acetonitrile in 0.1% trifluoroacetic acid/water to afford the title compound. LCMS: 333.11 (M+H)$^+$. $^1$H NMR (400 MHz, DMSO-d$_6$) δ 1.63-1.80 (m, 2H) 1.88 (d, 1H) 2.11 (d, 1H) 2.77-2.89 (m, 1H) 3.02-3.12 (m, 1H) 3.14-3.22 (m, 1H) 3.29 (d, 1H) 3.81 (s, 3H) 6.05 (d, 1H) 7.07 (d, 1H) 7.54 (s, 2H) 7.67 (s, 1H) 8.21 (d, 1H) 8.70 (d, 1H) 8.87 (s, 1H) 11.83 (s, 1H).

Example 138

N-(2-phenylethyl)-6-[2-(piperidin-4-yl)-1H-pyrrolo[2,3-b]pyridin-4-yl]pyridin-2-amine The title compound was prepared using the procedure described in Example 88C, using 2-phenylethanamine (54 mg, 0.44 mmol) in place of (tetrahydro-2H-pyran-4-yl)methanamine. $^1$H NMR (400 MHz, DMSO-d$_6$): δ 1H 1.73-1.88 (m, 2H), 2.21 (d, J=14.92 Hz, 2H), 2.87-2.97 (m, 2H), 3.00-3.12 (m, 3H), 3.15 (d, J=9.16 Hz, 2H), 3.58-3.65 (m, 2H), 6.57 (d, J=8.14 Hz, 1H), 6.80 (d, J=1.02 Hz, 1H), 7.19 (d, J=7.12 Hz, 2H), 7.26-7.31 (m, 5H), 7.30-7.34 (m, 1H), 7.52 (d, J=5.09 Hz, 1H). LCMS: 398 (M+H)$^+$.

Example 139

N-methyl-6-[2-(1-methylpiperidin-4-yl)-1H-pyrrolo[2,3-b]pyridin-4-yl]-N-(2-phenylethyl)pyridin-2-amine The title compound was obtained as a byproduct from Example 150. $^1$H NMR (400 MHz, DMSO-d$_6$): δ 1.74-1.92 (m, 2H), 2.28 (d, J=13.22 Hz, 2H), 2.82 (d, J=4.75 Hz, 3H), 2.85-2.95 (m, 2H), 2.96-3.03 (m, 1H), 3.06 (s, 3H), 3.11 (d, J=12.89 Hz, 2H), 3.53 (d, J=11.87 Hz, 2H), 3.78-3.90 (m, 2H), 6.74 (d, J=8.48 Hz, 1H), 6.80 (d, J=1.36 Hz, 1H), 7.17-7.24 (m, 1H), 7.24-7.31 (m, 5H), 7.59 (d, J=5.43 Hz, 1H), 7.64-7.73 (m, 1H), 8.28 (d, J=5.43 Hz, 1H). LCMS: 426 (M+H)$^+$.

Example 140

N-(2-chlorobenzyl)-6-[2-(piperidin-4-yl)-1H-pyrrolo[2,3-b]pyridin-4-yl]pyridin-2-amine The title compound was prepared using the procedure described in Example 88C, using (2-chlorophenyl)methanamine (50 mg, 0.35 mmol) in place of (tetrahydro-2H-pyran-4-yl)methanamine. $^1$H NMR (400 MHz, DMSO-d$_6$): 1.48-1.83 (m, 2H), 2.12 (d, J=12.89 Hz, 2H), 2.88-3.12 (m, 3H), 3.36 (d, J=12.89 Hz, 2H), 4.71 (s, 2H), 6.57 (d, J=1.36 Hz, 1H), 6.70 (d, J=8.48 Hz, 1H), 7.22 (d, J=7.12 Hz, 1H), 7.25-7.33 (m, 2H), 7.41-7.54 (m, 3H), 7.61 (t, J=7.97 Hz, 1H), 8.21 (d, J=5.09 Hz, 1H). LCMS: 417 (M+H)$^+$.

Example 141

N-(2-chlorobenzyl)-6-[2-(1-methylpiperidin-4-yl)-1H-pyrrolo[2,3-b]pyridin-4-yl]pyridin-2-amine The title compound was prepared using the procedure described in Example 89, using Example 140 (20 mg, 0.05 mmol) in place of Example 88C. $^1$H NMR (400 MHz, DMSO-d$_6$): δ 1.60-1.80 (m, 2H), 2.06-2.21 (m, 2H), 2.83 (d, J=4.75 Hz, 3H), 2.93-3.16 (m, 1H), 3.36 (d, J=12.55 Hz, 2H), 3.53 (d, J=11.87 Hz, 2H), 4.71 (s, 2H), 6.53 (d, J=1.36 Hz, 1H), 6.69 (d, J=8.48 Hz, 1H), 7.21 (d, J=7.46 Hz, 1H), 7.28-7.33 (m, 2H), 7.40-7.46 (m, 2H), 7.46-7.54 (m, 1H), 7.60 (t, J=7.80 Hz, 1H), 8.20 (d, J=5.09 Hz, 1H). LCMS: 432 (M+H)$^+$.

Example 142

N-(2-chlorobenzyl)-N-methyl-6-[2-(1-methylpiperidin-4-yl)-1H-pyrrolo[2,3-b]pyridin-4-yl]pyridin-2-amine The title compound was obtained as a byproduct from Example 141. $^1$H NMR (400 MHz, DMSO-d$_6$): δ 1.51-1.77 (m, 2H), 2.02-2.20 (m, 2H), 2.83 (d, J=4.75 Hz, 3H), 3.00-3.11 (m, 1H), 3.19 (s, 3H), 3.24-3.42 (m, 2H), 3.52 (d, J=11.19 Hz, 2H), 5.00 (s, 2H), 6.50 (d, J=1.36 Hz, 1H), 6.76 (d, J=8.48 Hz, 1H), 7.07-7.15 (m, 1H), 7.24-7.35 (m, 3H), 7.44 (d, J=5.09 Hz, 1H), 7.51-7.58 (m, 1H), 7.67-7.77 (m, 1H), 8.20 (d, J=5.09 Hz, 1H). LCMS: 446 (M+H)$^+$.

Example 143

1-[2-({6-[2-(piperidin-4-yl)-1H-pyrrolo[2,3-b]pyridin-4-yl]pyridin-2-yl}amino)ethyl]pyrrolidin-2-one The title compound was prepared using the procedure described in Example 88C, using 1-(2-aminoethyl)pyrrolidin-2-one (113 mg, 0.9 mmol) in place of (tetrahydro-2H-pyran-4-yl)methanamine. $^1$H NMR (400 MHz, DMSO-d$_6$): δ 1.79-1.98 (m, 4H), 2.18 (t, J=7.97 Hz, 2H), 2.27 (d, J=13.56 Hz, 2H), 2.89-3.23 (m, 3H), 3.29-3.49 (m, 6H), 3.55 (t, J=6.27 Hz, 2H), 6.62 (d, J=8.48 Hz, 1H), 6.76 (s, 1H), 7.21 (d, J=6.78 Hz, 1H), 7.54 (d, J=5.09 Hz, 1H), 7.60 (t, J=7.63 Hz, 1H), 8.25 (d, J=5.09 Hz, 1H). LCMS: 405 (M+H)$^+$.

Example 144

1-[2-(methyl{6-[2-(1-methylpiperidin-4-yl)-1H-pyrrolo[2,3-b]pyridin-4-yl]pyridin-2-yl}amino)ethyl]pyrrolidin-2-one The title compound was obtained as a byproduct from Example 151. $^1$H NMR (400 MHz, DMSO-d$_6$): δ 1.62-1.73 (m, 2H), 1.86 (dd, J=12.72, 2.54 Hz, 2H), 2.03 (t, J=7.97 Hz, 2H), 2.34 (d, J=13.56 Hz, 2H), 2.83 (d, J=4.41 Hz, 3H), 3.08 (s, 3H), 3.10-3.21 (m, 3H), 3.33 (t, J=6.95 Hz, 2H), 3.42 (t, J=6.10 Hz, 2H), 3.56 (d, J=11.87 Hz, 2H), 3.81 (t, J=6.10 Hz, 2H), 6.70 (d, J=8.48 Hz, 1H), 6.75 (d, J=1.70 Hz, 1H), 7.25 (d, J=7.12 Hz, 1H), 7.56 (d, J=5.09 Hz, 1H), 7.62-7.71 (m, 1H), 8.24 (d, J=5.09 Hz, 1H). LCMS: 433 (M+H)$^+$.

Example 145

2-[({trans-4-[4-(5-fluoro-2-methoxyphenyl)-1H-pyrrolo[2,3-b]pyridin-2-yl]cyclohexyl}amino)methyl]cyclopropanecarboxylic acid The title compound was prepared using the procedure described in Example 131 using Example 121 in place of Example 120. $^1$H NMR (400 MHz, DMSO-d$_6$) δ 11.73 (br s, 1H), 8.18 (d, 1H), 7.25 (m, 3H), 7.08 (d, 1H), 6.01 (s, 1H), 3.97 (s, 3H), 3.05 (m, 2H), 2.95 (m, 1H), 2.73 (m, 1H), 2.14 (m, 4H), 1.66 (m, 1H), 1.03 (m, 5H), 1.08 (m, 1H), 0.97 (m, 1H). (ESI) m/e 438.1 (M+H)$^+$.

Example 146

2-(azetidin-3-yl)-4-(5-fluoro-2-methoxyphenyl)-1H-pyrrolo[2,3-b]pyridine

Example 146A tert-butyl 3-((2-((tert-butoxycarbonyl)amino)-4-chloropyridin-3-yl)ethynyl)azetidine-1-carboxylate The title compound was prepared using the procedure described in Example 1E, using tert-butyl-3-ethynylazetidine-1-carboxylate (2 g, 11.04 mmol) in place of Example 1D. MS (ESI$^+$) m/z 408.2 (M+H)$^+$.

Example 146B tert-butyl 3-(4-chloro-1H-pyrrolo[2,3-b]pyridin-2-yl)azetidine-1-carboxylate The title compound was prepared using the procedure described in Example 1F, using Example 146A (2.98 g, 7.31 mmol) in place of Example 1E. MS (ESI$^+$) m/z 307.8 (M+H)$^+$.

Example 146C tert-butyl 3-(4-(5-fluoro-2-methoxyphenyl)-1H-pyrrolo[2,3-b]pyridin-2-yl)azetidine-1-carboxylate The title compound was prepared using the procedure described in Example 94C, using Example 146B (68 mg, 0.221 mmol) in place of Example 94B. MS (ESI$^+$) m/z 397.9 (M+H)$^+$.

Example 146D 2-(azetidin-3-yl)-4-(5-fluoro-2-methoxyphenyl)-1H-pyrrolo[2,3-b]pyridine The title compound was prepared as the trifluoroacetate salt using the procedure described in Example 94D, using Example 146C (68 mg, 0.171 mmol) in place of Example 94C. $^1$H NMR (300 MHz, DMSO-d$_6$) δ 3.73 (s, 3H) 4.10-4.35 (m, 5H) 6.37 (d, J=2.03 Hz, 1H) 7.08 (d, J=4.75 Hz, 1H) 7.15-7.36 (m, 3H) 8.22 (d, J=5.09 Hz, 1H) 11.80 (br. s, 1H). MS (ESI$^+$) m/z 298.0 (M+H)$^+$.

Example 147

1-{4-[4-(5-fluoro-2-methoxyphenyl)-1H-pyrrolo[2,3-b]pyridin-2-yl]piperidin-1-yl}-2-(4-hydroxypiperidin-1-yl)ethanone

Example 147A 2-chloro-1-(4-(4-(5-fluoro-2-methoxyphenyl)-1H-pyrrolo[2,3-b]pyridin-2-yl)piperidin-1-yl)ethanone The title compound was prepared as described in Example 135C, using 2-chloroacetic acid (0.241 mmol, 22.78 mg) in place of acetic acid. MS (ESI$^+$) m/z 402.2 (M+H)$^+$.

Example 147B

1-{4-[4-(5-fluoro-2-methoxyphenyl)-1H-pyrrolo[2, 3-b]pyridin-2-yl]piperidin-1-yl}-2-(4-hydroxypiperidin-1-yl)ethanone A mixture of Example 147A (60.0 mg, 0.149 mmol), triethylamine (0.062 mL, 0.448 mmol) and piperidin-4-ol (22.65 mg, 0.224 mmol) in tetrahydrofuran (1.5 mL) was heated at 70° C. for 4 hours. The mixture was quenched with water and brine and extracted with ethyl acetate (twice). The combined organic layers were washed with brine, dried over magnesium sulfate, filtered, concentrated and purified by reverse-phase HPLC on a Zorbax RX-C18 column using a gradient of 15% to 100% methanol/0.1% aqueous trifluoroacetic acid to afford the title compound as a trifluoroacetic acid salt. $^1$H NMR (400 MHz, CD$_3$OD) δ 1.63-2.02 (m, 4H), 2.01-2.26 (m, 4H), 2.92 (td, J=13.0, 2.8 Hz, 1H), 3.03-3.26 (m, 2H), 3.35-3.51 (m, 3H), 3.60-3.70 (m, 1H), 3.81 (s, 3H), 3.82-3.90 (m, 1.5H), 4.10 (bs, 0.5H), 4.19-4.37 (m, 2H), 4.59-4.68 (m, 1H), 6.39 (s, 1H), 7.19-7.32 (m, 3H), 7.51 (d, J=6.0 Hz, 1H), 8.29 (d, J=6.0 Hz, 1H). MS (ESI$^+$) m/z 467.2 (M+H)$^+$.

Example 148

4-(5-fluoro-2-methoxyphenyl)-2-[1-(methylsulfonyl) piperidin-4-yl]-1H-pyrrolo[2,3-b]pyridine To a solution of Example 135B (75 mg, 0.188 mmol) in N,N-dimethylformamide (1.5 mL) was added methanesulfonyl chloride (0.026 mL, 0.339 mmol) and triethylamine (0.157 mL, 1.130 mmol) and the mixture was stirred for 3 hours. The mixture was treated with water/brine and extracted with ethyl acetate (twice). The combined organic layers were dried over magnesium sulfate, filtered and concentrated. The residue was treated with ethyl acetate and ether (9:1) and sonicated. The suspension was filtered, washed with ether/ethyl acetate and oven-dried to afford the title compound. $^1$H NMR (400 MHz, DMSO-d$_6$) δ 1.67-1.82 (m, 2H), 2.05-2.13 (m, 2H), 2.79-2.92 (m, 6H), 3.60-3.69 (m, 2H), 3.73 (s, 3H), 6.01 (d, J=2.0 Hz, 1H), 7.02 (d, J=4.9 Hz, 1H), 7.15-7.28 (m, 3H), 8.15 (d, J=4.9 Hz, 1H), 11.63 (bs, 1H). MS (ESI$^+$) m/z 404.1 (M+H)$^+$.

Example 149

3-{4-[4-(5-fluoro-2-methoxyphenyl)-1H-pyrrolo[2, 3-b]pyridin-2-yl]piperidin-1-yl}propane-1,2-diol To a mixture of Example 135B (60 mg, 0.151 mmol), triethylamine (0.046 mL, 0.331 mmol) and acetic acid (0.043 mL, 0.753 mmol) in dichloromethane (2.5 mL) was added 2,3-dihydroxypropanal (27.1 mg, 0.301 mmol) and MP-cyanoborohydride (2.49 mmol/g, 242 mg, 0.603 mmol) and the mixture was stirred for 5 hours. The solid material was filtered and rinsed with dichloromethane/methanol. The filtrate was concentrated and purified by reverse-phase HPLC on a Zorbax RX-C18 column using a gradient of 15% to 100% methanol/0.1% aqueous trifluoroacetic acid to afford the title compound as a trifluoroacetic acid salt. $^1$H NMR (400 MHz, CD$_3$OD) δ ppm 1.95-2.25 (m, 2H), 2.23-2.48 (m, 2H), 3.12-3.27 (m, 4H), 3.40-3.65 (m, 3H), 3.78-3.85 (m, 5H), 3.96-4.13 (m, 1H), 6.42 (s, 1H), 7.19-7.33 (m, 3H), 7.50 (d, J=5.9 Hz, 1H), 8.31 (d, J=5.9 Hz, 1H). MS (ESI$^+$) m/z 400.1 (M+H)$^+$.

Example 150

6-[2-(1-methylpiperidin-4-yl)-1H-pyrrolo[2,3-b] pyridin-4-yl]-N-(2-phenylethyl)pyridin-2-amine The title compound was prepared using the procedure described in Example 89, using Example 138 (25 mg, 0.06 mmol) in place of Example 88C. $^1$H NMR (400 MHz, DMSO-d$_6$): δ 1.72-1.94 (m, 2H), 2.28 (d, J=13.56 Hz, 2H), 2.82 (d, J=4.75 Hz, 3H), 2.90-2.96 (m, 2H), 3.00-3.19 (m, 3H), 3.52 (d, J=11.87 Hz, 2H), 3.63 (t, J=7.46 Hz, 2H), 6.63 (d, J=8.14 Hz, 1H), 6.78 (s, 1H), 7.17-7.25 (m, 2H), 7.25-7.34 (m, 4H), 7.52 (d, J=5.09 Hz, 1H), 7.59 (t, J=7.80 Hz, 1H), 8.25 (d, J=5.09 Hz, 1H). LCMS: 412 (M+H)$^+$.

Example 151

1-[2-({6-[2-(1-methylpiperidin-4-yl)-1H-pyrrolo[2, 3-b]pyridin-4-yl]pyridin-2-yl}amino)ethyl]pyrrolidin-2-one The title compound was prepared using the procedure described in Example 89, using Example 143 (30 mg, 0.07 mmol) in place of Example 88C. $^1$H NMR (400 MHz, DMSO-d$_6$): δ 1.82-1.96 (m, 4H), 2.13-2.22 (m, 4H), 2.34 (d, J=13.73 Hz, 2H), 2.83 (d, J=3.66 Hz, 3H), 3.02-3.21 (m, 3H), 3.39-3.43 (m, 2H), 3.40-3.45 (m, 2H), 3.56 (t, J=5.95 Hz, 2H), 6.72 (d, J=7.93 Hz, 1H), 6.79 (s, 1H), 7.25 (d, J=7.32 Hz, 1H), 7.58 (d, J=5.19 Hz, 1H), 7.68 (t, J=7.63 Hz, 1H), 8.31 (d, J=5.19 Hz, 1H). LCMS: 419 (M+H)$^+$.

Example 152

5-chloro-N-(cyclopropylmethyl)-6-[2-(1-methylpiperidin-4-yl)-1H-pyrrolo[2,3-b]pyridin-4-yl]pyridin-2-amine The title compound was prepared using the procedure described in Example 11B, using Example 132 (20 mg, 0.06 mmol) in place of Example 11A and cyclopropanecarbaldehyde (10 mg, 0.09 mmol) in place of benzaldehyde. $^1$H NMR (400 MHz, DMSO-d$_6$): δ 0.12-0.25 (m, 2H), 0.37-0.47 (m, 2H), 0.98-1.10 (m, 1H), 1.73-1.88 (m, 2H), 2.30 (d, J=13.73 Hz, 2H), 2.81 (d, J=4.27 Hz, 3H), 2.96-3.20 (m, 3H), 3.09 (d, J=6.41 Hz, 2H), 3.53 (d, J=11.60 Hz, 2H), 6.11 (s, 1H), 6.62 (d, J=8.85 Hz, 1H), 7.17 (d, J=5.19 Hz, 1H), 7.57 (d, J=8.85 Hz, 1H), 8.23 (d, J=5.19 Hz, 1H). LCMS: 396 (M+H)$^+$.

Example 153

N-{4-[2-(dimethylamino)ethoxy]benzyl}-6-[2-(1-methylpiperidin-4-yl)-1H-pyrrolo[2,3-b]pyridin-4-yl]pyridin-2-amine A solution of Example 90B (20 mg, 0.065 mmol) and 2-(4-(aminomethyl)phenoxy)-N,N-dimethylethanamine (88 mg, 0.45 mmol) in dimethylsulfoxide (1 mL) was heated in a sealed tube at 110° C. overnight. The mixture was diluted with dichloromethane (20 mL) and the organic phase was washed with water, concentrated and purified by HPLC (Zorbax XDB C-18 (32) using a gradient of 5-40% acetonitrile/water (containing 0.1% trifluoroacetic acid) to afford the title compound. $^1$H NMR (400 MHz, DMSO-d$_6$): δ 1.71-1.95 (m, 2H), 2.20-2.38 (m, 2H), 2.83 (s, 3H), 2.85 (s, 6H), 2.96-3.24 (m, 3H), 3.43-3.57 (m, 2H), 4.22-4.35 (m, 4H), 4.58 (s, 2H), 6.69 (d, J=8.24 Hz, 1H), 6.74 (s, 1H), 6.96 (d, J=8.54 Hz, 2H), 7.24 (d, J=7.32 Hz, 1H), 7.35 (d, J=8.54 Hz, 2H), 7.54 (d, J=5.19 Hz, 1H), 7.61 (d, J=10.38 Hz, 1H), 8.27 (d, J=5.19 Hz, 1H). LCMS: 485 (M+H)$^+$.

Example 154

5-chloro-N-[(2,2-dimethyltetrahydro-2H-pyran-4-yl) methyl]-6-[2-(1-methylpiperidin-4-yl)-1H-pyrrolo[2, 3-b]pyridin-4-yl]pyridin-2-amine The title compound was prepared using the procedure described in Example 11B, using Example 132 (20 mg, 0.06 mmol) in place of Example 11A and 2,2-dimethyltetrahydro-2H-pyran-4-carbaldehyde (10 mg, 0.09 mmol) in place of benzaldehyde. $^1$H NMR (400 MHz, DMSO-d$_6$): δ 0.93-1.06 (m, 2H), 1.11 (s, 6H), 1.57 (dd, J=12.97, 2.90 Hz, 2H), 1.73-1.88 (m, 2H), 1.89-1.98 (m, 2H), 2.30 (d, J=13.73 Hz, 2H), 2.81 (d, J=4.27 Hz, 3H), 2.95-3.20 (m, 4H), 3.53 (d, J=12.21 Hz, 2H), 3.56-3.64 (m, 2H), 6.09 (s, 1H), 6.61 (d, J=8.85 Hz, 1H), 7.14 (d, J=4.88 Hz, 1H), 7.56 (d, J=8.85 Hz, 1H), 8.23 (d, J=4.88 Hz, 1H). LCMS: 468 (M+H)$^+$.

Example 155

5-chloro-6-[2-(1-methylpiperidin-4-yl)-1H-pyrrolo [2,3-b]pyridin-4-yl]-N-(pyridin-4-ylmethyl)pyridin-2-amine The title compound was prepared using the procedure described in Example 11B, using Example 132 (20 mg, 0.06 mmol) in place of Example 11A and isonicotinaldehyde (10 mg, 0.09 mmol) in place of benzaldehyde. $^1$H NMR (400 MHz, DMSO-d$_6$): δ 1.82-2.01 (m, 2H), 2.34 (d, J=13.43 Hz, 2H), 2.82 (s, 3H), 3.05-3.21 (m, 3H), 3.55 (t, J=12.82 Hz, 2H), 4.73 (d, J=7.02 Hz, 2H), 6.44 (s, 1H), 6.79 (d, J=8.85 Hz, 1H), 7.51 (d, J=5.19 Hz, 1H), 7.69 (d, J=8.85 Hz, 1H), 7.83 (d, J=6.41 Hz, 2H), 8.34 (d, J=5.19 Hz, 1H), 8.79 (d, J=6.10 Hz, 2H). LCMS: 433 (M+H)$^+$.

Example 156

6-[2-(1-methylpiperidin-4-yl)-1H-pyrrolo[2,3-b] pyridin-4-yl]-N-(1H-pyrazol-3-ylmethyl)pyridin-2-amine The title compound was prepared using the procedure described in Example 153, using (1H-pyrazol-3-yl)methanamine (44 mg, 0.45 mmol) in place of 2-(4-(aminomethyl) phenoxy)-N,N-dimethylethanamine. $^1$H NMR (400 MHz, DMSO-d$_6$): δ 1.81 (d, J=10.38 Hz, 2H), 2.29 (d, J=14.34 Hz, 2H), 2.82 (d, J=3.97 Hz, 3H), 2.98-3.18 (m, 3H), 3.55 (d, J=12.21 Hz, 2H), 4.62 (s, 2H), 6.21 (d, J=2.14 Hz, 1H), 6.34 (d, J=2.14 Hz, 1H), 6.71 (d, J=8.24 Hz, 1H), 7.21-7.25 (m, 1H), 7.52 (d, J=5.19 Hz, 1H), 7.59-7.62 (m, 1H), 7.76 (d, J=2.44 Hz, 1H), 8.25 (d, J=5.19 Hz, 1H). LCMS: 388 (M+H)$^+$.

Example 157

N-(2,3-dihydro-1H-isoindol-5-ylmethyl)-6-[2-(1-methylpiperidin-4-yl)-1H-pyrrolo[2,3-b]pyridin-4-yl]pyridin-2-amine The title compound was prepared using the procedure described in Example 88C, using Example 90B (20 mg, 0.06 mmol) in place of Example 88B and using tert-butyl 5-(aminomethyl)isoindoline-2-carboxylate (112 mg, 0.45 mmol) in place of (tetrahydro-2H-pyran-4-yl)methanamine. $^1$H NMR (400 MHz, DMSO-d$_6$): δ 1.72-1.94 (m, 2H), 2.18-2.35 (m, 2H), 2.83 (d, J=4.41 Hz, 3H), 2.93-3.16 (m, 3H), 3.54 (d, J=12.21 Hz, 2H), 4.47 (t, J=4.92 Hz, 4H), 4.65 (s, 2H), 6.59 (d, J=8.14 Hz, 1H), 6.68 (d, J=1.36 Hz, 1H), 7.20 (d, J=7.12 Hz, 1H), 7.31-7.41 (m, 3H), 7.47 (d, J=5.09 Hz, 1H), 7.52-7.59 (m, 1H), 8.20 (d, J=5.09 Hz, 1H). LCMS: 439 (M+H)$^+$.

Example 158

6-[2-(1-methylpiperidin-4-yl)-1H-pyrrolo[2,3-b] pyridin-4-yl]-N-[(1-methylpyrrolidin-3-yl)methyl] pyridin-2-amine The title compound was prepared using the procedure described in Example 153, using (1-methylpyrrolidin-3-yl) methanamine (51 mg, 0.45 mmol) in place of 2-(4-(aminomethyl)phenoxy)-N,N-dimethylethanamine. $^1$H NMR (400 MHz, DMSO-d$_6$): δ 1.80-1.95 (m, 2H), 2.03-2.20 (m, 1H), 2.35 (d, J=12.21 Hz, 2H), 2.54 (s, 3H) 2.83 (d, J=4.07 Hz, 3H), 2.85-2.95 (m, 3H), 2.98-3.22 (m, 4H), 3.32-3.46 (m, 2H), 3.52-3.58 (m, 2H), 3.93-4.05 (m, 2H), 6.60 (d, J=3.05 Hz, 1H), 6.63 (d, J=5.09 Hz, 1H), 7.27 (d, J=6.10 Hz, 1H), 7.54 (d, J=5.09 Hz, 1H), 7.59-7.65 (m, 1H), 8.24 (d, J=4.75 Hz, 1H). LCMS: 405 (M+H)$^+$.

Example 159

N-(1H-indol-6-ylmethyl)-6-[2-(1-methylpiperidin-4-yl)-1H-pyrrolo[2,3-b]pyridin-4-yl]pyridin-2-amine The title compound was prepared using the procedure described in Example 153, using (1H-indol-6-yl)methanamine (65 mg, 0.45 mmol) in place of 2-(4-(aminomethyl) phenoxy)-N,N-dimethylethanamine. $^1$H NMR (400 MHz, DMSO-d$_6$): δ 1.69-1.83 (m, 2H), 2.11-2.25 (m, 2H), 2.80 (d, J=4.75 Hz, 3H), 2.87-3.17 (m, 3H), 3.47 (d, J=12.21 Hz, 2H), 4.70 (s, 2H), 6.38 (t, J=2.03 Hz, 1H), 6.68-6.72 (m, 2H), 7.13 (dd, J=8.31, 1.53 Hz, 1H), 7.20 (d, J=7.12 Hz, 1H), 7.30-7.33 (m, 1H), 7.36 (d, J=8.48 Hz, 1H), 7.48-7.52 (m, 1H), 7.55 (s, 1H), 7.59 (d, J=7.46 Hz, 1H), 8.23 (d, J=5.09 Hz, 1H). LCMS: 437 (M+H)$^+$.

Example 160

5-chloro-6-[2-(1-methylpiperidin-4-yl)-1H-pyrrolo [2,3-b]pyridin-4-yl]-N-[4-(methylsulfonyl)benzyl] pyridin-2-amine The title compound was prepared using the procedure described in Example 11B, using Example 132 (20 mg, 0.06 mmol) in place of Example 11A and 4-(methylsulfonyl)benzaldehyde (17 mg, 0.09 mmol) in place of benzaldehyde. $^1$H NMR (400 MHz, DMSO-d$_6$): δ 1.64-1.82 (m, 2H), 2.18 (d, J=13.90 Hz, 2H), 2.80 (d, J=4.75 Hz, 3H), 2.84-2.97 (m, 1H), 3.09 (d, J=12.55 Hz, 2H), 3.19 (s, 3H), 3.51 (d, J=11.87 Hz, 2H), 4.59 (d, J=4.07 Hz, 2H), 5.91 (d, J=1.36 Hz, 1H), 6.68 (d, J=8.82 Hz, 1H), 7.08 (d, J=4.75 Hz, 1H), 7.55 (d, J=8.48 Hz, 2H), 7.63 (d, J=8.82 Hz, 1H), 7.88 (d, J=8.48 Hz, 2H), 8.19 (d, J=4.75 Hz, 1H). LCMS: 510 (M+H)$^+$.

Example 161

4-[({5-chloro-6-[2-(1-methylpiperidin-4-yl)-1H-pyrrolo[2,3-b]pyridin-4-yl]pyridin-2-yl}amino)methyl]benzenesulfonamide The title compound was prepared using the procedure described in Example 11B, using Example 132 (20 mg, 0.06 mmol) in place of Example 11A and 4-formylbenzenesulfonamide (16 mg, 0.09 mmol) in place of benzaldehyde. $^1$H NMR (400 MHz, DMSO-d$_6$): δ 1.62-1.83 (m, 2H), 2.17 (d, J=12.21 Hz, 2H), 2.80 (d, J=4.75 Hz, 3H), 2.84-2.99 (m, 1H), 3.09 (d, J=12.21 Hz, 2H), 3.51 (d, J=11.19 Hz, 2H), 4.56 (s, 2H), 5.92 (d, J=1.36 Hz, 1H), 6.67 (d, J=8.82 Hz, 1H), 7.10 (d, J=5.09 Hz, 1H), 7.47 (d, J=8.48 Hz, 2H), 7.63 (d, J=8.82 Hz, 1H), 7.77 (d, J=8.48 Hz, 2H), 8.19 (d, J=4.75 Hz, 1H). LCMS: 511 (M+H)$^+$.

Example 162

4-[({5-chloro-6-[2-(1-methylpiperidin-4-yl)-1H-pyrrolo[2,3-b]pyridin-4-yl]pyridin-2-yl}amino)methyl]benzamide The title compound was prepared using the procedure described in Example 11B, using Example 132 (20 mg, 0.06 mmol) in place of Example 11A and 4-formylbenzamide (13 mg, 0.09 mmol) in place of benzaldehyde. $^1$H NMR (400 MHz, DMSO-d$_6$): δ 1.58-1.80 (m, 2H), 2.12 (d, J=14.58 Hz, 2H), 2.81 (d, J=4.75 Hz, 3H), 2.96-3.16 (m, 3H), 3.50 (d, J=11.53 Hz, 2H), 4.52 (s, 2H), 5.80 (d, J=1.70 Hz, 1H), 6.68 (d, J=8.82 Hz, 1H), 7.11 (d, J=5.09 Hz, 1H), 7.35 (d, J=8.48 Hz, 2H), 7.62 (d, J=8.82 Hz, 1H), 7.83 (d, J=8.48 Hz, 2H), 8.19 (d, J=5.09 Hz, 1H). LCMS: 475 (M+H)$^+$.

Example 163

6-[2-(1-methylpiperidin-4-yl)-1H-pyrrolo[2,3-b]pyridin-4-yl]-N-[2-(morpholin-4-yl)ethyl]pyridin-2-amine The title compound was prepared using the procedure described in Example 153, using 2-morpholinoethanamine (59 mg, 0.45 mmol) in place of 2-(4-(aminomethyl)phenoxy)-N,N-dimethylethanamine. $^1$H NMR (400 MHz, DMSO-d$_6$): δ 1.69-1.99 (m, 2H), 2.20-2.40 (m, 2H), 2.83 (s, 3H), 2.96-3.07 (m, 1H), 3.14 (d, J=16.62 Hz, 4H), 3.32-3.68 (m, 6H), 3.68-3.87 (m, 2H), 3.89-4.07 (m, 2H), 6.59 (s, 1H), 6.80 (d, J=8.82 Hz, 1H), 7.17-7.35 (m, 1H), 7.51 (d, J=5.09 Hz, 1H), 7.67-7.82 (m, 1H), 8.25 (d, J=5.09 Hz, 1H). LCMS: 421 (M+H)$^+$.

Example 164

2-({6-[2-(1-methylpiperidin-4-yl)-1H-pyrrolo[2,3-b]pyridin-4-yl]pyridin-2-yl}amino)ethanol The title compound was prepared using the procedure described in Example 153, using 2-aminoethanol (28 mg, 0.45 mmol) in place of 2-(4-(aminomethyl)phenoxy)-N,N-dimethylethanamine. $^1$H NMR (400 MHz, DMSO-d$_6$): δ 1.77-1.97 (m, 2H), 2.35 (d, J=14.34 Hz, 2H), 2.83 (d, J=4.88 Hz, 3H), 3.01-3.17 (m, 3H), 3.47-3.52 (m, 2H), 3.52-3.59 (m, 2H), 3.62-3.66 (m, 2H), 6.75 (s, 1H), 6.76-6.81 (m, 1H), 7.21 (d, J=7.32 Hz, 1H), 7.50 (t, J=4.43 Hz, 1H), 7.64-7.82 (m, 1H), 8.28 (d, J=5.19 Hz, 1H). LCMS: 352 (M+H)$^+$.

Example 165

5-chloro-6-[2-(1-methylpiperidin-4-yl)-1H-pyrrolo[2,3-b]pyridin-4-yl]-N-(piperidin-4-ylmethyl)pyridin-2-amine A solution of Example 132 (30 mg, 0.09 mmol) in 1,2-dichloroethane (1 mL) and acetic acid (0.5 mL) was treated with tert-butyl 4-formylpiperidine-1-carboxylate (28.1 mg, 0.13 mmol) and stirred at room temperature for 2 hours. Sodium triacetoxyborohydride (28 mg, 0.13 mmol) was added and the mixture was stirred at room temperature for 12 hours. The mixture was diluted with dichloromethane (20 mL), treated with saturated sodium bicarbonate solution and the organic layer was concentrated. The residue was dissolved in dichloromethane (5 mL), trifluoroacetic acid (0.5 mL) was added and the mixture stirred at room temperature for 1 hour. Concentration and purification by HPLC (Zorbax XDB C-18 (32) using a gradient of 5-40% acetonitrile/water (containing 0.1% trifluoroacetic acid) afforded the title compound. $^1$H NMR (400 MHz, DMSO-d$_6$): δ 1.20-1.34 (m, 4H), 1.75-1.83 (m, 4H), 2.29 (d, J=13.73 Hz, 2H), 2.81 (d, J=4.27 Hz, 3H), 2.84-2.94 (m, 1H), 2.98-3.06 (m, 1H), 3.11 (d, J=12.51 Hz, 2H), 3.14-3.20 (m, 2H), 3.27 (d, J=6.10 Hz, 2H), 3.54 (d, J=11.90 Hz, 2H), 6.08 (s, 1H), 6.62 (d, J=8.85 Hz, 1H), 7.15 (d, J=4.88 Hz, 1H), 7.58 (d, J=8.85 Hz, 1H), 8.24 (d, J=5.19 Hz, 1H). LCMS: 439 (M+H)$^+$.

Example 166

4-[4-(5-fluoro-2-methoxyphenyl)-1H-pyrrolo[2,3-b]pyridin-2-yl]tetrahydro-2H-pyran-4-ol Example 166A 4-(4-(5-fluoro-2-methoxyphenyl)-1-tosyl-1H-pyrrolo[2,3-b]pyridin-2-yl)tetrahydro-2H-pyran-4-ol To a solution of Example 87A (200 mg, 0.504 mmol) in tetrahydrofuran (5 mL) at −78° C. was added 1.6M n-butyllithium in hexanes (0.473 mL, 0.757 mmol) under nitrogen. The mixture was stirred for 5 minutes and dihydro-2H-pyran-4(3H)-one (101 mg, 1.009 mmol) was added. Stirring was continued at −78° C. for 1 hour and the mixture was warmed to room temperature overnight. The mixture was quenched with water, extracted with ethyl acetate, dried over magnesium sulfate, filtered and purified by flash chromatography (silica gel, 20-100% ethyl acetate/heptanes to afford the title compound. MS (ESI$^+$) m/z 497.0 (M+H)$^+$.

Example 166B

4-[4-(5-fluoro-2-methoxyphenyl)-1H-pyrrolo[2,3-b]pyridin-2-yl]tetrahydro-2H-pyran-4-ol The title compound was prepared as the trifluoroacetate salt using the procedure described in Example 126C, using Example 166A in place of Example 126B. $^1$H NMR (300 MHz, DMSO-d$_6$) δ 1.71-1.78 (m, 2H), 1.84-2.43 (m, 2H), 3.62-3.71 (m, 2H), 3.74 (s, 3H), 3.76-3.83 (m, 2H), 3.84 (bs, 1H), 6.15 (d, J=2.1 Hz, 1H), 7.08 (d, J=5.0 Hz, 1H), 7.15-7.33 (m, 3H), 8.16-8.22 (m, 1H), 11.69 (bs, 1H). MS (ESI$^+$) m/z 497.0 (M+H)$^+$.

Example 167

4-(5-fluoro-2-methoxyphenyl)-2-[1-(pyridin-4-ylmethyl)azetidin-3-yl]-1H-pyrrolo[2,3-b]pyridine The title compound was prepared as the trifluoroacetate salt using the procedure described in Example 110, using Example 146D (0.11 g, 0.209 mmol) in place of Example 59F and isonicotinaldehyde (55 mg, 0.513 mmol) in place of tetrahydro-4H-pyran-4-one. $^1$H NMR (500 MHz, DMSO-d$_6$) δ 3.73 (s, 3H) 4.23-4.46 (m, 5H) 4.59 (s, 2H) 6.44 (s, 1H) 7.12

(d, J=4.88 Hz, 1H) 7.19-7.25 (m, 2H) 7.27-7.33 (m, 1H) 7.59 (d, J=5.80 Hz, 2H) 8.25 (d, J=4.88 Hz, 1H) 8.74 (d, J=5.80 Hz, 2H) 11.94 (br. s, 1H). MS (ESI$^+$) m/z 389.0 (M+H)$^+$.

Example 168

1-{3-[4-(5-fluoro-2-methoxyphenyl)-1H-pyrrolo[2,3-b]pyridin-2-yl]azetidin-1-yl}ethanone The title compound was prepared as the trifluoroacetate salt using the procedure described in Example 108, using Example 146D (0.05 g, 0.095 mmol) in place of Example 59F. $^1$H NMR (500 MHz, DMSO-d$_6$) δ 1.79 (s, 3H) 3.74 (s, 3H) 3.92-4.05 (m, 2H) 4.16-4.31 (m, 2H) 4.46 (t, J=8.54 Hz, 1H) 6.29 (d, J=1.53 Hz, 1H) 7.13 (d, J=4.88 Hz, 1H) 7.18-7.25 (m, 2H) 7.26-7.32 (m, 1H) 8.23 (d, J=4.88 Hz, 1H) 12.02 (br. s, 1H)). MS (ESI$^+$) m/z 340.0 (M+H)$^+$.

Example 169

2-{3-[4-(5-fluoro-2-methoxyphenyl)-1H-pyrrolo[2,3-b]pyridin-2-yl]azetidin-1-yl}ethanamine Example 169A tert-butyl (2-(3-(4-(5-fluoro-2-methoxyphenyl)-1H-pyrrolo[2,3-b]pyridin-2-yl)azetidin-1-yl)ethyl)carbamate The title compound was prepared using the procedure described in Example 110, using tert-butyl (2-oxoethyl) carbamate (50 mg, 0.314 mmol) in place of tetrahydro-4H-pyran-4-one and Example 146D (110 mg, 0.209 mmol) in place of Example 59F. MS (APCl$^+$) m/z 440.5 (M+H)$^+$.

Example 169B

2-{3-[4-(5-fluoro-2-methoxyphenyl)-1H-pyrrolo[2,3-b]pyridin-2-yl]azetidin-1-yl}ethanamine The title compound was prepared as the trifluoroacetate salt using the procedure described in Example 109B, using Example 169A (92 mg, 0.209 mmol) in place of Example 109A. $^1$H NMR (400 MHz, DMSO-d$_6$) δ 3.03-3.12 (m, 2H) 3.46-3.55 (m, 2H) 3.74 (s, 3H) 4.17-4.60 (m, 5H) 6.41 (s, 1H) 7.12 (d, J=4.88 Hz, 1H) 7.18-7.25 (m, 2H) 7.26-7.34 (m, 1H) 8.14 (s, 2H) 8.25 (d, J=4.88 Hz, 1H) 11.94 (s, 1H). MS (ESI$^+$) m/z 341.1 (M+H)$^+$.

Example 170

4-(5-fluoro-2-methoxyphenyl)-2-[1-(tetrahydro-2H-pyran-4-ylmethyl)azetidin-3-yl]-1H-pyrrolo[2,3-b]pyridine The title compound was prepared as the trifluoroacetate salt using the procedure described in Example 110, using tetrahydro-2H-pyran-4-carbaldehyde (58 mg, 0.508 mmol) in place of tetrahydro-4H-pyran-4-one and Example 146D (110 mg, 0.209 mmol) in place of Example 59F. $^1$H NMR (500 MHz, DMSO-d$_6$) δ 1.15-1.28 (m, 2H) 1.53-1.63 (m, 2H) 1.80-1.91 (m, 1H) 3.15-3.32 (m, 4H) 3.73 (s, 3H) 4.18-4.31 (m, 2H) 4.39-4.53 (m, 2H) 6.38-6.47 (m, 1H) 7.10 (d, J=5.19 Hz, 1H) 7.18-7.24 (m, 2H) 7.26-7.32 (m, 1H) 8.24 (d, J=4.88 Hz, 1H) 9.62-10.28 (m, 1H) 11.88-11.98 (m, 1H). MS (ESI$^+$) m/z 396.0 (M+H)$^+$.

Example 171

4-(5-fluoro-2-methoxyphenyl)-2-{1-[2-(morpholin-4-yl)ethyl]azetidin-3-yl}-1H-pyrrolo[2,3-b]pyridine The title compound was prepared as the trifluoroacetate salt using the procedure described in Example 110, using tetrahydro-2-morpholinoacetaldehyde hydrochloride hydrate (50 mg, 0.387 mmol) in place of tetrahydro-4H-pyran-4-one and Example 146D (50 mg, 0.095 mmol) in place of Example 59F. $^1$H NMR (500 MHz, DMSO-d$_6$) δ 3.00-3.27 (m, 4H) 3.29-3.42 (m, 1H) 3.59-3.68 (m, 2H) 3.74 (s, 3H) 3.76-3.83 (m, 2H) 4.19-4.56 (m, 6H) 6.36-6.51 (m, 1H) 7.10-7.15 (m, 1H) 7.18-7.26 (m, 2H) 7.26-7.34 (m, 1H) 8.26 (d, J=4.88 Hz, 1H) 11.83-12.07 (m, 1H). MS (ESI$^+$) m/z 411.0 (M+H)$^+$.

Example 172

2-{3-[4-(5-fluoro-2-methoxyphenyl)-1H-pyrrolo[2,3-b]pyridin-2-yl]azetidin-1-yl}ethanol Example 172A 2-(1-(2-((tert-butyldimethylsilyl)oxy)ethyl)azetidin-3-yl)-4-(5-fluoro-2-methoxyphenyl)-1H-pyrrolo[2,3-b]pyridine The title compound was prepared as the trifluoroacetate salt using the procedure described in Example 109A, using Example 146D (50 mg, 0.095 mmol) in place of the product of Example 59F. MS (APCl$^+$) m/z 456.5 (M+H)$^+$.

Example 172B

2-{3-[4-(5-fluoro-2-methoxyphenyl)-1H-pyrrolo[2,3-b]pyridin-2-yl]azetidin-1-yl}ethanol The title compound was prepared as the trifluoroacetate salt using the procedure described in Example 109B, using Example 172A (40 mg, 0.088 mmol) in place of Example 109A. $^1$H NMR (500 MHz, DMSO-d$_6$) δ 3.27-3.41 (m, 2H) 3.60-3.64 (m, 2H) 3.73 (s, 3H) 4.16-4.52 (m, 6H) 6.34-6.48 (m, 1H) 7.07-7.13 (m, 1H) 7.17-7.25 (m, 2H) 7.25-7.33 (m, 1H) 8.23 (d, J=4.88 Hz, 1H) 11.73-11.96 (m, 1H). MS (ESI) m/z 342.0 (M+H)$^+$.

Example 173 tert-butyl 3-[({5-chloro-6-[2-(1-methylpiperidin-4-yl)-1H-pyrrolo[2,3-b]pyridin-4-yl]pyridin-2-yl}amino)methyl]pyrrolidine-1-carboxylate The title compound was prepared using the procedure described in Example 11B, using Example 132 (20 mg, 0.06 mmol) in place of Example 11A and tert-butyl 3-formylpyrrolidine-1-carboxylate (18 mg, 0.09 mmol) in place of benzaldehyde. $^1$H NMR (400 MHz, DMSO-d$_6$): δ 1.35 (s, 9H), 1.50-1.68 (m, 2H), 1.80 (d, J=12.21 Hz, 2H), 1.93-2.09 (m, 1H), 2.28 (d, J=13.12 Hz, 2H), 2.80 (d, J=3.36 Hz, 3H), 2.89-3.04 (m, 1H), 3.10 (d, J=11.60 Hz, 2H), 3.19-3.29 (m, 2H), 3.26-3.40 (m, 2H), 3.52 (d, J=11.90 Hz, 2H), 3.78-3.98 (m, 2H), 6.09 (s, 1H), 6.61 (d, J=9.16 Hz, 1H), 7.13-7.16 (m, 1H), 7.57 (d, J=9.16 Hz, 1H), 8.23 (d, J=4.88 Hz, 1H). LCMS: 525 (M+H)$^+$.

Example 174

5-chloro-N-[(1,1-dioxidotetrahydro-2H-thiopyran-4-yl)methyl]-6-[2-(1-methylpiperidin-4-yl)-1H-pyrrolo[2,3-b]pyridin-4-yl]pyridin-2-amine The title compound was prepared using the procedure described in Example 11B, using Example 132 (20 mg, 0.06 mmol) in place of Example 11A and tetrahydro-2H-thiopyran-4-carbaldehyde 1,1-dioxide (15 mg, 0.09 mmol) in place of benzaldehyde. $^1$H NMR (400 MHz, DMSO-d$_6$): δ 1.60 (d, J=11.90 Hz, 2H), 1.72-1.90 (m, 2H), 2.02 (d, J=13.12 Hz, 2H), 2.28 (d, J=13.12 Hz, 2H), 2.80 (s, 3H), 2.94-3.15 (m, 6H), 3.15-3.25 (m, 2H), 3.52 (d, J=11.60 Hz, 2H), 3.83-3.98 (m, 2H), 6.11 (s, 1H), 6.61 (d, J=8.85 Hz, 1H), 7.17 (d, J=4.88 Hz, 1H), 7.57 (d, J=8.85 Hz, 1H), 8.23 (d, J=4.88 Hz, 1H). LCMS: 488 (M+H)$^+$.

Example 175

{3-[({5-chloro-6-[2-(1-methylpiperidin-4-yl)-1H-pyrrolo[2,3-b]pyridin-4-yl]pyridin-2-yl}amino)methyl]phenoxy}acetic acid The title compound was prepared using the procedure described in Example 11B, using Example 132 (20 mg, 0.06 mmol) in place of Example 11A and 2-(3-formylphenoxy)acetic acid (16 mg, 0.09 mmol) in place of benzaldehyde. $^1$H NMR (400 MHz, DMSO-d$_6$): δ 1.65-1.85 (m, 2H), 2.20 (d, J=10.99 Hz, 2H), 2.79 (s, 3H), 2.89-2.97 (m, 1H), 3.00-3.17 (m, 2H), 3.51 (d, J=11.90 Hz, 2H), 4.38 (s, 2H), 4.63 (s, 2H), 5.99 (s, 1H), 6.58-6.64 (m, 1H), 6.85 (d, J=8.54 Hz, 2H), 7.09 (d, J=8.54 Hz, 1H), 7.12-7.19 (m, 1H), 7.21 (d, J=8.54 Hz, 1H), 7.54-7.63 (m, 1H), 8.21 (d, J=5.19 Hz, 1H). LCMS: 506 (M+H)$^+$.

Example 176

{4-[({5-chloro-6-[2-(1-methylpiperidin-4-yl)-1H-pyrrolo[2,3-b]pyridin-4-yl]pyridin-2-yl}amino)methyl]phenoxy}acetic acid The title compound was prepared using the procedure described in Example 11B, using Example 132 (20 mg, 0.06 mmol) in place of Example 11A and 2-(4-formylphenoxy)acetic acid (16 mg, 0.09 mmol) in place of benzaldehyde. $^1$H NMR (400 MHz, DMSO-d$_6$): δ 1.63-1.83 (m, 2H), 2.20 (d, J=13.43 Hz, 2H), 2.80 (s, 3H), 2.94 (t, J=12.21 Hz, 1H), 3.02-3.17 (m, 2H), 3.50 (d, J=12.21 Hz, 2H), 4.38 (s, 2H), 4.63 (s, 2H), 5.99 (s, 1H), 6.63 (d, J=8.85 Hz, 1H), 6.85 (d, J=8.54 Hz, 2H), 7.15 (d, J=5.19 Hz, 1H), 7.18-7.27 (d, J=8.54 Hz, 2H), 7.58 (d, J=8.85 Hz, 1H), 8.21 (d, J=4.88 Hz, 1H). LCMS: 506 (M+H)$^+$.

Example 177

1-{4-[({5-chloro-6-[2-(1-methylpiperidin-4-yl)-1H-pyrrolo[2,3-b]pyridin-4-yl]pyridin-2-yl}amino)methyl]piperidin-1-yl}ethanone To a solution of Example 165 (20 mg, 0.05 mmol) in N,N-dimethylformamide (1 mL) was added acetic acid (4 mg, 0.07 mmol) and triethylamine (0.1 mL) at room temperature. 1-Ethyl-3-(3-dimethylaminopropyl)carbodiimide hydrochloride (11 mg, 0.07 mmol) and N-hydroxybenzotriazole (10 mg, 0.07 mmol) were added and the mixture was stirred overnight. Purification by HPLC (Zorbax XDB C-18 (32) using a gradient of 5-40% acetonitrile/water (containing 0.1% trifluoroacetic acid) afforded the title compound. $^1$H NMR (400 MHz, DMSO-d$_6$): δ 1.57-1.93 (m, 5H), 1.96 (s, 3H), 2.28 (d, J=13.73 Hz, 2H), 2.80 (d, J=3.97 Hz, 3H), 2.87-3.01 (m, 2H), 3.02-3.22 (m, 5H), 3.52 (d, J=11.60 Hz, 2H), 3.77 (d, J=13.12 Hz, 2H), 4.34 (d, J=12.82 Hz, 2H), 6.10 (s, 1H), 6.61 (d, J=9.16 Hz, 1H), 7.11-7.18 (m, 1H), 7.56 (d, J=9.16 Hz, 1H), 8.23 (d, J=5.19 Hz, 1H). LCMS: 481 (M+H)$^+$.

Example 178

5-chloro-6-[2-(1-methylpiperidin-4-yl)-1H-pyrrolo[2,3-b]pyridin-4-yl]-N-(4H-1,2,4-triazol-3-ylmethyl)pyridin-2-amine The title compound was prepared using the procedure described in Example 11B, using Example 132 (20 mg, 0.06 mmol) in place of Example 11A and 4H-1,2,4-triazole-3-carbaldehyde (9 mg, 0.09 mmol) in place of benzaldehyde. $^1$H NMR (400 MHz, DMSO-d$_6$): δ 1.66-1.90 (m, 2H), 2.26 (d, J=13.73 Hz, 2H), 2.82 (s, 3H), 2.90-3.03 (m, 1H), 3.04-3.15 (m, 2H), 3.54 (d, J=12.21 Hz, 2H), 4.55-4.63 (m, 2H), 6.04 (s, 1H), 6.74 (d, J=8.85 Hz, 1H), 7.14-7.18 (m, 1H), 7.66 (d, J=8.85 Hz, 1H), 8.24 (d, J=4.88 Hz, 1H), 8.38 (s, 1H). LCMS: 423 (M+H)$^+$.

Example 179

4-fluoro-3-[2-(1-methylpiperidin-4-yl)-1H-pyrrolo[2,3-b]pyridin-4-yl]-N-(tetrahydro-2H-pyran-4-ylmethyl)aniline

Example 179A tert-butyl 3-bromo-4-fluorophenylcarbamate

A solution of 6-bromo-5-fluoropyridin-2-amine (5 g, 26 mmol) in dichloromethane (150 mL) was treated with di-tert-butyl dicarbonate (6 mL, 26 mmol), triethylamine (5.3 mL, 52 mmol) and 4-dimethylaminopyridine (0.8 g, 6.6 mmol) and the mixture was stirred at room temperature overnight. The mixture was concentrated and purified by flash column (silica) using 30% ethyl acetate in hexane to afford the title compound. LCMS: 290 (M+H)$^+$.

Example 179B tert-butyl 4-fluoro-3-(4,4,5,5-tetramethyl-1,3,2-dioxaborolan-2-yl)phenylcarbamate The title compound was prepared using the procedure described in Example 88A, using Example 179A (3 g, 10.3 mmol) in place of 2-bromo-6-fluoropyridine. LCMS: 338 (M+H)$^+$.

Example 179C tert-butyl 4-fluoro-3-(2-(1-methylpiperidin-4-yl)-1H-pyrrolo[2,3-b]pyridin-4-yl)phenylcarbamate The title compound was prepared using the procedure described in Example 1G, using Example 132A (200 mg, 0.8 mmol) in place of Example 1F and Example 179B (405 mg, 1.2 mmol) in place of 5-fluoro-2-methoxyphenylboronic acid. LCMS: 425 (M+H)$^+$.

Example 179D 4-fluoro-3-(2-(1-methylpiperidin-4-yl)-1H-pyrrolo[2,3-b]pyridin-4-yl)aniline To a solution of Example 179C (102 mg, 0.24 mmol) in dichloromethane (2 mL) was added trifluoroacetic acid (1 mL) and the mixture was stirred for 2 hours. Concentration and purification by HPLC (Zorbax XDB C-18 (32) using a gradient of 5-40% acetonitrile/water (containing 0.1% trifluoroacetic acid) afforded the title compound. LCMS: 325 (M+H)$^+$.

Example 179E 4-fluoro-3-(2-(1-methylpiperidin-4-yl)-1H-pyrrolo[2,3-b]pyridin-4-yl)-N-((tetrahydro-2H-pyran-4-yl)methyl)aniline The title compound was prepared using the procedure described in Example 11B, using Example 179D (20 mg, 0.06 mmol) in place of Example 11A and tetrahydro-2H-pyran-4-carbaldehyde (10 mg, 0.09 mmol) in place of benzaldehyde. $^1$H NMR (400 MHz, DMSO-d$_6$): δ 1.13-1.32 (m, 4H), 1.53 (d, J=11.60 Hz, 2H), 1.70-1.86 (m, 1H), 1.93 (dd, J=7.17, 3.51 Hz, 2H), 2.29 (d, J=13.73 Hz, 2H), 2.82 (d, J=4.27 Hz, 3H), 2.94-3.06 (m, 1H), 3.06-3.14 (m, 2H), 3.18-3.25 (m, 2H), 3.54 (d, J=11.60 Hz, 2H), 3.84 (dd, J=10.99, 2.75 Hz, 2H), 6.13 (s, 1H), 6.75-6.85 (m, 1H), 7.00-7.29 (m, 3H), 8.25 (d, J=4.88 Hz, 1H). LCMS: 423 (M+H)$^+$.

Example 180

1-{4-[4-(5-fluoro-2-methoxyphenyl)-1H-pyrrolo[2,3-b]pyridin-2-yl]piperidin-1-yl}-2-(piperidin-1-yl)ethanone The title compound was prepared as described in Example 147B, using piperidine (0.299 mmol, 25.4 mg) in place of piperidin-4-ol. $^1$H NMR (400 MHz, CD$_3$OD) δ 1.47-1.63 (m, 1H), 1.61-2.02 (m, 7H), 2.14-2.23 (m, 2H), 2.83-3.11 (m, 3H), 3.15-3.27 (m, 1H), 3.30-3.33 (m, 1H), 3.53-3.62 (m, 2H), 3.79-3.86 (m, 4H), 4.16-4.29 (m, 2H), 4.59-4.68 (m, 1H), 6.39 (s, 1H), 7.19-7.32 (m, 3H), 7.52 (d, J=6.0 Hz, 1H), 8.29 (d, J=6.0 Hz, 1H). MS (ESI$^+$) m/z 451.2 (M+H)$^+$.

Example 181

1-{4-[4-(5-fluoro-2-methoxyphenyl)-1H-pyrrolo[2,3-b]pyridin-2-yl]piperidin-1-yl}-2-(morpholin-4-yl)ethanone The title compound was prepared as described in Example 147B, using morpholine (0.299 mmol, 26.0 mg) in place of piperidin-4-ol. $^1$H NMR (400 MHz, CD$_3$OD) δ 1.63-1.90 (m, 2H), 2.13-2.25 (m, 2H), 2.92 (td, J=13.0, 2.9 Hz, 1H), 3.13-3.26 (m, 2H), 3.26-3.36 (m, 2H), 3.37-3.78 (m, 2H), 3.80 (s, 3H), 3.83-3.41 (m, 5H), 4.27-4.41 (m, 2H), 4.60-4.68 (m, 1H), 6.38 (s, 1H), 7.19-7.32 (m, 3H), 7.49 (d, J=6.0 Hz, 1H), 8.28 (d, J=6.0 Hz, 1H). MS (ESI$^+$) m/z 453.2 (M+H)$^+$.

Example 182

1-{4-[4-(5-fluoro-2-methoxyphenyl)-1H-pyrrolo[2,3-b]pyridin-2-yl]piperidin-1-yl}-2-[(4-hydroxycyclohexyl)amino]ethanone The title compound was prepared as described in Example 147B, using 4-aminocyclohexanol (3 eq., 0.597 mmol, 68.8 mg) in place of piperidin-4-ol. Heating overnight was also required. $^1$H NMR (400 MHz, CD$_3$OD) δ 1.26-1.41 (m, 2H), 1.42-1.89 (m, 4H), 1.97-2.11 (m, 2H), 2.09-2.31 (m, 4H), 2.87-2.98 (m, 1H), 3.04-3.24 (m, 2H), 3.25-3.35 (m, 1H), 3.50-3.64 (m, 1H), 3.80 (s, 3H), 3.84-4.00 (m, 1H), 4.05-4.21 (m, 2H), 4.58-4.66 (m, 1H), 6.35 (s, 1H), 7.18-7.31 (m, 3H), 7.47 (d, J=5.9 Hz, 1H), 8.27 (d, J=5.9 Hz, 1H). MS (ESI$^+$) m/z 481.1 (M+H)$^+$.

Example 183

1-{4-[4-(5-fluoro-2-methoxyphenyl)-1H-pyrrolo[2,3-b]pyridin-2-yl]piperidin-1-yl}-2-[(2-hydroxyethyl)amino]ethanone A mixture of Example 147A (80 mg, 0.199 mmol) and 2-aminoethanol (0.096 mL, 1.593 mmol) in tetrahydrofuran (2 mL) was heated at 70° C. for 4 hours. The mixture was quenched with water and brine and was extracted with ethyl acetate (twice). The combined organic layers were washed with brine, dried over magnesium sulfate, filtered, concentrated and purified by reverse-phase HPLC on a Zorbax RX-C18 column using a gradient of 15% to 100% methanol/0.1% aqueous trifluoroacetic acid to afford the title compound as a trifluoroacetic acid salt. $^1$H NMR (400 MHz, CD$_3$OD) δ 1.63-1.89 (m, 2H), 2.13-2.24 (m, 2H), 2.93 (td, J=13.0, 2.8 Hz, 1H), 3.16-3.22 (m, 3H), 3.25-3.36 (m, 1H), 3.80 (s, 3H), 3.82-3.90 (m, 3H), 4.07-4.21 (m, 2H), 4.58-4.67 (m, 1H), 6.37 (s, 1H), 7.18-7.32 (m, 3H), 7.49 (d, J=6.0 Hz, 1H), 8.28 (d, J=6.0 Hz, 1H). MS (ESI$^+$) m/z 427.1 (M+H)$^+$.

Example 184

4-(5-fluoro-2-methoxyphenyl)-2-(1-methylazetidin-3-yl)-1H-pyrrolo[2,3-b]pyridine The title compound was prepared as the trifluoroacetate salt using the procedure described in Example 110, using formaldehyde (37% in water) (200 mg, 2.465 mmol) in place of tetrahydro-4H-pyran-4-one and Example 146D (110 mg, 0.209 mmol) in place of Example 59F. $^1$H NMR (400 MHz, DMSO-d$_6$) δ 2.87-2.96 (m, 3H) 3.74 (s, 3H) 4.14-4.54 (m, 5H) 6.36-6.44 (m, 1H) 7.07-7.13 (m, 1H) 7.17-7.25 (m, 2H) 7.25-7.34 (m, 1H) 8.24 (d, J=4.88 Hz, 1H) 11.78-11.99 (m, 1H). MS (ESI$^+$) m/z 311.9 (M+H)$^+$.

Example 185

4-(5-fluoro-2-methoxyphenyl)-2-[1-(methylsulfonyl)azetidin-3-yl]-1H-pyrrolo[2,3-b]pyridine The title compound was prepared as the trifluoroacetate salt using the procedure described in Example 108, using methanesulfonyl chloride (21 mg, 0.180 mmol) in place of acetyl chloride and Example 146D (93 mg, 0.177 mmol) in place of Example 59F. $^1$H NMR (400 MHz, DMSO-d$_6$) δ 3.05 (s, 3H) 3.74 (s, 3H) 4.01-4.22 (m, 5H) 6.32 (d, J=1.83 Hz, 1H) 7.08 (d, J=4.88 Hz, 1H) 7.17-7.24 (m, 2H) 7.24-7.32 (m, 1H) 8.21 (d, J=4.88 Hz, 1H) 11.80 (s, 1H). MS (ESI$^+$) m/z 376.0 (M+H)$^+$.

Example 186

3-{4-[4-(5-fluoro-2-methoxyphenyl)-1H-pyrrolo[2,3-b]pyridin-2-yl]-3,6-dihydropyridin-1(2H)-yl}propane-1,2-diol The title compound was prepared as described in Example 149, using Example 87D (0.202 mmol, 80.0 mg) in place of Example 135B. The mixture was heated at 40° C. for 3 hours. ¹H NMR (400 MHz, CD₃OD) δ 2.91-2.99 (m, 2H), 3.25-3.51 (m, 3H), 3.59 (qd, J=11.3, 5.1 Hz, 2H), 3.78-3.89 (m, 1H), 3.79 (s, 3H), 3.89-4.30 (m, 3H), 6.47 (bs, 1H), 6.58 (s, 1H), 7.16-7.28 (m, 3H), 7.33 (d, J=5.5 Hz, 1H), 8.29 (d, J=5.5 Hz, 1H). MS (ESI⁺) m/z 397.9 (M+H)⁺.

Example 187

4-fluoro-3-[2-(piperidin-4-yl)-1H-pyrrolo[2,3-b]pyridin-4-yl]aniline

Example 187A tert-butyl 4-(4-(5-(tert-butoxycarbonylamino)-2-fluorophenyl)-1H-pyrrolo[2,3-b]pyridin-2-yl)piperidine-1-carboxylate The title compound was prepared using the procedure described in Example 1G, using Example 17E (50 mg, 0.15 mmol) in place of Example 1F and Example 179B (75 mg, 0.22 mmol) in place of 5-fluoro-2-methoxyphenylboronic acid. LCMS: 511 (M+H)⁺.

Example 187B 4-fluoro-3-(2-(piperidin-4-yl)-1H-pyrrolo[2,3-b]pyridin-4-yl)aniline The title compound was prepared using the procedure described in Example 179D, using Example 187A (38 mg, 0.07 mmol) in place of Example 179C. ¹H NMR (400 MHz, DMSO-d₆): δ 1.13-1.32 (m, 4H), 1.53 (d, J=11.60 Hz, 2H), 1.70-1.86 (m, 1H), 1.93 (dd, J=7.17, 3.51 Hz, 2H), 2.29 (d, J=13.73 Hz, 2H), 2.82 (d, J=4.27 Hz, 3H), 2.94-3.06 (m, 1H), 3.06-3.14 (m, 2H), 3.18-3.25 (m, 2H), 3.54 (d, J=11.60 Hz, 2H), 3.84 (dd, J=10.99, 2.75 Hz, 2H), 6.13 (s, 1H), 6.75-6.85 (m, 1H), 7.00-7.29 (m, 3H), 8.25 (d, J=4.88 Hz, 1H). LCMS: 311 (M+H)⁺.

Example 188

5-chloro-6-[2-(1-methylpiperidin-4-yl)-1H-pyrrolo[2,3-b]pyridin-4-yl]-N-[3-(methylsulfonyl)benzyl]pyridin-2-amine The title compound was prepared using the procedure described in Example 11B, using Example 132 (25 mg, 0.07 mmol) in place of Example 11A and 3-(methylsulfonyl)benzaldehyde (27 mg, 0.14 mmol) in place of benzaldehyde. ¹H NMR (400 MHz, DMSO-d₆): δ 1.62-1.82 (m, 2H), 2.14-2.24 (m, 2H), 2.81 (d, J=4.75 Hz, 3H), 2.87-2.98 (m, 1H), 2.99-3.11 (m, 2H), 3.11 (s, 3H), 3.51 (d, J=11.53 Hz, 2H), 4.57 (d, J=3.39 Hz, 2H), 5.95 (d, J=1.36 Hz, 1H), 6.68 (d, J=8.82 Hz, 1H), 7.09 (d, J=4.75 Hz, 1H), 7.55-7.66 (m, 3H), 7.78-7.83 (m, 1H), 7.85 (s, 1H), 8.19 (d, J=4.75 Hz, 1H). LCMS: 510 (M+H)⁺.

Example 189

4-fluoro-3-[2-(1-methylpiperidin-4-yl)-1H-pyrrolo[2,3-b]pyridin-4-yl]-N-(pyridin-4-ylmethyl)aniline The title compound was prepared using the procedure described in Example 11B, using Example 179D (25 mg, 0.08 mmol) in place of Example 11A and isonicotinaldehyde (17 mg, 0.15 mmol) in place of benzaldehyde. ¹H NMR (400 MHz, DMSO-d₆): δ 1.72-1.81 (m, 2H), 2.24 (d, J=13.73 Hz, 2H), 2.83 (s, 3H), 2.98 (t, J=12.21 Hz, 1H), 3.12 (t, J=11.90 Hz, 2H), 3.55 (d, J=11.90 Hz, 2H), 4.62 (s, 2H), 5.93 (s, 1H), 6.69 (dd, J=5.95, 2.90 Hz, 2H), 7.03 (d, J=3.97 Hz, 1H), 7.07-7.20 (m, 1H), 7.91 (d, J=6.10 Hz, 2H), 8.21 (d, J=4.88 Hz, 1H), 8.83 (d, J=6.10 Hz, 2H). LCMS: 416 (M+H)⁺.

Example 190

4-fluoro-3-[2-(1-methylpiperidin-4-yl)-1H-pyrrolo[2,3-b]pyridin-4-yl]-N-[4-(methylsulfonyl)benzyl]aniline The title compound was prepared using the procedure described in Example 11B, using Example 179D (20 mg, 0.06 mmol) in place of Example 11A and 4-(methylsulfonyl)benzaldehyde (17 mg, 0.09 mmol) in place of benzaldehyde. ¹H NMR (400 MHz, DMSO-d₆): δ 1.74-1.86 (m, 2H), 2.24 (d, J=13.73 Hz, 2H), 2.82 (d, J=4.58 Hz, 3H), 2.93-3.01 (m, 1H), 3.06-3.15 (m, 2H), 3.20 (s, 3H), 3.54 (d, J=11.90 Hz, 2H), 4.43 (s, 2H), 5.94 (s, 1H), 6.62-6.73 (m, 2H), 7.01-7.04 (m, 1H), 7.07-7.14 (m, 1H), 7.63 (d, J=8.24 Hz, 2H), 7.90 (d, J=8.54 Hz, 2H), 8.21 (d, J=4.88 Hz, 1H). LCMS: 493 (M+H)⁺.

Example 191

4-[({4-fluoro-3-[2-(1-methylpiperidin-4-yl)-1H-pyrrolo[2,3-b]pyridin-4-yl]phenyl}amino)methyl]benzamide The title compound was prepared using the procedure described in Example 11B, using Example 179D (20 mg, 0.06 mmol) in place of Example 11A and 4-formylbenzamide (14 mg, 0.09 mmol) in place of benzaldehyde. ¹H NMR (400 MHz, DMSO-d₆): δ 1.70-1.84 (m, 2H) 2.17 (d, J=13.73 Hz, 2H) 2.84 (d, J=4.58 Hz, 3H) 2.91 (t, J=12.21 Hz, 1H) 3.05-3.16 (m, 2H) 3.55 (d, J=11.60 Hz, 2H) 4.36 (s, 2H) 5.76 (s, 1H) 6.62 (dd, J=6.10, 3.05 Hz, 1H) 6.69-6.79 (m, 1H) 7.04 (d, J=6.41 Hz, 1H) 7.10 (t, J=9.46 Hz, 1H) 7.44 (d, J=8.24 Hz, 2H) 7.86 (d, J=8.24 Hz, 2H) 8.20 (d, J=4.88 Hz, 1H). LCMS: 458 (M+H)⁺.

Example 192

(3S,5R)-5-[({5-chloro-6-[2-(piperidin-4-yl)-1H-pyrrolo[2,3-b]pyridin-4-yl]pyridin-2-yl}amino)methyl]pyrrolidin-3-ol Example 192A (2R,4S)-tert-butyl 2-(((6-bromo-5-chloropyridin-2-yl)amino)methyl)-4-hydroxypyrrolidine-1-carboxylate The title compound was prepared using the procedure described in Example 11B, using (2R,4S)-tert-butyl 2-formyl-4-hydroxypyrrolidine-1-carboxylate (500 mg, 2.32 mmol) in place of benzaldehyde. LCMS: 408.1 (M+3)⁺.

Example 192B 4-(4-{6-[((2R,4S)-1-tert-butoxycarbonyl-4-hydroxy-pyrrolidin-2-ylmethyl)-amino]-3-chloro-pyridin-2-yl}-1H-pyrrolo[2,3-b]pyridin-2-yl)-piperidine-1-carboxylic acid tert-butyl ester The title compound was prepared using the procedure described in Example 42B, using Example 192A (286 mg, 0.702 mmol) in place of Example 42A. LCMS: 627.3 (M+H)$^+$.

Example 192C (3S,5R)-5-[({5-chloro-6-[2-(piperidin-4-yl)-1H-pyrrolo[2,3-b]pyridin-4-yl]pyridin-2-yl}amino)methyl]pyrrolidin-3-ol The title compound was prepared as the trifluoroacetate salt using the procedure described in Example 1H, using Example 192B (150 mg, 0.239 mmol) in place of Example 1G. LCMS: 427.2 (M+H)$^+$. $^1$H NMR (400 MHz, DMSO-d$_6$/D$_2$O): δ 1.75-1.78 (m, 4H), 1.9-1.96 (m, 1H), 2.20-2.23 (m, 2H), 3.02-3.07 (m, 4H), 3.18-3.22 (m, 1H), 3.34-3.39 (m, 4H), 4.35 (brs, 1H), 6.06 (s, 1H), 6.70 (d, J=9.2 Hz, 1H), 7.11 (d, J=5.2 Hz, 1H), 7.22 (brs, 1H), 7.67 (d, J=8.8 Hz, 1H), 8.22 (d, J=4.8 Hz, 1H), 8.62-8.78 (m, 1H), 9.2-9.3 (m, 1H), 11.8 (s, 1H).

Example 193

2-(azepan-3-yl)-4-(5-fluoro-2-methoxyphenyl)-1H-pyrrolo[2,3-b]pyridine

Example 193A tert-butyl 3-ethynylazepane-1-carboxylate

The title compound was prepared using the procedure described in Example 1D, using tert-butyl 3-formylazepane-1-carboxylate (1.5 g, 6.6 mmol) in place of Example 1C. LCMS: 224.4 (M+H)$^+$.

Example 193B tert-butyl 3-((2-((tert-butoxycarbonyl)amino)-4-chloropyridin-3-yl)ethynyl)azepane-1-carboxylate The title compound was prepared using the procedure described in Example 1E, using Example 193A (756 mg, 3.38 mmol) in place of Example 1D. LCMS: 450.2 (M+H)$^+$.

Example 193C tert-butyl 3-(4-chloro-1H-pyrrolo[2,3-b]pyridin-2-yl)azepane-1-carboxylate The title compound was prepared using the procedure described in Example 1F, using Example 193B (1 g, 2.22 mmol) in place of Example 1E. LCMS: 352.2 (M+2)$^+$.

Example 193D tert-butyl 3-(4-(5-fluoro-2-methoxyphenyl)-1H-pyrrolo[2,3-b]pyridin-2-yl)azepane-1-carboxylate The title compound was prepared using the procedure described in Example 1G, using Example 193C (200 mg, 0.57 mmol) in place of Example 1F. LCMS: 440.2 (M+H)$^+$.

Example 193E 2-(azepan-3-yl)-4-(5-fluoro-2-methoxyphenyl)-1H-pyrrolo[2,3-b]pyridine The title compound was prepared as the hydrochloride salt using the procedure described in Example 1H, using Example 193D (120 mg, 0.273 mmol) in place of Example 1G. LCMS: 340.2 (M+H)$^+$. $^1$H NMR (400 MHz, DMSO-d$_6$/D$_2$O): δ 1.6-1.7 (m, 1H), 1.81-1.84 (m, 4H), 2.08-2.14 (m, 1H), 3.1-3.2 (m, 4H), 3.73 (s, 3H), 6.23 (s, 1H), 7.20-7.26 (m, 3H), 7.29-7.34 (m, 1H), 8.27 (d, J=5.6 Hz, 1H).

Example 194

N-benzyl-5-chloro-6-(2-cyclohexyl-1H-pyrrolo[2,3-b]pyridin-4-yl)pyridin-2-amine

Example 194A tert-butyl (4-chloro-3-(cyclohexylethynyl)pyridin-2-yl)carbamate The title compound was prepared using the procedure described in Example 1E, using cyclohexyl acetylene (305 mg, 2.82 mmol) in place of Example 1D. LCMS: 335.1 (M+H)$^+$.

Example 194B 4-chloro-2-cyclohexyl-1H-pyrrolo[2,3-b]pyridine

The title compound was prepared using the procedure described in Example 1F, using Example 194A (800 mg, 2.38 mmol) in place of Example 1E. LCMS: 235.1 (M+H)$^+$.

Example 194C 2-cyclohexyl-4-(4,4,5,5-tetramethyl-1,3,2-dioxaborolan-2-yl)-1H-pyrrolo[2,3-b]pyridine The title compound was prepared using the procedure described in Example 5A, using Example 194B (200 mg, 0.852 mmol) in place of Example 1F. LCMS: 327.3 (M+H)$^+$.

Example 194D

N-benzyl-5-chloro-6-(2-cyclohexyl-1H-pyrrolo[2,3-b]pyridin-4-yl)pyridin-2-amine

The title compound was prepared using the procedure described in Example 5B, using Example 194C (200 mg, 0.613 mmol) in place of product of Example 5A and Example 11B (274 mg, 0.92 mmol) in place of 6-bromo-5-methoxy-pyridin-2-amine. LCMS: 417.1 (M+H)$^+$. $^1$H NMR (400 MHz, DMSO-d$_6$): δ 1.16-1.22 (m, 1H), 1.29-1.31 (m, 4H), 1.65-1.73 (m, 2H), 1.87-1.88 (m, 2H), 2.58-2.66 (m, 2H), 4.47 (s, 2H), 5.90 (d, J=1.6 Hz, 1H), 6.64 (d, J=9.2 Hz, 1H), 7.17 (d, J=5.6 Hz, 1H), 7.21-7.24 (m, 1H), 7.27-7.33 (m, 4H), 7.48-7.52 (m, 1H), 7.60 (d, J=8.8 Hz, 1H), 8.17 (d, J=5.2 Hz, 1H), 11.8 (s, 1H).

Example 195

N-benzyl-3-[5-chloro-2-(piperidin-4-yl)-1H-pyrrolo[2,3-b]pyridin-4-yl]-4-fluoroaniline

Example 195A tert-butyl 4-(4-(5-(benzylamino)-2-fluorophenyl)-5-chloro-1H-pyrrolo[2,3-b]pyridin-2-yl)piperidine-1-carboxylate The title compound was prepared using the procedure described in Example 1G, using Example 51B (133 mg, 0.407 mmol) in place of the product of 5-fluoro-2-methoxyphenylboronic acid and Example 77C (130 mg, 0.313 mmol) in place of Example 1F. LCMS: 479.1 (M+H—NCOOH)+.

Example 195B

N-benzyl-3-[5-chloro-2-(piperidin-4-yl)-1H-pyrrolo[2,3-b]pyridin-4-yl]-4-fluoroaniline The title compound was prepared as the trifluoroacetate salt using the procedure described in Example 1H, using Example 195A (140 mg, 0.262 mmol) in place of Example 1G, and purified using preparative HPLC (Zorbax XDB C-18 column with gradient elution from 0.1% trifluoroacetic acid in water to 1:1 methanol/acetonitrile). LCMS: 435.4 (M+H)+. $^1$H NMR (400 MHz, CD$_3$OD): δ 1.85-1.93 (m, 2H), 2.26-2.33 (m, 2H), 3.09-3.20 (m, 3H), 3.48-3.53 (m, 2H), 4.34 (s, 2H), 5.90 (s, 1H), 6.6-6.63 (m, 1H), 6.79-6.83 (m, 1H), 7.03 (t, J=9.2 Hz, 1H), 7.23-7.27 (m, 1H), 7.31-7.35 (m, 2H), 7.38-7.40 (m, 2H), 8.20 (s, 1H).

Example 196

5-chloro-N-{[(2S,4S)-4-fluoropyrrolidin-2-yl]methyl}-6-[2-(piperidin-4-yl)-1H-pyrrolo[2,3-b]pyridin-4-yl]pyridin-2-amine

Example 196A (2R,4R)-tert-butyl 2-(((6-bromo-5-chloropyridin-2-yl)amino)methyl)-4-fluoropyrrolidine-1-carboxylate The title compound was prepared using the procedure described in Example 11B, using (2R,4R)-tert-butyl 4-fluoro-2-formylpyrrolidine-1-carboxylate (500 mg, 2.74 mmol) in place of benzaldehyde. LCMS: 410.3 (M+3)+.

Example 196B tert-butyl 4-(4-(6-((((2R,4R)-1-(tert-butoxycarbonyl)-4-fluoropyrrolidin-2-yl)methyl)amino)-3-chloropyridin-2-yl)-1H-pyrrolo[2,3-b]pyridin-2-yl)piperidine-1-carboxylate The title compound was prepared using the procedure described in Example 7A, using Example 21A (200 mg, 0.468 mmol) in place of Example 5A and Example 196A (128 mg, 0.312 mmol) in place of 2-bromo-4-cyclopropyl-1-methoxybenzene. LCMS: 629.6 (M+H)+.

Example 196C 5-chloro-N-{[(2S,4S)-4-fluoropyrrolidin-2-yl]methyl}-6-[2-(piperidin-4-yl)-1H-pyrrolo[2,3-b]pyridin-4-yl]pyridin-2-amine The title compound was prepared as trifluoroacetate salt using the procedure described in Example 1H, using Example 196B (150 mg, 0.238 mmol) in place of Example 1G, and purified using preparative HPLC (SEMI-C-18 column with gradient elution from 0.1% trifluoroacetic acid in water to 1:1 methanol/acetonitrile). LCMS: 429.2 (M+H)+. $^1$H NMR (400 MHz, CD$_3$OD): δ 1.95-2.02 (m, 3H), 2.17-2.22 (m, 2H), 2.36-2.38 (m, 2H), 3.14-3.22 (m, 3H), 3.48-3.70 (m, 2H), 3.68-3.70 (m, 2H), 4.06-4.08 (m, 1H), 5.27 (brs, 1H), 5.40 (brs, 1H), 6.22 (s, 1H), 6.79 (d, J=9.2 Hz, 1H), 7.25 (d, J=5.2 Hz, 1H), 7.71 (d, J=8.8 Hz, 1H), 8.30 (d, J=5.2 Hz, 1H).

Example 197

4-[({5-chloro-4-[2-(piperidin-4-yl)-1H-pyrrolo[2,3-b]pyridin-4-yl]pyridin-2-yl}amino)methyl]tetrahydro-2H-pyran-4-carbonitrile

Example 197A 4-(((5-chloro-4-iodopyridin-2-yl)amino)methyl)tetrahydro-2H-pyran-4-carbonitrile A solution of 5-chloro-2-fluoro-4-iodopyridine (1 g, 3.88 mmol) and 4-(aminomethyl)tetrahydro-2H-pyran-4-carbonitrile (1.634 g, 11.65 mmol) in 4 mL of dimethylsulfoxide was heated at 100° C. for 8 hours. The mixture was quenched with 100 mL of ice-cold water and was extracted with ethyl acetate (50 mL×2). The organic layer was washed with water and brine, dried over sodium sulfate, filtered, and concentrated. Purification by column chromatography (silica gel, 20% ethyl acetate in hexane) afforded the title compound.

Example 197B

4-[({5-chloro-4-[2-(piperidin-4-yl)-1H-pyrrolo[2,3-b]pyridin-4-yl]pyridin-2-yl}amino)methyl]tetrahydro-2H-pyran-4-carbonitrile To a solution of Example 197A (1 g, 2.65 mmol) and Example 21A (1.132 g, 2.65 mmol) in 10 mL ethanol was added potassium acetate (0.780 g, 7.94 mmol). The mixture was degassed for 5 minutes with nitrogen and bis(di-tert-butyl(4-dimethylaminophenyl)phosphine)dichloropalladium(II) (0.073 g, 0.132 mmol) was added. The mixture was heated at 80° C. for 2 hours and was cooled to room temperature. The mixture was quenched into ice-cold water and extracted with ethyl acetate (100 mL×3). The organic layer was washed with brine, concentrated and purified by preparative HPLC (Agilent AD/SP/C18-25/011 reversed phase column and gradient elution from 10 mM ammonium acetate to 1:1 methanol/acetonitrile) to afford the title compound as the acetate salt. LCMS: 452.1 (M+H)+. $^1$H NMR (400 MHz, CD$_3$OD): δ 1.84-1.88 (m, 2H), 2.01-2.05 (m, 4H), 3.32-3.36 (m, 2H), 3.14-3.20 (m, 3H), 3.49-3.52 (m, 2H), 3.69-3.75 (m, 2H), 4.0-4.03 (m, 2H), 4.49 (s, 2H), 6.13 (s, 1H), 7.0 (s, 1H), 7.11 (d, J=5.2 Hz, 1H), 8.26 (d, J=4.8 Hz, 1H), 8.34 (s, 1H).

Example 198

5-chloro-N-{[(2S)-4,4-difluoropyrrolidin-2-yl]methyl}-6-[2-(piperidin-4-yl)-1H-pyrrolo[2,3-b]pyridin-4-yl]pyridin-2-amine

Example 198A (R)-tert-butyl 2-(((6-bromo-5-chloropyridin-2-yl)amino)methyl)-4,4-difluoropyrrolidine-1-carboxylate The title compound was prepared using the procedure described in Example 11B, using (R)-tert-butyl 4,4-difluoro-2-formylpyrrolidine-1-carboxylate (200 mg, 0.850 mmol) in place of benzaldehyde. LCMS: 326 (M+H-Boc)$^+$.

Example 198B (R)-tert-butyl 4-(4-(6-(((1-(tert-butoxycarbonyl)-4,4-difluoropyrrolidin-2-yl)methyl)amino)-3-chloropyridin-2-yl)-1H-pyrrolo[2,3-b]pyridin-2-yl)piperidine-1-carboxylate The title compound was prepared using the procedure described in Example 7A, using Example 21A (400 mg, 0.936 mmol) in place of Example 5A and Example 198A (186 mg, 0.624 mmol) in place of 2-bromo-4-cyclopropyl-1-methoxybenzene. LCMS: 647.2 (M+H)$^+$.

Example 198C 5-chloro-N-{[(2S)-4,4-difluoropyrrolidin-2-yl]methyl}-6-[2-(piperidin-4-yl)-1H-pyrrolo[2,3-b]pyridin-4-yl]pyridin-2-amine The title compound was prepared as the acetate salt using the procedure described in Example 6E, using Example 198B (400 mg, 0.618 mmol) in place of Example 6D, and purified using preparative HPLC (Zorbax XDB C-18 column with gradient elution from 10M ammonium acetate in water to 1:1 methanol/acetonitrile). LCMS: 447.4 (M+H)$^+$. $^1$H NMR (400 MHz, CD$_3$OD): δ 1.95-1.97 (m, 2H), 2.33-2.37 (m, 3H), 3.14-3.23 (m, 3H), 3.34-3.36 (m, 3H), 3.47-3.51 (m, 4H), 3.58-3.61 (m, 1H), 6.21 (s, 1H), 6.61-6.63 (m, 1H), 7.19 (d, J=4.8 Hz, 1H), 7.57 (d, J=8.8 Hz, 1H), 8.22 (d, J=5.2 Hz, 1H).

Example 199

N-benzyl-4-chloro-3-[2-(piperidin-3-yl)-1H-pyrrolo[2,3-b]pyridin-4-yl]aniline

Example 199A tert-butyl 3-(4-(5-(benzylamino)-2-chlorophenyl)-1H-pyrrolo[2,3-b]pyridin-2-yl)piperidine-1-carboxylate The title compound was prepared using the procedure described in Example 7A, using Example 53A (200 mg, 0.677 mmol) in place of 2-bromo-4-cyclopropyl-1-methoxybenzene. LCMS: 517.6 (M+H)$^+$.

Example 199B

N-benzyl-4-chloro-3-[2-(piperidin-3-yl)-1H-pyrrolo[2,3-b]pyridin-4-yl]aniline

The title compound was prepared as the hydrochloride salt using the procedure described in Example 6E, using Example 199A (400 mg, 0.618 mmol) in place of Example 6D. LCMS: 417.2 (M+H)$^+$. $^1$H NMR (400 MHz, CD$_3$OD): δ 1.88-2.0 (m, 2H), 2.10-2.13 (m, 1H), 2.28-2.31 (m, 1H), 3.06-3.11 (m, 1H), 3.47-3.50 (m, 2H), 3.68-3.71 (m, 1H), 4.58 (s, 2H), 6.49 (s, 1H), 7.30-7.32 (m, 2H), 7.38-7.47 (m, 5H), 7.60 (d, J=6 Hz, 1H), 7.65 (d, J=8.4 Hz, 1H), 8.48 (d, J=6 Hz, 1H).

Example 200

N-benzyl-5-chloro-N-methyl-6-[2-(piperidin-3-yl)-1H-pyrrolo[2,3-b]pyridin-4-yl]pyridin-2-amine

Example 200A tert-butyl 3-(4-(6-(benzyl(methyl)amino)-3-chloropyridin-2-yl)-1H-pyrrolo[2,3-b]pyridin-2-yl)piperidine-1-carboxylate The title compound was prepared using the procedure described in Example 5B, using Example 46A (219 mg, 0.702 mmol)) in place of 6-bromo-5-methoxypyridin-2-amine.

Example 200B

N-benzyl-5-chloro-N-methyl-6-[2-(piperidin-3-yl)-1H-pyrrolo[2,3-b]pyridin-4-yl]pyridin-2-amine The title compound was prepared as trifluoroacetate salt using the procedure described in Example 1H, using Example 200A (100 mg, 0.188 mmol) in place of Example 1G, and purified using preparative HPLC (Zorbax XDB C-18 column with gradient elution from 0.1% trifluoroacetic acid in water to acetonitrile). LCMS: 432.2 (M+H)$^+$. $^1$H NMR (400 MHz, DMSO-d$_6$): δ 1.5-1.6 (m, 1H), 1.68-1.74 (m, 1H), 1.85-1.9 (m, 1H), 1.98-2.02 (m, 1H), 2.78-2.82 (m, 1H), 2.9-3.0 (m, 1H), 3.05 (s, 3H), 3.28-3.31 (m, 1H), 3.45-3.48 (m, 2H), 4.80 (s, 2H), 6.06 (d, J=1.6 Hz, 1H), 6.78 (d, J=8.8 Hz, 1H), 7.18-7.21 (m, 3H), 7.24-7.27 (m, 1H), 7.32-7.35 (m, 2H), 7.73 (d, J=9.2 Hz, 1H), 8.22 (d, J=5.2 Hz, 1H), 8.60-8.62 (m, 1H), 11.8 (s, 1H).

Example 201

4-(4,5-difluoro-2-methoxyphenyl)-2-(piperidin-3-yl)-1H-pyrrolo[2,3-b]pyridine

Example 201A tert-butyl 3-(4-(4,5-difluoro-2-methoxyphenyl)-1H-pyrrolo[2,3-b]pyridin-2-yl)piperidine-1-carboxylate The title compound was prepared using the procedure described in Example 1G, using (4,5-difluoro-2-methoxyphenyl)boronic acid (95 mg, 0.503 mmol) in place of 5-fluoro-2-methoxyphenylboronic acid.

Example 201B 4-(4,5-difluoro-2-methoxyphenyl)-2-(piperidin-3-yl)-1H-pyrrolo[2,3-b]pyridine The title compound was prepared as trifluoroacetate salt using the procedure described in Example 1H, using Example 201A (100 mg, 0.22 mmol) in place of Example 1G, and purified using preparative HPLC (Zorbax XDB C-18 column with gradient elution from 0.1% trifluoroacetic acid in water to 1:1 methanol/acetonitrile). LCMS: 344.1 (M+H)$^+$. $^1$H NMR (400 MHz, DMSO-$d_6$/$D_2O$): δ 1.70-1.74 (m, 2H), 1.89-1.90 (m, 1H), 2.07-2.12 (m, 1H), 2.82-2.84 (m, 1H), 3.09-3.16 (m, 2H), 3.28-3.32 (m, 1H), 3.50-3.52 (m, 1H), 3.74 (s, 3H), 6.10 (s, 1H), 7.05 (d, J=5.2 Hz, 1H), 7.32-7.37 (m, 1H), 7.41-7.46 (m, 1H), 8.19 (s, 1H).

Example 202

5-chloro-N-(3,4-difluorobenzyl)-6-[2-(piperidin-3-yl)-1H-pyrrolo[2,3-b]pyridin-4-yl]pyridin-2-amine Example 202A tert-butyl 3-(4-(3-chloro-6-((3,4-difluorobenzyl)amino)pyridin-2-yl)-1H-pyrrolo[2,3-b]pyridin-2-yl)piperidine-1-carboxylate The title compound was prepared using the procedure described in Example 7A, using Example 39A (200 mg, 0.60 mmol) in place of 2-bromo-4-cyclopropyl-1-methoxybenzene. LCMS: 454.5 (M+H)$^+$.

Example 202B 5-chloro-N-(3,4-difluorobenzyl)-6-[2-(piperidin-3-yl)-1H-pyrrolo[2,3-b]pyridin-4-yl]pyridin-2-amine The title compound was prepared as trifluoroacetate salt using the procedure described in Example 1H, using Example 202A (150 mg, 0.271 mmol) in place of Example 1G, and purified using preparative HPLC (Zorbax XDB C-18 column with gradient elution from 0.1% trifluoroacetic acid in water to 1:1 methanol/acetonitrile). LCMS: 454.5 (M+H)$^+$. $^1$H NMR (400 MHz, DMSO-$d_6$/$D_2O$): δ 1.58-1.75 (m, 2H), 1.87-1.90 (m, 1H), 2.0-2.02 (m, 1H), 2.79-2.84 (m, 1H), 2.96-3.02 (m, 1H), 3.08-3.11 (m, 1H), 3.29-3.32 (m, 1H), 4.42 (s, 2H), 5.98 (s, 1H), 6.65 (d, J=8.8 Hz, 1H), 7.08-7.12 (m, 2H), 7.32-7.37 (m, 2H), 7.62 (d, J=8.8 Hz, 1H), 8.21 (d, J=5.2 Hz, 1H).

Example 203

5-chloro-N-(3-fluorobenzyl)-6-[2-(piperidin-3-yl)-1H-pyrrolo[2,3-b]pyridin-4-yl]pyridin-2-amine Example 203A tert-butyl 3-(4-(3-chloro-6-((3-fluorobenzyl)amino)pyridin-2-yl)-1H-pyrrolo[2,3-b]pyridin-2-yl)piperidine-1-carboxylate The title compound was prepared using the procedure described in Example 7A, using Example 33A (49.2 mg, 0.156 mmol) in place of 2-bromo-4-cyclopropyl-1-methoxybenzene. LCMS: 536.5 (M+H)$^+$.

Example 203B 5-chloro-N-(3-fluorobenzyl)-6-[2-(piperidin-3-yl)-1H-pyrrolo[2,3-b]pyridin-4-yl]pyridin-2-amine The title compound was prepared as trifluoroacetate salt using the procedure described in Example 1H, using Example 203A (75 mg, 0.14 mmol) in place of Example 1G, and purified using preparative HPLC (Zorbax XDB C-18 column with gradient elution from 0.1% trifluoroacetic acid in water to 1:1 methanol/acetonitrile). LCMS: 436.5 (M+H)$^+$. $^1$H NMR (400 MHz, DMSO-$d_6$/$D_2O$): δ 1.52-1.6 (m, 1H), 1.7-1.78 (m, 1H), 1.85-1.92 (m, 1H), 1.98-2.02 (m, 1H), 2.8-2.84 (m, 1H), 2.97-3.0 (m, 1H), 3.05-3.1 (m, 1H), 3.28-3.31 (m, 1H), 3.43-3.46 (m, 1H), 4.46 (s, 2H), 5.91 (s, 1H), 6.66 (d, J=9.2 Hz, 1H), 7.06-7.13 (m, 4H), 7.35-7.36 (m, 1H), 7.61 (d, J=8.8 Hz, 1H), 8.20 (d, J=4.8 Hz).

Example 204

5-chloro-N-(4-fluorobenzyl)-6-[2-(piperidin-3-yl)-1H-pyrrolo[2,3-b]pyridin-4-yl]pyridin-2-amine Example 204A 6-bromo-5-chloro-N-(4-fluorobenzyl)pyridin-2-amine The title compound was prepared using the procedure described in Example 11B, using 4-fluorobenzaldehyde (329 mg, 2.65 mmol) in place of benzaldehyde. LCMS: 316.85 (M+3)$^+$.

Example 204B tert-butyl 3-(4-(3-chloro-6-((4-fluorobenzyl)amino)pyridin-2-yl)-1H-pyrrolo[2,3-b]pyridin-2-yl)piperidine-1-carboxylate The title compound was prepared using the procedure described in Example 5B, using Example 204A (222 mg, 0.702 mmol) in place of 6-bromo-5-methoxypyridin-2-amine. LCMS: 537.1 (M+2)$^+$.

Example 204C 5-chloro-N-(4-fluorobenzyl)-6-[2-(piperidin-3-yl)-1H-pyrrolo[2,3-b]pyridin-4-yl]pyridin-2-amine The title compound was prepared as trifluoroacetate salt using the procedure described in Example 1H, using Example 204B (100 mg, 0.187 mmol) in place of Example 1G, and purified using preparative HPLC (Zorbax XDB C-18 column with gradient elution from 0.1% trifluoroacetic acid in water to 1:1 methanol/acetonitrile). LCMS: 436.1 (M+H)$^+$. $^1$H NMR (400 MHz, DMSO-$d_6$/$D_2O$): δ 1.57-1.60 (m, 1H), 1.71-1.75 (m, 1H), 1.87-1.90 (m, 1H), 2.0-2.03 (m, 1H), 2.79-2.85 (m, 1H), 2.97-3.03 (m, 1H), 3.09-3.12 (m, 1H), 3.29-3.38 (m, 1H), 3.48-3.51 (m, 1H), 4.43 (s, 2H), 6.03 (s, 1H), 6.64 (d, J=8.8 Hz, 1H), 7.11-7.16 (m, 3H), 7.30-7.34 (m, 2H), 7.61 (d, J=8.8 Hz, 1H), 8.23 (d, J=5.2 Hz, 1H).

Example 205

N-benzyl-5-chloro-4-[2-(piperidin-3-yl)-1H-pyrrolo[2,3-b]pyridin-4-yl]pyridin-2-amine Example 205A tert-butyl 3-(4-(2-(benzylamino)-5-chloropyridin-4-yl)-1H-pyrrolo[2,3-b]pyridin-2-yl)piperidine-1-carboxylate The title compound was prepared using the procedure described in Example 5B, using Example 52B (150 mg, 0.504 mmol) in place of 6-bromo-5-methoxypyridin-2-amine. LCMS: 518.2 (M+H)$^+$.

Example 205B

N-benzyl-5-chloro-4-[2-(piperidin-3-yl)-1H-pyrrolo[2,3-b]pyridin-4-yl]pyridin-2-amine The title compound was prepared as trifluoroacetate salt using the procedure described in Example 1H, using Example 205A (180 mg, 0.34 mmol) in place of Example 1G, and purified using preparative HPLC (Zorbax XDB C-18 column with gradient elution from 0.1% trifluoroacetic acid in water to 1:1 methanol/acetonitrile). LCMS: 418.2 (M+H)$^+$. $^1$H NMR (400 MHz, DMSO-d$_6$): δ 1.64-1.71 (m, 2H), 1.88-2.0 (m, 2H), 2.83-2.86 (m, 2H), 3.03-3.09 (m, 2H), 3.28-3.32 (m, 1H), 4.48 (s, 2H), 5.97 (s, 1H), 6.57 (s, 1H), 7.01 (d, J=5.2 Hz, 1H), 7.24-7.25 (m, 1H), 7.32-7.33 (m, 4H), 8.13 (s, 1H), 8.23 (d, J=4.8 Hz, 1H).

Example 206

N-benzyl-4-fluoro-3-[2-(piperidin-3-yl)-1H-pyrrolo[2,3-b]pyridin-4-yl]aniline

Example 206A tert-butyl 3-(4-(5-(benzylamino)-2-fluorophenyl)-1H-pyrrolo[2,3-b]pyridin-2-yl)piperidine-1-carboxylate The title compound was prepared using the procedure described in Example 1G, using Example 51B (190 mg, 0.581 mmol) in place of 5-fluoro-2-methoxyphenylboronic acid. LCMS: 501.6 (M+H)$^+$.

Example 206B

N-benzyl-4-fluoro-3-[2-(piperidin-3-yl)-1H-pyrrolo[2,3-b]pyridin-4-yl]aniline

The title compound was prepared as trifluoroacetate salt using the procedure described in Example 1H, using Example 206A (150 mg, 0.30 mmol) in place of Example 1G, and purified using preparative HPLC (Zorbax XDB C-18 column with gradient elution from 0.1% trifluoroacetic acid in water to 1:1 methanol/acetonitrile). LCMS: 401.3 (M+H)$^+$. $^1$H NMR (400 MHz, CD$_3$OD): δ 1.30-1.35 (m, 1H), 1.8-1.94 (m, 2H), 2.10-2.14 (m, 1H), 2.24-2.28 (m, 1H), 3.01-3.08 (m, 1H), 3.15-3.21 (m, 1H), 3.46-3.49 (m, 1H), 3.62-3.65 (m, 1H), 4.40 (s, 2H), 6.25 (s, 1H), 6.81-6.89 (m, 2H), 7.11 (t, J=9.2 Hz, 1H), 7.27-7.31 (m, 2H), 7.34-7.46 (m, 4H), 8.27 (d, J=5.6 Hz, 1H).

Example 207

5-chloro-N-(2-fluorobenzyl)-6-[2-(piperidin-3-yl)-1H-pyrrolo[2,3-b]pyridin-4-yl]pyridin-2-amine

Example 207A tert-butyl 3-(4-(3-chloro-6-((2-fluorobenzyl)amino)pyridin-2-yl)-1H-pyrrolo[2,3-b]pyridin-2-yl)piperidine-1-carboxylate The title compound was prepared using the procedure described in Example 5B, using Example 38A (222 mg, 0.702 mmol) in place of 6-bromo-5-methoxypyridin-2-amine. LCMS: 536.2 (M+H)$^+$.

Example 207B 5-chloro-N-(2-fluorobenzyl)-6-[2-(piperidin-3-yl)-1H-pyrrolo[2,3-b]pyridin-4-yl]pyridin-2-amine The title compound was prepared as trifluoroacetate salt using the procedure described in Example 1H, using Example 207A (100 mg, 0.187 mmol) in place of Example 1G, and purified using preparative HPLC (Zorbax XDB C-18 column with gradient elution from 0.1% trifluoroacetic acid in water to 1:1 methanol/acetonitrile). LCMS: 436.4 (M+H)$^+$. $^1$H NMR (400 MHz, DMSO-d$_6$): δ 1.57-1.61 (m, 1H), 1.71-1.75 (m, 1H), 1.87-1.91 (m, 1H), 1.99-2.03 (m, 1H), 2.80-2.83 (m, 1H), 2.99-3.12 (m, 2H), 3.30-3.38 (m, 1H), 3.45-3.48 (m, 1H), 4.50 (s, 2H) 5.97 (s, 1H), 6.69 (d, J=8.8 Hz, 1H), 7.11-7.20 (m, 3H), 7.29-7.38 (m, 2H), 7.47 (brs, 1H), 7.61 (dd, J=1.6, 8.8 Hz, 1H), 8.62 (brs, 1H), 11.8 (s, 1H).

Example 208

5-chloro-6-[2-(piperidin-3-yl)-1H-pyrrolo[2,3-b]pyridin-4-yl]-N-(pyridin-3-ylmethyl)pyridin-2-amine

Example 208A tert-butyl 3-(4-(3-chloro-6-((pyridin-3-ylmethyl)amino)pyridin-2-yl)-1H-pyrrolo[2,3-b]pyridin-2-yl)piperidine-1-carboxylate The title compound was prepared using the procedure described in Example 7A, using Example 34A (200 mg, 0.67 mmol) in place of 2-bromo-4-cyclopropyl-1-methoxybenzene. LCMS: 519.4 (M+H)$^+$.

Example 208B 5-chloro-6-[2-(piperidin-3-yl)-1H-pyrrolo[2,3-b]pyridin-4-yl]-N-(pyridin-3-ylmethyl)pyridin-2-amine The title compound was prepared as the trifluoroacetate salt using the procedure described in Example 1H, using Example 208A (200 mg, 0.385 mmol) in place of Example 1G, and purified using preparative HPLC (Zorbax XDB C-18 column with gradient elution from 0.1% trifluoroacetic acid in water to 1:1 methanol/acetonitrile). LCMS: 419.1 (M+H)$^+$. $^1$H NMR (400 MHz, CD$_3$OD): δ 1.82-1.95 (m, 2H), 2.08-2.12 (m, 1H), 2.26-2.29 (m, 1H), 3.02-3.09 (m, 1H), 3.17-3.23 (m, 1H), 3.46-3.49 (m, 2H), 4.73 (s, 2H), 6.33 (s, 1H), 6.77 (d, J=8.8 Hz, 1H), 7.23 (d, J=5.6 Hz, 1H), 7.65 (d, J=8.8 Hz, 1H), 7.93 (dd, J=5.6, 8.4 Hz, 1H), 8.30 (d, J=5.6 Hz, 1H), 8.49 (d, J=8 Hz, 1H), 8.67 (d, J=5.2 Hz, 1H), 8.72 (d, J=1.6 Hz, 1H).

Example 209

4-[3-chloro-6-(pyridin-3-ylmethoxy)pyridin-2-yl]-2-(piperidin-3-yl)-1H-pyrrolo[2,3-b]pyridine

Example 209A 2-bromo-3-chloro-6-(pyridin-3-ylmethoxy)pyridine 6-(benzyloxy)-2-bromo-3-chloropyridine The title compound was prepared using the procedure described in Example 58B, using pyridin-3-ylmethanol (352 mg, 3.26 mmol) in place of benzyl alcohol. LCMS: 300 (M+3)$^+$.

Example 209B tert-butyl 3-(4-(3-chloro-6-(pyridin-3-ylmethoxy) pyrrolo[2,3-b]pyridin-2-yl)-1H-pyrrolo[2,3-b]pyridin-2-yl)piperidine-1-carboxylate The title compound was prepared using the procedure described in Example 7A, using Example 209A (300 mg, 1.0 mmol) in place of 2-bromo-4-cyclopropyl-1-methoxybenzene. LCMS: 520.1 (M+H)$^+$.

Example 209C

4-[3-chloro-6-(pyridin-3-ylmethoxy)pyridin-2-yl]-2-(piperidin-3-yl)-1H-pyrrolo[2,3-b]pyridine The title compound was prepared as the trifluoroacetate salt using the procedure described in Example 1H, using Example 209B (250 mg, 0.481 mmol) in place of Example 1G, and purified using preparative HPLC (Zorbax XDB C-18 column with gradient elution from 0.1% trifluoroacetic acid in water to 1:1 methanol/acetonitrile). LCMS: 420.15 (M+H)$^+$. $^1$H NMR (400 MHz, DMSO-d$_6$/D$_2$O): δ 1.65-1.75 (m, 2H), 1.88-1.91 (m, 1H), 2.07-2.10 (m, 1H), 2.80-2.87 (m, 1H), 3.04-3.15 (m, 2H), 3.29-3.32 (m, 1H), 3.50-3.52 (m, 1H), 5.41 (s, 2H), 6.08 (s, 1H), 7.07 (d, J=8.8 Hz, 1H), 7.18 (d, J=4.8 Hz, 1H), 7.60 (dd, J=5.6, 8 Hz, 1H), 8.02 (d, J=8.8 Hz, 1H), 8.07 (d, J=7.6 Hz, 1H), 8.27 (d, J=4.8 Hz, 1H), 8.64 (dd, J=1.2, 5.2 Hz, 1H), 8.72 (d, J=1.6 Hz, 1H).

Example 210

5-chloro-N-[(5-fluoropyridin-3-yl)methyl]-6-[2-(piperidin-3-yl)-1H-pyrrolo[2,3-b]pyridin-4-yl]pyridin-2-amine

Example 210A tert-butyl 3-(4-(3-chloro-6-(((5-fluoropyridin-3-yl)methyl)amino)pyridin-2-yl)-1H-pyrrolo[2,3-b]pyridin-2-yl)piperidine-1-carboxylate The title compound was prepared using the procedure described in Example 7A, using Example 37A (200 mg, 0.63 mmol) in place of 2-bromo-4-cyclopropyl-1-methoxybenzene. LCMS: 537.5 (M+H)$^+$.

Example 210B 5-chloro-N-[(5-fluoropyridin-3-yl)methyl]-6-[2-(piperidin-3-yl)-1H-pyrrolo[2,3-b]pyridin-4-yl]pyridin-2-amine The title compound was prepared as trifluoroacetate salt using the procedure described in Example 1H, using Example 210A (200 mg, 0.458 mmol) in place of Example 1G, and purified using preparative HPLC (Agilent XDB C-18 column with gradient elution from 0.1% trifluoroacetic acid in water to 1:1 methanol/acetonitrile). LCMS: 437.1 (M+H)$^+$. $^1$H NMR (400 MHz, CD$_3$OD): δ 1.31-1.35 (m, 1H), 1.82-1.94 (m, 2H), 2.08-2.13 (m, 1H), 2.23-2.27 (m, 1H), 3.05-3.07 (m, 1H), 3.17-3.23 (m, 1H), 3.46-3.49 (m, 1H), 3.65-3.68 (m, 1H), 4.62 (s, 2H), 6.26 (s, 1H), 6.73 (d, J=8.8 Hz, 1H), 7.38 (d, J=6 Hz, 1H), 7.63 (d, J=9.2 Hz, 2H), 8.32 (d, J=5.2 Hz, 1H), 8.37-8.38 (m, 2H).

Example 211

N-benzyl-5-fluoro-4-[2-(piperidin-3-yl)-1H-pyrrolo[2,3-b]pyridin-4-yl]pyridin-2-amine

Example 211A tert-butyl 3-(4-(2,5-difluoropyridin-4-yl)-1H-pyrrolo[2,3-b]pyridin-2-yl)piperidine-1-carboxylate To a solution of Example 5A (100 mg, 0.234 mmol) and 2,5-difluoro-4-iodopyridine (200 mg, 0.830 mmol) in 3.5 mL of 1,2-dimethoxyethane was added 1.5 mL saturated sodium bicarbonate solution and the mixture was degassed with nitrogen. 1,1'-Bis(diphenylphosphino)ferrocene-palladium(II) dichloride dichloromethane complex (33.9 mg, 0.041 mmol) was added and the mixture was heated at 100° C. for 2 hours. The mixture was cooled to room temperature, diluted with ethyl acetate and filtered through diatomaceous earth. The combined organic layers were washed with water and brine (25 mL each) and dried over sodium sulfate. Filtration, concentration and purification by column chromatography (silica gel, 50% ethyl acetate-hexane) afforded the title compound. LCMS: 415.4 (M+H)$^+$.

Example 211B tert-butyl 3-(4-(2-(benzylamino)-5-fluoropyridin-4-yl)-1H-pyrrolo[2,3-b]pyridin-2-yl)piperidine-1-carboxylate To Example 211A (120 mg, 0.290 mmol) and phenylmethanamine (62.1 mg, 0.579 mmol) in 2 mL dimethylsulfoxide was added N-ethyl-N-isopropylpropan-2-amine (0.076 ml, 0.434 mmol). The mixture was heated in sealed tube at 120° C. for 4 hours, cooled to room temperature and diluted with water. The mixture was extracted with ethyl acetate (50 mL×3), dried over sodium sulfate, filtered and concentrated to provide the crude product which was recrystallised from 1:10 ethyl acetate-hexane to afford the title compound. LCMS: 502.4 (M+H)$^+$.

Example 211C

N-benzyl-5-fluoro-4-[2-(piperidin-3-yl)-1H-pyrrolo[2,3-b]pyridin-4-yl]pyridin-2-amine The title compound was prepared as the trifluoroacetate salt using the procedure described in Example 1H, using Example 211B (100 mg, 0.199 mmol) in place of Example 1G, and purified using preparative HPLC (AG/AD/PP/C-18 column with gradient elution from 0.1% trifluoroacetic acid in water to 1:1 methanol/acetonitrile). LCMS: 402.3 (M+H)$^+$. $^1$H NMR (400 MHz, CD$_3$OD): δ 1.31-1.35 (m, 1H), 1.83-1.95 (m, 2H), 2.10-2.13 (m, 1H), 2.25-2.29 (m, 1H), 3.01-3.07 (m, 1H), 3.16-3.22 (m, 1H), 3.47-3.50 (m, 1H), 3.64-3.68 (m, 1H), 4.61 (s, 2H), 6.29 (d, J=2 Hz, 1H), 7.02 (d, J=5.2 Hz, 1H), 7.27 (dd, J=1.2, 5.2 Hz, 1H), 7.34-7.44 (m, 5H), 8.12 (d, J=3.2 Hz, 1H), 8.32 (d, J=5.6 Hz, 1H).

Example 212

N-benzyl-4-fluoro-6-[2-(piperidin-3-yl)-1H-pyrrolo[2,3-b]pyridin-4-yl]pyridin-2-amine

Example 212A

N-benzyl-6-chloro-4-nitropyridin-2-amine

To a solution of 2,6-dichloro-4-nitropyridine (0.1 g, 0.518 mmol) and benzyl amine (0.062 mL, 0.570 mmol) in 10 mL toluene was added cesium carbonate (0.253 g, 0.777 mmol).

The mixture was degassed with nitrogen and 2,2'-bis(diphenylphosphino)-1,1'-binaphthalene (0.016 g, 0.026 mmol) and palladium acetate (5.82 mg, 0.026 mmol) were added. The mixture was heated at 100° C. for 2 hours, filtered through diatomaceous earth and concentrated. The residue was dissolved in ethyl acetate, washed with water and brine, dried over sodium sulfate, filtered, and concentrated. Recrystallization from 1:10 ethyl acetate-hexane afforded the title compound.

Example 212B

N-benzyl-6-chloro-4-fluoropyridin-2-amine

A solution of Example 212A (70 mg, 0.265 mmol) in 3 mL of N,N-dimethylformamide was treated with 1M tetra-n-butyl ammonium fluoride in tetrahydrofuran (0.531 mL, 0.531 mmol) and the mixture was heated at 65° C. for 12 hours. The mixture was poured into 30 mL 1:1 water/ethyl acetate and the organic layer was washed with water and brine, dried over sodium sulfate, filtered, and concentrated. Purification by column chromatography (silica, 5% ethyl acetate-hexane) afforded the title compound. LCMS: 236.8 (M+H)$^+$.

Example 212C tert-butyl 3-(4-(6-(benzylamino)-4-fluoropyridin-2-yl)-1H-pyrrolo[2,3-b]pyridin-2-yl)piperidine-1-carboxylate The title compound was prepared using the procedure described in Example 5B, using Example 212B (61 mg, 0.257 mmol) in place of 6-bromo-5-methoxypyridin-2-amine. LCMS: 502.2 (M+H)$^+$.

Example 212D

N-benzyl-4-fluoro-6-[2-(piperidin-3-yl)-1H-pyrrolo[2,3-b]pyridin-4-yl]pyridin-2-amine The title compound was prepared as the trifluoroacetate salt using the procedure described in Example 1H, using Example 212C (60 mg, 0.119 mmol) in place of Example 1G, and purified using preparative HPLC (Waters 'X'Bridge column with gradient elution from 0.1% trifluoroacetic acid in water to acetonitrile). LCMS: 402.2 (M+H)$^+$. $^1$H NMR (400 MHz, CD$_3$OD): δ 1.65-1.69 (m, 1H), 1.88-1.92 (m, 1H), 2.05-2.09 (m, 1H), 2.16-2.19 (m, 1H), 2.96-3.08 (m, 2H), 3.26-3.3.29 (m, 1H), 3.44-3.47 (m, 1H), 3.61-3.63 (m, 1H), 4.74 (s, 2H), 6.46 (dd, J=2, 11.2 Hz, 1H), 6.93 (s, 1H), 7.14 (dd, J=2, 9.2 Hz, 1H), 7.28-7.31 (m, 1H), 7.36-7.44 (m, 4H), 7.70 (d, J=5.6 Hz, 1H), 8.32 (d, J=5.6 Hz, 1H).

Example 213

N-benzyl-4-[5-chloro-2-(piperidin-3-yl)-1H-pyrrolo[2,3-b]pyridin-4-yl]pyridin-2-amine

Example 213A

N-benzyl-4-(4,4,5,5-tetramethyl-1,3,2-dioxaborolan-2-yl)pyridin-2-amine

The title compound was prepared using the procedure described in Example 6C, using N-benzyl-4-bromopyridin-2-amine (250 mg, 0.95 mmol) in place of Example 6B. LCMS: 296.7 (M+H)$^+$.

Example 213B tert-butyl 3-(4-(2-(benzylamino)pyridin-4-yl)-5-chloro-1H-pyrrolo[2,3-b]pyridin-2-yl)piperidine-1-carboxylate The title compound was prepared using the procedure described in Example 7A, using Example 213A (292 mg, 0.940 mmol) in place of Example 5A and Example 78B (300 mg, 0.723 mmol) in place of 2-bromo-4-cyclopropyl-1-methoxybenzene. LCMS: 518.2 (M+H)$^+$.

Example 213C

N-benzyl-4-[5-chloro-2-(piperidin-3-yl)-1H-pyrrolo[2,3-b]pyridin-4-yl]pyridin-2-amine The title compound was prepared as the acetate salt using the procedure described in Example 6E, using Example 213B (250 mg, 0.483 mmol) in place of Example 6D, and purified using preparative HPLC (AG/AD/PP/C-18 column with gradient elution from 10M ammonium acetate in water to 1:1 methanol/acetonitrile). LCMS: 418.1 (M+H)$^+$. $^1$H NMR (400 MHz, DMSO-d$_6$/D$_2$O): δ 1.50-1.52 (m, 2H), 1.6-1.66 (m, 1H), 1.98-2.05 (m, 1H), 2.55-2.66 (m, 2H), 2.82-2.84 (m, 1H), 2.92-2.95 (m, 1H), 3.13-3.15 (m, 1H), 4.48 (s, 2H), 5.82 (s, 1H), 6.53-6.56 (m, 2H), 7.1-7.22 (m, 1H), 7.28-7.35 (m, 4H), 8.07 (d, J=5.2 Hz, 1H), 8.17 (s, 1H).

Example 214

4-fluoro-N-(3-fluorobenzyl)-3-[2-(piperidin-3-yl)-1H-pyrrolo[2,3-b]pyridin-4-yl]aniline

Example 214A tert-butyl 3-(4-(2-fluoro-5-((3-fluorobenzyl)amino)phenyl)-1H-pyrrolo[2,3-b]pyridin-2-yl)piperidine-1-carboxylate The title compound was prepared using the procedure described in Example 1G, using Example 51B (308 mg, 0.893 mmol) in place of 5-fluoro-2-methoxyphenylboronic acid. LCMS: 519.4 (M+H)$^+$.

Example 214B 4-fluoro-N-(3-fluorobenzyl)-3-[2-(piperidin-3-yl)-1H-pyrrolo[2,3-b]pyridin-4-yl]aniline The title compound was prepared as the trifluoroacetate salt using the procedure described in Example 1H, using Example 214A (150 mg, 0.28 mmol) in place of Example 1G, and purified using preparative HPLC (Agilent XDB C-18 column with gradient elution from 0.1% trifluoroacetic acid in water to 1:1 methanol/acetonitrile). LCMS: 419.55 (M+H)$^+$. $^1$H NMR (400 MHz, CD$_3$OD): δ 1.81-1.94 (m, 2H), 2.10-2.14 (m, 1H), 2.25-2.28 (m, 1H), 3.05-3.08 (m, 1H), 3.14-3.22 (m, 1H), 3.46-3.51 (m, 2H), 3.63-3.66 (m, 1H), 4.40 (s, 2H), 6.26 (d, J=2 Hz, 1H), 6.74-6.76 (m, 1H), 6.79-6.83 (m, 1H), 7.0-7.02 (m, 1H), 7.06-7.09 (m, 1H), 7.15 (d, J=10.4 Hz, 1H), 7.23 (d, J=7.6 Hz, 1H), 7.28 (dd, J=1.2, 5.2 Hz, 1H), 7.34-7.38 (m, 1H), 8.28 (d, J=5.6 Hz, 1H).

Example 215

4-[4-(5-fluoro-2-methoxyphenyl)-1H-pyrrolo[2,3-b]pyridin-2-yl]-N-methyl-3,6-dihydropyridine-1(2H)-carboxamide To a suspension of Example 87 (70.0 mg, 0.177 mmol) in N,N-dimethylformamide (2 mL) was added n-succinimidyl-n-methylcarbamate (45.6 mg, 0.265 mmol) and triethylamine (0.148 mL, 1.06 mmol) and the mixture was stirred overnight. Water was slowly added and the solids were filtered, rinsed with water, and oven-dried to give the title compound. $^1$H NMR (400 MHz, DMSO-$d_6$) δ 2.44 (bs, 2H), 2.59 (d, J=3.3 Hz, 3H), 3.50 (t, J=5.6 Hz, 2H), 3.74 (s, 3H), 3.97-4.03 (m, 2H), 6.22-6.27 (m, 1H), 6.41-6.54 (m, 2H), 7.04 (d, J=4.9 Hz, 1H), 7.15-7.31 (m, 3H), 8.20 (d, J=4.9 Hz, 1H), 11.81 (bs, 1H) MS (ESI$^+$) m/z 381.1 (M+H)$^+$.

Example 216

4-[4-(5-fluoro-2-methoxyphenyl)-1H-pyrrolo[2,3-b]pyridin-2-yl]-3,6-dihydropyridine-1(2H)-sulfonamide Example 216A tert-butyl (4-(4-(5-fluoro-2-methoxyphenyl)-1H-pyrrolo[2,3-b]pyridin-2-yl)-5,6-dihydropyridin-1(2H)-yl)sulfonylcarbamate To a solution of Example 87 (235 mg, 0.727 mmol) in dichloromethane (10 mL) was added triethylamine (0.203 mL, 1.453 mmol) and (tert-butoxycarbonyl)((4-(dimethylamino)pyridin-1-ium-1-yl)sulfonyl)amide (219 mg, 727 mmol). The mixture was stirred at room temperature overnight and directly loaded onto a silica gel cartridge, eluting with a gradient of 0-15% methanol in dichloromethane to provide the title compound. MS (DCI/NH$_3$) m/z 503 (M+H)$^+$.

Example 216B

4-[4-(5-fluoro-2-methoxyphenyl)-1H-pyrrolo[2,3-b]pyridin-2-yl]-3,6-dihydropyridine-1(2H)-sulfonamide To a solution of Example 216A (209 mg, 0.416 mmol) in dichloromethane (5 mL) was added trifluoroacetic acid (1 mL) and the solution was stirred at room temperature for 2 hours. After concentration, the residue was dissolved in methanol (3 mL) and the crystallized material that formed was collected by filtration. The filtrate was concentrated and the residue was purified by HPLC (Zorbax, C-18 column), eluting with a gradient of 0-100% 0.1% trifluoroacetic acid in water/acetonitrile. The combined material was suspended in 1:1 methanol/dichloromethane (10 mL), treated with 2M hydrogen chloride in ether and concentrated to provide the title compound as the hydrochloride salt. $^1$H NMR (400 MHz, DMSO-$d_6$): 2.63 (m, 2H), 3.21 (t, J=5.80 Hz, 2H), 3.76 (s, 3H), 6.43 (d, J=1.53 Hz, 1H), 6.65 (s, 1H), 6.89 (s, 2H), 7.21-7.38 (m, 4H), 8.30 (d, J=5.49 Hz, 1H), 12.56 (s, 1H); MS (DCI/NH$_3$) m/z 403 (M+H)$^+$.

Example 217

N-[4-({4-[4-(5-fluoro-2-methoxyphenyl)-1H-pyrrolo[2,3-b]pyridin-2-yl]-3,6-dihydropyridin-1(2H)-yl}methyl)phenyl]acetamide To a mixture of Example 87 (80.0 mg, 0.202 mmol) and triethylamine (0.062 mL, 0.444 mmol) in dichloromethane (2 mL) and methanol (2 mL) was added acetic acid (0.058 mL, 1.009 mmol), N-(4-formylphenyl)acetamide (65.9 mg, 0.404 mmol), and MP-cyanoborohydride (Biotage, 324 mg, 2.49 mmol/g) and the mixture was stirred overnight. The solid was filtered and rinsed with dichloromethane/methanol. The filtrate was concentrated and purified by by reverse-phase HPLC on a Zorbax RX-C18 column (250×21.2 mm, 7 μm particle size) using a gradient of 10-95% acetonitrile in 0.1% aqueous trifluoroacetic acid to provide the title compound as a trifluoroacetic acid salt. $^1$H NMR (400 MHz, Methanol-$d_4$) δ 2.15 (s, 3H), 2.93 (bs, 2H), 3.59-3.73 (m, 1H), 3.79 (s, 3H), 3.98 (s, 3H), 4.43 (s, 2H), 6.45-6.51 (m, 1H), 6.62 (s, 1H), 7.16-7.29 (m, 3H), 7.40 (d, J=5.7 Hz, 1H), 7.46-7.53 (m, 2H), 7.68-7.74 (m, 2H), 8.31 (d, J=5.7 Hz, 1H). MS (ESI$^+$) m/z 471.1 (M+H)$^+$.

Example 218 tert-butyl({4-[4-(5-fluoro-2-methoxyphenyl)-1H-pyrrolo[2,3-b]pyridin-2-yl]-3,6-dihydropyridin-1(2H)-yl}sulfonyl)carbamate Example 218A (tert-butoxycarbonyl)((4-(dimethylamino)pyridin-1-ium-1-yl)sulfonyl)amide To a solution of t-butanol (2.6 mL, 27.2 mmol) in dichloromethane (20 mL) was added dropwise with ice cooling chlorosulfonyl isocyanate (2.4 mL, 27.6 mL) over 15 minutes. After stirring for 15 minutes, 4-(dimethylamino)pyridine (6.9 g, 56.5 mmol) was added, the cooling bath was removed and dichloromethane (100 mL) was added. The mixture was stirred at room temperature for 1 hour and diluted with 130 mL of dichloromethane. The mixture was washed with water and brine, dried over sodium sulfate, filtered, and concentrated in vacuo to yield the title compound as a crystalline solid. MS (DCI/NH$_3$) m/z 301 (M+H)$^+$.

Example 218B tert-butyl({4-[4-(5-fluoro-2-methoxyphenyl)-1H-pyrrolo[2,3-b]pyridin-2-yl]-3,6-dihydropyridin-1(2H)-yl}sulfonyl)carbamate To a solution of Example 87 (235 mg, 0.727 mmol) in dichloromethane (10 mL) was added triethylamine (0.203 mL, 1.453 mmol) and Example 218A (219 mg, 727 mmol). The mixture was stirred at room temperature overnight and directly loaded onto silica gel (Teledyne Combinflash Rf) eluting with a gradient of 0-15% methanol in dichloromethane to provide the title compound. $^1$H NMR (400 MHz, DMSO-$d_6$): δ 1.39 (s, 9H), 2.57 (br s, 2H), 3.46 (t, J=5.65 Hz, 2H), 3.74 (s, 3H), 4.02 (d, J=2.14 Hz, 2H), 6.26 (d, J=1.83 Hz, 1H), 6.51 (s, 1H), 7.04 (d, J=4.88 Hz, 1H), 7.17-7.31 (m, 3H), 8.21 (d, J=4.88 Hz, 1H), 11.07 (s, 1H), 11.86 (d, J=1.83 Hz, 1H). MS (DCI/NH$_3$) m/z 503 (M+H)$^+$.

Example 219

4-[4-(5-fluoro-2-methoxyphenyl)-1H-pyrrolo[2,3-b]pyridin-2-yl]cyclohex-3-ene-1-carboxylic acid

Example 219A

4-(5-fluoro-2-methoxyphenyl)-2-iodo-1H-pyrrolo[2,3-b]pyridine

To a solution of Example 87B (4 g, 7.87 mmol) in 75 mL dioxane was added 6M aqueous sodium hydroxide (13.12 mL, 79 mmol). The mixture was heated at 100° C. for 1 hour, cooled, and reduced to half volume in vacuo. The residue was diluted with 50 mL ethyl acetate, washed with saturated sodium bicarbonate and brine, dried over magnesium sulfate, filtered, and concentrated to give the title compound. LCMS: 369.53 $(M+H)^+$.

Example 219B ethyl 4-(4-(5-fluoro-2-methoxyphenyl)-1H-pyrrolo[2,3-b]pyridin-2-yl)cyclohex-3-enecarboxylate To a solution of Example 219A (500 mg, 1.358 mmol), ethyl 4-(4,4,5,5-tetramethyl-1,3,2-dioxaborolan-2-yl)cyclohex-3-enecarboxylate (495 mg, 1.766 mmol), and bis(triphenylphosphine)palladium(II) dichloride (95 mg, 0.136 mmol) in 30 mL 7:2:3 1,2-dimethoxyethane/ethanol/water was added sodium carbonate (432 mg, 4.07 mmol). The mixture was heated at 100° C. for 4 hours, cooled to room temperature, and diluted with 50 mL ethyl acetate. The mixture was washed with saturated sodium bicarbonate, water and brine, dried over magnesium sulfate, filtered, and concentrated. The residue was triturated with ethyl acetate and the solid was filtered and dried in vacuo to give the title compound. MS (ESI): 395.2 $(M+H)^+$.

Example 219C

4-[4-(5-fluoro-2-methoxyphenyl)-1H-pyrrolo[2,3-b]pyridin-2-yl]cyclohex-3-ene-1-carboxylic acid To a solution of Example 219B (350 mg, 0.887 mmol) in 10 mL dioxane was added 6M aqueous sodium hydroxide (1.479 mL, 8.87 mmol). The mixture was heated at 50° C. for 12 hours, cooled and diluted with 25 mL water. The basic aqueous layer was extracted with ethyl acetate (twice) and the organics were discarded. To the basic aqueous layer was added 25 mL ethyl acetate and the aqueous layer made slightly acidic with 2.5M hydrochloric acid. The aqueous layer was extracted with ethyl acetate (twice) and the combined organics were washed with brine, dried over magnesium sulfate, filtered and concentrated to give the title compound. $^1$H NMR (400 MHz, DMSO-$d_6$) δ 1.60-1.77 (m, 1H) 1.99-2.12 (m, 1H) 2.28-2.46 (m, 3H) 2.53 (dd, J=7.78, 2.90 Hz, 2H) 3.62-3.89 (m, 3H) 6.18 (d, J=1.83 Hz, 1H) 6.53 (s, 1H) 7.02 (d, J=4.88 Hz, 1H) 7.08-7.42 (m, 3H) 8.17 (d, J=4.88 Hz, 1H) 11.73 (d, J=1.53 Hz, 1H) 11.96-12.37 (m, J=2.44 Hz, 1H); MS (ESI): 367.2 $(M+H)^+$.

Example 220

4-(2,3-difluorophenyl)-2-[1-(methylsulfonyl)-1,2,3,6-tetrahydropyridin-4-yl]-1H-pyrrolo[2,3-b]pyridine

Example 220A

4-bromo-1-tosyl-1H-pyrrolo[2,3-b]pyridine

To a suspension of 4-bromo-1H-pyrrolo[2,3-b]pyridine (15 g, 76 mmol) and p-toluenesulfonyl chloride (21.77 g, 114 mmol) in toluene (200 mL) was added a solution of tetrabutylammonium hydrogen sulfate (2.58 g, 7.61 mmol) in water (10 mL) and the mixture was cooled to 0° C. A solution of sodium hydroxide (9.13 g, 228 mmol) in water (30 mL) was added and the mixture was stirred at room temperature overnight. The mixture was diluted with ethyl acetate and the solution was washed with saturated sodium chloride. The organic layer was dried over sodium sulfate, filtered and concentrated to give the title compound. MS (CI) m/z 352 $(M+H)^+$.

Example 220B

4-bromo-2-iodo-1-tosyl-1H-pyrrolo[2,3-b]pyridine

To a solution of Example 220A (25 g, 71.2 mmol) in tetrahydrofuran (600 mL) at −78° C. was added slowly 2M lithium diisopropylamide (39.1 mL, 78 mmol) and the mixture was stirred at −78° C. for 1 hour. A solution of iodine (19.87 g, 78 mmol) in tetrahydrofuran (100 mL) was added slowly and the reaction was allowed to warm to room temperature gradually. The reaction mixture was stirred at room temperature for 3 hours and was quenched with saturated aqueous sodium thiosulfate, water and ethyl acetate. The aqueous layer was extracted with ethyl acetate and the combined organics were dried over sodium sulfate, filtered and concentrated to give the title compound. MS (CI) m/z 477 $(M+H)^+$.

Example 220C tert-butyl 4-(4-bromo-1-tosyl-1H-pyrrolo[2,3-b]pyridin-2-yl)-5,6-dihydropyridine-1(2H)-carboxylate To as solution of Example 220B (20 g, 41.9 mmol), tert-butyl 4-(4,4,5,5-tetramethyl-1,3,2-dioxaborolan-2-yl)-5,6-dihydropyridine-1(2H)-carboxylate (16.85 g, 54.5 mmol), and tetrakis(triphenylphosphine)palladium (4.84 g, 4.19 mmol) in N,N-dimethylformamide (500 mL) was added a solution of sodium bicarbonate (7.04 g, 84 mmol) in water (40 mL) and the mixture was stirred at 80° C. for 12 hours. The reaction was quenched by the addition of saturated aqueous sodium thiosulfate, water and ethyl acetate. The aqueous layer was extracted with ethyl acetate and the combined organics were dried over sodium sulfate, filtered and concentrated to give the title compound. MS (CI) m/z 532 $(M+H)^+$.

Example 220D

4-bromo-2-(1,2,3,6-tetrahydropyridin-4-yl)-1-tosyl-1H-pyrrolo[2,3-b]pyridine A mixture of Example 220C (8 g, 15.02 mmol) and trifluoroacetic acid (11.58 mL, 150 mmol) in dichloromethane (100 mL) was stirred at 20° C. for 12 hours. The mixture was concentrated to give the title compound as a trifluoroacetate salt. MS (CI) m/z 432 $(M+H)^+$.

Example 220E

4-bromo-2-(1-(methylsulfonyl)-1,2,3,6-tetrahydropyridin-4-yl)-1-tosyl-1H-pyrrolo[2,3-b]pyridine A mixture of Example 220D (6 g, 13.88 mmol) and triethylamine (9.67 mL, 69.4 mmol) in N,N-dimethylformamide (150 mL) was cooled to 0° C. in an ice bath. Methanesulfonyl chloride (2.16 mL, 27.8 mmol) was added and the mixture was stirred at 0° C. for 2 hours. The mixture was diluted with water and filtered and the precipitate was washed with water to give the title compound. MS (CI) m/z 511 (M+H)+.

Example 220F

4-bromo-2-(1-(methylsulfonyl)-1,2,3,6-tetrahydropyridin-4-yl)-1H-pyrrolo[2,3-b]pyridine To a solution of Example 220E (6.5 g, 12.73 mmol) in 1,4-dioxane (50 mL) was added a solution of sodium hydroxide (1.528 g, 38.2 mmol) in water (5 mL) and the mixture was stirred at 60° C. for 12 hours. The mixture was concentrated and the residue was suspended in water and N,N-dimethylformamide. The mixture was filtered and the solid was washed with ethyl acetate to give the title compound. MS (CI) m/z 356 (M+H)+.

Example 220G

4-(2,3-difluorophenyl)-2-[1-(methylsulfonyl)-1,2,3,6-tetrahydropyridin-4-yl]-1H-pyrrolo[2,3-b]pyridine A mixture of Example 220F (120 mg, 0.337 mmol), (2,3-difluorophenyl)boronic acid (53.2 mg, 0.337 mmol), sodium carbonate (89 mg, 0.842 mmol), and [1,1'-bis(diphenylphosphino)ferrocene]dichloropalladium(II)-dichloromethane adduct (27.5 mg, 0.034 mmol) in toluene (4 mL), water (1 mL), and butan-1-ol (2 mL) was degassed with nitrogen and the mixture was heated at 100° C. for 3 hours. The solvent was removed under reduced pressure and the residue was purified by reverse-phase HPLC on a SunFire C18 column using a gradient of 25-52% acetonitrile in 0.05% aqueous trifluoroacetic acid to give the title compound as a trifluoroacetate salt. $^1$H NMR (400 MHz, DMSO-$d_6$) δ 2.63 (s, 2H), 2.95 (s, 3H), 3.36 (t, J=5.6 Hz, 2H), 3.92 (d, J=2.0 Hz, 2H), 6.42 (s, 1H), 6.58 (s, 1H), 7.14 (d, J=5.2 Hz, 1H), 7.38-7.41 (m, 1H), 7.44-7.47 (m, 1H), 7.55-7.58 (m, 1H), 8.29 (d, J=5.2 Hz, 1H), 12.07 (s, 1H). MS (ESI+) m/z 390.1 (M+H)+.

Example 221

3-{4-[4-(5-fluoro-2-methoxyphenyl)-1H-pyrrolo[2,3-b]pyridin-2-yl]-3,6-dihydropyridin-1(2H)-yl}-3-oxopropanenitrile The title compound was prepared essentially as described in Example 100, substituting 2-cyanoacetic acid for acetic acid. The crude compound was purified by reverse-phase HPLC performed on a Zorbax RX-C18 column using a gradient of 15-100% methanol in 0.1% aqueous trifluoroacetic acid to afford the title compound as a trifluoroacetate salt. $^1$H NMR (400 MHz, DMSO-$d_6$) δ 2.46-2.49 (m, 1H), 2.60 (bs, 1H), 3.55 (t, J=5.7 Hz, 1H), 3.67 (t, J=5.7 Hz, 1H), 3.74 (d, J=1.3 Hz, 3H), 4.09 (s, 1H), 4.14-4.18 (m, 3H), 6.31 (dd, J=5.2, 2.0 Hz, 1H), 6.52 (dt, J=6.5, 3.5 Hz, 1H), 7.10 (dd, J=5.1, 3.5 Hz, 1H), 7.15-7.39 (m, 3H), 8.24 (d, J=5.0 Hz, 1H), 11.89-12.19 (m, 1H). MS (ESI+) m/z 391.2 (M+H)+.

Example 222

4-[4-(2,3-difluorophenyl)-1H-pyrrolo[2,3-b]pyridin-2-yl]-N-methyl-3,6-dihydropyridine-1(2H)-carboxamide

Example 222A tert-butyl 4-(4-(2,3-difluorophenyl)-1-tosyl-1H-pyrrolo[2,3-b]pyridin-2-yl)-5,6-dihydropyridine-1(2H)-carboxylate A mixture of Example 220C (750.0 mg, 1.409 mmol), (2,3-difluorophenyl)boronic acid (267 mg, 1.690 mmol), bis(triphenylphosphine)palladium(II)dichloride (39.5 mg, 0.056 mmol), and 1M sodium carbonate (1409 μL, 1.409 mmol) in 10 mL 1,2-dimethoxyethane/ethanol/water (7:2:3) was heated in a Biotage Initiator microwave reactor at 150° C. for 15 minutes. The mixture was concentrated, treated with ethyl acetate and washed with aqueous sodium bicarbonate. The organic layer was washed with water, dried over magnesium sulfate, filtered, concentrated and purified on silica gel using an ISCO Companion eluting with heptanes/ethyl acetate (7:3 to 6:4) to give the title compound. MS (ESI+) m/z 566.1 (M+H)+.

Example 222B tert-butyl 4-(4-(2,3-difluorophenyl)-1H-pyrrolo[2,3-b]pyridin-2-yl)-5,6-dihydropyridine-1(2H)-carboxylate A mixture Example 222A (0.820 g, 1.450 mmol) and 5M sodium hydroxide (1.015 mL, 5.07 mmol) in dioxane (10 mL) was heated at 90° C. for 7 hours. The mixture was concentrated and the residue was treated with ethyl acetate and washed with aqueous sodium bicarbonate. The organic layer was dried over magnesium sulfate, filtered, and concentrated until most of solvent was removed. The precipitate was filtered, washed with ethyl acetate/ether, and dried under vacuum to give the title compound. MS (ESI+) m/z 412.1 (M+H)+.

Example 222C

4-(2,3-difluorophenyl)-2-(1,2,3,6-tetrahydropyridin-4-yl)-1H-pyrrolo[2,3-b]pyridine A solution of Example 222B (0.255 g, 0.620 mmol) in dichloromethane (5 mL) was treated with trifluoroacetic acid (0.477 mL, 6.20 mmol) and the mixture was stirred for 3 hours and concentrated. The residue was dissolved in 2 mL methanol and treated slowly with 2 mL 2M hydrogen chloride in ether. The suspension was diluted with ether and stirred for 10 minutes. The solids were filtered, washed with ether, and dried to give the title compound as a hydrochloride salt. MS (ESI+) m/z 312.1 (M+H)+.

Example 222D

4-[4-(2,3-difluorophenyl)-1H-pyrrolo[2,3-b]pyridin-2-yl]-N-methyl-3,6-dihydropyridine-1(2H)-carboxamide To a suspension of Example 222C (72.0 mg, 0.187 mmol) and N-succinimidyl-N-methylcarbamate (48.4 mg, 0.281 mmol) in dimethylformamide (2.5 mL) was added triethylamine (0.157 mL, 1.124 mmol) and the mixture was stirred for 3 hours and treated slowly with water. The precipitate was filtered, washed with water, dried over magnesium sulfate, filtered, and purified by HPLC (same protocol as Example 221) to give the title compound as a trifluoroacetate salt. $^1$H NMR (400 MHz, Methanol-$d_4$) δ 2.56-2.62 (m, 2H), 2.76 (s, 3H), 3.63 (t, J=5.6 Hz, 2H), 4.13 (q, J=2.8 Hz, 2H), 6.48-6.54 (m, 1H), 6.57 (d, J=2.1 Hz, 1H), 7.29-7.53 (m, 4H), 8.31 (d, J=5.6 Hz, 1H). MS (ESI$^+$) m/z 369.1 (M+H)$^+$.

Example 223

4-(5-fluoro-2-methoxyphenyl)-2-[8-(methylsulfonyl)-8-azabicyclo[3.2.1]oct-2-en-3-yl]-1H-pyrrolo[2,3-b]pyridine Example 223A tert-butyl 3-(((trifluoromethyl)sulfonyl)oxy)-8-azabicyclo[3.2.1]oct-3-ene-8-carboxylate To a solution of tert-butyl 3-oxo-8-azabicyclo[3.2.1]octane-8-carboxylate (10 g, 44.4 mmol) in tetrahydrofuran (100 mL) was added 2M lithium diisopropylamide (26.6 mL, 53.3 mmol) dropwise at −60° C. under argon and the mixture was stirred at −60° C. for 1 hour. A solution of 1,1,1-trifluoro-N-phenyl-N-((trifluoromethyl)sulfonyl)methanesulfonamide (17.44 g, 48.8 mmol) in tetrahydrofuran (100 mL) was added dropwise at −60° C. and the mixture was stirred at −60° C. for 30 minutes, and was allowed to warm to room temperature. The mixture was stirred under argon overnight, quenched with water (200 mL), and extracted with ethyl acetate (three times). The organic extracts were washed with 5% aqueous citric acid (twice) and stirred with 1M aqueous sodium hydroxide (200 mL) for 30 minutes. The wash process was repeated one additional time. The organic phase was dried over sodium sulfate, filtered, concentrated, and purified by flash chromatography on silica gel using an ISCO Companion eluting with ethyl acetate/petroleum ether (1:20) to give the title compound.

Example 223B tert-butyl 3-(4,4,5,5-tetramethyl-1,3,2-dioxaborolan-2-yl)-8-azabicyclo[3.2.1]oct-3-ene-8-carboxylate A mixture of Example 223A (10 g, 28.0 mmol), 4,4,4',4',5,5,5',5'-octamethyl-2,2'-bi(1,3,2-dioxaborolane) (7.82 g, 30.8 mmol), potassium acetate (7.42 g, 76 mmol), and [1,1'-bis(diphenylphosphino)ferrocene]dichloropalladium(II)-dichloromethane adduct (1.024 g, 1.399 mmol) in 1,4-dioxane (500 mL) was degassed with argon and the mixture was stirred at 80° C. under argon overnight. The mixture was cooled to room temperature and filtered. The filtrate was concentrated in vacuo and the residue was purified by flash chromatography on silica gel using an ISCO Companion eluting with ethyl acetate/petroleum ether (1:50 to 1:20) to give the title compound. MS (DCI$^+$) m/z 336.2 (M+H)$^+$.

Example 223C 2-(8-azabicyclo[3.2.1]oct-2-en-3-yl)-4-(5-fluoro-2-methoxyphenyl)-1H-pyrrolo[2,3-b]pyridine The title compound was prepared essentially as described in Example 87C and 87, substituting Example 223B for tert-butyl 4-(4,4,5,5-tetramethyl-1,3,2-dioxaborolan-2-yl)-5,6-dihydropyridine-1(2H)-carboxylate in Example 87C. MS (ESI$^+$) m/z 350.1 (M+H)$^+$.

Example 223D 4-(5-fluoro-2-methoxyphenyl)-2-[8-(methylsulfonyl)-8-azabicyclo[3.2.1]oct-2-en-3-yl]-1H-pyrrolo[2,3-b]pyridine To a solution of Example 223C (80.0 mg, 0.189 mmol) in N,N-dimethylformamide (2 mL) was added methanesulfonyl chloride (0.030 mL, 0.379 mmol) and triethylamine (0.158 mL, 1.137 mmol) and the mixture was stirred for 3 hours. The mixture was treated with brine and aqueous sodium bicarbonate and extracted with ethyl acetate (twice). The combined organic layers were dried over magnesium sulfate, filtered, concentrated, and purified on silica gel using an ISCO Companion eluting with heptanes/ethyl acetate (1:9 to 0:10) to give the title compound. $^1$H NMR (400 MHz, DMSO-$d_6$) δ 1.63-1.74 (m, 1H), 1.91-2.14 (m, 2H), 2.15-2.27 (m, 1H), 2.92-3.00 (m, 4H), 3.74 (s, 3H), 4.32-4.40 (m, 1H), 4.44 (t, J=5.8 Hz, 1H), 6.22 (s, 1H), 6.79 (d, J=6.0 Hz, 1H), 7.03 (d, J=4.9 Hz, 1H), 7.15-7.31 (m, 3H), 8.20 (d, J=4.9 Hz, 1H), 11.73-11.86 (m, 1H). MS (ESI$^+$) m/z 428.1 (M+H)$^+$.

Example 224

2-{4-[4-(5-fluoro-2-methoxyphenyl)-1H-pyrrolo[2,3-b]pyridin-2-yl]-3,6-dihydropyridin-1(2H)-yl}-N,N-dimethylacetamide A suspension of Example 87 (0.05 g, 0.126 mmol) and triethylamine (0.088 mL, 0.631 mmol) in N,N-dimethylformamide (1.051 mL) was treated with 2-chloro-N,N-dimethylacetamide (0.018 g, 0.145 mmol) and the mixture was heated at 75° C. for 4 hours. The mixture was purified by reverse phase HPLC on a Phenomenex Luna C8(2) 5 um 100 Å AXIA column eluting with a gradient of 10-70% acetonitrile in 0.1% trifluoroacetic acid/water to afford the title compound as the trifluoroacetate salt. $^1$H NMR (400 MHz, CD$_3$OD) δ 2.94-3.07 (m, 8H), 3.42-3.77 (m, 2H), 3.82 (s, 3H), 4.02-4.25 (m, 2H), 4.36 (s, 2H), 6.48-6.57 (m, 1H), 6.70 (s, 1H), 7.17-7.34 (m, 3H), 7.48 (d, J=5.9 Hz, 1H), 8.34 (d, J=5.9 Hz, 1H). MS (ESI$^+$) m/z 409.0 (M+H)$^+$.

Example 225

4-[4-(5-fluoro-2-methoxyphenyl)-1H-pyrrolo[2,3-b]pyridin-2-yl]-N-(1-methyl-1H-pyrazol-4-yl)-3,6-dihydropyridine-1(2H)-carboxamide A solution of 1-methyl-1H-pyrazol-4-amine (0.0105 g, 0.108 mmol), bis(2,5-dioxopyrrolidin-1-yl) carbonate (0.035 g, 0.135 mmol), and pyridine (8.73 µL, 0.108 mmol) in N,N-dimethylformamide (0.3 mL) was stirred at ambient temperature for 2 hours. N-ethyl-N-isopropylpropan-2-amine (0.056 mL, 0.324 mmol) was added and the solution was added to a suspension of Example 87 (0.043 g, 0.108 mmol) and N-ethyl-N-isopropylpropan-2-amine (0.075 mL, 0.432 mmol) in N,N-dimethylformamide (0.5 mL) dropwise over 3 minutes. The mixture was stirred for 16 hours at ambient temperature and purified by reverse phase HPLC on a Phenomenex Luna C8(2) 5 um 100 Å AXIA column eluting with a gradient of 10-70% acetonitrile in 0.1% trifluoroacetic acid/water to afford the title compound as the trifluoroacetate salt.

¹H NMR (400 MHz, DMSO-d₆) δ 2.47-2.53 (m, 2H), 3.58-3.64 (m, 2H), 3.75 (s, 3H), 3.76 (s, 3H), 4.10-4.18 (m, 2H), 6.29-6.33 (m, 1H), 6.54-6.59 (m, 1H), 7.09 (d, J=5.0 Hz, 1H), 7.18-7.32 (m, 3H), 7.33-7.37 (m, 1H), 7.65-7.69 (m, 1H), 8.23 (d, J=5.1 Hz, 1H), 8.51-8.56 (m, 1H), 11.94-12.01 (m, 1H). MS (ESI⁺) m/z 447.1 (M+H)⁺.

Example 226

{4-[4-(5-fluoro-2-methoxyphenyl)-1H-pyrrolo[2,3-b]pyridin-2-yl]-3,6-dihydropyridin-1(2H)-yl}acetic acid Example 226A tert-butyl 2-(4-(4-(5-fluoro-2-methoxyphenyl)-1H-pyrrolo[2,3-b]pyridin-2-yl)-5,6-dihydropyridin-1(2H)-yl)acetate A mixture of Example 87 (0.5 g, 1.262 mmol) and triethylamine (0.879 mL, 6.31 mmol) in N,N-dimethylformamide (12.62 mL) was treated with tert-butyl 2-bromoacetate (0.214 mL, 1.451 mmol) and the mixture was heated at 75° C. for 4 hours. The mixture was cooled to ambient temperature and poured into water. The suspension was filtered and the solid was washed with water (twice) and dried under vacuum. Purification by flash chromatography on silica gel (AnaLogix IntelliFlash 280) eluting with a gradient of 0-6% methanol in dichloromethane afforded the title compound. MS (ESI⁺) m/z 438.1 (M+H)⁺.

Example 226B

{4-[4-(5-fluoro-2-methoxyphenyl)-1H-pyrrolo[2,3-b]pyridin-2-yl]-3,6-dihydropyridin-1(2H)-yl}acetic acid A solution of Example 226A (0.43 g, 0.983 mmol) and trifluoroacetic acid (1.817 mL, 23.59 mmol) in dichloromethane (9.83 mL) was stirred at ambient temperature for 24 hours. The mixture was concentrated, dissolved in 5 mL dichloromethane and 2N hydrogen chloride in ether (20 mL) was added. The suspension was stirred for 20 minutes, treated with ether (50 mL), and filtered. The solid was washed with ether and dried under vacuum to afford the title compound as a hydrochloride salt. ¹H NMR (400 MHz, DMSO-d₆) δ 2.84-2.92 (m, 2H), 3.50-3.63 (m, 2H), 3.74 (s, 3H), 4.03-4.11 (m, 2H), 4.14 (s, 2H), 6.40 (s, 1H), 6.46-6.56 (m, 1H), 7.13 (d, J=5.2 Hz, 1H), 7.16-7.29 (m, 3H), 8.26 (d, J=5.1 Hz, 1H), 12.07 (bs, 1H). MS (ESI⁺) m/z 382.1 (M+H)⁺.

Example 227

2-{4-[4-(5-fluoro-2-methoxyphenyl)-1H-pyrrolo[2,3-b]pyridin-2-yl]-3,6-dihydropyridin-1(2H)-yl}acetamide The title compound was prepared according to the procedure described in Example 224 substituting 2-bromoacetamide for 2-chloro-N,N-dimethylacetamide. ¹H NMR (400 MHz, CD₃OD) δ 2.90-3.02 (m, 2H), 3.52-3.74 (m, 2H), 3.81 (s, 3H), 4.01-4.22 (m, 4H), 6.46-6.54 (m, 1H), 6.65 (s, 1H), 7.15-7.32 (m, 3H), 7.41 (d, J=5.8 Hz, 1H), 8.32 (d, J=5.7 Hz, 1H). MS (ESI⁺) m/z 381.1 (M+H)⁺.

Example 228 ethyl({4-[4-(5-fluoro-2-methoxyphenyl)-1H-pyrrolo[2,3-b]pyridin-2-yl]-3,6-dihydropyridin-1(2H)-yl}sulfonyl)carbamate The title compound was prepared essentially as described in Example 218, substituting ethanol for t-butanol in Example 218A. ¹H NMR (400 MHz, DMSO-d₆): δ 1.15 (t, J=7.17 Hz, 3H), 2.58 (s, 2H), 3.47 (t, J=5.65 Hz, 2H), 3.74 (s, 3H), 4.02 (d, J=2.14 Hz, 2H), 4.07 (q, J=7.22 Hz, 2H), 6.26 (d, J=1.83 Hz, 1H), 6.50 (s, 1H), 7.04 (d, J=4.88 Hz, 1H), 7.17-7.30 (m, 3H), 8.21 (d, J=4.88 Hz, 1H), 11.37 (s, 1H), 11.86 (d, J=1.22 Hz, 1H). MS (DCI/NH₃) m/z 475 (M+H)⁺.

Example 229

4-[5-chloro-4-(5-fluoro-2-methoxyphenyl)-1H-pyrrolo[2,3-b]pyridin-2-yl]-N-methyl-3,6-dihydropyridine-1(2H)-carboxamide Example 229A 4,5-dichloro-1-tosyl-1H-pyrrolo[2,3-b]pyridine To 60% sodium hydride in mineral oil (1.390 g, 34.8 mmol) in N,N-dimethylformamide (60 mL) at 0° C. was added a solution of 4,5-dichloro-1H-pyrrolo[2,3-b]pyridine (Adesis, 5.0 g, 26.7 mmol) in N,N-dimethylformamide (20 mL) slowly over 5 minutes. The mixture was allowed to warm to room temperature and was stirred for 30 minutes. The mixture was cooled to 0° C. and a solution of p-toluenesulfonyl chloride (5.35 g, 28.1 mmol) in N,N-dimethylformamide (20 mL) was added. The mixture was allowed to warm to room temperature and stirred for 2 hours. Additional p-toluenesulfonyl chloride (500 mg, 2.62 mmol) was added, and the mixture was stirred another 1 hour at room temperature. The reaction was quenched with saturated aqueous ammonium chloride (25 mL) and extracted with ethyl acetate (twice). The combined organic layers were washed with water and brine, dried over sodium sulfate, filtered and concentrated. The residue was purified by flash chromatography on silica gel (AnaLogix IntelliFlash 280) eluting with a gradient of 40-70% ethyl acetate in hexanes to afford the title compound. MS (ESI⁺) m/z 341.6 (M+H)⁺.

Example 229B 4,5-dichloro-2-iodo-1-tosyl-1H-pyrrolo[2,3-b]pyridine

To a solution of diisopropylamine (4.85 mL, 34.1 mmol) in tetrahydrofuran (50 mL) at −10° C. under nitrogen was added dropwise 2.5M n-butyllithium in hexane (13.62 mL, 34.1 mmol) and the mixture was stirred at −10° C. for 30 minutes. A solution of Example 229A (8.3 g, 24.33 mmol) in tetrahydrofuran (220 mL) cooled to −78° C. was treated with the lithium diisopropylamide solution dropwise over 20 minutes and the mixture was stirred for 50 minutes at −78° C. A solution of iodine (8.64 g, 34.1 mmol) in tetrahydrofuran (30 mL) was added and the mixture was stirred for 20 minutes at −78° C. and allowed to warm to room temperature. The reaction was quenched with saturated aqueous sodium thiosulfate and extracted with ethyl acetate (150 mL). The organic layer was washed with water and brine, dried over sodium sulfate, filtered, and concentrated. The residue was purified by flash chromatography on silica gel (AnaLogix IntelliFlash 280) eluting with a gradient of 30-60% ethyl acetate in hexanes. The solid was triturated with 100 mL 15% ethyl acetate/hexane, filtered and dried under vacuum to afford the title compound. MS (ESI$^+$) m/z 466.7 (M+H)$^+$.

Example 229C tert-butyl 4-(4,5-dichloro-1-tosyl-1H-pyrrolo[2,3-b]pyridin-2-yl)-5,6-dihydropyridine-1(2H)-carboxylate A mixture of Example 229B (0.808 g, 1.730 mmol), tert-butyl 4-(4,4,5,5-tetramethyl-1,3,2-dioxaborolan-2-yl)-5,6-dihydropyridine-1(2H)-carboxylate (Frontier Scientific, 0.588 g, 1.903 mmol) and sodium hydrogencarbonate (0.436 g, 5.19 mmol) in degassed N,N-dimethylformamide (10.81 mL) and water (3.6 mL) was treated with bis(triphenylphosphine)palladium(II) chloride (0.121 g, 0.173 mmol) under nitrogen and the mixture was heated at 72° C. for 24 hours. The mixture was cooled to ambient temperature, suspended in 80 mL water, stirred for 30 minutes and filtered. Purification by flash chromatography on silica gel (AnaLogix IntelliFlash 280) eluting with a gradient of 0-20% ethyl acetate in hexanes afforded the title compound. MS (ESI$^+$) m/z 522.2 (M+H)$^+$.

Example 229D tert-butyl 4-(5-chloro-4-(5-fluoro-2-methoxyphenyl)-1-tosyl-1H-pyrrolo[2,3-b]pyridin-2-yl)-5,6-dihydropyridine-1(2H)-carboxylate A mixture of Example 229C (0.16 g, 0.306 mmol), (5-fluoro-2-methoxyphenyl)boronic acid (0.062 g, 0.368 mmol) and sodium hydrogencarbonate (0.103 g, 1.225 mmol) in degassed N,N-dimethylformamide (2.55 mL) and water (0.851 mL) was treated with 1,1'-bis(di-t-butylphosphino)ferrocenepalladium dichloride (TCI, 0.014 g, 0.021 mmol) under nitrogen and the mixture was heated at 110° C. for 10 minutes in a Biotage Initiator microwave reactor. Water and ethyl acetate was added and the aqueous layer was extracted with ethyl acetate. The combined organic layers were washed with brine, dried over sodium sulfate, filtered, and concentrated. Purification by flash chromatography on silica gel (AnaLogix IntelliFlash 280) eluting with a gradient of 0-45% ethyl acetate in heptanes afforded the title compound. MS (ESI$^+$) m/z 612.2 (M+H)$^+$.

Example 229E tert-butyl 4-(5-chloro-4-(5-fluoro-2-methoxyphenyl)-1H-pyrrolo[2,3-b]pyridin-2-yl)-5,6-dihydropyridine-1(2H)-carboxylate A mixture of Example 229D (0.16 g, 0.261 mmol) and 3N sodium hydroxide (0.261 mL, 0.784 mmol) in 1,4-dioxane (1.743 mL), ethanol (1.743 mL) and water (0.7 mL) was heated at 75° C. for 2.5 hours. The mixture was concentrated and the residue was partitioned in ethyl acetate and water. The organic layer was dried over sodium sulfate, filtered, and concentrated. Purification by flash chromatography on silica gel (AnaLogix IntelliFlash 280) eluting with a gradient of from 0-4% methanol in dichloromethane afforded the title compound. MS (ESI$^+$) m/z 458.1 (M+H)$^+$.

Example 229F 5-chloro-2-(1-ethyl-1,2,3,6-tetrahydropyridin-4-yl)-4-(5-fluoro-2-methoxyphenyl)-1H-pyrrolo[2,3-b]pyridine A solution of Example 229E (0.072 g, 0.157 mmol) in dichloromethane (1.429 mL) was treated with 2,2,2-trifluoroacetic acid (0.121 mL, 1.572 mmol) and the mixture was stirred at room temperature for 8 hours. The mixture was concentrated and the residue was partitioned in ethyl acetate and saturated aqueous sodium bicarbonate. The aqueous layer was back-extracted with additional ethyl acetate and the combined organic layers were washed with brine, dried over sodium sulfate, filtered, and concentrated to provide the title compound. MS (ESI$^+$) m/z 358.1 (M+H)$^+$.

Example 229G

4-[5-chloro-4-(5-fluoro-2-methoxyphenyl)-1H-pyrrolo[2,3-b]pyridin-2-yl]-N-methyl-3,6-dihydropyridine-1(2H)-carboxamide A solution of Example 229F (0.049 g, 0.137 mmol) and triethylamine (0.057 mL, 0.411 mmol) in N,N-dimethylformamide (1.4 mL) was treated with 2,5-dioxopyrrolidin-1-yl methylcarbamate (0.035 g, 0.205 mmol) and the mixture was stirred at room temperature for 16 hours. The mixture was poured into water and the solid was filtered and dried under vacuum to afford the title compound. $^1$H NMR (500 MHz, DMSO-d$_6$) δ 2.32-2.43 (m, 2H), 2.58 (d, J=4.3 Hz, 3H), 3.46 (t, J=5.7 Hz, 2H), 3.70 (s, 3H), 3.96-4.03 (m, 2H), 6.01-6.08 (m, 1H), 6.40-6.47 (m, 1H), 6.47-6.55 (m, 1H), 7.14 (dd, J=8.6, 3.1 Hz, 1H), 7.20 (dd, J=9.2, 4.5 Hz, 1H), 7.26-7.39 (m, 1H), 8.24 (s, 1H), 12.03 (bs, 1H). MS (ESI$^+$) m/z 415.1 (M+H)$^+$.

Example 230

4-(5-fluoro-2-methoxyphenyl)-2-[1-(5-methylsulfonimidoyl)-1,2,3,6-tetrahydropyridin-4-yl]-1H-pyrrolo[2,3-b]pyridine Example 230A N-[{4-[4-(5-fluoro-2-methoxyphenyl)-1H-pyrrolo[2,3-b]pyridin-2-yl]-3,6-dihydropyridin-1(2H)-yl}(methyl)oxido-λ$^6$-sulfanylidene]-4-methylbenzenesulfonamide To a solution of Example 87 (200 mg, 0.618 mmol) in dichloromethane (20 mL) was added triethylamine (0.259 mL, 0.188 mmol) and N-tosylmethanesulfonimidoyl chloride (SynChem, 331 mg, 1.237 mmol) at room temperature and the mixture was heated at 50° C. overnight. After cooling, the solid was filtered, washed with dichloromethane and dried in vacuo to provide the title compound. MS (DCI/NH$_3$) m/z 555 (M+H)$^+$.

Example 230B 4-(5-fluoro-2-methoxyphenyl)-2-[1-(5-methylsulfonimidoyl)-1,2,3,6-tetrahydropyridin-4-yl]-1H-pyrrolo[2,3-b]pyridine To a suspension of sodium (140 mg, 6.09 mmol) in anhydrous 1,2-dimethoxyethane (10 mL) was added anthracene (1.08 g, 6.09 mmol) and the suspension was placed in an ultrasonic cleaner overnight to form a blue solution. A solution of Example 230A (220 mg, 0.395 mmol) in 1,2-dimethyoxyethane (6 mL) was added dropwise to the freshly prepared sodium anthracenide solution at 0° C. After addition, the mixture was stirred at 0° C. for 30 minutes and quenched with water and 2N aqueous hydrochloric acid (5 mL) at 0° C. The cooling bath was removed, and the mixture was partitioned between ethyl acetate and brine. The aqueous phase was made basic with aqueous sodium hydroxide, extracted with ethyl acetate, and the combined organic phase was washed with water and concentrated. The residue was purified by flash chromatography (Teledyne Combinflash Rf) on silica (0-15% methanol in dichloromethane) and further purified by HPLC (Zorbax, C-18, eluting with a 0-100% gradient of 0.1% trifluoroacetic acid in water/0.1% trifluoroacetic acid in acetonitrile) to provide the title compound as the trifluoroacetate salt. $^1$H NMR (400 MHz, CD$_3$OD): δ 2.77 (s, 2H), 3.34 (s, 3H), 3.60-3.66 (m, 1H), 3.68-3.75 (m, 1H), 3.81 (s, 3H), 4.17-4.20 (m, J=3.05 Hz, 2H), 6.56-6.58 (m, 2H), 7.20-7.29 (m, 3H), 7.42 (d, J=5.80 Hz, 1H), 8.29 (d, J=5.80 Hz, 1H). MS (DCI/NH$_3$) m/z 401 (M+H)$^+$.

Example 231

2-{4-[5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide Example 231A 4-chloro-5-fluoro-1-(phenylsulfonyl)-1H-pyrrolo[2,3-b]pyridine To a solution of 4-chloro-5-fluoro-1H-pyrrolo[2,3-b]pyridine (Adesis, 4.60 g, 27.0 mmol) in N,N-dimethylformamide (70 mL) was added 60% sodium hydride in mineral oil (1.186 g, 29.7 mmol) at 0° C. and the mixture was warmed to room temperature and stirred for 30 minutes. Benzenesulfonyl chloride (3.79 mL, 29.7 mmol) was added and after stirring 3 hours, the mixture was quenched with water and aqueous sodium bicarbonate. The suspension was filtered, washed with aqueous sodium bicarbonate, water, and heptanes, and vacuum oven-dried to give the title compound. MS (ESI$^+$) m/z 311.0 (M+H)$^+$.

Example 231B 4-chloro-5-fluoro-2-iodo-1-(phenylsulfonyl)-1H-pyrrolo[2,3-b]pyridine To a solution of Example 231A (3.560 g, 11.46 mmol) in tetrahydrofuran (75 mL) at 78° C. was added dropwise 2M lithium diisopropylamide in tetrahydrofuran/heptane/ethylbenzene (11.46 mL, 22.91 mmol). The mixture was stirred at −78° C. for 30 minutes and iodine (5.82 g, 22.91 mmol) in tetrahydrofuran (25 mL) was added. After stirring at −78° C. for 3 hours, the reaction was quenched with aqueous sodium thiosulfate and extracted with ethyl acetate (twice). The combined organic layers were dried over magnesium sulfate, filtered, concentrated until most solvent was removed. The suspension was diluted with ethyl acetate and warmed with a heat gun. Heptanes were added to the suspension and the mixture was stirred for 1 hour. The solid was filtered, washed with heptanes/ethyl acetate (1:1), and vacuum oven-dried to give the title compound. The filtrate was concentrated and triturated with heptanes/ethyl acetate (1:1) to give additional title compound. MS (ESI$^+$) m/z 436.9 (M+H)$^+$.

Example 231C tert-butyl 4-(4-chloro-5-fluoro-1-(phenylsulfonyl)-1H-pyrrolo[2,3-b]pyridin-2-yl)-5,6-dihydropyridine-1(2H)-carboxylate A mixture of Example 231B (6.70 g, 15.34 mmol), tert-butyl 4-(4,4,5,5-tetramethyl-1,3,2-dioxaborolan-2-yl)-5,6-dihydropyridine-1(2H)-carboxylate (4.89 g, 15.81 mmol), tetrakis(triphenylphosphine)palladium (0.532 g, 0.460 mmol), and sodium bicarbonate solution (40 mL, 15.34 mmol) in N,N-dimethylformamide (160 mL) was degassed and heated at 80° C. overnight. The mixture was diluted with water/brine and extracted with ethyl acetate (twice). The combined organic layers were washed with water, dried over magnesium sulfate, filtered, concentrated, and purified on silica gel using an ISCO Companion eluting with heptanes/ethyl acetate (8:2 to 7:3) to give the title compound. MS (ESI$^+$) m/z 492.0 (M+H)$^+$.

Example 231D tert-butyl 4-(5-fluoro-4-(5-fluoro-2-methoxyphenyl)-1-(phenylsulfonyl)-1H-pyrrolo[2,3-b]pyridin-2-yl)-5,6-dihydropyridine-1(2H)-carboxylate A mixture of Example 231C (2000 mg, 4.07 mmol), (5-fluoro-2-methoxyphenyl)boronic acid (898 mg, 5.28 mmol), potassium phosphate tribasic (2589 mg, 12.20 mmol), and phenylallylchloro[1,3-bis(diisopropylphenyl)-2-imidazol-2-ylidene]palladium(II) (79 mg, 0.122 mmol) in tetrahydrofuran (60 mL) and water (20 mL) was degassed and heated at 60° C. for 3 hours. The mixture was treated with water and brine and extracted with ethyl acetate. The organic layer was washed with water, dried over magnesium sulfate, filtered, concentrated, and purified on silica gel using an ISCO Companion eluting with heptanes/ethyl acetate (7:3 to 6:4) to give the title compound. MS (ESI$^+$) m/z 582.1 (M+H)$^+$.

Example 231E 5-fluoro-4-(5-fluoro-2-methoxyphenyl)-2-(1,2,3,6-tetrahydropyridin-4-yl)-1H-pyrrolo[2,3-b]pyridine A mixture of Example 231D (2.00 g, 3.44 mmol) and 5M sodium hydroxide (2.407 mL, 12.04 mmol) in dioxane (20 mL) was heated at 90° C. for 8 hours. After concentration, the residue was treated with ethyl acetate and washed with water. The organic layer was dried over magnesium sulfate, filtered, concentrated, and purified on silica gel using an ISCO Companion eluting with heptanes/ethyl acetate (6:4 to 4:6) to give the protected intermediate. A solution of the intermediate in dichloromethane (25 mL) was treated with trifluoroacetic acid (2.27 mL, 29.4 mmol) and the mixture was stirred for 3 hours and concentrated. The residue was dissolved in 6 mL methanol and treated slowly with 5 mL 2M hydrogen chloride in ether. The suspension was sonicated, diluted with ether and stirred for 10 minutes. The solid was filtered, washed with ether and vacuum oven-dried to give the title compound as a hydrochloride salt. MS (ESI$^+$) m/z 342.1 (M+H)$^+$.

Example 231F

2-{4-[5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide A mixture of Example 231E (80.0 mg, 0.193 mmol), 2-chloro-N,N-dimethylacetamide (0.023 mL, 0.222 mmol), and triethylamine (0.135 mL, 0.966 mmol) in N,N-dimethylformamide (1.5 mL) was heated at 75° C. for 4 hours. The mixture was treated with water and brine and extracted with ethyl acetate (twice). The combined organic layers were dried over magnesium sulfate, filtered, concentrated, and purified by HPLC (same protocol as Example 221) to give the title compound as a trifluoroacetic acid salt. $^1$H NMR (500 MHz, Methanol-$d_4$) δ 2.83-3.00 (m, 2H), 3.01 (s, 6H), 3.35-3.49 (m, 1H), 3.67-3.81 (m, 1H), 3.77 (s, 3H), 3.87-4.30 (m, 2H), 4.34 (bs, 2H), 6.36 (s, 1H), 6.38 (bs, 1H), 7.09-7.29 (m, 3H), 8.16 (d, J=2.8 Hz, 1H). MS (ESI$^+$) m/z 427.0 (M+H)$^+$.

Example 232

4-[4-(4,5-difluoro-2-methoxyphenyl)-1H-pyrrolo[2,3-b]pyridin-2-yl]-N-methyl-3,6-dihydropyridine-1(2H)-carboxamide

Example 232A 4-(4,5-difluoro-2-methoxyphenyl)-2-(1,2,3,6-tetrahydropyridin-4-yl)-1H-pyrrolo[2,3-b]pyridine The title compound was prepared as in Example 87, substituting 4,5-difluoro-2-methoxyphenylboronic acid for 5-fluoro-2-methoxyphenylboronic acid in Example 87A. MS (ESI$^+$) m/z 342 (M+H)$^+$.

Example 232B 4-(4-(4,5-difluoro-2-methoxyphenyl)-1H-pyrrolo[2,3-b]pyridin-2-yl)-N-methyl-5,6-dihydropyridine-1(2H)-carboxamide The title compound was prepared using the procedure described in Example 215, using Example 232A in place of Example 87. $^1$H NMR (400 MHz, DMSO-$d_6$) δ 2.37-2.50 (m, 2H), 2.60 (s, 3H), 3.50 (t, J=5.7 Hz, 2H), 3.76 (s, 3H), 4.01 (q, J=2.8 Hz, 2H), 6.32 (d, J=2.0 Hz, 1H), 6.53 (d, J=3.7 Hz, 1H), 7.09 (d, J=5.1 Hz, 1H), 7.36 (dd, J=12.9, 6.9 Hz, 1H), 7.49 (dd, J=11.0, 9.2 Hz, 1H), 8.23 (d, J=5.1 Hz, 1H), 12.01 (d, J=2.7 Hz, 1H). MS (ESI) m/z 406 (M+H)$^+$.

Example 233

2-{3-[4-(5-fluoro-2-methoxyphenyl)-1H-pyrrolo[2,3-b]pyridin-2-yl]-8-azabicyclo[3.2.1]oct-2-en-8-yl}-N,N-dimethylacetamide The title compound was prepared essentially as described in Example 231F, substituting Example 223C for Example 231E. $^1$H NMR (500 MHz, Methanol-$d_4$) δ 2.04-2.14 (m, 1H), 2.34-2.59 (m, 3H), 2.76-2.90 (m, 1H), 2.94-3.05 (m, 6H), 3.21-3.42 (m, 1H), 3.81 (s, 3H), 4.12-4.35 (m, 3H), 4.36-4.47 (m, 1H), 6.60-6.80 (m, 1H), 7.19-7.25 (m, 1H), 7.23-7.33 (m, 2H), 7.44 (d, J=5.7 Hz, 1H), 8.33 (d, J=5.7 Hz, 1H). MS (ESI$^+$) m/z 435.1 (M+H)$^+$.

Example 234

2-{4-[4-(2,3-difluorophenyl)-1H-pyrrolo[2,3-b]pyridin-2-yl]-3,6-dihydropyridin-1(2H)-yl}-N,N-dimethylacetamide The title compound was prepared essentially as described in Example 231F, substituting Example 222C for Example 231E. $^1$H NMR (400 MHz, Methanol-$d_4$) δ 3.00-3.04 (m, 8H), 3.43-3.79 (m, 2H), 3.99-4.31 (m, 2H), 4.35 (s, 2H), 6.45-6.50 (m, 1H), 6.65 (d, J=2.3 Hz, 1H), 7.29-7.52 (m, 4H), 8.36 (d, J=5.3 Hz, 1H). MS (ESI$^+$) m/z 397.1 (M+H)$^+$.

Example 235

2-{4-[4-(5-fluoro-2-methoxyphenyl)-1H-pyrrolo[2,3-b]pyridin-2-yl]piperidin-1-yl}-N,N-dimethylacetamide To a mixture of Example 17 (300 mg, 0.922 mmol), 2-chloro-N,N-dimethylacetamide (118 mg, 0.968 mmol) in N,N-dimethylformamide (2.5 mL) was added N-ethyl-N-isopropylpropan-2-amine (0.644 mL, 3.69 mmol) and the mixture was stirred at 70° C. for 2 hours. Water was added and the mixture was extracted with ethyl acetate. The combined organic layers were washed with brine, dried over sodium sulfate, filtered and concentrated. The residue was purified by flash chromatography (AnaLogix IntelliFlash 280) on silica gel, eluting with 5-15% methanol in dichloromethane (linear gradient) to afford the title compound. $^1$H NMR (400 MHz, DMSO-$d_6$) δ 1.61-1.80 (m, 2H) 1.89-2.02 (m, 2H) 2.09-2.22 (m, 2H) 2.62-2.73 (m, 1H) 2.81 (s, 3H) 2.85-2.95 (m, 2H) 3.03 (s, 3H) 3.14 (s, 2H) 3.73 (s, 3H) 5.96 (d, J=1.83 Hz, 1H) 7.00 (d, J=4.88 Hz, 1H) 7.14-7.30 (m, 3H) 8.13 (d, J=5.19 Hz, 1H) 11.55 (s, 1H). MS (ESI$^+$) m/z 411 (M+H)$^+$.

Example 236

2-{4-[5-cyano-4-(5-fluoro-2-methoxyphenyl)-1H-pyrrolo[2,3-b]pyridin-2-yl]-3,6-dihydropyridin-1(2H)-yl}-N,N-dimethylacetamide

Example 236A 4-chloro-1-(phenylsulfonyl)-1H-pyrrolo[2,3-b]pyridine-5-carbonitrile 4-Chloro-1H-pyrrolo[2,3-b]pyridine-5-carbonitrile (2.6 g, 14.64 mmol) and triethylamine (3.06 mL, 21.96 mmol) in tetrahydrofuran (100 mL) was cooled to 0° C. and benzenesulfonyl chloride (2.253 mL, 17.57 mmol) was added dropwise. The mixture was stirred at 0° C. for 1 hour and at room temperature for 10 hours and the mixture was concentrated. Water was added and the mixture was extracted with dichloromethane (three times). The organic phase was washed with water and brine, dried over sodium sulfate, filtered and concentrated. The residue was triturated with diethyl ether to afford the title compound. MS (ESI(+)) m/e 318 (M+H)$^+$.

Example 236B 4-(5-fluoro-2-methoxyphenyl)-1-(phenylsulfonyl)-1H-pyrrolo[2,3-b]pyridine-5-carbonitrile A mixture of Example 236A (2 g, 6.29 mmol), (5-fluoro-2-methoxyphenyl)boronic acid (1.284 g, 7.55 mmol), sodium hydrogencarbonate (1.586 g, 18.88 mmol) and [1,1'-bis (diphenylphosphino)ferrocene]-dichloropalladium(II)-dichloromethane adduct (0.276 g, 0.378 mmol) in 80 mL N,N-dimethylformamide and 20 mL water was degassed with nitrogen and heated at 100° C. for 3 hours. The mixture was cooled to room temperature, diluted with water, and extracted with ethyl acetate. The organic phase was washed with brine, dried over magnesium sulfate, filtered and concentrated. Purification by silica-gel flash chromatography (AnaLogix IntelliFlash 280) eluting with dichloromethane afforded the title compound. MS (ESI$^+$) m/z 408 (M+H)$^+$.

Example 236C 4-(5-fluoro-2-methoxyphenyl)-2-iodo-1-(phenylsulfonyl)-1H-pyrrolo[2,3-b]pyridine-5-carbonitrile The title compound was prepared essentially as described in Example 87B, substituting Example 236B for Example 87A. MS (ESI$^+$) m/z 534 (M+H)$^+$.

Example 236D tert-butyl 4-(5-cyano-4-(5-fluoro-2-methoxyphenyl)-1-(phenylsulfonyl)-1H-pyrrolo[2,3-b]pyridin-2-yl)-5,6-dihydropyridine-1(2H)-carboxylate The title compound was prepared according to the procedure described in Example 87C, substituting Example 236C for Example 87B. MS (ESI$^+$) m/z 589 (M+H)$^+$.

Example 236E tert-butyl 4-(5-cyano-4-(5-fluoro-2-methoxyphenyl)-1H-pyrrolo[2,3-b]pyridin-2-yl)-5,6-dihydropyridine-1(2H)-carboxylate To a solution of Example 236D (400 mg, 0.680 mmol) in 5 mL methanol and 5 mL tetrahydrofuran was added 1N aqueous sodium hydroxide (3398 µL, 3.40 mmol) and the mixture was stirred at room temperature overnight and at 70° C. for 1 hour. The mixture was diluted with water, neutralized to pH 5-6 and extracted with ethyl acetate. The organic phase was washed with water and brine, dried over magnesium sulfate, filtered and concentrated. The residue was purified by flash chromatography (AnaLogix IntelliFlash 280) eluting with 0-3% methanol in dichloromethane to afford the title compound. MS (ESI$^+$) m/z 449 (M+H)$^+$.

Example 236F 4-(5-fluoro-2-methoxyphenyl)-2-(1,2,3,6-tetrahydropyridin-4-yl)-1H-pyrrolo[2,3-b]pyridine-5-carbonitrile To a solution of Example 236E (110 mg, 0.245 mmol) in dichloromethane (2 mL) was added trifluoroacetic acid (0.5 mL) and the mixture was stirred at room temperature for 3 hours and concentrated. The residue was triturated with diethyl ether and filtered to obtain the title compound as the trifluoroacetic acid salt. MS (ESI(+)) m/e 349 (M+H)$^+$.

Example 236G

2-{4-[5-cyano-4-(5-fluoro-2-methoxyphenyl)-1H-pyrrolo[2,3-b]pyridin-2-yl]-3,6-dihydropyridin-1(2H)-yl}-N,N-dimethylacetamide The title compound was prepared according to the procedure described in Example 235, substituting Example 236F for Example 17. $^1$H NMR (400 MHz, DMSO-d$_6$) δ 2.40-2.50 (m, 2H), 2.65-2.72 (m, 2H), 2.82 (s, 3H), 3.01 (s, 3H), 3.19-3.24 (m, 4H), 3.76 (s, 3H), 6.25 (s, 1H), 6.56 (bs, 1H), 7.22-7.43 (m, 3H), 8.60 (s, 1H), 12.43 (bs, 1H). MS (ESI(+)) m/e 434 (M+H)$^+$.

Example 237 ethyl({4-[5-fluoro-4-(5-fluoro-2-methoxyphenyl)-1H-pyrrolo[2,3-b]pyridin-2-yl]-3,6-dihydropyridin-1(2H)-yl}sulfonyl)carbamate The title compound was prepared essentially as described in Example 218, substituting ethanol for tert-butanol in Example 218A and substituting Example 231E for Example 87 in Example 218B. The crude compound was purified by HPLC (same protocol as Example 217) to give the title compound as a trifluoroacetic acid salt. $^1$H NMR (500 MHz, DMSO-d$_6$) δ 1.15 (t, J=7.1 Hz, 3H), 2.56 (bs, 2H), 3.42-3.49 (m, 2H), 3.73 (s, 3H), 3.99-4.04 (m, 2H), 4.07 (q, J=7.1 Hz, 2H), 6.20 (d, J=2.1 Hz, 1H), 6.51 (bs, 1H), 7.16-7.30 (m, 2H), 7.33 (td, J=8.6, 3.2 Hz, 1H), 8.21 (d, J=2.5 Hz, 1H), 11.37 (s, 1H), 11.97-12.02 (m, 1H). MS (ESI$^+$) m/z 493.1 (M+H)$^+$.

Example 238

2-{4-[4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone A solution of Example 226B (2 g, 4.40 mmol), N-ethyl-N-isopropylpropan-2-amine (3.84 mL, 22.01 mmol) and azetidin-3-ol hydrochloride (0.555 g, 5.06 mmol) in N,N-dimethylformamide (33.9 mL) was treated with 1-[bis(dimethylamino)methylene]-1H-1,2,3-triazolo[4,5-b]pyridinium 3-oxide hexafluorophosphate (1.724 g, 4.53 mmol) and the mixture was stirred at room temperature for 20 hours. The mixture was concentrated under vacuum and the residue was purified by flash chromatography on silica gel (AnaLogix IntelliFlash 280) eluting with a gradient of 0-10% methanol in dichloromethane followed by a gradient of 0-10% methanol in dichloromethane containing 1% ammonium hydroxide to afford the title compound. $^1$H NMR (500 MHz, DMSO-d$_6$) δ 2.44-2.50 (m, 2H), 2.64-2.72 (m, 2H), 3.04-3.14 (m, 2H), 3.14-3.22 (m, 2H), 3.55-3.63 (m, 1H), 3.74 (s, 3H), 3.87-3.96 (m, 1H), 4.00-4.09 (m, 1H), 4.30-4.40 (m, 1H), 4.40-4.50 (m, 1H), 5.69 (d, J=6.1 Hz, 1H), 6.17-6.24 (m, 1H), 6.44-6.51 (m, 1H), 7.02 (d, J=4.9 Hz, 1H), 7.14-7.34 (m, 3H), 8.19 (d, J=4.9 Hz, 1H), 11.77 (bs, 1H). MS (ESI$^+$) m/z 437.0 (M+H)$^+$.

Example 239

2-{4-[4-(5-fluoro-2-methoxyphenyl)-1H-pyrrolo[2,3-b]pyridin-2-yl]-3,6-dihydropyridin-1(2H)-yl}-1-[(2S)-2-(hydroxymethyl)pyrrolidin-1-yl]ethanone The title compound was prepared according to the procedure described in Example 238 substituting (S)-pyrrolidin-2-ylmethanol for azetidin-3-ol hydrochloride. $^1$H NMR (400 MHz, CD$_3$OD) δ 1.84-2.10 (m, 4H), 2.56-2.65 (m, 2H), 2.78-2.90 (m, 2H), 3.33-3.36 (m, 3H), 3.38-3.71 (m, 5H), 3.76 (s, 3H), 4.03-4.28 (m, 1H), 6.26 (s, 1H), 6.33-6.42 (m, 1H), 7.07 (d, J=5.1 Hz, 1H), 7.11-7.21 (m, 3H), 8.14 (d, J=5.1 Hz, 1H). MS (ESI$^+$) m/z 465.1 (M+H)$^+$.

Example 240

{4-[4-(5-fluoro-2-methoxyphenyl)-1H-pyrrolo[2,3-b]pyridin-2-yl]-3,6-dihydropyridin-1(2H)-yl}[(2R,4R)-4-hydroxypyrrolidin-2-yl]methanone

Example 240A (2R,4R)-tert-butyl 2-(4-(4-(5-fluoro-2-methoxyphenyl)-1H-pyrrolo[2,3-b]pyridin-2-yl)-1,2,3,6-tetrahydropyridine-1-carbonyl)-4-hydroxypyrrolidine-1-carboxylate A mixture of Example 87 (200 mg, 0.505 mmol), N-Boc-cis-4-hydroxy-D-proline (152 mg, 0.656 mmol), $N^1$-((ethylimino)methylene)-$N^3,N^3$-dimethylpropane-1,3-diamine hydrochloride (126 mg, 0.656 mmol), 1H-benzo[d][1,2,3]triazol-1-ol hydrate (100 mg, 0.656 mmol) and triethylamine (0.35 mL) in 6 mL N,N-dimethylformamide was heated at 100° C. overnight. The mixture was diluted with water and extracted with dichloromethane. The organic phase was washed with water and brine, dried over magnesium sulfate, filtered and concentrated under reduced pressure. The residue was purified by silica-gel column chromatography (AnaLogix IntelliFlash 280) eluting with 0-5% methanol in dichloromethane to afford the title compound. MS (ESI(+)) m/e 537 (M+H)$^+$.

Example 240B

{4-[4-(5-fluoro-2-methoxyphenyl)-1H-pyrrolo[2,3-b]pyridin-2-yl]-3,6-dihydropyridin-1(2H)-yl}[(2R,4R)-4-hydroxypyrrolidin-2-yl]methanone To a solution of Example 240A (100 mg, 0.186 mmol) in dichloromethane (2 mL) was added trifluoroacetic acid (0.2 mL, 2.60 mmol) and the mixture was stirred at room temperature for 4 hours and concentrated. The residue was dissolved in dichloromethane (2 mL) and treated with 2M hydrogen chloride in ether (2.5 mL) and filtered. The solid was washed with diethyl ether and concentrated to obtain the title compound as the hydrochloride salt. $^1$H NMR (500 MHz, DMSO-$d_6$) δ 1.70-1.80 (m, 1H), 2.53-2.79 (m, 2H), 3.09-3.32 (m, 2H), 4.60-4.06 (m, 7H) 4.37-4.43 (m, 2H), 4.44 (dd, J=38.4, 9.5 Hz, 1H), 4.57-4.77 (m, 1H), 6.44 (bs, 1H), 6.62-6.69 (m, 1H), 7.01-7.38 (m, 3H), 8.29 (d, J=5.3 Hz, 1H), 8.46-8.80 (m, 1H), 10.24 (bs, 1H), 12.57-12.65 (m, 1H). MS (ESI(+)) m/e 437 (M+H)$^+$.

Example 241

N-{4-[4-(5-fluoro-2-methoxyphenyl)-1H-pyrrolo[2,3-b]pyridin-2-yl]cyclohex-3-en-1-yl}-D-valine

Example 241A 4-(5-fluoro-2-methoxyphenyl)-2-(1,4-dioxaspiro[4.5]dec-7-en-8-yl)-1H-pyrrolo[2,3-b]pyridine The title compound was prepared essentially as described in Example 219B, substituting Example 219A with Example 87B and ethyl 4-(4,4,5,5-tetramethyl-1,3,2-dioxaborolan-2-yl)cyclohex-3-enecarboxylate with 4,4,5,5-tetramethyl-2-(1,4-dioxaspiro[4.5]dec-7-en-8-yl)-1,3,2-dioxaborolane. A solution of the crude material in 50 mL dioxane was treated with 6M aqueous sodium hydroxide (8.20 mL, 49.2 mmol) at 100° C. for 3 hours. The mixture was cooled, diluted with ethyl acetate, washed with saturated sodium bicarbonate, water, and brine, dried over magnesium sulfate, filtered and concentrated to give the title compound as a solid which was used in the next step without further purification. MS (ESI): 381.2 (M+H)$^+$.

Example 241B 4-(4-(5-fluoro-2-methoxyphenyl)-1H-pyrrolo[2,3-b]pyridin-2-yl)cyclohex-3-enone To a solution of Example 241A (3.7 g, 9.73 mmol) in 30 mL dichloromethane was added excess trifluoroacetic acid (6 mL). The mixture was stirred at room temperature overnight and the solvent was removed in vacuo. The residue was dissolved in 50 mL ethyl acetate and washed with saturated sodium bicarbonate, water, and brine, dried over magnesium sulfate, filtered and concentrated. The crude material was triturated with ethyl acetate and the solid was filtered and dried in vacuo to give the title compound. MS (ESI): 337.2 (M+H)$^+$.

Example 241C

N-{4-[4-(5-fluoro-2-methoxyphenyl)-1H-pyrrolo[2,3-b]pyridin-2-yl]cyclohex-3-en-1-yl}-D-valine To a mixture of Example 241B (125 mg, 0.372 mmol), triethylamine (0.114 mL, 0.818 mmol), acetic acid (0.106 mL, 1.858 mmol) and (R)-tert-butyl 2-amino-3-methylbutanoate hydrochloride (0.401 mL, 1.858 mmol) in 4 mL 1:1 dichloromethane/methanol was added Biotage MP-cyanoborohydride resin (2.17 mmol/g, 678 mg, 1.487 mmol) and the mixture was shaken at room temperature overnight. The mixture was diluted with dichloromethane and the resin was filtered off, rinsing with dichloromethane and methanol. The crude material was purified by flash chromatography (Analogix280, eluting with a 0-4% methanol/dichloromethane gradient). The tert-butyl ester in 5 mL dichloromethane was treated with excess trifluoroacetic acid for 10 hours. The solvent was removed and the residue was dissolved in 5 mL methanol and treated with 2M hydrogen chloride in diethyl ether for 1 hour. The mixture was diluted with 50 mL diethyl ether and the solid was filtered and dried in vacuo to give the title compound as the hydrochloride salt. $^1$H NMR (400 MHz, DMSO-$d_6$) δ 0.87-1.16 (m, 6H) 1.76-2.02 (m, 1H) 2.09-2.40 (m, 2H) 2.56-2.87 (m, 3H) 3.20-3.45 (m, 1H) 3.64-3.86 (m, 3H) 4.05 (s, 1H) 6.40 (s, 1H) 6.60 (s, 1H) 7.13-7.44 (m, 4H) 8.22-8.33 (m, 1H) 8.40 (d, J=1.83 Hz, 1H) 8.65-9.88 (m, 2H) 12.70 (d, J=3.97 Hz, 1H). MS (ESI): 438.1 (M+H)$^+$.

Example 242

1-{4-[4-(5-fluoro-2-methoxyphenyl)-1H-pyrrolo[2,3-b]pyridin-2-yl]cyclohex-3-en-1-yl}-L-proline The title compound was prepared essentially as described in Example 241C, substituting (R)-tert-butyl 2-amino-3-methylbutanoate hydrochloride with (S)-tert-butyl pyrrolidine-2-carboxylate. The material was purified by preparative HPLC on a Waters prep system using a Phenomenex Luna C8(2) 5 um 100 Å AXIA column using a 10-95% gradient of acetonitrile and 0.1% trifluoroacetic acid in water, to provide the title compound as the trifluoroacetate salt. $^1$H NMR (400 MHz, DMSO-$d_6$) δ 1.66-1.94 (m, 2H) 1.97-2.28 (m, 3H) 2.33-2.49 (m, 2H) 2.57-2.84 (m, 2H) 3.35 (d, J=2.44 Hz, 1H)

3.49-3.71 (m, 2H) 3.70-3.79 (m, 3H) 4.47-4.73 (m, 1H) 6.14-6.35 (m, 1H) 6.46 (s, 1H) 7.09 (d, J=4.88 Hz, 1H) 7.16-7.34 (m, 3H) 8.24 (d, J=4.88 Hz, 1H) 9.29-9.96 (m, 1H) 11.98 (s, 1H). MS (ESI): 436.1 (M+H)$^+$.

Example 243

N-cyano-4-[4-(5-fluoro-2-methoxyphenyl)-1H-pyrrolo[2,3-b]pyridin-2-yl]-3,6-dihydropyridine-1(2H)-carboxamide To a solution of cyanamide (98 mg, 2.32 mmol) and N-ethyl-N-isopropylpropan-2-amine (0.5 mL, 5.73 mmol) in N,N-dimethylformamide (5 mL) at 0° C., was added 4-nitrophenyl carbonochloridate (450 mg, 2.24 mmol) and the mixture was stirred at room temperature for 2 hours. A solution of Example 87 (304 mg, 0.767 mmol) and N-ethyl-N-isopropylpropan-2-amine (1 mL, 5.73 mmol) in N,N-dimethylformamide (5 mL) was added and the mixture was stirred at room temperature overnight. The crude product was purified by HPLC using a SunFire, C8 column and eluting with a gradient of 30-100% acetonitrile/water containing 0.1% trifluoroacetic acid. The solid was suspended in water, adjusted to ~pH 9 with sodium hydroxide, and extracted with ethyl acetate. The organic phase was washed with saturated sodium carbonate, water and brine, dried over sodium sulfate, filtered, and concentrated. The residue was further purified by HPLC using a SunFire, C8 column and eluted with a gradient of 30-100% acetonitrile/water containing 0.1% trifluoroacetic acid. After concentration, the residue was dissolved in methanol and treated with 1M hydrogen chloride in ether (5 mL). Ether (100 mL) was added and the solid was filtered, washed with ether and dried under vacuum to afford the title compound as the hydrochloride salt. $^1$H NMR (500 MHz, methanol-d$_4$) δ 2.64 (m, 2H) 3.74 (t, J=5.49 Hz, 2H) 3.82 (s, 3H) 4.26 (m, 2H) 6.57 (m, 1H) 6.62 (s, 1H) 7.27 (m, 3H) 7.52 (d, J=6.10 Hz, 1H) 8.30 (d, J=6.10 Hz, 1H). MS (ESI$^+$) m/z 392.1 (M+H)$^+$.

Example 244

1-({4-[4-(5-fluoro-2-methoxyphenyl)-1H-pyrrolo[2,3-b]pyridin-2-yl]-3,6-dihydropyridin-1(2H)-yl}acetyl)-L-prolinamide The title compound was prepared according to the procedure described in Example 238 substituting (S)-pyrrolidine-2-carboxamide for azetidin-3-ol hydrochloride. $^1$H NMR (400 MHz, pyridine-d$_5$) δ 1.61-2.09 (m, 3H), 2.14-2.31 (m, 1H), 2.57-2.69 (m, 2H), 2.82-2.95 (m, 2H), 3.32-3.49 (m, 4H), 3.55-3.78 (m, 5H), 4.74-4.96 (m, 1H), 6.46-6.62 (m, 2H), 7.06 (dd, J=9.0, 4.6 Hz, 1H), 7.13-7.25 (m, 2H), 7.38 (dd, J=9.0, 3.2 Hz, 1H), 8.46 (d, J=5.0 Hz, 1H), 12.11-12.34 (m, 1H). MS (ESI$^+$) m/z 478.1 (M+H)$^+$.

Example 245

2-{4-[4-(5-fluoro-2-methoxyphenyl)-1H-pyrrolo[2,3-b]pyridin-2-yl]piperidin-1-yl}acetamide A mixture of Example 135B (free base, 0.06 g, 0.184 mmol) and triethylamine (0.077 mL, 0.553 mmol) in N,N-dimethylformamide (1.537 mL) was treated with 2-bromoacetamide (0.029 g, 0.212 mmol) and the mixture was heated at 75° C. for 3.5 hours. The mixture was purified by reverse phase HPLC on a Phenomenex Luna C8(2) 5 um 100 Å AXIA column eluting with a gradient of 10-70% acetonitrile in 0.1% trifluoroacetic acid/water to afford the title compound. $^1$H NMR (400 MHz, CD$_3$OD) δ 2.02-2.28 (m, 2H), 2.32-2.46 (m, 2H), 3.18-3.35 (m, 3H), 3.64-3.85 (m, 2H), 3.82 (s, 3H), 4.00 (s, 2H), 6.47 (bs, 1H), 7.18-7.36 (m, 3H), 7.54 (d, J=6.1 Hz, 1H), 8.33 (d, J=6.1 Hz, 1H). MS (ESI$^+$) m/z 383.2 (M+H)$^+$.

Example 246

2-{4-[4-(5-fluoro-2-methoxyphenyl)-1H-pyrrolo[2,3-b]pyridin-2-yl]piperidin-1-yl}-N-methylacetamide The title compound was prepared according to the procedure described in Example 245 substituting 2-bromo-N-methylacetamide (Oakwood Chemical) for 2-bromoacetamide. $^1$H NMR (500 MHz, CD$_3$OD) δ 2.03-2.25 (m, 2H), 2.33-2.44 (m, 2H), 2.81 (s, 3H), 3.15-3.34 (m, 3H), 3.62-3.78 (m, 2H), 3.81 (s, 3H), 3.96 (s, 2H), 6.41 (bs, 1H), 7.17-7.33 (m, 3H), 7.46 (d, J=5.9 Hz, 1H), 8.30 (d, J=5.8 Hz, 1H). MS (ESI$^+$) m/z 397.2 (M+H)$^+$.

Example 247

2-{4-[4-(5-fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone Example 247A tert-butyl 2-(4-(4-(5-fluoro-2-methoxyphenyl)-1H-pyrrolo[2,3-b]pyridin-2-yl)piperidin-1-yl)acetate The title compound was prepared according to the procedure described in Example 226A substituting Example 135B for Example 87. MS (ESI$^+$) m/z 440.1 (M+H)$^+$.

Example 247B 2-(4-(4-(5-fluoro-2-methoxyphenyl)-1H-pyrrolo[2,3-b]pyridin-2-yl)piperidin-1-yl)acetic acid The title compound was prepared according to the procedure described in Example 226B substituting Example 247A for Example 226A. MS (ESI$^+$) m/z 384.1 (M+H)$^+$.

Example 247C

2-{4-[4-(5-fluoro-2-methoxyphenyl)-1H-pyrrolo[2,3-b]pyridin-2-yl]piperidin-1-yl}-1-[(2S)-2-(hydroxymethyl)pyrrolidin-1-yl]ethanone The title compound was prepared according to the procedure described in Example 238 substituting Example 247B for Example 226B and (S)-pyrrolidin-2-ylmethanol for azetidin-3-ol hydrochloride. $^1$H NMR (400 MHz, pyridine-d$_5$) δ 1.60-1.75 (m, 1H), 1.79-1.94 (m, 3H), 1.96-2.10 (m, 4H), 2.25-2.41 (m, 2H), 2.78-2.94 (m, 1H), 3.05-3.56 (m, 5H), 3.58-3.73 (m, 4H), 3.72-4.05 (m, 2H), 4.33-4.44 (m, 1H), 6.28-6.31 (m, 1H), 7.05 (dd, J=9.0, 4.6 Hz, 1H), 7.12-7.18 (m, 1H), 7.22 (d, J=4.9 Hz, 1H), 7.38 (dd, J=9.0, 3.2 Hz, 1H), 8.45 (d, J=4.9 Hz, 1H), 12.13 (bs, 1H). MS (ESI$^+$) m/z 467.2 (M+H)$^+$.

Example 248

4-(5-fluoro-2-methoxyphenyl)-2-[1-(methylsulfonyl)-1,2,3,6-tetrahydropyridin-4-yl]-1H-pyrrolo[2,3-b]pyridine-3-carbonitrile

Example 248A 4-chloro-1-((2-(trimethylsilyl)ethoxy)methyl)-1H-pyrrolo[2,3-b]pyridine-3-carbonitrile A solution of 4-chloro-1H-pyrrolo[2,3-b]pyridine-3-carbonitrile (2.5 g, 14.08 mmol) in tetrahydrofuran (200 mL) was cooled to 0° C. and treated with sodium hydride (0.5 g, 21.1 mmol). The mixture was stirred at 0° C. for 30 minutes and (2-(chloromethoxy)ethyl)trimethylsilane (2.8 g, 16.9 mmol) was added. After stirring at room temperature for 2 hours, the mixture was treated with brine and extracted with ethyl acetate (three times) and the organic layers were dried over sodium sulfate. Filtration, concentration and purification by flash chromatography (Combi Flash Rf) (silica gel, 40% ethyl acetate in hexane) afforded the title compound. MS (ESI$^+$) m/z 308 (M+H)$^+$.

Example 248B 4-(5-fluoro-2-methoxyphenyl)-1-((2-(trimethylsilyl)ethoxy)methyl)-1H-pyrrolo[2,3-b]pyridine-3-carbonitrile A mixture of Example 248A (3.0 g, 9.78 mmol), (5-fluoro-2-methoxyphenyl)boronic acid (2.5 g, 14.6 mmol), phenylallylchloro(1,3-bis(diisopropylphenyl)-2-imidazol-2-yliden)palladium(II) (0.19 g, 0.29 mmol) and potassium phosphate (4.1 g, 19.6 mmol) in tetrahydrofuran (60 mL) and water (18 mL) was purged with nitrogen and heated at 60° C. for 3 hours. The mixture was treated with brine, extracted with ethyl acetate (three times) and the organic layer was dried over sodium sulfate. Filtration, concentration and purification by flash chromatography (Combi Flash Rf) (silica gel, 30% ethyl acetate in hexane) afforded the title compound. MS (ESI$^+$) m/z 398 (M+H)$^+$.

Example 248C 4-(5-fluoro-2-methoxyphenyl)-2-iodo-1-((2-(trimethylsilyl)ethoxy)methyl)-1H-pyrrolo[2,3-b]pyridine-3-carbonitrile A solution of Example 248B (0.7 g, 1.76 mmol) in tetrahydrofuran (50 mL) was cooled to –75° C. and treated dropwise with 2N lithium diisopropylamide in tetrahydrofuran (1.7 mL, 3.40 mmol). The mixture was stirred at –75° C. for 30 minutes and iodine (0.85 g, 3.52 mmol) in 2.5 mL tetrahydrofuran was added. The mixture was slowly brought to room temperature and quenched with aqueous ammonium chloride (100 mL) and extracted with ethyl acetate (twice). The organic layers were concentrated and purified by column chromatography (Combi Flash Rf) (silica gel, 30% ethyl acetate in hexane) to afford the title compound. MS (ESI$^+$) m/z 524 (M+H)$^+$.

Example 248D tert-butyl 4-(3-cyano-4-(5-fluoro-2-methoxyphenyl)-1H-pyrrolo[2,3-b]pyridin-2-yl)-5,6-dihydropyridine-1(2H)-carboxylate The title compound was prepared using the procedure described in Example 87C, using Example 248C in place of Example 87B. MS (ESI$^+$) m/z 449 (M+H)$^+$.

Example 248E 4-(5-fluoro-2-methoxyphenyl)-2-(1,2,3,6-tetrahydropyridin-4-yl)-1H-pyrrolo[2,3-b]pyridine-3-carbonitrile The title compound was prepared using the procedure described in Example 1H, using Example 248D in place of Example 1G. MS (ESI$^+$) m/z 449 (M+H)$^+$.

Example 248F 4-(5-fluoro-2-methoxyphenyl)-2-(1-(methylsulfonyl)-1,2,3,6-tetrahydropyridin-4-yl)-1H-pyrrolo[2,3-b]pyridine-3-carbonitrile The title compound was prepared using the procedure described in Example 148, using Example 248E in place of Example 135B. $^1$H NMR (400 MHz, DMSO-d$_6$/D$_2$O): δ 2.76-2.91 (m, 2H), 3.48 (t, J=5.7 Hz, 2H), 3.78 (s, 3H), 3.96, 4.03 (q, J=3.0 Hz, 2H), 6.70-6.78 (m, 1H), 7.13-7.30 (m, 2H), 7.24 (dd, J=8.7, 3.1 Hz, 1H), 7.36 (td, J=8.6, 3.1 Hz, 1H), 8.46 (d, J=4.9 Hz, 1H), 12.94 (s, 1H). MS (ESI$^+$) m/z 427 (M+H)$^+$.

Example 249

4-[3-cyano-4-(5-fluoro-2-methoxyphenyl)-1H-pyrrolo[2,3-b]pyridin-2-yl]-N-methyl-3,6-dihydropyridine-1(2H)-carboxamide The title compound was prepared using the procedure described in Example 215, using Example 248E in place of Example 87. $^1$H NMR (400 MHz, DMSO-d$_6$) δ 2.60 (s, 3H), 2.61-2.68 (m, 2H), 3.54 (t, J=5.6 Hz, 2H), 3.72 (s, 3H), 4.07 (q, J=3.0 Hz, 2H), 6.62-6.78 (m, 1H), 7.09-7.15 (m, 2H), 7.18 (dd, J=8.7, 3.2 Hz, 1H), 7.29 (td, J=8.7, 3.2 Hz, 1H), 8.39 (d, J=4.9 Hz, 1H). MS (ESI$^+$) m/z 406 (M+H)$^+$.

Example 250 ethyl({4-[4-(5-fluoro-2-methoxyphenyl)-1H-pyrrolo[2,3-b]pyridin-2-yl]cyclohex-3-en-1-yl}sulfamoyl)carbamate

Example 250A 4-(4-(5-fluoro-2-methoxyphenyl)-1H-pyrrolo[2,3-b]pyridin-2-yl)cyclohex-3-enamine The title compound was prepared essentially as described in Example 223A-C, substituting tert-butyl (4-oxocyclohexyl)carbamate for tert-butyl 3-oxo-8-azabicyclo[3.2.1]octane-8-carboxylate in Example 223A. MS (DCI/NH₃) m/z 489 (M+H)⁺.

Example 250B ethyl({4-[4-(5-fluoro-2-methoxyphenyl)-1H-pyrrolo[2,3-b]pyridin-2-yl]cyclohex-3-en-1-yl}sulfamoyl)carbamate The title compound was prepared essentially as described in Example 218, substituting Example 250A for Example 87 in Example 218B and ethanol for tert-butanol in Example 218A. ¹H NMR (400 MHz, DMSO-d₆) δ 1.21 (t, J=7.02 Hz, 3H), 1.59-1.68 (m, 1H), 1.92-1.98 (m, 1H), 2.17-2.25 (m, 1H), 2.37-2.46 (m, 1H), 2.55-2.61 (m, 1H), 3.38-3.43 (m, 1H), 3.73 (s, 3H), 4.13 (q, J=7.02 Hz, 2H), 6.18 (d, J=1.53 Hz, 1H), 6.41 (s, 1H), 7.02 (d, J=5.19 Hz, 1H), 7.16-7.29 (m, 3H), 7.86 (d, J=7.02 Hz, 1H), 8.18 (d, J=4.88 Hz, 1H), 11.12 (s, 1H), 11.71 (s, 1H). MS (DCI/NH₃) m/z 489 (M+H)⁺.

Example 251

2-{4-[4-(5-fluoro-2-methoxyphenyl)-1H-pyrrolo[2,3-b]pyridin-2-yl]piperidin-1-yl}-N-(2-hydroxyethyl)-N-methylacetamide Stock solutions (in N,N-dimethylacetamide) of Example 247B (0.27M, 286 μL, 0.078 mmol), N,N-di-isopropylethylamine (0.81M, 0.234 mmol), 1-[bis(dimethylamino)methylene]-1H-1,2,3-triazolo[4,5-b]pyridinium 3-oxid hexafluorophosphate (0.32M, 286 μL, 0.094 mmol), and 2-(methylamino)ethanol (0.41M, 235 μL, 0.094 mmol) were mixed through a PFA mixing tube (0.2 mm inner diameter), and loaded into an injection loop. The reaction segment was injected into a flow reactor (Hastelloy coil, 0.75 mm inner diameter, 1.8 mL internal volume) set at 100° C., and passed through the reactor at 180 μL min⁻¹ (10 minute residence time). Upon exiting the reactor, the reaction was loaded directly into an injection loop and purified by preparative HPLC on a Phenomenex Luna C8(2) 5 um 100 Å AXIA column, eluting with a 5-100% gradient of acetonitrile/0.1% ammonium acetate in water. ¹H NMR (400 MHz, DMSO-d₆) δ 1.63-1.82 (m, 2H), 1.91-2.12 (m, 2H), 2.24 (td, J=11.6, 2.5 Hz, 2H), 2.66-3.22 (m, 8H), 3.44 (s, 4H), 3.72 (s, 3H), 5.96 (s, 1H), 7.00 (d, J=5.0 Hz, 1H), 7.09-7.27 (m, 3H), 8.13 (d, J=5.0 Hz, 1H). MS (APCI) m/z 441.3 [M+H]⁺.

Example 252

2-{4-[4-(5-fluoro-2-methoxyphenyl)-1H-pyrrolo[2,3-b]pyridin-2-yl]piperidin-1-yl}-N-(3-hydroxycyclobutyl)acetamide The title compound was prepared according to the procedure described in Example 251 substituting 3-aminocyclobutanol hydrochloride (Synthonix) for 2-(methylamino)ethanol. ¹H NMR (400 MHz, DMSO-d₆) δ 1.66-1.84 (m, 3H), 1.98 (d, J=12.9 Hz, 2H), 2.05-2.33 (m, 4H), 2.56 (ddd, J=7.0, 4.5, 2.6 Hz, 2H), 2.61-2.83 (m, 1H), 2.83-2.96 (m, 4H), 3.72 (s, 4H), 4.18-4.41 (m, 1H), 5.98 (s, 1H), 7.01 (d, J=5.0 Hz, 1H), 7.09-7.28 (m, 3H), 8.13 (d, J=4.9 Hz, 1H). MS (APCI) m/z 453.3 [M+H]⁺.

Example 253

2-{4-[4-(5-fluoro-2-methoxyphenyl)-1H-pyrrolo[2,3-b]pyridin-2-yl]piperidin-1-yl}-1-(3-hydroxyazetidin-1-yl)ethanone The title compound was prepared according to the procedure described in Example 238 substituting Example 247B for Example 226B. ¹H NMR (400 MHz, DMSO-d₆) δ 1.65-1.78 (m, 2H), 1.90-2.00 (m, 2H), 2.07-2.20 (m, 2H), 2.62-2.71 (m, 1H), 2.84-2.92 (m, 2H), 2.92-3.03 (m, 2H), 3.52-3.62 (m, 1H), 3.73 (s, 3H), 3.87-3.96 (m, 1H), 3.96-4.08 (m, 1H), 4.25-4.50 (m, 2H), 5.96 (s, 1H), 7.00 (d, J=4.9 Hz, 1H), 7.12-7.32 (m, 3H), 8.13 (d, J=4.9 Hz, 1H), 11.57 (bs, 1H). MS (ESI⁺) m/z 439.2 (M+H)⁺.

Example 254

N-{4-[4-(5-fluoro-2-methoxyphenyl)-1H-pyrrolo[2,3-b]pyridin-2-yl]cyclohex-3-en-1-yl}-3-methyl-L-valine The title compound was prepared essentially as described in Example 241C, substituting (R)-tert-butyl 2-amino-3-methylbutanoate hydrochloride with (S)-tert-butyl 2-amino-3,3-dimethylbutanoate hydrochloride to give the title compound as the hydrochloride salt. ¹H NMR (500 MHz, DMSO-d₆) δ 1.02-1.24 (m, 9H) 1.78-2.17 (m, 1H) 2.31 (s, 1H) 2.45 (d, J=12.82 Hz, 1H) 2.54-2.88 (m, 3H) 3.28 (s, 1H) 3.65-3.85 (m, 3H) 4.00 (d, J=10.68 Hz, 2H) 6.41 (s, 1H) 6.61 (s, 1H) 7.07-7.53 (m, 4H) 8.29 (d, J=5.49 Hz, 1H) 8.87 (s, 1H) 12.76 (d, J=13.43 Hz, 1H). MS (ESI): 452.1 (M+H)⁺.

Example 255

2-{4-[5-fluoro-4-(5-fluoro-2-methoxyphenyl)-1H-pyrrolo[2,3-b]pyridin-2-yl]piperidin-1-yl}-N,N-dimethylacetamide Example 255A tert-butyl 4-((4-chloro-5-fluoro-2-pivalamidopyridin-3-yl)ethynyl)piperidine-1-carboxylate A mixture of N-(4-chloro-5-fluoro-3-iodopyridin-2-yl)pivalamide (1 g, 2.80 mmol), tert-butyl 4-ethynylpiperidine-1-carboxylate (0.880 g, 4.21 mmol), copper(I) iodide (0.053 g, 0.28 mmol), and bis(triphenylphosphine)palladium(II) dichloride (0.197 g, 0.280 mmol) in 50 mL tetrahydrofuran was degassed with nitrogen. The mixture was stirred at room temperature for 48 hours and at 50° C. for 8 hours. The mixture was filtered and the filtrate was diluted with water and extracted with ethyl acetate. The organic phase was washed with brine, dried over sodium sulfate, filtered and concentrated. The residue was purified by silica-gel column chromatography eluting with 0-40% ethyl acetate in heptane to afford the title compound. MS (ESI(+)) m/e 438 (M+H)⁺.

Example 255B tert-butyl 4-(4-chloro-5-fluoro-1H-pyrrolo[2,3-b]pyridin-2-yl)piperidine-1-carboxylate A mixture of Example 255A (1000 mg, 2.283 mmol), 18-crown-6 (302 mg, 1.142 mmol), and potassium 2-methylpropan-2-olate (512 mg, 4.57 mmol) in 15 mL t-butanol was heated under microwave (Biotage) conditions at 135° C. for 35 minutes. Water was added and the mixture was extracted with dichloromethane. The organic phase was washed with water and brine, dried over sodium sulfate, filtered and concentrated. The residue was triturated with diethyl ether and filtered to afford the title compound. MS (ESI(+)) m/e 354 (M+H)$^+$.

Example 255C tert-butyl 4-(5-fluoro-4-(5-fluoro-2-methoxyphenyl)-1H-pyrrolo[2,3-b]pyridin-2-yl)piperidine-1-carboxylate A mixture of Example 255B (600 mg, 1.696 mmol), (5-fluoro-2-methoxyphenyl)boronic acid (403 mg, 2.374 mmol), phenylallylchloro[1,3-bis(diisopropylphenyl)-2-imidazol-2-ylidene]palladium(II) (110 mg, 0.170 mmol), and potassium phosphate (1080 mg, 5.09 mmol) in 12 mL tetrahydrofuran and 3 mL water was degassed with nitrogen and heated in a Biotage microwave for 40 minutes at 120° C. The mixture was extracted with ethyl acetate and purified by silica gel column chromatography eluting with 0-5% methanol in dichloromethane to afford the title compound. MS (ESI(+)) m/e 444 (M+H)$^+$.

Example 255D 5-fluoro-4-(5-fluoro-2-methoxyphenyl)-2-(piperidin-4-yl)-1H-pyrrolo[2,3-b]pyridine The title compound was prepared using the procedure described in Example 236F, substituting Example 255C for Example 236D. MS (ESI(+)) m/e 344 (M+H)$^+$.

Example 255E

2-{4-[5-fluoro-4-(5-fluoro-2-methoxyphenyl)-1H-pyrrolo[2,3-b]pyridin-2-yl]piperidin-1-yl}-N,N-dimethylacetamide The title compound was prepared using the procedure described in Example 235, substituting Example 255D for Example 17. $^1$H NMR (400 MHz, DMSO-d$_6$) δ 0.85-1.83 (m, 2H), 1.93-2.03 (m, 2H), 2.15-2.25 (m, 2H), 2.66-2.81 (m, 1H), 2.86 (s, 3H), 2.91-2.99 (m, 2H), 3.08 (s, 3H), 3.19 (bs, 2H), 3.78 (s, 3H), 5.95 (bs, 1H), 7.22-7.29 (m, 2H), 7.37 (td, J=8.6, 3.2 Hz, 1H), 8.17 (d, J=2.5 Hz, 1H), 11.75 (bs, 1H). MS (ESI(+)) m/e 429 (M+H)$^+$.

Example 256

2-{4-[3-cyano-4-(5-fluoro-2-methoxyphenyl)-1H-pyrrolo[2,3-b]pyridin-2-yl]-3,6-dihydropyridin-1(2H)-yl}-N,N-dimethylacetamide To a suspension of Example 248E (125 mg, 0.359 mmol) in N,N-dimethylformamide (6 mL) was added triethylamine (0.30 mL, 2.153 mmol) and 2-chloro-N,N-dimethylacetamide (56 mg, 0.466 mmol) and the mixture was heated at 70° C. for 3 hours. After cooling, the mixture was partitioned between ethyl acetate and sodium bicarbonate and the organic phase was washed with brine and concentrated. The residue was purified by flash chromatography (5-20% methanol in 2:1 ethyl acetate/hexane) to provide the title compound. $^1$H NMR (400 MHz, DMSO-d$_6$): δ 2.77-2.80 (m, 2H), 2.86 (t, J=5.65 Hz, 2H), 2.95 (s, 3H), 3.11 (s, 3H), 3.37 (q, J=2.75 Hz, 2H), 3.77 (s, 3H), 6.65-6.67 (m, 1H), 7.04-7.12 (m, 3H), 7.15-7.21 (m, 1H), 8.34 (d, J=4.88 Hz, 1H). MS (DCI/NH$_3$) m/z 434 (M+H)$^+$.

Example 257

2-{4-[4-(2-methoxyphenyl)-1H-pyrrolo[2,3-b]pyridin-2-yl]piperidin-1-yl}-N,N-dimethylacetamide Example 257A tert-butyl 4-(4-(2-methoxyphenyl)-1-(phenylsulfonyl)-1H-pyrrolo[2,3-b]pyridin-2-yl)-5,6-dihydropyridine-1(2H)-carboxylate The title compound was prepared as described in Example 87A-C, substituting 2-methoxyphenylboronic acid for 5-fluoro-2-methoxyphenylboronic acid in Example 87A.

Example 257B 4-(2-methoxyphenyl)-2-(piperidin-4-yl)-1H-pyrrolo[2,3-b]pyridine

The title compound was prepared as in Example 135A-B, substituting Example 257A for Example 87C in Example 135A.

Example 257C

2-{4-[4-(2-methoxyphenyl)-1H-pyrrolo[2,3-b]pyridin-2-yl]piperidin-1-yl}-N,N-dimethylacetamide The title compound was prepared as described in Example 224, substituting Example 257B for Example 87. $^1$H NMR (500 MHz, DMSO-d$_6$) δ 1.69 (qd, J=12.4, 3.7 Hz, 2H), 1.90-1.99 (m, 2H), 2.11-2.22 (m, 2H), 2.67 (tt, J=11.9, 3.8 Hz, 1H), 2.81 (s, 3H), 2.90 (dt, J=11.7, 3.1 Hz, 2H), 3.03 (s, 3H), 3.14 (s, 2H), 3.75 (s, 3H), 5.93 (d, J=2.1 Hz, 1H), 6.99 (d, J=4.9 Hz, 1H), 7.07 (t, J=7.4 Hz, 1H), 7.17 (d, J=8.2 Hz, 1H), 7.29-7.47 (m, 2H), 8.12 (d, J=4.9 Hz, 1H), 11.50 (d, J=2.2 Hz, 1H). MS (ESI) m/z 393 (M+H)$^+$.

Example 258

4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine Example 258A (S)-tert-butyl 2-methyl-4-(((trifluoromethyl)sulfonyl)oxy)-5,6-dihydropyridine-1(2H)-carboxylate and (S)-tert-butyl 6-methyl-4-(((trifluoromethyl)sulfonyl)oxy)-5,6-dihydropyridine-1(2H)-carboxylate (4:1)

A solution of (S)-tert-butyl-2-methyl-4-oxopiperidine-1-carboxylate (5 g, 23.44 mmol) in tetrahydrofuran (100 mL) was cooled to −78° C. and lithium bis(trimethylsilyl)amide (1M in hexanes, 28.1 mL, 28.1 mmol) was added dropwise. The mixture was stirred at −78° C. for 30 minutes and a solution of 1,1,1-trifluoro-N-phenyl-N-((trifluoromethyl)sulfonyl)methanesulfonamide (10.89 g, 30.5 mmol) in tetrahydrofuran (25 mL) was added dropwise. The mixture was allowed to warm to room temperature and after 24 hours, the reaction was quenched with saturated ammonium chloride and extracted with ethyl acetate. The extracts were dried over sodium sulfate, filtered, and concentrated. Purification by flash chromatography on silica gel eluting with 0-40% ethyl acetate-hexanes gave an oil as a mixture of enol isomers. This material also contained 25% by weight 1,1,1-trifluoro-N-phenylmethanesulfonamide. The mixture was carried on in the next step without any further purification. MS (ESI) m/e 246.0 (M-BOC)+.

Example 258B 4-(5-fluoro-2-methoxyphenyl)-1-tosyl-1H-pyrrolo[2,3-b]pyridine

To a mixture of 4-bromo-1-(4-methylphenylsulfonyl)-1H-pyrrolo[2,3-b]pyridine (100 g, 284.7 mmol) and (5-fluoro-2-methoxyphenyl)boronic acid (58.05 g, 341.6 mmol) in dimethoxyethane (1600 mL) and water (440 mL) was added potassium carbonate (106.2 g, 768.6 mmol). The mixture was purged with nitrogen and [1,1'-bis(diphenylphosphino)ferrocene]dichloropalladium(II)-dichloromethane adduct (13.95 g, 17.08 mmol) was added. The mixture was purged with nitrogen for 10 minutes and stirred at 100° C. for 1 hour. After concentration, the residue was diluted with ethyl acetate (1500 mL) and washed with aqueous sodium bicarbonate (twice) and brine. The organic layer was dried over sodium sulfate, filtered and concentrated under reduced pressure. The residue was purified by flash chromatography on silica gel eluting with 30-60% ethyl acetate in petroleum ether to afford the title compound.

Example 258C 4-(5-fluoro-2-methoxyphenyl)-2-iodo-1-tosyl-1H-pyrrolo[2,3-b]pyridine To a solution of Example 258B (98 g, 247.2 mmol) in tetrahydrofuran (3528 mL) was added lithium diisopropylamide (1.8M in tetrahydrofuran/heptane/ethylbenzene, 233.4 mL, 420.2 mmol) at −78° C. The mixture was stirred for 20 minutes and a solution of iodine (116.07 g, 457.3 mmol) in tetrahydrofuran (392 mL) was added drop wise over 20 minutes, maintaining the temperature below −70° C. After 30 minutes, the mixture was poured into a saturated ammonium chloride (980 mL) and extracted with ethyl acetate (twice). The combined extracts were washed with saturated sodium thiosulfate (twice) and brine, dried over sodium sulfate, filtered, and concentrated. The residue was purified by flash chromatography on silica gel eluting with 0-11% ethyl acetate in 10% dichloromethane/petroleum ether to afford the title compound.

Example 258D (S)-tert-butyl 4-(4-(5-fluoro-2-methoxyphenyl)-1-tosyl-1H-pyrrolo[2,3-b]pyridin-2-yl)-2-methyl-5,6-dihydropyridine-1(2H)-carboxylate and (S)-tert-butyl 4-(4-(5-fluoro-2-methoxyphenyl)-1-tosyl-1H-pyrrolo[2,3-b]pyridin-2-yl)-6-methyl-5,6-dihydropyridine-1(2H)-carboxylate (4:1)

A mixture of Example 258A (1.75 g, 6.89 mmol), bis(diphenylphosphino)ferrocene]dichloropalladium(II)-dichloromethane adduct (0.235 g, 0.287 mmol), 4,4,4',4',5,5,5',5'-octamethyl-2,2'-bi(1,3,2-dioxaborolane) (1.75 g, 28.7 mmol), and potassium acetate (2.82 g, 28.7 mmol) in dioxane (40 mL) was degassed and heated at reflux for 90 minutes. After cooling to room temperature, Example 258C (3 g, 5.74 mmol), additional bis(diphenylphosphino)ferrocene]dichloropalladium(II)-dichloromethane adduct (0.235 g, 0.287 mmol) and a solution of sodium carbonate (3.35 g, 31.6 mmol) in water (0.5 mL) was added and the mixture was heated to 65° C. for 24 hours. The mixture was partitioned between water and ethyl acetate and the organic layer was dried over sodium sulfate, filtered, and concentrated. Purification by flash chromatography on silica gel eluting with 0-30% ethyl acetate in heptanes over 50 minutes provided the title compound as a mixture of regioisomers which was used in the next step without any further purification. MS (ESI) m/e 592.1 (M+1)+.

Example 258E (S)-tert-butyl 4-(4-(5-fluoro-2-methoxyphenyl)-1H-pyrrolo[2,3-b]pyridin-2-yl)-2-methyl-5,6-dihydropyridine-1(2H)-carboxylate and (S)-tert-butyl 4-(4-(5-fluoro-2-methoxyphenyl)-1H-pyrrolo[2,3-b]pyridin-2-yl)-6-methyl-5,6-dihydropyridine-1(2H)-carboxylate (4:1)

To a solution of Example 258D (3.06 g, 5.17 mmol) in dioxane (29.6 mL) was added a solution of sodium hydroxide (0.724 g, 18.1 mmol) in water (3.62 mL) and the mixture was heated at 90° C. for 24 hours. The mixture was cooled to room temperature, diluted with saturated sodium bicarbonate and extracted with ethyl acetate. The combined extracts were dried over sodium sulfate, filtered, and concentrated. Purification by flash chromatography on silica gel eluting with 0-50% methanol in dichloromethane provided the title compound as a mixture of regioisomers which was used in the next step without any further purification. MS (ESI) m/e 438.1 (M+1)+.

Example 258F (S)-4-(5-fluoro-2-methoxyphenyl)-2-(6-methyl-1,2,3,6-tetrahydropyridin-4-yl)-1H-pyrrolo[2,3-b]pyridine To a solution of Example 258E (0.600 g, 1.37 mmol) in 4 mL 1:1 methanol:ethyl acetate was added 2M hydrogen chloride in diethyl ether (5 mL) and the mixture was stirred at 40° C. for 2 hours and concentrated. Purification by reverse phase-HPLC (Sunfire 5 µM, 50×250 mm) eluting with 5-40% acetonitrile in water (containing 0.1% trifluoroacetic acid), provided the title compound as trifluoroacetate salt. To a solution of this salt in methanol was added 2M hydrogen chloride in diethyl ether. Concentration afforded the title compound as the hydrochloride salt. MS (ESI) m/e 338.1 (M+1)+.

Example 258G 4-(5-fluoro-2-methoxyphenyl)-2-[(6S)-6-methyl-1-(methylsulfonyl)-1,2,3,6-tetrahydropyridin-4-yl]-1H-pyrrolo[2,3-b]pyridine Methanesulfonyl chloride (0.03 mL, 0.38 mmol) was added to Example 258F (96.4 mg, 0.235 mmol) and triethylamine (0.2 mL, 1.43 mmol) in N,N-dimethylformamide (2 mL). After stirring at room temperature for 24 hours, the mixture was concentrated. Purification by reverse phase-HPLC (Sunfire 5 µM, 50×250 mm) eluting with 5-50% acetonitrile in water (containing 0.1% trifluoroacetic acid) provided the trifluoroacetate salt. The salt was dissolved in methanol and eluted from a SCX column with 0.5M ammonia in methanol to give the free base of the title compound. $^1$H NMR (500 MHz, DMSO-$d_6$) δ 1.31 (d, 3H), 2.53 (m, 2H), 2.93 (s, 3H), 3.22 (m, 1H), 3.74 (s, 3H), 3.77 (m, 1H), 4.44 (m, 1H), 6.28 (d, 1H), 6.51 (m, 1H), 7.04 (d, 1H), 7.25 (m, 3H), 8.21 (d, 1H), 11.83 (br s, 1H). MS (ESI) m/e 416.1 (M+1)$^+$.

Example 259

2-{4-[5-fluoro-4-(5-fluoro-2-methoxyphenyl)-1H-pyrrolo[2,3-b]pyridin-2-yl]piperidin-1-yl}-1-(3-hydroxyazetidin-1-yl)ethanone Example 259A tert-butyl 2-(4-(5-fluoro-4-(5-fluoro-2-methoxyphenyl)-1H-pyrrolo[2,3-b]pyridin-2-yl)piperidin-1-yl) acetate The title compound was prepared using the procedure described in Example 226A, substituting Example 255D for Example 87. MS (ESI(+)) m/e 458 (M+H)$^+$.

Example 259B 2-(4-(5-fluoro-4-(5-fluoro-2-methoxyphenyl)-1H-pyrrolo[2,3-b]pyridin-2-yl)piperidin-1-yl)acetic acid The title compound was prepared using the procedure described in Example 226B, substituting Example 259A for Example 226A. MS (ESI(+)) m/e 402 (M+H)$^+$.

Example 259C

2-{4-[5-fluoro-4-(5-fluoro-2-methoxyphenyl)-1H-pyrrolo[2,3-b]pyridin-2-yl]piperidin-1-yl}-1-(3-hydroxyazetidin-1-yl)ethanone The title compound was prepared using the procedure described in Example 238, substituting Example 259B for 226B. $^1$H NMR (500 MHz, DMSO-$d_6$) 1.67-1.91 (m, 2H), 1.91-2.01 (m, 2H), 2.04-2.42 (m, 2H), 2.58-3.26 (m, 5H), 3.59 (dd, J=10.1, 4.3 Hz, 1H), 3.72 (s, 3H), 3.93 (dd, J=9.4, 4.3 Hz, 1H), 3.99-4.08 (m, 1H), 4.37 (d, J=8.7 Hz, 1H), 4.39-4.48 (m, 1H), 5.69 (d, J=6.0 Hz, 1H), 5.91 (d, J=2.0 Hz, 1H), 7.15-7.27 (m, 2H), 7.32 (td, J=8.6, 3.2 Hz, 1H), 8.13 (d, J=2.5 Hz, 1H), 11.73 (bs, 1H). MS (ESI(+)) m/e 457 (M+H)$^+$.

Example 260

2-[(2S)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide Example 260A (2S)-tert-butyl 4-hydroxy-2-(hydroxymethyl)piperidine-1-carboxylate A solution of (S)-1-(tert-butoxycarbonyl)-4-oxopiperidine-2-carboxylic acid (5 g, 20.55 mmol) in tetrahydrofuran (100 mL) under nitrogen was cooled in an ice bath. 1N Borane-tetrahydrofuran in tetrahydrofuran (61.7 mL, 61.7 mmol) was added dropwise over 25 minutes and the mixture was stirred at room temperature for 3 hours, cooled to 0° C. and quenched with 10 mL water. Potassium carbonate (5 g) was added and the mixture was stirred overnight at room temperature, and partitioned between water and ether (three times). The ether extracts were dried over sodium sulfate, filtered, concentrated onto silica gel, and purified by flash chromatography (gradient of 0-100% ethyl acetate-heptanes) to give the title compound as a mixture of diastereomers. MS (ESI+) m/z 231.9 (M+H)+.

Example 260B (2S)-tert-butyl 4-hydroxy-2-(((triisopropylsilyl)oxy) methyl)piperidine-1-carboxylate Chlorotriisopropylsilane (2.284 g, 11.85 mmol) was added dropwise to a 0° C. solution of Example 260A (2.65 g, 10.77 mmol), triethylamine (1.253 g, 12.39 mmol) and 4-(dimethylamino)pyridine (0.263 g, 2.154 mmol) in dichloromethane (25 mL). The mixture was stirred at 0° C. for 20 minutes and at room temperature for 16 hours. Water (50 mL) was added and the layers were separated. The aqueous layer was extracted with dichloromethane (twice), and the combined extracts were dried over sodium sulfate, filtered, and concentrated. The residue was purified by flash chromatography on silica gel (gradient of 0-30% ethyl acetate/heptanes) to give the title compound as a mixture of diastereomers. MS (ESI+) m/z 388.0 (M+H)+.

Example 260C (S)-tert-butyl 4-oxo-2-(((triisopropylsilyl)oxy)methyl)piperidine-1-carboxylate To a solution of Example 260B (3.32 g, 8.56 mmol) in dichloromethane (28.5 mL) was added activated powdered 4 Å molecular sieves (9 g), tetrapropylammonium perruthenate (0.150 g, 0.428 mmol) and N-methylmorpholine-N-oxide (1.505 g, 12.85 mmol), and the mixture was stirred overnight at room temperature. The mixture was filtered through a pad of silica, rinsing with ethyl acetate. The filtrate was concentrated and purified by flash chromatography on silica gel (gradient from 0-20% ethyl acetate-heptanes) to give the title compound. MS (ESI+) m/z 385.8 (M+H)+.

Example 260D (S)-tert-butyl 4-(((trifluoromethyl)sulfonyl)oxy)-6-(((triisopropylsilyl)oxy)methyl)-5,6-dihydropyridine-1(2H)-carboxylate and (5)-tert-butyl 4-(((trifluoromethyl)sulfonyl)oxy)-2-(((triisopropylsilyl)oxy) methyl)-5,6-dihydropyridine-1(2H)-carboxylate A solution of Example 260C (2.27 g, 5.89 mmol) in tetrahydrofuran (24 mL) at −78° C. was treated dropwise with a 1M solution of sodium bis(trimethylsilyl)amide in tetrahydrofuran (7.06 ml, 7.06 mmol). The mixture was stirred for 30 minutes at −78° C. and a solution of 1,1,1-trifluoro-N-phenyl-N-((trifluoromethyl)sulfonyl)methanesulfonamide (2.73 g, 7.65 mmol) in tetrahydrofuran (6 mL) was added dropwise. The mixture allowed to warm to room temperature and stirred for 3 hours. The reaction was quenched with saturated aqueous ammonium chloride (50 mL) and extracted with ethyl acetate (three times). The organic extracts were dried over sodium sulfate, filtered, and concentrated and the residue was purified by flash chromatography on silica gel, eluting with a gradient from 0-40% ethyl acetate-heptanes to give a mixture of the two diastereomers, which was used in the next step without further purification. MS (ESI+) m/z 418.1 (M-Boc+H)+.

Example 260E (S)-tert-butyl 4-(4-(5-fluoro-2-methoxyphenyl)-1H-pyrrolo[2,3-b]pyridin-2-yl)-6-(((triisopropylsilyl)oxy)methyl)-5,6-dihydropyridine-1(2H)-carboxylate The mixture of Example 260D (2.66 g, 4.62 mmol), bis(pinacolatodiboron) (1.173 g, 4.62 mmol), and potassium acetate (2.266 g, 23.09 mmol) in dioxane (25 mL) was degassed with nitrogen for 30 minutes. Bis(diphenylphosphino)ferrocene]dichloropalladium(II)-dichloromethane complex (0.189 g, 0.231 mmol) was added and the mixture was heated at reflux for 1.5 hours and cooled to room temperature. To this mixture was added Example 219A (1.7 g, 4.62 mmol), bis(diphenylphosphino)ferrocene]dichloropalladium(II)-dichloromethane complex (0.189 g, 0.231 mmol) and a degassed solution of sodium carbonate (2.69 g, 25.4 mmol) in water (12.5 mL). Nitrogen was bubbled through the mixture for 10 minutes, followed by heating at 75° C. for 16 hours. After cooling to room temperature, the mixture was partitioned between water and ethyl acetate (three times). The combined extracts were dried over sodium sulfate, filtered, and concentrated, and the residue was purified by flash chromatography on silica gel, eluting with a gradient from 0-5% methanol in dichloromethane, to provide the two diastereomers, Example 260E (eluting last) and Example 260F (eluting first). Example 260E: MS (ESI+) m/z 610.2 (M+H)+; Example 260F: MS (ESI+) m/z 610.2 (M+H)+.

Example 260F (S)-tert-butyl 4-(4-(5-fluoro-2-methoxyphenyl)-1H-pyrrolo[2,3-b]pyridin-2-yl)-2-(((triisopropylsilyl)oxy)methyl)-5,6-dihydropyridine-1(2H)-carboxylate The mixture of Example 260D (2.66 g, 4.62 mmol), bis(pinacolatodiboron) (1.173 g, 4.62 mmol), and potassium acetate (2.266 g, 23.09 mmol) in dioxane (25 mL) was degassed with nitrogen for 30 minutes. Bis(diphenylphosphino)ferrocene]dichloropalladium(II)-dichloromethane complex (0.189 g, 0.231 mmol) was added and the mixture was heated at reflux for 1.5 hours and cooled to room temperature. To this mixture was added Example 219A (1.7 g, 4.62 mmol), bis(diphenylphosphino)ferrocene]dichloropalladium(II)-dichloromethane complex (0.189 g, 0.231 mmol) and a degassed solution of sodium carbonate (2.69 g, 25.4 mmol) in water (12.5 mL). Nitrogen was bubbled through the mixture for 10 minutes, followed by heating at 75° C. for 16 hours. After cooling to room temperature, the mixture was partitioned between water and ethyl acetate (three times). The combined extracts were dried over sodium sulfate, filtered, and concentrated, and the residue was purified by flash chromatography on silica gel, eluting with a gradient from 0-5% methanol in dichloromethane, to provide the two diastereomers, Example 260E (eluting last) and Example 260F (eluting first). Example 260E: MS (ESI+) m/z 610.2 (M+H)+; Example 260F: MS (ESI+) m/z 610.2 (M+H)+.

Example 260G (S)-tert-butyl 4-(4-(5-fluoro-2-methoxyphenyl)-1H-pyrrolo[2,3-b]pyridin-2-yl)-6-(hydroxymethyl)-5,6-dihydropyridine-1(2H)-carboxylate A solution of 1M tetrabutylammonium fluoride in tetrahydrofuran (3.1 mL, 3.10 mmol) was added to a solution of Example 260E (627 mg, 1.028 mmol) in tetrahydrofuran (5 mL) and the mixture was stirred at room temperature for 1 hour and concentrated. The residue was purified by flash chromatography on silica gel, eluting with a gradient of 0-7% methanol-dichloromethane to give the title compound. MS (ESI+) m/z 454.1 (M+H)+.

Example 260H (S)-(4-(4-(5-fluoro-2-methoxyphenyl)-1H-pyrrolo[2,3-b]pyridin-2-yl)-1,2,3,6-tetrahydropyridin-2-yl)methanol The title compound was prepared as the hydrochloride salt using the procedure described in Example 1H, using Example 260G (334 mg, 0.736 mmol) in place of Example 1G. MS (ESI+) m/z 354.0 (M+H)+.

Example 260I

2-[(2S)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide To a solution of Example 260H (150 mg, 0.352 mmol) in N,N-dimethylformamide (1.8 mL) was added N-ethyl-N-isopropylpropan-2-amine (227 mg, 1.759 mmol) and 2-chloro-N,N-dimethylacetamide (39.9 µL, 0.387 mmol). The mixture was stirred for 3 days at room temperature and for 2 hours at 70° C., and partitioned between water and ethyl acetate (three times). The extracts were dried over sodium sulfate, filtered, and concentrated, and the residue was purified by flash chromatography on silica gel, eluting with a gradient of 0-8% methanol/dichloromethane to afford the title compound. $^1$H NMR (400 MHz, DMSO-d$_6$) δ 11.77 (s, 1H), 8.18 (d, J=5.0 Hz, 1H), 7.31-7.16 (m, 3H), 7.02 (d, J=5.0 Hz, 1H), 6.46 (s, 1H), 6.18 (d, J=1.8 Hz, 1H), 4.61 (t, J=5.3 Hz, 1H), 3.74 (s, 3H), 3.60-3.27 (m, 6H), 3.33 (s, 3H), 3.02 (s, 3H), 2.93 (dd, J=11.1, 5.7 Hz, 1H), 2.81 (s, 3H), 2.48-2.32 (m, 2H); MS (ESI+) m/z 439.0 (M+H)+.

Example 261

2-[(6S)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide Example 261 was prepared essentially as described in Example 260, substituting Example 260F for Example 260E in Example 260G. $^1$H NMR (500 MHz, DMSO-d$_6$) δ 11.75 (s, 1H), 8.19 (d, J=4.9 Hz, 1H), 7.35-7.11 (m, 3H), 7.02 (d, J=5.0 Hz, 1H), 6.48-6.45 (m, 1H), 6.23 (d, J=1.8 Hz, 1H), 4.81 (t, J=5.3 Hz, 1H), 3.74 (s, 3H), 3.61 (d, J=15.0 Hz, 1H), 3.57-3.49 (m, 1H), 3.43 (dt, J=9.9, 5.0 Hz, 1H), 3.37 (dd, J=11.3, 4.2 Hz, 1H), 3.23 (s, 1H), 3.01 (s, 3H), 2.99-2.92 (m, 1H), 2.83 (s, 3H), 2.76-2.69 (m, 1H), 2.43 (d, J=17.2 Hz, 1H), 2.32 (d, J=17.2 Hz, 1H); MS (ESI+) m/z 439.0 (M+H)+.

Example 262

4-(5-fluoro-2-methoxyphenyl)-2-((3aS,6aR)-2-(methylsulfonyl)-1,2,3,3a,4,6a-hexahydrocyclopenta[c]pyrrol-5-yl)-1H-pyrrolo[2,3-b]pyridine Example 262A tert-butyl 5-(((trifluoromethyl)sulfonyl)oxy)-3,3a,6,6a-tetrahydrocyclopenta[c]pyrrole-2(1H)-carboxylate To a solution of sodium bis(trimethylsilyl)amide (1M in tetrahydrofuran, 14.65 mL, 14.65 mmol) in tetrahydrofuran (12 mL) at −78° C. was slowly added tert-butyl 5-oxohexahydrocyclopenta[c]pyrrole-2(1H)-carboxylate (3.00 g, 13.32 mmol) in tetrahydrofuran (7.5 mL). The mixture was stirred for 30 minutes and treated over 15 minutes with a solution of 1,1,1-trifluoro-N-phenyl-N-((trifluoromethyl)sulfonyl) methanesulfonamide (5.23 g, 14.65 mmol) in tetrahydrofuran (12 mL). The mixture was stirred at −78° C. for 90 minutes and allowed to warm to room temperature for 1 hour. The mixture was quenched with water (7.5 mL) and extracted with ethyl acetate. The organic layer was washed with brine, dried over sodium sulfate, filtered, and concentrated in vacuo. The residue was purified by flash chromatography on silica gel, eluting with a gradient of 10-80% ethyl acetate/hexanes to afford the title compound (~75% purity), which was used in the next step without further purification. MS (ESI$^+$) m/z 380 (M+Na)$^+$.

Example 262B tert-butyl 5-(4,4,5,5-tetramethyl-1,3,2-dioxaborolan-2-yl)-3,3a,6,6a-tetrahydrocyclopenta[c]pyrrole-2 (1H)-carboxylate A pressure vial was charged with Example 262A (2000 mg, ~4.20 mmol), 4,4,4',4',5,5,5',5'-octamethyl-2,2'-bi(1,3,2-dioxaborolane) (1173 mg, 4.62 mmol), potassium acetate (1236 mg, 12.59 mmol), [1,1'-bis(diphenylphosphino)ferrocene]dichloropalladium(II)-dichloromethane complex (171 mg, 0.210 mmol) and dioxane (16 mL). The vial was capped with a septa, flushed with nitrogen, stirred at 90° C. for 4 hours and used directly in the next step.

Example 262C tert-butyl 5-(4-(5-fluoro-2-methoxyphenyl)-1-(phenylsulfonyl)-1H-pyrrolo[2,3-b]pyridin-2-yl)-3,3a,6,6a-tetrahydrocyclopenta[c]pyrrole-2(1H)-carboxylate To Example 262B (~4.20 mmol) was added Example 87B (2.14 g, 4.20 mmol), aqueous 2M sodium carbonate (10.50 mL, 21.0 mmol) and [1,1'-bis(diphenylphosphino)ferrocene] dichloropalladium(II)-dichloromethane complex (0.171 g, 0.210 mmol). The vial was capped with a septa, flushed with nitrogen and stirred at 65° C. for 6 hours. Water was added and the mixture was extracted with ethyl acetate. The combined organic layers were washed with brine, dried over sodium sulfate, filtered, and concentrated in vacuo. The residue was purified by flash chromatography on silica gel, eluting with a gradient of 0-5% methanol in dichloromethane to give the title compound (~80% purity), which was used in the next step without further purification. MS (ESI$^+$) m/z 590 (M+H)$^+$.

Example 262D tert-butyl 5-(4-(5-fluoro-2-methoxyphenyl)-1H-pyrrolo[2,3-b]pyridin-2-yl)-3,3a,6,6a-tetrahydrocyclopenta[c]pyrrole-2(1H)-carboxylate To a solution of Example 262C (~3.93 mmol) in tetrahydrofuran (28 mL) and methanol (20 mL) was added 1M aqueous sodium hydroxide (23.61 mL, 23.61 mmol) and the mixture was stirred at 60° C. for 3 hours. The mixture was extracted with ethyl acetate and the organic layer was washed with brine, dried over sodium sulfate, filtered and concentrated in vacuo. The residue was purified by flash chromatography on silica gel, eluting with a gradient of 6-15% methanol in dichloromethane to give the title compound. LC-MS: 450 (M+H)$^+$.

Example 262E 4-(5-fluoro-2-methoxyphenyl)-2-(1,2,3,3a,4,6a-hexahydrocyclopenta[c]pyrrol-5-yl)-1H-pyrrolo[2,3-b]pyridine To Example 262D (966 mg, 2.15 mmol) was added dichloromethane (6 mL) and trifluoroacetic acid (2 mL). The mixture was stirred at room temperature for 1 hour and concentrated in vacuo. The residue was diluted with ethyl acetate, washed with aqueous sodium bicarbonate and brine, and the organic layer was dried over sodium sulfate, filtered and concentrated in vacuo to give the title compound. MS (ESI$^+$) m/z 350 (M+H)$^+$.

Example 262F 4-(5-fluoro-2-methoxyphenyl)-2-(2-(methylsulfonyl)-1,2,3,3a,4,6a-hexahydrocyclopenta[c]pyrrol-5-yl)-1H-pyrrolo[2,3-b]pyridine To Example 262E (300 mg, 0.86 mmol) in N,N-dimethylformamide (3 mL) was added methanesulfonyl chloride (0.10 mL, 1.29 mmol) and triethylamine (0.36 mL, 2.57 mmol). The mixture was stirred at room temperature for 30 minutes and concentrated in vacuo. The residue was purified by reverse-phase HPLC on a Phenomenex Luna C8 AXIA column (30×75 mm, 100 Å) using a gradient of 10-95% acetonitrile:0.1% trifluoroacetic acid in water to afford the title compound as the trifluoroacetic acid salt. The salt was diluted with ethyl acetate and neutralized with aqueous sodium bicarbonate. The organic layer was washed with brine, dried over sodium sulfate, filtered, and concentrated in vacuo to afford the title compound as the free base. MS (ESI$^+$) m/z 428 (M+H)$^+$.

Example 262G 4-(5-fluoro-2-methoxyphenyl)-2-43aS,6aR)-2-(methylsulfonyl)-1,2,3,3a,4,6a-hexahydrocyclopenta[c] pyrrol-5-yl)-1H-pyrrolo[2,3-b]pyridine Preparative SFC chiral separation of Example 262F (29 mg) was performed on a THAR/Waters SFC 80 system running under SuperChrom software control and equipped with an S-way preparative column switcher, carbon dioxide pump, modifier pump, automated back pressure regulator, UV detector, and 6-position fraction collector. The mobile phase comprised of supercritical carbon dioxide supplied by a Dewar of bone-dry non-certified carbon dioxide pressurized to 350 psi with a modifier of methanol at a flow rate of 70 g/minutes. UV detection was set to collect at a wavelength of 220 nm, the column was at ambient temperature, and the backpressure regulator was set to maintain 100 bar. The sample was dissolved in methanol/dichloromethane (1/2) at a concentration of 20 mg/mL. The sample was loaded into the modifier stream in 1 mL (20 mg) injections. The mobile phase was held isocratically at 20% methanol:carbon dioxide. Fraction collection was time triggered. The instrument was fitted with a CHIRALPAK IC column (21 mm i.d.×250 mm length with 5 µm particles). The chiral separation afforded the title compound (which corresponded to the slower eluting enantiomer) and Example 264 (see below). For the title compound: $^1$H NMR (400 MHz, DMSO-d$_6$) δ 2.57-2.68 (m, 1H) 2.87 (s, 3H) 2.89-3.48 (m, 6H) 3.55-3.67 (m, 1H) 3.74 (s, 3H) 6.19 (s, 1H) 6.30 (s, 1H) 7.04 (d, J=4.88 Hz, 1H) 7.14-7.35 (m, 3H) 8.21 (d, J=4.58 Hz, 1H) 11.92 (s, 1H). MS (ESI$^+$) m/z 428 (M+H)$^+$.

Example 263

2-{4-[3-cyano-5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide Example 263A 4-chloro-5-fluoro-3-iodo-1H-pyrrolo[2,3-b]pyridine To a solution of 4-chloro-5-fluoro-1H-pyrrolo[2,3-b]pyridine (1.8 g, 10.5 mmol) in N,N-dimethylformamide (25 mL) at 0° C. was added N-iodosuccinimide (2.37 g, 10.55 mmol). The mixture was slowly brought to room temperature, quenched with brine and extracted with ethyl acetate (twice). The organic phase was concentrated and purified by column chromatography (silica gel, 30% ethyl acetate in hexane) to afford the title compound. MS (ESI$^+$) m/z 297 (M+H)$^+$.

Example 263B 4-chloro-5-fluoro-3-iodo-1-((2-(trimethylsilyl)ethoxy)methyl)-1H-pyrrolo[2,3-b]pyridine A solution of Example 263A (2.8 g, 9.44 mmol) in tetrahydrofuran (200 mL) was cooled to 0° C. and sodium hydride (0.34 g, 14.17 mmol) was added. The mixture was stirred at 0° C. for 30 minutes and (2-(chloromethoxy)ethyl)trimethylsilane (2.5 mL, 14.17 mmol) was added. The mixture was warmed to room temperature, stirred for 2 hours, quenched with brine and extracted with ethyl acetate (twice). The organic phase was concentrated and purified by flash chromatography (silica gel, 30% ethyl acetate in hexane) to afford the title compound. MS (ESI$^+$) m/z 427 (M+H)$^+$.

Example 263C 4-chloro-5-fluoro-1-((2-(trimethylsilyl)ethoxy)methyl)-1H-pyrrolo[2,3-b]pyridine-3-carbonitrile A mixture of Example 263B (2.5 g, 5.86 mmol), zinc cyanide (0.8 g, 7.0 mmol), 1,1'-bis(diphenylphosphino)ferrocene (0.4 g, 0.7 mmol) and tris(dibenzylideneacetone)dipalladium(0) (0.27 g, 0.3 mmol) in N,N-dimethylformamide (50 mL) and water (0.5 mL) was flushed with nitrogen and heated at 80° C. overnight. The reaction was quenched with brine and extracted with ethyl acetate (twice). The organic phase was concentrated and purified by flash chromatography (silica gel, 30% ethyl acetate in hexane) to afford the title compound. MS (ESI$^+$) m/z 326 (M+H)$^+$.

Example 263D 5-fluoro-4-(5-fluoro-2-methoxyphenyl)-1-((2-(trimethylsilyl)ethoxy)methyl)-1H-pyrrolo[2,3-b]pyridine-3-carbonitrile The title compound was prepared using the procedure described in Example 87A, using Example 263C (750 mg, 2.3 mmol) in place of 4-bromo-1-(phenylsulfonyl)-1H-pyrrolo[2,3-b]pyridine. LCMS: 416 (M+H)$^+$.

Example 263E 5-fluoro-4-(5-fluoro-2-methoxyphenyl)-2-iodo-1-((2-(trimethylsilyl)ethoxy)methyl)-1H-pyrrolo[2,3-b]pyridine-3-carbonitrile A solution of Example 263D (0.72 g, 1.7 mmol) in tetrahydrofuran (50 mL) was cooled to −75° C. and 2N lithium diisopropylamide (2.6 mL, 5.2 mmol) was added dropwise. The mixture was stirred at −75° C. for 30 minutes and a solution of iodine (0.88 g, 3.47 mmol) in tetrahydrofuran (2.5 mL) was added. The mixture was slowly brought to room temperature, quenched with aqueous ammonium chloride (100 mL) and extracted with ethyl acetate (twice). The organic phase was concentrated and purified by flash chromatography (silica gel, 30% ethyl acetate in hexane) to afford the title compound. MS (ESI$^+$) m/z 542 (M+H)$^+$.

Example 263F tert-butyl 4-(3-cyano-5-fluoro-4-(5-fluoro-2-methoxyphenyl)-1-((2-(trimethylsilyl)ethoxy)methyl)-1H-pyrrolo[2,3-b]pyridin-2-yl)-5,6-dihydropyridine-1(2H)-carboxylate The title compound was prepared using the procedure described in Example 87C, using Example 263E (0.5 mg, 0.9 mmol) in place of Example 87B. LCMS: 597 (M+H)$^+$.

Example 263G 5-fluoro-4-(5-fluoro-2-methoxyphenyl)-2-(1,2,3,6-tetrahydropyridin-4-yl)-1H-pyrrolo[2,3-b]pyridine-3-carbonitrile To a solution of Example 263F (0.42 g, 0.7 mmol) in tetrahydrofuran (10 mL) was added 35% hydrochloric acid (6 mL) and the mixture was heated at 65° C. overnight. Concentration and purification by HPLC (Zorbax C-18, using a 0-100% gradient of water/acetonitrile, containing 0.1% trifluoroacetic acid) afforded the title compound. $^1$H NMR (400 MHz, Methanol-d$_4$) δ 3.00 (tq, J=6.2, 2.3 Hz, 2H), 3.58 (td, J=6.5, 2.8 Hz, 2H), 3.77 (s, 3H), 3.77 (s, 3H), 3.98 (q, J=2.7 Hz, 2H), 6.68 (tt, J=3.5, 1.7 Hz, 1H), 7.06-7.17 (m, 2H) 7.19-7.29 (m, 1H), 8.35 (d, J=2.3 Hz, 1H). MS (ESI$^+$) m/z 367 (M+H)$^+$.

Example 263H

2-{4-[3-cyano-5-fluoro-4-(5-fluoro-2-methoxyphenyl)-1H-pyrrolo[2,3-b]pyridin-2-yl]-3,6-dihydropyridin-1(2H)-yl}-N,N-dimethylacetamide The title compound was prepared using the procedure described in Example 231F, using Example 263G (60 mg, 0.17 mmol) in place of Example 231E. $^1$H NMR (500 MHz, Methanol-d$_4$) δ 3.02 (s, 6H), 3.13 (d, J=6.8 Hz, 2H), 3.46-3.73 (m, 2H), 3.77 (s, 3H), 4.15 (s, 2H), 4.37 (s, 2H), 6.67 (dt, J=3.5, 1.9 Hz, 1H), 7.02-7.18 (m, 2H), 7.24 (ddd, J=9.2, 8.2, 3.1 Hz, 1H), 8.36 (d, J=2.3 Hz, 1H). MS (ESI$^+$) m/z 452 (M+H)$^+$.

Example 264

4-(5-fluoro-2-methoxyphenyl)-2-43aR,6aS)-2-(methylsulfonyl)-1,2,3,3a,4,6a-hexahydrocyclopenta[c]pyrrol-5-yl)-1H-pyrrolo[2,3-b]pyridine The title compound was prepared as described in Example 262G. The title compound corresponded to the faster eluting enantiomer under the SFC conditions described. $^1$H NMR (400 MHz, DMSO-d$_6$) δ 2.57-2.66 (m, 1H) 2.87 (s, 3H) 2.88-3.49 (m, 6H) 3.57-3.67 (m, 1H) 3.74 (s, 3H) 6.19 (s, 1H) 6.31 (s, 1H) 7.04 (d, J=4.88 Hz, 1H) 7.14-7.33 (m, 3H) 8.21 (d, J=4.88 Hz, 1H) 11.92 (s, 1H). MS (ESI$^+$) m/z 428 (M+H)$^+$.

Example 265

5-fluoro-4-(5-fluoro-2-methoxyphenyl)-2-[1-(methylsulfonyl)-1,2,3,6-tetrahydropyridin-4-yl]-1H-pyrrolo[2,3-b]pyridine-3-carbonitrile The title compound was prepared using the procedure described in Example 148, using Example 263G (50 mg, 0.14 mmol) in place of Example 135B. $^1$H NMR (400 MHz, Methanol-d$_4$) δ 2.82 (tt, J=5.8, 2.5 Hz, 2H), 2.92 (s, 3H), 3.54 (t, J=5.7 Hz, 2H), 3.78 (s, 3H), 4.05 (q, J=3.0 Hz, 2H), 6.69 (t, J=1.8 Hz, 1H), 7.11 (ddd, J=8.1, 6.0, 3.7 Hz, 2H), 7.23 (ddd, J=9.1, 8.2, 3.1 Hz, 1H), 8.30 (d, J=2.3 Hz, 1H). MS (ESI$^+$) m/z 445 (M+H)$^+$.

Example 266

4-[3-cyano-5-fluoro-4-(5-fluoro-2-methoxyphenyl)-1H-pyrrolo[2,3-b]pyridin-2-yl]-N-methyl-3,6-dihydropyridine-1(2H)-carboxamide The title compound was prepared using the procedure described in Example 215, using Example 263G (50 mg, 0.14 mmol) in place of Example 87. $^1$H NMR (400 MHz, Methanol-d$_4$) δ 2.67-2.74 (m, 2H), 2.77 (s, 3H), 3.63-3.68 (m, 2H), 3.78 (s, 3H), 4.14 (q, J=3.0 Hz, 2H), 6.64-6.70 (m, 1H), 7.11 (ddd, J=8.6, 5.2, 3.6 Hz, 2H), 7.23 (td, J=8.6, 3.1 Hz, 1H), 8.30 (d, J=2.4 Hz, 1H). MS (ESI$^+$) m/z 424 (M+H)$^+$.

Example 267

5-fluoro-4-(5-fluoro-2-methoxyphenyl)-2-{1-[2-(3-hydroxyazetidin-1-yl)-2-oxoethyl]-1,2,3,6-tetrahydropyridin-4-yl}-1H-pyrrolo[2,3-b]pyridine-3-carbonitrile

Example 267A tert-butyl 2-(4-(3-cyano-5-fluoro-4-(5-fluoro-2-methoxyphenyl)-1H-pyrrolo[2,3-b]pyridin-2-yl)-5,6-dihydropyridin-1(2H)-yl)acetate The title compound was prepared using the procedure described in Example 226A, using Example 263G (50 mg, 0.14 mmol) in place of Example 87. MS (ESI$^+$) m/z 481 (M+H)$^+$.

Example 267B 2-(4-(3-cyano-5-fluoro-4-(5-fluoro-2-methoxyphenyl)-1H-pyrrolo[2,3-b]pyridin-2-yl)-5,6-dihydropyridin-1(2H)-yl)acetic acid The title compound was prepared using the procedure described in Example 226B, using Example 267A (105 mg, 0.22 mmol) in place of Example 226A. MS (ESI$^+$) m/z 425 (M+H)$^+$.

Example 267C 5-fluoro-4-(5-fluoro-2-methoxyphenyl)-2-(1-(2-(3-hydroxyazetidin-1-yl)-2-oxoethyl)-1,2,3,6-tetrahydropyridin-4-yl)-1H-pyrrolo[2,3-b]pyridine-3-carbonitrile The title compound was prepared using the procedure described in Example 238, using Example 267B (60 mg, 0.14 mmol) in place of Example 226B. $^1$H NMR (500 MHz, Methanol-d$_4$) δ 3.03-3.18 (m, 2H), 3.53-3.69 (m, 2H), 3.77 (s, 3H), 3.86 (dd, J=10.6, 4.4 Hz, 1H), 3.99-4.05 (m, 1H), 4.13-4.17 (m, 2H), 4.28-4.34 (m, 1H), 4.44 (td, J=7.5, 3.7 Hz, 1H), 4.66 (ddd, J=6.8, 4.4, 2.5 Hz, 1H), 6.66 (dq, J=3.8, 2.0 Hz, 1H), 7.08-7.16 (m, 2H), 7.24 (td, J=8.6, 3.1 Hz, 1H), 8.36 (d, J=2.2 Hz, 1H). MS (ESI$^+$) m/z 424 (M+H)$^+$.

Example 268

5-fluoro-4-(5-fluoro-2-methoxyphenyl)-2-(1-{2-[(2R)-2-(hydroxymethyl)pyrrolidin-1-yl]-2-oxoethyl}-1,2,3,6-tetrahydropyridin-4-yl)-1H-pyrrolo[2,3-b]pyridine-3-carbonitrile The title compound was prepared using the procedure described in Example 238, using Example 267B (50 mg, 0.11 mmol) in place of Example 226B and (R)-pyrrolidin-2-yl-methanol in place of azetidin-3-ol hydrochloride. $^1$H NMR (400 MHz, DMSO-d$_6$) δ 1.77-2.03 (m, 4H), 2.93-3.13 (m, 2H), 3.17 (s, 2H), 3.33-3.48 (m, 2H), 3.49-3.56 (m, 1H), 3.74 (s, 3H), 3.95-4.09 (m, 2H), 4.33 (d, J=6.1 Hz, 2H), 4.46 (s, 1H), 6.68 (d, J=4.3 Hz, 1H), 7.21 (d, J=4.4 Hz, 1H), 7.29 (dd, J=8.6, 3.1 Hz, 1H), 7.33-7.41 (m, 1H), 8.48 (s, 1H). MS (ESI$^+$) m/z 508 (M+H)$^+$.

Example 269

2-[(6R)-4-[4-(5-fluoro-2-methoxyphenyl)-1H-pyrrolo[2,3-b]pyridin-2-yl]-6-(hydroxymethyl)-3,6-dihydropyridin-1(2H)-yl]-N,N-dimethylacetamide The title compound was prepared essentially as described in Example 260, substituting (R)-1-(tert-butoxycarbonyl)-4-oxopiperidine-2-carboxylic acid for (S)-1-(tert-butoxycarbonyl)-4-oxopiperidine-2-carboxylic acid in the procedure described for Example 260A. $^1$H NMR (400 MHz, DMSO-d$_6$) δ 11.73 (s, 1H), 8.18 (d, J=4.9 Hz, 1H), 7.36-7.07 (m, 3H), 7.02 (d, J=4.9 Hz, 1H), 6.46 (d, J=3.0 Hz, 1H), 6.23 (d, J=1.8 Hz, 1H), 4.79 (t, J=5.2 Hz, 1H), 3.74 (s, 3H), 3.61 (d, J=15.0 Hz, 1H), 3.57-3.48 (m, 1H), 3.43 (dt, J=10.8, 5.4 Hz, 1H), 3.37-3.27 (m, 1H), 3.23 (s, 1H), 3.01 (s, 3H), 2.96 (dd, J=12.5, 6.2 Hz, 1H), 2.82 (s, 3H), 2.77-2.68 (m, 1H), 2.43 (d, J=16.9 Hz, 1H), 2.31 (d, J=17.6 Hz, 1H); MS (ESI+) m/z 439.0 (M+H)+.

Example 270

2-[(2R)-4-[4-(5-fluoro-2-methoxyphenyl)-1H-pyrrolo[2,3-b]pyridin-2-yl]-2-(hydroxymethyl)-3,6-dihydropyridin-1(2H)-yl]-N,N-dimethylacetamide The title compound was prepared essentially as described in Example 260, substituting (R)-1-(tert-butoxycarbonyl)-4-oxopiperidine-2-carboxylic acid for (S)-1-(tert-butoxycarbonyl)-4-oxopiperidine-2-carboxylic acid in the procedure described for Example 260A. $^1$H NMR (400 MHz, DMSO-d$_6$) δ 11.77 (d, J=1.5 Hz, 1H), 8.18 (d, J=5.0 Hz, 1H), 7.35-7.12 (m, 3H), 7.02 (d, J=4.9 Hz, 1H), 6.46 (s, 1H), 6.18 (d, J=1.9 Hz, 1H), 4.61 (t, J=5.4 Hz, 1H), 3.74 (s, 3H), 3.60-3.27 (m, 6H), 3.02 (s, 3H), 2.97-2.88 (m, 1H), 2.81 (s, 3H), 2.48-2.34 (m, 2H); MS (ESI+) m/z 439.1 (M+H)+.

Example 271

2-[6,6-dimethyl-1-(methylsulfonyl)-1,2,3,6-tetrahydropyridin-4-yl]-4-(5-fluoro-2-methoxyphenyl)-1H-pyrrolo[2,3-b]pyridine

Example 271A tert-butyl 2,2-dimethyl-4-(((trifluoromethyl)sulfonyl)oxy)-5,6-dihydropyridine-1(2H)-carboxylate and tert-butyl 6,6-dimethyl-4-(((trifluoromethyl)sulfonyl)oxy)-5,6-dihydropyridine-1(2H)-carboxylate (4:1)

The title compound was prepared using the procedure described in Example 258A using tert-butyl 2,2-dimethyl-4-oxopiperidine-1-carboxylate (2.51 g, 11.04 mmol) in place of (S)-tert-butyl-2-methyl-4-oxopiperidine-1-carboxylate. Purification by flash chromatography on silica gel eluting with 1:1 dichloromethane:hexanes gave the title compound as a mixture of isomers. MS (ESI) m/e 260.0 (M-BOC)$^+$.

Example 271B tert-butyl 4-(4-(5-fluoro-2-methoxyphenyl)-1-tosyl-1H-pyrrolo[2,3-b]pyridin-2-yl)-2,2-dimethyl-5,6-dihydropyridine-1(2H)-carboxylate and tert-butyl 4-(4-(5-fluoro-2-methoxyphenyl)-1-tosyl-1H-pyrrolo[2,3-b]pyridin-2-yl)-6,6-dimethyl-5,6-dihydropyridine-1(2H)-carboxylate (4:1)

The title compound was prepared as a mixture of regioisomers using the procedure described in Example 258D using Example 271A (0.848 mg, 2.36 mmol) in place of Example 258A. The mixture was used in the next step without further purification. MS (ESI) m/e 606.1 (M+1)$^+$.

Example 271C tert-butyl 4-(4-(5-fluoro-2-methoxyphenyl)-1H-pyrrolo[2,3-b]pyridin-2-yl)-2,2-dimethyl-5,6-dihydropyridine-1(2H)-carboxylate The title compound was prepared using the procedure described in Example 258E using Example 271B (1.61 g, 2.66 mmol) in place of Example 258D. Purification by flash chromatography on silica gel eluting with 40% ethyl acetate in hexanes gave the single isomer title compound (the other regioisomer is described in Example 272A). MS (ESI) m/e 452.1 (M+1)$^+$.

Example 271D 2-(6,6-dimethyl-1,2,3,6-tetrahydropyridin-4-yl)-4-(5-fluoro-2-methoxyphenyl)-1H-pyrrolo[2,3-b]pyridine A mixture of Example 271C (0.249 g, 0.551 mmol) and 2,2,2-trifluoroacetic acid (1 mL, 12.98 mmol) in dichloromethane (1 mL) was stirred for 24 hours at room temperature and concentrated. The hydrochloride salt was prepared by dissolving the resultant solid in methanol and adding 2M hydrogen chloride in diethyl ether. After concentrating under reduced pressure, the title compound was obtained. MS (ESI) m/e 352.1 (M+1)$^+$.

Example 271E

2-[6,6-dimethyl-1-(methylsulfonyl)-1,2,3,6-tetrahydropyridin-4-yl]-4-(5-fluoro-2-methoxyphenyl)-1H-pyrrolo[2,3-b]pyridine The title compound was prepared using the procedure described in Example 258G using Example 271D (0.101 g, 0.239 mmol) in place of Example 258F. $^1$H NMR (500 MHz, DMSO-d$_6$) δ 1.56 (s, 6H), 2.52 (m, 2H), 3.01 (s, 3H), 3.43 (t, 2H), 3.74 (s, 3H), 6.28 (m, 2H), 7.04 (d, 1H), 7.24 (m, 3H), 8.21 (d, 1H), 11.80 (br s, 1H). MS (ESI) m/e 430.1 (M+1)$^+$.

Example 272

2-[2,2-dimethyl-1-(methylsulfonyl)-1,2,3,6-tetrahydropyridin-4-yl]-4-(5-fluoro-2-methoxyphenyl)-1H-pyrrolo[2,3-b]pyridine

Example 272A tert-butyl 4-(4-(5-fluoro-2-methoxyphenyl)-1H-pyrrolo[2,3-b]pyridin-2-yl)-6,6-dimethyl-5,6-dihydropyridine-1(2H)-carboxylate The title compound was prepared using the procedure described in Example 258E using Example 271B (1.61 g, 2.66 mmol) in place of Example 258D. Purification by flash chromatography on silica gel eluting with 40% ethyl acetate in hexanes gave the single isomer title compound (the other regioisomer is described in Example 271C). MS (ESI) m/e 452.1 (M+1)$^+$.

Example 272B 2-(2,2-dimethyl-1,2,3,6-tetrahydropyridin-4-yl)-4-(5-fluoro-2-methoxyphenyl)-1H-pyrrolo[2,3-b]pyridine The title compound was prepared using the procedure described in Example 271D using Example 272A (0.600 g, 1.32 mmol) in place of Example 271C. MS (ESI) m/e 352.1 (M+1)$^+$.

Example 272C 2-(2,2-dimethyl-1-(methylsulfonyl)-1,2,3,6-tetrahydropyridin-4-yl)-4-(5-fluoro-2-methoxyphenyl)-1H-pyrrolo[2,3-b]pyridine The title compound was prepared using the procedure described in Example 258G substituting Example 272B (0.106 g, 0.251 mmol) in place of Example 258F. $^1$H NMR (500 MHz, DMSO-d$_6$) δ 1.44 (s, 6H), 2.53 (m, 2H), 3.01 (s, 3H), 3.73 (s, 3H), 4.08 (m, 2H), 6.26 (d, 1H), 6.54 (m, 1H), 7.03 (d, 1H), 7.24 (m, 3H), 8.20 (d, 1H), 11.87 (br s, 1H). MS (ESI) m/e 430.2 (M+1)⁺.

Example 273

2-{4-[4-(5-fluoro-2-methoxyphenyl)-1H-pyrrolo[2,3-b]pyridin-2-yl]-2,2-dimethyl-3,6-dihydropyridin-1(2H)-yl}-N,N-dimethylacetamide A mixture of Example 272B (0.102 g, 0.241 mmol), 2-chloro-N,N-dimethylacetamide (0.047 g, 0.387 mmol) and triethylamine (0.2 mL, 1.43 mmol) was stirred in N,N-dimethylformamide (2 mL) at room temperature for 24 hours and concentrated under reduced pressure. Purification by reverse phase-HPLC (Sunfire 5 μM, 50×250 mm) eluting with 5-50% acetonitrile in water (containing 0.1% trifluoroacetic acid) provided the trifluoroacetate salt, which was dissolved in methanol and eluted from a SCX column with 0.5M ammonia in methanol to give the free base of the title compound. ¹H NMR (500 MHz, DMSO-d₆) δ 1.12 (br s, 6H), 2.38 (br s, 2H), 2.88 (s, 3H), 3.13 (s, 3H), 3.25 (br s, 1H), 3.32 (br s, 1H), 3.44 (m, 2H), 3.79 (s, 3H), 6.24 (m, 1H), 6.51 (m, 1H), 7.07 (d, 1H), 7.29 (m, 3H), 8.24 (d, 1H), 11.84 (br s, 1H). MS (ESI) m/e 437.1 (M+1)⁺.

Example 274

4-(5-fluoro-2-methoxyphenyl)-2-{2-[(2-methoxyethyl)sulfonyl]-1,2,3,3a,4,6a-hexahydrocyclopenta[c]pyrrol-5-yl}-1H-pyrrolo[2,3-b]pyridine The title compound was prepared using the procedure described in Example 262F using 2-methoxyethanesulfonyl chloride in place of methanesulfonyl chloride. ¹H NMR (400 MHz, DMSO-d₆) δ) d 2.60 (d, J=17.70 Hz, 1H) 2.98 (m, 3H) 3.21 (s, 3H) 3.46 (m, 2H) 3.61 (m, 3H) 3.73 (s, 3H) 6.18 (d, J=1.83 Hz, 1H) 6.30 (d, J=1.53 Hz, 1H) 7.04 (d, J=4.88 Hz, 1H) 7.23 (m, 3H) 8.21 (d, J=4.88 Hz, 1H) 11.91 (s, 1H). MS (ESI⁺) m/z 471.2 (M+H)⁺.

Example 275

2-{4-[5-cyano-4-(5-fluoro-2-methoxyphenyl)-1H-pyrrolo[2,3-b]pyridin-2-yl]piperidin-1-yl}-N,N-dimethylacetamide A solution of Example 236G (80 mg, 0.185 mmol) in methanol (10 mL) was added to 20% palladium hydroxide on carbon (wet) (40 mg, 0.029 mmol) in a pressure bottle. The mixture was stirred at 50° C. under 30 psi hydrogen for 16 hours and filtered. The filtrate was concentrated and the residue was purified by reverse-phase HPLC on a Phenomenex Luna C8 AXIA column (100 Å) using a gradient of 10-95% acetonitrile/0.1% trifluoroacetic acid in water to afford the title compound. ¹H NMR (400 MHz, DMSO-d₆) δ 2.00-2.20 (m, 2H), 2.21-2.30 (m, 2H), 2.90-2.98 (m, 6H), 2.98-3.45 (m, 5H), 3.75 (s, 3H), 4.21 (s, 2H), 6.09 (bs, 1H), 7.20 (dd, J=8.6, 3.1 Hz, 1H), 7.26 (dd, J=9.1, 4.5 Hz, 1H), 7.29-7.38 (m, 1H), 8.54 (s, 1H), 12.12 (bs, 1H). MS (ESI(+)) m/e 436 (M+H)⁺

Example 276

2-{4-[4-(5-fluoro-2-methoxyphenyl)-1H-pyrrolo[2,3-b]pyridin-2-yl]piperidin-1-yl}-N-(3-hydroxycyclobutyl)-N-methylacetamide The title compound was prepared according to the procedure described in Example 238 substituting Example 247B for Example 226B and 3-(methylamino)cyclobutanol hydrochloride (Enamine) for azetidin-3-ol hydrochloride. ¹H NMR (500 MHz, CD₃OD) δ 1.83-2.30 (m, 6H), 2.39-2.65 (m, 4H), 2.78-2.91 (m, 1H), 2.91-3.04 (m, 3H), 3.09-3.23 (m, 2H), 3.41-3.53 (m, 2H), 3.76 (s, 3H), 3.91-4.43 (m, 2H), 6.07 (d, J=4.0 Hz, 1H), 7.08 (d, J=5.1 Hz, 1H), 7.10-7.20 (m, 3H), 8.11 (d, J=5.1 Hz, 1H). MS (ESI⁺) m/z 467.2 (M+H)⁺.

Example 277

4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine-5-carbonitrile Example 277A 4-(5-fluoro-2-methoxyphenyl)-2-iodo-1H-pyrrolo[2,3-b]pyridine-5-carbonitrile To a solution of Example 236C (3 g, 5.63 mmol) in 20 mL tetrahydrofuran and 20 mL methanol was added 2N lithium hydroxide (8.44 mL, 16.88 mmol) and the mixture was stirred at room temperature for 4 hours. The mixture was neutralized with 2N aqueous hydrochloric acid, extracted with ethyl acetate and purified by flash chromatography eluting with 0-50% ethyl acetate in heptane to afford the title compound. MS (ESI(+)) m/e 394 (M+H)⁺.

Example 277B tert-butyl 5-(5-cyano-4-(5-fluoro-2-methoxyphenyl)-1H-pyrrolo[2,3-b]pyridin-2-yl)-3,3a,6,6a-tetrahydrocyclopenta[c]pyrrole-2(1H)-carboxylate The title compound was prepared using the procedure described in Example 87C, substituting Example 277A for Example 87B and Example 262B in place of tert-butyl 4-(4,4,5,5-tetramethyl-1,3,2-dioxaborolan-2-yl)-5,6-dihydropyridine-1(2H)-carboxylate. MS (ESI⁺) m/z 475 (M+H)⁺.

Example 277C 4-(5-fluoro-2-methoxyphenyl)-2-(1,2,3,3a,4,6a-hexahydrocyclopenta[c]pyrrol-5-yl)-1H-pyrrolo[2,3-b]pyridine-5-carbonitrile The title compound was prepared as the procedure described in Example 236F, substituting Example 277B for Example 236E. MS (ESI⁺) m/z 375 (M+H)⁺.

Example 277D 4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine-5-carbonitrile The title compound was prepared using the procedure described in Example 262F, substituting Example 277C for Example 262E. ¹H NMR (500 MHz, DMSO-d₆) δ 2.56-2.68 (m, 1H), 2.81-3.14 (m, 6H), 3.15-3.21 (m, 1H), 3.43 (dd, J=9.8, 8.1 Hz, 2H), 3.57-3.67 (m, 1H), 3.76 (s, 3H), 6.25 (dd, J=3.8, 1.9 Hz, 1H), 6.40 (d, J=2.3 Hz, 1H), 7.21-7.36 (m, 3H), 7.35-7.44 (m, 1H), 12.60 (bs, 1H). MS (ESI(+)) m/e 453 (M+H)$^+$.

Example 278

2-{5-[5-cyano-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide The title compound was prepared using the procedure described in Example 235, substituting Example 277C for Example 17. $^1$H NMR (400 MHz, DMSO-d$_6$) δ 2.40-2.50 (m, 3H), 2.55-2.64 (m, 2H), 2.77 (d, J=3.5 Hz, 3H), 2.82-2.99 (m, 5H), 3.16-3.21 (m, 2H), 3.40-3.50 (br, 1H), 3.75 (s, 3H), 6.17 (s, 1H), 6.40 (d, J=2.5 Hz, 1H), 7.23-7.34 (m, 2H), 7.39 (td, J=8.7, 3.2 Hz, 1H), 8.60 (d, J=0.7 Hz, 1H), 12.51 (bs, 1H). MS (ESI(+)) m/e 460 (M+H)$^+$.

Example 279

4-[5-fluoro-4-(5-fluoro-2-methoxyphenyl)-1H-pyrrolo[2,3-b]pyridin-2-yl]cyclohex-3-ene-1-carboxylic acid Example 279A ethyl 4-(4-chloro-5-fluoro-1-(phenylsulfonyl)-1H-pyrrolo[2,3-b]pyridin-2-yl)cyclohex-3-enecarboxylate The title compound was prepared essentially as described in Example 219B, substituting Example 219A with Example 231B. MS (ESI): 463.1 (M+H)$^+$.

Example 279B ethyl 4-(5-fluoro-4-(5-fluoro-2-methoxyphenyl)-1-(phenylsulfonyl)-1H-pyrrolo[2,3-b]pyridin-2-yl)cyclohex-3-enecarboxylate To a solution of Example 279A (1250 mg, 2.86 mmol) in 13.3 mL tetrahydrofuran/water (3:1) was added 5-fluoro-2-methoxyphenylboronic acid (1043 mg, 3.72 mmol), sodium carbonate (1214 mg, 11.45 mmol) and phenylallylchloro[1,3-bix(diisopropylphenyl)-2-imidazol-2-ylidene]palladium (II) (60.3 mg, 0.086 mmol) and the mixture was heated at 75° C. for 2 hours. The mixture was cooled to room temperature, and diluted with ethyl acetate, and the organics washed with saturated sodium bicarbonate, water, and brine, dried over magnesium sulfate, filtered, and concentrated. Purification by flash chromatography (Analogix280, SF 40-80 column, 10-60% ethyl acetate/hexane gradient) gave the title compound. MS (ESI): 553.1 (M+H)$^+$.

Example 279C

4-[5-fluoro-4-(5-fluoro-2-methoxyphenyl)-1H-pyrrolo[2,3-b]pyridin-2-yl]cyclohex-3-ene-1-carboxylic acid A suspension of Example 279B (1.1 g, 1.991 mmol) in 20 mL dioxane was treated with 6M aqueous sodium hydroxide (4.98 mL, 29.9 mmol) at 80° C. for 1 hour and at 100° C. for 2 hours. The mixture was cooled and most solvent removed in vacuo. The residue was diluted with 15 mL water and the basic layer extracted with ethyl acetate (twice). The organic layer was discarded. The basic aqueous layer was adjusted to ~pH 7 with 1M hydrochloric acid, and extracted with ethyl acetate (twice) and dichloromethane (twice). The combined organics were washed with brine, dried over magnesium sulfate, filtered, and concentrated. Trituration with ethyl acetate, filtration and drying in vacuo gave the title compound. $^1$H NMR (500 MHz, DMSO-d$_6$) δ 1.60-1.78 (m, 1H) 1.95-2.11 (m, 1H) 2.27-2.48 (m, 3H) 3.39-3.52 (m, 1H) 3.53-3.62 (m, 1H) 3.67-3.81 (m, 3H) 6.12 (s, 1H) 6.54 (s, 1H) 7.07-7.44 (m, 3H) 8.17 (d, J=2.14 Hz, 1H) 11.86 (s, 1H). MS (ESI): 385.2 (M+H)$^+$.

Example 280

1-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-2-hydroxyethanone A mixture of Example 262E (60 mg, 0.172 mmol), 2-hydroxyacetic acid (22.39 mg, 0.206 mmol), 1-[bis(dimethylamino)methylene]-1H-1,2,3-triazolo[4,5-b]pyridinium 3-oxide hexafluorophosphate (78 mg, 0.206 mmol) and triethylamine (47.9 µL, 0.343 mmol) in dimethylformamide (2 mL) was stirred at room temperature overnight. The mixture was concentrated in vacuo and the residue was purified by reverse-phase HPLC on a Phenomenex Luna C8 AXIA column (100 Å) using a gradient of 10-95% acetonitrile/0.1% trifluoroacetic acid in water to afford the title compound as the trifluoroacetate salt. $^1$H NMR (500 MHz, DMSO-d$_6$) δ 2.58-3.16 (m, 4H) 3.39-3.72 (m, 4H) 3.74 (s, 3H) 3.88-4.04 (m, 3H) 6.17-6.31 (m, 1H) 6.35 (s, 1H) 7.14 (d, J=5.19 Hz, 1H) 7.18-7.36 (m, 3H) 8.26 (d, J=5.19 Hz, 1H) 12.16 (s, 1H). MS (ESI$^+$) m/z 408 (M+H)$^+$.

Example 281

3-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-3-oxopropanenitrile The title compound was prepared as the trifluoroacetate salt using the procedure described in Example 280, substituting 2-hydroxyacetic acid with 2-cyanoacetic acid. $^1$H NMR (400 MHz, DMSO-d$_6$) δ 2.58-3.16 (m, 4H) 3.46-3.64 (m, 4H) 3.74 (s, 3H) 3.89-3.95 (m, 2H) 6.25 (dd, J=4.12, 1.98 Hz, 1H) 6.34 (s, 1H) 7.11 (d, J=4.88 Hz, 1H) 7.18-7.34 (m, 3H) 8.24 (d, J=5.19 Hz, 1H) 12.10 (s, 1H). MS (ESI$^+$) m/z 417 (M+H)$^+$.

Example 282

5-fluoro-4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine Example 282A 5-fluoro-4-(5-fluoro-2-methoxyphenyl)-2-(1,2,3,3a,4,6a-hexahydrocyclopenta[c]pyrrol-5-yl)-1H-pyrrolo[2,3-b]pyridine The title compound was prepared essentially as described in Example 231C-E, substituting Example 262B for tert-butyl 4-(4,4,5,5-tetramethyl-1,3,2-dioxaborolan-2-yl)-5,6-dihydropyridine-1(2H)-carboxylate in Example 231C. MS (ESI$^+$) m/z 368.2 (M+H)$^+$.

Example 282B 5-fluoro-4-(5-fluoro-2-methoxyphenyl)-2-[2-(methylsulfonyl)-1,2,3,3a,4,6a-hexahydrocyclopenta[c]pyrrol-5-yl]-1H-pyrrolo[2,3-b]pyridine To a solution of Example 282A in 1-methyl-2-pyrrolidinone (2 mL) was added triethylamine (0.177 mL, 1.267 mmol) and methanesulfonyl chloride (0.033 mL, 0.422 mmol) and the mixture was stirred for 3 hours. The mixture was treated with water and stirred for 10 minutes and the precipitate was filtered, washed with water, and vacuum oven-dried. The solid was suspended in 1 mL methanol and treated with 1 mL 2M hydrogen chloride in ether. The suspension was diluted with 4 mL ether, stirred for 10 minutes, filtered, washed with ether, and vacuum oven-dried to give the title compound as a hydrochloride salt. $^1$H NMR (400 MHz, Methanol-$d_4$) δ 2.63-2.76 (m, 1H), 2.85 (s, 3H), 3.00-3.13 (m, 1H), 3.11-3.24 (m, 2H), 3.37-3.54 (m, 3H), 3.68-3.77 (m, 1H), 3.80 (s, 3H), 6.39-6.48 (m, 2H), 7.20-7.29 (m, 2H), 7.28-7.37 (m, 1H), 8.43 (d, J=3.9 Hz, 1H). MS (ESI$^+$) m/z 446.2 (M+H)$^+$.

Example 283

4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-5-carbonitrile

Example 283A tert-butyl 2-(4-(5-cyano-4-(5-fluoro-2-methoxyphenyl)-1H-pyrrolo[2,3-b]pyridin-2-yl)-5,6-dihydropyridin-1(2H)-yl)acetate The title compound was prepared using the procedure described in Example 226A, substituting Example 236F for Example 87. MS (ESI(+)) m/e 463 (M+H)$^+$.

Example 283B 2-(4-(5-cyano-4-(5-fluoro-2-methoxyphenyl)-1H-pyrrolo[2,3-b]pyridin-2-yl)-5,6-dihydropyridin-1 (2H)-yl)acetic acid The title compound was prepared using the procedure described in Example 226B, substituting Example 283A for Example 226A. MS (ESI(+)) m/e 407 (M+H)$^+$.

Example 283C 4-(5-fluoro-2-methoxyphenyl)-2-(1-{2-[(2S)-2-(hydroxymethyl)pyrrolidin-1-yl]-2-oxoethyl}-1,2,3,6-tetrahydropyridin-4-yl)-1H-pyrrolo[2,3-b]pyridine-5-carbonitrile The title compound was prepared using the procedure described in Example 238, substituting Example 283B for Example 226B and (S)-pyrrolidin-2-ylmethanol for azetidin-3-ol hydrochloride. $^1$H NMR (400 MHz, DMSO-$d_6$) δ 1.72-1.95 (m, 4H), 2.40-2.77 (m, 4H), 3.16-3.42 (m, 7H), 3.76 (s, 3H), 4.18-4.2 (m, 3H), 6.25 (s, 1H), 6.56 (bs, 1H), 7.20-7.44 (m, 3H), 8.59 (s, 1H). MS (ESI(+)) m/e 490 (M+H)$^+$.

Example 284

(3aS,6aR)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide

Example 284A (3aS,6aR)-tert-butyl 5-(4-(5-fluoro-2-methoxyphenyl)-1H-pyrrolo[2,3-b]pyridin-2-yl)-3,3a,6,6a-tetrahydrocyclopenta[c]pyrrole-2(1H)-carboxylate Preparative SFC chiral separation of Example 262D (4.0 g) was performed on a THAR/Waters SFC 80 system running under SuperChrom software control and equipped with an S-way preparative column switcher, carbon dioxide pump, modifier pump, automated back pressure regulator, UV detector, and 6-position fraction collector. The mobile phase comprised of supercritical carbon dioxide supplied by a Dewar of bone-dry non-certified carbon dioxide pressurized to 350 psi with a modifier of methanol at a flow rate of 70 g/min. UV detection was set to collect at a wavelength of 220 nm, the column was at ambient temperature, and the back-pressure regulator was set to maintain 100 bar. The sample was dissolved in methanol at a concentration of 100 mg/mL. The sample was loaded into the modifier stream in 1 mL (100 mg) injections. The mobile phase was held isocraticly at 20% methanol:carbon dioxide. Fraction collection was time triggered. The instrument was fitted with a CHIRALPAK OD-H column (21 mm i.d.×250 mm length with 5 μm particles). The chiral separation afforded the title compound as the slower eluting enantiomer and Example 285A (see below, faster eluting enantiomer). Optical rotation for the title compound was obtained using an Autopol IV® automatic polarimeter (c=10 mg/mL in choloform at 24.8° C.) [α]$_D$=+165.20. LC-MS: 450 (M+H)$^+$.

Example 284B (3aS,6aR)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide To a solution of Example 284A (2.14 g, 4.76 mmol) in ethyl acetate (13 mL) was added methanol (13 mL) and 2M hydrogen chloride in diethyl ether (2 mL, 4.00 mmol). The mixture was stirred at 35° C. for 2 hours and cooled. Diethyl ether (50 mL) was added and the suspension was stirred vigorously at room temperature for 10 minutes and filtered. The solid was washed with 50 mL of diethyl ether and 50 mL of heptane and the solid was collected and dried under high vacuum to provide the deprotected intermediate as the hydrochloride salt. To a solution of this intermediate (100 mg, 0.237 mmol) in N,N-dimethylformamide (1.5 mL) was added 2,5-dioxopyrrolidin-1-yl methylcarbamate (44.8 mg, 0.260 mmol) and triethylamine (0.165 mL, 1.184 mmol) and the mixture was stirred at room temperature for 3 hours. Water was slowly added, and the precipitate was collected by filtration, washed with diethyl ether and dried in vacuo to provide the title compound. $^1$H NMR (500 MHz, DMSO-$d_6$) δ 2.51-2.60 (m, 4H) 2.84-3.07 (m, 3H) 3.35-3.40 (m, 2H) 3.46-3.55 (m, 2H) 3.73 (s, 3H) 5.96-6.07 (m, 1H) 6.15-6.20 (m, 1H) 6.31 (s, 1H)

7.03 (d, J=4.88 Hz, 1H) 7.16-7.32 (m, 3H) 8.21 (d, J=4.88 Hz, 1H) 11.89 (d, J=1.53 Hz, 1H). MS (ESI$^+$) m/z 407 (M+H)$^+$.

Example 285

(3aR,6aS)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide

Example 285A (3aR,6aS)-tert-butyl 5-(4-(5-fluoro-2-methoxyphenyl)-1H-pyrrolo[2,3-b]pyridin-2-yl)-3,3a,6,6a-tetrahydrocyclopenta[c]pyrrole-2(1H)-carboxylate The title compound was prepared in Example 284A, and corresponds to the faster eluting enantiomer under the SFC conditions described in Example 284A. Optical rotation was obtained using an Autopol IV® automatic polarimeter (c=10 mg/mL in choloform at 24.8° C.) $[\alpha]_D$=−161.10. LC-MS: 450 (M+H)$^+$.

Example 285B (3aR,6aS)-5-(4-(5-fluoro-2-methoxyphenyl)-1H-pyrrolo[2,3-b]pyridin-2-yl)-N-methyl-3,3a,6,6a-tetrahydrocyclopenta[c]pyrrole-2(1H)-carboxamide The title compound was prepared using the condition described in Example 284B, substituting Example 284A with Example 285A. $^1$H NMR (500 MHz, DMSO-d$_6$) δ 2.51-2.58 (m, 4H) 2.83-3.06 (m, 3H) 3.35-3.40 (m, 2H) 3.47-3.55 (m, 2H) 3.73 (s, 3H) 6.00-6.08 (m, 1H) 6.15-6.20 (m, 1H) 6.31 (s, 1H) 7.03 (d, J=4.88 Hz, 1H) 7.16-7.30 (m, 3H) 8.21 (d, J=4.88 Hz, 1H) 11.89 (d, J=1.22 Hz, 1H). MS (ESI$^+$) m/z 407 (M+H)$^+$.

Example 286

5-[5-fluoro-4-(5-fluoro-2-methoxyphenyl)-1H-pyrrolo[2,3-b]pyridin-2-yl]-N-methyl-3,3a,4,6a-tetrahydrocyclopenta[c]pyrrole-2(1H)-carboxamide To a suspension of Example 282A (80.0 mg, 0.182 mmol) and N-succinimidyl-N-methylcarbamate (46.9 mg, 0.273 mmol) in N,N-dimethylformamide (2.5 mL) was added triethylamine (0.152 mL, 1.090 mmol) and the mixture was stirred for 3 hours. The mixture was treated with water and brine and extracted with ethyl acetate (twice). The combined organic layers were washed with water and brine, dried over magnesium sulfate, filtered, and concentrated until most of the solvent was removed. The suspension was filtered, washed with ethyl acetate and vacuum oven-dried to give the title compound. $^1$H NMR (400 MHz, Pyridine-d$_5$) δ 2.56-2.86 (m, 1H), 2.86-2.95 (m, 5H), 3.31-3.42 (m, 1H), 3.47 (bs, 1H), 3.61-3.75 (m, 4H), 3.73-3.91 (m, 2H), 6.40 (bs, 2H), 6.48 (d, J=2.0 Hz, 1H), 7.12 (dd, J=9.1, 4.5 Hz, 1H), 7.31 (td, J=8.5, 3.2 Hz, 1H), 7.48-7.54, (m, 1H), 8.53 (d, J=2.6 Hz, 1H), 13.12 (bs, 1H). MS (ESI$^+$) m/z 425.1 (M+H)$^+$.

Example 287

2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N,N-dimethylacetamide A mixture of Example 282A (80.0 mg, 0.182 mmol), 2-chloro-N,N-dimethylacetamide (0.021 mL, 0.209 mmol), and triethylamine (0.127 mL, 0.908 mmol) in N,N-dimethylformamide (2 mL) was heated at 75° C. for 4 hours. The mixture was treated with water and brine and extracted with ethyl acetate (twice). The combined organic layers were washed with brine, dried over magnesium sulfate, filtered, concentrated, and purified by HPLC (same protocol as Example 221). The trifluoroacetic acid salt was flushed through an SCX column eluting with 2M ammonia in methanol to give the free base of the title compound. $^1$H NMR (400 MHz, Pyridine-d$_5$) δ 2.58-3.06 (m, 13H), 3.31 (d, J=5.4 Hz, 2H), 3.39-3.44 (m, 1H), 3.71 (s, 3H), 6.43 (bs, 1H), 6.48 (bs, 1H), 7.12 (dd, J=9.1, 4.5 Hz, 1H), 7.27-7.36 (m, 1H), 7.50 (d, J=8.8 Hz, 1H), 8.51 (d, J=2.6 Hz, 1H), 13.13 (bs, 1H). MS (ESI$^+$) m/z 453.2 (M+H)$^+$.

Example 288

(cis-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid

Example 288A methyl 2-((1s,4s)-4-(4-(4-(5-fluoro-2-methoxyphenyl)-1H-pyrrolo[2,3-b]pyridin-2-yl)-5,6-dihydropyridin-1(2H)-yl)cyclohexyl)acetate A solution of Example 87 (0.15 g, 0.379 mmol) and triethylamine (0.132 mL, 0.946 mmol) in dichloromethane (3.15 mL) and methanol (3.15 mL) was treated with methyl 2-(4-oxocyclohexyl)acetate (J&W PharmLab, 0.084 g, 0.492 mmol), acetic acid (0.130 mL, 2.271 mmol), and MP-cyanoborohydride (Biotage, 2.49 mmol/g, 0.608 g, 1.514 mmol) and the mixture was stirred at room temperature for 20 hours. The mixture was diluted with 40 mL 50% methanol in dichloromethane and filtered. The filtrate was concentrated and the residue was partitioned in ethyl acetate and saturated aqueous sodium bicarbonate. The organic layer was washed with brine, dried over sodium sulfate, filtered, and concentrated. Purification by flash chromatography on silica gel (AnaLogix IntelliFlash 280) eluting with a gradient of 0-9% methanol in dichloromethane afforded the title compound. MS (ESI$^+$) m/z 478.1 (M+H)$^+$.

Example 288B (cis-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid A solution of Example 288A (0.025 g, 0.052 mmol) in tetrahydrofuran (0.262 mL) and methanol (0.262 mL) was treated with aqueous 2M lithium hydroxide (0.079 mL, 0.157 mmol) and the mixture was stirred at room temperature for 16 hours. The mixture was purified by reverse phase HPLC on a Phenomenex Luna C8(2) 5 um 100 Å AXIA column eluting with a gradient of 10-70% acetonitrile in 0.1% trifluoroacetic acid/water to afford the cis-isomer title compound (along with the trans-isomer described in Example 289) as the trifluoroacetate salt. $^1$H NMR (400 MHz, DMSO-d$_6$) δ 1.48-1.78 (m, 6H), 1.78-1.94 (m, 2H), 2.07-2.16 (m, 1H), 2.33 (d, J=7.6 Hz, 2H), 2.72-2.93 (m, 2H), 3.14-3.33 (m, 2H), 3.67-3.77 (m, 4H), 3.90-4.02 (m, 2H), 6.40 (d, J=1.9 Hz, 1H), 6.48-6.56 (m, 1H), 7.09 (d, J=5.0 Hz, 1H), 7.16-7.36 (m, 3H), 8.26 (d, J=5.0 Hz, 1H), 9.51 (bs, 1H), 12.07 (d, J=1.6 Hz, 1H). MS (ESI$^+$) m/z 464.0 (M+H)$^+$.

Example 289

(trans-4-{4-[4-(5-fluoro-2-methoxyphenyl)-1H-pyrrolo[2,3-b]pyridin-2-yl]-3,6-dihydropyridin-1(2H)-yl}cyclohexyl)acetic acid The trans-isomer title compound was obtained as the trifluoroacetate salt in the purification described in Example 288B. $^1$H NMR (400 MHz, DMSO-$d_6$) δ 1.00-1.17 (m, 2H), 1.44-1.71 (m, 3H), 1.81-1.94 (m, 2H), 1.99-2.19 (m, 4H), 2.67-2.93 (m, 2H), 3.13-3.30 (m, 2H), 3.61-3.72 (m, 1H), 3.74 (s, 3H), 3.90-4.02 (m, 2H), 6.40 (d, J=1.9 Hz, 1H), 6.47-6.55 (m, 1H), 7.09 (d, J=5.0 Hz, 1H), 7.16-7.36 (m, 3H), 8.26 (d, J=5.0 Hz, 1H), 9.61 (bs, 1H), 12.06 (d, J=1.7 Hz, 1H). MS (ESI$^+$) m/z 464.0 (M+H)$^+$.

Example 290

4-(5-fluoro-2-methoxyphenyl)-2-(1-{2-[(2S)-2-(hydroxymethyl)pyrrolidin-1-yl]-2-oxoethyl}piperidin-4-yl)-1H-pyrrolo[2,3-b]pyridine-5-carbonitrile

Example 290A tert-butyl 2-(4-(5-cyano-4-(5-fluoro-2-methoxyphenyl)-1H-pyrrolo[2,3-b]pyridin-2-yl)piperidin-1-yl)acetate The title compound was prepared as described in Example 275, substituting Example 283A for Example 236G. MS (ESI (+)) m/e 465 (M+H)$^+$.

Example 290B 2-(4-(5-cyano-4-(5-fluoro-2-methoxyphenyl)-1H-pyrrolo[2,3-b]pyridin-2-yl)piperidin-1-yl)acetic acid The title compound was prepared using the procedure described in Example 226B, substituting Example 290A for Example 226A. MS (ESI(+)) m/e 409 (M+H)$^+$.

Example 290C 4-(5-fluoro-2-methoxyphenyl)-2-(1-{2-[(2S)-2-(hydroxymethyl)pyrrolidin-1-yl]-2-oxoethyl}piperidin-4-yl)-1H-pyrrolo[2,3-b]pyridine-5-carbonitrile The title compound was prepared using the procedure described in Example 238, substituting Example 290B for Example 226B and (S)-pyrrolidin-2-ylmethanol for azetidin-3-ol hydrochloride. $^1$H NMR (400 MHz, DMSO-$d_6$) δ 1.86 (s, 8H), 2.12-2.28 (m, 1H), 2.89-2.98 (m, 1H), 3.10 (d, J=9.1 Hz, 1H), 3.12-3.69 (m, 7H), 3.76 (s, 3H) 3.90-4.30 (m, 3H), 6.04 (d, J=2.9 Hz, 1H), 7.19-7.30 (m, 2H). 7.33-7.47 (m, 1H), MS (ESI(+)) m/e 492 (M+H)$^+$.

Example 291

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-N-methyl-2-oxoethanesulfonamide The title compound was prepared using the conditions described in Example 280, substituting 2-hydroxyacetic acid with 2-(N-methylsulfamoyl)acetic acid. $^1$H NMR (400 MHz, DMSO-$d_6$) δ 2.55-2.69 (m, 5H) 2.81-3.12 (m, 3H) 3.47-3.66 (m, 2H) 3.73 (s, 3H) 3.74-3.97 (m, 2H) 4.06-4.22 (m, 2H) 6.32 (s, 1H) 6.97-7.09 (m, J=5.49, 5.49 Hz, 2H) 7.15-7.32 (m, 3H) 8.21 (d, J=4.88 Hz, 1H) 11.92 (dd, J=4.73, 1.68 Hz, 1H). MS (ESI$^+$) m/z 485 (M+H)$^+$.

Example 292

4-{4-[4-(5-fluoro-2-methoxyphenyl)-1H-pyrrolo[2,3-b]pyridin-2-yl]-3,6-dihydropyridin-1(2H)-yl}cyclohexanecarboxylic acid

Example 292A tert-butyl 4-(4-(4-(5-fluoro-2-methoxyphenyl)-1H-pyrrolo[2,3-b]pyridin-2-yl)-5,6-dihydropyridin-1(2H)-yl)cyclohexanecarboxylate The title compound was prepared according to the procedure described in Example 288A substituting tert-butyl 4-oxocyclohexanecarboxylate (Astatech) for methyl 2-(4-oxocyclohexyl)acetate. MS (ESI$^+$) m/z 506.1 (M+H)$^+$.

Example 292B 4-(4-(4-(5-fluoro-2-methoxyphenyl)-1H-pyrrolo[2,3-b]pyridin-2-yl)-5,6-dihydropyridin-1(2H)-yl)cyclohexanecarboxylic acid The title compound was prepared according to the procedure described in Example 226B substituting Example 292A for Example 226A. $^1$H NMR (500 MHz, CD$_3$OD) δ 1.52-1.88 (m, 4H), 2.05-2.45 (m, 5H), 2.91-3.05 (m, 2H), 3.32-3.46 (m, 2H), 3.76-3.86 (m, 4H), 4.02-4.13 (m, 2H), 6.57-6.66 (m, 1H), 6.75 (d, J=6.1 Hz, 1H), 7.21-7.37 (m, 3H), 7.59 (dd, J=6.1, 0.9 Hz, 1H), 8.37 (d, J=6.0 Hz, 1H). MS (ESI$^+$) m/z 450.1 (M+H)$^+$.

Example 293

2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone

Example 293A tert-butyl 2-(5-(5-fluoro-4-(5-fluoro-2-methoxyphenyl)-1H-pyrrolo[2,3-b]pyridin-2-yl)-3,3a,6,6a-tetrahydrocyclopenta[c]pyrrol-2(1H)-yl)acetate A mixture of Example 282A (400 mg, 0.908 mmol), tert-butyl 2-bromoacetate (0.157 mL, 1.090 mmol), and triethylamine (0.633 mL, 4.54 mmol) in N,N-dimethylformamide (7 mL) was heated at 85° C. for 30 minutes in a Biotage Initiator microwave reactor. The mixture was treated with water and brine and extracted with ethyl acetate (twice). The combined organic layers were washed with water and brine, dried over magnesium sulfate, filtered, concentrated, and purified on silica gel using the ISCO Companion eluting with ethyl acetate/heptanes (7:3 to 8:2) to give the title compound. MS (ESI$^+$) m/z 481.9 (M+H)$^+$.

Example 293B 2-(5-(5-fluoro-4-(5-fluoro-2-methoxyphenyl)-1H-pyrrolo[2,3-b]pyridin-2-yl)-3,3a,6,6a-tetrahydrocyclopenta[c]pyrrol-2(1H)-yl)acetic acid A solution of Example 293A (0.685 g, 1.423 mmol) and trifluoroacetic acid (2.74 mL, 35.6 mmol) in dichloromethane (12 mL) was stirred for 18 hours. The mixture was concentrated and the residue was dissolved in 5 mL dichloromethane and treated with 8 mL 2M hydrogen chloride in ether. The suspension was sonicated, diluted with ether, and stirred for 1 hour. The solid was filtered, washed with ether and vacuum oven-dried to give the title compound as a hydrochloride salt. MS (trifluoroacetic acid salt via HPLC) (ESI$^+$) m/z 426.2 (M+H)$^+$.

Example 293C

2-{5-[5-fluoro-4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone A mixture of Example 293B (0.100 g, 0.217 mmol), (benzotriazol-1-yl-oxytripyrrolidinophosphonium hexafluorophosphate (0.135 g, 0.260 mmol), triethylamine (0.151 mL, 1.083 mmol), and azetidin-3-ol.hydrochloride (0.028 g, 0.260 mmol) in N,N-dimethylformamide (2.5 mL) was stirred for 3 hours. The mixture was treated with water and brine and extracted with ethyl acetate (twice). The combined organic layers were washed with water and brine, dried over magnesium sulfate, filtered, concentrated, and purified on silica gel using the ISCO Companion eluting with dichloromethane/methanol/ammonium hydroxide (18:1:0.1 to 9:1:0.1) to give the title compound. $^1$H NMR (400 MHz, Methanol-d$_4$) δ 2.47-2.67 (m, 3H), 2.67-2.76 (m, 2H), 2.93-3.01 (m, 2H), 3.05-3.19 (m, 2H), 3.71-3.76 (m, 4H), 3.92-4.01 (m, 1H), 4.13-4.21 (m, 1H), 4.35-4.44 (m, 1H), 4.45-4.62 (m, 1H), 6.09 (s, 1H), 6.19 (bs, 1H), 6.99-7.24 (m, 3H), 8.07 (d, J=2.9 Hz, 1H). (ESI$^+$) m/z 481.2 (M+H)$^+$.

Example 294

2-{4-[5-fluoro-4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone Example 294A 2-(4-(5-fluoro-4-(5-fluoro-2-methoxyphenyl)-1H-pyrrolo[2,3-b]pyridin-2-yl)-5,6-dihydropyridin-1(2H)-yl)acetic acid The title compound was prepared essentially as described in Examples 293A and B, substituting Example 231E for Example 282A in Example 293A. MS (ESI$^+$) m/z 400.1 (M+H)$^+$.

Example 294B

2-{4-[5-fluoro-4-(5-fluoro-2-methoxyphenyl)-1H-pyrrolo[2,3-b]pyridin-2-yl]-3,6-dihydropyridin-1(2H)-yl}-1-(3-hydroxyazetidin-1-yl)ethanone A mixture of Example 294A (0.100 g, 0.229 mmol), (benzotriazol-1-yl-oxytripyrrolidinophosphonium hexafluorophosphate (0.143 g, 0.275 mmol), triethylamine (0.160 mL, 1.147 mmol), and azetidin-3-ol.hydrochloride (0.030 g, 0.275 mmol) in N,N-dimethylformamide (2.5 mL) was stirred for 3 hours and was treated slowly with water. The solid was filtered, washed with water, dried in a vacuum oven, heated in 6 mL ethyl acetate/heptanes (1:1) at 70° C. for 2 hours, filtered, washed with ethyl acetate/heptanes (1:1), and vacuum oven-dried to give the title compound. $^1$H NMR (500 MHz, Methanol-d$_4$) δ 2.54-2.60 (m, 2H), 2.78 (t, J=5.7 Hz, 2H), 3.21 (d, J=2.9 Hz, 2H), 3.29 (d, J=3 Hz, 1H), 3.76 (s, 4H), 4.02-4.08 (m, 1H), 4.22 (dd, J=10.7, 6.8 Hz, 1H), 4.44-4.52 (m, 1H), 4.52-4.62 (m, 2H), 6.16 (s, 1H), 6.34-6.39 (m, 1H), 7.08-7.24 (m, 3H), 8.07 (d, J=2.8 Hz, 1H). MS (ESI$^+$) m/z 455.0 (M+H)$^+$.

Example 295

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-(3-hydroxyazetidin-1-yl)ethanone The title compound was prepared essentially as described in Examples 293A-C, substituting Example 262E for Example 282A in Example 293A. The mixture was concentrated in vacuo and the residue was purified by reverse-phase HPLC on a Phenomenex Luna C8 AXIA column (100 Å) using a gradient of 10-95% acetonitrile/10 mM ammonium acetate in water to afford the title compound. $^1$H NMR (400 MHz, DMSO-d$_6$) δ 2.44-2.96 (m, 8H) 3.00 (s, 2H) 3.48-4.47 (m, 6H) 3.73 (s, 3H) 6.12 (s, 1H) 6.30 (s, 1H) 7.03 (d, J=4.88 Hz, 1H) 7.13-7.33 (m, 3H) 8.19 (d, J=4.88 Hz, 1H) 11.84 (s, 1H). (ESI$^+$) m/z 463 (M+H)$^+$.

Example 296

2-{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}-1-[(2S)-2-(hydroxymethyl)pyrrolidin-1-yl]ethanone The title compound was prepared essentially as described in Examples 293A-C, substituting Example 262E for Example 282A in Example 293A and azetidin-3-ol hydrochloride with (S)-pyrrolidin-2-ylmethanol. $^1$H NMR (400 MHz, DMSO-D6) δ 1.66-1.84 (m, 4H) 2.41-3.52 (m, 15H) 3.73 (s, 3H) 3.86-4.07 (m, 1H) 6.11 (s, 1H) 6.28-6.33 (m, 1H) 7.03 (d, J=4.88 Hz, 1H) 7.15-7.31 (m, 3H) 8.19 (d, J=4.88 Hz, 1H) 11.85 (s, 1H). MS (ESI$^+$) m/z 491 (M+H)$^+$.

Example 297

2-{4-[5-fluoro-4-(5-fluoro-2-methoxyphenyl)-1H-pyrrolo[2,3-b]pyridin-2-yl]-3,6-dihydropyridin-1(2H)-yl}-1-(4-hydroxypiperidin-1-yl)ethanone A mixture of Example 294A (0.085 g, 0.195 mmol), (benzotriazol-1-yl-oxytripyrrolidinophosphonium hexafluorophosphate (0.122 g, 0.234 mmol), triethylamine (0.109 mL, 0.780 mmol), and piperidin-4-ol.hydrochloride (0.032 g, 0.234 mmol) in N,N-dimethylformamide (2 mL) was stirred for 3 hours. The mixture was treated with water and brine and extracted with ethyl acetate (twice). The combined organic layers were washed with brine, dried over magnesium sulfate, filtered, concentrated, and purified on silica gel using the ISCO Companion eluting with dichloromethane/methanol/ammonium hydroxide (18:1:0.1 to 9:1:0.1) to give the title compound. $^1$H NMR (400 MHz, Methanol-d$_4$) δ 1.33-1.60 (m, 2H), 1.79-1.94 (m, 2H), 2.56 (bs, 2H), 2.73-2.80 (m, 2H), 3.06-3.18 (m, 1H), 3.27-3.30 (m, 2H), 3.32-3.43 (m, 2H), 3.76 (s, 3H), 3.78-3.98 (m, 2H), 4.03-4.12 (m, 1H), 4.56 (d, J=1.1 Hz, 1H), 6.16 (s, 1H), 6.34-6.40 (m, 1H), 6.99-7.24 (m, 3H), 8.06 (d, J=2.9 Hz, 1H). MS (ESI$^+$) m/z 483.1 (M+H)$^+$.

Example 298

(4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid

Example 298A methyl 2-(4-(4-(5-fluoro-4-(5-fluoro-2-methoxyphenyl)-1H-pyrrolo[2,3-b]pyridin-2-yl)-5,6-dihydropyridin-1(2H)-yl)cyclohexyl)acetate To a mixture of Example 231E (0.150 g, 0.362 mmol) and triethylamine (0.111 mL, 0.797 mmol) in dichloromethane (2 mL) and methanol (2 mL) was added acetic acid (0.104 mL, 1.810 mmol), methyl 2-(4-oxocyclohexyl)acetate (0.116 mL, 0.724 mmol) and MP-cyanoborohydride (Biotage, 582 mg, 2.49 mmol/g). The mixture was heated at 40° C. for 3 hours and the solid was filtered and rinsed with dichloromethane/methanol. The filtrate was concentrated and the residue was partitioned in ethyl acetate and saturated aqueous sodium bicarbonate. The organic layer was washed with brine, dried over anhydrous sodium sulfate, filtered and concentrated. The residue was purified on silica gel using the ISCO Companion eluting with methanol/ethyl acetate (5:95) to give the title compound. MS (ESI$^+$) m/z 496.1 (M+H)$^+$.

Example 298B (4-{4-[5-fluoro-4-(5-fluoro-2-methoxyphenyl)-1H-pyrrolo[2,3-b]pyridin-2-yl]-3,6-dihydropyridin-1(2H)-yl}cyclohexyl)acetic acid A mixture of Example 298A (0.115 g, 0.232 mmol) and lithium hydroxide (0.011 g, 0.464 mmol) in tetrahydrofuran (3 mL), methanol (1.2 mL), and water (0.9 mL) was stirred overnight and concentrated. The residue was dissolved in 4 mL water and treated with 2M aqueous hydrogen chloride. The suspension was diluted with water, stirred for 15 minutes, filtered, washed with water, and vacuum oven-dried to give the title compound as a hydrochloride salt. $^1$H NMR (400 MHz, Methanol-d$_4$) δ 1.13-1.28 (m, 1H), 1.55-1.95 (m, 4H), 1.95-2.07 (m, 2H), 2.17-2.27 (m, 3H), 2.43 (d, J=7.6 Hz, 1H), 2.87-2.95 (m, 2H), 3.30-3.38 (m, 2H), 3.77 (s, 4H), 4.00-4.08 (m, 2H), 6.33 (s, 1H), 6.41 (bs, 1H), 7.08-7.26 (m, 3H), 8.15 (d, J=2.8 Hz, 1H). MS (ESI$^+$) m/z 482.0 (M+H)$^+$.

Example 299

2-{4-[4-(5-fluoro-2-methoxyphenyl)-1H-pyrrolo[2,3-b]pyridin-2-yl]-2,2-dimethyl-3,6-dihydropyridin-1(2H)-yl}-1-(3-hydroxyazetidin-1-yl)ethanone

Example 299A tert-butyl 2-(4-(4-(5-fluoro-2-methoxyphenyl)-1H-pyrrolo[2,3-b]pyridin-2-yl)-6,6-dimethyl-5,6-dihydropyridin-1(2H)-yl)acetate A mixture of Example 272B (0.388 g, 0.915 mmol), tert-butyl bromoacetate (0.264 g, 1.35 mmol) and triethylamine (0.7 mL, 5.02 mmol) in N,N-dimethylformamide (2 mL) was heated at 70° C. for 8 hours and was concentrated. The residue was partitioned between ethyl acetate and water and the organic layer was dried over sodium sulfate, filtered and concentrated. Purification by flash chromatography on silica gel eluting with 50% ethyl acetate in hexanes gave the title compound. MS (ESI) m/e 466.4 (M+1)[1].

Example 299B 2-(4-(4-(5-fluoro-2-methoxyphenyl)-1H-pyrrolo[2,3-b]pyridin-2-yl)-6,6-dimethyl-5,6-dihydropyridin-1(2H)-yl)acetic acid Example 299A (0.136 g, 0.294 mmol) and trifluoroacetic acid (2 mL, 26 mmol) were stirred in dichloromethane (2 mL) for 24 hours at room temperature and concentrated under reduced pressure. The hydrochloride salt was prepared by dissolving the solid in methanol and adding 2M hydrogen chloride in diethyl ether. After concentration, the title compound was obtained. MS (ESI) m/e 410.4 (M+1)$^+$.

Example 299C

2-{4-[4-(5-fluoro-2-methoxyphenyl)-1H-pyrrolo[2,3-b]pyridin-2-yl]-2,2-dimethyl-3,6-dihydropyridin-1(2H)-yl}-1-(3-hydroxyazetidin-1-yl)ethanone A mixture of Example 299B (0.172 g, 0.357 mmol), 3-hydroxyazetidine hydrochloride (0.047 g, 0.429 mmol), 2-(3H-[1,2,3]triazolo[4,5-b]pyridin-3-yl)-1,1,3,3-tetramethylisouronium hexafluorophosphate(V) (0.164 g, 0.431 mmol) and triethylamine (0.3 mL, 2.15 mmol) in N,N-dimethylformamide (4 mL) was stirred for 24 hours at room temperature. The mixture was concentrated and purified by reverse phase-HPLC (Sunfire 5 µM, 50×250 mm) eluting with 5-40% acetonitrile in water (containing 0.1% trifluoroacetic acid). The trifluoroacetate salt was dissolved in methanol and eluted from a SCX column with 0.5M ammonia in methanol to give the title compound. $^1$H NMR (500 MHz, DMSO-d$_6$) δ 1.03 (br s, 6H), 2.32 (br s, 2H), 3.11 (m, 4H), 3.57 (m, 1H), 3.73 (s, 3H), 3.95 (m, 1H), 4.04 (m, 1H), 4.39 (m, 2H), 6.54 (m, 1H), 6.19 (br s, 1H), 6.46 (m, 1H), 7.02 (d, 1H), 7.23 (m, 3H), 8.18 (d, 1H), 11.79 (br s, 1H). MS (ESI) m/e 465.0 (M+1)$^+$.

Example 300

{5-[4-(5-fluoro-2-methoxyphenyl)-1H-pyrrolo[2,3-b]pyridin-2-yl]-3,3a,4,6a-tetrahydrocyclopenta[c]pyrrol-2(1H)-yl}(3-hydroxycyclobutyl)methanone The title compound was prepared using the conditions described in Example 280, substituting 2-hydroxyacetic acid with 3-hydroxycyclobutanecarboxylic acid. $^1$H NMR (500 MHz, DMSO-d$_6$) d 1.78-2.38 (m, 4H) 2.53-3.13 (m, 5H) 3.41-3.69 (m, 4H) 3.73 (s, 3H) 3.84-4.02 (m, 1H) 5.03 (dd, J=9.16, 7.02 Hz, 1H) 6.18 (dd, J=4.73, 1.68 Hz, 1H) 6.30 (s, 1H) 7.04 (d, J=4.88 Hz, 1H) 7.15-7.33 (m, 3H) 8.21 (d, J=4.88 Hz, 1H) 11.90 (s, 1H)). (ESI$^+$) m/z 462 (M+H)$^+$.

Example 301

2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide

Example 301A tert-butyl 3-(5-cyano-4-(5-fluoro-2-methoxyphenyl)-1H-pyrrolo[2,3-b]pyridin-2-yl)-8-azabicyclo[3.2.1]oct-3-ene-8-carboxylate A mixture of Example 236C (0.4 g, 0.750 mmol), Example 223B (0.302 g, 0.900 mmol), sodium carbonate (0.238 g, 2.250 mmol), and [1,1'-bis(diphenylphosphino)ferrocene]dichloro-palladium(II) dichloromethane adduct (0.043 g, 0.053 mmol) in 10 mL tetrahydrofuran and 3 mL water was heated at 80° C. for 4 hours. The mixture was cooled to room temperature and treated with 2N lithium hydroxide (1.875 mL, 3.75 mmol) for 4 hours. The mixture was neutralized with 2N aqueous hydrochloric acid and extracted with ethyl acetate. The organic phase was washed with water and brine, dried over sodium sulfate, filtered and concentrated. The residue was purified by flash chromatography eluting with 0-5% methanol in dichloromethane to afford the title compound. MS (ESI(+)) m/e 475 (M+H)$^+$.

Example 301B 2-(8-azabicyclo[3.2.1]oct-3-en-3-yl)-4-(5-fluoro-2-methoxyphenyl)-1H-pyrrolo[2,3-b]pyridine-5-carbonitrile To a solution of Example 301A (380 mg, 0.801 mmol) in dichloromethane (5 mL) was added trifluoroacetic acid (617 µL, 8.01 mmol) and the mixture was stirred at room temperature overnight and concentrated. The residue was triturated with diethyl ether, filtered, and dried under reduced pressure to afford the title compound as the trifluoroacetate salt. MS (ESI(+)) m/e 375 (M+H)$^+$.

Example 301C

2-{3-[5-cyano-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide The title compound was prepared using the procedure described in Example 235, substituting Example 301B for Example 17. $^1$H NMR (400 MHz, DMSO-d$_6$) δ 1.39-2.40 (m, 6H), 2.68-2.78 (m, 1H), 2.78-2.83 (m, 4H), 3.00 (d, J=3.3 Hz, 3H), 3.40-3.63 (m, 2H), 3.75 (s, 3H), 6.21 (bs, 1H), 6.67-6.73 (m, 1H), 7.21-7.34 (m, 2H), 7.38 (td, J=8.6, 3.2 Hz, 1H), 8.59 (s, 1H), 12.42 (bs, 1H). MS (ESI(+)) m/e 460 (M+H)$^+$.

Example 302

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide Example 302A 2-(8-azabicyclo[3.2.1]oct-2-en-3-yl)-5-fluoro-4-(5-fluoro-2-methoxyphenyl)-1H-pyrrolo[2,3-b]pyridine, 2Hydrochloric Acid The title compound was prepared essentially as described in Examples 231C-E, substituting Example 223B for tert-butyl 4-(4,4,5,5-tetramethyl-1,3,2-dioxaborolan-2-yl)-5,6-dihydropyridine-1(2H)-carboxylate in Example 231C. MS (ESI$^+$) m/z 368.0 (M+H)$^+$.

Example 302B

2-{3-[5-fluoro-4-(5-fluoro-2-methoxyphenyl)-1H-pyrrolo[2,3-b]pyridin-2-yl]-8-azabicyclo[3.2.1]oct-2-en-8-yl}-N,N-dimethylacetamide A mixture of Example 302A (110.0 mg, 0.250 mmol), 2-chloro-N,N-dimethylacetamide (0.030 mL, 0.287 mmol), and triethylamine (0.174 mL, 1.249 mmol) in N,N-dimethylformamide (2.5 mL) was heated at 75° C. for 4 hours. The mixture was treated with water and brine and extracted with ethyl acetate (twice). The combined organic layers were washed with brine, dried over magnesium sulfate, filtered, concentrated, and purified on silica gel using the ISCO Companion eluting with dichloromethane methanol/ammonium hydroxide (18:1:0.1) to give the title compound. $^1$H NMR (500 MHz, Methanol-d$_4$) δ 1.58-1.69 (m, 1H), 1.90-1.98 (m, 1H), 2.01-2.26 (m, 2H), 2.83-3.01 (m, 5H), 3.05 (d, J=2.8 Hz, 3H), 3.39-3.65 (m, 3H), 3.69 (t, J=5.7 Hz, 1H), 3.76 (s, 3H), 6.13 (s, 1H), 6.48-6.53 (m, 1H), 7.07-7.25 (m, 3H), 8.06 (d, J=2.8 Hz, 1H). MS (ESI$^+$) m/z 453.1 (M+H)$^+$.

Example 303

4-(5-fluoro-2-methoxyphenyl)-2-(2-{2-[(2S)-2-(hydroxymethyl)pyrrolidin-1-yl]-2-oxoethyl}-1,2,3,3a,4,6a-hexahydrocyclopenta[c]pyrrol-5-yl)-1H-pyrrolo[2,3-b]pyridine-5-carbonitrile Example 303A tert-butyl 2-(5-(5-cyano-4-(5-fluoro-2-methoxyphenyl)-1H-pyrrolo[2,3-b]pyridin-2-yl)-3,3a,6,6a-tetrahydrocyclopenta[c]pyrrol-2(1H)-yl)acetate The title compound was prepared using the procedure described in Example 226A, substituting Example 277C for Example 87. MS (ESI(+)) m/e 489.

Example 303B 2-(5-(5-cyano-4-(5-fluoro-2-methoxyphenyl)-1H-pyrrolo[2,3-b]pyridin-2-yl)-3,3a,6,6a-tetrahydrocyclopenta[c]pyrrol-2(1H)-yl)acetic acid The title compound was prepared using the procedure described in Example 226B, substituting Example 303A for Example 226A. MS (ESI(+)) m/e 433 (M+H)$^+$.

Example 303C 4-(5-fluoro-2-methoxyphenyl)-2-(2-{2-[(2S)-2-(hydroxymethyl)pyrrolidin-1-yl]-2-oxoethyl}-1,2,3,3a,4,6a-hexahydrocyclopenta[c]pyrrol-5-yl)-1H-pyrrolo[2,3-b]pyridine-5-carbonitrile The title compound was prepared according to the procedure described in Example 238 substituting Example 303B for Example 226B and (S)-pyrrolidin-2-ylmethanol for azetidin-3-ol hydrochloride. $^1$H NMR (400 MHz, DMSO-d$_6$) δ 1.25 (s, 1H), 1.64-1.99 (m, 4H), 2.59-2.81 (m, 4H), 3.12-3.72 (m, 9H), 3.74 (s, 3H), 3.78-4.62 (m, 2H), 6.16 (s, 1H), 6.36 (bs, 1H), 7.15-7.29 (m, 3H), 7.33 (td, J=8.6, 3.1 Hz, 1H), 12.23 (bs, 1H). MS (ESI(+)) m/e 516 (M+H)$^+$.

Example 304

2-{3-[4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone

Example 304A 2-(3-(4-(5-fluoro-2-methoxyphenyl)-1H-pyrrolo[2,3-b]pyridin-2-yl)-8-azabicyclo[3.2.1]oct-2-en-8-yl) acetic acid The title compound was prepared essentially as described in Examples 293A and B, substituting Example 223C for Example 282A in Example 293A. MS (ESI$^+$) m/z 408.1 (M+H)$^+$.

Example 304B

2-{3-[4-(5-fluoro-2-methoxyphenyl)-1H-pyrrolo[2,3-b]pyridin-2-yl]-8-azabicyclo[3.2.1]oct-2-en-8-yl}-1-(3-hydroxyazetidin-1-yl)ethanone A mixture of Example 304A (0.100 g, 0.225 mmol), (benzotriazol-1-yl-oxytripyrrolidinophosphonium hexafluorophosphate (0.141 g, 0.270 mmol), triethylamine (0.157 mL, 1.126 mmol), and azetidin-3-ol.hydrochloride (0.030 g, 0.270 mmol) in N,N-dimethylformamide (2.5 mL) was stirred for 3 hours. The mixture was treated with water and brine and extracted with ethyl acetate (twice). The combined organic layers were washed with brine, dried over magnesium sulfate, filtered, concentrated, and purified on silica gel using the ISCO Companion flash system eluting with dichloromethane/methanol/ammonium hydroxide (18:1:0.1 to 12:1:0.1) to give the title compound. $^1$H NMR (500 MHz, Methanol-d$_4$) δ 1.60-1.70 (m, 1H), 1.91-1.99 (m, 1H), 2.06-2.17 (m, 2H), 2.16-2.27 (m, 1H), 2.82-2.91 (m, 1H), 3.26-3.34 (m, 1H), 3.51-3.58 (m, 1H), 3.63-3.70 (m, 1H), 3.76-3.78 (m, 4H), 4.00 (td, J=9.9, 4.3 Hz, 1H), 4.21 (dd, J=10.6, 6.9 Hz, 1H), 4.33-4.46 (m, 1H), 4.49-4.69 (m, 2H), 6.23 (s, 1H), 6.48-6.53 (m, 1H), 7.07 (d, J=5.1 Hz, 1H), 7.09-7.20 (m, 3H), 8.15 (d, J=5.1 Hz, 1H). MS (ESI$^+$) m/z 463.1 (M+H)$^+$.

Example 305

2-{3-[4-(5-fluoro-2-methoxyphenyl)-1H-pyrrolo[2,3-b]pyridin-2-yl]-8-azabicyclo[3.2.1]oct-2-en-8-yl}-1-[(2S)-2-(hydroxymethyl)pyrrolidin-1-yl]ethanone The title compound was prepared essentially as described in Example 304B, substituting (S)-pyrrolidin-2-ylmethanol for azetidin-3-ol hydrochloride. $^1$H NMR (400 MHz, Methanol-d$_4$) δ 1.60-1.72 (m, 1H), 1.79-2.07 (m, 5H), 2.05-2.31 (m, 3H), 2.85-2.94 (m, 1H), 3.41-3.67 (m, 7H), 3.76 (s, 4H), 4.05-4.20 (m, 1H), 6.24 (s, 1H), 6.48-6.54 (m, 1H), 7.07 (d, J=5.1 Hz, 1H), 7.10-7.20 (m, 3H), 8.14 (d, J=5.1 Hz, 1H). MS (ESI$^+$) m/z 491.2 (M+H)$^+$.

Example 306

2-{3-[4-(5-fluoro-2-methoxyphenyl)-1H-pyrrolo[2,3-b]pyridin-2-yl]-8-azabicyclo[3.2.1]oct-2-en-8-yl}-N-(2-hydroxyethyl)-N-methylacetamide The title compound was prepared essentially as described in Example 304B, substituting 2-(methylamino)ethanol for azetidin-3-ol hydrochloride. MS (ESI$^+$) m/z 408.1 (M+H)$^+$.

$^1$H NMR (400 MHz, Methanol-d$_4$) δ 1.60-1.73 (m, 1H), 1.91-2.01 (m, 1H), 2.02-2.28 (m, 3H), 2.89-2.95 (m, 3H), 3.10 (s, 1H), 3.42-3.95 (m, 11H), 6.24 (s, 1H), 6.51 (d, J=5.5 Hz, 1H), 7.07 (d, J=5.1 Hz, 1H), 7.10-7.19 (m, 3H), 8.14 (d, J=5.1 Hz, 1H). MS (ESI$^+$) m/z 465.1 (M+H)$^+$.

Example 307

5-chloro-N-(3-fluorobenzyl)-4-[2-(piperidin-4-yl)-1H-pyrrolo[2,3-b]pyridin-4-yl]pyridin-2-amine

Example 307A tert-butyl 4-(4-(2-amino-5-chloropyridin-4-yl)-1H-pyrrolo[2,3-b]pyridin-2-yl)piperidine-1-carboxylate A mixture of Example 17E (565 mg, 1.682 mmol), (2-((tert-butoxycarbonyl)amino)-5-chloropyridin-4-yl)boronic acid (550 mg, 2.02 mmol), (PPh$_3$)$_2$PdCl$_2$—CH$_2$Cl$_2$ adduct (70.9 mg, 0.10 mmol), tricyclohexylphosphine (28.3 mg, 0.10 mmol), Pd(dppf)$_2$Cl$_2$ (82 mg, 0.10 mmol), cesium carbonate (1.64 g, 5.05 mmol) and 1M Na$_2$CO$_3$ aqueous solution (5.05 mL, 5.05 mmol) in dioxane (18 mL) in a sealed tube was heated at 10° C. for 3 days. After cooling, the reaction mixture was diluted with ethyl acetate and washed with brine. The organic layer was concentrated and the residue was purified by reverse phase chromatography (C18 column), eluted with a gradient of 10%-70% acetonitrile in 0.1% TFA water solution to provide the title compound. LC/MS: 428 (M+H)$^+$.

Example 307B tert-butyl 4-(4-(5-chloro-2-((3-fluorobenzyl)amino)pyridin-4-yl)-1H-pyrrolo[2,3-b]pyridin-2-yl)piperidine-1-carboxylate To a solution of Example 307A (74 mg, 0.17 mmol) and 3-fluorobenzaldehyde (107 mg, 0.86 mmol) in dichloromethane was added acetic acid (0.05 mL, 0.86 mmol) and MP-CNBH$_3$ (2.49 mmol/g) (278 mg, 0.69 mmol). The mixture was stirred overnight and the insoluble material was filtered off. The filtrated was concentrated. The residue was purified by flash chromatograph eluting with a gradient of 10%-50% ethyl acetate in hexanes to provide the title compound. LCMS: 537 (M+H)$^+$.

Example 307C 5-chloro-N-(3-fluorobenzyl)-4-[2-(piperidin-4-yl)-1H-pyrrolo[2,3-b]pyridin-4-yl]pyridin-2-amine A solution of Example 307B (50 mg, 0.09 mmol) in dichloromethane (5 mL) and trifluoroacetic acid (1 mL) was stirred for 15 minutes and concentrated. The residue was purified by reverse phase chromatography (C18 column) eluting with 10%-70% acetonitrile in 0.1% TFA water solution to provide the title compound. $^1$H NMR (400 MHz, DMSO-d$_6$) δ 1.69-1.86 (m, 2H), 2.21 (d, 2H), 2.96-3.13 (m, 3H), 3.37 (d, 2H), 4.53 (s, 3H), 5.96 (s, 1H), 6.63 (s, 1H), 7.02 (d, 1H), 7.04-7.12 (m, 1H), 7.12-7.23 (m, 2H), 7.34-7.42 (m, 1H), 7.51 (s, 1H), 8.15 (s, 1H), 8.24 (d, 1H), 8.26-8.39 (m, 1H), 8.66 (d, 1H), 11.89 (s, 1H), LCMS: 436 (M+H)$^+$.

Example 308

6-[2-(3-aminocyclohexyl)-1H-pyrrolo[2,3-b]pyridin-4-yl]-N-(3-fluorobenzyl)pyridin-2-amine

Example 308A tert-butyl[3-({2-[(tert-butoxycarbonyl)amino]-4-chloropyridin-3-yl}ethynyl)cyclohexyl]carbamate To a solution of tert-butyl (3-ethynylcyclohexyl) carbamate (SynChem, 1.706 g, 7.64 mmol) in THF (20 mL) was added tert-butyl 4-chloro-3-iodopyridin-2-ylcarbamate (2.98 g, 8.4 mmol), CuI (58 mg, 0.3 mmol), bis(triphenylphosphine)palladium chloride (268 mg, 0.38 mmol) and triethylamine (2.3 g, 23 mmol). The mixture was purged with $N_2$ and was stirred at room temperature for two days. The reaction mixture was diluted with 60 mL of methylene chloride and washed with water. The organic phase was dried over magnesium sulfate, filtered, and concentrated. The residue was purified by flash chromatography (20-50% ethyl acetate in heptane) to provide the title compound. MS (DCI, $NH_3$) m/z 450 $(M+H)^+$.

Example 308B tert-butyl 2-(3-((tert-butoxycarbonyl)amino)cyclohexyl)-4-chloro-1H-pyrrolo[2,3-b]pyridine-1-carboxylate To a solution of Example 308A (0.82 g, 1.822 mmol) in toluene (15 mL) was added potassium t-butoxide (0.511 g, 4.56 mmol) and 18-Crown-6 (48.2 mg, 0.182 mmol). The reaction mixture was heated at 80° C. overnight. The reaction was quenched with water and the mixture was extracted with ethyl acetate three times. The combined organic phases were concentrated. The residue was dissolved in methylene chloride (40 mL). Di-tert-butyl dicarbonate (589 mg, 1.8 mmol), triethylamine (0.753 mL, 5.40 mmol) and 4-(dimethylamino)pyridine (22 mg, 0.18 mmol) were then added. This mixture was stirred at room temperature overnight. Volatiles were removed and the residue was directly separated by flash chromatography (10-50% gradient ethyl acetate in heptane) to provide the title compound. MS (DCI, $NH_3$) m/z 350 $(M+H)^+$.

Example 308C tert-butyl 2-(3-((tert-butoxycarbonyl)amino)cyclohexyl)-4-(6-fluoropyridin-2-yl)-1H-pyrrolo[2,3-b]pyridine-1-carboxylate A mixture of Example 308B (128 mg, 0.284 mmol), Example 309A (95 mg, 0.427 mmol), dichlorobis(triphenylphosphine)palladium (II) (20 mg, 0.028 mmol), tricyclohexylphosphine (8 mg, 0.028 mmol) and cesium carbonate (278 mg, 0.853 mmol) in anhydrous dioxane (6 mL) was purged with nitrogen, and heated at 95° C. overnight. The organic phase was washed with brine, and concentrated. The residue was separated by flash chromatography (20-70 gradient ethyl acetate in heptane) to provide the title compound. MS (DCI, $NH_3$) m/z 510 $(M+H)^+$.

Example 308D tert-butyl (3-(4-(6-((3-fluorobenzyl)amino)pyridin-2-yl)-1H-pyrrolo[2,3-b]pyridin-2-yl)cyclohexyl)carbamate To a solution of Example 308C (100 mg, 0.196 mmol) in DMSO (0.1 mL) was added 3-fluorobenzylamine (98 mg, 0.783 mmol). The mixture was heated in a microwave reactor (Biotage, Initiator) at 150° C. three times for one hour. After cooling, the reaction mixture was partitioned between ethyl acetate and brine. The organic phase was washed with brine and concentrated. The residue was separated by flash chromatography (0-15% gradient methanol in methylene chloride) to provide the title compound. MS (DCI, $NH_3$) m/z 516 $(M+H)^+$.

Example 308E

6-[2-(3-aminocyclohexyl)-1H-pyrrolo[2,3-b]pyridin-4-yl]-N-(3-fluorobenzyl)pyridin-2-amine To a solution of Example 308D (60 mg, 0.116 mmol) in methylene chloride (5 mL) was added trifluoroacetic acid (1 mL). The mixture was stirred at room temperature for 1 hour, and concentrated. The residue was purified by HPLC (Zorbax, C-18, 250×2.54 column, Mobile phase A: 0.1% TFA in $H_2O$; B: 0.1% TFA in $CH_3CN$; 0-100% gradient) to provide the title compound as TFA salt. $^1H$ NMR (400 MHz, $CD_3OD$): δ 1.39-1.48 (m, 2H), 1.55-1.66 (m, 2H), 2.01-2.06 (m, 2H), 2.13 (d, J=12.21 Hz, 1H), 2.38 (d, J=12.21 Hz, 1H), 2.93-3.02 (m, 1H), 4.73 (s, 2H), 6.76 (s, 1H), 6.89 (d, J=8.54 Hz, 1H), 6.98-7.05 (m, 1H), 7.16 (d, J=10.07 Hz, 1H), 7.24 (d, J=7.63 Hz, 1H), 7.33-7.40 (m, 3H), 7.68 (d, J=5.80 Hz, 1H), 7.77-7.82 (m, 1H), 8.29 (d, J=5.80 Hz, 1H); MS (DCI, $NH_3$) m/z 416 $(M+H)^+$.

Example 309

4-(6-fluoropyridin-2-yl)-2-(1,2,3,6-tetrahydropyridin-4-yl)-1H-pyrrolo[2,3-b]pyridine

Example 309A 2-fluoro-6-(4,4,5,5-tetramethyl-1,3,2-dioxaborolan-2-yl)pyridine A mixture of 2-bromo-6-fluoropyridine (15 g, 85 mmol), potassium acetate (25.10 g, 256 mmol), $PdCl_2(dppf)$-$CH_2Cl_2$ adduct (3.48 g, 4.26 mmol) and bis(pinacolato)diboron (22.73 g, 89 mmol) in 1,4-dioxane (200 mL) was stirred at 100° C. overnight. The mixture was filtered and the filtrate was concentrated. The concentrate was dissolved in ethyl acetate and washed with water followed by brine. The organic phase was dried over magnesium sulfate, filtered and concentrated to afford the title compound. MS $(ESI^+)$ m/z 142.1 $(M-81)^+$, for the corresponding boronic acid.

Example 309B 4-(6-fluoropyridin-2-yl)-1-(phenylsulfonyl)-1H-pyrrolo[2,3-b]pyridine A mixture of 4-bromo-1-(phenylsulfonyl)-1H-pyrrolo[2,3-b]pyridine (16 g, 47.5 mmol), Example 309A (22.68 g, 71.2 mmol), and PdCl$_2$(dppf)-CH$_2$Cl$_2$ adduct (1.938 g, 2.373 mmol) in 1,2-dimethoxyethane (10 mL) was treated with a solution of potassium carbonate (32.8 g, 237 mmol) in water (5 mL) and stirred at 100° C. for 3 hours. The reaction mixture was diluted with ethyl acetate and washed with brine. The organic layer was dried with Na$_2$SO$_4$, filtered, and concentrated. The residue was purified by flash column chromatography eluting with ethyl acetate/petroleum ether (1:3) to provide the title compound. MS (ESI$^+$) m/z 354.1 (M+H)$^+$.

Example 309C 4-(6-fluoropyridin-2-yl)-2-iodo-1-(phenylsulfonyl)-1H-pyrrolo[2,3-b]pyridine To Example 309B (5 g, 14.15 mmol) in tetrahydrofuran (100 mL) at −78° C. was added 2M lithium diisopropylamide in tetrahydrofuran (9.20 mL, 18.39 mmol) slowly. The resulting mixture was stirred at −78° C. for 1 hour. A solution of I$_2$ (5.39 g, 21.22 mmol) in THF (50 mL) was added slowly. The reaction was stirred at −78° C. for 2 hours. The reaction was quenched with aqueous sodium thiosulfate and extracted with ethyl acetate. The organic layer was washed with water and brine, dried over Na$_2$SO$_4$, filtered, and concentrated. The residue was washed with ethyl acetate to give the title compound. MS (ESI$^+$) m/z 479.9 (M+H)$^+$.

Example 309D tert-butyl 4-(4-(6-fluoropyridin-2-yl)-1-(phenylsulfonyl)-1H-pyrrolo[2,3-b]pyridin-2-yl)-5,6-dihydropyridine-1(2H)-carboxylate A mixture of Example 309C (4 g, 7.09 mmol), tert-butyl 4-(4,4,5,5-tetramethyl-1,3,2-dioxaborolan-2-yl)-5,6-dihydropyridine-1(2H)-carboxylate (2.63 g, 8.51 mmol), Pd(Ph$_3$P)$_4$ (0.410 g, 0.355 mmol), and an aqueous solution (15 mL) of sodium bicarbonate (1.788 g, 21.28 mmol) in dimethylformamide (50 mL) was stirred at 80° C. overnight. The reaction mixture was cooled, treated with water, and extracted with ethyl acetate (three times). The combined organic phases were washed with brine, dried over anhydrous Na$_2$SO$_4$, filtered, and concentrated. The residue was triturated with a mixture of ethyl acetate and petroleum ether (1:1). The solids were filtered and vacuum oven-dried to give the title compound. MS (ESI$^+$) m/z 535 (M+H)$^+$.

Example 309E tert-butyl 4-(4-(6-fluoropyridin-2-yl)-1H-pyrrolo[2,3-b]pyridin-2-yl)-5,6-dihydropyridine-1(2H)-carboxylate A mixture of Example 309D (3.0 g, 5.61 mmol) in 1,4-dioxane (50 mL) was treated with a solution of sodium hydroxide (0.673 g, 16.83 mmol) in water (10 mL). The resulting mixture was stirred at 80° C. overnight. Most solvent was evaporated. The solids were filtered, washed with water/ethyl acetate/ether, and vacuum oven-dried to give the title compound. MS (ESI$^+$) m/z 395.1 (M+H)$^+$.

Example 309F 4-(6-fluoropyridin-2-yl)-2-(1,2,3,6-tetrahydropyridin-4-yl)-1H-pyrrolo[2,3-b]pyridine A mixture of Example 309E (4.0 g, 10.14 mmol) and 4M HCl in dioxane (25.4 ml, 101 mmol) in methanol (10 mL) was stirred at room temperature for 4 hours. The mixture was concentrated and the solid was washed with ethyl acetate and vacuum dried to provide the title compound as an HCl salt. $^1$H NMR (400 MHz, DMSO-d$_6$) δ 2.81 (s, 2H), 3.33 (s, 2H), 3.83 (s, 2H), 6.62 (s, 1H), 7.17 (d, J=1.6 Hz, 1H), 7.30 (dd, J=7.9, 2.6 Hz, 1H), 7.68 (d, J=5.2 Hz, 1H), 8.08-8.25 (m, 2H), 8.37 (d, J=5.2 Hz, 1H), 9.46 (s, 2H), 12.44 (s, 1H). MS (ESI$^+$) m/z 295.1 (M+H)$^+$.

Example 310

4-(6-fluoropyridin-2-yl)-2-[1-(methylsulfonyl)-1,2,3,6-tetrahydropyridin-4-yl]-1H-pyrrolo[2,3-b]pyridine A mixture of Example 309F (0.6 g, 1.486 mmol) and triethylamine (1.243 ml, 8.92 mmol) in dimethylformamide (10 mL) was cooled to 0° C. and treated with methanesulfonyl chloride (0.232 ml, 2.97 mmol). The resulting mixture was stirred at room temperature for 3 hours. The reaction mixture was diluted with water. The aqueous layer was extracted with ethyl acetate (2×50 mL). The combined organic layers were washed with H$_2$O and brine, dried with Na$_2$SO$_4$, filtered and concentrated. The concentrate was washed with ethyl acetate/petroleum ether (1:3) to provide the title compound. $^1$H NMR (400 MHz, DMSO) δ 2.71 (s, 2H), 2.97 (s, 3H), 3.41 (t, J=5.6 Hz, 2H), 3.95 (d, J=2.5 Hz, 2H), 6.61 (s, 1H), 7.06 (d, J=1.9 Hz, 1H), 7.26 (dd, J=8.0, 2.6 Hz, 1H), 7.59 (d, J=5.1 Hz, 1H), 8.08-8.10 (m, 1H), 8.14-8.20 (m, 1H), 8.32 (d, J=5.1 Hz, 1H), 12.07 (s, 1H). MS (ESI$^+$) m/z 373.1 (M+H)$^+$.

Example 311

N-(2,6-difluorobenzyl)-6-{2-[1-(methylsulfonyl)-1,2,3,6-tetrahydropyridin-4-yl]-1H-pyrrolo[2,3-b]pyridin-4-yl}pyridin-2-amine A mixture of Example 310 (50.0 mg, 0.134 mmol) and (2,6-difluorophenyl)methanamine (0.096 mL, 0.806 mmol) in DMSO (1.5 mL) was heated at 100° C. for four days. The reaction mixture was purified by reverse-phase HPLC performed on a Zorbax RX-C18 column using a gradient of 15-100% methanol in 0.1% aqueous trifluoroacetic acid at a flow rate of 15 mL/minute to afford the title compound as a trifluoroacetic acid salt. $^1$H NMR (400 MHz, Methanol-d$_4$) δ ppm 2.75 (m, 2H), 2.92 (s, 3H), 3.52 (t, J=5.7 Hz, 2H), 4.04 (d, J=3.1 Hz, 2H), 4.80 (s, 2H), 6.55 (p, J=2.1 Hz, 1H), 6.87-7.15 (m, 4H), 7.27-7.47 (m, 2H), 7.68 (d, J=5.8 Hz, 1H), 7.85 (dd, J=8.7, 7.3 Hz, 1H), 8.34 (d, J=5.8 Hz, 1H). MS (ESI$^+$) m/z 496.2 (M+H)$^+$.

Example 312

N-(2-chlorobenzyl)-6-{2-[1-(methylsulfonyl)-1,2,3,6-tetrahydropyridin-4-yl]-1H-pyrrolo[2,3-b]pyridin-4-yl}pyridin-2-amine A mixture of Example 310 (75.0 mg, 0.201 mmol) and (2-chlorophenyl)methanamine (0.196 mL, 1.611 mmol) in DMSO (1.3 mL) was heated at 100° C. for 4 days. The crude material was first purified by HPLC performed on a Zorbax RX-C18 column using a gradient of 15-100% methanol in 0.1% aqueous trifluoroacetic acid at a flow rate of 15 mL/minute to afford the title compound as a trifluoroacetic acid salt. The trifluoroacetic acid salt of the title compound was suspended in hot DMSO/CH$_3$OH (1:1). After cooling, the solids were filtered, washed with CH$_3$OH, and vacuum oven-dried to provide the title compound as a trifluoroacetic acid salt. $^1$H NMR (500 MHz, DMSO-d$_6$) δ 2.29-2.35 (m, 2H), 2.95 (s, 3H), 3.33 (t, J=5.7 Hz, 2H), 3.87-3.93 (m, 2H), 4.75 (s, 2H), 6.47 (bs, 1H), 6.69-6.75 (m, 1H), 6.87 (s, 1H), 7.19-7.51 (m, 7H), 7.59-7.66 (m, 1H), 8.24 (d, J=5.2 Hz, 1H), 11.94 (bs, 1H). MS (ESI$^+$) m/z 494.2 (M+H)$^+$.

Example 313

N-(cyclopropylmethyl)-6-{2-[1-(methylsulfonyl)-1,2,3,6-tetrahydropyridin-4-yl]-1H-pyrrolo[2,3-b]pyridin-4-yl}pyridin-2-amine A mixture of Example 310 (75.0 mg, 0.201 mmol) and cyclopropylmethanamine (0.188 mL, 2.417 mmol) in DMSO (1.3 mL) was heated at 100° C. for two days. The reaction mixture was treated with water and extracted with ethyl acetate. The organic layer was concentrated and purified by HPLC performed on a Zorbax RX-C18 column using a gradient of 15-100% methanol in 0.1% aqueous trifluoroacetic acid at a flow rate of 15 mL/minute to afford the title compound as a trifluoroacetic acid salt. The trifluoroacetic acid salt of the title compound was treated with aqueous NaHCO$_3$ and extracted with ethyl acetate. The suspension in the organic layer was filtered and vacuum oven-dried to give the title compound. $^1$H NMR (500 MHz, DMSO-d$_6$) δ 0.22-0.28 (m, 2H), 0.41-0.50 (m, 2H), 1.09-1.21 (m, 1H), 2.65-2.72 (m, 2H), 2.96 (s, 3H), 3.41 (t, J=5.7 Hz, 2H), 3.91-3.96 (m, 2H), 6.55 (d, J=8.6 Hz, 2H), 6.80 (t, J=5.6 Hz, 1H), 7.18-7.21 (m, 2H), 7.48-7.55 (m, 2H), 8.23 (d, J=5.0 Hz, 1H), 11.80-11.91 (m, 1H). MS (ESI$^+$) m/z 424.2 (M+H)$^+$.

Example 314

N-benzyl-6-{2-[1-(methylsulfonyl)piperidin-4-yl]-1H-pyrrolo[2,3-b]pyridin-4-yl}pyrazin-2-amine Example 314A N-benzyl-6-(2-(piperidin-4-yl)-1H-pyrrolo[2,3-b]pyridin-4-yl)pyrazin-2-amine A mixture of Example 21A (400 mg, 0.94 mmol), N-benzyl-6-bromopyrazin-2-amine (297 mg, 1.12 mmol), bis(triphenylphosphine)palladium(ii) chloride (66 mg, 0.094 mmol), tricyclohexylphosphine (26 mg, 0.094 mmol) and cesium carbonate (921 mg, 2.8 mmol) was purged with nitrogen, then anhydrous dioxane (50 mL) was added. The mixture was heated at 100° C. overnight. The reaction was cooled to room temperature and filtrated; and the solid was washed with dichloromethane (200 mL). The filtrate was concentrated and purified by flash chromatography on silica gel using an ISCO Companion eluting with heptanes/ethyl acetate (30%) to give Boc-protected intermediate that was dissolved in CH$_2$Cl$_2$ (10 mL) then treated with trifluoroacetic acid (1 mL). The mixture was stirred at room temperature for 5 hours and concentrated. The residue was purified by reverse-phase HPLC on Zorbax XDB C-18 using a gradient of 5-40% acetonitrile/water (containing 0.1% trifluoroacetic acid) to afford the title compound as trifluoroacetate salt. MS (DCI/NH$_3$) m/z 385 (M+H)$^+$.

Example 314B

N-benzyl-6-{2-[1-(methylsulfonyl)piperidin-4-yl]-1H-pyrrolo[2,3-b]pyridin-4-yl}pyrazin-2-amine The title compound was prepared essentially as described in Example 220E, substituting Example 314A (30 mg, 0.08 mmol) for Example 220D. $^1$H NMR (500 MHz, DMSO-d$_6$) δ 1.53-1.72 (m, 2H), 1.91-2.05 (m, 2H), 2.71-2.88 (m, 3H), 2.90 (s, 3H), 3.63 (dt, J=12.3, 3.5 Hz, 2H), 4.53-4.77 (m, 2H), 6.59 (d, J=2.1 Hz, 1H), 7.18-7.30 (m, 1H), 7.29-7.43 (m, 4H), 7.54 (d, J=5.2 Hz, 1H), 8.06 (s, 1H), 8.21 (d, J=5.2 Hz, 1H), 8.39 (s, 1H). MS (ESI$^+$) m/z 463 (M+H)$^+$.

Example 315

N-benzyl-6-[2-(piperidin-4-yl)-1H-pyrrolo[2,3-b]pyrazin-2-yl]pyrazin-2-amine

The title compound was prepared essentially as described in Example 314A. $^1$H NMR (500 MHz, DMSO-d$_6$) δ 1.66-1.81 (m, 2H), 2.08-2.23 (m, 2H), 3.04 (qt, J=11.2, 2.7 Hz, 3H), 3.36 (dt, J=13.0, 3.1 Hz, 2H), 4.66 (s, 2H), 6.67 (d, J=2.0 Hz, 1H), 7.20-7.31 (m, 1H), 7.31-7.44 (m, 4H), 7.56 (d, J=5.2 Hz, 1H), 8.07 (s, 1H), 8.25 (d, J=5.1 Hz, 1H), 8.40 (s, 1H). MS (ESI$^+$) m/z 385 (M+H)$^+$.

Example 316

6-[2-(piperidin-4-yl)-1H-pyrrolo[2,3-b]pyridin-4-yl]-N-(tetrahydro-2H-pyran-4-ylmethyl)pyrazin-2-amine The title compound was prepared essentially as described in Example 314A, substituting 6-bromo-N-((tetrahydro-2H-pyran-4-yl)methyl)pyrazin-2-amine (200 mg, 0.74 mmol) for N-benzyl-6-bromopyrazin-2-amine. $^1$H NMR (400 MHz, DMSO-d$_6$) δ 1.16-1.42 (m, 2H), 1.70 (ddd, J=13.1, 4.1, 2.0 Hz, 2H), 1.76-1.94 (m, 3H), 2.29 (dd, J=14.6, 3.8 Hz, 2H), 2.92-3.22 (m, 4H), 3.20-3.49 (m, 5H), 3.88 (ddd, J=11.5, 4.5, 1.9 Hz, 2H), 6.83 (d, J=2.0 Hz, 1H), 7.59 (d, J=5.2 Hz, 1H), 7.99 (s, 1H), 8.26 (d, J=5.1 Hz, 1H), 8.35 (s, 1H). MS (ESI$^+$) m/z 393 (M+H)$^+$.

Example 317

N-(3,5-difluorobenzyl)-6-[2-(piperidin-4-yl)-1H-pyrrolo[2,3-b]pyridin-4-yl]pyrazin-2-amine The title compound was prepared essentially as described in Example 314A, substituting 6-bromo-N-(3,5-difluorobenzyl)pyrazin-2-amine (354 mg, 1.2 mmol) for N-benzyl-6-bromopyrazin-2-amine. $^1$H NMR (400 MHz, DMSO-d$_6$) δ 1.76 (dd, J=13.3, 3.5 Hz, 2H), 2.07-2.25 (m, 2H), 3.05 (dp, J=11.4, 3.8, 3.2 Hz, 3H), 3.30-3.42 (m, 2H), 4.68 (d, J=4.2 Hz, 2H), 6.58 (d, J=2.0 Hz, 1H), 7.05-7.16 (m, 3H), 7.54 (d, J=5.2 Hz, 1H), 8.10 (s, 1H), 8.24 (d, J=5.2 Hz, 1H), 8.44 (s, 1H). MS (ESI$^+$) m/z 421 (M+H)$^+$.

Example 318

N-(3-fluorobenzyl)-6-[2-(piperidin-4-yl)-1H-pyrrolo[2,3-b]pyridin-4-yl]pyrazin-2-amine The title compound was prepared essentially as described in Example 314A, substituting 6-bromo-N-(3-fluorobenzyl)pyrazin-2-amine (317 mg, 1.1 mmol) for N-benzyl-6-bromopyrazin-2-amine. $^1$H NMR (500 MHz, DMSO-d$_6$) δ 1.75 (qd, J=12.9, 3.8 Hz, 2H), 2.05-2.24 (m, 2H), 3.05 (dtt, J=10.9, 7.4, 3.2 Hz, 3H), 3.37 (d, J=12.8 Hz, 2H), 4.68 (s, 2H), 6.63 (d, J=2.1 Hz, 1H), 7.10 (qd, J=8.6, 7.8, 2.0 Hz, 1H), 7.16-7.29 (m, 2H), 7.40 (td, J=7.9, 6.1 Hz, 1H), 7.56 (d, J=5.2 Hz, 1H), 8.09 (s, 1H), 8.25 (d, J=5.2 Hz, 1H), 8.42 (s, 1H). MS (ESI$^+$) m/z 421 (M+H)$^+$.

Example 319

6-[2-(piperidin-4-yl)-1H-pyrrolo[2,3-b]pyridin-4-yl]-N-(pyridin-3-ylmethyl)pyrazin-2-amine

Example 319A tert-butyl 4-(4-(6-aminopyrazin-2-yl)-1H-pyrrolo[2,3-b]pyridin-2-yl)piperidine-1-carboxylate A mixture of Example 21A (500 mg, 1.2 mmol), 6-bromopyrazin-2-amine (244 mg, 1.4 mmol), bis(triphenylphosphine)palladium(ii) chloride (82 mg, 0.1 mmol), tricyclohexylphosphine (33 mg, 0.1 mmol) and cesium carbonate (1.2 g, 3.5 mmol) was purged with nitrogen, then anhydrous dioxane (60 ml) was added. The mixture was heated at 100° C. overnight. The reaction was cooled to room temperature and filtrated, and the solid was washed with dichloromethane (200 mL). The filtrate was concentrated and purified by flash chromatography on silica gel using an ISCO Companion eluting with heptanes/ethyl acetate (30%) to provide the title compound. MS (ESI$^+$) m/z 395 (M+H)$^+$.

Example 319B

6-[2-(piperidin-4-yl)-1H-pyrrolo[2,3-b]pyridin-4-yl]-N-(pyridin-3-ylmethyl)pyrazin-2-amine A solution of Example 319A (50 mg, 0.13 mmol) in a mixed solvent of 1,2-dichloroethane (1 ml) and acetic acid (0.5 ml) was added nicotinaldehyde (20 mg, 0.19 mmol). The mixture was stirred at room temperature for 2 hours and sodium triacetoxyborohydride (40 mg, 0.19 mmol) was added. The mixture was stirred overnight. The reaction mixture was partitioned between water and ethyl acetate. The organic phase was concentrated and purified by flash chromatography on silica gel using an ISCO Companion eluting with heptanes/ethyl acetate (30%) to give Boc-protected intermediate which was dissolved in CH$_2$Cl$_2$ (10 mL) then treated with trifluoroacetic acid (1 mL). The mixture was stirred at room temperature for 5 hours and concentrated. The residue was purified by reverse-phase HPLC on Zorbax XDB C-18 using a gradient of 5-40% acetonitrile/water (containing 0.1% trifluoroacetic acid) to afford the title compound as a trifluoroacetate salt. $^1$H NMR (400 MHz, DMSO-d$_6$) δ 1.64-1.86 (m, 2H), 2.02-2.25 (m, 2H), 3.05 (dd, J=13.0, 8.4 Hz, 3H), 3.38 (d, J=12.4 Hz, 2H), 4.77 (d, J=4.5 Hz, 2H), 6.57 (s, 1H), 7.51 (d, J=5.1 Hz, 1H), 7.77 (dd, J=8.0, 5.3 Hz, 1H), 8.12 (s, 1H), 8.24 (t, J=6.3 Hz, 2H), 8.45 (s, 1H), 8.68 (d, J=5.3 Hz, 1H), 8.82 (s, 1H). MS (ESI$^+$) m/z 386 (M+H)$^+$.

Example 320

6-[2-(piperidin-4-yl)-1H-pyrrolo[2,3-b]pyridin-4-yl]-N-(pyridin-4-ylmethyl)pyrazin-2-amine The title compound was prepared essentially as described in Example 319B, substituting isonicotinaldehyde (20 mg, 0.2 mmol) for nicotinaldehyde. $^1$H NMR (400 MHz, DMSO-d$_6$) δ 1.73 (qd, J=12.7, 3.9 Hz, 2H), 2.09-2.19 (m, 2H), 2.98-3.14 (m, 3H), 3.41 (d, J=12.4 Hz, 2H), 4.93 (d, J=4.5 Hz, 2H), 6.46 (d, J=1.8 Hz, 1H), 7.46 (d, J=5.2 Hz, 1H), 8.01 (d, J=5.8 Hz, 2H), 8.23 (d, J=5.1 Hz, 2H), 8.49 (s, 1H), 8.86 (d, J=6.0 Hz, 2H). MS (ESI$^+$) m/z 386 (M+H)$^+$.

Example 321

N-(3,4-difluorobenzyl)-6-[2-(piperidin-4-yl)-1H-pyrrolo[2,3-b]pyridin-4-yl]pyrazin-2-amine The title compound was prepared essentially as described in Example 319B, substituting 3,4-difluorobenzaldehyde (27 mg, 0.19 mmol) for nicotinaldehyde. $^1$H NMR (400 MHz, DMSO-d$_6$) δ 1.69-1.85 (m, 2H), 2.06-2.27 (m, 2H), 2.97-3.14 (m, 3H), 3.37 (d, J=11.9 Hz, 2H), 4.64 (d, J=3.2 Hz, 2H), 6.62 (d, J=2.0 Hz, 1H), 7.20-7.30 (m, 1H), 7.42 (ddt, J=13.4, 10.8, 5.3 Hz, 2H), 7.55 (d, J=5.2 Hz, 1H), 8.08 (s, 1H), 8.25 (d, J=5.1 Hz, 1H), 8.42 (s, 1H). MS (ESI$^+$) m/z 421 (M+H)$^+$.

Example 322

1-[4-(4-{6-[(3,5-difluorobenzyl)amino]pyrazin-2-yl}-1H-pyrrolo[2,3-b]pyridin-2-yl)piperidin-1-yl]-2-hydroxyethanone A mixture of Example 317 (50 mg, 0.12 mmol), 2-hydroxyacetic acid (11 mg, 0.13 mmol), N-(3-dimethylaminopropyl)-N'-ethylcarbodiimide hydrochloride (28 mg, 0.15 mmol), 1-hydroxybenzotriazole hydrate (23 mg, 0.15 mmol) and triethylamine (15 mg, 0.15 mmol) in N,N'-dimethylformamide (2 mL) was stirred at room temperature overnight. The mixture was concentrated in vacuo and the residue was purified by reverse-phase HPLC on Zorbax XDB C-18 using a gradient of 5-40% acetonitrile/water (containing 0.1% trifluoroacetic acid) to afford the title compound as trifluoroacetic acid salt. $^1$H NMR (400 MHz, DMSO-d$_6$) δ 1.51 (dt, J=37.8, 12.7 Hz, 2H), 1.82-1.99 (m, 2H), 2.74 (dd, J=14.6, 10.1 Hz, 1H), 2.95 (ddd, J=11.7, 8.1, 3.6 Hz, 1H), 3.09 (t, J=12.9 Hz, 1H), 3.76 (d, J=13.8 Hz, 1H), 4.13 (s, 2H), 4.46 (d, J=13.4 Hz, 1H), 4.67 (s, 2H), 6.52 (d, J=2.0 Hz, 1H), 7.11 (td, J=7.8, 7.0, 3.4 Hz, 3H), 7.57 (d, J=5.4 Hz, 1H), 8.10 (d, J=5.3 Hz, 1H), 8.24 (d, J=5.3 Hz, 1H), 8.44 (d, J=5.4 Hz, 1H). MS (ESI$^+$) m/z 479 (M+H)$^+$.

Example 323

1-[4-(4-{6-[(3-fluorobenzyl)amino]pyrazin-2-yl}-1H-pyrrolo[2,3-b]pyridin-2-yl)piperidin-1-yl]-2-hydroxyethanone The title compound was prepared essentially as described in Example 322, substituting Example 318 (50 mg, 0.12 mmol) for Example 317. $^1$H NMR (400 MHz, DMSO-d$_6$) δ 1.40-1.62 (m, 2H), 1.91 (dd, J=13.3, 3.7 Hz, 2H), 2.74 (dd, J=14.5, 10.4 Hz, 1H), 2.94 (ddt, J=11.8, 7.4, 3.6 Hz, 1H), 3.08 (t, J=12.9 Hz, 1H), 3.76 (d, J=13.9 Hz, 1H), 4.13 (s, 2H), 4.67 (s, 2H), 6.55 (d, J=1.9 Hz, 1H), 7.02-7.14 (m, 1H), 7.15-7.26 (m, 2H), 7.39 (td, J=8.0, 6.2 Hz, 1H), 7.56 (t, J=5.7 Hz, 1H), 8.10 (d, J=5.7 Hz, 1H), 8.23 (d, J=5.2 Hz, 1H), 8.43 (d, J=5.7 Hz, 1H). MS (ESI$^+$) m/z 461 (M+H)$^+$.

Example 324

1-(4-{4-[6-(benzylamino)pyrazin-2-yl]-1H-pyrrolo[2,3-b]pyridin-2-yl}piperidin-1-yl)-2-hydroxyethanone The title compound was prepared essentially as described in Example 322, substituting Example 315 (50 mg, 0.13 mmol) for Example 317. $^1$H NMR (400 MHz, DMSO-d$_6$) δ 1.36-1.59 (m, 2H), 1.87-1.95 (m, 2H), 2.74 (dd, J=14.2, 10.7

Hz, 1H), 2.95 (ddt, J=11.8, 7.4, 3.7 Hz, 1H), 3.08 (t, J=12.5 Hz, 1H), 3.75 (d, J=14.0 Hz, 1H), 4.13 (s, 2H), 4.44 (d, J=13.3 Hz, 1H), 4.66 (s, 2H), 6.62 (d, J=2.0 Hz, 1H), 7.20-7.30 (m, 1H), 7.30-7.42 (m, 4H), 7.60 (d, J=5.3 Hz, 1H), 8.08 (s, 1H), 8.24 (d, J=5.3 Hz, 1H), 8.41 (s, 1H). MS (ESI+) m/z 443 (M+H)+.

Example 325

N-benzyl-N-methyl-6-[2-(1-methylpiperidin-4-yl)-1H-pyrrolo[2,3-b]pyridin-4-yl]pyrazin-2-amine The title compound was prepared essentially as described in Example 89, substituting Example 315 (50 mg, 0.13 mmol) for Example 88. $^1$H NMR (400 MHz, DMSO-d$_6$) δ 1.87 (t, J=13.0 Hz, 2H), 2.28 (d, J=14.7 Hz, 2H), 2.83 (s, 3H), 2.85 (s, 3H), 3.12 (t, J=11.8 Hz, 3H), 3.53-3.61 (m, 2H), 4.32 (s, 2H), 6.40 (d, J=1.9 Hz, 1H), 6.92 (d, J=5.0 Hz, 1H), 7.31 (d, J=7.3 Hz, 1H), 7.36-7.47 (m, 4H), 7.61 (d, J=5.1 Hz, 1H), 8.15 (d, J=5.0 Hz, 1H), 8.34 (d, J=5.2 Hz, 1H). MS (ESI+) m/z 413 (M+H)+.

Example 326

N-benzyl-6-[2-(1-methylpiperidin-4-yl)-1H-pyrrolo[2,3-b]pyridin-4-yl]pyrazin-2-amine The title compound was prepared essentially as described in Example 89, substituting Example 315 (50 mg, 0.13 mmol) for Example 88. $^1$H NMR (400 MHz, DMSO-d$_6$) δ 1.68-1.85 (m, 2H), 2.20 (d, J=13.5 Hz, 2H), 2.81 (s, 3H), 2.91-3.03 (m, 1H), 3.03-3.20 (m, 2H), 3.53 (d, J=11.6 Hz, 2H), 4.66 (s, 2H), 6.64 (d, J=1.9 Hz, 1H), 7.18-7.30 (m, 1H), 7.37 (dt, J=14.9, 7.3 Hz, 4H), 7.55 (d, J=5.2 Hz, 1H), 8.07 (s, 1H), 8.25 (t, J=4.8 Hz, 1H), 8.39 (s, 1H). MS (ESI+) m/z 399 (M+H)+.

Example 327

1-(4-{4-[6-(benzylamino)pyrazin-2-yl]-1H-pyrrolo[2,3-b]pyridin-2-yl}piperidin-1-yl)ethanone The title compound was prepared essentially as described in Example 135C, substituting Example 315 (50 mg, 0.13 mmol) for Example 135B. $^1$H NMR (400 MHz, DMSO-d$_6$) δ 1.31-1.61 (m, 2H), 1.90 (td, J=15.4, 14.9, 3.7 Hz, 2H), 2.04 (s, 3H), 2.63 (td, J=12.9, 2.8 Hz, 1H), 2.85-3.00 (m, 1H), 3.14 (td, J=13.2, 12.7, 2.4 Hz, 1H), 3.88 (d, J=14.1 Hz, 1H), 4.47 (d, J=13.3 Hz, 1H), 4.67 (s, 2H), 6.64 (d, J=1.9 Hz, 1H), 7.21-7.29 (m, 1H), 7.30-7.44 (m, 4H), 7.63 (d, J=5.4 Hz, 1H), 8.09 (s, 1H), 8.26 (d, J=5.4 Hz, 1H), 8.42 (s, 1H). MS (ESI) m/z 399 (M+H)+.

Example 328

3-(4-{4-[6-(benzylamino)pyrazin-2-yl]-1H-pyrrolo[2,3-b]pyridin-2-yl}piperidin-1-yl)propane-1,2-diol The title compound was prepared essentially as described in Example 149, substituting Example 315 (50 mg, 0.13 mmol) for Example 135B. $^1$H NMR (400 MHz, DMSO-d$_6$) δ 1.71-1.85 (m, 1H), 1.92 (d, J=12.5 Hz, 1H), 2.08-2.26 (m, 2H), 2.91-3.14 (m, 2H), 3.19 (dt, J=13.2, 4.9 Hz, 1H), 3.34 (dd, J=10.9, 6.0 Hz, 1H), 3.40-3.53 (m, 1H), 3.56-3.68 (m, 2H), 3.96 (m, 2H), 4.66 (d, J=3.3 Hz, 2H), 6.63 (d, J=2.0 Hz, 1H), 7.21-7.31 (m, 1H), 7.31-7.45 (m, 4H), 7.55 (dd, J=5.1, 3.5 Hz, 1H), 8.06 (d, J=1.8 Hz, 1H), 8.24 (dd, J=5.1, 2.4 Hz, 1H), 8.40 (d, J=9.9 Hz, 1H). MS (ESI+) m/z 459 (M+H)+.

Example 329 ethyl[(4-{4-[6-(benzylamino)pyrazin-2-yl]-1H-pyrrolo[2,3-b]pyridin-2-yl}piperidin-1-yl)sulfonyl]carbamate Example 329A ((4-(dimethylamino)pyridin-1-ium-1-yl)sulfonyl)(ethoxycarbonyl)amide Chlorosulfonyl isocyanate (2.4 mL, 27.6 mL) was added to a solution of ethanol (1.61 mL, 27.2 mmol) in anhydrous methylene chloride (100 mL) dropwise with cooling over 15 minutes. After stirring for 15 minutes, 4-(dimethylamino)pyridine (6.9 g, 56.5 mmol) was then added. The cooling bath was removed, and the reaction mixture was stirred at room temperature for 1 hour. The reaction mixture was washed with water and brine. After drying with sodium sulfate and filtration, the organic layer was concentrated under vacuum to provide the title compound. MS (DCI/NH$_3$) m/z 274 (M+H)+.

Example 329B ethyl[(4-{4-[6-(benzylamino)pyrazin-2-yl]-1H-pyrrolo[2,3-b]pyridin-2-yl}piperidin-1-yl)sulfonyl]carbamate To a suspension of Example 315 (50 mg, 0.100 mmol) in CH$_2$Cl$_2$ (5 mL) was added triethylamine (0.056 mL, 0.402 mmol) and Example 329A (27 mg, 0.100 mmol) at room temperature. The mixture was stirred at room temperature overnight, and was directly purified by flash chromatography (0-15% CH$_3$OH in CH$_2$Cl$_2$) to provide the title compound. $^1$H NMR (400 MHz, DMSO-d$_6$): δ 1.21 (t, J=7.17 Hz, 3H), 1.52-1.63 (m, 2H), 1.96 (d, J=10.99 Hz, 2H), 2.77-2.82 (m, 1H), 2.92-2.99 (m, 2H), 3.71 (d, J=12.21 Hz, 2H), 4.12 (q, J=7.22 Hz, 2H), 4.67 (d, J=5.80 Hz, 2H), 6.55 (d, J=1.53 Hz, 1H), 7.24 (t, J=7.17 Hz, 1H), 7.32-7.40 (m, 4H), 7.49 (d, J=4.88 Hz, 1H), 7.83 (t, J=6.10 Hz, 1H), 8.04 (s, 1H), 8.19 (d, J=4.88 Hz, 1H), 8.37 (s, 1H), 11.28 (s, 1H), 11.64 (s, 1H). MS (DCI, NH$_3$) m/z 536 (M+H)+.

Example 330

4-(6-chloro-3-fluoropyridin-2-yl)-2-(piperidin-4-yl)-1H-pyrrolo[2,3-b]pyridine

The title compound was prepared essentially as described in Example 314A, substituting 2-bromo-6-chloro-3-fluoropyridine (148 mg, 0.74 mmol) for N-benzyl-6-bromopyrazin-2-amine. $^1$H NMR (400 MHz, DMSO-d$_6$) δ 1.76-1.92 (m, 2H), 2.13-2.34 (m, 2H), 2.96-3.24 (m, 3H), 3.31-3.50 (m, 2H), 6.45 (t, J=1.8 Hz, 1H), 7.39 (dd, J=5.0, 1.8 Hz, 1H), 7.71 (dd, J=8.7, 3.1 Hz, 1H), 8.04 (dd, J=10.0, 8.7 Hz, 1H), 8.32 (d, J=5.1 Hz, 1H). MS (ESI+) m/z 331 (M+H)+.

Example 331

4-{6-[(3-fluorobenzyl)oxy]pyrazin-2-yl}-2-(piperidin-4-yl)-1H-pyrrolo[2,3-b]pyridine The title compound was prepared essentially as described in Example 314A, substituting 2-bromo-6-((3-fluorobenzyl)

oxy)pyrazine (238 mg, 0.84 mmol) for N-benzyl-6-bromopyrazin-2-amine $^1$H NMR (400 MHz, DMSO-$d_6$) δ 1.75-1.96 (m, 2H), 2.13-2.40 (m, 2H), 2.94-3.23 (m, 3H), 3.40 (d, J=12.5 Hz, 2H), 5.60 (s, 2H), 6.76 (d, J=2.0 Hz, 1H), 7.12-7.27 (m, 1H), 7.32-7.44 (m, 2H), 7.47 (td, J=7.8, 6.0 Hz, 1H), 7.68 (d, J=5.1 Hz, 1H), 8.31 (d, J=5.1 Hz, 1H), 8.47 (s, 1H), 8.97 (s, 1H). MS (ESI$^+$) m/z 404 (M+H)$^+$.

Example 332

N-(3-fluorobenzyl)-6-[2-(1-methylpiperidin-4-yl)-1H-pyrrolo[2,3-b]pyridin-4-yl]pyrazin-2-amine The title compound was prepared essentially as described in Example 89, substituting Example 318 (50 mg, 0.13 mmol) for Example 88. $^1$H NMR (400 MHz, DMSO-$d_6$) δ 1.77 (qd, J=13.3, 3.8 Hz, 2H), 2.13-2.31 (m, 2H), 2.83 (d, J=4.5 Hz, 3H), 2.98 (ddd, J=12.2, 8.7, 3.3 Hz, 1H), 3.11 (dd, J=10.3, 3.1 Hz, 2H), 3.54 (d, J=12.2 Hz, 2H), 4.59-4.71 (m, 2H), 6.60 (d, J=1.9 Hz, 1H), 7.09 (td, J=8.7, 2.6 Hz, 1H), 7.16-7.29 (m, 3H), 7.40 (td, J=7.9, 6.1 Hz, 1H), 7.55 (t, J=5.2 Hz, 1H), 8.09 (s, 1H), 8.24 (d, J=5.1 Hz, 1H), 8.41 (s, 1H). MS (ESI$^+$) m/z 417 (M+H)$^+$.

Example 333

1-[4-(4-{6-[(3-fluorobenzyl)amino]pyrazin-2-yl}-1H-pyrrolo[2,3-b]pyridin-2-yl)piperidin-1-yl]ethanone The title compound was prepared essentially as described in Example 135C, substituting Example 318 (50 mg, 0.13 mmol) for Example 135B. $^1$H NMR (400 MHz, DMSO-$d_6$) δ 1.30-1.60 (m, 2H), 1.82-1.98 (m, 2H), 2.04 (s, 3H), 2.63 (td, J=12.9, 2.8 Hz, 1H), 2.84-3.02 (m, 1H), 3.14 (td, J=13.5, 13.1, 2.6 Hz, 1H), 3.83-3.94 (m, 1H), 4.41-4.51 (m, 2H), 4.68 (s, 2H), 6.55 (d, J=2.0 Hz, 1H), 7.07 (td, J=8.7, 2.7 Hz, 1H), 7.13-7.27 (m, 2H), 7.39 (td, J=7.9, 6.1 Hz, 1H), 7.56 (d, J=5.2 Hz, 1H), 8.09 (s, 1H), 8.22 (d, J=5.2 Hz, 1H), 8.42 (s, 1H). MS (ESI$^+$) m/z 445 (M+H)$^+$.

Example 334

4-{6-[(3-fluorobenzyl)oxy]pyrazin-2-yl}-2-(1-methylpiperidin-4-yl)-1H-pyrrolo[2,3-b]pyridine The title compound was prepared essentially as described in Example 89, substituting Example 331 (50 mg, 0.12 mmol) for Example 88. $^1$H NMR (400 MHz, DMSO-$d_6$) δ 1.74-2.00 (m, 2H), 2.20 (dd, J=21.1, 14.1 Hz, 2H), 2.94-3.25 (m, 3H), 3.28-3.52 (m, 2H), 3.63 (s, 3H), 4.68 (d, J=3.5 Hz, 2H), 6.60 (d, J=2.2 Hz, 1H), 7.09 (td, J=8.7, 2.6 Hz, 1H), 7.15-7.30 (m, 2H), 7.40 (td, J=8.0, 6.0 Hz, 1H), 7.54 (dd, J=5.2, 1.9 Hz, 1H), 8.08 (s, 1H), 8.24 (d, J=5.1 Hz, 1H), 8.42 (d, J=9.8 Hz, 1H). MS (ESI$^+$) m/z 417 (M+H)$^+$.

Example 335

N-benzyl-6-[2-(1,2,3,6-tetrahydropyridin-4-yl)-1H-pyrrolo[2,3-b]pyridin-4-yl]pyrazin-2-amine Example 335A tert-butyl 4-(4-(4,4,5,5-tetramethyl-1,3,2-dioxaborolan-2-yl)-1-tosyl-1H-pyrrolo[2,3-b]pyridin-2-yl)-5,6-dihydropyridine-1(2H)-carboxylate A mixture of potassium acetate (5.53 g, 56.3 mmol), 1,1'-bis(diphenylphosphino)ferrocene-palladium(II)dichloride dichloromethane complex (0.920 g, 1.127 mmol), bis(pinacolato)diboron (11.92 g, 47.0 mmol), and Example 220C (10 g, 18.78 mmol) in 1,2-dimethoxyethane (200 mL) was stirred at 80° C. for 6 hours. The reaction mixture was diluted with water. The aqueous layer was extracted with ethyl acetate (3×200 mL). The combined organic layers were washed with water and brine, dried with $Na_2SO_4$, filtered, concentrated, and recrystallized with ethyl acetate/petroleum ether (1:4) to provide the title compound. MS (ESI$^+$) m/z 580.3 (M+H)$^+$.

Example 335B

N-benzyl-6-[2-(1,2,3,6-tetrahydropyridin-4-yl)-1H-pyrrolo[2,3-b]pyridin-4-yl]pyrazin-2-amine The title compound was prepared essentially as described in Example 314A, substituting Example 335A (500 mg, 1.2 mmol) for Example 21A. $^1$H NMR (400 MHz, DMSO-$d_6$) δ 2.45 (q, J=5.6, 5.1 Hz, 2H), 3.23-3.35 (m, 2H), 3.82 (d, J=5.2 Hz, 2H), 4.69 (s, 2H), 6.40-6.53 (m, 1H), 6.99 (d, J=2.0 Hz, 1H), 7.19-7.30 (m, 1H), 7.30-7.47 (m, 5H), 7.58 (d, J=5.1 Hz, 1H), 8.08 (s, 1H), 8.30 (d, J=5.1 Hz, 1H), 8.44 (s, 1H). MS (ESI$^+$) m/z 383 (M+H)$^+$.

Example 336

1-[4-(4-{6-[(3-fluorobenzyl)oxy]pyrazin-2-yl}-1H-pyrrolo[2,3-b]pyridin-2-yl)piperidin-1-yl]-2-hydroxyethanone The title compound was prepared essentially as described in Example 322, substituting Example 331 (50 mg, 0.12 mmol) for Example 317. $^1$H NMR (400 MHz, DMSO-$d_6$) δ 1.51-1.80 (m, 2H), 1.93-2.07 (m, 2H), 2.71-2.84 (m, 1H), 2.99-3.21 (m, 2H), 3.78 (d, J=13.8 Hz, 1H), 4.12 (d, J=7.2 Hz, 2H), 4.46 (d, J=13.2 Hz, 1H), 5.60 (s, 2H), 6.70 (d, J=1.9 Hz, 1H), 7.06-7.26 (m, 1H), 7.33-7.39 (m, 2H), 7.46 (td, J=8.1, 6.1 Hz, 1H), 7.69 (d, J=5.2 Hz, 1H), 8.30 (d, J=5.2 Hz, 1H), 8.47 (s, 1H), 8.96 (s, 1H). MS (ESI$^+$) m/z 462 (M+H)$^+$.

Example 337

3-[4-(4-{6-[(3-fluorobenzyl)oxy]pyrazin-2-yl}-1H-pyrrolo[2,3-b]pyridin-2-yl)piperidin-1-yl]propane-1,2-diol The title compound was prepared essentially as described in Example 149, substituting Example 331 (50 mg, 0.12 mmol) for Example 135B. $^1$H NMR (400 MHz, DMSO-$d_6$) δ 1.77-2.14 (m, 2H), 2.31 (dd, J=20.1, 14.4 Hz, 2H), 3.00-3.14 (m, 2H), 3.13-3.29 (m, 1H), 3.34 (dd, J=11.0, 6.1 Hz, 1H), 3.45 (ddd, J=14.4, 10.9, 4.8 Hz, 2H), 3.65 (d, J=11.9 Hz, 2H), 3.83-4.06 (m, 2H), 5.60 (s, 2H), 6.75 (d, J=1.9 Hz, 1H), 7.20 (td, J=8.7, 2.1 Hz, 1H), 7.32-7.41 (m, 2H), 7.47 (dt, J=7.8, 6.5 Hz, 1H), 7.68 (d, J=4.9 Hz, 1H), 8.32 (dd, J=5.2, 2.3 Hz, 1H), 8.47 (s, 1H), 8.97 (d, J=9.9 Hz, 1H). MS (ESI$^+$) m/z 478 (M+H)$^+$.

Example 338 ethyl {[4-(4-{6-[(3-fluorobenzyl)amino]pyrazin-2-yl}-1H-pyrrolo[2,3-b]pyridin-2-yl)piperidin-1-yl]sulfonyl}carbamate The title product was prepared essentially as described in Example 329B, substituting Example 318 for Example 315.

¹H NMR (500 MHz, DMSO-d₆): δ 1.21 (t, J=7.02 Hz, 3H), 1.56-1.64 (m, 2H), 1.97 (d, J=10.99 Hz, 2H), 2.78-2.83 (m, 1H), 2.93-2.99 (m, 2H), 3.73 (d, J=12.21 Hz, 2H), 4.13 (q, J=7.22 Hz, 2H), 4.68 (d, J=6.10 Hz, 2H), 6.51 (d, J=1.53 Hz, 1H), 7.03-7.09 (m, 1H), 7.18-7.26 (m, 2H), 7.36-7.42 (m, 1H), 7.49 (d, J=5.19 Hz, 1H), 7.87 (t, J=6.10 Hz, 1H), 8.06 (s, 1H), 8.19 (d, J=5.19 Hz, 1H), 8.39 (s, 1H), 11.28 (s, 1H), 11.66 (s, 1H). MS (DCI/NH₃) m/z 554 (M+H)⁺.

Example 339

4-{4-[6-(benzylamino)pyrazin-2-yl]-1H-pyrrolo[2,3-b]pyridin-2-yl}-N-methylpiperidine-1-carboxamide The title compound was prepared essentially as described in Example 222D, substituting Example 314A (50 mg, 0.12 mmol) for Example 222C. ¹H NMR (400 MHz, DMSO-d₆) δ 1.36-1.57 (m, 2H), 1.70-1.99 (m, 2H), 2.60 (s, 3H), 2.68-2.93 (m, 2H), 4.04 (dt, J=13.2, 3.0 Hz, 2H), 4.66 (s, 2H), 6.62 (d, J=1.9 Hz, 1H), 7.19-7.30 (m, 1H), 7.30-7.46 (m, 4H), 7.61 (d, J=5.4 Hz, 1H), 8.09 (s, 1H), 8.25 (d, J=5.4 Hz, 1H), 8.42 (s, 1H). MS (DCl/NH₃) m/z 442 (M+H)⁺.

Example 340

4-(4-{6-[(3-fluorobenzyl)amino]pyrazin-2-yl}-1H-pyrrolo[2,3-b]pyridin-2-yl)-N-methylpiperidine-1-carboxamide The title compound was prepared essentially as described in Example 222D, substituting Example 318 (70 mg, 0.2 mmol) for Example 222C. ¹H NMR (400 MHz, DMSO-d₆) δ 1.49 (td, J=12.4, 4.0 Hz, 2H), 1.74-1.92 (m, 2H), 2.60 (s, 3H), 2.78 (ddd, J=25.6, 12.7, 3.1 Hz, 3H), 4.03 (d, J=23.3 Hz, 2H), 4.67 (d, J=3.5 Hz, 2H), 6.52 (d, J=2.0 Hz, 1H), 7.07 (td, J=8.6, 2.7 Hz, 1H), 7.15-7.28 (m, 2H), 7.39 (td, J=8.0, 6.1 Hz, 1H), 7.54 (d, J=5.2 Hz, 1H), 8.08 (s, 1H), 8.21 (d, J=5.2 Hz, 1H), 8.41 (s, 1H). MS (DCl/NH₃) m/z 459 (M+H)⁺.

Example 341

4-{6-[(3-fluorobenzyl)oxy]pyrazin-2-yl}-2-[1-(methylsulfonyl)piperidin-4-yl]-1H-pyrrolo[2,3-b]pyridine The title compound was prepared essentially as described in Example 220E, substituting Example 331 (50 mg, 0.12 mmol) for Example 220D. ¹H NMR (400 MHz, DMSO-d₆) δ 1.77 (dd, J=12.6, 3.9 Hz, 2H), 2.03-2.16 (m, 2H), 2.87 (d, J=2.6 Hz, 3H), 2.91 (s, 3H), 3.58-3.71 (m, 2H), 5.61 (s, 2H), 6.71 (d, J=2.0 Hz, 1H), 7.15-7.26 (m, 1H), 7.32-7.41 (m, 2H), 7.46 (td, J=7.7, 5.8 Hz, 1H), 7.67 (d, J=5.1 Hz, 1H), 8.28 (d, J=5.1 Hz, 1H), 8.46 (s, 1H), 8.95 (s, 1H). MS (ESI⁺) m/z 482 (M+H)⁺.

Example 342

1-[4-(4-{6-[(3-fluorobenzyl)oxy]pyrazin-2-yl}-1H-pyrrolo[2,3-b]pyridin-2-yl)piperidin-1-yl]ethanone The title compound was prepared essentially as described in Example 135C, substituting Example 331 (50 mg, 0.12 mmol) for Example 135B. ¹H NMR (400 MHz, DMSO-d₆) δ 1.53 (dd, J=12.4, 4.1 Hz, 1H), 1.62-1.73 (m, 1H), 1.97 (d, J=14.7 Hz, 2H), 2.04 (s, 3H), 2.61-2.72 (m, 1H), 2.96-3.05 (m, 1H), 3.17 (ddd, J=15.1, 12.6, 2.7 Hz, 1H), 3.87-3.96 (m, 1H), 4.44-4.53 (m, 1H), 5.61 (s, 2H), 6.69 (d, J=2.0 Hz, 1H), 7.14-7.24 (m, 1H), 7.36 (ddd, J=7.6, 4.1, 2.0 Hz, 2H), 7.46 (td, J=8.1, 6.0 Hz, 1H), 7.68 (d, J=5.2 Hz, 1H), 8.29 (d, J=5.2 Hz, 1H), 8.47 (s, 1H), 8.96 (s, 1H). MS (ESI⁺) m/z 446 (M+H)⁺.

Example 343

4-(4-{6-[(3-fluorobenzyl)oxy]pyrazin-2-yl}-1H-pyrrolo[2,3-b]pyridin-2-yl)-N-methylpiperidine-1-carboxamide The title compound was prepared essentially as described in Example 222D, substituting Example 331 (50 mg, 0.12 mmol) for Example 222C. ¹H NMR (400 MHz, DMSO-d₆) δ 1.51-1.65 (m, 2H), 1.88-1.98 (m, 2H), 2.59 (s, 3H), 2.79 (td, J=12.8, 2.5 Hz, 2H), 2.87-2.96 (m, 1H), 4.05 (dt, J=13.5, 3.1 Hz, 2H), 5.60 (s, 2H), 6.68 (d, J=2.0 Hz, 1H), 7.19 (td, J=8.3, 7.5, 1.8 Hz, 1H), 7.32-7.39 (m, 2H), 7.46 (td, J=7.6, 5.7 Hz, 1H), 7.67 (d, J=5.2 Hz, 1H), 8.28 (d, J=5.2 Hz, 1H), 8.46 (s, 1H), 8.95 (s, 1H). MS (DCl/NH₃) m/z 461 (M+H)⁺.

Example 344

1-[4-{4-[6-(benzylamino)pyrazin-2-yl]-1H-pyrrolo[2,3-b]pyridin-2-yl}-3,6-dihydropyridin-1(2H)-yl]-2-hydroxyethanone The title compound was prepared essentially as described in Example 322, substituting Example 335 (200 mg, 0.47 mmol) for Example 317. ¹H NMR (400 MHz, DMSO-d₆) δ 2.26 (d, J=26.2 Hz, 2H), 3.50 (t, J=5.6 Hz, 1H), 3.63 (m, 1H), 3.97 (d, J=3.2 Hz, 2H), 4.07-4.21 (m, 2H), 4.69 (s, 2H), 6.39-6.58 (m, 1H), 6.93 (d, J=9.9 Hz, 1H), 7.26 (t, J=7.1 Hz, 1H), 7.32-7.44 (m, 4H), 7.56 (d, J=5.1 Hz, 1H), 8.08 (s, 1H), 8.26 (d, J=5.2 Hz, 1H), 8.44 (s, 1H). MS (ESI⁺) m/z 441 (M+H)⁺.

Example 345

N-(3-fluorobenzyl)-6-[2-(1,2,3,6-tetrahydropyridin-4-yl)-1H-pyrrolo[2,3-b]pyridin-4-yl]pyrazin-2-amine The title compound was prepared essentially as described in Example 314A, substituting Example 335A (500 mg, 1.2 mmol) for Example 21A and 6-bromo-N-(3-fluorobenzyl)pyrazin-2-amine for N-benzyl-6-bromopyrazin-2-amine ¹H NMR (400 MHz, DMSO-d₆) δ 2.48 (d, J=7.5 Hz, 2H), 3.23-3.41 (m, 2H), 3.73-3.90 (m, 2H), 4.70 (d, J=3.7 Hz, 2H), 6.47 (d, J=3.7 Hz, 1H), 6.95 (d, J=2.1 Hz, 1H), 7.09 (td, J=8.7, 2.6 Hz, 1H), 7.15-7.31 (m, 2H), 7.40 (td, J=7.9, 6.1 Hz, 1H), 7.56 (d, J=5.1 Hz, 1H), 8.10 (s, 1H), 8.29 (d, J=5.1 Hz, 1H), 8.46 (s, 1H). MS (ESI⁺) m/z 401 (M+H)⁺.

Example 346

3-[4-(4-{6-[(3-fluorobenzyl)amino]pyrazin-2-yl}-1H-pyrrolo[2,3-b]pyridin-2-yl)-3,6-dihydropyridin-1(2H)-yl]propane-1,2-diol The title compound was prepared essentially as described in Example 149, substituting Example 345 (50 mg, 0.12 mmol) for Example 135B. ¹H NMR (400 MHz, DMSO-d₆) δ 2.53-2.74 (m, 2H), 3.08-3.21 (m, 1H), 3.32 (ddd, J=27.0, 11.9, 6.2 Hz, 3H), 3.47 (dd, J=11.0, 4.8 Hz, 1H), 3.63 (d, J=12.2 Hz, 1H), 3.96 (m, 2H), 4.70 (t, J=5.4 Hz, 2H), 6.43 (t, J=3.2 Hz, 1H), 6.95 (d, J=2.1 Hz, 1H), 7.09 (td, J=8.8, 2.6 Hz, 1H), 7.22 (dd, J=17.2, 8.6 Hz, 2H), 7.34-7.45 (m, 1H), 7.56

(d, J=5.1 Hz, 1H), 8.09 (s, 1H), 8.29 (d, J=5.1 Hz, 1H), 8.45 (s, 1H). MS (ESI+) m/z 475 (M+H)+.

Example 347

4-{6-[(3-fluorobenzyl)oxy]pyrazin-2-yl}-2-(1,2,3,6-tetrahydropyridin-4-yl)-1H-pyrrolo[2,3-b]pyridine The title compound was prepared essentially as described in Example 314A, substituting Example 335A (500 mg, 1.2 mmol) for Example 21A and 2-bromo-6-((3-fluorobenzyl) oxy)pyrazine for N-benzyl-6-bromopyrazin-2-amine. $^1$H NMR (400 MHz, DMSO-d$_6$) δ 2.70 (t, J=5.8 Hz, 2H), 3.36 (dq, J=7.4, 4.8 Hz, 2H), 3.86 (d, J=4.5 Hz, 2H), 5.62 (s, 2H), 6.55 (t, J=3.3 Hz, 1H), 7.10 (d, J=2.0 Hz, 1H), 7.20 (td, J=8.1, 7.4, 2.2 Hz, 1H), 7.34-7.42 (m, 2H), 7.47 (td, J=7.8, 6.0 Hz, 1H), 7.70 (d, J=5.0 Hz, 1H), 8.37 (d, J=5.0 Hz, 1H), 8.49 (s, 1H), 9.00 (d, J=5.2 Hz, 1H). MS (ESI+) m/z 402 (M+H)+.

Example 348

4-(4-{6-[(3-fluorobenzyl)amino]pyrazin-2-yl}-1H-pyrrolo[2,3-b]pyridin-2-yl)-N-methyl-3,6-dihydropyridine-1(2H)-carboxamide The title compound was prepared essentially as described in Example 222D, substituting Example 345 (50 mg, 0.13 mmol) for Example 222C. $^1$H NMR (400 MHz, DMSO-d$_6$) δ 2.26 (d, J=5.6 Hz, 2H), 2.61 (s, 3H), 3.47 (m, 2H), 3.47 (t, J=5.7 Hz, 2H), 4.00 (q, J=2.9 Hz, 2H), 4.70 (s, 2H), 6.48 (d, J=3.6 Hz, 1H), 6.88 (d, J=2.1 Hz, 1H), 7.08 (td, J=8.6, 2.6 Hz, 1H), 7.14-7.29 (m, 2H), 7.40 (td, J=7.9, 6.1 Hz, 1H), 7.54 (d, J=5.2 Hz, 1H), 8.08 (s, 1H), 8.25 (d, J=5.1 Hz, 1H), 8.45 (s, 1H). MS (DCl/NH$_3$) m/z 458 (M+H)+.

Example 349

6-[2-(1-methylpiperidin-4-yl)-1H-pyrrolo[2,3-b]pyridin-4-yl]-N-(pyridin-3-ylmethyl)pyrazin-2-amine The title compound was prepared essentially as described in Example 89, substituting Example 319 (50 mg, 0.13 mmol) for Example 88. $^1$H NMR (500 MHz, DMSO-d$_6$) δ 1.69-1.81 (m, 2H), 2.24 (dd, J=14.4, 3.5 Hz, 2H), 2.83 (s, 3H), 2.94-3.02 (m, 1H), 3.10 (d, J=12.8 Hz, 2H), 3.54 (d, J=12.2 Hz, 2H), 4.77 (d, J=4.7 Hz, 3H), 6.56 (d, J=2.0 Hz, 1H), 7.50 (dd, J=5.1, 2.7 Hz, 1H), 7.76 (dd, J=8.1, 5.1 Hz, 1H), 8.02 (t, J=5.6 Hz, 1H), 8.12 (s, 1H), 8.24 (t, J=6.6 Hz, 2H), 8.44 (s, 1H), 8.68 (d, J=5.2 Hz, 1H), 8.81 (d, J=2.1 Hz, 1H). MS (ESI+) m/z 400 (M+H)+.

Example 350

3-[4-(4-{6-[(pyridin-3-ylmethyl)amino]pyrazin-2-yl}-1H-pyrrolo[2,3-b]pyridin-2-yl)piperidin-1-yl]propane-1,2-diol The title compound was prepared essentially as described in Example 149, substituting Example 319 (50 mg, 0.12 mmol) for Example 135B. $^1$H NMR (500 MHz, DMSO-d$_6$) δ 1.77-1.88 (m, 1H), 1.89-2.00 (m, 1H), 2.23 (dd, J=28.5, 14.0 Hz, 2H), 2.97-3.15 (m, 2H), 3.16-3.28 (m, 1H), 3.35 (dd, J=10.8, 6.1 Hz, 1H), 3.45 (ddd, J=16.6, 11.1, 5.0 Hz, 1H), 3.60-3.69 (m, 2H), 3.98 (d, J=11.9 Hz, 2H), 4.73-4.85 (m, 2H), 6.56 (d, J=2.1 Hz, 1H), 7.51 (d, J=5.2 Hz, 1H), 7.82 (dt, J=8.0, 4.7 Hz, 1H), 8.13 (s, 1H), 8.24 (d, J=5.1 Hz, 1H), 8.31 (d, J=7.8 Hz, 1H), 8.45 (s, 1H), 8.71 (d, J=5.1 Hz, 1H), 8.84 (d, J=2.2 Hz, 1H). MS (ESI+) m/z 460 (M+H)+

Example 351

2-hydroxy-1-[4-(4-{6-[(pyridin-3-ylmethyl)amino]pyrazin-2-yl}-1H-pyrrolo[2,3-b]pyridin-2-yl)piperidin-1-yl]ethanone The title compound was prepared essentially as described in Example 322, substituting Example 319 (50 mg, 0.13 mmol) for Example 317. $^1$H NMR (500 MHz, DMSO-d$_6$) δ 1.47 (q, J=13.1 Hz, 1H), 1.53-1.64 (m, 1H), 1.95 (d, J=12.9 Hz, 2H), 2.99 (q, J=12.0, 9.7 Hz, 1H), 3.10 (dq, J=18.9, 10.9, 8.8 Hz, 2H), 3.77 (d, J=13.9 Hz, 1H), 4.09-4.20 (m, 2H), 4.46 (d, J=12.8 Hz, 1H), 4.82 (s, 2H), 6.53 (s, 1H), 7.53 (d, J=5.3 Hz, 1H), 7.93 (dd, J=14.3, 7.6 Hz, 2H), 8.15 (s, 1H), 8.24 (d, J=5.2 Hz, 1H), 8.42-8.49 (m, 2H), 8.77 (d, J=5.5 Hz, 1H), 8.89 (s, 1H). MS (ESI+) m/z 444 (M+H)+.

Example 352

N-methyl-4-(4-{6-[(pyridin-3-ylmethyl)amino]pyrazin-2-yl}-1H-pyrrolo[2,3-b]pyridin-2-yl)piperidine-1-carboxamide The title compound was prepared essentially as described in Example 222D, substituting Example 319 (50 mg, 0.13 mmol) for Example 222C. $^1$H NMR (500 MHz, DMSO-d$_6$) δ 1.47 (qd, J=12.5, 4.0 Hz, 2H), 1.87 (dd, J=13.4, 3.6 Hz, 2H), 2.60 (s, 3H), 2.78 (ddd, J=14.0, 9.1, 2.4 Hz, 2H), 3.10 (dd, J=7.3, 4.8 Hz, 1H), 3.99-4.11 (m, 2H), 4.76-4.89 (m, 2H), 6.50 (d, J=2.0 Hz, 1H), 7.51 (d, J=5.2 Hz, 1H), 7.89 (dd, J=8.0, 5.5 Hz, 1H), 8.14 (s, 1H), 8.22 (d, J=5.2 Hz, 1H), 8.41 (dt, J=8.3, 1.6 Hz, 1H), 8.46 (s, 1H), 8.75 (d, J=5.3 Hz, 1H), 8.81-8.98 (m, 1H). MS (DCl/NH$_3$) m/z 443 (M+H)+.

Example 353

1-[4-(4-{6-[(3-fluorobenzyl)amino]pyrazin-2-yl}-1H-pyrrolo[2,3-b]pyridin-2-yl)-3,6-dihydropyridin-1(2H)-yl]-2-hydroxyethanone The title compound was prepared essentially as described in Example 322, substituting Example 345 (50 mg, 0.13 mmol) for Example 317. $^1$H NMR (400 MHz, DMSO-d$_6$) δ 2.19-2.37 (m, 2H), 3.51 (t, J=5.7 Hz, 1H), 3.66 (t, J=5.7 Hz, 1H), 4.09-4.15 (m, 2H), 4.18 (d, J=8.8 Hz, 2H), 4.71 (s, 2H), 6.42-6.55 (m, 1H), 6.90 (d, J=11.1 Hz, 1H), 7.02-7.15 (m, 1H), 7.17-7.28 (m, 2H), 7.40 (q, J=7.0, 6.3 Hz, 1H), 8.09 (s, 1H), 8.27 (d, J=5.2 Hz, 1H), 8.46 (s, 1H). MS (ESI+) m/z 459 (M+H)+.

Example 354

4-{6-[(3-fluorobenzyl)oxy]pyrazin-2-yl}-2-[1-(methylsulfonyl)-1,2,3,6-tetrahydropyridin-4-yl]-1H-pyrrolo[2,3-b]pyridine The title compound was prepared essentially as described in Example 220E, substituting Example 347 (50 mg, 0.13 mmol) for Example 220D. $^1$H NMR (500 MHz, DMSO-d$_6$) δ 2.61 (q, J=4.7 Hz, 2H), 2.96 (s, 3H), 3.39 (t, J=5.8 Hz, 2H), 3.93 (q, J=2.8 Hz, 2H), 5.62 (s, 2H), 6.49-6.70 (m, 1H), 7.03 (d, J=2.1 Hz, 1H), 7.19 (td, J=8.7, 2.6 Hz, 1H), 7.30-7.42 (m, 2H), 7.46 (td, J=8.0, 6.0 Hz, 1H), 7.69 (d, J=5.1 Hz, 1H), 8.33 (d, J=5.1 Hz, 1H), 8.47 (s, 1H), 8.99 (s, 1H). MS (ESI$^+$) m/z 480 (M+H)$^+$.

Example 355

3,5-difluoro-N-(3-fluorobenzyl)-6-[2-(piperidin-4-yl)-1H-pyrrolo[2,3-b]pyridin-4-yl]pyridin-2-amine The title compound was prepared essentially as described in Example 314A, substituting Example 335A (500 mg, 1.2 mmol) for Example 21A and 6-bromo-3,5-difluoro-N-(3-fluorobenzyl)pyridin-2-amine for N-benzyl-6-bromopyrazin-2-amine. $^1$H NMR (400 MHz, DMSO-d$_6$) δ 1.70 (qd, J=12.8, 3.8 Hz, 2H), 2.09 (dd, J=14.4, 3.8 Hz, 2H), 3.02 (tt, J=11.6, 9.0 Hz, 3H), 3.35 (d, J=12.8 Hz, 2H), 4.67 (d, J=3.3 Hz, 2H), 6.24 (s, 1H), 7.00-7.19 (m, 3H), 7.25 (dd, J=5.2, 2.1 Hz, 1H), 7.36 (td, J=7.9, 6.2 Hz, 1H), 7.83 (t, J=10.2 Hz, 1H), 8.22 (d, J=5.1 Hz, 1H). MS (ESI$^+$) m/z 438 (M+H)$^+$.

Example 356

4-(4-{6-[(3-fluorobenzyl)oxy]pyrazin-2-yl}-1H-pyrrolo[2,3-b]pyridin-2-yl)-N-methyl-3,6-dihydropyridine-1(2H)-carboxamide The title compound was prepared essentially as described in Example 222D, substituting Example 347 (50 mg, 0.13 mmol) for Example 222C. $^1$H NMR (500 MHz, DMSO-d$_6$) δ 2.45 (qd, J=5.1, 3.0 Hz, 2H), 2.61 (s, 3H), 3.52 (t, J=5.6 Hz, 2H), 4.03 (q, J=2.7 Hz, 2H), 5.61 (s, 2H), 6.57 (dt, J=3.7, 2.2 Hz, 1H), 7.02 (d, J=2.0 Hz, 1H), 7.12-7.25 (m, 1H), 7.37 (ddd, J=7.0, 3.9, 1.7 Hz, 2H), 7.47 (td, J=8.1, 6.2 Hz, 1H), 7.69 (d, J=5.1 Hz, 1H), 8.32 (d, J=5.1 Hz, 1H), 8.47 (s, 1H), 8.99 (s, 1H). MS (DCl/NH$_3$) m/z 459 (M+H)$^+$.

Example 357

1-[4-(4-{6-[(3-fluorobenzyl)oxy]pyrazin-2-yl}-1H-pyrrolo[2,3-b]pyridin-2-yl)-3,6-dihydropyridin-1(2H)-yl]-2-hydroxyethanone The title compound was prepared essentially as described in Example 322, substituting Example 347 (50 mg, 0.13 mmol) for Example 317. $^1$H NMR (500 MHz, DMSO-d$_6$) δ 2.39-2.60 (m, 2H), 3.56 (t, J=5.7 Hz, 1H), 3.70 (t, J=5.8 Hz, 1H), 4.09-4.20 (m, 4H), 5.62 (s, 2H), 6.52-6.64 (m, 1H), 7.01 (dd, J=16.4, 2.3 Hz, 1H), 7.19 (td, J=8.9, 2.5 Hz, 1H), 7.37 (ddd, J=6.5, 5.3, 2.0 Hz, 2H), 7.47 (td, J=8.0, 6.0 Hz, 1H), 7.69 (d, J=5.1 Hz, 1H), 8.33 (d, J=5.1 Hz, 1H), 8.48 (s, 1H), 8.99 (s, 1H). MS (ESI$^+$) m/z 460 (M+H)$^+$.

Example 358

3,5-difluoro-N-(3-fluorobenzyl)-6-{2-[1-(methylsulfonyl)-1,2,3,6-tetrahydropyridin-4-yl]-1H-pyrrolo[2,3-b]pyridin-4-yl}pyridin-2-amine The title compound was prepared essentially as described in Example 220E, substituting Example 345 (50 mg, 0.11 mmol) for Example 220D. $^1$H NMR (400 MHz, DMSO-d$_6$) δ 1.53 (dqd, J=25.1, 12.5, 4.0 Hz, 2H), 1.87-2.01 (m, 2H), 2.73 (s, 3H), 2.97 (ddd, J=19.7, 10.7, 5.6 Hz, 2H), 4.66 (d, J=3.8 Hz, 2H), 6.13 (s, 1H), 7.04 (d, J=2.6 Hz, 1H), 7.09-7.18 (m, 3H), 7.25 (dd, J=5.2, 2.3 Hz, 1H), 7.35 (td, J=7.9, 6.0 Hz, 1H), 7.83 (d, J=10.2 Hz, 1H), 8.19 (d, J=5.1 Hz, 1H). MS (ESI$^+$) m/z 516 (M+H)$^+$.

Example 359

4-(4-{3,5-difluoro-6-[(3-fluorobenzyl)amino]pyridin-2-yl}-1H-pyrrolo[2,3-b]pyridin-2-yl)-N-methylpiperidine-1-carboxamide The title compound was prepared essentially as described in Example 222D, substituting Example 355 (50 mg, 0.11 mmol) for Example 222C. $^1$H NMR (400 MHz, DMSO-d$_6$) δ 1.33-1.51 (m, 2H), 1.77 (dd, J=13.4, 3.6 Hz, 2H), 2.61 (s, 3H), 2.75 (ddt, J=12.8, 10.6, 2.7 Hz, 4H), 3.98-4.13 (m, 2H), 4.65 (s, 2H), 6.13 (s, 1H), 6.98-7.19 (m, 4H), 7.28 (dd, J=5.3, 2.3 Hz, 1H), 7.36 (td, J=7.9, 6.1 Hz, 1H), 7.83 (t, J=10.2 Hz, 1H), 8.21 (d, J=5.2 Hz, 1H). MS (DCl/NH$_3$) m/z 495 (M+H)$^+$.

Example 360

1-[4-(4-{3,5-difluoro-6-[(3-fluorobenzyl)amino]pyridin-2-yl}-1H-pyrrolo[2,3-b]pyridin-2-yl)piperidin-1-yl]-2-hydroxyethanone The title compound was prepared essentially as described in Example 322, substituting Example 355 (50 mg, 0.11 mmol) for Example 317. $^1$H NMR (400 MHz, DMSO-d$_6$) δ 1.43 (dtd, J=36.5, 12.2, 5.8 Hz, 2H), 1.85 (dd, J=13.1, 4.0 Hz, 2H), 2.72 (t, J=12.6 Hz, 1H), 2.87 (tt, J=11.8, 3.6 Hz, 1H), 3.06 (t, J=12.7 Hz, 1H), 3.74 (d, J=13.6 Hz, 1H), 4.44 (d, J=12.8 Hz, 1H), 4.66 (s, 2H), 6.15 (s, 1H), 6.98-7.19 (m, 4H), 7.29 (dd, J=5.3, 2.3 Hz, 1H), 7.36 (td, J=7.9, 6.0 Hz, 1H), 7.83 (t, J=10.2 Hz, 1H), 8.21 (d, J=5.3 Hz, 1H). MS (ESI$^+$) m/z 496 (M+H)$^+$.

Example 361

4-{4-[6-(benzylamino)pyrazin-2-yl]-1H-pyrrolo[2,3-b]pyridin-2-yl}cyclohex-3-ene-1-carboxylic acid Example 361A ethyl 4-(4-chloro-1-tosyl-1H-pyrrolo[2,3-b]pyridin-2-yl)cyclohex-3-enecarboxylate A solution of 4-chloro-2-iodo-1-tosyl-1H-pyrrolo[2,3-b]pyridine (2.0 g, 4.4 mmol), ethyl 4-(4,4,5,5-tetramethyl-1,3,2-dioxaborolan-2-yl)cyclohex-3-enecarboxylate (1.6 g, 5.5 mmol) and bis(triphenylphosphine)palladium(ii) chloride (324 mg, 0.5 mmol) in a mixed solvent of 1,2-dimethoxyethane/ethanol/water with ratio of 7/3/2 (200 mL) was purged with N$_2$ and heated at 100° C. overnight. After cooling, the reaction mixture was partitioned between water and ethyl acetate. The organic phase was concentrated and purified by flash chromatography on silica gel using an ISCO Companion eluting with heptanes/ethyl acetate (50%) to give desired product. MS (ESI$^+$) m/z 460 (M+H)$^+$.

Example 361B ethyl 4-(4-(4,4,5,5-tetramethyl-1,3,2-dioxaborolan-2-yl)-1-tosyl-1H-pyrrolo[2,3-b]pyridin-2-yl)cyclohex-3-enecarboxylate The title compound was prepared essentially as described in Example 5A, substituting Example 361A (1.4 g, 3.1 mmol) for Example 1F. MS (ESI$^+$) m/z 551 (M+H)$^+$.

Example 361C 4-(4-(6-(benzylamino)pyrazin-2-yl)-1H-pyrrolo[2,3-b]pyridin-2-yl)cyclohex-3-enecarboxylic acid A mixture of Example 361B (400 mg, 0.7 mmol), N-benzyl-6-bromopyrazin-2-amine (230 mg, 0.9 mmol), bis(triphenylphosphine)palladium(ii) chloride (51 mg, 0.07 mmol), tricyclohexylphosphine (21 mg, 0.07 mmol) and cesium carbonate (715 mg, 2.2 mmol) was degased and filled with $N_2$, then anhydrous dioxane (50 ml) was added. The mixture was heated at 100° C. overnight. The reaction mixture was cooled to room temperature and filtrated; the solid was washed with dichloromethane (200 mL). The filtrate was concentrated and purified by flash chromatography on silica gel using an ISCO Companion eluting with heptanes/ethyl acetate (30%) to provide an ester which was dissolved in dioxane (20 mL) and treated with 20% sodium hydroxide (80 mg, 2 mmol). The reaction was heated at 90° C. for 6 hours. The mixture was acidified with HCl solution to a pH 7.0 and concentrated. The residue was partitioned between ethyl acetate and water. The organic layer was dried over magnesium sulfate, filtered and concentrated to about 10 mL. The formed solid was collected by filtration, washed with 1:1 ethyl acetate/heptane, and dried under vacuum to afford the title compound. $^1$H NMR (400 MHz, DMSO-$d_6$) δ 1.64 (dtd, J=12.6, 10.0, 5.7 Hz, 1H), 2.00 (dt, J=12.3, 3.6 Hz, 1H), 2.20 (dd, J=24.6, 15.7 Hz, 2H), 2.28-2.46 (m, 3H), 4.69 (d, J=5.9 Hz, 2H), 6.49 (t, J=3.9 Hz, 1H), 6.85 (d, J=2.1 Hz, 1H), 7.25 (t, J=7.2 Hz, 1H), 7.28-7.44 (m, 3H), 7.50 (d, J=5.1 Hz, 1H), 7.87 (t, J=6.2 Hz, 1H), 8.06 (s, 1H), 8.21 (d, J=5.1 Hz, 1H), 8.40 (s, 1H). MS (ESI$^+$) m/z 426 (M+H)$^+$.

Example 362

4-{4-[6-(benzylamino)pyrazin-2-yl]-1H-pyrrolo[2,3-b]pyridin-2-yl}-N-methylcyclohex-3-ene-1-carboxamide To a solution of Example 361C (50 mg, 0.12 mmol) in anhydrous N,N-dimethylformamide (2 mL) was added methylamine HCl salt (13 mg, 1.8 mmol), 1-ethyl-3-[3-(dimethylamino)propyl]-carbodiimide hydrochloride (34 mg, 0.18 mmol), 1-hydroxybenzotriazolemonohydrate (27 mg, 0.18 mmol), and triethylamine (18 mg, 0.18 mmol). The reaction mixture was stirred at room temperature overnight. The mixture was purified by reverse-phase HPLC on Zorbax XDB C-18 (32) using a gradient of 5-40% acetonitrile/water (containing 0.1% trifluoroacetic acid) to afford the title compound as the trifluoroacetate salt. $^1$H NMR (400 MHz, DMSO-$d_6$) δ 1.59 (dt, J=11.8, 5.8 Hz, 1H), 1.87 (d, J=12.6 Hz, 1H), 2.13 (d, J=18.4 Hz, 1H), 2.30 (td, J=18.7, 17.7, 6.6 Hz, 4H), 2.61 (d, J=4.5 Hz, 3H), 4.69 (d, J=6.0 Hz, 2H), 6.49 (d, J=4.3 Hz, 1H), 6.85 (d, J=2.2 Hz, 1H), 7.25 (t, J=7.1 Hz, 1H), 7.36 (dt, J=14.9, 7.6 Hz, 3H), 7.50 (d, J=5.1 Hz, 1H), 7.79 (dt, J=18.2, 5.3 Hz, 1H), 8.04 (s, 1H), 8.21 (d, J=5.1 Hz, 1H), 8.40 (s, 1H). MS (DCl/NH$_3$) m/z 439 (M+H)$^+$.

Example 363

4-(4-{6-[(3-fluorobenzyl)amino]pyrazin-2-yl}-1H-pyrrolo[2,3-b]pyridin-2-yl)cyclohex-3-ene-1-carboxylic acid The title compound was prepared essentially as described in Example 361C, substituting 6-bromo-N-(3-fluorobenzyl)pyrazin-2-amine for N-benzyl-6-bromopyrazin-2-amine $^1$H NMR (500 MHz, DMSO-$d_6$) δ 1.65 (ddt, J=13.7, 6.9, 4.2 Hz, 1H), 1.97-2.06 (m, 1H), 2.10-2.27 (m, 2H), 2.32-2.48 (m, 2H), 2.51 (p, J=1.9 Hz, 1H), 4.71 (s, 2H), 6.59 (t, J=4.0 Hz, 1H), 6.89 (d, J=2.1 Hz, 1H), 7.03-7.16 (m, 1H), 7.18-7.28 (m, 1H), 7.39 (td, J=7.9, 6.1 Hz, 1H), 7.46-7.54 (m, 1H), 7.66 (d, J=5.5 Hz, 1H), 8.18 (s, 1H), 8.26 (d, J=5.5 Hz, 1H), 8.49 (s, 1H). MS (DCl/NH$_3$) m/z 444 (M+H)$^+$.

Example 364

4-(4-{6-[(3-fluorobenzyl)oxy]pyrazin-2-yl}-1H-pyrrolo[2,3-b]pyridin-2-yl)cyclohex-3-ene-1-carboxylic acid The title compound was prepared essentially as described in Example 361C, substituting 2-bromo-6-((3-fluorobenzyl)oxy)pyrazine for N-benzyl-6-bromopyrazin-2-amine $^1$H NMR (400 MHz, DMSO-$d_6$) δ 1.71 (tdd, J=10.1, 8.4, 6.8, 4.7 Hz, 1H), 1.94-2.15 (m, 1H), 2.28-2.63 (m, 7H), 5.62 (s, 2H), 6.58 (t, J=3.5 Hz, 1H), 6.94 (d, J=1.9 Hz, 1H), 7.19 (td, J=8.6, 2.5 Hz, 1H), 7.31-7.40 (m, 2H), 7.46 (td, J=8.0, 6.1 Hz, 1H), 7.65 (d, J=5.1 Hz, 1H), 8.29 (d, J=5.1 Hz, 1H), 8.46 (s, 1H), 8.97 (s, 1H). MS (DCl/NH$_3$) m/z 445 (M+H)$^+$.

Example 365

4-(4-{6-[(3-fluorobenzyl)oxy]pyrazin-2-yl}-1H-pyrrolo[2,3-b]pyridin-2-yl)-N-methylcyclohex-3-ene-1-carboxamide The title compound was prepared essentially as described in Example 362, substituting Example 364 (50 mg, 0.11 mmol) for Example 361C. $^1$H NMR (400 MHz, DMSO-$d_6$) δ 1.53-1.71 (m, 1H), 1.92 (d, J=12.6 Hz, 1H), 2.23-2.42 (m, 4H), 2.54 (d, J=5.6 Hz, 1H), 2.60 (d, J=4.5 Hz, 3H), 5.62 (s, 2H), 6.58 (d, J=4.6 Hz, 1H), 6.93 (d, J=2.0 Hz, 1H), 7.19 (td, J=8.7, 2.8 Hz, 1H), 7.31-7.42 (m, 2H), 7.44 (s, 1H), 7.65 (d, J=5.1 Hz, 1H), 7.79 (q, J=4.4 Hz, 1H), 8.29 (d, J=5.1 Hz, 1H), 8.46 (s, 1H), 8.98 (s, 1H). MS (DCl/NH$_3$) m/z 458 (M+H)$^+$.

Example 366

4-(4-{6-[(3-fluorobenzyl)oxy]pyrazin-2-yl}-1H-pyrrolo[2,3-b]pyridin-2-yl)cyclohex-3-ene-1-carboxamide The title compound was prepared essentially as described in Example 362, substituting Example 364 (50 mg, 0.11 mmol) for Example 361C and ammonium hydroxide for methylamine HCl salt. $^1$H NMR (400 MHz, DMSO-$d_6$) δ 1.63 (dd, J=12.5, 5.6 Hz, 1H), 1.86-2.01 (m, 1H), 2.35 (q, J=10.0, 5.8 Hz, 4H), 2.48-2.57 (m, 6H), 5.62 (s, 2H), 6.48-6.68 (m, 1H), 6.80 (s, 1H), 6.94 (d, J=2.0 Hz, 1H), 7.19 (td, J=8.9, 3.0 Hz, 1H), 7.27-7.41 (m, 1H), 7.46 (td, J=8.0, 5.9 Hz, 1H), 7.65 (d, J=5.1 Hz, 1H), 8.29 (d, J=5.1 Hz, 1H), 8.46 (s, 1H), 8.98 (s, 1H). MS (DCl/NH$_3$) m/z 444 (M+H)$^+$.

Example 367

4-(4-{6-[(3-fluorobenzyl)amino]pyrazin-2-yl}-1H-pyrrolo[2,3-b]pyridin-2-yl)cyclohex-3-ene-1-carboxamide The title compound was prepared essentially as described in Example 362, substituting Example 363 (80 mg, 0.18 mmol) for Example 361C and ammonium hydroxide for methanamine HCl salt. $^1$H NMR (400 MHz, DMSO-$d_6$) δ

1.58 (dt, J=12.3, 5.5 Hz, 1H), 1.85-1.95 (m, 1H), 2.16 (dd, J=12.2, 5.0 Hz, 1H), 2.19-2.41 (m, 4H), 4.70 (d, J=5.1 Hz, 2H), 6.50 (d, J=4.6 Hz, 1H), 7.08 (td, J=8.6, 2.7 Hz, 1H), 7.15-7.28 (m, 2H), 7.32 (s, 1H), 7.39 (td, J=7.9, 6.0 Hz, 1H), 7.51 (d, J=5.1 Hz, 1H), 8.07 (s, 1H), 8.22 (d, J=5.2 Hz, 1H), 8.43 (s, 1H). MS (DCI/NH$_3$) m/z 443 (M+H)$^+$.

Example 368

4-{4-[6-(benzylamino)pyrazin-2-yl]-1H-pyrrolo[2,3-b]pyridin-2-yl}cyclohex-3-ene-1-carboxamide The title compound was prepared essentially as described in Example 362, substituting ammonium hydroxide (20 mg, 0.6 mmol) for methanamine HCl salt. $^1$H NMR (400 MHz, DMSO-d$_6$) δ 1.48-1.65 (m, 1H), 1.84-1.99 (m, 1H), 2.09-2.22 (m, 1H), 2.23-2.43 (m, 4H), 4.69 (s, 2H), 6.51 (t, J=3.3 Hz, 1H), 6.89 (d, J=2.0 Hz, 1H), 7.20-7.29 (m, 1H), 7.29-7.43 (m, 4H), 7.56 (d, J=5.2 Hz, 1H), 8.07 (s, 1H), 8.24 (d, J=5.3 Hz, 1H), 8.43 (s, 1H). MS (DCI/NH$_3$) m/z 425 (M+H)$^+$.

Example 369 tert-butyl {4-[4-(5-fluoro-2-methoxyphenyl)-1H-pyrrolo[2,3-b]pyridin-2-yl]-3,6-dihydropyridin-1(2H)-yl}acetate Example 369A 4-bromo-1-tosyl-1H-pyrrolo[2,3-b]pyridine To a suspension of 4-bromo-1H-pyrrolo[2,3-b]pyridine (15 g, 76 mmol) and p-toluenesulfonyl chloride (21.77 g, 114 mmol) in toluene (200 mL) was added a solution of tetrabutylammonium hydrogen sulfate (2.58 g, 7.61 mmol) in water (10 mL) and the mixture was cooled to 0° C. A solution of sodium hydroxide (9.13 g, 228 mmol) in water (30 mL) was added and the mixture was stirred at room temperature overnight. The mixture was diluted with ethyl acetate and the solution was washed with saturated sodium chloride. The organic layer was dried over sodium sulfate, filtered and concentrated to give the title compound. MS (CI) m/z 352 (M+H)$^+$.

Example 369B 4-bromo-2-iodo-1-tosyl-1H-pyrrolo[2,3-b]pyridine

To a solution of Example 369A (25 g, 71.2 mmol) in tetrahydrofuran (600 mL) at −78° C. was slowly added 2M lithium diisopropylamide in heptane/tetrahydrofuran/ethylbenzene (39.1 mL, 78 mmol) and the mixture was stirred at −78° C. for 1 hour. A solution of iodine (19.87 g, 78 mmol) in tetrahydrofuran (100 mL) was added slowly and the reaction was allowed to warm to room temperature gradually. The reaction mixture was stirred at room temperature for 3 hours and was quenched with saturated aqueous sodium thiosulfate, water and ethyl acetate. The aqueous layer was extracted with ethyl acetate and the combined organics were dried over sodium sulfate, filtered and concentrated to give the title compound. MS (CI) m/z 477 (M+H)$^+$.

Example 369C tert-butyl 4-(4-bromo-1-tosyl-1H-pyrrolo[2,3-b]pyridin-2-yl)-5,6-dihydropyridine-1(2H)-carboxylate To as solution of Example 369B (20 g, 41.9 mmol), tert-butyl 4-(4,4,5,5-tetramethyl-1,3,2-dioxaborolan-2-yl)-5,6-dihydropyridine-1(2H)-carboxylate (16.85 g, 54.5 mmol), and tetrakis(triphenylphosphine)palladium (4.84 g, 4.19 mmol) in N,N-dimethylformamide (500 mL) was added a solution of sodium bicarbonate (7.04 g, 84 mmol) in water (40 mL) and the mixture was stirred at 80° C. for 12 hours. The reaction was quenched by the addition of saturated aqueous sodium thiosulfate, water and ethyl acetate. The aqueous layer was extracted with ethyl acetate and the combined organics were dried over sodium sulfate, filtered and concentrated to provide the title compound. MS (CI) m/z 532 (M+H)$^+$.

Example 369D tert-butyl 4-(4-(4,4,5,5-tetramethyl-1,3,2-dioxaborolan-2-yl)-1-tosyl-1H-pyrrolo[2,3-b]pyridin-2-yl)-5,6-dihydropyridine-1(2H)-carboxylate A mixture of potassium acetate (5.53 g, 56.3 mmol), 1,1'-bis(diphenylphosphino)ferrocene-palladium(II)dichloride dichloromethane complex (0.920 g, 1.127 mmol), bis(pinacolato)diboron (11.92 g, 47.0 mmol), and Example 369C (10 g, 18.78 mmol) in 1,2-dimethoxyethane (200 mL) was stirred at 80° C. for 6 hours. The reaction mixture was diluted with water. The aqueous layer was extracted with ethyl acetate (3×200 mL). The combined organic layers were washed with H$_2$O and brine, dried with Na$_2$SO$_4$, filtered, concentrated, and recrystallized in 100 mL of ethyl acetate/petroleum ether (1:4) to give the title compound. MS (ESI$^+$) m/z 580.3 (M+H)$^+$.

Example 369E tert-butyl 4-(4-(6-(methylcarbamoyl)pyridin-3-yl)-1-tosyl-1H-pyrrolo[2,3-b]pyridin-2-yl)-5,6-dihydropyridine-1(2H)-carboxylate A mixture of Example 369D (1.700 g, 2.93 mmol), 5-bromo-N-methylpicolinamide (0.757 g, 3.52 mmol), 1,1'-bis(diphenylphosphino)ferrocene-palladium(II)dichloride dichloromethane complex (0.096 g, 0.117 mmol), and saturated sodium bicarbonate solution (10 mL, 2.93 mmol) in N,N-dimethylformamide (40 mL) was degassed and heated at 80° C. for 2 hours. The reaction mixture was filtered, treated with water and brine and extracted twice with ethyl acetate. The combined organic layers were washed with water, dried over MgSO$_4$, filtered, concentrated, and purified on an 80 g silica column using the ISCO Companion flash system eluting with heptanes/ethyl acetate (3:7 to 2:8) to give the title compound. MS (ESI$^+$) m/z 588.1 (M+H)$^+$.

Example 369F

A mixture of Example 369E (0.890 g, 1.514 mmol) and 5M sodium hydroxide (1.363 mL, 6.81 mmol) solution in dioxane (10 mL) was heated at 90° C. for 8 hours. The reaction mixture was slowly cooled while stirring was continued. Precipitate formed and the mixture was diluted with water (30 mL). The suspension was stirred for 30 minutes, filtered, washed with water, and vacuum oven-dried to give the title compound. MS (ESI$^+$) m/z 434.1 (M+H)$^+$.

Example 369G tert-butyl {4-[4-(5-fluoro-2-methoxyphenyl)-1H-pyrrolo[2,3-b]pyridin-2-yl]-3,6-dihydropyridin-1(2H)-yl}acetate A suspension of Example 369F (0.590 g, 1.361 mmol) in CH$_2$Cl$_2$ (10 mL) was treated with trifluoroacetic acid (1.258 mL, 16.33 mmol). The mixture was stirred at 35° C. for 6 hours and concentrated. The residue was suspended in 5 mL of methanol and treated with 5 mL of 2M HCl in ether slowly. The suspension was diluted with ether and stirred for 10 minutes. The solids were filtered, washed with ether, and vacuum oven-dried to give the title compound as HCl salt. $^1$H NMR (400 MHz, CD$_3$OD) δ 2.91-2.97 (m, 2H), 3.02 (s, 3H), 3.53 (t, J=6.1 Hz, 2H), 3.99-4.04 (m, 2H), 6.68-6.74 (m, 1H), 7.12 (s, 1H), 7.79 (d, J=6.2 Hz, 1H), 8.35 (d, J=8.1 Hz, 1H), 8.46-8.53 (m, 2H), 9.12 (d, J=2.2 Hz, 1H). MS (ESI$^+$) m/z 334.1 (M+H)$^+$.

BIOLOGICAL EXAMPLES

CDK9 Enzyme Protocol

CDK9 enzyme activities were measured using LANCE ULight TR-FRET kinase assay reagents (PerkinElmer, Waltham, Mass.). Compounds were diluted in 100% DMSO then diluted with 1:10 in serine/threonine kinase assay buffer containing 20 mM HEPES, 10 mM MgCl$_2$, 100 mM Na$_3$VO$_4$, and 0.0075% Triton X-100. Equal volume of the compound dilutions was added to a final reaction mixture containing LANCE detection buffer (PerkinElmer CR97-100), 100 nM ULight MBP (PerkinElmer TRF0109M), 1000 μM ATP, and CDK9/Cyclin T1 (Carna Biosciences 04-110). The kinase reaction was carried out for 1 hour before addition of stopping buffer to a final of 20 mM EDTA and 0.5 nM of LANCE Ultra Europium anti-phospho-MBP antibody (PerkinElmer TRF0201M) in LANCE detection buffer. The reaction was incubated for 1 hour and the signal was read in Envision in TR-FRET mode (excitation at 320 nm and emission at 615/665 nm).

CDK9 Enzyme Protocol

CDK9 enzyme activities were measured using LANCE ULight TR-FRET kinase assay reagents (PerkinElmer, Waltham, Mass.). Compounds were directly added in 100% DMSO to white low volume assay plates (Perkin Elmer Proxiplate 6008289) using a Labcyte Echo acoustic dispenser. Assay reagents in serine/threonine kinase assay buffer containing 20 mM HEPES, 10 mM MgCl$_2$, 100 mM Na$_3$VO$_4$, and 0.0075% Triton X-100. were added for final reaction mixture concentrations of 1000 μM ATP, 100 nM U-light MBP peptide (Perkin Elmer TRF0109M) and reaction initiated with 4 nM CDK9/Cyclin T1 (Carna Biosciences 04-110). The kinase reaction was carried out for 30 minutes before addition of stopping buffer to a final of 20 mM EDTA and 0.5 nM of LANCE Ultra Europium anti-phospho-MBP antibody (PerkinElmer TRF0201M) in LANCE detection buffer (PerkinElmer CR97-100). The reaction was equilibrated for 1 hour and the signal read in the Perkin Elmer Envision in TR-FRET mode (excitation at 320 nm and emission at 615/665 nm).

Cell Viability Protocol

Cell viability assays were performed using A431 or H929 cells. A431 cells were seeded in 96-well plates at 10,000 cells/well and, after overnight incubation, treated with compounds at 2-times the final concentration to result in a dose response of 3-fold dilutions from 10 μM to 0.0005 μM (50 μL/well, 0.1% final DMSO concentration). H929 cells were seeded in 96-well plates at 10,000 cells/well and treated immediately with compounds as described above. After 24 hours at 37° C., cell viability was measured Cell TiterGlo reagent (Promega) with a luminescence reader. Alternately, cell viability assays were performed in 384-well format. A431 cells were seeded in 384-well plates at 2500 cells/well and, after overnight incubation, treated with compounds in a dose response of 3-fold dilutions from 10 μM to 0.0005 μM (25 nL/well, 0.1% final DMSO concentration). For the H929 viability assay, 25 nL/well of the compounds was dispensed into 384-well plates in a dose response as described above and cells were immediately seeded in 384-well plates at 2500 cells/well. After 24 hours at 37° C., cell viability was measured using Cell TiterGlo reagent (Promega) with a luminescence reader. The results are reported in Table 1.

In-Cell Western

In-cell Western assays were used to measure phosphorylation of RNA polymerase II C-terminal domain Ser2. A431 cells were seeded in 96-well black plates at 15,000 cells/well, 50 μL/well and, after overnight incubation, treated with compounds at 2-times the final concentration to result in a dose response of 3-fold dilutions from 10 μM to 0.0005 μM. After 4 hours, cells were washed with PBS and fixed at room temperature for 1 hour with 4% paraformaldehyde in PBS. Cells were washed with PBST (PBS with 0.1% Triton X100), blocked in 5% BSA in 1×PBST, and incubated with rabbit anti-RNA Polymerase II CTD phosphorylated Ser 2 (Bethyl) overnight at 4° C. Cells were then washed with Delfia/Autodelfia wash buffer and incubated for 2 hours at room temperature in the dark with Delfia Eu-N1 anti-rabbit antibody diluted in Delfia Assay Buffer. Cells were washed with Delfia/Autodelfia wash buffer, incubated for 20 minutes at room temperature in the dark with Delfia Enhancement solution, and the plate was read at the Europium settings on a Victor plate reader. The Delfia signal was normalized for cell density using Hoechst staining.

Alternate In-Cell Western Protocol

In-cell Western assays were used to measure phosphorylation of RNA polymerase II C-terminal domain Ser2. A431 cells were seeded in 96-well black walled Viewplates (Perkin Elmer) at 10,000 cells/well 50 μl per well and, after overnight incubation, treated with compounds at 2 times the final concentration to result in a final dose response of 3-fold dilutions from 10 μM to 0.0005 μM. After 4 hours, cells were fixed at room temperature for 10 minutes with the addition of 100 μl of 4% paraformaldehyde in PBS. Cells were washed with PBST, blocked in 1% BSA in 1×PBST for 30 minutes, and incubated with rabbit anti-RNA Polymerase II CTD phosphorylated Ser 2 (Bethyl) overnight at 4° C. Cells were then washed with Delfia/Autodelfia wash buffer and incubated for 1 hour at room temperature in the dark with Alexa Fluor 488 conjugated goat anti-rabbit antibody and Hoechst (Invitrogen) diluted in blocking buffer. Cells were washed with Delfia/Autodelfia wash buffer, followed by the addition of 200 μl of PBS. The plates were read on a CellInsight high content instrument (Thermo Scientific). The Alexa Fluor 488 signal was normalized for by subtracting background staining and collecting images from 400 cells. The In-cell Western (ICW) IC$_{50}$ values are reported in Table 1.

TABLE 1

| EXAMPLE | CDK9/Cyclin T1 IC$_{50}$ (μM) | Cell Viability A-431 IC$_{50}$ (μM) | Cell Viability H929 IC$_{50}$ (μM) | ICW IC$_{50}$ (μM) |
|---|---|---|---|---|
| 1 | 0.016 | 0.089 | 0.28 | 0.085 |
| 2 | 0.022 | 0.18 | 0.17 | 0.22 |
| 3 | 0.023 | 0.11 | ND | 0.2 |
| 4 | 0.015 | 0.04 | ND | 0.076 |
| 5 | 6.9 | ND | ND | ND |
| 6 | >12.5 | >10 | ND | ND |
| 7 | 4.7 | ND | ND | ND |
| 8 | 0.049 | 0.3 | 1.08 | 0.47 |

TABLE 1-continued

| EXAMPLE | CDK9/Cyclin T1 IC$_{50}$ (μM) | Cell Viability A-431 IC$_{50}$ (μM) | Cell Viability H929 IC$_{50}$ (μM) | ICW IC$_{50}$ (μM) |
|---|---|---|---|---|
| 9 | 0.035 | 0.17 | ND | 0.26 |
| 10 | 0.32 | 1 | ND | ND |
| 11 | 0.033 | 0.041 | 0.32 | 0.26 |
| 12 | 0.093 | ND | ND | ND |
| 13 | 0.13 | ND | ND | ND |
| 14 | 0.49 | 0.96 | ND | ND |
| 15 | 1.4 | 3.3 | ND | ND |
| 16 | 0.77 | 0.33 | ND | ND |
| 17 | 0.011 | 0.022 | 0.16 | 0.02 |
| 18 | 0.019 | 0.052 | ND | 0.052 |
| 19 | 0.019 | 0.076 | ND | 0.32 |
| 20 | 0.031 | 0.12 | ND | 0.52 |
| 21 | 6.6 | ND | ND | ND |
| 22 | 0.012 | 0.15 | ND | 0.076 |
| 23 | 0.077 | 0.45 | ND | 2.7 |
| 24 | 0.068 | 0.55 | ND | 1.6 |
| 25 | 0.3 | ND | ND | ND |
| 26 | 0.077 | ND | ND | ND |
| 27 | 0.027 | 0.2 | ND | 0.039 |
| 28 | 0.017 | 0.064 | 0.18 | 0.052 |
| 29 | 0.023 | 0.12 | ND | 0.074 |
| 30 | 0.12 | ND | ND | ND |
| 31 | 2.6 | ND | ND | ND |
| 32 | 0.021 | 0.025 | 0.077 | 0.17 |
| 33 | 0.015 | 0.016 | ND | 0.035 |
| 34 | 0.018 | 0.1 | ND | 0.66 |
| 35 | 0.021 | 0.14 | ND | 0.36 |
| 36 | 0.017 | 0.085 | ND | 0.17 |
| 37 | 0.01 | 0.19 | ND | 0.14 |
| 38 | 0.033 | 0.3 | ND | 0.45 |
| 39 | 0.019 | 0.035 | ND | 0.03 |
| 40 | 0.025 | 0.28 | ND | 0.15 |
| 41 | 0.06 | 7.2 | ND | >10 |
| 42 | 0.55 | ND | ND | ND |
| 43 | 0.17 | ND | ND | ND |
| 44 | 5.1 | ND | ND | ND |
| 45 | 19 | ND | ND | ND |
| 46 | 0.021 | 0.14 | ND | 0.76 |
| 47 | 0.048 | 1.1 | 0.64 | 0.89 |
| 48 | 0.081 | 4.8 | ND | 4.3 |
| 49 | 0.087 | 0.28 | ND | 0.74 |
| 50 | 0.57 | ND | ND | ND |
| 51 | 0.049 | 0.011 | 0.053 | 0.027 |
| 52 | 0.014 | 0.049 | ND | 0.085 |
| 53 | 0.025 | 0.46 | ND | 0.15 |
| 54 | 0.019 | 0.11 | ND | 0.11 |
| 55 | 0.049 | 2.1 | ND | 4.1 |
| 56 | 0.015 | 0.24 | ND | 0.19 |
| 57 | 0.015 | 0.019 | ND | 0.024 |
| 58 | 0.024 | 1.1 | ND | 0.89 |
| 59 | 0.017 | 0.075 | 0.2 | 0.042 |
| 60 | 0.025 | 0.12 | ND | 0.26 |
| 61 | 0.023 | 0.13 | ND | 0.27 |
| 62 | 0.015 | 0.048 | ND | 0.045 |
| 63 | 0.022 | 0.042 | ND | 0.06 |
| 64 | 0.025 | 0.089 | ND | 0.13 |
| 65 | 0.2 | ND | ND | ND |
| 66 | 0.042 | 0.65 | 0.51 | 0.54 |
| 67 | 0.037 | 0.63 | ND | 0.23 |
| 68 | 0.51 | ND | ND | ND |
| 69 | 0.25 | ND | ND | ND |
| 70 | 0.065 | 0.66 | ND | 0.48 |
| 71 | 0.063 | 0.76 | ND | 0.66 |
| 72 | 0.36 | ND | ND | ND |
| 73 | 0.12 | ND | ND | ND |
| 74 | 0.024 | 0.61 | 0.38 | 0.3 |
| 75 | 0.023 | 0.76 | ND | 0.52 |
| 76 | 0.017 | 0.089 | ND | 0.17 |
| 77 | 0.025 | 0.18 | ND | 0.14 |
| 78 | 0.063 | 0.32 | ND | 0.42 |
| 79 | 0.84 | 0.52 | ND | ND |
| 80 | 0.039 | 0.68 | 0.56 | 0.34 |
| 81 | 0.64 | 0.3 | ND | ND |
| 82 | 0.18 | ND | ND | ND |
| 83 | 1.3 | 3.3 | ND | ND |
| 84 | 0.6 | 0.89 | ND | ND |
| 85 | 0.1 | ND | ND | ND |
| 86 | 0.12 | ND | ND | ND |
| 87 | 0.01 | 0.014 | 0.034 | 0.025 |
| 88 | 0.03 | ND | 1 | ND |
| 89 | 0.034 | 0.15 | 0.39 | 0.16 |
| 90 | 0.035 | ND | 3.4 | ND |
| 91 | 0.029 | ND | 0.51 | ND |
| 92 | 0.051 | ND | 0.91 | ND |
| 93 | 0.034 | ND | 0.53 | ND |
| 94 | 0.58 | ND | ND | ND |
| 95 | 0.15 | ND | 1.1 | ND |
| 96 | 0.05 | 0.71 | 0.7 | 0.44 |
| 97 | 0.014 | 0.046 | 0.15 | 0.1 |
| 98 | 0.27 | ND | 4.1 | ND |
| 99 | 1.3 | ND | ND | ND |
| 100 | 0.033 | 0.09 | 0.11 | 0.033 |
| 101 | 0.036 | 0.055 | 0.13 | 0.072 |
| 102 | 0.012 | ND | 0.16 | ND |
| 103 | 0.43 | ND | ND | ND |
| 104 | 0.044 | ND | 1.5 | ND |
| 105 | 0.013 | ND | 0.36 | ND |
| 106 | 0.18 | ND | 3.7 | ND |
| 107 | 0.036 | ND | 2.1 | ND |
| 108 | 0.074 | ND | 0.79 | ND |
| 109 | 0.044 | ND | 0.55 | ND |
| 110 | 0.044 | ND | 1 | ND |
| 111 | 0.038 | ND | 0.72 | ND |
| 112 | 0.014 | ND | 0.79 | ND |
| 113 | 0.023 | ND | 1.1 | ND |
| 114 | 0.036 | ND | 0.76 | ND |
| 115 | 0.029 | ND | 1 | ND |
| 116 | 0.1 | ND | 3 | ND |
| 117 | 0.061 | ND | 0.89 | ND |
| 118 | 0.043 | ND | 0.86 | ND |
| 119 | 0.037 | 0.089 | 0.13 | 0.16 |
| 120 | 0.022 | 0.1 | 0.19 | 0.11 |
| 121 | 0.034 | ND | 0.26 | ND |
| 122 | 0.04 | ND | 0.29 | ND |
| 123 | 0.028 | ND | 0.79 | ND |
| 124 | 0.039 | ND | 1.1 | ND |
| 125 | 0.046 | ND | 2 | ND |
| 126 | 0.075 | ND | 0.9 | ND |
| 127 | 0.023 | ND | 1.2 | ND |
| 128 | 0.021 | ND | 1.4 | ND |
| 129 | 0.014 | ND | 1.8 | ND |
| 130 | 0.05 | ND | 1.2 | ND |
| 131 | 0.064 | ND | 2.3 | ND |
| 132 | 0.13 | ND | 2.7 | ND |
| 133 | 1.5 | ND | ND | ND |
| 134 | 0.12 | ND | 1.4 | ND |
| 135 | 0.044 | ND | 0.65 | ND |
| 136 | 0.023 | 0.29 | 0.23 | 0.14 |
| 137 | 0.039 | ND | 1.1 | ND |
| 138 | 0.033 | ND | 1.2 | ND |
| 139 | 0.12 | ND | 3.9 | ND |
| 140 | 0.02 | ND | 0.57 | ND |
| 141 | 0.024 | ND | 0.74 | ND |
| 142 | 0.069 | ND | 1.3 | ND |
| 143 | 0.32 | ND | >10 | ND |
| 144 | 0.37 | ND | ND | ND |
| 145 | 0.029 | ND | 2.6 | ND |
| 146 | 0.012 | ND | 0.6 | ND |
| 147 | 0.031 | ND | 1.27 | ND |
| 148 | 0.021 | ND | 0.77 | ND |
| 149 | 0.021 | 0.028 | 0.13 | 0.098 |
| 150 | 0.017 | ND | 1.3 | ND |
| 151 | 0.34 | ND | 4 | ND |
| 152 | 0.096 | ND | <3.3 | ND |
| 153 | 0.047 | ND | 1.1 | ND |
| 154 | 0.15 | ND | 0.47 | ND |
| 155 | 0.051 | 0.046 | 0.25 | 0.11 |
| 156 | 0.015 | ND | 0.96 | ND |

TABLE 1-continued

| EXAMPLE | CDK9/Cyclin T1 IC$_{50}$ (µM) | Cell Viability A-431 IC$_{50}$ (µM) | Cell Viability H929 IC$_{50}$ (µM) | ICW IC$_{50}$ (µM) |
|---|---|---|---|---|
| 157 | 0.049 | ND | 2.4 | ND |
| 158 | 0.091 | ND | 4.2 | ND |
| 159 | 0.086 | ND | 0.62 | ND |
| 160 | 0.041 | 0.054 | 0.19 | 0.18 |
| 161 | 0.045 | 0.089 | 0.22 | 0.21 |
| 162 | 0.028 | ND | 0.49 | ND |
| 163 | 0.11 | ND | 2.9 | ND |
| 164 | 0.03 | ND | 1.8 | ND |
| 165 | 0.45 | 8.53 | 10 | >10 |
| 166 | 0.27 | ND | 3.8 | ND |
| 167 | 0.073 | ND | 1.5 | ND |
| 168 | 0.16 | ND | 3 | ND |
| 169 | 0.034 | ND | 0.76 | ND |
| 170 | 0.29 | ND | 5 | ND |
| 171 | 0.09 | ND | ND | ND |
| 172 | 0.076 | ND | 1.4 | ND |
| 173 | 0.075 | ND | 2.6 | ND |
| 174 | 0.025 | ND | 2.1 | ND |
| 175 | 0.1 | ND | 6.1 | ND |
| 176 | 0.035 | ND | 0.63 | ND |
| 177 | 0.055 | ND | 1.1 | ND |
| 178 | 0.078 | ND | 3.2 | ND |
| 179 | 0.052 | ND | 0.66 | ND |
| 180 | 0.023 | ND | 0.71 | ND |
| 181 | 0.019 | ND | 0.73 | ND |
| 182 | 0.022 | ND | 0.47 | ND |
| 183 | 0.022 | ND | 0.54 | ND |
| 184 | 0.03 | ND | 0.8 | ND |
| 185 | 0.14 | ND | 2.2 | ND |
| 186 | 0.004 | 0.017 | 0.047 | 0.026 |
| 187 | 0.067 | ND | 3.4 | ND |
| 188 | 0.046 | 0.068 | 0.28 | 0.15 |
| 189 | 0.023 | 0.007 | 0.061 | 0.016 |
| 190 | 0.008 | 0.021 | 0.057 | 0.044 |
| 191 | 0.025 | 0.055 | 0.25 | 0.077 |
| 192 | 0.81 | ND | ND | ND |
| 193 | 0.033 | 0.063 | 0.71 | 0.089 |
| 194 | ND | ND | ND | ND |
| 195 | 0.033 | 0.037 | 0.057 | 0.04 |
| 196 | 0.91 | ND | ND | ND |
| 197 | 0.73 | ND | ND | ND |
| 198 | 0.16 | ND | 7.27 | ND |
| 199 | 0.029 | 0.13 | 0.16 | 0.14 |
| 200 | 0.055 | 1.31 | 1.4 | 1.1 |
| 201 | 0.026 | 0.093 | 0.14 | 0.063 |
| 202 | 0.02 | 0.19 | 0.28 | 0.37 |
| 203 | 0.008 | 0.047 | 0.11 | 0.052 |
| 204 | 0.027 | 0.56 | 0.57 | 0.2 |
| 205 | 0.023 | 0.52 | 0.33 | 0.28 |
| 206 | 0.011 | 0.12 | 0.18 | 0.093 |
| 207 | 0.066 | 1.36 | 0.82 | ND |
| 208 | 0.043 | 0.063 | ND | 0.17 |
| 209 | 0.08 | 0.17 | ND | 0.29 |
| 210 | 0.017 | 0.024 | ND | 0.079 |
| 211 | 0.018 | 0.1 | ND | 0.033 |
| 212 | 0.021 | 0.048 | ND | 0.036 |
| 213 | 0.025 | 0.029 | ND | 0.093 |
| 214 | 0.021 | 0.021 | ND | 0.027 |
| 215 | 0.019 | 0.025 | 0.074 | 0.059 |
| 216 | 0.03 | 0.02 | 0.059 | 0.12 |
| 217 | 0.056 | 0.011 | 0.02 | ND |
| 218 | 0.064 | 0.07 | 0.066 | ND |
| 219 | 0.062 | 1.61 | 1.15 | 1.79 |
| 220 | 0.053 | ND | 0.463 | ND |
| 221 | 0.021 | 0.026 | 0.044 | ND |
| 222 | 0.084 | ND | 0.48 | ND |
| 223 | 0.038 | ND | 0.316 | ND |
| 224 | 0.039 | 0.053 | 0.151 | 0.028 |
| 225 | 0.037 | 0.044 | 0.073 | 0.123 |
| 226 | 0.033 | 0.187 | 0.243 | 0.087 |
| 227 | 0.028 | 0.13 | 0.2 | 0.105 |
| 228 | 0.019 | 0.145 | 0.206 | 0.47 |
| 229 | 0.101 | 0.096 | 0.105 | 0.244 |
| 230 | 0.022 | 0.046 | 0.148 | 0.176 |
| 231 | 0.045 | 0.015 | 0.073 | 0.03 |
| 232 | 0.023 | 0.018 | 0.059 | 0.108 |
| 233 | 0.114 | 0.056 | 0.084 | 0.073 |
| 234 | 0.047 | 0.139 | 0.098 | 0.154 |
| 235 | 0.038 | 0.046 | 0.06 | 0.035 |
| 236 | 0.126 | 0.07 | 0.057 | 0.124 |
| 237 | 0.13 | 0.162 | 0.105 | 0.333 |
| 238 | 0.062 | 0.213 | 0.212 | 0.177 |
| 239 | 0.053 | 0.038 | 0.026 | 0.032 |
| 240 | 0.056 | ND | 0.1 | ND |
| 241 | 0.08 | 0.333 | 0.076 | 0.371 |
| 242 | 0.07 | 1.83 | 0.341 | 1.32 |
| 243 | 0.027 | 0.077 | 0.045 | 0.17 |
| 244 | 0.118 | ND | 0.195 | ND |
| 245 | 0.032 | 0.127 | 0.089 | 0.09 |
| 246 | 0.039 | 0.139 | 0.094 | 0.12 |
| 247 | 0.045 | ND | 0.01 | ND |
| 248 | 0.023 | 0.025 | 0.014 | 0.035 |
| 249 | 0.028 | 0.031 | 0.019 | 0.048 |
| 250 | 0.047 | ND | 0.303 | ND |
| 251 | 0.056 | 0.024 | 0.029 | 0.022 |
| 252 | 0.045 | 0.176 | 0.119 | 0.092 |
| 253 | 0.077 | ND | 0.156 | ND |
| 254 | 0.095 | 0.054 | 0.048 | 0.091 |
| 255 | 0.09 | ND | 0.02 | ND |
| 256 | 0.045 | 0.041 | 0.029 | 0.056 |
| 257 | 0.082 | ND | 0.083 | ND |
| 258 | 0.085 | ND | 0.238 | ND |
| 259 | 0.102 | ND | 0.051 | ND |
| 260 | 0.111 | ND | 0.156 | ND |
| 261 | 0.093 | ND | 0.322 | ND |
| 262 | 0.091 | 0.138 | 0.138 | 0.168 |
| 263 | 0.101 | 0.014 | 0.015 | 0.029 |
| 264 | 0.07 | 0.028 | 0.026 | 0.043 |
| 265 | 0.049 | 0.014 | 0.017 | 0.034 |
| 266 | 0.085 | 0.016 | 0.012 | 0.046 |
| 267 | 0.135 | 0.141 | 0.049 | 0.184 |
| 268 | 0.149 | 0.119 | 0.037 | 0.199 |
| 269 | 0.115 | 0.182 | 0.144 | 0.156 |
| 270 | 0.082 | 0.242 | 0.133 | 0.172 |
| 271 | 0.104 | 0.39 | 0.252 | 0.555 |
| 272 | 0.122 | ND | 0.373 | ND |
| 273 | 0.081 | 0.09 | 0.023 | 0.041 |
| 274 | 0.078 | 0.055 | 0.044 | 0.055 |
| 275 | 0.09 | 0.043 | 0.041 | 0.088 |
| 276 | 0.066 | 0.05 | 0.023 | 0.03 |
| 277 | 0.087 | 0.083 | 0.057 | 0.198 |
| 278 | 0.086 | 0.126 | 0.117 | 0.305 |
| 279 | 0.124 | 0.707 | 0.433 | 1.09 |
| 280 | 0.071 | 0.037 | 0.03 | 0.106 |
| 281 | 0.077 | 0.036 | 0.03 | 0.161 |
| 282 | 0.117 | 0.028 | 0.032 | 0.088 |
| 283 | 0.172 | 0.093 | 0.057 | 0.18 |
| 284 | 0.071 | 0.024 | 0.019 | 0.105 |
| 285 | 0.093 | 0.069 | 0.072 | 0.144 |
| 286 | 0.201 | 0.014 | 0.023 | 0.047 |
| 287 | 0.104 | 0.043 | 0.051 | 0.101 |
| 288 | 0.071 | ND | 0.099 | ND |
| 289 | 0.057 | 0.229 | 0.111 | 0.379 |
| 290 | 0.078 | 0.046 | 0.035 | 0.113 |
| 291 | 0.093 | 0.06 | 0.055 | 0.196 |
| 292 | 0.139 | 0.236 | 0.129 | 0.277 |
| 293 | 0.07 | 0.117 | 0.096 | 0.241 |
| 294 | 0.042 | 0.118 | 0.131 | 0.176 |
| 295 | 0.119 | ND | 0.183 | ND |
| 296 | 0.125 | ND | 0.196 | ND |
| 297 | 0.083 | 0.042 | 0.042 | 0.06 |
| 298 | 0.099 | 0.093 | 0.059 | 0.302 |
| 299 | 0.083 | 0.298 | 0.206 | 0.142 |
| 300 | 0.115 | 0.063 | 0.081 | 0.164 |
| 301 | 0.12 | 0.043 | 0.057 | 0.083 |
| 302 | 0.09 | 0.013 | 0.027 | 0.024 |
| 303 | 0.138 | 0.294 | 0.194 | 0.421 |
| 304 | 0.131 | ND | 0.254 | ND |

TABLE 1-continued

| EXAMPLE | CDK9/Cyclin T1 IC$_{50}$ (μM) | Cell Viability A-431 IC$_{50}$ (μM) | Cell Viability H929 IC$_{50}$ (μM) | ICW IC$_{50}$ (μM) |
|---|---|---|---|---|
| 305 | 0.061 | ND | 0.064 | ND |
| 306 | 0.114 | ND | 0.032 | ND |
| 307 | 0.015 | ND | 0.16 | ND |
| 308 | 0.009 | ND | 0.39 | ND |
| 309 | 0.24 | ND | 1 | ND |
| 310 | 0.25 | ND | 3.1 | ND |
| 311 | 0.17 | ND | 1.1 | ND |
| 312 | 0.49 | ND | ND | ND |
| 313 | 0.26 | ND | 0.96 | ND |
| 314 | 0.015 | ND | 0.64 | ND |
| 315 | 0.005 | 0.004 | 0.047 | ND |
| 316 | 0.031 | ND | 0.27 | ND |
| 317 | 0.005 | 0.002 | 0.039 | 0.003 |
| 318 | 0.01 | 0.004 | 0.059 | 0.008 |
| 319 | 0.029 | 0.080 | 0.082 | 0.20 |
| 320 | 0.036 | ND | 0.12 | ND |
| 321 | 0.009 | 0.005 | 0.037 | 0.021 |
| 322 | 0.031 | ND | 0.042 | ND |
| 323 | 0.011 | ND | 0.076 | ND |
| 324 | 0.04 | ND | 0.12 | ND |
| 325 | 0.62 | ND | ND | ND |
| 326 | 0.01 | ND | 0.053 | ND |
| 327 | 0.03 | ND | 0.12 | ND |
| 328 | 0.028 | ND | 0.11 | ND |
| 329 | 0.015 | 0.77 | 0.83 | ND |
| 330 | 2.6 | ND | ND | ND |
| 331 | 0.012 | ND | 0.12 | ND |
| 332 | 0.014 | ND | 0.011 | ND |
| 333 | 0.021 | ND | 0.11 | ND |
| 334 | 0.013 | 0.023 | 0.025 | 0.10 |
| 335 | 0.015 | ND | 0.031 | ND |
| 336 | 0.027 | 0.13 | 0.061 | 0.26 |
| 337 | 0.011 | 0.044 | 0.089 | 0.12 |
| 338 | 0.014 | 0.42 | 0.42 | ND |
| 339 | 0.035 | ND | 0.13 | ND |
| 340 | 0.019 | 0.097 | 0.1 | 0.26 |
| 341 | 0.06 | ND | 0.19 | ND |
| 342 | 0.024 | ND | 0.3 | ND |
| 343 | 0.045 | ND | 0.13 | ND |
| 344 | 0.023 | 0.011 | 0.021 | 0.030 |
| 345 | 0.009 | ND | 0.014 | ND |
| 346 | 0.014 | ND | 0.010 | ND |
| 347 | 0.007 | ND | 0.040 | ND |
| 348 | 0.017 | 0.035 | 0.010 | 0.038 |
| 349 | 0.041 | ND | 0.19 | ND |
| 350 | 0.043 | ND | 0.20 | ND |
| 351 | 0.081 | ND | 1.4 | ND |
| 352 | 0.066 | ND | 1.1 | ND |
| 353 | 0.009 | 0.013 | 0.006 | 0.017 |
| 354 | 0.008 | 0.085 | 0.097 | 0.13 |
| 355 | 0.002 | ND | 0.056 | ND |
| 356 | 0.002 | 0.031 | 0.049 | 0.039 |
| 357 | 0.002 | 0.026 | 0.024 | 0.044 |
| 358 | 0.11 | ND | 1.2 | ND |
| 359 | 0.01 | ND | 0.35 | ND |
| 360 | 0.006 | ND | 0.43 | ND |
| 361 | 0.021 | ND | 1.5 | ND |
| 362 | 0.011 | 0.045 | 0.036 | 0.087 |
| 363 | 0.044 | ND | 0.90 | ND |
| 364 | 0.018 | ND | 0.52 | ND |
| 365 | 0.084 | ND | 0.17 | ND |
| 366 | 0.087 | ND | 0.076 | ND |
| 367 | 0.044 | ND | 0.061 | ND |
| 368 | 2.2 | ND | 0.057 | ND |
| 369 | 0.57 | ND | 6.4 | ND |

ND = not determined

It is meant to be understood that the examples and embodiments described herein are for illustrative purposes only and that various modifications or changes in light thereof will be suggested to persons skilled in the art and are to be included within the spirit and purview of the appended claims. All publications, patents, and patent applications cited herein are hereby incorporated by reference in their entirety for all purposes.

Xenograft Tumor Growth Inhibition Assay

The effect of Examples 1 and 32 to inhibit the growth of H929 xenograft tumors implanted in mice was evaluated. NCI-H929 cells obtained from either tumor brei or culture were suspended in cell culture medium (MEM, no calcium, no glutamine, Life Technologies Corporation) and diluted 1:1 with a solution of Matrigel™ (BD Biosciences, Franklin Lakes, N.J.). Tumor cells 5 million per site were inoculated subcutaneously into the right hind flank of female nude or SCID-beige mice (Charles River Labs). Randomization into treatment and vehicle control groups (9-10/group) occurred when the mean tumor volume reached approximately 200 mm$^3$. Compounds were formulated in 2.5% DMSO, 2.5% Tween80, 25% PEG400, 70% phosphate-buffered saline or in 2% DMSO, 5% Tween80, 20% PEG400, 73% HPMC. Administration of compound or vehicle was initiated on the day following randomization and continued for the indicated time. Tumors were measured twice a week throughout the treatment period using a pair of calipers and tumor volumes were calculated according to the formula V=L×W$^2$/2 (V: volume, mm$^3$; L: length, mm. W: width, mm). Tumor growth inhibition was calculated based on the mean tumor volume measured at the end of the treatment period according to the formula % TGI=100−mean tumor volume of treatment group/mean tumor volume of control group×100. Results are given in Table 2.

TABLE 2

H929 human multiple myeloma cancer xenograft model.

| example | Dose mg/kg | route, regimen | % TGI[a] | % TGD[b] | % removed from study[c] |
|---|---|---|---|---|---|
| 1 | 12.5 | IP, TW[d] × 2 | 72* | Nd[e] | 0 |
| 32 | 1.85 | IP, TW × 4 | 27* | Nd | 10 |
| 32 | 3.75 | IP, TW × 4 | 57*** | Nd | 0 |
| 32 | 5.00 | IP, TW × 4 | 66*** | Nd | 10 |

[a]The p values (as indicated by asterisks) are derived from Student's T test comparison of treatment group vs. control group: *p < 0.05, p < 0.01, *p < 0.001.
[b]Tumor growth delay, % TGD = (T − C)/C × 100, where T = median time to reach 500 mm$^3$ of treatment group and C = median time to endpoint of control group. The p values (as indicated by asterisks) derived from Kaplan Meier log-rank comparison of treatment group vs. treatment control group based on an endpoint of 1000 mm$^3$. *p < 0.05, p < 0.01, *p < 0.001.
[c]Percentage of treatment group that were removed from study due to morbidity or weight loss in excess of 20%.
[d]Twice a week, 3 and 4 days apart.
[e]Not determined. End point not achieved by end of study (day 27).

What is claimed is:

1. A compound of formula (IIIa), or a pharmaceutically acceptable salt thereof,

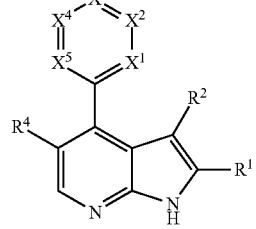

Formula (IIIa)

wherein $X^1$, and $X^4$ are N; and the remaining are $CR^{3A}$;

$R^1$ is selected from the group consisting of cycloalkyl, cycloalkenyl, heterocycloalkyl, and heterocycloalkenyl; wherein the $R^1$ cycloalkyl, cycloalkenyl, heterocycloalkyl and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $S(O)(N)R^5SO_2R^5$, $C(O)H$, $C(O)OH$, $(O)$, $OH$, $CN$, $NO_2$, $F$, $Cl$, $Br$ and $I$;

$R^2$ is selected from the group consisting of hydrogen, $C_1$-$C_4$ alkyl, $NO_2$, $CN$, $C(O)NH_2$, $C(O)OR^{2A}$, $F$, $Cl$, $Br$, and $I$;

$R^{2A}$ is selected from the group consisting of $C_1$-$C_6$ alkyl, $C_2$-$C_6$ alkenyl, and $C_2$-$C_6$ alkynyl;

$R^{3A}$, at each occurrence, is each independently selected from the group consisting of H, $R^6$, $OR^6$, $SR^6$, $S(O)R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $C(O)H$, $C(O)OH$, $(O)$, $OH$, $CN$, $NO_2$, $F$, $Cl$, $Br$ and $I$;

$R^4$ is selected from the group consisting of $R^{4A}$, $OR^{4A}$, $C(O)NH_2$, $CN$, $F$, $Cl$, $Br$, and $I$;

$R^{4A}$ is selected from the group consisting of hydrogen, $C_1$-$C_6$ alkyl, $C_2$-$C_6$ alkenyl, and $C_2$-$C_6$ alkynyl;

$R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $B(OH)_2$, $C(O)H$, $C(O)OH$, $OH$, $CN$, $NO_2$, $F$, $Cl$, $Br$ and $I$; wherein each $R^5$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $(O)$, $OH$, $CN$, $NO_2$, $F$, $Cl$, $Br$ and $I$;

$R^6$, at each occurrence, is independently selected from the group consisting of $C_1$-$C_6$ alkyl, $C_2$-$C_6$ alkenyl, $C_2$-$C_6$ alkynyl, phenyl, heteroaryl, heterocycloalkyl, heterocycloalkenyl, cycloalkyl, and cycloalkenyl; wherein each $R^6C_1$-$C_6$ alkyl, $C_2$-$C_6$ alkenyl, and $C_2$-$C_6$ alkynyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $OH$, $CN$, $NO_2$, $F$, $Cl$, $Br$ and $I$; wherein each $R^6$ phenyl, cycloalkyl, cycloalkenyl, heteroaryl, heterocycloalkyl, and heterocycloalkenyl is optionally substituted with one or more substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $(O)$, $OH$, $CN$, $NO_2$, $F$, $Cl$, $Br$ and $I$;

$R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $NH_2$, $NHR^{13}$, $N(R^{13})_2$, $C(O)H$, $C(O)OH$, $OH$, $CN$, $NO_2$, $F$, $Cl$, $Br$ and $I$; wherein each $R^7$ aryl, cycloalkyl, cycloalkenyl, heteroaryl, heterocycloalkyl, and heterocycloalkenyl is optionally substituted with one or more substituents independently selected from the group consisting of $R^{11}$, $OR^{11}$, $SR^{11}$, $S(O)R^{11}$, $SO_2R^{11}$, $C(O)R^{11}$, $CO(O)R^{11}$, $OC(O)R^{11}$, $OC(O)OR^{11}$, $NH_2$, $NHR^{11}$, $N(R^{11})_2$, $NHC(O)R^{11}$, $NR^{11}C(O)R^{11}$, $NHS(O)_2R^{11}$, $NR^{11}S(O)_2R^{11}$, $NHC(O)OR^{11}$, $NR^{11}C(O)OR^{11}$, $NHC(O)NH_2$, $NHC(O)NHR^{11}$, $NHC(O)N(R^{11})_2$, $NR^{11}C(O)NHR^{11}$, $NR^{11}C(O)N(R^{11})_2$, $C(O)NH_2$, $C(O)NHR^{11}$, $C(O)N(R^{11})_2$, $C(O)NHOH$, $C(O)NHOR^{11}$, $C(O)NHSO_2R^{11}$, $C(O)NR^{11}SO_2R^{11}$, $SO_2NH_2$, $SO_2NHR^{11}$, $SO_2N(R^{11})_2$, $C(O)H$, $C(O)OH$, $(O)$, $OH$, $CN$, $NO_2$, $F$, $Cl$, $Br$ and $I$;

$R^8$, at each occurrence, is independently selected from the group consisting of $C_1$-$C_6$ alkyl, $C_2$-$C_6$ alkenyl, $C_2$-$C_6$ alkynyl, and heterocycloalkyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, $SO_2R^{8A}$, $C(O)OR^{8A}$, $C(O)NH_2$, $C(O)NHR^{8A}$, $C(O)N(R^{8A})_2$, $C(O)NHSO_2R^{8A}$, $C(O)NR^{8A}SO_2R^{8A}$, $NH_2$, $C(O)H$, $C(O)OH$, $OH$, $CN$, $NO_2$, $F$, $Cl$, $Br$ and $I$; wherein each $R^8$ heterocycloalkyl is optionally substituted with one or more substituents independently selected from the group consisting of $NH_2$, $C(O)H$, $C(O)OH$, $OH$, $CN$, $NO_2$, $F$, $Cl$, $Br$ and $I$;

$R^{8A}$, at each occurrence, is independently selected from the group consisting of $C_1$-$C_6$ alkyl, $C_2$-$C_6$ alkenyl, and $C_2$-$C_6$ alkynyl;

$R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ aryl, cycloalkyl, cycloalkenyl, heteroaryl, heterocycloalkyl, and heterocycloalkenyl is optionally substituted with one or more substituents independently selected from the group consisting of $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $(O)$, $OH$, $CN$, $NO_2$, $F$, $CI$, $Br$ and $I$;

$R^{10}$, at each occurrence, is independently selected from the group consisting of $C_1$-$C_6$ alkyl, $C_2$-$C_6$ alkenyl, and $C_2$-$C_6$ alkynyl; wherein each $R^{10}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, $OH$, $CN$, $NO_2$, $F$, $CI$, $Br$ and $I$;

$R^{11}$, at each occurrence, is independently selected from the group consisting of $C_1$-$C_6$ alkyl, $C_2$-$C_6$ alkenyl, $C_2$-$C_6$ alkynyl, aryl, and heteroaryl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $OR^{11A}$, $NH_2$, $NHR^{11A}$, $N(R^{11A})_2$, $C(O)H$, $C(O)OH$, $OH$, $CN$, $NO_2$, $F$, $CI$, $Br$ and $I$; wherein each $R^{11}$ aryl and heteroaryl is optionally substituted with one or more substituents independently selected from the group consisting of $C_1$-$C_6$ alkyl, $C_1$-$C_6$ haloalkyl, $NH_2$, $C(O)H$, $C(O)OH$, $OH$, $CN$, $NO_2$, $F$, $CI$, $Br$ and $I$;

$R^{11A}$, at each occurrence, is independently selected from the group consisting of $C_1$-$C_6$ alkyl, $C_2$-$C_6$ alkenyl, and $C_2$-$C_6$ alkynyl;

$R^{12}$, at each occurrence, is independently selected from the group consisting of $C_1$-$C_6$ alkyl, $C_2$-$C_6$ alkenyl, and $C_2$-$C_6$ alkynyl; wherein each $R^{12}$ $C_1$-$C_6$ alkyl, $C_2$-$C_6$ alkenyl, and $C_2$-$C_6$ alkynyl is optionally substituted with one or more substituents independently selected from the group consisting of $NH_2$, $NHR^{14}$, $N(R^{14})_2$, $C(O)H$, $C(O)OH$, $OH$, $CN$, $NO_2$, $F$, $CI$, $Br$ and $I$;

$R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, cycloalkyl, cycloalkenyl, and heterocycloalkyl, heterocycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of $R^{15}$, $OR^{15}$, $C(O)H$, $C(O)OH$, $OH$, $CN$, $NO_2$, $F$, $CI$, $Br$ and $I$; wherein each $R^{13}$ aryl, cycloalkyl, cycloalkenyl, heteroaryl, heterocycloalkyl, and heterocycloalkenyl is optionally substituted with one or more substituents independently selected from the group consisting of $R^{16}$, $OR^{16}$, $C(O)H$, $C(O)OH$, $(O)$, $OH$, $CN$, $NO_2$, $F$, $CI$, $Br$ and $I$;

$R^{14}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl;

$R^{15}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl; wherein each $R^{15}$ $C_1$-$C_6$ alkyl, $C_2$-$C_6$ alkenyl, and $C_2$-$C_6$ alkynyl is optionally substituted with one or more $OCH_3$; and $R^{16}$, at each occurrence, is independently selected from the group consisting of $C_1$-$C_6$ haloalkyl, $C_1$-$C_6$ alkyl, $C_2$-$C_6$ alkenyl, and $C_2$-$C_6$ alkynyl.

2. The compound of claim 1, or a pharmaceutically acceptable salt thereof, wherein $R^2$ is hydrogen, $R^4$ is $R^{4A}$, and $R^{4A}$ is hydrogen.

3. The compound of claim 2, or a pharmaceutically acceptable salt thereof, wherein $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $SO_2NHC(O)R^5$, $SO_2NR^5C(O)R^5$, $NHS(O)_2R^5$, $NR^5S(O)_2R^5$, $NHC(O)OR^5$, $NR^5C(O)OR^5$, $SO_2NHC(O)OR^5$, $SO_2NR^5C(O)OR^5$, $NHSO_2NHC(O)OR^5$, $NHSO_2NR^5C(O)OR^5$, $NR^5SO_2NR^5C(O)OR^5$, $NR^5SO_2NHC(O)OR^5$, $NHC(O)NH_2$, $NHC(O)NHR^5$, $NHC(O)N(R^5)_2$, $NR^5C(O)NHR^5$, $NR^5C(O)N(R^5)_2$, $OC(O)NH_2$, $OC(O)NHR^5$, $OC(O)N(R^5)_2$, $OC(O)NHSO_2R^5$, $OC(O)NR^5SO_2R^5$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $OSO_2NH_2$, $OSO_2NHR^5$, $OSO_2N(R^5)_2$, $C(O)NHCN$, $C(O)NR^5CN$, $S(O)(N)R^5$, $S(O)(N)R^5SO_2R^5$, $C(O)H$, $C(O)OH$, $(O)$, $OH$, $CN$, $NO_2$, $F$, $Cl$, $Br$ and $I$.

4. The compound of claim 2, or a pharmaceutically acceptable salt thereof, wherein $R^1$ is selected from the group consisting of pyrrolidinyl, morpholinyl, piperidinyl, 1,2,3,6-tetrahydropyridinyl, cyclohexyl, and cyclohexenyl; wherein the $R^1$ pyrrolidinyl, morpholinyl, piperidinyl, 1,2,3,6-tetrahydropyridinyl, cyclohexyl, and cyclohexenyl are optionally substituted with one or more substituents independently selected from the group consisting of $R^5$, $SO_2R^5$, $C(O)R^5$, $CO(O)R^5$, $NH_2$, $SO_2NHC(O)OR^5$, $C(O)NH_2$, $C(O)NHR^5$, and $C(O)OH$.

5. The compound of claim 3, or a pharmaceutically acceptable salt thereof, wherein $R^{3A}$, at each occurrence, is independently selected from the group consisting of H, $R^6$, $OR^6$, $NH_2$, $NHR^6$, $N(R^6)_2$, $NHC(O)R^6$, $C(O)NHR^6$, F, and Cl.

6. The compound of claim 5, or a pharmaceutically acceptable salt thereof, wherein $R^6$, at each occurrence, is independently selected from the group consisting of $C_1$-$C_6$ alkyl, phenyl, and heteroaryl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of $R^9$, $SR^9$, and OH; wherein each $R^6$ phenyl and heteroaryl is optionally substituted with one or more substituents independently selected from the group consisting of $NH_2$, and Cl.

7. The compound of claim 1, selected from the group consisting of:
N-benzyl-6-{2-[1-(methylsulfonyl)piperidin-4-yl]-1H-pyrrolo[2,3-b]pyridin-4-yl}pyrazin-2-amine;
N-benzyl-6-[2-(piperidin-4-yl)-1H-pyrrolo[2,3-b]pyridin-4-yl]pyrazin-2-amine;
6-[2-(piperidin-4-yl)-1H-pyrrolo[2,3-b]pyridin-4-yl]-N-(tetrahydro-2H-pyran-4-ylmethyl)pyrazin-2-amine;
N-(3,5-difluorobenzyl)-6-[2-(piperidin-4-yl)-1H-pyrrolo[2,3-b]pyridin-4-yl]pyrazin-2-amine;
N-(3-fluorobenzyl)-6-[2-(piperidin-4-yl)-1H-pyrrolo[2,3-b]pyridin-4-yl]pyrazin-2-amine;

6-[2-(piperidin-4-yl)-1H-pyrrolo[2,3-b]pyridin-4-yl]-N-(pyridin-3-ylmethyl)pyrazin-2-amine;
6-[2-(piperidin-4-yl)-1H-pyrrolo[2,3-b]pyridin-4-yl]-N-(pyridin-4-ylmethyl)pyrazin-2-amine;
N-(3,4-difluorobenzyl)-6-[2-(piperidin-4-yl)-1H-pyrrolo[2,3-b]pyridin-4-yl]pyrazin-2-amine;
1-[4-(4-{6-[(3,5-difluorobenzyl)amino]pyrazin-2-yl}-1H-pyrrolo[2,3-b]pyridin-2-yl)piperidin-1-yl]-2-hydroxyethanone;
1-[4-(4-{6-[(3-fluorobenzyl)amino]pyrazin-2-yl}-1H-pyrrolo[2,3-b]pyridin-2-yl)piperidin-1-yl]-2-hydroxyethanone;
1-(4-{4-[6-(benzylamino)pyrazin-2-yl]-1H-pyrrolo[2,3-b]pyridin-2-yl}piperidin-1-yl)-2-hydroxyethanone;
N-benzyl-N-methyl-6-[2-(1-methylpiperidin-4-yl)-1H-pyrrolo[2,3-b]pyridin-4-yl]pyrazin-2-amine;
N-benzyl-6-[2-(1-methylpiperidin-4-yl)-1H-pyrrolo[2,3-b]pyridin-4-yl]pyrazin-2-amine;
1-(4-{4-[6-(benzylamino)pyrazin-2-yl]-1H-pyrrolo[2,3-b]pyridin-2-yl}piperidin-1-yl)ethanone;
3-(4-{4-[6-(benzylamino)pyrazin-2-yl]-1H-pyrrolo[2,3-b]pyridin-2-yl}piperidin-1-yl)propane-1,2-diol;
ethyl [(4-{4-[6-(benzylamino)pyrazin-2-yl]-1H-pyrrolo[2,3-b]pyridin-2-yl}piperidin-1-yl)sulfonyl]carbamate;
4-{6-[(3-fluorobenzyl)oxy]pyrazin-2-yl}-2-(piperidin-4-yl)-1H-pyrrolo[2,3-b]pyridine;
N-(3-fluorobenzyl)-6-[2-(1-methylpiperidin-4-yl)-1H-pyrrolo[2,3-b]pyridin-4-yl]pyrazin-2-amine;
1-[4-(4-{6-[(3-fluorobenzyl)amino]pyrazin-2-yl}-1H-pyrrolo[2,3-b]pyridin-2-yl)piperidin-1-yl]ethanone;
4-{6-[(3-fluorobenzyl)oxy]pyrazin-2-yl}-2-(1-methylpiperidin-4-yl)-1H-pyrrolo[2,3-b]pyridine;
N-benzyl-6-[2-(1,2,3,6-tetrahydropyridin-4-yl)-1H-pyrrolo[2,3-b]pyridin-4-yl]pyrazin-2-amine;
1-[4-(4-{6-[(3-fluorobenzyl)oxy]pyrazin-2-yl}-1H-pyrrolo[2,3-b]pyridin-2-yl)piperidin-1-yl]-2-hydroxyethanone;
3-[4-(4-{6-[(3-fluorobenzyl)oxy]pyrazin-2-yl}-1H-pyrrolo[2,3-b]pyridin-2-yl)piperidin-1-yl]propane-1,2-diol;
ethyl {[4-(4-{6-[(3-fluorobenzyl)amino]pyrazin-2-yl}-1H-pyrrolo[2,3-b]pyridin-2-yl)piperidin-1-yl]sulfonyl}carbamate;
4-{4-[6-(benzylamino)pyrazin-2-yl]-1H-pyrrolo[2,3-b]pyridin-2-yl}-N-methylpiperidine-1-carboxamide;
4-(4-{6-[(3-fluorobenzyl)amino]pyrazin-2-yl}-1H-pyrrolo[2,3-b]pyridin-2-yl)-N-methylpiperidine-1-carboxamide;
4-{6-[(3-fluorobenzyl)oxy]pyrazin-2-yl}-2-[1-(methylsulfonyl)piperidin-4-yl]-1H-pyrrolo[2,3-b]pyridine;
1-[4-(4-{6-[(3-fluorobenzyl)oxy]pyrazin-2-yl}-1H-pyrrolo[2,3-b]pyridin-2-yl)piperidin-1-yl]ethanone;
4-(4-{6-[(3-fluorobenzyl)oxy]pyrazin-2-yl}-1H-pyrrolo[2,3-b]pyridin-2-yl)-N-methylpiperidine-1-carboxamide;
1-[4-{4-[6-(benzylamino)pyrazin-2-yl]-1H-pyrrolo[2,3-b]pyridin-2-yl}-3,6-dihydropyridin-1(2H)-yl]-2-hydroxyethanone;
N-(3-fluorobenzyl)-6-[2-(1,2,3,6-tetrahydropyridin-4-yl)-1H-pyrrolo[2,3-b]pyridin-4-yl]pyrazin-2-amine;
3-[4-(4-{6-[(3-fluorobenzyl)amino]pyrazin-2-yl}-1H-pyrrolo[2,3-b]pyridin-2-yl)-3,6-dihydropyridin-1(2H)-yl]propane-1,2-diol;
4-{6-[(3-fluorobenzyl)oxy]pyrazin-2-yl}-2-(1,2,3,6-tetrahydropyridin-4-yl)-1H-pyrrolo[2,3-b]pyridine;
4-(4-{6-[(3-fluorobenzyl)amino]pyrazin-2-yl}-1H-pyrrolo[2,3-b]pyridin-2-yl)-N-methyl-3,6-dihydropyridin-1(2H)-carboxamide;
6-[2-(1-methylpiperidin-4-yl)-1H-pyrrolo[2,3-b]pyridin-4-yl]-N-(pyridin-3-ylmethyl)pyrazin-2-amine;
3-[4-(4-{6-[(pyridin-3-ylmethyl)amino]pyrazin-2-yl}-1H-pyrrolo[2,3-b]pyridin-2-yl)piperidin-1-yl]propane-1,2-diol;
2-hydroxy-1-[4-(4-{6-[(pyridin-3-ylmethyl)amino]pyrazin-2-yl}-1H-pyrrolo[2,3-b]pyridin-2-yl)piperidin-1-yl]ethanone;
N-methyl-4-(4-{6-[(pyridin-3-ylmethyl)amino]pyrazin-2-yl}-1H-pyrrolo[2,3-b]pyridin-2-yl)piperidine-1-carboxamide;
1-[4-(4-{6-[(3-fluorobenzyl)amino]pyrazin-2-yl}-1H-pyrrolo[2,3-b]pyridin-2-yl)-3,6-dihydropyridin-1(2H)-yl]-2-hydroxyethanone;
4-{6-[(3-fluorobenzyl)oxy]pyrazin-2-yl}-2-[1-(methylsulfonyl)-1,2,3,6-tetrahydropyridin-4-yl]-1H-pyrrolo[2,3-b]pyridine;
4-(4-{6-[(3-fluorobenzyl)oxy]pyrazin-2-yl}-1H-pyrrolo[2,3-b]pyridin-2-yl)-N-methyl-3,6-dihydropyridine-1(2H)-carboxamide;
1-[4-(4-{6-[(3-fluorobenzyl)oxy]pyrazin-2-yl}-1H-pyrrolo[2,3-b]pyridin-2-yl)-3,6-dihydropyridin-1(2H)-yl]-2-hydroxyethanone;
4-{4-[6-(benzylamino)pyrazin-2-yl]-1H-pyrrolo[2,3-b]pyridin-2-yl}cyclohex-3-ene-1-carboxylic acid;
4-{4-[6-(benzylamino)pyrazin-2-yl]-1H-pyrrolo[2,3-b]pyridin-2-yl}-N-methylcyclohex-3-ene-1-carboxamide;
4-(4-{6-[(3-fluorobenzyl)amino]pyrazin-2-yl}-1H-pyrrolo[2,3-b]pyridin-2-yl)cyclohex-3-ene-1-carboxylic acid;
4-(4-{6-[(3-fluorobenzyl)oxy]pyrazin-2-yl}-1H-pyrrolo[2,3-b]pyridin-2-yl)cyclohex-3-ene-1-carboxylic acid;
4-(4-{6-[(3-fluorobenzyl)oxy]pyrazin-2-yl}-1H-pyrrolo[2,3-b]pyridin-2-yl)-N-methylcyclohex-3-ene-1-carboxamide;
4-(4-{6-[(3-fluorobenzyl)oxy]pyrazin-2-yl}-1H-pyrrolo[2,3-b]pyridin-2-yl)cyclohex-3-ene-1-carboxamide;
4-(4-{6-[(3-fluorobenzyl)amino]pyrazin-2-yl}-1H-pyrrolo[2,3-b]pyridin-2-yl)cyclohex-3-ene-1-carboxamide;
4-{4-[6-(benzylamino)pyrazin-2-yl]-1H-pyrrolo[2,3-b]pyridin-2-yl}cyclohex-3-ene-1-carboxamide;
and pharmaceutically acceptable salts thereof.

8. A pharmaceutical composition comprising a pharmaceutically acceptable excipient and a therapeutically effective amount of a compound of claim 1 or a pharmaceutically acceptable salt thereof.

* * * * *